United States Patent [19]
Adams et al.

[11] Patent Number: 6,060,432
[45] Date of Patent: *May 9, 2000

[54] HERBICIDAL SULFONAMIDES

[75] Inventors: Edward John Adams, Elkton, Md.; Karlheinz Drauz, Freigericht, Germany; Wonpyo Hong, Lutherville, Md.; Balreddy Kamireddy; Wallace Christian Petersen, both of Hockessin, Del.; Matthias Schaefer, Goldbach; Christoph Weckbecker, Hanau, both of Germany

[73] Assignees: E. I. du Pont de Nemours and Company, Wilmington, Del.; Degussa Aktiengesellschaft, Frankfurt, Germany

[ * ] Notice: This patent issued on a continued prosecution application filed under 37 CFR 1.53(d), and is subject to the twenty year patent term provisions of 35 U.S.C. 154(a)(2).

[21] Appl. No.: 08/736,636

[22] Filed: Oct. 24, 1996

Related U.S. Application Data

[60] Provisional application No. 60/007,031, Oct. 25, 1995, and provisional application No. 60/012,329, Feb. 27, 1996.

[51] Int. Cl.[7] ............ C07D 403/02; C07D 471/00; C07D 487/00; A01N 43/50
[52] U.S. Cl. ............ 504/276; 504/197; 504/245; 504/246; 546/23; 546/84; 546/121; 548/113; 548/302.4; 548/302.7
[58] Field of Search ............ 504/197, 245, 504/246, 276; 546/23, 84, 121; 548/113, 302.4, 302.7

[56] References Cited

U.S. PATENT DOCUMENTS

| | | | |
|---|---|---|---|
| 4,666,507 | 5/1987 | Yanagi et al. | 71/92 |
| 5,356,863 | 10/1994 | Satow et al. | 504/243 |
| 5,605,877 | 2/1997 | Schafer et al. | 504/266.2 |
| 5,883,049 | 3/1999 | Hirai et al. | 504/246 |

FOREIGN PATENT DOCUMENTS

| | | |
|---|---|---|
| 2119673 | 9/1994 | Canada . |
| 0 077 938 A2 | 5/1983 | European Pat. Off. . |
| 0 364 797 A2 | 4/1990 | European Pat. Off. . |
| 3813884 | 11/1989 | Germany . |
| 4327027 | 8/1994 | Germany . |
| 06345743 | 12/1994 | Japan . |
| 2230261 | 10/1990 | United Kingdom . |
| WO 93/15074 | 8/1993 | WIPO . |
| WO 94/03454 | 2/1994 | WIPO . |
| WO 94/03459 | 2/1994 | WIPO . |
| WO 94/04511 | 3/1994 | WIPO . |
| WO 94/05668 | 3/1994 | WIPO . |
| WO 94/10173 | 5/1994 | WIPO . |
| WO 94/22860 | 10/1994 | WIPO . |
| WO 95/00521 | 1/1995 | WIPO . |
| WO 95/23509 | 9/1995 | WIPO . |
| WO 95/29158 | 11/1995 | WIPO . |

*Primary Examiner*—Mukund J. Shah
*Assistant Examiner*—Brenda Coleman

[57] ABSTRACT

Compounds of Formula I, and their N-oxides and agriculturally suitable salts, are disclosed which are useful for controlling undesired vegetation

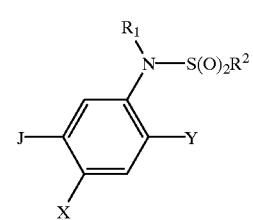

I wherein X, Y, J, $R^1$, and $R^2$ are as defined in the disclosure.

Also disclosed are compositions containing the compounds of Formula I and a method for controlling undesired vegetation which involves contacting the vegetation or its environment with an effective amount of a compound of Formula I.

9 Claims, No Drawings

HERBICIDAL SULFONAMIDES

CROSS-REFERENCE TO RELATED APPLICATIONS

This application claims the benefit of U.S. Provisional Application No. 60/007,031, filed Oct. 25, 1995, and U.S. Provisional Application No. 60/012,329, filed Feb. 27, 1996.

BACKGROUND OF THE INVENTION

This invention relates to certain sulfonamides, their N-oxides, agriculturally suitable salts and compositions, and methods of their use for controlling undesirable vegetation.

The control of undesired vegetation is extremely important in achieving high crop efficiency. Achievement of selective control of the growth of weeds especially in such useful crops as rice, soybean, sugar beet, corn (maize), potato, wheat, barley, tomato and plantation crops, among others, is very desirable. Unchecked weed growth in such useful crops can cause significant reduction in productivity and thereby result in increased costs to the consumer. The control of undesired vegetation in noncrop areas is also important. Many products are commercially available for these purposes, but the need continues for new compounds which are more effective, less costly, less toxic, environmentally safer or have different modes of action.

U.S. Pat. No. 4,818,275 discloses herbicidal acyclic sulfonamides of the formula

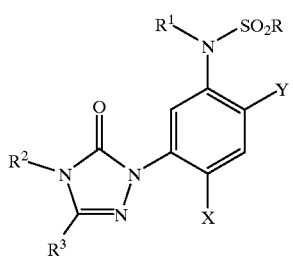

wherein, inter alia

X and Y are Br, Cl or F;

R is alkyl, haloalkyl or dialkylamino;

$R^1$ is H, Na, lower alkyl or $SO_2R$;

$R^2$ is alkyl, haloalkyl or lower alkoxy; and $R^3$ is halogen, alkyl or haloalkyl.

The sulfonamides of the present invention are not disclosed therein.

SUMMARY OF THE INVENTION

This invention is directed to compounds of Formula I including all geometric and stereoisomers, N-oxides, and agriculturally suitable salts thereof, agricultural compositions containing them and their use for controlling undesirable vegetation:

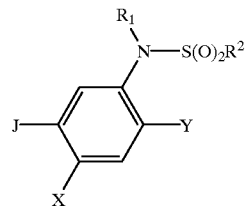

wherein

X is H, F or Cl;

Y is F, Cl, Br, cyano, nitro, $C_1$–$C_3$ haloalkyl, $C_1$–$C_3$ alkoxy, $C_1$–$C_3$ haloalkoxy or $C(S)NH_2$;

$R^1$ is H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, $C_2$–$C_6$ alkoxyalkyl, $C_2$–$C_6$ haloalkoxyalkyl, formyl, $C_2$–$C_{20}$ alkylcarbonyl, $C_4$–$C_7$ cycloalkylcarbonyl, $C_2$–$C_6$ haloalkylcarbonyl, $C_2$–$C_6$ alkoxycarbonyl, $C_3$–$C_6$ alkoxyalkylcarbonyl, $C_2$–$C_6$ haloalkoxycarbonyl, $C_3$–$C_6$ cycloalkyl, $C_3$–$C_6$ halocycloalkyl, $C_4$–$C_7$ cycloalkylalkyl, $C_4$–$C_7$ halocycloalkylaLkyl, $S(O)_2R^2$, $C(O)SR^3$, $C(O)NR^4R^5$ or benzoyl;

$R^2$ is $C_1$–$C_6$ alkoxy, $C_1$–$C_6$ haloalkoxy, $C_1$–$C_6$ haloalkyl, $C_3$–$C_6$ cylcloalkyl, $C_3$–$C_6$ halocycloalkyl, $C_2$–$C_6$ alkoxyalkyl, $C_2$–$C_6$ haloalkoxyalkyl, $C_2$–$C_6$ alkenyl, $C_2$–$C_6$ haloalkenyl, $C_3$–$C_6$ alkoxyalkenyl, $C_2$–$C_6$ alkynyl, $C_2$–$C_6$ haloalkynyl, $C_2$–$C_6$ cyanoalkyl, $C_1$–$C_6$ nitroalkyl, $(CH_2)_p$—$OR^6$, $C$=$CH(CH_2)_q$—$OR^6$, $C$≡$C(CH_2)_q$—$OR^6$, $C_2$–$C_6$ alkylthioalkyl, $C_2$–$C_6$ alkylsulfinylalkyl, $C_2$–$C_6$ alkylsulfonylalkyl, $C_3$–$C_8$ alkloxycarbonylalkyl, $C_3$–$C_8$ alkylcarbonyloxyalkyl or oxiranyl optionally substituted with 1–3 $C_1$–$C_3$ alkyl;

$R^3$ is H, $C_1$–$C_3$ alkyl or $C_1$–$C_3$ haloalkyl; or $R^3$ is phenyl optionally substituted with $C_1$–$C_3$ alkyl, 1–3 halogen, 4–5 fluorine, 1–2 nitro, $C_1$–$C_3$ alkoxy or $CF_3$;

$R^4$ is H, $C_1$–$C_3$ alkyl or $C_1$–$C_3$ haloalkyl; or $R^4$ is phenyl optionally substituted with $C_1$–$C_3$ alkyl, 1–3 halogen, 4–5 fluorine, 1–2 nitro, $C_1$–$C_3$ alkoxy or $CF_3$;

$R^5$ is $C_1$–$C_3$ alkyl or $C_1$–$C_3$ haloalkyl; or $R^4$ and $R^5$ are taken together as —CH—$CH_2$—, —$CH_2CH_2CH_2$—, —$CH_2CH_2CH_2CH_2$—, —$CH_2CH_2CH_2CH_2CH_2$— or —$CH_2CH_2OCH_2CH_2$—;

$R^6$ is $C_1$–$C_3$ alkylsulfonyl, $C_1$–$C_3$ haloalkylsulfonyl or $P$(=$O$)($OR^7$)($OR^8$); or $R^6$ is phenylsulfonyl optionally substituted with $C_1$–$C_6$ alkyl, 1–3 halogen, 4–5 fluorine, $C_1$–$C_6$ alkoxy, $CF_3$ or $C_2$–$C_4$ alkylcarbonyl;

$R^7$ and $R^8$ are each independently H, $C_1$–$C_3$ alkyl or $C_1$–$C_3$ haloalkyl;

J is

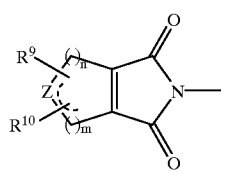

J-1

-continued
J-2 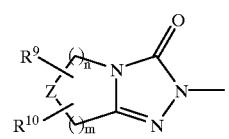
J-3 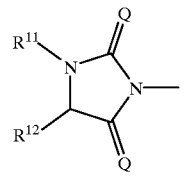
J-4 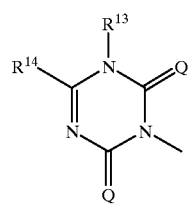
J-5 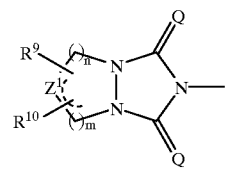
J-6 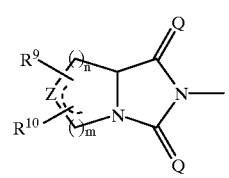
J-7 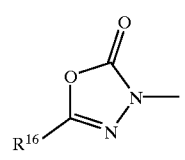
J-8 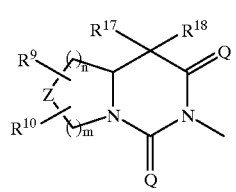
J-9 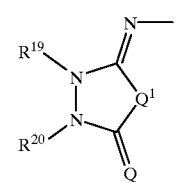
J-10 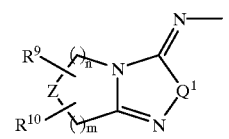
-continued
J-11 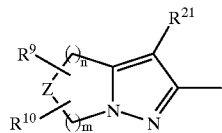
J-12 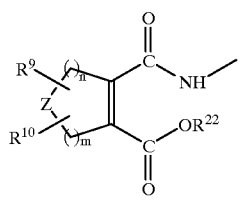
J-13 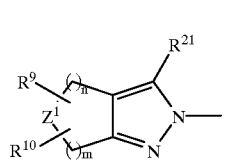
J-14 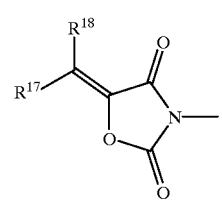
J-15 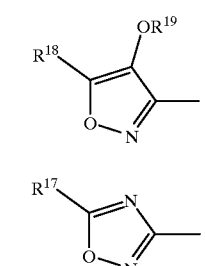
J-16 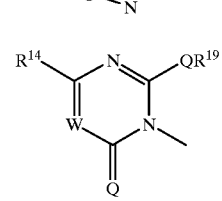
J-17 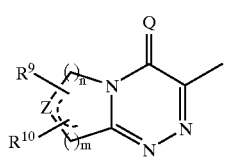
J-18 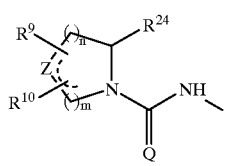
J-19
wherein the dashed line in J-1, J-5, J-6, J-18, and J-19 indicates that the left-hand ring contains only single bonds or one bond in the ring is a carbon-carbon double bond;

m and n are each independently 0, 1, 2 or 3, provided that m+n is 2 or 3;

Z is $CR^9R^{10}$, O, S, S(O), $S(O)_2$, $N(C_1–C_4$ alkyl) or

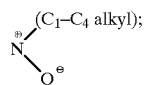

$Z^1$ is $CR^9R^{23}$, O, S, S(O), $S(O)_2$, $N(C_1–C_4$ alkyl) or

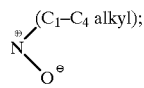

each $R^9$ is independently H, $C_1–C_6$ alkyl, halogen, hydroxy, $C_1–C_6$ alkoxy, $C_1–C_6$ haloalkyl, $C_1–C_6$ haloalkoxy, $C_2–C_6$ alkylcarbonyloxy or $C_2–C_6$ haloalkylcarbonyloxy;

each $R^{10}$ is independently H, $C_1–C_6$ alkyl, hydroxy or halogen; or when $R^9$ and $R^{10}$ are bonded to adjacent carbon atoms they can be taken together with the carbons to which they are attached to form

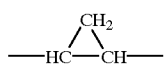

optionally substituted with at least one member selected from 1–2 halogen and 1–2 $C_1–C_3$ alkyl;

each $R^{11}$ is independently H, $C_1–C_6$ alkyl, $C_3–C_6$ alkenyl, $C_1–C_6$ haloalkyl or $C_2–C_6$ alkoxyalkyl;

$R^{12}$ is H, halogen, $C_1–C_6$ alkyl, $C_3–C_6$ alklenyl, $C_1–C_6$ haloalkyl or $C_2–C_6$ alkoxyalkyl;

$R^{13}$ is H, $C_1–C_6$ alkyl, $C_1–C_6$ haloallyl, $C_3–C_6$ alkenyl, $C_3–C_6$ haloalkenyl, $C_3–C_6$ alkynyl, $C_3–C_6$ haloalkynyl, HC(=O), $C_2–C_5$ alkylcarbonyl or $N(R^{11})_2$;

$R^{14}$ is $C_1–C_6$ alkyl, $C_1–C_6$ alkylthio, $C_1–C_6$ haloalkyl or $N(CH_3)_2$;

W is N or $CR^{15}$;

$R^{15}$ is H, $C_1–C_6$ alkyl or halogen; or $R^{15}$ is phenyl optionally substituted with $C_1–C_6$ alkyl, 1–3 halogen, 4–5 fluorine, $C_1–C_6$ alkoxy or $CF_3$;

$R^{16}$ is $C_1–C_6$ alkyl, halogen or $C_1–C_6$ haloalkyl;

$R^{17}$ and $R^{18}$ are each independently H, $C_1–C_6$ alkyl or $C_1–C_6$ haloalkyl;

$R^{19}$ and $R^{20}$ are each independently $C_1–C_6$ alkyl, $C_1–C_6$ haloalkyl, $C_3–C_6$ alkenyl, $C_3–C_6$ haloalkenyl, $C_3–C_6$ alkynyl or $C_3–C_6$ haloalkynyl;

$R^{21}$ is H, halogen, cyano, $C_1–C_3$ alkoxy or $C_1–C_3$ haloalkoxy;

$R^{22}$ is $C_1–C_6$ alkyl or $C_1–C_6$ haloalkyl; or $R^{22}$ is phenyl optionally substituted with $C_1–C_6$ alkyl, 1–3 halogen, 4–5 fluorine, 1–2 nitro, $C_1–C_6$ alkoxy or $CF_3$;

$R^{23}$ is $C_1–C_3$ alkyl, hydroxy or halogen;

$R^{24}$ is cyano or $C(Q)R^{25}$;

$R^{25}$ is $OR^{26}$ or $NR^{27}R^{28}$;

$R^{26}$ is $C_1–C_6$ alkyl or $C_1–C_6$ haloalkyl;

each $R^{27}$ is independently H or $C_1–C_6$ alkyl;

$R^{28}$ is H, $C_1–C_6$ alkyl, $C_1–C_6$ alkoxy or $NR^{27}R^{29}$; or $R^{27}$ and $R^{28}$ can be taken together as $—CH_2CH_2—$, $—CH_2CH_2CH_2—$, $—CH_2CH_2CH_2CH_2—$, $—CH_2CH_2CH_2CH_2CH_2—$ or $—CH_2CH_2OCH_2CH_2—$;

$R^{29}$ is H, $C_1–C_3$ alkyl, $C_2–C_4$ alkylcarbonyl, $C_2–C_4$ alkoxycarbonyl or $C_1–C_3$ alkylsulfonyl;

Q is independently O or S;

$Q^1$ is O or S;

p is 1,2 or 3; and q is 0, 1, 2 or 3;

provided that,
(a) when J is J-5, X is F, Y is Cl, $R^1$ is H, Q is O, $R^9$ and $R^{10}$ are H, $Z^1$ is O, n is 2, and m is 1, then $R^2$ is other than $CF_3$;
(b) when J is J-6, X is F, Y is Cl, $R^1$ is H, Q is O, $R^9$ and $R^{10}$ are H, Z is CHCl or CHBr, n is 1, and m is 1, then $R^2$ is other than $CF_3$;
(c) when J is J-8, X is F, Y is Cl, $R^1$ is H, $R^{17}$ and $R^{18}$ are H, Q is O, $R^9$ and $R^{10}$ are H, Z is $CH_2$, and (m+n) is 2 or 3, then $R^2$ is other than $CF_3$;
(d) when J is J-8, X is F, Y is Cl, $R^1$ is H, $R^{17}$ and $R^{18}$ are H, Q is O, $R^9$ and $R^{10}$ are H, Z is O, n is 1, and m is 2, then $R^2$ is other than $CF_3$; and
(e) when J is J-11, X is F, Y is Cl, $R^1$ is H, $R^{21}$ is Cl, $R^9$ and $R^{10}$ are H, Z is $CH_2$, and (m+n) is 3, then $R^2$ is other than $CF_3$.

In the above recitations, the term "alkyl", used either alone or in compound words such as "alkylthio" or "haloalkyl" includes straight-chain or branched alkyl, such as, methyl, ethyl, n-propyl, i-propyl, or the different butyl, pentyl or hexyl isomers. The term "1–2 alkyl" indicates that one or two of the available positions for that substituent may be alkyl which are independently selected. "Alkenyl" includes straight-chain or branched alkenes such as vinyl, 1-propenyl, 2-propenyl, and the different butenyl, pentenyl and hexenyl isomers. "Alkenyl" also includes polyenes such as 1,2-propadienyl and 2,4-hexadienyl. "Alkynyl" includes straight-chain or branched alkynes such as ethynyl, 1-propynyl, 2-propynyl and the different butynyl, pentynyl and hexynyl isomers. "Alkynyl" can also include moieties comprised of multiple triple bonds such as 2,5-hexadiynyl. "Alkoxy" includes, for example, methoxy, ethoxy, n-propyloxy, isopropyloxy and the different butoxy, pentoxy and hexyloxy isomers. "Alkoxyalkyl" denotes alkoxy substitution on alkyl. "Alkoxyalkoxy" denotes alkoxy substitution on alkoxy. Examples of "alkoxyalkyl" include $CH_3OCH_2$, $CH_3OCH_2CH_2$, $CH_3CH_2OCH_2$, $CH_3CH_2CH_2CH_2OCH_2$ and $CH_3CH_2OCH_2CH_2$. "Alkylthio" includes branched or straight-chain alkylthio moieties such as methylthio, ethylthio, and the different propylthio, butylthio, pentylthio and hexylthio isomers. "Alkylthioalkyl" denotes alkylthio substitution on alkyl. Examples of "alkylthioalkyl" include $CH_3SCH_2$, $CH_3SCH_2CH_2$, $CH_3CH_2SCH_2$, $CH_3CH_2CH_2CH_2SCH_2$ an $CH_3CH_2SCH_2CH_2$. "Alkylsulfinyl" includes both enantiomers of an alkylsulfinyl group. Examples of "alklylsulfinyl" include $CH_3S(O)$, $CH_3CH_2S(O)$, $CH_3CH_2CH_2S(O)$, $(CH_3)_2CHS(O)$ and the different butylsulfinyl, pentylsulfinyl and hexylsulfinyl isomers. Examples of "alkylsulfonyl" include $CH_3S(O)_2$, $CH_3CH_2S(O)_2$, $CH_3CH_2CH_2S(O)_2$, $(CH_3)_2CHS(O)_2$ and the different butylsulfonyl, pentylsulfonyl and hexylsulfonyl isomers. "Cyanoalklyl" denotes an alkyl group substituted with one cyano group. Examples of "cyanoalkyl" include $NCCH_2$, $NCCH_2CH_2$ and $CH_3CH(CN)CH_2$. "Alkylamino", "dialkylamino", and the like, are defined analogously to the above examples. "Cycloalkyl" includes, for example, cyclopropyl, cyclobutyl, cyclopentyl, and cyclohexyl. One skilled in the art will appreciate that not all nitrogen containing heterocycles can form N-oxides since the nitrogen requires an available lone pair for oxidation to the oxide; one skilled in the art will recognize those nitrogen containing heterocycles which can form N-oxides.

The term "halogen", either alone or in compound words such as "haloalkyl", includes fluorine, chlorine, bromine or iodine. The term "1–2 halogen" indicates that one or two of the available positions for that substituent may be halogen which are independently selected. Further, when used in compound words such as "haloalkyl", said alkyl may be partially or fully substituted with halogen atoms which may be the same or different. Examples of "haloalkyl" include $F_3C$, $ClCH_2$, $CF_3CH_2$ and $CF_3CCl_2$. The terms "haloalkenyl", "haloalkynyl", "haloalkoxy", and the like, are defined analogously to the term "haloalkyl". Examples of "haloalkenyl" include $(Cl)_2C=CHCH_2$ and $CF_3CH_2C=CHCH_2$. Examples of "haloalkynyl" include $HC\equiv CCHCl$, $CF_3C\equiv C$, $CCl_3C\equiv C$ and $FCH_2C\equiv CCH_2$. Examples of "haloalkoxy" include $CF_3O$, $CCl_3CH_2O$, $HCF_2CH_2CH_2O$ and $CF_3CH_2O$. Examples of "haloalkylthio" include $CCl_3S$, $CF_3S$, $CCl_3CH_2S$ and $ClCH_2CH_2CH_2S$. Examples of "haloalkylsulfinyl" include $CF_3S(O)$, $CCl_3S(O)$, $CF_3CH_2S(O)$ and $CF_3CF_2S(O)$. Examples of "haloalkylsulfonyl" include $CF_3S(O)_2$, $CCl_3S(O)_2$, $CF_3CH_2S(O)_2$ and $CF_3CF_2S(O)_2$. Examples of "haloalkoxyalkoxy" include $CF_3OCH_2O$, $ClCH_2CH_2OCH_2CH_2O$, $Cl_3CCH_2OCH_2O$ as well as branched alkyl derivatives.

The total number of carbon atoms in a substituent group is indicated by the "$C_i–C_j$" prefix where i and j are numbers from 1 to 20. For example, $C_1–C_3$ alkylsulfonyl designates methylsulfonyl through propylsulfonyl; $C_2$ alkoxyalkyl designates $CH_3OCH_2$; $C_3$ alkoxyalkyl designates, for example, $CH_3CH(OCH_3)$, $CH_3OCH_2CH_2$ or $CH_3CH_2OCH_2$; and $C_4$ alkoxyalkyl designates the various isomers of an alkyl group substituted with an alkoxy group containing a total of four carbon atoms, examples including $CH_3CH_2CH_2OCH_2$ and $CH_3CH_2OCH_2CH_2$. Examples of "alkylcarbonyl" include $C(O)CH_3$, $C(O)CH_2CH_2CH_3$ and $C(O)CH(CH_3)_2$. Examples of "alkoxycarbonyl" include $CH_3OC(=O)$, $CH_3CH_2OC(=O)$, $CH_3CH_2CH_2OC(=O)$, $(CH_3)_2CHOC(=O)$ and the different butoxy- or pentoxycarbonyl isomers. In the above recitations, when a compound of Formula I is comprised of one or more heterocyclic rings, all substituents are attached to these rings through any available carbon or nitrogen by replacement of a hydrogen on said carbon or nitrogen.

When a compound is substituted with a substituent bearing a subscript that indicates the number of said substituents can exceed 1, said substituents (when they exceed 1) are independently selected from the group of defined substituents. Further, when the subscript indicates a range, e.g., $(R)_{i-j}$, then the number of substituents may be selected from the integers between i and j inclusive.

When a group contains a substituent which can be hydrogen, for example $R^1$ or $R^{13}$, then, when this substituent is taken as hydrogen, it is recognized that this is equivalent to said group being unsubstituted.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula I, N-oxides and agriculturally suitable salts thereof. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. The salts of the compounds of the invention also include those formed with organic bases (e.g., pyridine, ammonia, triethylamine or dicyclohexylamine) or inorganic bases (e.g., hydrides, hydroxides, or carbonates of sodium, potassium, lithium, calcium, magnesium or barium) when the compound contains an acidic group such as a carboxylic acid or an amide.

Preferred compounds for reasons of better activity and/or ease of synthesis are:

Preferred 1. Compounds of Formula I above, and N-oxides and agriculturally suitable salts thereof, wherein:

X is F or Cl;

Y is F, Cl or Br;

$R^1$ is H, $C_1–C_6$ alkyl, $C_3–C_6$ cycloalkyl, $C_3–C_6$ alkenyl, $C_3–C_6$ alkynyl, $C_1–C_6$ haloalkyl, $C_2–C_6$ alkoxyalkyl, $C_3–C_6$ haloalkenyl, $C_3–C_6$ alkoxyalkylcarbonyl, $C_2–C_6$ alkylcarbonyl, $C_2–C_6$ alkoxycarbonyl, $S(O)_2R^2$ or $C(O)NR^4R^5$;

$R^2$ is $C_1–C_6$ alkoxy, $C_1–C_6$ haloalkoxy, $C_1–C_6$ haloalkyl, $C_3–C_6$ cylcloalkyl, $C_3–C_6$ halocycloalkyl, $C_2–C_6$ alkoxyalkyl or $C_2–C_6$ haloalkoxyalkyl;

J is J-5, J-6, J-11, J-17 or J-19;

Z is $CR^9R^{10}$, O, S or $N(C_1–C_4$ alkyl);

each $R^9$ is independently H, halogen or $C_1–C_6$ haloalkoxy;

each $R^{10}$ is independently H, hydroxy or halogen;

each Q is O;

$Z^1$ is $CR^9R^{23}$, O, S or $N(C_1–C_4$ alkyl); and $R^{23}$ is halogen.

Preferred 2. Compounds of Preferred 1 wherein:

Y is F or Cl;

$R^1$ is H, $C_1–C_6$ alkyl, $C_3–C_6$ cycloalkyl, $C_3–C_6$ alkenyl, $C_3–C_6$ alkynyl, $C_1–C_6$ haloalkyl, $C_2–C_6$ alkoxyalkyl, $C_3–C_6$ haloalkenyl, $C_2–C_6$ alkylcarbonyl or $C_2–C_6$ alkoxycarbonyl;

$R^2$ is $C_1–C_6$ haloalkoxy, $C_1–C_6$ haloalkyl, $C_3–C_6$ halocycloalkyl, $C_2–C_6$ alkoxyalkyl or $C_2–C_6$ haloalkoxyalkyl;

Z is $CR^9R^{10}$ or O; and $Z^1$ is $CR^9R^{23}$ or O.

Preferred 3. Compounds of Preferred 1 wherein:

J is J-19;

$R^1$ is H, $C_1–C_6$ alkyl, $C_3–C_6$ alkenyl, $C_3–C_6$ alkynyl, $C_2–C_6$ alkoxyalkyl, $C_2–C_6$ alkylcarbonyl or $C_2–C_6$ alkoxycarbonyl;

$R^2$ is $C_1–C_6$ haloalkyl;

$R^9$ is H;

$R^{10}$ is hydroxy or halogen;

Z is $CR^9R^{10}$;

n is 1; and m is 1.

Preferred 4. Compounds of Preferred 2 wherein:

J is J-6; and

Z is $CR^9R^{10}$.

Most preferred are compounds of Preferred 4 selected from the group:
a) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide;
b) (6S-cis)-N-[2-chloro-4-fluoro-5-(6-fluorotetrahydro-1,3-dioxo-1H-pyrrolo[1,2-c]imidazol-2(3H)-yl)phenyl]-N-[(chloromethyl)sulfonyl]acetamide;
c) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide;
d) (6S-cis)-N-[2-chloro-5-(6-chlorotetrahydro-1,3-dioxo-1H-pyrrolo[1,2-c]imidazol-2(3H)-yl)-4-fluorophenyl]-N-[(chloromethyl)sulfonyl]acetamide;
e) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide monosodium salt;
f) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide monopotassium salt;
g) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide monosodium salt; and
h) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide monopotassium salt.

This invention also relates to herbicidal compositions comprising herbicidally effective amounts of the compounds of the invention and at least one of a surfactant, a solid diluent or a liquid diluent. The preferred compositions of the present invention are those which comprise the above preferred compounds.

This invention also relates to a method for controlling undesired vegetation comprising applying to the locus of the vegetation herbicidally effective amounts of the compounds of the invention (e.g., as a composition described herein). The preferred methods of use are those involving the above preferred compounds.

DETAILS OF THE INVENTION

The compounds of Formula I can be prepared by one or more of the following methods and variations as described in Schemes 1–10. The definitions of X, Y, J, $R^1$–$R^{29}$ Z, $Z^1$, n, m, W, Q, $Q^1$, p, and q in the compounds of Formulae 1–23 below are as defined above in the Summary of the Invention. Compounds of Formulae Ia–If are various subsets of the compounds of Formula I, and all substituents for Formulae Ia–If are as defined above for Formula I.

Compounds of Formula I are prepared from the corresponding anilines of Formula 1 as represented in Scheme 1.

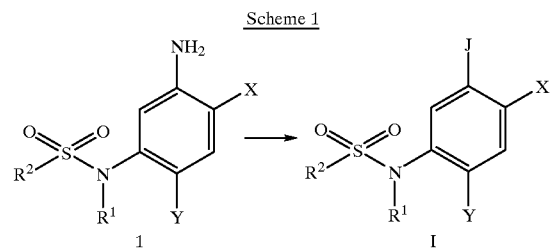

Synthesis of Anilines of Formula 1

Anilines of Formula 1 are prepared by the method illustrated in Scheme 2. Nitration of acetanilide 2 using a nitric acid/sulfuric acid mixture affords the nitro compound of Formula 3. Reduction of the nitro group to the aniline of Formula 4 can be achieved by catalytic hydrogenation over a metal catalyst such as palladium, iridium or Raney® nickel. The preferred catalyst is 5% iridium adsorbed onto charcoal. The aniline of Formula 4 is contacted with a sulfonyl chloride to give the sulfonamide of Formula 5. For compounds wherein $R^1$ is other than H, the sulfonamide nitrogen can be alkylated, acylated or sulfonylated to give the $R^{1a}$-substituted compound of Formula 1. The alkylation is performed using an alkyl halide or alkyl sulfonate in the presence of a base such as potassium carbonate, sodium methoxide, potassium t-butoxide (t-BuOK) or sodium hydride in an anhydrous solvent such as dimethylformamide (DMF), tetrahydrofuran or acetonitrile at ambient temperature to 80° C. Acylations to form the carbonyl-substituted sulfonamides are accomplished by condensing the sulfonamide of Formula 5 with the appropriate acylating agent, for example an acyl chloride, isocyanate or carbamoyl chloride. Sulfonylations to form the sulfonyl-substituted sulfonamides are accomplished in an analogous manner by reacting the sulfonamide of Formula 5 with the appropriate sulfonylating agent, for example a sulfonyl chloride.

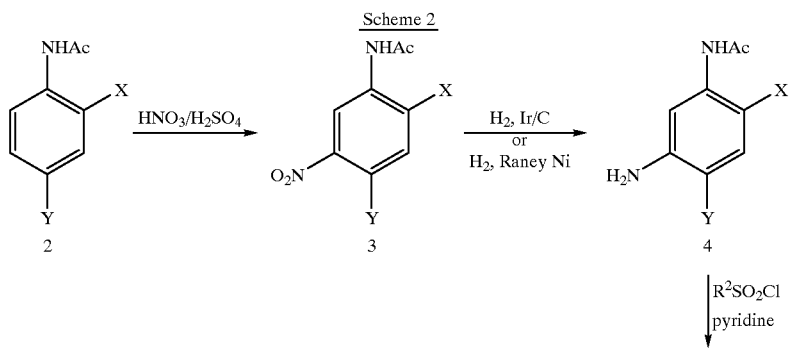

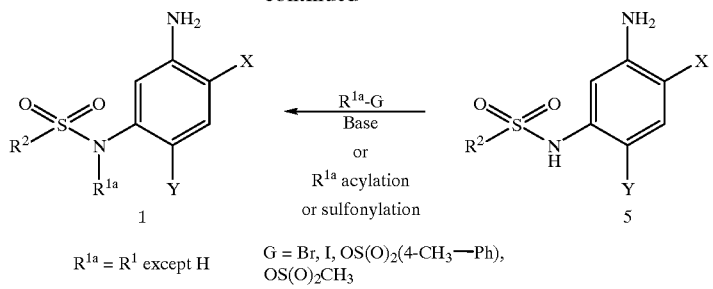

Anilines of Formula I can also be prepared by the method illustrated in Scheme 3. The nitro aniline of Formula 6 is sulfonylated to afford the compound of Formula 7. Further alkylation, acylation or sulfonylation gives the nitro compound of Formula 8. Reduction of the nitro group to the aniline of Formula 9 can be achieved by iron in acetic acid or by catalytic hydrogenation over a metal catalyst such as palladium or iridium. The preferred method is by hydrogenation over 5% iridium adsorbed onto charcoal. Chlorination of the phenyl ring provides the compound of Formula 1 wherein $R^{1a}$ is $R^1$ as defined in the Summary of the Invention except H.

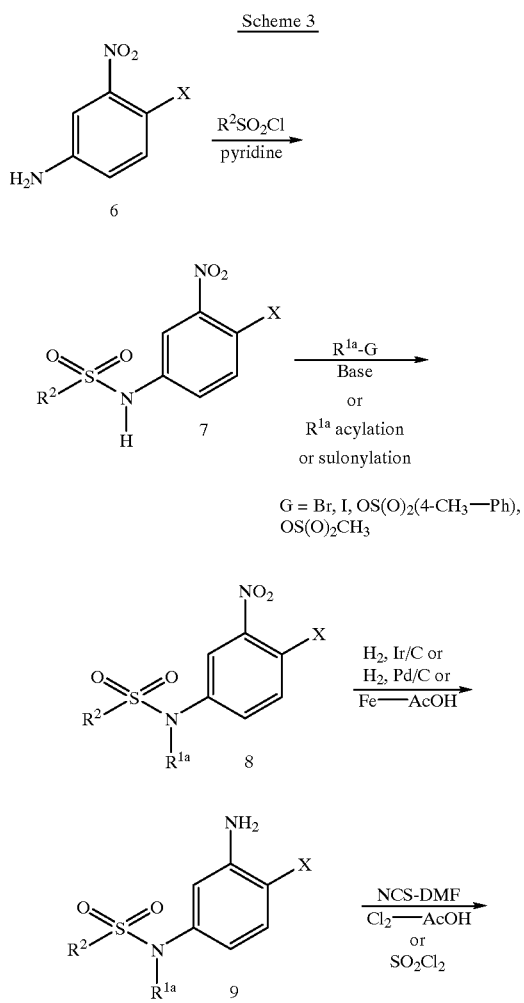

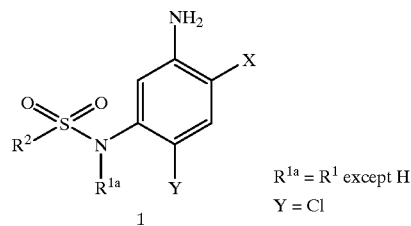

Converting Anilines of Formula 1 to Compounds of Formula I

The anilines prepared by the methods outlined in Schemes 2 and 3 are used in the condensation with J group derivatives to form compounds of Formula I. In some instances, the anilines are used directly in the condensation reactions. In other instances and depending on the nature of the J-group, the $NH_2$ of the aniline is first converted to another functional group prior to condensation. For example, the aniline may be converted first to a hydrazine, an isocyanate or an aryl iodide. These methods are described in more detail below.

Direct Coupling with the Anilines

In some instances where the aniline is used directly, the compounds of Formula I are prepared by condensation of the aniline with an anhydride precursor to the J group. For example, as illustrated in Scheme 4, the anhydride of Formula 10 is condensed with the aniline of Formula 1 to give compounds of Formula Ia wherein J=J-1. This method is disclosed in EP-A-170,191.

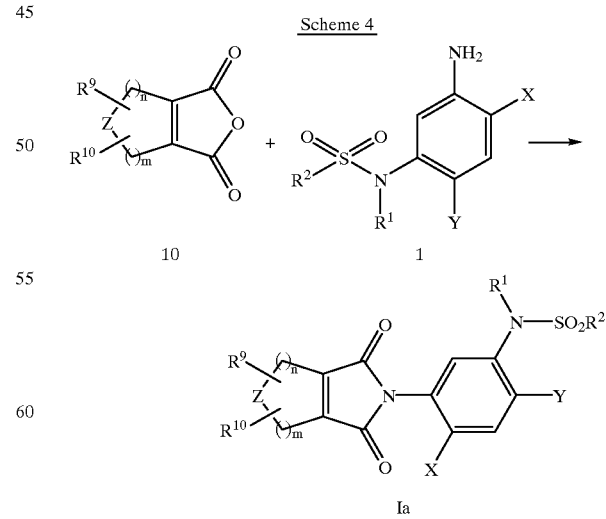

The anhydride of Formula 10 can be prepared by methods disclosed in EP493,721, and WO 91/06216. Compounds of Formula I wherein J=J-8 and J-12 can be prepared using similar methodology. The aniline is condensed with the appropriate J-group anhydride, diester, or other bis-electrophile to form the compound of Formula I. The J-8 group precursor and the aniline condensation reaction are described in WO94/03459. The J-12 group anhydride and the aniline condensation reaction are described in U.S. Pat. No. 4,003,926.

Hydrazines

For some compounds of Formula I, the appropriate aniline is first converted to the corresponding hydrazine, and then the hydrazine is condensed with the J-group derivative, or precursor thereof, to form the desired material. The conversion of an aniline of Formula 1 to a hydrazine of Formula 11 is illustrated in Scheme 5. Subsequent condensation of the hydrazine with the iminoether precursor to J-2 followed by cyclization with phosgene forms the sulfonamide of Formula Ib. The preparation of the iminoether J-2 precursor and the condensation procedure is described in U.S. Pat. No. 4,315,767.

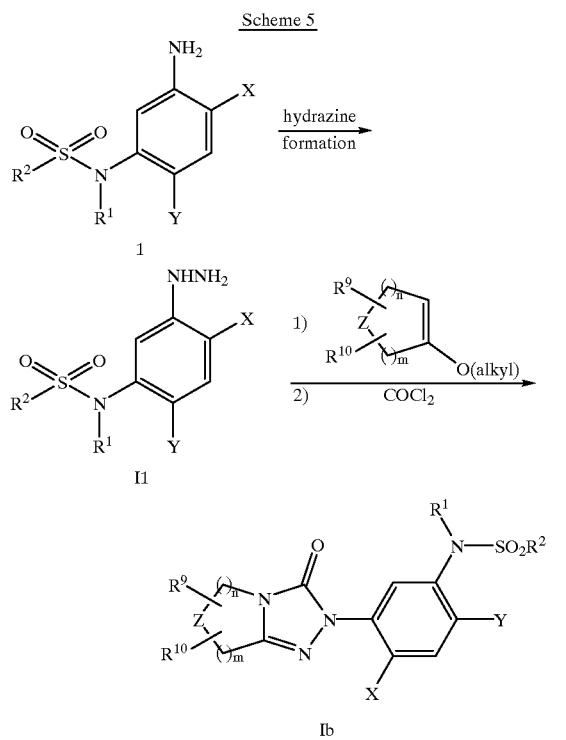

Anilines can be converted to the hydrazines by diazotization and then reduction as is well-known in the literature (for example, see U.S. Pat. No. 4,695,312).

Compounds of Formula I wherein J=J-7 are also prepared by first converting the aniline to the appropriate hydrazine, and then condensation with the appropriate J-group precursor. Methods for the preparation of the J-7 precursor and the condensation with a hydrazine are described in WO 92/12139 and U.S. Pat. No. 4,560,752.

The retrosynthetic analysis for the synthesis of the J-2 group is shown below in Scheme 6 for compounds of Formula I wherein J=J-2 and Z is $CR^9R^{10}$. The formation of ring A can be accomplished by intramolecular cyclization between the nitrogen in ring B and the terminal double bond of the triazolinone with the sulfonamide group already in place. The synthesis of the triazolinone ring B is known in the art and can be prepared by methods such as those described in U.S. Pat. No. 4,818,275 and U.S. Pat. No. 4,818,276.

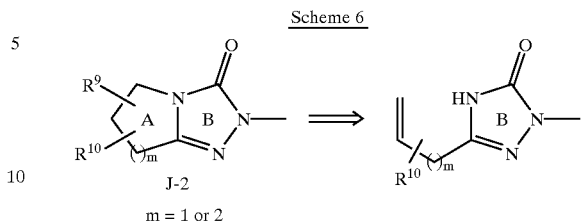

m = 1 or 2

Isocyanates

In some instances, the appropriate aniline is first converted to the corresponding isocyanate, and then the isocyanate is condensed with the J-group derivative, or precursor thereof, to form compounds of Formula I. In Scheme 7, the conversion of aniline of Formula 1 to isocyanate of Formula 12 is illustrated. Subsequent condensation of the isocyanate with the aminoester of Formula 13 followed by cyclization forms the sulfonamide of Formula Ic. The preparation of some aminoester precursors to J-6 and the condensation procedure are described in U.S. Pat. No. 4,179,276.

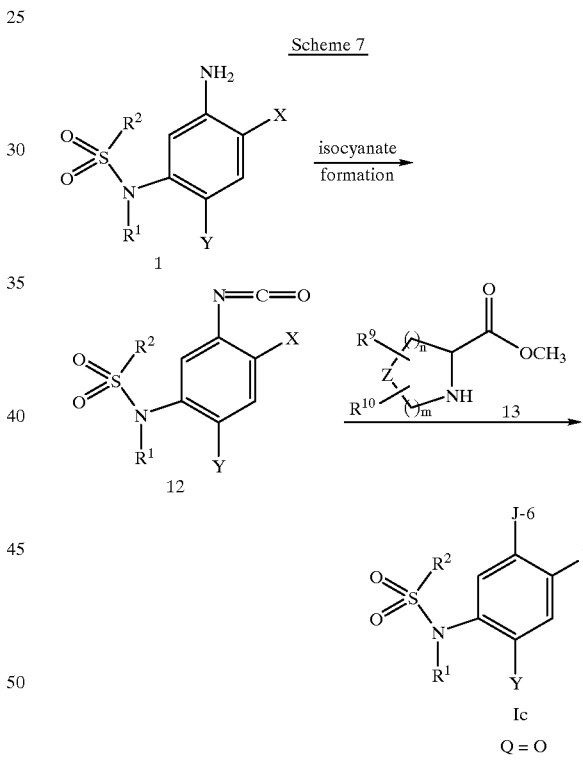

Q = O

Compounds of Formula I wherein J=J-3, J4, J-5, J-9, J-10 and J-19 are also prepared by first converting the aniline to the appropriate isocyanate, and then condensation with the appropriate J-group precursor. Methods for the preparation of the J-4 precursor and the condensation are described in WO 92/11244, EP 476,697, ZA 91/00466, JP 377,874, and U.S. Pat. No. 3,902,887. The synthesis of the J-5 precursor and the condensation with isocyanates is described in WO 92/13453 and EP 230,874. Methods for the preparation of the J-3 precursor and the condensation with isocyanates are described in EP 484,776. Methods for the preparation of the J-19 precursor and its condensation with isocyanates are described in EP 493,323. The synthesis of the J-10 precursor and the condensation with isocyanates is described in *J. Pesticide Sci.*, (1993), 18, 309. In a similar vein, the imino compounds of Formula I wherein J=J-9 can be prepared from the corresponding isocyanates of the anilines. The condensation procedure and J-group precursor preparation for compounds containing J-9 are disclosed in EP 457,151, JP 4,145,087, EP 480,871 and DE 3,927,388.

One skilled in the art will recognize that when Q or $Q^1$ is S in the desired product, the appropriate isothiocyanate is used instead of the isocyanate in the synthesis.

For some compounds of Formula I wherein J=J-3, J4, J-5, J-6, J-10, and J-19, the coupling can also be accomplished starting with the aniline rather than the isocyanate. For example, the synthesis of compounds of Formula Id (compounds of Formula I wherein $R^9$ and $R^{10}$ are taken together to form a cyclopropane ring) is illustrated in Scheme 8.

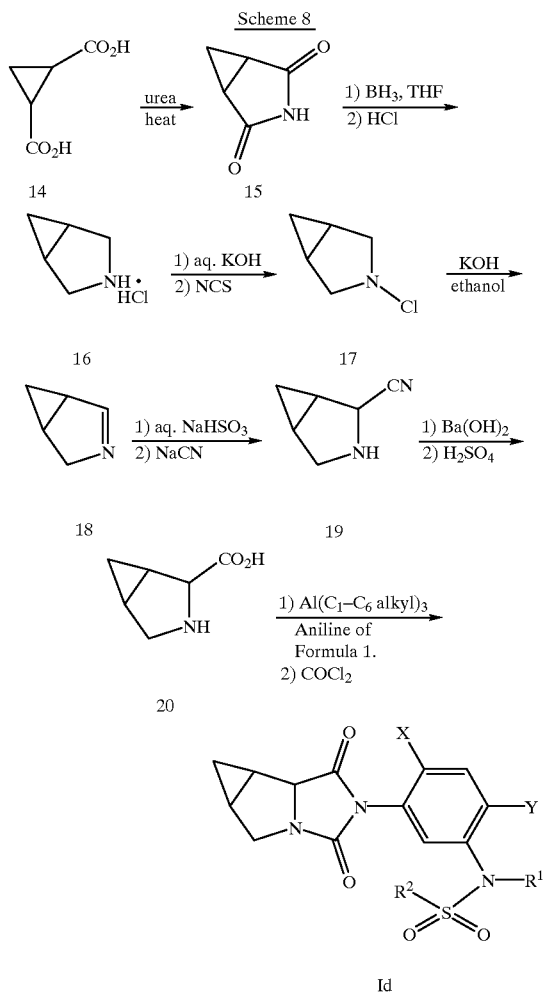

Treatment of cyclopropane dicarboxylic acid of Formula 14 with urea and heating to 175–185° C. affords the dicarboximide of Formula 15 as described by G. C. Crockett et al. in *Synth. Commun.* (1981), 11, 447454. The diester of the diacid of Formula 14 is prepared by the method described by L. L. McCoy in *J. Am. Chem. Soc.*, (1958), 80, 65–68. The diacid can be obtained by saponification of the diester using well-known methods. Reduction of the dicarboximide of Formula 15 with borane in an inert solvent, such as tetrahydrofuran (THF), followed by work-up with aqueous hydrochloric acid affords the azabicyclo[3.1.0]hexane hydrochloride of Formula 16. The reduction is preferably conducted with heating, for example in THF at reflux, as described by H. C. Brown and P. Heim in *J. Org. Chem.*, (1973), 38,912–916.

The amine hydrochloride of Formula 16 is converted via a five step sequence to the α-amimoacid of Formula 20 as illustrated. Purification of the intermediates is not necessary. Neutralization of the amine hydrochloride with a base, such as concentrated aqueous potassium hydroxide, liberates the free amine. Dissolution of the amine in an inert solvent, such as diethyl ether, and treatment with a solution of N-chlorosuccinimide (NCS) in an inert solvent such as ether, produces the chloramine of Formula 17. The solution of the chloramine is then treated with ethanolic potassium hydroxide to effect dehydrochlorination and give the imine of Formula 18. Once again, the imine is not purified but treated directly first with aqueous sodium bisulfite, and then with solid sodium cyanide to afford the aminonitrile of Formula 19. The reaction mixture is poured into water and extracted with a water-immiscible solvent such as ether. The organic layers are dried and evaporated under reduced pressure to afford the aminonitrile. No additional purification is necessary. The aminonitrile can be converted to the aminoacid of Formula 20 by hydrolysis with aqueous barium hydroxide followed by neutralization with sulfuric acid. A mixture of epimers at the carboxylic acid centers is obtained, and the individual diastereomers can be separated by chromatography.

The acid of Formula 20 is reacted with the aniline of Formula 1 and a trialkylaluminum reagent (e.g., trimethylaluminum), in a non-coordinating solvent such as an aromatic hydrocarbon (e.g., benzene and toluene) or halogenated hydrocarbon (e.g., methylene chloride, chloroform, and dichloroethane) to obtain the amide. Generally, the reaction requires 0.1 to 48 hours at a temperature of 0° C. to 25° C. to proceed to completion. The amides are isolated by extraction into an organic solvent, aqueous wash, and removal of the solvent under reduced pressure. Purification can be accomplished by chromatography or recrystallization. The condensation with the amine can also be performed starting with the ester of the acid of Formula 20.

The tricyclic imide of Formula Id can be prepared from the α-aminoamide by condensation with phosgene or a phosgene equivalent. Treatment of the α-aminoamide with phosgene is preferably carried out in the presence of a tertiary-amine base such as triethylamine, pyridine, or N,N-diisopropylethylamine, in an inert solvent such as dichloromethane or 1-chlorobutane. The phosgene can be added as a gas or as a solution in an inert solvent such as toluene. Suitable temperatures range from about 0° C. to the reflux temperature of the solvent. 1,1'-Carbonyldiimidazole, diphosgene (ClC(=O)OCCl$_3$) and triphosgene (Cl$_3$COC(=O)OCCl$_3$) can also be used in a similar manner.

The tricyclic imide of Formula Id can be isolated by extraction into an organic solvent, aqueous wash, and removal of the solvent under reduced pressure. Additional purification can be accomplished by chromatography or recrystallization.

The preparation of compounds of Formula I wherein J=J-6 and Z is CR$^9$R$^{10}$ is also described in WO94/05668.

Aryl Iodides

For the preparation of compounds of Formula I wherein J=J-11, the appropriate aniline is first converted to the aryl alkyne as illustrated in Scheme 9. The aniline of Formula 1 is converted to the aryl iodide of Formula 21 via diazotization followed by treatment with a metal iodide salt. The aryl iodide is linked by a palladium coupling reaction to give the trimethylsilyl (TMS) alkyne. Hydrolysis of the TMS group with base affords the terminal alkyne of Formula 22. In the case of J-11, a [3+2] cycloaddition using a sydnone as the dipole and the alkyne as the dipolarophile affords the bicyclic pyrazole compounds. Introduction of the $R^{21}$ group affords the sulfonamides of Formula Ie. For example, treatment with N-chlorosuccinimide affords the $R^{21}$=Cl compound. These methods are described in WO 93/15074, JP 4,059,706, WO 92/06962, and JP 3,163,063.

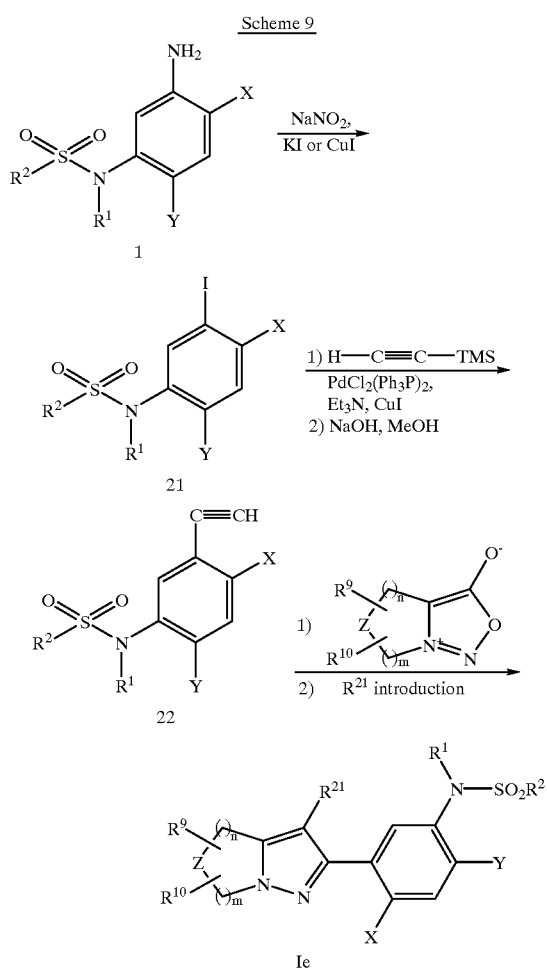

For compounds of Formula I wherein J=J-5, the coupling can also be accomplished starting with the aniline rather than the isocyanate. This method is described in WO 94/10173. For example, the synthesis of compounds of Formula If is illustrated in Scheme 10. Treatment of a diester of Formula 23 with an aniline of Formula 1 in the presence of a trialkylaluminum reagent (e.g., trimethylaluminum) in a non-coordinating solvent such as an aromatic hydrocarbon (e.g., benzene, toluene) or a halogenated hydrocarbon (e.g., methylene chloride, chloroform, and dichloroethane) affords a compound of Formula If.

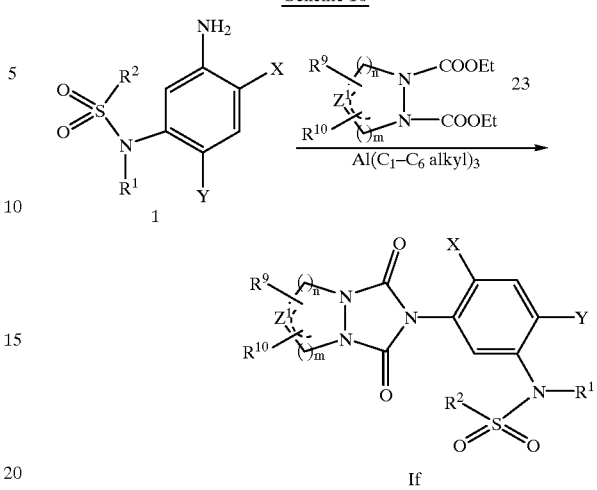

Methods for the preparation of compounds of Formula I wherein J=J-13 are described in EP 379,911, U.S. Pat. No. 4,123,252, and U.S. Pat. No. 4,042,373. Methods for the preparation of compounds of Formula I wherein J=J-14 are described in U.S. Pat. No. 4,818,272. Methods for the preparation of compounds of Formula I wherein J=J-17 are described in WO 95/25725 and DE 4,437,295. Methods for the preparation of compounds of Formula I wherein J=J-18 are described in DE 3,340,296 and U.S. Pat. No. 93/06132. Compounds of Formula I wherein J=15 and J=16 can be prepared by methods known in the art or by obvious modifications of these methods.

It is recognized that some reagents and reaction conditions described above for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis (see, for example, Greene, T. W.; Wuts, P. G. M. *Protective Group in Organic Synthesis*, 2nd ed.; Wiley: New York, 1991). One skilled in the art will recognize that, in some cases, after the introduction of a given reagent as it is depicted in any individual scheme, it may be necessary to perform additional routine synthetic steps not described in detail to complete the synthesis of compounds of Formula I.

One skilled in the art will also recognize that compounds of Formula I and the intermediates described herein can be subjected to various electrophilic, nucleophilic, radical, organometallic, oxidation, and reduction reactions to add substituents or modify existing substituents.

Without further elaboration, it is believed that one skilled in the art using the preceding description can utilize the present invention to its fullest extent. The following Examples are, therefore, to be construed as merely illustrative, and not limiting of the disclosure in any way whatsoever. Percentages are by weight except for chromatographic solvent mixtures or where otherwise indicated. Parts and percentages for chromatographic solvent mixtures are by volume unless otherwise indicated. $^1$H NMR data are in ppm downfield from tetrarnethylsilane. Couplings are designated by (s)-singlet, (d)-doublet, (t)-triplet, (q)-quartet, (m)-multiplet, (dd) -doublet of doublets, (ddd)-doublet of doublet of doublets, (dt)-doublet of triplets, and (br s)-broad singlet.

EXAMPLE 1

Step A: Preparation of N-(4-chloro-2-fluoro-5-nitrophenyl) acetamide

To a stirred solution of N-(4-chloro-2-fluorophenyl) acetamide (180.6 g, 0.96 mol) in concentrated sulfuric acid (1L) was added a mixture of 175 mL of concentrated $HNO_3$ and 175 mL of concentrated sulfuric acid at 0 to 5° C. in 1.5 h. After the addition was finished, the reaction mixture was stirred for another 0.5 h. The solution was poured into 5 L of ice water. After the product precipitated, it was isolated by filtration and then was dissolved in 2.5 L of ethyl acetate. After separation of the water layer, the organic layer was dried over sodium sulfate and then the solvent was evaporated. The crude product was triturated in diisopropyl ether (1.5 L), isolated by filtration, and dried under reduced pressure to afford the title compound of Step A (196.2 g, 87.6%) melting at 145–146° C. $^1H$ NMR ($Me_2SO-d_6$) δ 10.3–10.2 (s, 1H), 8.9 (d, 1H), 7.9–7.8 (d, 2.2–2.1 (s, 3H).

Step B: Preparation of N-(5-amino-4-chloro-2-fluorophenyl)acetamide

To a supension of the title compound of Step A (116 g, 500 mmol) in 500 mL of ethyl acetate was added 3.63 g of iridium (5%) on charcoal. The hydrogenation was performed at 4 bar of hydrogen pressure in an autoclave for 4.5 h at 60° C. The reaction was then filtered and the solvent removed under reduced pressure. Drying of the crystalline product yielded the title compound of Step B (99.4 g, 98%) melting at 142–143° C. $^1H$ NMR ($CDCl_3$) δ 7.9 (d, 1H), 7.3–7.2 (br s, 1H), 7.1–7.0 (s, 2H), 2.2–2.1 (s, 3H).

Step C: Preparation of N-[4-chloro-5-[[(chloromethyl) sulfonyl]amino]-2-fluorophenyl]acetamide

To a stirred solution of the title compound of Step B (8.10 g, 40 mmol) in pyridine (50 mL) was added chloromethyl-sulfonyl chloride (3.84 mL, 40.45 mmol) over 30 minutes at 0° C. After stirring at room temperature for 14 h, chloromethylsulfonyl chloride (0.38 mL, 4.05 mmol) was added to complete the reaction. Water was added so that the product precipitated. After filtration and washing with water and petroleum ether, the title compound of Step C was isolated as a bright powder (11.17 g, 89%) melting at 208–210° C. $^1H$ NMR ($Me_2SO-d_6$) δ 10.2–10.1 (s, 1H), 9.9 (s, 1H), 8.1 (d, 1H), 7.6–7.5 (d, 1H), 5.0–4.9 (s, 2H), 2.1 (s, 3H).

Step D: Preparation of N-(5-amino-2-chloro-4-fluorophenyl)-1-chloromethanesulfonamide

The title compound of Step C (10.3 g, 32.6 mmol) was suspended in 450 mL of 2M HCl. The temperature was raised to the boiling point of the reaction mixture under an argon atmosphere. After 45 minutes of stirring at this temperature, the reaction was cooled to room temperature, neutralized with $NaHCO_3$, and the product was extracted into ethyl acetate. After drying of the solution over sodium sulfate, the solvent was evaporated under reduced pressure yielding 8.9 g (98%) of the title compound of Step D as bright crystals melting at 105–107° C. $^1H$ NMR ($Me_2SO-d_6$) δ 9.9–9.8 (br s, 1H), 7.2 (d, 1H), 6.9 (d, 1H), 5.5–5.4 (s, 2H), 4.9 (s, 2H).

Step E: Preparation of 1-chloro-N-(2-chloro-4-fluoro-5-isocyanatophenyl)methanesulfonamide

To a stirred solution of phosgene (68 mmol) in 35 mL toluene was added the title compound of Step D (4.2 g, 15.4 mmol) in 80 mL toluene at 0° C. and the reaction was stirred at room temperature overnight. The temperature was then raised to 70° C. for 4 h. After cooling to room temperature, the reaction mixture was filtrated and the solvent was removed under reduced pressure. Drying of the white precipitate under reduced pressure yielded the title compound of Step E (4.4 g, 95%) melting at 101.5–102.5° C. $^1H$ NMR ($CDCl_3$) δ 7.5 (d, 1H), 7.3 (d, 1H), 7.0–6.9 (br s, 1H), 4.64.5 (s, 2H).

Step F: Preparation of (2R-cis)-1-[[[4-chloro-5-[[(chloromethyl)sulfonyl]amino]-2-fluorophenyl]amino] carbonyl]-4-hydroxy-2-pyrrolidinecarboxylic acid

To a stirred slurry of the title compound of Step E (34 mmol) in 550 mL toluene was added 4-cis-D-hydroxyproline (4.55 g, 35 mmol) at room temperature. 500 mL of dimethoxyethane was added and the temperature was raised to 70° C. After 1 h the temperature was raised to 90° C. for 6 h, and then the reaction mixture was stirred at room temperature overnight. The solvent was removed under reduced pressure and after the addition of water, petroleum ether and ethyl acetate, the product was extracted into the water phase. The product was precipitated by removal of the water under reduced pressure, dissolved in ethyl acetate, and dried over $Na_2SO_4$. The solvent was removed under reduced pressure furnishing the title compound of Step F (8.06 g, 50%). $^1H$ NMR ($Me_2SO-d_6$) δ 12.4 (br s, 1H), 10.1 (br s, 1H), 8.2 (s, 1H), 7.7 (d, 1H), 7.5 (d, 1H), 5.1–5.0 (br s, 1H), 5.04.9 (s, 2H), 4.4 (m, 1H), 4.3 (m, 1H), 3.7–3.6 (m, 1), 3.4–3.3 (m, 2H), 2.4–2.3 (m, 1H).

Step G: Preparation of (6R-trans)-1-chloro-N-[2-chloro-4-fluoro-5-(tetrahydro-6-hydroxy-1,3-dioxo-1H-pyrrolo[1.2-c]imidazol-2(3H)-yl)phenyl]methanesulfonamide

To a stirred solution of the title compound of Step F (2.7 g, 5.4 mmol) and N-hydroxysuccinimide (0.621 g, 5.4 mmol) in acetonitrile (50 mL) was added a solution of N,N-dicyclohexylcarbodiimide (1.14 g, 5.4 mmol) in acetonitrile (30 mL) over 30 minutes at 0 to −5° C. The reaction was stirred at room temperature for 14 h. The by-products were removed by filtration and the solvent was evaporated under reduced pressure to yield the title compound of Step G (2.6 g, quantitative yield) as a crude product melting at 198–200° C. $^1H$ NMR ($Me_2SO-d_6$) δ 10.2 (br s, 1H), 7.8–7.7 (d, 1H), 7.5–7.4 (d, 1H), 5.2–5.1 (br s, 1H), 5.1–5.0 (s, 2H), 4.5 (m, 1H), 4.34.2 (m, 1H), 3.1 (m, 1H), 2.3 (m, 1H), 2.0 (m, 1H).

Step H: Preparation of (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide

A suspension of the title compound of Step G (4.12 g, 10 mmol) in chlorobenzene (20 mL) was heated to 120° C. and a solution of Ishikawa's reagent ($Et_2NCF_2CHFCF_3$, 4.9 g) in chlorobenzene (5 mL) was added dropwise over 15 minutes. Heating at 120° C. was continued for another 15 minutes, after which time all of the solids had dissolved and the reaction mixture was then allowed to cool to room temperature. The mixture was concentrated under reduced pressure, the residue was dissolved in $CHCl_3$ (20 mL) and dicyclohexylamine (4.0 mL) was added dropwise at room temperature. This mixture was stirred for 10 minutes, hexanes (40 mL) was added slowly, and the mixture was stirred for another 10 minutes. The mixture was then filtered and the white solids were washed with 2:1 hexanes:$CHCl_3$, then with hexanes, and finally dried under nitrogen. The dried solids were suspended in $CH_2Cl_2$ (60 mL), cooled to 0° C., and 10% sulfuric acid (20 g) was added dropwise at 0–10° C. The mixture was stirred for 15 minutes at 0–10° C., then the organic phase was separated, washed with water (20 mL) and brine (20 mL), dried over magnesium sulfate, filtered, and concentrated under reduced pressure to yield a crude product containing the title product of Step H (3.59 g, 86 %). $^1H$ NMR ($CDCl_3$) δ 7.62 (d, 1H), 7.34 (d, 1H), 7.26 (br s, 1H), 5.5 (m, 1H), 4.60 (dd, 1H), 4.52 (s, 2H), 4.12 (m, 1H), 3.62 (dd, 1H), 2.64 (m, 1H), 2.06

EXAMPLE 2

Step A: Preparation of (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide To a stirred suspension of the title compound of Example 1, Step G (3.3 g, 8 mmol) in 25 mL toluene and 0.02 g DMF was added at 80° C. thionyl chloride (1.31 g, 11 mmol) over a period of 15 minutes. The suspension was stirred at the same temperature for 2 h and at 105° C. for 30 minutes. After cooling to room temperature, the organic layer was washed with water, dried, and the solvent was evaporated under reduced pressure to yield the title compound of Step A, a compound of this invention, in quantitative yield as a crude powdery product melting at 169–170° C. $^1$H NMR (CDCl$_3$) δ 7.64 (d, 1H), 7.36 (d, 1H), 7.20 (br s, 1H), 4.78 (m, 2H), 4.56 (s, 2H), 4.24 (dd, 1H), 3.62 (dd, 1H), 2.62 (m, 1H), 2.38 (m, 1H).

EXAMPLE 3

Step A: Preparation of (6S-cis)-N-[2-chloro-4-fluoro-5-(6-fluorotetrahydro-1H-dioxo-1H-pyrrolo[1,2-c]imidazol-2(3H)-yl)phenyl]-N-[(chloromethyl)sulfonyl]acetamide To a solution of the title compound of Example 1, Step H (4.14 g, 10 mmol) in anhydrous dichloromethane (200 mL) and pyridine (5 mL) was added a solution of acetyl chloride (0.863 g, 11 mmol) in dichloromethane (10 mL) dropwise at room temperature. After completion of the reaction (monitored by tlc), the organic phase was washed with water (50 mL) and diluted with HCl (5%, 50 mL). The organic layer was separated, dried (MgSO$_4$), and the solvent was removed in vacuo to give the title compound of Step A, a compound of this invention, as a white solid (4.3 g, 94%) melting at 198–200° C. $^1$H NMR (CDCl$_3$) δ 7.56 (m, 2H), 5.52 (m, 1H), 5.40 (dd, 1H), 4.84 (d, 1H), 4.62 (dd, 1H), 4.08 (m, 1H), 3.62 (m, 1H), 2.68 (m, 1H), 2.05 (s, 3H), 1.98 (m, 1H).

EXAMPLE 4

Step A: Preparation of (6S-cis)-N-[2-chloro-5-(6-fluorotetrahydro-1,3-dioxo-1H-pyrrolor[2-c]imidazol-2(3H)-yl)-4-fluorophenyl]-N-[(chloromethyl)sulfonyl]acetamide To a solution of the title compound of Example 2, Step A (4.29 g, 10 mmol) in anhydrous dichloromethane (200 mL) and pyridine (5 mL) was added a solution of acetyl chloride (0.862 g, 11 mmol) in dichloromethane (10 mL) dropwise at room temperature. After completion of the reaction (monitored by tlc), the organic phase was washed with water (50 mL) and diluted with HCl (5%, 50 mL) and water (50 mL). The organic layer was separated, dried (MgSO$_4$), and the removed the solvent to give the title compound of Step A, a compound of this invention, as a white solid (4.4 g, 93%) melting at 180–181° C. $^1$H NMR (CDCl$_3$) δ 7.50 (m, 2H), 5.38 (dd, 1H), 4.92 (d, 1H), 4.78 (m, 2H), 4.24 (dd, 1H), 3.62 (dd, 1H), 2.62 (m, 1H), 2.26 (m, 1H), 2.04 (s, 3H)

EXAMPLE 5

Step A: Preparation of (6S-cis)-1-chloro-N-[2-chloro-4-fluoro-5-(6-fluorotetrahydro-1,3-dioxo-1H-pyrrolo[2-c]imidazol-2(3H)-yl)phenyl]-N-methyl methanesulfonamide A mixture of the title compound of Example 1, Step H (0.414 g, 1 mmol), dimethyl sulfate (0.14 g, 1.1 mmol), and potassium carbonate (0.27 g) in acetone (10 mL) was stirred at room temperature for 4 h. After completion of the reaction, the potassium carbonate was filtered off and the solvent was removed on a rotary evaporator. The title compound of Step A, a compound of this invention, was isolated by flash chromatography (0.41 g, 95%) as a white solid melting at 90–92° C. $^1$H NMR (CDCl$_3$) δ 7.52 (d, 1H), 7.39 (d, 1H), 5.54 (m, 1H), 4.62 (s, 2H), 4.60 (m, 1H), 4.08 (m, 1H), 3.60 (dd, 1H), 3.42 (s, 3H), 2.64 (m, 1H), 2.01 (m, 1H).

EXAMPLE 6

Step A: Preparation of (6S-cis)-1-chloro-N-[2-chloro-4-fluoro-5-(6-fluorotetrahydro-1,3-dioxo-1H-pyrrolo[1,2-c]imidazol-2(3H)-yl)phenyl]-N-ethylmethanesulfonamide A mixture of the title compound of Example 1, Step H (0.414 g, 1 mmol), diethylsulfate (0.17 g, 1.1 mmol), and potassium carbonate (0.27 g) in acetone (10 mL) was stirred at room temperature for 4 h. After completion of the reaction, the potassium carbonate was filtered off and the solvent was removed on a rotary evaporator. The title compound of Step A, a compound of this invention, was isolated by flash chromatography (0.41 g, 92%) as a white solid melting at 198–200° C. $^1$H NMR (CDCl$_3$) δ 7.46 (d, 1H), 7.42 (d, 1H), 5.52 (m, 1H), 4.62 (dd, 1H), 4.59 (s, 2H), 4.02 (dd, 1H), 3.80 (m, 4H), 3.60 (dd, 1H), 2.64 (m, 1H), 2.01 (m, 1H), 1.20 (t, 6).

EXAMPLE 7

Step A: Preparation of (6S-cis)-methyl [2-chloro-4-fluoro-5-(6-fluorotetrahydro-1,3-dioxo-1H-pyrrolo[1,2-c]imidazol-2(3H)-yl)phenyl][(chloromethyl)sulfonyl]carbamate To a mixture of the title compound of Example 1, Step H (0.32 g, 0.7 mmol) and pyridine (0.5 mL) in dichloromethane (5 mL) was added a solution of methyl chloroformate (0.09 g, 0.95 mmol) in dichloromethane (1 mL) at room temperature. After completion of the reaction (2 h), the solvents were removed in vacuo and the title compound of Step A, a compound of this invention, was isolated by flash chromatography (0.31 g, 95%) as a white solid melting at 108–115° C. $^1$H NMR (CDCl$_3$) δ 7.40 (m, 2H), 5.42 (m, 1H), 5.36 (dd, 1H), 4.92 (dd, 1H), 4.60 (m, 1H), 4.04 (m, 1H), 3.82 (s, 3H), 3.60 (dd, 1H), 2.64 (m, 1H), 2.02 (m, 1H).

EXAMPLE 8

Step A: Preparation of (6S-cis)-1-chloro-N-[2-chloro-5-(6-chlorotetrahydro-1,3-dioxo 1H-pyrrolo[1,2-c]imidazol-2(3H)-yl)-4-fluorophenyl]-N-methyl methanesulfonamide A mixture of the title compound of Example 2, Step A (0.43 g, 1 mmol), dimethyl sulfate (0.17 g, 1.1 mmol), and potassium carbonate (0.27 g) in acetone (10 mL) was stirred at room temperature for 4 h. After completion of the reaction, potassium carbonate was filtered off and the solvent was removed on a rotary evaporator to yield the title compound of Step A, a compound of this invention, as a white solid purified by flash chromatography (0.40 g, 90%) and melting at 119–124° C. $^1$H NMR (CDCl$_3$) δ 7.52 (d, 1H), 7.42 (d, 1H), 4.76 (m, 2H), 4.62 (s, 2H), 4.24 (dd, 1H), 3.64 (dd, 1H) 3.42 (s, 3H), 2.62 (m, 1H), 2.22 (m, 1H).

EXAMPLE 9

Step A: Preparation of (6S-cis)-1-chloro-N-[2-chloro-5-(6-chlorotetrahydro-1,3-dioxo-1-pyrrolo[1,2-c]imidazol-2(3H)-yl)-4-fluorophenyl]-N-ethylmethanesulfonamide A mixture of the title compound of Example 2, Step A (0.43 g, 1 mmol), diethyl sulfate (0.17 g, 1.1 mmol), and potassium carbonate (0.27 g) in acetone (10 mL) was stirred at room temperature for 4 h. After completion of the reaction, potassium carbonate was filtered off and the solvent was removed on a rotary evaporator to yield the title compound of Step A, a compound of this invention, as a white solid purified by flash chromatography (0.4 g, 89%) and melting at 152–154° C. $^1$H NMR (CDCl$_3$) δ 7.40 (m, 2H), 5.30 (s, 2H), 4.72 (m, 2H), 4.22 (dd, 1H), 3.82 (m, 4H), 3.60 (dd, 1H), 2.24 (m, 1H), 1.40 (t, 3H), 1.20 (t, 3H).

EXAMPLE 10

Step A: Preparation of (6S-cis)-methyl [2-chloro-5-(6-chlorotetrahydro-1,3-dioxo-1H-pyrrolo[1,2-c]imidazol-2(3H)-yl)-4-fluorophenyl][(chloromethyl)sulfonyl]carbamate To a mixture of the title compound of Example 2, Step A (0.34 g, 0.79 mmol) and pyridine (0.5 mL) in dichloromethane (5 mL) was added a solution of methyl chloroformate (85 mg, 0.9 mmol) in dichloromethane (1 mL) at room temperature. After completion of the reaction (2 h), the solvents were removed and the title compound of Step A, a compound of this invention, was isolated by flash chromatography (0.34 g, 93%) as a white solid melting at 117–124° C. $^1$H NMR (CDCl$_3$) δ 7.40 (m, 2H), 5.40 (dd, 1H), 4.96 (dd, 1H), 4.76 (m, 2H), 4.24 (dd, 1H), 3.84 (s, 3H), 3.62 (dd, 1H), 2.60 (m, 1H), 2.24 (m, 1H).

EXAMPLE 11

Step A: Preparation of 1-chloro-N-[2-chloro-4-fluoro-5-(hexahydro-7-hydroxy-1,3-dioxoimidazo[1,5-a]pyridin-2(3H)-yl)phenyl]methanesulfonamide To a solution of the title compound of Example 1, Step E (4.54 g, 15.2 mmol) in dichloromethane (20 mL) was added dropwise a solution of methyl cis-4-hydroxy-2-piperidinecarboxylate (2.41 g, 15.2 mmol, prepared as described in *J. Org. Chem.* (1991), 4084) in dichloromethane (20 mL) at room temperature. The reaction was stirred at room temperature for 20 hours, quenched by the addition of water, and the aqueous layer was extracted with dichloromethane. The combined organic layers were washed with water and dried over magnesium sulfate. The solvent was removed under reduced pressure and the title compound of Step A, a compound of this invention, was isolated as a foam by flash chromatography (4.98 g). $^1$H NMR (Me$_2$SO-d$_6$) δ 10.1 (br s, 1H), 7.75 (m, 1H), 7.4 (dd, 1H), 5.1 (m, 1H), 4.9 (s, 2H), 4.1–3.9 (m, 3H), 3.75 (m, 1H), 2.95 (m, 1H), 2.05 (m, 1H), 1.9 (br d, 1H), 1.2 (m, 1H).

EXAMPLE 12

Step A: Preparation of cis-1-chloro-N-[2-chloro-4-fluoro-5-(7-fluorohexahydro-1,3-dioxoimidazo[1,5-a]pyridin-2(3H)-yl)phenyl]methanesulfonamide To a solution of the title compound of Example 11, Step A (771 mg, 1–80 mmol) in dichloromethane (10 mL) was added dropwise diethylaminosulfur trifluoride (0.48 mL, 3.60 mmol) at 0° C. The reaction was stirred at 0° C. for 1 hour, quenched with cold water, and extracted with dichloromethane. The combined organic layers were washed with water, dried over magnesium sulfate, and concentrated under reduced pressure. The title compound of Step A, a compound of this invention, was isolated by flash chromatography (332 mg) as a foam melting at 60–64° C. $^1$H NMR (CDCl$_3$) δ7.7 (d, 1H), 7.4 (d, 1H), 7.1 (br s, 1H), 5.28 and 5.12 (two br s, 1 H), 4.6 (s, 2H), 1H), 4.2 (dd, 1H), 3.3 (ddd, 1H), 2.65 (m, 1H), 2.2 (m, 1H), 1.9–1.6 (m, 2H).

EXAMPLE 13

Step A: Preparation of ethyl [(dimethylamino)[[[(4-chloro-2-fluoro-5-nitrophenyl)amino]carbonyl]imino]methyl]methylcarbamate To a solution of 1-chloro-5-fluoro-4-isocyanato-2-nitrobenzene (3.4 g, 15.7 mmol) in toluene (50 mL) was added dropwise a solution of ethyl [(dimethylamino)iminomethyl]methylcarbamate (2.41 g, 15.2 mmol, prepared as described in U.S. Pat. No. 3,902,887) in toluene (50 mL) at room temperature. The reaction was stirred at room temperature for 2 hours, quenched by the addition of water, and the aqueous layer was extracted with dichloromethane. The excess solvent was removed under reduced pressure and the title compound of Step A was isolated by flash chromatography as a yellow solid (5.07 g) melting at 158–159° C.

$^1$H NMR (CDCl$_3$) δ 9.05 (d, 1H), 7.3 (br s, 1H), 7.2 (d, 1H), 4.2 (q, 2H), 3.15 (s, 3H), 3.0 (s, 6H), 1.2 (br s, 3H).

Step B: Preparation of 3-(4-chloro-2-fluoro-5-nitrophenyl)-6-(dimethylamino)-5-methyl-1,3,5-triazine-2,4(1H,3H)-dione A mixture of the title compound of Step A (3.0 g, 7.7 mmol) in methanol (150 mL) was stirred at room temperature overnight The excess solvent was removed under reduced pressure to provide the title compound of Step B as a white solid (2.8 g). $^1$H NMR (CDCl$_3$) δ 8.05 (d, 1H), 7.4 (d, 1H), 3.45 (s, 3H), 3.1 (s, 6H).

Step C: Preparation of 3-(5-amino-4-chloro-2-fluorophenyl)-6-(dimethylamino)-5-methyl-1,3,5-triazine-2,4(1H,3H)-dione To a slurry of iron powder (5.3 g) in 5% aqueous acetic acid (30 mL) was added dropwise a solution of the title compound of step B (2.8 g, 8.1 mmol) in a mixture of concentrated acetic acid (25 mL) and ethyl acetate (25 mL) at room temperature. The reaction was stirred at room temperature for 30 minutes, diluted with excess ethyl acetate, filtered through Celite®, and washed with water. The aqueous phase was extracted with ethyl acetate and the combined organic layers were washed with saturated aqueous sodium bicarbonate solution and water. The organic layers were then dried over magnesium sulfate and concentrated under reduced pressure. The title compound of Step C was isolated by flash chromatography as a foam (1.59 g). $^1$H NMR (CDCl$_3$) δ 7.15 (d, 1H), 6.65 (d, 1H), 3.95 (br s, 2H), 3.4 (s, 3H), 3.1 (s, 6H).

Step D: Preparation of 1-chloro-N-[2-chloro-5-[4 (dimethylamino)-3,6-dihydro-3-methyl-2,6-dioxo-1,3,5-triazin-1(2H)-yl]-4-fluorophenyl]methanesulfonamide To a solution of the title compound of Step C (359 mg, 1.15 mmol), pyridine (0.50 mL), and a catalytic amount of 4-dimethylamino pyridine in dichloromethane was added chloromethylsulfonyl chloride (0.136 mL, 1,37 mmol) at 0° C. The reaction was stirred at 0° C. for 90 minutes and then concentrated under reduced pressure. The crude oil was dissolved in dichloromethane and washed sequentially with water, 1N aqueous HCl, and water. The organic phase was then dried over magnesium sulfate and concentrated under reduced pressure. The title compound of Step D, a compound of this invention, was isolated by flash chromatography as a foam (126 mg) melting at 234–237° C. $^1$H NMR (CDCl$_3$) δ 7.7 (d, 1H), 7.35 (d, 1H), 7.0 (br s, 1H), 4.55 (q, 2H), 3.45 (s, 3H), 3.15 (s, 6H).

By the procedures described herein together with methods known in the art, the following compounds of Table 1 can be prepared. The following abbreviations are used in the Table which follows: CN=cyano and Ph=phenyl.

TABLE 1

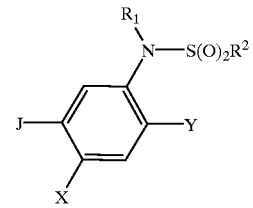

J = 1, Y = Cl, and R$^2$ = CH$_2$Cl

| X | R$^1$ | Z | n | m |
|---|---|---|---|---|
| F | H | CH$_2$ | 1 | 1 |
| F | C(=O)CH$_3$ | CH$_2$ | 1 | 1 |
| F | CO$_2$CH$_3$ | CH$_2$ | 1 | 1 |
| F | H | CHF | 1 | 1 |

TABLE 1-continued

| | | | | |
|---|---|---|---|---|
| F | C(=O)CH$_3$ | CHF | 1 | 1 |
| F | CO$_2$CH$_3$ | CHF | 1 | 1 |
| F | H | CH$_2$ | 1 | 2 |
| F | C(=O)CH$_3$ | CH$_2$ | 1 | 2 |
| F | CO$_2$CH$_3$ | CH$_2$ | 1 | 2 |
| F | H | CHF | 1 | 2 |
| F | C(=O)CH$_3$ | CHF | 1 | 2 |
| F | CO$_2$CH$_3$ | CHF | 1 | 2 |
| Cl | H | CH$_2$ | 1 | 2 |
| Cl | C(=O)CH$_3$ | CH$_2$ | 1 | 1 |
| Cl | CO$_2$CH$_3$ | CH$_2$ | 1 | 1 |
| Cl | H | CHF | 1 | 1 |
| Cl | C(=O)CH$_3$ | CHF | 1 | 1 |
| Cl | CO$_2$CH$_3$ | CHF | 1 | 1 |
| Cl | H | CH$_2$ | 1 | 2 |
| Cl | C(=O)CH$_3$ | CH$_2$ | 1 | 2 |
| Cl | CO$_2$CH$_3$ | CH$_2$ | 1 | 2 |
| Cl | H | CHF | 1 | 2 |
| Cl | C(=O)CH$_3$ | CHF | 1 | 2 |
| Cl | CO$_2$CH$_3$ | CHF | 1 | 2 |

J 2, Y = Cl, and R$^2$ = CH$_2$Cl

| x | R$^1$ | z | n | m |
|---|---|---|---|---|
| F | H | CH$_2$ | 1 | 1 |
| F | C(=O)CH$_3$ | CH$_2$ | 1 | 1 |
| F | CO$_2$CH$_3$ | CH$_2$ | 1 | 1 |
| F | H | CHF | 1 | 1 |
| F | C(=O)CH$_3$ | CHF | 1 | 1 |
| F | CO$_2$CH$_3$ | CHF | 1 | 1 |
| F | H | CH$_2$ | 1 | 2 |
| F | C(=O)CH$_3$ | CH$_2$ | 1 | 2 |
| F | CO$_2$CH$_3$ | CH$_2$ | 1 | 2 |
| F | H | CHF | 1 | 2 |
| F | C(=O)CH$_3$ | CHF | 1 | 2 |
| F | CO$_2$CH$_3$ | CHF | 1 | 2 |
| Cl | H | CH$_2$ | 1 | 1 |
| Cl | C(=O)CH$_3$ | CH$_2$ | 1 | 1 |
| Cl | CO$_2$CH$_3$ | CH$_2$ | 1 | 1 |
| Cl | H | CHF | 1 | 1 |
| Cl | C(=O)CH$_3$ | CHF | 1 | 1 |
| Cl | CO$_2$CH$_3$ | CHF | 1 | 1 |
| Cl | H | CH$_2$ | 1 | 2 |
| Cl | C(=O)CH$_3$ | CH$_2$ | 1 | 2 |
| Cl | CO$_2$CH$_3$ | CH$_2$ | 1 | 2 |
| Cl | H | CHF | 1 | 2 |
| Cl | C(=O)CH$_3$ | CHF | 1 | 2 |
| Cl | CO$_2$CH$_3$ | CHF | 1 | 2 |

J = 3, Q = O, Y = Cl, and R$^2$ = CH$_2$Cl

| X | R$^1$ | R$^{11}$ | R$^{12}$ |
|---|---|---|---|
| F | H | CH$_3$ | CH$_2$Cl |
| F | C(=O)CH$_3$ | CH$_3$ | CH$_2$Cl |
| F | CO$_2$CH$_3$ | CH$_3$ | CH$_2$Cl |
| F | H | CH$_2$CH$_2$CH$_2$F | CH$_2$Cl |
| F | C(=O)CH$_3$ | CH$_2$CH$_2$CH$_2$F | CH$_2$Cl |
| F | CO$_2$CH$_3$ | CH$_2$CH$_2$CH$_2$F | CH$_2$Cl |
| F | H | CH$_3$ | CH$_2$F |
| F | C(=O)CH$_3$ | CH$_3$ | CH$_2$F |
| F | CO$_2$CH$_3$ | CH$_3$ | CH$_2$F |
| F | H | CH$_2$CH$_2$CH$_2$F | CH$_2$F |
| F | C(=O)CH$_3$ | CH$_2$CH$_2$CH$_2$F | CH$_2$F |
| F | CO$_2$CH$_3$ | CH$_2$CH$_2$CH$_2$F | CH$_2$F |
| Cl | H | CH$_3$ | CH$_2$Cl |
| Cl | C(=O)CH$_3$ | CH$_3$ | CH$_2$Cl |
| Cl | CO$_2$CH$_3$ | CH$_3$ | CH$_2$Cl |
| Cl | H | CH$_2$CH$_2$CH$_2$F | CH$_2$Cl |
| Cl | C(=O)CH$_3$ | CH$_2$CH$_2$CH$_2$F | CH$_2$Cl |
| Cl | CO$_2$CH$_3$ | CH$_2$CH$_2$CH$_2$F | CH$_2$Cl |
| Cl | H | CH$_3$ | CH$_2$F |
| Cl | C(=O)CH$_3$ | CH$_3$ | CH$_2$F |
| Cl | CO$_2$CH$_3$ | CH$_3$ | CH$_2$F |
| Cl | H | CH$_2$CH$_2$CH$_2$F | CH$_2$F |
| Cl | C(=O)CH$_3$ | CH$_2$CH$_2$CH$_2$F | CH$_2$F |
| Cl | CO$_2$CH$_3$ | CH$_2$CH$_2$CH$_2$F | CH$_2$F |

J = 4, Q = O, Y = Cl, and R$^2$ = CH$_2$Cl

| X | R$^1$ | R$^{13}$ | R$^{14}$ |
|---|---|---|---|
| F | H | CH$_3$ | CF$_3$ |
| F | C(=O)CH$_3$ | CH$_3$ | CF$_3$ |
| F | CO$_2$CH$_3$ | CH$_3$ | CF$_3$ |
| F | H | CHF$_2$ | CF$_3$ |
| F | C(=O)CH$_3$ | CHF$_2$ | CF$_3$ |
| F | CO$_2$CH$_3$ | CHF$_2$ | CF$_3$ |
| F | H | CH$_3$ | N(CH$_3$)$_2$ |
| F | C(=O)CH$_3$ | CH$_3$ | N(CH$_3$)$_2$ |
| F | CO$_2$CH$_3$ | CH$_3$ | N(CH$_3$)$_2$ |
| F | H | CHF$_2$ | N(CH$_3$)$_2$ |
| F | C(=O)CH$_3$ | CHF$_2$ | N(CH$_3$)$_2$ |
| F | CO$_2$CH$_3$ | CHF$_2$ | N(CH$_3$)$_2$ |
| Cl | H | CH$_3$ | CF$_3$ |
| Cl | C(=O)CH$_3$ | CH$_3$ | CF$_3$ |
| Cl | CO$_2$CH$_3$ | CH$_3$ | CF$_3$ |
| Cl | H | CHF$_2$ | CF$_3$ |
| Cl | C(=O)CH$_3$ | CHF$_2$ | CF$_3$ |
| Cl | CO$_2$CH$_3$ | CHF$_2$ | CF$_3$ |
| Cl | H | CH$_3$ | N(CH$_3$)$_2$ |
| Cl | C(=O)CH$_3$ | CH$_3$ | N(CH$_3$)$_2$ |
| Cl | CO$_2$CH$_3$ | CH$_3$ | N(CH$_3$)$_2$ |
| Cl | H | CHF$_2$ | N(CH$_3$)$_2$ |
| Cl | C(=O)CH$_3$ | CHF$_2$ | N(CH$_3$)$_2$ |
| Cl | CO$_2$CH$_3$ | CHF$_2$ | N(CH$_3$)$_2$ |

J = 5 and Q = O

| X | Y | Z$^1$ | n | m | R$^1$ | R$^2$ |
|---|---|---|---|---|---|---|
| F | H | CH$_2$ | 1 | 1 | H | CH$_2$Cl |
| F | H | CH$_2$ | 1 | 1 | H | CH$_2$Br |
| F | H | CH$_2$ | 1 | 2 | H | CH$_2$Cl |
| F | H | CH$_2$ | 1 | 2 | H | CH$_2$Br |
| F | H | CHF | 1 | 1 | H | CH$_2$Cl |
| F | H | CHF | 1 | 1 | H | CH$_2$Br |
| F | H | CHF | 1 | 2 | H | CH$_2$Cl |
| F | H | CHF | 1 | 2 | H | CH$_2$Br |
| F | H | CHCl | 1 | 1 | H | CH$_2$Cl |
| F | H | CHCl | 1 | 1 | H | CH$_2$Br |
| F | H | CHCl | 1 | 2 | H | CH$_2$Cl |
| F | H | CHCl | 1 | 2 | H | CH$_2$Br |
| F | Cl | CH$_2$ | 1 | 1 | H | CH$_2$Cl |
| F | Cl | CH$_2$ | 1 | 1 | H | CH$_2$Br |
| F | Cl | CH$_2$ | 1 | 1 | C(=O)CH$_3$ | CH$_2$Cl |
| F | Cl | CH$_2$ | 1 | 1 | C(=O)CH$_3$ | CH$_2$Br |
| F | Cl | CH$_2$ | 1 | 1 | CO$_2$CH$_3$ | CH$_2$Cl |
| F | Cl | CH$_2$ | 1 | 1 | CO$_2$CH$_3$ | CH$_2$Br |
| F | Cl | CH$_2$ | 1 | 1 | CH$_2$C≡CH | CH$_2$Cl |
| F | Cl | CH$_2$ | 1 | 1 | CH$_2$C≡CH | CH$_2$Br |
| F | Cl | CH$_2$ | 1 | 2 | H | CH$_2$Cl |
| F | Cl | CH$_2$ | 1 | 2 | H | CH$_2$Br |
| F | Cl | CH$_2$ | 1 | 2 | C(=O)CH$_3$ | CH$_2$Cl |
| F | Cl | CH$_2$ | 1 | 2 | C(=O)CH$_3$ | CH$_2$Br |
| F | Cl | CH$_2$ | 1 | 2 | CO$_2$CH$_3$ | CH$_2$Cl |
| F | Cl | CH$_2$ | 1 | 2 | CO$_2$CH$_3$ | CH$_2$Br |
| F | Cl | CH$_2$ | 1 | 2 | CH$_2$C≡CH | CH$_2$Cl |
| F | Cl | CH$_2$ | 1 | 2 | CH$_2$C≡CH | CH$_2$Br |
| F | Cl | CHF | 1 | 1 | H | CH$_2$Cl |
| F | Cl | CHF | 1 | 1 | H | CH$_2$Br |
| F | Cl | CHF | 1 | 1 | C(=O)CH$_3$ | CH$_2$Cl |
| F | Cl | CHF | 1 | 1 | C(=O)CH$_3$ | CH$_2$Br |
| F | Cl | CHF | 1 | 1 | CO$_2$CH$_3$ | CH$_2$Cl |
| F | Cl | CHF | 1 | 1 | CO$_2$CH$_3$ | CH$_2$Br |
| F | Cl | CHF | 1 | 1 | CH$_2$C≡CH | CH$_2$Cl |
| F | Cl | CHF | 1 | 1 | CH$_2$C≡CH | CH$_2$Br |
| F | Cl | CHF | 1 | 2 | H | CH$_2$Cl |
| F | Cl | CHF | 1 | 2 | H | CH$_2$Br |
| F | Cl | CHF | 1 | 2 | C(=O)CH$_3$ | CH$_2$Cl |
| F | Cl | CHF | 1 | 2 | C(=O)CH$_3$ | CH$_2$Br |
| F | Cl | CHF | 1 | 2 | CO$_2$CH$_3$ | CH$_2$Cl |
| F | Cl | CHF | 1 | 2 | CO$_2$CH$_3$ | CH$_2$Br |
| F | Cl | CHF | 1 | 2 | CH$_2$C≡CH | CH$_2$Cl |
| F | Cl | CHF | 1 | 2 | CH$_2$C≡CH | CH$_2$Br |
| F | Cl | CHCl | 1 | 1 | H | CH$_2$Cl |
| F | Cl | CHCl | 1 | 1 | H | CH$_2$Br |

TABLE 1-continued

| | | | | | | |
|---|---|---|---|---|---|---|
| F | Cl | CHCl | 1 | 1 | C(=O)CH₃ | CH₂Cl |
| F | Cl | CHCl | 1 | 1 | C(=O)CH₃ | CH₂Br |
| F | Cl | CHCl | 1 | 1 | CO₂CH₃ | CH₂Cl |
| F | Cl | CHCl | 1 | 1 | CO₂CH₃ | CH₂Br |
| F | Cl | CHCl | 1 | 1 | CH₂C≡CH | CH₂Cl |
| F | Cl | CHCl | 1 | 1 | CH₂C≡CH | CH₂Br |
| F | Cl | CHCl | 1 | 2 | H | CH₂Cl |
| F | Cl | CHCl | 1 | 2 | H | CH₂Br |
| F | Cl | CHCl | 1 | 2 | C(=O)CH₃ | CH₂Cl |
| F | Cl | CHCl | 1 | 2 | C(=O)CH₃ | CH₂Br |
| F | Cl | CHCl | 1 | 2 | CO₂CH₃ | CH₂Cl |
| F | Cl | CHCl | 1 | 2 | CO₂CH₃ | CH₂Br |
| F | Cl | CHCl | 1 | 2 | CH₂C≡CH | CH₂Cl |
| F | Cl | CHCl | 1 | 2 | CH₂C≡CH | CH₂Br |
| F | Br | CH₂ | 1 | 1 | H | CH₂Cl |
| F | Br | CH₂ | 1 | 1 | H | CH₂Br |
| F | Br | CH₂ | 1 | 1 | C(=O)CH₃ | CH₂Cl |
| F | Br | CH₂ | 1 | 1 | C(=O)CH₃ | CH₂Br |
| F | Br | CH₂ | 1 | 1 | CO₂CH₃ | CH₂Cl |
| F | Br | CH₂ | 1 | 1 | CO₂CH₃ | CH₂Br |
| F | Br | CH₂ | 1 | 1 | CH₂C≡CH | CH₂Cl |
| F | Br | CH₂ | 1 | 1 | CH₂C≡CH | CH₂Br |
| F | Br | CH₂ | 1 | 2 | H | CH₂Cl |
| F | Br | CH₂ | 1 | 2 | H | CH₂Br |
| F | Br | CH₂ | 1 | 2 | C(=O)CH₃ | CH₂Cl |
| F | Br | CH₂ | 1 | 2 | C(=O)CH₃ | CH₂Br |
| F | Br | CH₂ | 1 | 2 | CO₂CH₃ | CH₂Cl |
| F | Br | CH₂ | 1 | 2 | CO₂CH₃ | CH₂Br |
| F | Br | CH₂ | 1 | 2 | CH₂C≡CH | CH₂Cl |
| F | Br | CH₂ | 1 | 2 | CH₂C≡CH | CH₂Br |
| F | Br | CHF | 1 | 1 | H | CH₂Cl |
| F | Br | CHF | 1 | 1 | H | CH₂Br |
| F | Br | CHF | 1 | 1 | C(=O)CH₃ | CH₂Cl |
| F | Br | CHF | 1 | 1 | C(=O)CH₃ | CH₂Br |
| F | Br | CHF | 1 | 1 | CO₂CH₃ | CH₂Cl |
| F | Br | CHF | 1 | 1 | CO₂CH₃ | CH₂Br |
| F | Br | CHF | 1 | 1 | CH₂C≡CH | CH₂Cl |
| F | Br | CHF | 1 | 1 | CH₂C≡CH | CH₂Br |
| F | Br | CHF | 1 | 2 | H | CH₂Cl |
| F | Br | CHF | 1 | 2 | H | CH₂Br |
| F | Br | CHF | 1 | 2 | C(=O)CH₃ | CH₂Cl |
| F | Br | CHF | 1 | 2 | C(=O)CH₃ | CH₂Br |
| F | Br | CHF | 1 | 2 | CO₂CH₃ | CH₂Cl |
| F | Br | CHF | 1 | 2 | CO₂CH₃ | CH₂Br |
| F | Br | CHF | 1 | 2 | CH₂C≡CH | CH₂Cl |
| F | Br | CHF | 1 | 2 | CH₂C≡CH | CH₂Br |
| F | Br | CHCl | 1 | 1 | H | CH₂Cl |
| F | Br | CHCl | 1 | 1 | H | CH₂Br |
| F | Br | CHCl | 1 | 1 | C(=O)CH₃ | CH₂Cl |
| F | Br | CHCl | 1 | 1 | C(=O)CH₃ | CH₂Br |
| F | Br | CHCl | 1 | 1 | CO₂CH₃ | CH₂Cl |
| F | Br | CHCl | 1 | 1 | CO₂CH₃ | CH₂Br |
| F | Br | CHCl | 1 | 1 | CH₂C≡CH | CH₂Cl |
| F | Br | CHCl | 1 | 1 | CH₂C≡CH | CH₂Br |
| F | Br | CHCl | 1 | 2 | H | CH₂Cl |
| F | Br | CHCl | 1 | 2 | H | CH₂Br |
| F | Br | CHCl | 1 | 2 | C(=O)CH₃ | CH₂Cl |
| F | Br | CHCl | 1 | 2 | C(=O)CH₃ | CH₂Br |
| F | Br | CHCl | 1 | 2 | CO₂CH₃ | CH₂Cl |
| F | Br | CHCl | 1 | 2 | CO₂CH₃ | CH₂Br |
| F | Br | CHCl | 1 | 2 | CH₂C≡CH | CH₂Cl |
| F | Br | CHCl | 1 | 2 | CH₂C≡CH | CH₂Br |
| F | CN | CH₂ | 1 | 1 | H | CH₂Cl |
| F | CN | CH₂ | 1 | 1 | H | CH₂Br |
| F | CN | CH₂ | 1 | 1 | C(=O)CH₃ | CH₂Cl |
| F | CN | CH₂ | 1 | 1 | C(=O)CH₃ | CH₂Br |
| F | CN | CH₂ | 1 | 1 | CO₂CH₃ | CH₂Cl |
| F | CN | CH₂ | 1 | 1 | CO₂CH₃ | CH₂Br |
| F | CN | CH₂ | 1 | 1 | CH₂C≡CH | CH₂Cl |
| F | CN | CH₂ | 1 | 1 | CH₂C≡CH | CH₂Br |
| F | CN | CH₂ | 1 | 2 | H | CH₂Cl |
| F | CN | CH₂ | 1 | 2 | H | CH₂Br |
| F | CN | CH₂ | 1 | 2 | C(=O)CH₃ | CH₂Cl |
| F | CN | CH₂ | 1 | 2 | C(=O)CH₃ | CH₂Br |
| F | CN | CH₂ | 1 | 2 | CO₂CH₃ | CH₂Cl |
| F | CN | CH₂ | 1 | 2 | CO₂CH₃ | CH₂Br |
| F | CN | CH₂ | 1 | 2 | CH₂C≡CH | CH₂Cl |
| F | CN | CH₂ | 1 | 2 | CH₂C≡CH | CH₂Br |
| F | CN | CHF | 1 | 1 | H | CH₂Cl |
| F | CN | CHF | 1 | 1 | H | CH₂Br |
| F | CN | CHF | 1 | 1 | C(=O)CH₃ | CH₂Cl |
| F | CN | CHF | 1 | 1 | C(=O)CH₃ | CH₂Br |
| F | CN | CHF | 1 | 1 | CO₂CH₃ | CH₂Cl |
| F | CN | CHF | 1 | 1 | CO₂CH₃ | CH₂Br |
| F | CN | CHF | 1 | 1 | CH₂C≡CH | CH₂Cl |
| F | CN | CHF | 1 | 1 | CH₂C≡CH | CH₂Br |
| F | CN | CHF | 1 | 2 | H | CH₂Cl |
| F | CN | CHF | 1 | 2 | H | CH₂Br |
| F | CN | CHF | 1 | 2 | C(=O)CH₃ | CH₂Cl |
| F | CN | CHF | 1 | 2 | C(=O)CH₃ | CH₂Br |
| F | CN | CHF | 1 | 2 | CO₂CH₃ | CH₂Cl |
| F | CN | CHF | 1 | 2 | CO₂CH₃ | CH₂Br |
| F | CN | CHF | 1 | 2 | CH₂C≡CH | CH₂Cl |
| F | CN | CHF | 1 | 2 | CH₂C≡CH | CH₂Br |
| F | CN | CHCl | 1 | 1 | H | CH₂Cl |
| F | CN | CHCl | 1 | 1 | H | CH₂Br |
| F | CN | CHCl | 1 | 1 | C(=O)CH₃ | CH₂Cl |
| F | CN | CHCl | 1 | 1 | C(=O)CH₃ | CH₂Br |
| F | CN | CHCl | 1 | 1 | CO₂CH₃ | CH₂Cl |
| F | CN | CHCl | 1 | 1 | CO₂CH₃ | CH₂Br |
| F | CN | CHCl | 1 | 1 | CH₂C≡CH | CH₂Cl |
| F | CN | CHCl | 1 | 1 | CH₂C≡CH | CH₂Br |
| F | CN | CHCl | 1 | 2 | H | CH₂Cl |
| F | CN | CHCl | 1 | 2 | H | CH₂Br |
| F | CN | CHCl | 1 | 2 | C(=O)CH₃ | CH₂Cl |
| F | CN | CHCl | 1 | 2 | C(=O)CH₃ | CH₂Br |
| F | CN | CHCl | 1 | 2 | CO₂CH₃ | CH₂Cl |
| F | CN | CHCl | 1 | 2 | CO₂CH₃ | CH₂Br |
| F | CN | CHCl | 1 | 2 | CH₂C≡CH | CH₂Cl |
| F | CN | CHCl | 1 | 2 | CH₂C≡CH | CH₂Br |
| Cl | H | CH₂ | 1 | 1 | H | CH₂Cl |
| Cl | H | CH₂ | 1 | 1 | H | CH₂Br |
| Cl | H | CH₂ | 1 | 2 | H | CH₂Cl |
| Cl | H | CH₂ | 1 | 2 | H | CH₂Br |
| Cl | H | CHF | 1 | 1 | H | CH₂Cl |
| Cl | H | CHF | 1 | 1 | H | CH₂Br |
| Cl | H | CHF | 1 | 2 | H | CH₂Cl |
| Cl | H | CHF | 1 | 2 | H | CH₂Br |
| Cl | H | CHCl | 1 | 1 | H | CH₂Cl |
| Cl | H | CHCl | 1 | 1 | H | CH₂Br |
| Cl | H | CHCl | 1 | 2 | H | CH₂Cl |
| Cl | H | CHCl | 1 | 2 | H | CH₂Br |
| Cl | Cl | CH₂ | 1 | 1 | H | CH₂Cl |
| Cl | Cl | CH₂ | 1 | 1 | H | CH₂Br |
| Cl | Cl | CH₂ | 1 | 1 | C(=O)CH₃ | CH₂Cl |
| Cl | Cl | CH₂ | 1 | 1 | C(=O)CH₃ | CH₂Br |
| Cl | Cl | CH₂ | 1 | 1 | CO₂CH₃ | CH₂Cl |
| Cl | Cl | CH₂ | 1 | 1 | CO₂CH₃ | CH₂Br |
| Cl | Cl | CH₂ | 1 | 1 | CH₂C≡CH | CH₂Cl |
| Cl | Cl | CH₂ | 1 | 1 | CH₂C≡CH | CH₂Br |
| Cl | Cl | CH₂ | 1 | 2 | H | CH₂Cl |
| Cl | Cl | CH₂ | 1 | 2 | H | CH₂Br |
| Cl | Cl | CH₂ | 1 | 2 | C(=O)CH₃ | CH₂Cl |
| Cl | Cl | CH₂ | 1 | 2 | C(=O)CH₃ | CH₂Br |
| Cl | Cl | CH₂ | 1 | 2 | CO₂CH₃ | CH₂Cl |
| Cl | Cl | CH₂ | 1 | 2 | CO₂CH₃ | CH₂Br |
| Cl | Cl | CH₂ | 1 | 2 | CH₂C≡CH | CH₂Cl |
| Cl | Cl | CH₂ | 1 | 2 | CH₂C≡CH | CH₂Br |
| Cl | Cl | CHF | 1 | 1 | H | CH₂Cl |
| Cl | Cl | CHF | 1 | 1 | H | CH₂Br |
| Cl | Cl | CHF | 1 | 1 | C(=O)CH₃ | CH₂Cl |
| Cl | Cl | CHF | 1 | 1 | C(=O)CH₃ | CH₂Br |
| Cl | Cl | CHF | 1 | 1 | CO₂CH₃ | CH₂Cl |
| Cl | Cl | CHF | 1 | 1 | CO₂CH₃ | CH₂Br |
| Cl | Cl | CHF | 1 | 1 | CH₂C≡CH | CH₂Cl |
| Cl | Cl | CHF | 1 | 1 | CH₂C≡CH | CH₂Br |
| Cl | Cl | CHF | 1 | 2 | H | CH₂Cl |
| Cl | Cl | CHF | 1 | 2 | H | CH₂Br |
| Cl | Cl | CHF | 1 | 2 | C(=O)CH₃ | CH₂Cl |
| Cl | Cl | CHF | 1 | 2 | C(=O)CH₃ | CH₂Br |
| Cl | Cl | CHF | 1 | 2 | CO₂CH₃ | CH₂Cl |
| Cl | Cl | CHF | 1 | 2 | CO₂CH₃ | CH₂Br |
| Cl | Cl | CHF | 1 | 2 | CH₂C≡CH | CH₂Cl |
| Cl | Cl | CHF | 1 | 2 | CH₂C≡CH | CH₂Br |
| Cl | Cl | CHCl | 1 | 1 | H | CH₂Cl |
| Cl | Cl | CHCl | 1 | 1 | H | CH₂Br |
| Cl | Cl | CHCl | 1 | 1 | C(=O)CH₃ | CH₂Cl |
| Cl | Cl | CHCl | 1 | 1 | C(=O)CH₃ | CH₂Br |

TABLE 1-continued

| X | Y | X | n | m | R¹ | R² |
|---|---|---|---|---|---|---|
| Cl | Cl | CHCl | 1 | 1 | CO$_2$CH$_3$ | CH$_2$Cl |
| Cl | Cl | CHCl | 1 | 1 | CO$_2$CH$_3$ | CH$_2$Br |
| Cl | Cl | CHCl | 1 | 1 | CH$_2$C≡CH | CH$_2$Cl |
| Cl | Cl | CHCl | 1 | 1 | CH$_2$C≡CH | CH$_2$Br |
| Cl | Cl | CHCl | 1 | 2 | H | CH$_2$Cl |
| Cl | Cl | CHCl | 1 | 2 | H | CH$_2$Br |
| Cl | Cl | CHCl | 1 | 2 | C(=O)CH$_3$ | CH$_2$Cl |
| Cl | Cl | CHCl | 1 | 2 | C(=O)CH$_3$ | CH$_2$Br |
| Cl | Cl | CHCl | 1 | 2 | CO$_2$CH$_3$ | CH$_2$Cl |
| Cl | Cl | CHCl | 1 | 2 | CO$_2$CH$_3$ | CH$_2$Br |
| Cl | Cl | CHCl | 1 | 2 | CH$_2$C≡CH | CH$_2$Cl |
| Cl | Cl | CHCl | 1 | 2 | CH$_2$C≡CH | CH$_2$Br |
| Cl | Br | CH$_2$ | 1 | 1 | H | CH$_2$Cl |
| Cl | Br | CH$_2$ | 1 | 1 | H | CH$_2$Br |
| Cl | Br | CH$_2$ | 1 | 1 | C(=O)CH$_3$ | CH$_2$Cl |
| Cl | Br | CH$_2$ | 1 | 1 | C(=O)CH$_3$ | CH$_2$Br |
| Cl | Br | CH$_2$ | 1 | 1 | CO$_2$CH$_3$ | CH$_2$Cl |
| Cl | Br | CH$_2$ | 1 | 1 | CO$_2$CH$_3$ | CH$_2$Br |
| Cl | Br | CH$_2$ | 1 | 1 | CH$_2$C≡CH | CH$_2$Cl |
| Cl | Br | CH$_2$ | 1 | 1 | CH$_2$C≡CH | CH$_2$Br |
| Cl | Br | CH$_2$ | 1 | 2 | H | CH$_2$Cl |
| Cl | Br | CH$_2$ | 1 | 2 | H | CH$_2$Br |
| Cl | Br | CH$_2$ | 1 | 2 | C(=O)CH$_3$ | CH$_2$Cl |
| Cl | Br | CH$_2$ | 1 | 2 | C(=O)CH$_3$ | CH$_2$Br |
| Cl | Br | CH$_2$ | 1 | 2 | CO$_2$CH$_3$ | CH$_2$Cl |
| Cl | Br | CH$_2$ | 1 | 2 | CO$_2$CH$_3$ | CH$_2$Br |
| Cl | Br | CH$_2$ | 1 | 2 | CH$_2$C≡CH | CH$_2$Cl |
| Cl | Br | CH$_2$ | 1 | 2 | CH$_2$C≡CH | CH$_2$Br |
| Cl | Br | CHF | 1 | 1 | H | CH$_2$Cl |
| Cl | Br | CHF | 1 | 1 | H | CH$_2$Br |
| Cl | Br | CHF | 1 | 1 | C(=O)CH$_3$ | CH$_2$Cl |
| Cl | Br | CHF | 1 | 1 | C(=O)CH$_3$ | CH$_2$Br |
| Cl | Br | CHF | 1 | 1 | CO$_2$CH$_3$ | CH$_2$Cl |
| Cl | Br | CHF | 1 | 1 | CO$_2$CH$_3$ | CH$_2$Br |
| Cl | Br | CHF | 1 | 1 | CH$_2$C≡CH | CH$_2$Cl |
| Cl | Br | CHF | 1 | 1 | CH$_2$C≡CH | CH$_2$Br |
| Cl | Br | CHF | 1 | 2 | H | CH$_2$Cl |
| Cl | Br | CHF | 1 | 2 | H | CH$_2$Br |
| Cl | Br | CHF | 1 | 2 | C(=O)CH$_3$ | CH$_2$Cl |
| Cl | Br | CHF | 1 | 2 | C(=O)CH$_3$ | CH$_2$Br |
| Cl | Br | CHF | 1 | 2 | CO$_2$CH$_3$ | CH$_2$Cl |
| Cl | Br | CHF | 1 | 2 | CO$_2$CH$_3$ | CH$_2$Br |
| Cl | Br | CHF | 1 | 2 | CH$_2$C≡CH | CH$_2$Cl |
| Cl | Br | CHF | 1 | 2 | CH$_2$C≡CH | CH$_2$Br |
| Cl | Br | CHCl | 1 | 1 | H | CH$_2$Cl |
| Cl | Br | CHCl | 1 | 1 | H | CH$_2$Br |
| Cl | Br | CHCl | 1 | 1 | C(=O)CH$_3$ | CH$_2$Cl |
| Cl | Br | CHCl | 1 | 1 | C(=O)CH$_3$ | CH$_2$Br |
| Cl | Br | CHCl | 1 | 1 | CO$_2$CH$_3$ | CH$_2$Cl |
| Cl | Br | CHCl | 1 | 1 | CO$_2$CH$_3$ | CH$_2$Br |
| Cl | Br | CHCl | 1 | 1 | CH$_2$C≡CH | CH$_2$Cl |
| Cl | Br | CHCl | 1 | 1 | CH$_2$C≡CH | CH$_2$Br |
| Cl | Br | CHCl | 1 | 2 | H | CH$_2$Cl |
| Cl | Br | CHCl | 1 | 2 | H | CH$_2$Br |
| Cl | Br | CHCl | 1 | 2 | C(=O)CH$_3$ | CH$_2$Cl |
| Cl | Br | CHCl | 1 | 2 | C(=O)CH$_3$ | CH$_2$Br |
| Cl | Br | CHCl | 1 | 2 | CO$_2$CH$_3$ | CH$_2$Cl |
| Cl | Br | CHCl | 1 | 2 | CO$_2$CH$_3$ | CH$_2$Br |
| Cl | Br | CHCl | 1 | 2 | CH$_2$C≡CH | CH$_2$Cl |
| Cl | Br | CHCl | 1 | 2 | CH$_2$C≡CH | CH$_2$Br |
| Cl | CN | CH$_2$ | 1 | 1 | H | CH$_2$Cl |
| Cl | CN | CH$_2$ | 1 | 1 | H | CH$_2$Br |
| Cl | CN | CH$_2$ | 1 | 1 | C(=O)CH$_3$ | CH$_2$Cl |
| Cl | CN | CH$_2$ | 1 | 1 | C(=O)CH$_3$ | CH$_2$Br |
| Cl | CN | CH$_2$ | 1 | 1 | CO$_2$CH$_3$ | CH$_2$Cl |
| Cl | CN | CH$_2$ | 1 | 1 | CO$_2$CH$_3$ | CH$_2$Br |
| Cl | CN | CH$_2$ | 1 | 1 | CH$_2$C≡CH | CH$_2$Cl |
| Cl | CN | CH$_2$ | 1 | 1 | CH$_2$C≡CH | CH$_2$Br |
| Cl | CN | CH$_2$ | 1 | 2 | H | CH$_2$Cl |
| Cl | CN | CH$_2$ | 1 | 2 | H | CH$_2$Br |
| Cl | CN | CH$_2$ | 1 | 2 | C(=O)CH$_3$ | CH$_2$Cl |
| Cl | CN | CH$_2$ | 1 | 2 | C(=O)CH$_3$ | CH$_2$Br |
| Cl | CN | CH$_2$ | 1 | 2 | CO$_2$CH$_3$ | CH$_2$Cl |
| Cl | CN | CH$_2$ | 1 | 2 | CO$_2$CH$_3$ | CH$_2$Br |
| Cl | CN | CH$_2$ | 1 | 2 | CH$_2$C≡CH | CH$_2$Cl |
| Cl | CN | CH$_2$ | 1 | 2 | CH$_2$C≡CH | CH$_2$Br |
| Cl | CN | CHF | 1 | 1 | H | CH$_2$Cl |
| Cl | CN | CHF | 1 | 1 | H | CH$_2$Br |
| Cl | CN | CHF | 1 | 1 | C(=O)CH$_3$ | CH$_2$Cl |
| Cl | CN | CHF | 1 | 1 | C(=O)CH$_3$ | CH$_2$Br |
| Cl | CN | CHF | 1 | 1 | CO$_2$CH$_3$ | CH$_2$Cl |
| Cl | CN | CHF | 1 | 1 | CO$_2$CH$_3$ | CH$_2$Br |
| Cl | CN | CHF | 1 | 1 | CH$_2$C≡CH | CH$_2$Cl |
| Cl | CN | CHF | 1 | 1 | CH$_2$C≡CH | CH$_2$Br |
| Cl | CN | CHF | 1 | 2 | H | CH$_2$Cl |
| Cl | CN | CHF | 1 | 2 | H | CH$_2$Br |
| Cl | CN | CHF | 1 | 2 | C(=O)CH$_3$ | CH$_2$Cl |
| Cl | CN | CHF | 1 | 2 | C(=O)CH$_3$ | CH$_2$Br |
| Cl | CN | CHF | 1 | 2 | CO$_2$CH$_3$ | CH$_2$Cl |
| Cl | CN | CHF | 1 | 2 | CO$_2$CH$_3$ | CH$_2$Br |
| Cl | CN | CHF | 1 | 2 | CH$_2$C≡CH | CH$_2$Cl |
| Cl | CN | CHF | 1 | 2 | CH$_2$C≡CH | CH$_2$Br |
| Cl | CN | CHCl | 1 | 1 | H | CH$_2$Cl |
| Cl | CN | CHCl | 1 | 1 | H | CH$_2$Br |
| Cl | CN | CHCl | 1 | 1 | C(=O)CH$_3$ | CH$_2$Cl |
| Cl | CN | CHCl | 1 | 1 | C(=O)CH$_3$ | CH$_2$Br |
| Cl | CN | CHCl | 1 | 1 | CO$_2$CH$_3$ | CH$_2$Cl |
| Cl | CN | CHCl | 1 | 1 | CO$_2$CH$_3$ | CH$_2$Br |
| Cl | CN | CHCl | 1 | 1 | CH$_2$C≡CH | CH$_2$Cl |
| Cl | CN | CHCl | 1 | 1 | CH$_2$C≡CH | CH$_2$Br |
| Cl | CN | CHCl | 1 | 2 | H | CH$_2$Cl |
| Cl | CN | CHCl | 1 | 2 | H | CH$_2$Br |
| Cl | CN | CHCl | 1 | 2 | C(=O)CH$_3$ | CH$_2$Cl |
| CJ | CN | CHCl | 1 | 2 | C(=O)CH$_3$ | CH$_2$Br |
| Cl | CN | CHCl | 1 | 2 | CO$_2$CH$_3$ | CH$_2$Cl |
| Cl | CN | CHCl | 1 | 2 | CO$_2$CH$_3$ | CH$_2$Br |
| Cl | CN | CHCl | 1 | 2 | CH$_2$C≡CH | CH$_2$Cl |
| Cl | CN | CHCl | 1 | 2 | CH$_2$C≡CH | CH$_2$Br |

J = 6 and Q = O

| X | Y | X | n | m | R¹ | R² |
|---|---|---|---|---|---|---|
| F | H | CH$_2$ | 1 | 1 | H | CH$_2$Cl |
| F | H | CH$_2$ | 1 | 1 | H | CH$_2$Br |
| F | H | CH$_2$ | 1 | 1 | C(=O)CH$_3$ | CH$_2$Cl |
| F | H | CH$_2$ | 1 | 1 | C(=O)CH$_3$ | CH$_2$Br |
| F | H | CH$_2$ | 1 | 1 | CO$_2$CH$_3$ | CH$_2$Cl |
| F | H | CH$_2$ | 1 | 1 | CO$_2$CH$_3$ | CH$_2$Br |
| F | H | CH$_2$ | 1 | 1 | CH$_2$C≡CH | CH$_2$Cl |
| F | H | CH$_2$ | 1 | 1 | CH$_2$C≡CH | CH$_2$Br |
| F | H | CH$_2$ | 1 | 2 | H | CH$_2$Cl |
| F | H | CH$_2$ | 1 | 2 | H | CH$_2$Br |
| F | H | CH$_2$ | 1 | 2 | C(=O)CH$_3$ | CH$_2$Cl |
| F | H | CH$_2$ | 1 | 2 | C(=O)CH$_3$ | CH$_2$Br |
| F | H | CH$_2$ | 1 | 2 | CO$_2$CH$_3$ | CH$_2$Cl |
| F | H | CH$_2$ | 1 | 2 | CO$_2$CH$_3$ | CH$_2$Br |
| F | H | CH$_2$ | 1 | 2 | CH$_2$C≡CH | CH$_2$Cl |
| F | H | CH$_2$ | 1 | 2 | CH$_2$C≡CH | CH$_2$Br |
| F | H | CHF | 1 | 1 | H | CH$_2$Cl |
| F | H | CHF | 1 | 1 | H | CH$_2$Br |
| F | H | CHF | 1 | 1 | C(=O)CH$_3$ | CH$_2$Cl |
| F | H | CHF | 1 | 1 | C(=O)CH$_3$ | CH$_2$Br |
| F | H | CHF | 1 | 1 | CO$_2$CH$_3$ | CH$_2$Cl |
| F | H | CHF | 1 | 1 | CO$_2$CH$_3$ | CH$_2$Br |
| F | H | CHF | 1 | 1 | CH$_2$C≡CH | CH$_2$Cl |
| F | H | CHF | 1 | 1 | CH$_2$C≡CH | CH$_2$Br |
| F | H | CHF | 1 | 2 | H | CH$_2$Cl |
| F | H | CHF | 1 | 2 | H | CH$_2$Br |
| F | H | CHF | 1 | 2 | C(=O)CH$_3$ | CH$_2$Cl |
| F | H | CHF | 1 | 2 | C(=O)CH$_3$ | CH$_2$Br |
| F | H | CHF | 1 | 2 | CO$_2$CH$_3$ | CH$_2$Cl |
| F | H | CHF | 1 | 2 | CO$_2$CH$_3$ | CH$_2$Br |
| F | H | CHF | 1 | 2 | CH$_2$C≡CH | CH$_2$Cl |
| F | H | CHF | 1 | 2 | CH$_2$C≡CH | CH$_2$Br |
| F | H | CHCl | 1 | 1 | H | CH$_2$Cl |
| F | H | CHCl | 1 | 1 | H | CH$_2$Br |
| F | H | CHCl | 1 | 1 | C(=O)CH$_3$ | CH$_2$Cl |
| F | H | CHCl | 1 | 1 | C(=O)CH$_3$ | CH$_2$Br |
| F | H | CHCl | 1 | 1 | CO$_2$CH$_3$ | CH$_2$Cl |
| F | H | CHCl | 1 | 1 | CO$_2$CH$_3$ | CH$_2$Br |
| F | H | CHCl | 1 | 1 | CH$_2$C≡CH | CH$_2$Cl |
| F | H | CHCl | 1 | 1 | CH$_2$C≡CH | CH$_2$Br |
| F | H | CHCl | 1 | 2 | H | CH$_2$Cl |
| F | H | CHCl | 1 | 2 | H | CH$_2$Br |
| F | H | CHCl | 1 | 2 | C(=O)CH$_3$ | CH$_2$Cl |
| F | H | CHCl | 1 | 2 | C(=O)CH$_3$ | CH$_2$Br |
| F | H | CHCl | 1 | 2 | CO$_2$CH$_3$ | CH$_2$Cl |

TABLE 1-continued

| | | | | | | |
|---|---|---|---|---|---|---|
| F | H | CHCl | 1 | 2 | CO$_2$CH$_3$ | CH$_2$Br |
| F | H | CHCl | 1 | 2 | CH$_2$C≡CH | CH$_2$Cl |
| F | H | CHCl | 1 | 2 | CH$_2$C≡CH | CH$_2$Br |
| F | Cl | CH$_2$ | 1 | 1 | H | CH$_2$Cl |
| F | Cl | CH$_2$ | 1 | 1 | H | CH$_2$Br |
| F | Cl | CH$_2$ | 1 | 1 | C(=O)CH$_3$ | CH$_2$Cl |
| F | Cl | CH$_2$ | 1 | 1 | C(=O)CH$_3$ | CH$_2$Br |
| F | Cl | CH$_2$ | 1 | 1 | CO$_2$CH$_3$ | CH$_2$Cl |
| F | Cl | CH$_2$ | 1 | 1 | CO$_2$CH$_3$ | CH$_2$Br |
| F | Cl | CH$_2$ | 1 | 1 | CH$_2$C≡CH | CH$_2$Cl |
| F | Cl | CH$_2$ | 1 | 1 | CH$_2$C≡CH | CH$_2$Br |
| F | Cl | CH$_2$ | 1 | 2 | H | CH$_2$Cl |
| F | Cl | CH$_2$ | 1 | 2 | H | CH$_2$Br |
| F | Cl | CH$_2$ | 1 | 2 | C(=O)CH$_3$ | CH$_2$Cl |
| F | Cl | CH$_2$ | 1 | 2 | C(=O)CH$_3$ | CH$_2$Br |
| F | Cl | CH$_2$ | 1 | 2 | CO$_2$CH$_3$ | CH$_2$Cl |
| F | Cl | CH$_2$ | 1 | 2 | CO$_2$CH$_3$ | CH$_2$Br |
| F | Cl | CH$_2$ | 1 | 2 | CH$_2$C≡CH | CH$_2$Cl |
| F | Cl | CH$_2$ | 1 | 2 | CH$_2$C≡CH | CH$_2$Br |
| F | Cl | CHF | 1 | 1 | H | CH$_2$Cl |
| F | Cl | CHF | 1 | 1 | H | CH$_2$Br |
| F | Cl | CHF | 1 | 1 | C(=O)CH$_3$ | CH$_2$Cl |
| F | Cl | CHF | 1 | 1 | C(=O)CH$_3$ | CH$_2$Br |
| F | Cl | CHF | 1 | 1 | CO$_2$CH$_3$ | CH$_2$Cl |
| F | Cl | CHF | 1 | 1 | CO$_2$CH$_3$ | CH$_2$Br |
| F | Cl | CHF | 1 | 1 | CH$_2$C≡CH | CH$_2$Cl |
| F | Cl | CHF | 1 | 1 | CH$_2$C≡CH | CH$_2$Br |
| F | Cl | CHF | 1 | 2 | H | CH$_2$Cl |
| F | Cl | CHF | 1 | 2 | H | CH$_2$Br |
| F | Cl | CHF | 1 | 2 | C(=O)CH$_3$ | CH$_2$Cl |
| F | Cl | CHF | 1 | 2 | C(=O)CH$_3$ | CH$_2$Br |
| F | Cl | CHF | 1 | 2 | CO$_2$CH$_3$ | CH$_2$Cl |
| F | Cl | CHF | 1 | 2 | CO$_2$CH$_3$ | CH$_2$Br |
| F | Cl | CHF | 1 | 2 | CH$_2$C≡CH | CH$_2$Cl |
| F | Cl | CHF | 1 | 2 | CH$_2$C≡CH | CH$_2$Br |
| F | Cl | CHCl | 1 | 1 | H | CH$_2$Cl |
| F | Cl | CHCl | 1 | 1 | H | CH$_2$Br |
| F | Cl | CHCl | 1 | 1 | C(=O)CH$_3$ | CH$_2$Cl |
| F | Cl | CHCl | 1 | 1 | C(=O)CH$_3$ | CH$_2$Br |
| F | Cl | CHCl | 1 | 1 | CO$_2$CH$_3$ | CH$_2$Cl |
| F | Cl | CHCl | 1 | 1 | CO$_2$CH$_3$ | CH$_2$Br |
| F | Cl | CHCl | 1 | 1 | CH$_2$C≡CH | CH$_2$Cl |
| F | Cl | CHCl | 1 | 1 | CH$_2$C≡CH | CH$_2$Br |
| F | Cl | CHCl | 1 | 2 | H | CH$_2$Cl |
| F | Cl | CHCl | 1 | 2 | H | CH$_2$Br |
| F | Cl | CRCl | 1 | 2 | C(=O)CH$_3$ | CH$_2$Cl |
| F | Cl | CHCl | 1 | 2 | C(=O)CH$_3$ | CH$_2$Br |
| F | Cl | CHCl | 1 | 2 | CO$_2$CH$_3$ | CH$_2$Cl |
| F | Cl | CHCl | 1 | 2 | CO$_2$CH$_3$ | CH$_2$Br |
| F | Cl | CHCl | 1 | 2 | CH$_2$C≡CH | CH$_2$Cl |
| F | Cl | CHCl | 1 | 2 | CH$_2$C≡CH | CH$_2$Br |
| F | Br | CH$_2$ | 1 | 1 | H | CH$_2$Cl |
| F | Br | CH$_2$ | 1 | 1 | H | CH$_2$Br |
| F | Br | CH$_2$ | 1 | 1 | C(=O)CH$_3$ | CH$_2$Cl |
| F | Br | CH$_2$ | 1 | 1 | C(=O)CH$_3$ | CH$_2$Br |
| F | Br | CH$_2$ | 1 | 1 | CO$_2$CH$_3$ | CH$_2$Cl |
| F | Br | CH$_2$ | 1 | 1 | CO$_2$CH$_3$ | CH$_2$Br |
| F | Br | CH$_2$ | 1 | 1 | CH$_2$C≡CH | CH$_2$Cl |
| F | Br | CH$_2$ | 1 | 1 | CH$_2$C≡CH | CH$_2$Br |
| F | Br | CH$_2$ | 1 | 2 | H | CH$_2$Cl |
| F | Br | CH$_2$ | 1 | 2 | H | CH$_2$Br |
| F | Br | CH$_2$ | 1 | 2 | C(=O)CH$_3$ | CH$_2$Cl |
| F | Br | CH$_2$ | 1 | 2 | C(=O)CH$_3$ | CH$_2$Br |
| F | Br | CH$_2$ | 1 | 2 | CO$_2$CH$_3$ | CH$_2$Cl |
| F | Br | CH$_2$ | 1 | 2 | CO$_2$CH$_3$ | CH$_2$Br |
| F | Br | CH$_2$ | 1 | 2 | CH$_2$C≡CH | CH$_2$Cl |
| F | Br | CH$_2$ | 1 | 2 | CH$_2$C≡CH | CH$_2$Br |
| F | Br | CHF | 1 | 1 | H | CH$_2$Cl |
| F | Br | CHF | 1 | 1 | H | CH$_2$Br |
| F | Br | CHF | 1 | 1 | C(=O)CH$_3$ | CH$_2$Cl |
| F | Br | CHF | 1 | 1 | C(=O)CH$_3$ | CH$_2$Br |
| F | Br | CHF | 1 | 1 | CO$_2$CH$_3$ | CH$_2$Cl |
| F | Br | CHF | 1 | 1 | CO$_2$CH$_3$ | CH$_2$Br |
| F | Br | CHF | 1 | 1 | CH$_2$C≡CH | CH$_2$Cl |
| F | Br | CHF | 1 | 1 | CH$_2$C≡CH | CH$_2$Br |
| F | Br | CHF | 1 | 2 | H | CH$_2$Cl |
| F | Br | CHF | 1 | 2 | H | CH$_2$Br |
| F | Br | CHF | 1 | 2 | C(=O)CH$_3$ | CH$_2$Cl |
| F | Br | CHF | 1 | 2 | C(=O)CH$_3$ | CH$_2$Br |

TABLE 1-continued

| | | | | | | |
|---|---|---|---|---|---|---|
| F | Br | CHF | 1 | 2 | CO$_2$CH$_3$ | CH$_2$Cl |
| F | Br | CHF | 1 | 2 | CO$_2$CH$_3$ | CH$_2$Br |
| F | Br | CHF | 1 | 2 | CH$_2$C≡CH | CH$_2$Cl |
| F | Br | CHF | 1 | 2 | CH$_2$C≡CH | CH$_2$Br |
| F | Br | CHCl | 1 | 1 | H | CH$_2$Cl |
| F | Br | CHCl | 1 | 1 | H | CH$_2$Br |
| F | Br | CHCl | 1 | 1 | C(=O)CH$_3$ | CH$_2$Cl |
| F | Br | CHCl | 1 | 1 | C(=O)CH$_3$ | CH$_2$Br |
| F | Br | CHCl | 1 | 1 | CO$_2$CH$_3$ | CH$_2$Cl |
| F | Br | CHCl | 1 | 1 | CO$_2$CH$_3$ | CH$_2$Br |
| F | Br | CHCl | 1 | 1 | CH$_2$=CH | CH$_2$Cl |
| F | Br | CHCl | 1 | 1 | CH$_2$=CH | CH$_2$Br |
| F | Br | CHCl | 1 | 2 | H | CH$_2$Cl |
| F | Br | CHCl | 1 | 2 | H | CH$_2$Br |
| F | Br | CHCl | 1 | 2 | C(=O)CH$_3$ | CH$_2$Cl |
| F | Br | CHCl | 1 | 2 | C(=O)CH$_3$ | CH$_2$Br |
| F | Br | CHCl | 1 | 2 | CO$_2$CH$_3$ | CH$_2$Cl |
| F | Br | CHCl | 1 | 2 | CO$_2$CH$_3$ | CH$_2$Br |
| F | Br | CHCl | 1 | 2 | CH$_2$=CH | CH$_2$Cl |
| F | Br | CHCl | 1 | 2 | CH$_2$=CH | CH$_2$Br |
| F | CN | CH$_2$ | 1 | 1 | H | CH$_2$Cl |
| F | CN | CH$_2$ | 1 | 1 | H | CH$_2$Br |
| F | CN | CH$_2$ | 1 | 1 | C(=O)CH$_3$ | CH$_2$Cl |
| F | CN | CH$_2$ | 1 | 1 | C(=O)CH$_3$ | CH$_2$Br |
| F | CN | CH$_2$ | 1 | 1 | CO$_2$CH$_3$ | CH$_2$Cl |
| F | CN | CH$_2$ | 1 | 1 | CO$_2$CH$_3$ | CH$_2$Br |
| F | CN | CH$_2$ | 1 | 1 | CH$_2$=CH | CH$_2$Cl |
| F | CN | CH$_2$ | 1 | 1 | CH$_2$=CH | CH$_2$Br |
| F | CN | CH$_2$ | 1 | 2 | H | CH$_2$Cl |
| F | CN | CH$_2$ | 1 | 2 | H | CH$_2$Br |
| F | CN | CH$_2$ | 1 | 2 | C(=O)CH$_3$ | CH$_2$Cl |
| F | CN | CH$_2$ | 1 | 2 | C(=O)CH$_3$ | CH$_2$Br |
| F | CN | CH$_2$ | 1 | 2 | CO$_2$CH$_3$ | CH$_2$Cl |
| F | CN | CH$_2$ | 1 | 2 | CO$_2$CH$_3$ | CH$_2$Br |
| F | CN | CH$_2$ | 1 | 2 | CH$_2$=CH | CH$_2$Cl |
| F | CN | CH$_2$ | 1 | 2 | CH$_2$=CH | CH$_2$Br |
| F | CN | CHF | 1 | 1 | H | CH$_2$Cl |
| F | CN | CHF | 1 | 1 | H | CH$_2$Br |
| F | CN | CHF | 1 | 1 | C(=O)CH$_3$ | CH$_2$Cl |
| F | CN | CHF | 1 | 1 | C(=O)CH$_3$ | CH$_2$Br |
| F | CN | CHF | 1 | 1 | CO$_2$CH$_3$ | CH$_2$Cl |
| F | CN | CHF | 1 | 1 | CO$_2$CH$_3$ | CH$_2$Br |
| F | CN | CHF | 1 | 1 | CH$_2$=CH | CH$_2$Cl |
| F | CN | CHF | 1 | 1 | CH$_2$=CH | CH$_2$Br |
| F | CN | CHF | 1 | 2 | H | CH$_2$Cl |
| F | CN | CHF | 1 | 2 | H | CH$_2$Br |
| F | CN | CHF | 1 | 2 | C(=O)CH$_3$ | CH$_2$Cl |
| F | CN | CHF | 1 | 2 | C(=O)CH$_3$ | CH$_2$Br |
| F | CN | CHF | 1 | 2 | CO$_2$CH$_3$ | CH$_2$Cl |
| F | CN | CHF | 1 | 2 | CO$_2$CH$_3$ | CH$_2$Br |
| F | CN | CHF | 1 | 2 | CH$_2$C≡CH | CH$_2$Cl |
| F | CN | CHF | 1 | 2 | CH$_2$C≡CH | CH$_2$Br |
| F | CN | CHCl | 1 | 1 | H | CH$_2$Cl |
| F | CN | CHCl | 1 | 1 | H | CH$_2$Br |
| F | CN | CHCl | 1 | 1 | C(=O)CH$_3$ | CH$_2$Cl |
| F | CN | CHCl | 1 | 1 | C(=O)CH$_3$ | CH$_2$Br |
| F | CN | CHCl | 1 | 1 | CO$_2$CH$_3$ | CH$_2$Cl |
| F | CN | CHCl | 1 | 1 | CO$_2$CH$_3$ | CH$_2$Br |
| F | CN | CHCl | 1 | 1 | CH$_2$C≡CH | CH$_2$Cl |
| F | CN | CHCl | 1 | 1 | CH$_2$C≡CH | CH$_2$Br |
| F | CN | CHCl | 1 | 2 | H | CH$_2$Cl |
| F | CN | CHCl | 1 | 2 | H | CH$_2$Br |
| F | CN | CHCl | 1 | 2 | C(=O)CH$_3$ | CH$_2$Cl |
| F | CN | CHCl | 1 | 2 | C(=O)CH$_3$ | CH$_2$Br |
| F | CN | CHCl | 1 | 2 | CO$_2$CH$_3$ | CH$_2$Cl |
| F | CN | CHCl | 1 | 2 | CO$_2$CH$_3$ | CH$_2$Br |
| F | CN | CHCl | 1 | 2 | CH$_2$C≡CH | CH$_2$Cl |
| F | CN | CHCl | 1 | 2 | CH$_2$C≡CH | CH$_2$Br |
| Cl | H | CH$_2$ | 1 | 1 | H | CH$_2$Cl |
| Cl | H | CH$_2$ | 1 | 1 | H | CH$_2$Br |
| Cl | H | CH$_2$ | 1 | 1 | C(=O)CH$_3$ | CH$_2$Cl |
| Cl | H | CH$_2$ | 1 | 1 | C(=O)CH$_3$ | CH$_2$Br |
| Cl | H | CH$_2$ | 1 | 1 | CO$_2$CH$_3$ | CH$_2$Cl |
| Cl | H | CH$_2$ | 1 | 1 | CO$_2$CH$_3$ | CH$_2$Br |
| Cl | H | CH$_2$ | 1 | 1 | CH$_2$C≡CH | CH$_2$Cl |
| Cl | H | CH$_2$ | 1 | 1 | CH$_2$C≡CH | CH$_2$Br |
| Cl | H | CH$_2$ | 1 | 2 | H | CH$_2$Cl |
| Cl | H | CH$_2$ | 1 | 2 | H | CH$_2$Br |
| Cl | H | CH$_2$ | 1 | 2 | C(=O)CH$_3$ | CH$_2$Cl |

TABLE 1-continued

| | | | | | | |
|---|---|---|---|---|---|---|
| Cl | H | CH$_2$ | 1 | 2 | C(=O)CH$_3$ | CH$_2$Br |
| Cl | H | CH$_2$ | 1 | 2 | CO$_2$CH$_3$ | CH$_2$Cl |
| Cl | H | CH$_2$ | 1 | 2 | CO$_2$CH$_3$ | CH$_2$Br |
| Cl | H | CH$_2$ | 1 | 2 | CH$_2$C≡CH | CH$_2$Cl |
| Cl | H | CH$_2$ | 1 | 2 | CH$_2$C≡CH | CH$_2$Br |
| Cl | H | CHF | 1 | 1 | H | CH$_2$Cl |
| Cl | H | CHF | 1 | 1 | H | CH$_2$Br |
| Cl | H | CHF | 1 | 1 | C(=O)CH$_3$ | CH$_2$Cl |
| Cl | H | CHF | 1 | 1 | C(=O)CH$_3$ | CH$_2$Br |
| Cl | H | CHF | 1 | 1 | CO$_2$CH$_3$ | CH$_2$Cl |
| Cl | H | CHF | 1 | 1 | CO$_2$CH$_3$ | CH$_2$Br |
| Cl | H | CHF | 1 | 1 | CH$_2$C≡CH | CH$_2$Cl |
| Cl | H | CHF | 1 | 1 | CH$_2$C≡CH | CH$_2$Br |
| Cl | H | CHF | 1 | 2 | H | CH$_2$Cl |
| Cl | H | CHF | 1 | 2 | H | CH$_2$Br |
| Cl | H | CHF | 1 | 2 | C(=O)CH$_3$ | CH$_2$Cl |
| Cl | H | CHF | 1 | 2 | C(=O)CH$_3$ | CH$_2$Br |
| Cl | H | CHF | 1 | 2 | CO$_2$CH$_3$ | CH$_2$Cl |
| Cl | H | CHF | 1 | 2 | CO$_2$CH$_3$ | CH$_2$Br |
| Cl | H | CHF | 1 | 2 | CH$_2$C≡CH | CH$_2$Cl |
| Cl | H | CHF | 1 | 2 | CH$_2$C≡CH | CH$_2$Br |
| Cl | H | CHCl | 1 | 1 | H | CH$_2$Cl |
| Cl | H | CHCl | 1 | 1 | H | CH$_2$Br |
| Cl | H | CHCl | 1 | 1 | C(=O)CH$_3$ | CH$_2$Cl |
| Cl | H | CHCl | 1 | 1 | C(=O)CH$_3$ | CH$_2$Br |
| Cl | H | CHCl | 1 | 1 | CO$_2$CH$_3$ | CH$_2$Cl |
| Cl | H | CHCl | 1 | 1 | CO$_2$CH$_3$ | CH$_2$Br |
| Cl | H | CHCl | 1 | 1 | CH$_2$C≡CH | CH$_2$Cl |
| Cl | H | CHCl | 1 | 1 | CH$_2$C≡CH | CH$_2$Br |
| Cl | H | CHCl | 1 | 2 | H | CH$_2$Cl |
| Cl | H | CHCl | 1 | 2 | H | CH$_2$Br |
| Cl | H | CHCl | 1 | 2 | C(=O)CH$_3$ | CH$_2$Cl |
| Cl | H | CHCl | 1 | 2 | C(=O)CH$_3$ | CH$_2$Br |
| Cl | H | CHCl | 1 | 2 | CO$_2$CH$_3$ | CH$_2$Cl |
| Cl | H | CHCl | 1 | 2 | CO$_2$CH$_3$ | CH$_2$Br |
| Cl | H | CHCl | 1 | 2 | CH$_2$C≡CH | CH$_2$Cl |
| Cl | H | CHCl | 1 | 2 | CH$_2$C≡CH | CH$_2$Br |
| Cl | Cl | CH$_2$ | 1 | 1 | H | CH$_2$Cl |
| Cl | Cl | CH$_2$ | 1 | 1 | H | CH$_2$Br |
| Cl | Cl | CH$_2$ | 1 | 1 | C(=O)CH$_3$ | CH$_2$Cl |
| Cl | Cl | CH$_2$ | 1 | 1 | C(=O)CH$_3$ | CH$_2$Br |
| Cl | Cl | CH$_2$ | 1 | 1 | CO$_2$CH$_3$ | CH$_2$Cl |
| Cl | Cl | CH$_2$ | 1 | 1 | CO$_2$CH$_3$ | CH$_2$Br |
| Cl | Cl | CH$_2$ | 1 | 1 | CH$_2$C≡CH | CH$_2$Cl |
| Cl | Cl | CH$_2$ | 1 | 1 | CH$_2$C≡CH | CH$_2$Br |
| Cl | Cl | CH$_2$ | 1 | 2 | H | CH$_2$Cl |
| Cl | Cl | CH$_2$ | 1 | 2 | H | CH$_2$Br |
| Cl | Cl | CH$_2$ | 1 | 2 | C(=O)CH$_3$ | CH$_2$Cl |
| Cl | Cl | CH$_2$ | 1 | 2 | C(=O)CH$_3$ | CH$_2$Br |
| Cl | Cl | CH$_2$ | 1 | 2 | CO$_2$CH$_3$ | CH$_2$Cl |
| Cl | Cl | CH$_2$ | 1 | 2 | CO$_2$CH$_3$ | CH$_2$Br |
| Cl | Cl | CH$_2$ | 1 | 2 | CH$_2$C≡CH | CH$_2$Cl |
| Cl | Cl | CH$_2$ | 1 | 2 | CH$_2$C≡CH | CH$_2$Br |
| Cl | Cl | CHF | 1 | 1 | H | CH$_2$Cl |
| Cl | Cl | CHF | 1 | 1 | H | CH$_2$Br |
| Cl | Cl | CHF | 1 | 1 | C(=O)CH$_3$ | CH$_2$Cl |
| Cl | Cl | CHF | 1 | 1 | C(=O)CH$_3$ | CH$_2$Br |
| Cl | Cl | CHF | 1 | 1 | CO$_2$CH$_3$ | CH$_2$Cl |
| Cl | Cl | CHF | 1 | 1 | CO$_2$CH$_3$ | CH$_2$Br |
| Cl | Cl | CHF | 1 | 1 | CH$_2$C≡CH | CH$_2$Cl |
| Cl | Cl | CHF | 1 | 1 | CH$_2$C≡CH | CH$_2$Br |
| Cl | Cl | CHF | 1 | 2 | H | CH$_2$Cl |
| Cl | Cl | CHF | 1 | 2 | H | CH$_2$Br |
| Cl | Cl | CHF | 1 | 2 | C(=O)CH$_3$ | CH$_2$Cl |
| Cl | Cl | CHF | 1 | 2 | C(=O)CH$_3$ | CH$_2$Br |
| Cl | Cl | CHF | 1 | 2 | CO$_2$CH$_3$ | CH$_2$Cl |
| Cl | Cl | CHF | 1 | 2 | CO$_2$CH$_3$ | CH$_2$Br |
| Cl | Cl | CHF | 1 | 2 | CH$_2$C≡CH | CH$_2$Cl |
| Cl | Cl | CHF | 1 | 2 | CH$_2$C≡CH | CH$_2$Br |
| Cl | Cl | CHCl | 1 | 1 | H | CH$_2$Cl |
| Cl | Cl | CHCl | 1 | 1 | H | CH$_2$Br |
| Cl | Cl | CHCl | 1 | 1 | C(=O)CH$_3$ | CH$_2$Cl |
| Cl | Cl | CHCl | 1 | 1 | C(=O)CH$_3$ | CH$_2$Br |
| Cl | Cl | CHCl | 1 | 1 | CO$_2$CH$_3$ | CH$_2$Cl |
| Cl | Cl | CHCl | 1 | 1 | CO$_2$CH$_3$ | CH$_2$Br |
| Cl | Cl | CHCl | 1 | 1 | CH$_2$C≡CH | CH$_2$Cl |
| Cl | Cl | CHCl | 1 | 1 | CH$_2$C≡CH | CH$_2$Br |
| Cl | Cl | CHCl | 1 | 2 | H | CH$_2$Cl |
| Cl | Cl | CHCl | 1 | 2 | H | CH$_2$Br |
| Cl | Cl | CHCl | 1 | 2 | C(=O)CH$_3$ | CH$_2$Cl |
| Cl | Cl | CHCl | 1 | 2 | C(=O)CH$_3$ | CH$_2$Br |
| Cl | Cl | CHCl | 1 | 2 | CO$_2$CH$_3$ | CH$_2$Cl |
| Cl | Cl | CHCl | 1 | 2 | CO$_2$CH$_3$ | CH$_2$Br |
| Cl | Cl | CHCl | 1 | 2 | CH$_2$C≡CH | CH$_2$Cl |
| Cl | Cl | CHCl | 1 | 2 | CH$_2$C≡CH | CH$_2$Br |
| Cl | Br | CH$_2$ | 1 | 1 | H | CH$_2$Cl |
| Cl | Br | CH$_2$ | 1 | 1 | H | CH$_2$Br |
| Cl | Br | CH$_2$ | 1 | 1 | C(=O)CH$_3$ | CH$_2$Cl |
| Cl | Br | CH$_2$ | 1 | 1 | C(=O)CH$_3$ | CH$_2$Br |
| Cl | Br | CH$_2$ | 1 | 1 | CO$_2$CH$_3$ | CH$_2$Cl |
| Cl | Br | CH$_2$ | 1 | 1 | CO$_2$CH$_3$ | CH$_2$Br |
| Cl | Br | CH$_2$ | 1 | 1 | CH$_2$C≡CH | CH$_2$Cl |
| Cl | Br | CH$_2$ | 1 | 1 | CH$_2$C≡CH | CH$_2$Br |
| Cl | Br | CH$_2$ | 1 | 2 | H | CH$_2$Cl |
| Cl | Br | CH$_2$ | 1 | 2 | H | CH$_2$Br |
| Cl | Br | CH$_2$ | 1 | 2 | C(=O)CH$_3$ | CH$_2$Cl |
| Cl | Br | CH$_2$ | 1 | 2 | C(=O)CH$_3$ | CH$_2$Br |
| Cl | Br | CH$_2$ | 1 | 2 | CO$_2$CH$_3$ | CH$_2$Cl |
| Cl | Br | CH$_2$ | 1 | 2 | CO$_2$CH$_3$ | CH$_2$Br |
| Cl | Br | CH$_2$ | 1 | 2 | CH$_2$C≡CH | CH$_2$Cl |
| Cl | Br | CH$_2$ | 1 | 2 | CH$_2$C≡CH | CH$_2$Br |
| Cl | Br | CHF | 1 | 1 | H | CH$_2$Cl |
| Cl | Br | CHF | 1 | 1 | H | CH$_2$Br |
| Cl | Br | CHF | 1 | 1 | C(=O)CH$_3$ | CH$_2$Cl |
| Cl | Br | CHF | 1 | 1 | C(=O)CH$_3$ | CH$_2$Br |
| Cl | Br | CHF | 1 | 1 | CO$_2$CH$_3$ | CH$_2$Cl |
| Cl | Br | CHF | 1 | 1 | CO$_2$CH$_3$ | CH$_2$Br |
| Cl | Br | CHF | 1 | 1 | CH$_2$C≡CH | CH$_2$Cl |
| Cl | Br | CHF | 1 | 1 | CH$_2$C≡CH | CH$_2$Br |
| Cl | Br | CHF | 1 | 2 | H | CH$_2$Cl |
| Cl | Br | CHF | 1 | 2 | H | CH$_2$Br |
| Cl | Br | CHF | 1 | 2 | C(=O)CH$_3$ | CH$_2$Cl |
| Cl | Br | CHF | 1 | 2 | C(=O)CH$_3$ | CH$_2$Br |
| Cl | Br | CHF | 1 | 2 | CO$_2$CH$_3$ | CH$_2$Cl |
| Cl | Br | CHF | 1 | 2 | CO$_2$CH$_3$ | CH$_2$Br |
| Cl | Br | CHF | 1 | 2 | CH$_2$C≡CH | CH$_2$Cl |
| Cl | Br | CHF | 1 | 2 | CH$_2$C≡CH | CH$_2$Br |
| Cl | Br | CHCl | 1 | 1 | H | CH$_2$Cl |
| Cl | Br | CHCl | 1 | 1 | H | CH$_2$Br |
| Cl | Br | CHCl | 1 | 1 | C(=O)CH$_3$ | CH$_2$Cl |
| Cl | Br | CHCl | 1 | 1 | C(=O)CH$_3$ | CH$_2$Br |
| Cl | Br | CHCl | 1 | 1 | CO$_2$CH$_3$ | CH$_2$Cl |
| Cl | Br | CHCl | 1 | 1 | CO$_2$CH$_3$ | CH$_2$Br |
| Cl | Br | CHCl | 1 | 1 | CH$_2$C≡CH | CH$_2$Cl |
| Cl | Br | CHCl | 1 | 1 | CH$_2$C≡CH | CH$_2$Br |
| Cl | Br | CHCl | 1 | 2 | H | CH$_2$Cl |
| Cl | Br | CHCl | 1 | 2 | H | CH$_2$Br |
| Cl | Br | CHCl | 1 | 2 | C(=O)CH$_3$ | CH$_2$Cl |
| Cl | Br | CHCl | 1 | 2 | C(=O)CH$_3$ | CH$_2$Br |
| Cl | Br | CHCl | 1 | 2 | CO$_2$CH$_3$ | CH$_2$Cl |
| Cl | Br | CHCl | 1 | 2 | CO$_2$CH$_3$ | CH$_2$Br |
| Cl | Br | CHCl | 1 | 2 | CH$_2$C≡CH | CH$_2$Cl |
| Cl | Br | CHCl | 1 | 2 | CH$_2$C≡CH | CH$_2$Br |
| Cl | CN | CH$_2$ | 1 | 1 | H | CH$_2$Cl |
| Cl | CN | CH$_2$ | 1 | 1 | H | CH$_2$Br |
| Cl | CN | CH$_2$ | 1 | 1 | C(=O)CH$_3$ | CH$_2$Cl |
| Cl | CN | CH$_2$ | 1 | 1 | C(=O)CH$_3$ | CH$_2$Br |
| Cl | CN | CH$_2$ | 1 | 1 | CO$_2$CH$_3$ | CH$_2$Cl |
| Cl | CN | CH$_2$ | 1 | 1 | CO$_2$CH$_3$ | CH$_2$Br |
| Cl | CN | CH$_2$ | 1 | 1 | CH$_2$C≡CH | CH$_2$Cl |
| Cl | CN | CH$_2$ | 1 | 1 | CH$_2$C≡CH | CH$_2$Br |
| Cl | CN | CH$_2$ | 1 | 2 | H | CH$_2$Cl |
| Cl | CN | CH$_2$ | 1 | 2 | H | CH$_2$Br |
| Cl | CN | CH$_2$ | 1 | 2 | C(=O)CH$_3$ | CH$_2$Cl |
| Cl | CN | CH$_2$ | 1 | 2 | C(=O)CH$_3$ | CH$_2$Br |
| Cl | CN | CH$_2$ | 1 | 2 | CO$_2$CH$_3$ | CH$_2$Cl |
| Cl | CN | CH$_2$ | 1 | 2 | CO$_2$CH$_3$ | CH$_2$Br |
| Cl | CN | CH$_2$ | 1 | 2 | CH$_2$C≡CH | CH$_2$Cl |
| Cl | CN | CH$_2$ | 1 | 2 | CH$_2$C≡CH | CH$_2$Br |
| Cl | CN | CHF | 1 | 1 | H | CH$_2$Cl |
| Cl | CN | CHF | 1 | 1 | H | CH$_2$Br |
| Cl | CN | CHF | 1 | 1 | C(=O)CH$_3$ | CH$_2$Cl |
| Cl | CN | CHF | 1 | 1 | C(=O)CH$_3$ | CH$_2$Br |
| Cl | CN | CHF | 1 | 1 | CO$_2$CH$_3$ | CH$_2$Cl |
| Cl | CN | CHF | 1 | 1 | CO$_2$CH$_3$ | CH$_2$Br |
| Cl | CN | CHF | 1 | 1 | CH$_2$C≡CH | CH$_2$Cl |
| Cl | CN | CHF | 1 | 1 | CH$_2$C≡CH | CH$_2$Br |
| Cl | CN | CHF | 1 | 2 | H | CH$_2$Cl |

TABLE 1-continued

| | | | | | | |
|---|---|---|---|---|---|---|
| Cl | CN | CHF | 1 | 2 | H | CH$_2$Br |
| Cl | CN | CHF | 1 | 2 | C(=O)CH$_3$ | CH$_2$Cl |
| Cl | CN | CHF | 1 | 2 | C(=O)CH$_3$ | CH$_2$Br |
| Cl | CN | CHF | 1 | 2 | CO$_2$CH$_3$ | CH$_2$Cl |
| Cl | CN | CHF | 1 | 2 | CO$_2$CH$_3$ | CH$_2$Br |
| Cl | CN | CHF | 1 | 2 | CH$_2$C≡CH | CH$_2$Cl |
| Cl | CN | CHF | 1 | 2 | CH$_2$C≡CH | CH$_2$Br |
| Cl | CN | CHCl | 1 | 1 | H | CH$_2$Cl |
| Cl | CN | CHCl | 1 | 1 | H | CH$_2$Br |
| Cl | CN | CHCl | 1 | 1 | C(=O)CH$_3$ | CH$_2$Cl |
| Cl | CN | CHCl | 1 | 1 | C(=O)CH$_3$ | CH$_2$Br |
| Cl | CN | CHCl | 1 | 1 | CO$_2$CH$_3$ | CH$_2$Cl |
| Cl | CN | CHCl | 1 | 1 | CO$_2$CH$_3$ | CH$_2$Br |
| Cl | CN | CHCl | 1 | 1 | CH$_2$C≡CH | CH$_2$Cl |
| Cl | CN | CHCl | 1 | 1 | CH$_2$C≡CH | CH$_2$Br |
| Cl | CN | CHCl | 1 | 2 | H | CH$_2$Cl |
| Cl | CN | CHCl | 1 | 2 | H | CH$_2$Br |
| Cl | CN | CHCl | 1 | 2 | C(=O)CH$_3$ | CH$_2$Cl |
| Cl | CN | CHCl | 1 | 2 | C(=O)CH$_3$ | CH$_2$Br |
| Cl | CN | CHCl | 1 | 2 | CO$_2$CH$_3$ | CH$_2$Cl |
| Cl | CN | CHCl | 1 | 2 | CO$_2$CH$_3$ | CH$_2$Br |
| Cl | CN | CHCl | 1 | 2 | CH$_2$C≡CH | CH$_2$Cl |
| Cl | CN | CHCl | 1 | 2 | CH$_2$C≡CH | CH$_2$Br |

| J = 6, X = F, Y = Cl, n = m = 1, and Q = O | | |
|---|---|---|
| Z | R$^1$ | R$^2$ |
| CHF | H | CH$_2$F |
| CHF | H | CH$_2$OCH$_3$ |
| CHF | H | CH$_2$CN |
| CHF | H | CH$_2$SCH$_3$ |
| CHF | H | CH$_2$SO$_2$CH$_3$ |
| CHF | H | CHCl$_2$ |
| CHF | H | CH$_2$CH$_2$Cl |
| CHF | C(=O)CH$_3$ | CH$_2$F |
| CHF | C(=O)CH$_3$ | CH$_2$OCH$_3$ |
| CHF | C(=O)CH$_3$ | CH$_2$CN |
| CHF | C(=O)CH$_3$ | CH$_2$SCH$_3$ |
| CHF | C(=O)CH$_3$ | CH$_2$SO$_2$CH$_3$ |
| CHF | C(=O)CH$_3$ | CHCl$_2$ |
| CHF | C(=O)CH$_3$ | CH$_2$CH$_2$Cl |
| CHF | CO$_2$CH$_3$ | CH$_2$F |
| CHF | CO$_2$CH$_3$ | CH$_2$OCH$_3$ |
| CHF | CO$_2$CH$_3$ | CH$_2$CN |
| CHF | CO$_2$CH$_3$ | CH$_2$SCH$_3$ |
| CHF | CO$_2$CH$_3$ | CH$_2$SO$_2$CH$_3$ |
| CHF | CO$_2$CH$_3$ | CHCl$_2$ |
| CHF | CO$_2$CH$_3$ | CH$_2$CH$_2$Cl |
| CHF | CH$_2$C≡CH | CH$_2$F |
| CHF | CH$_2$C≡CH | CH$_2$OCH$_3$ |
| CHF | CH$_2$C≡CH | CH$_2$CN |
| CHF | CH$_2$C≡CH | CH$_2$SCH$_3$ |
| CHF | CH$_2$C≡CH | CH$_2$SO$_2$CH$_3$ |
| CHF | CH$_2$C≡CH | CHCl$_2$ |
| CHF | CH$_2$C≡CH | CH$_2$CH$_2$Cl |
| CHCl | H | CH$_2$F |
| CHCl | H | CH$_2$OCH$_3$ |
| CHCl | H | CH$_2$CN |
| CHCl | H | CH$_2$SCH$_3$ |
| CHCl | H | CH$_2$SO$_2$CH$_3$ |
| CHCl | H | CHCl$_2$ |
| CHCl | H | CH$_2$CH$_2$Cl |
| CHCl | C(=O)CH$_3$ | CH$_2$F |
| CHCl | C(=O)CH$_3$ | CH$_2$OCH$_3$ |
| CHCl | C(=O)CH$_3$ | CH$_2$CN |
| CHCl | C(=O)CH$_3$ | CH$_2$SCH$_3$ |
| CHCl | C(=O)CH$_3$ | CH$_2$SO$_2$CH$_3$ |
| CHCl | C(=O)CH$_3$ | CHCl$_2$ |
| CHCl | C(=O)CH$_3$ | CH$_2$CH$_2$Cl |
| CHCl | CO$_2$CH$_3$ | CH$_2$F |
| CHCl | CO$_2$CH$_3$ | CH$_2$OCH$_3$ |
| CHCl | CO$_2$CH$_3$ | CH$_2$CN |
| CHCl | CO$_2$CH$_3$ | CH$_2$SCH$_3$ |
| CHCl | CO$_2$CH$_3$ | CH$_2$SO$_2$CH$_3$ |
| CHCl | CO$_2$CH$_3$ | CHCl$_2$ |
| CHCl | CO$_2$CH$_3$ | CH$_2$CH$_2$Cl |
| CHCl | CH$_2$C≡CH | CH$_2$F |
| CHCl | CH$_2$C≡CH | CH$_2$OCH$_3$ |
| CHCl | CH$_2$C≡CH | CH$_2$CN |
| CHCl | CH$_2$C≡CH | CH$_2$SCH$_3$ |
| CHCl | CH$_2$C≡CH | CH$_2$SO$_2$CH$_3$ |
| CHCl | CH$_2$C≡CH | CHCl$_2$ |
| CHCl | CH$_2$C≡CH | CH$_2$CH$_2$Cl |
| CHBr | H | CH$_2$Cl |
| CHBr | H | CH$_2$F |
| CHBr | H | CH$_2$OCH$_3$ |
| CHBr | H | CH$_2$CN |
| CHBr | H | CH$_2$SCH$_3$ |
| CHBr | H | CH$_2$SO$_2$CH$_3$ |
| CRBr | H | CHCl$_2$ |
| CHBr | H | CH$_2$CH$_2$Cl |
| CHBr | C(=O)CH$_3$ | CH$_2$Cl |
| CHBr | C(=O)CH$_3$ | CH$_2$F |
| CHBr | C(=O)CH$_3$ | CH$_2$OCH$_3$ |
| CHBr | C(=O)CH$_3$ | CH$_2$CN |
| CHBr | C(=O)CH$_3$ | CH$_2$SCH$_3$ |
| CHBr | C(=O)CH$_3$ | CH$_2$SO$_2$CH$_3$ |
| CHBr | C(=O)CH$_3$ | CHCl$_2$ |
| CHBr | C(=O)CH$_3$ | CH$_2$CH$_2$Cl |
| CHBr | CO$_2$CH$_3$ | CH$_2$Cl |
| CHBr | CO$_2$CH$_3$ | CH$_2$F |
| CHBr | CO$_2$CH$_3$ | CH$_2$OCH$_3$ |
| CHBr | CO$_2$CH$_3$ | CH$_2$CN |
| CHBr | CO$_2$CH$_3$ | CH$_2$SCH$_3$ |
| CHBr | CO$_2$CH$_3$ | CH$_2$SO$_2$CH$_3$ |
| CHBr | CO$_2$CH$_3$ | CHCl$_2$ |
| CHBr | CO$_2$CH$_3$ | CH$_2$CH$_2$Cl |
| CHBr | CH$_2$C≡CH | CH$_2$Cl |
| CHBr | CH$_2$C≡CH | CH$_2$F |
| CHBr | CH$_2$C≡CH | CH$_2$OCH$_3$ |
| CHBr | CH$_2$C≡CH | CH$_2$CN |
| CHBr | CH$_2$C≡CH | CH$_2$SCH$_3$ |
| CHBr | CH$_2$C≡CH | CH$_2$SO$_2$CH$_3$ |
| CHBr | CH$_2$C≡CH | CHCl$_2$ |
| CHBr | CH$_2$C≡CH | CH$_2$CH$_2$Cl |
| CHCl | C(=O)Ph | CH$_2$Cl |
| CHCl | C(=O)CHCl$_2$ | CH$_2$Cl |
| CHCl | C(=O)CH(Cl)CH$_3$ | CH$_2$Cl |
| CHCl | C(=O)(CH$_2$)$_{18}$CH$_3$ | CH$_2$Cl |
| CHCl | C(=O)CH$_2$Cl | CH$_2$Cl |
| CHCl | C(=O)CH$_2$CH$_3$ | CH$_2$Cl |
| CHCl | C(=O)CH(CH$_3$)$_2$ | CH$_2$Cl |
| CHCl | C(=O)CH(CH$_2$)2 | CH$_2$Cl |

| J = 7, Y = Cl, and R$^2$ = CH$_2$Cl | | |
|---|---|---|
| X | R$^1$ | R$^{16}$ |
| F | H | CH$_3$ |
| F | C(=O)CH$_3$ | CH$_3$ |
| F | CO$_2$CH$_3$ | CH$_3$ |
| F | H | CF$_3$ |
| F | C(=O)CH$_3$ | CF$_3$ |
| F | CO$_2$CH$_3$ | CF$_3$ |
| Cl | H | CH$_3$ |
| Cl | C(=O)CH$_3$ | CH$_3$ |
| Cl | CO$_2$CH$_3$ | CH$_3$ |
| Cl | H | CF$_3$ |
| Cl | C(=O)CH$_3$ | CF$_3$ |
| Cl | CO$_2$CH$_3$ | CF$_3$ |

| J = O, Y = Cl, Q = 0, n = m = 1, R$^2$ = CH$_2$Cl, and R$^{17}$ = R$^{18}$ = H | | |
|---|---|---|
| X | R$^1$ | Z |
| F | H | CH$_2$ |
| F | C(=O)CH$_3$ | CH$_2$ |
| F | CO$_2$CH$_3$ | CH$_2$ |
| F | H | CHF |
| F | C(=O)CH$_3$ | CHF |
| F | CO$_2$CH$_3$ | CHF |
| Cl | H | CH$_2$ |
| Cl | C(=O)CH$_3$ | CH$_2$ |
| Cl | CO$_2$CH$_3$ | CH$_2$ |
| Cl | H | CHF |
| Cl | C(=O)CH$_3$ | CHF |
| Cl | CO$_2$CH$_3$ | CHF |

TABLE 1-continued

J = O, Q = 0, Q¹ = S, Y = Cl, and R² = CH$_2$Cl

| X | R$^1$ | R$^{19}$ | R$^{20}$ |
|---|---|---|---|
| F | H | CH$_3$ | CH$_3$ |
| F | C(=O)CH$_3$ | CH$_3$ | CH$_3$ |
| F | CO$_2$CH$_3$ | CH$_3$ | CH$_3$ |
| F | H | CH$_2$CH$_3$ | CH$_3$ |
| F | C(=O)CH$_3$ | CH$_2$CH$_3$ | CH$_3$ |
| F | CO$_2$CH$_3$ | CH$_2$CH$_3$ | CH$_3$ |
| F | H | CH$_2$=CH | CH$_3$ |
| F | C(=O)CH$_3$ | CH$_2$=CH | CH$_3$ |
| F | CO$_2$CH$_3$ | CH$_2$=CH | CH$_3$ |
| F | H | CF$_3$ | CH$_3$ |
| F | C(=O)CH$_3$ | CF$_3$ | CH$_3$ |
| F | CO$_2$CH$_3$ | CF$_3$ | CH$_3$ |
| F | H | CH$_3$ | CH$_2$CH$_3$ |
| F | C(=O)CH$_3$ | CH$_3$ | CH$_2$CH$_3$ |
| F | CO$_2$CH$_3$ | CH$_3$ | CH$_2$CH$_3$ |
| F | H | CH$_2$CH$_3$ | CH$_2$CH$_3$ |
| F | C(=O)CH$_3$ | CH$_2$CH$_3$ | CH$_2$CH$_3$ |
| F | CO$_2$CH$_3$ | CH$_2$CH$_3$ | CH$_2$CH$_3$ |
| F | H | CH$_2$=CH | CH$_2$CH$_3$ |
| F | C(=O)CH$_3$ | CH$_2$=CH | CH$_2$CH$_3$ |
| F | CO$_2$CH$_3$ | CH$_2$=CH | CH$_2$CH$_3$ |
| F | H | CF$_3$ | CH$_2$CH$_3$ |
| F | C(=O)CH$_3$ | CF$_3$ | CH$_2$CH$_3$ |
| F | CO$_2$CH$_3$ | CF$_3$ | CH$_2$CH$_3$ |
| F | H | CH$_3$ | CH$_2$=CH |
| F | C(=O)CH$_3$ | CH$_3$ | CH$_2$=CH |
| F | CO$_2$CH$_3$ | CH$_3$ | CH$_2$=CH |
| F | H | CH$_2$CH$_3$ | CH$_2$=CH |
| F | C(=O)CH$_3$ | CH$_2$CH$_3$ | CH$_2$=CH |
| F | CO$_2$CH$_3$ | CH$_2$CH$_3$ | CH$_2$=CH |
| F | H | CH$_2$C≡CH | CH$_2$=CH |
| F | C(=O)CH$_3$ | CH$_2$C≡CH | CH$_2$=CH |
| F | CO$_2$CH$_3$ | CH$_2$C≡CH | CH$_2$=CH |
| F | H | CF$_3$ | CH$_2$=CH |
| F | C(=O)CH$_3$ | CF$_3$ | CH$_2$=CH |
| F | CO$_2$CH$_3$ | CF$_3$ | CH$_2$=CH |
| F | H | CH$_3$ | CF$_3$ |
| F | C(=O)CH$_3$ | CH$_3$ | CF$_3$ |
| F | CO$_2$CH$_3$ | CH$_3$ | CF$_3$ |
| F | H | CH$_2$CH$_3$ | CF$_3$ |
| F | C(=O)CH$_3$ | CH$_2$CH$_3$ | CF$_3$ |
| F | CO$_2$CH$_3$ | CH$_2$CH$_3$ | CF$_3$ |
| F | H | CH$_2$=CH | CF$_3$ |
| F | C(=O)CH$_3$ | CH$_2$=CH | CF$_3$ |
| F | CO$_2$CH$_3$ | CH$_2$=CH | CF$_3$ |
| F | H | CF$_3$ | CF$_3$ |
| F | C(=O)CH$_3$ | CF$_3$ | CF$_3$ |
| F | CO$_2$CH$_3$ | CF$_3$ | CF$_3$ |
| Cl | H | CH$_3$ | CH$_3$ |
| Cl | C(=O)CH$_3$ | CH$_3$ | CH$_3$ |
| Cl | CO$_2$CH$_3$ | CH$_3$ | CH$_3$ |
| Cl | H | CH$_2$CH$_3$ | CH$_3$ |
| Cl | C(=O)CH$_3$ | CH$_2$CH$_3$ | CH$_3$ |
| Cl | CO$_2$CH$_3$ | CH$_2$CH$_3$ | CH$_3$ |
| Cl | H | CH$_2$C≡CH | CH$_3$ |
| Cl | C(=O)CH$_3$ | CH$_2$C≡CH | CH$_3$ |
| Cl | CO$_2$CH$_3$ | CH$_2$C≡CH | CH$_3$ |
| Cl | H | CF$_3$ | CH$_3$ |
| Cl | C(=O)CH$_3$ | CF$_3$ | CH$_3$ |
| Cl | CO$_2$CH$_3$ | CF$_3$ | CH$_3$ |
| Cl | H | CH$_3$ | CH$_2$CH$_3$ |
| Cl | C(=O)CH$_3$ | CH$_3$ | CH$_2$CH$_3$ |
| Cl | CO$_2$CH$_3$ | CH$_3$ | CH$_2$CH$_3$ |
| Cl | H | CH$_2$CH$_3$ | CH$_2$CH$_3$ |
| Cl | C(=O)CH$_3$ | CH$_2$CH$_3$ | CH$_2$CH$_3$ |
| Cl | CO$_2$CH$_3$ | CH$_2$CH$_3$ | CH$_2$CH$_3$ |
| Cl | H | CH$_2$C≡CH | CH$_2$CH$_3$ |
| Cl | C(=O)CH$_3$ | CH$_2$C≡CH | CH$_2$CH$_3$ |
| Cl | CO$_2$CH$_3$ | CH$_2$=CH | CH$_2$CH$_3$ |
| Cl | H | CF$_3$ | CH$_2$CH$_3$ |
| Cl | C(=O)CH$_3$ | CF$_3$ | CH$_2$CH$_3$ |
| Cl | CO$_2$CH$_3$ | CF$_3$ | CH$_2$CH$_3$ |
| Cl | H | CH$_3$ | CH$_2$C≡CH |
| Cl | C(=O)CH$_3$ | CH$_3$ | CH$_2$C≡CH |
| Cl | CO$_2$CH$_3$ | CH$_3$ | CH$_2$C≡CH |
| Cl | H | CH$_2$CH$_3$ | CH$_2$C≡CH |
| Cl | C(=O)CH$_3$ | CH$_2$CH$_3$ | CH$_2$C≡CH |
| Cl | CO$_2$CH$_3$ | CH$_2$CH$_3$ | CH$_2$C≡CH |
| Cl | H | CH$_2$C≡CH | CH$_2$C≡CH |
| Cl | C(=O)CH$_3$ | CH$_2$C≡CH | CH$_2$C≡CH |
| Cl | CO$_2$CH$_3$ | CH$_2$C≡CH | CH$_2$C≡CH |
| Cl | H | CF$_3$ | CH$_2$C≡CH |
| Cl | C(=O)CH$_3$ | CF$_3$ | CH$_2$C≡CH |
| Cl | CO$_2$CH$_3$ | CF$_3$ | CH$_2$C≡CH |
| Cl | H | CH$_3$ | CF$_3$ |
| Cl | C(=O)CH$_3$ | CH$_3$ | CF$_3$ |
| Cl | CO$_2$CH$_3$ | CH$_3$ | CF$_3$ |
| Cl | H | CH$_2$CH$_3$ | CF$_3$ |
| Cl | C(=O)CH$_3$ | CH$_2$CH$_3$ | CF$_3$ |
| Cl | CO$_2$CH$_3$ | CH$_2$CH$_3$ | CF$_3$ |
| Cl | H | CH$_2$C≡CH | CF$_3$ |
| Cl | C(=O)CH$_3$ | CH$_2$C≡CH | CF$_3$ |
| Cl | CO$_2$CH$_3$ | CH$_2$C≡CH | CF$_3$ |
| Cl | H | CF$_3$ | CF$_3$ |
| Cl | C(=O)CH$_3$ | CF$_3$ | CF$_3$ |
| Cl | CO$_2$CH$_3$ | CF$_3$ | CF$_3$ |

J = 10, Q$^1$ = S, Y = Cl, and R$^2$ = CH$_2$Cl

| X | R$^1$ | Z | n | m |
|---|---|---|---|---|
| F | H | CH$_2$ | 1 | 1 |
| F | C(=O)CH$_3$ | CH$_2$ | 1 | 1 |
| F | CO$_2$CH$_3$ | CH$_2$ | 1 | 1 |
| F | H | CHF | 1 | 1 |
| F | C(=O)CH$_3$ | CHF | 1 | 1 |
| F | CO$_2$CH$_3$ | CHF | 1 | 1 |
| F | H | CH$_2$ | 1 | 2 |
| F | C(=O)CH$_3$ | CH$_2$ | 1 | 2 |
| F | CO$_2$CH$_3$ | CH$_2$ | 1 | 2 |
| F | H | CHF | 1 | 2 |
| F | C(=O)CH$_3$ | CHF | 1 | 2 |
| F | CO$_2$CH$_3$ | CHF | 1 | 2 |
| Cl | H | CH$_2$ | 1 | 1 |
| Cl | C(=O)CH$_3$ | CH$_2$ | 1 | 1 |
| Cl | CO$_2$CH$_3$ | CH$_2$ | 1 | 1 |
| Cl | H | CHF | 1 | 1 |
| Cl | C(=O)CH$_3$ | CHF | 1 | 1 |
| Cl | CO$_2$CH$_3$ | CHF | 1 | 1 |
| Cl | H | CH$_2$ | 1 | 2 |
| Cl | C(=O)CH$_3$ | CH$_2$ | 1 | 2 |
| Cl | CO$_2$CH$_3$ | CH$_2$ | 1 | 2 |
| Cl | H | CHF | 1 | 2 |
| Cl | C(=O)CH$_3$ | CHF | 1 | 2 |
| Cl | CO$_2$CH$_3$ | CHF | 1 | 2 |

J = 11 and R$^{21}$ = Cl

| X | Y | Z | n | m | R$^1$ | R$^2$ |
|---|---|---|---|---|---|---|
| F | H | CH$_2$ | 1 | 1 | H | CH$_2$Cl |
| F | H | CH$_2$ | 1 | 1 | H | CH$_2$Br |
| F | H | CH$_2$ | 1 | 2 | H | CH$_2$Cl |
| F | H | CH$_2$ | 1 | 2 | H | CH$_2$Br |
| F | H | CHF | 1 | 1 | H | CH$_2$Cl |
| F | H | CHF | 1 | 1 | H | CH$_2$Br |
| F | H | CHF | 1 | 2 | H | CH$_2$Cl |
| F | H | CHF | 1 | 2 | H | CH$_2$Br |
| F | H | CHCl | 1 | 1 | H | CH$_2$Cl |
| F | H | CHCl | 1 | 1 | H | CH$_2$Br |
| F | H | CHCl | 1 | 2 | H | CH$_2$Cl |
| F | H | CHCl | 1 | 2 | H | CH$_2$Br |
| F | Cl | CH$_2$ | 1 | 1 | H | CH$_2$Cl |
| F | Cl | CH$_2$ | 1 | 1 | H | CH$_2$Br |
| F | Cl | CH$_2$ | 1 | 1 | C(=O)CH$_3$ | CH$_2$Cl |
| F | Cl | CH$_2$ | 1 | 1 | C(=O)CH$_3$ | CH$_2$Br |
| F | Cl | CH$_2$ | 1 | 1 | CO$_2$CH$_3$ | CH$_2$Cl |
| F | Cl | CH$_2$ | 1 | 1 | CO$_2$CH$_3$ | CH$_2$Br |
| F | Cl | CH$_2$ | 1 | 1 | CH$_2$C≡CH | CH$_2$Cl |
| F | Cl | CH$_2$ | 1 | 1 | CH$_2$C≡CH | CH$_2$Br |
| F | Cl | CH$_2$ | 1 | 2 | H | CH$_2$Cl |
| F | Cl | CH$_2$ | 1 | 2 | H | CH$_2$Br |
| F | Cl | CH$_2$ | 1 | 2 | C(=O)CH$_3$ | CH$_2$Cl |
| F | Cl | CH$_2$ | 1 | 2 | C(=O)CH$_3$ | CH$_2$Br |

TABLE 1-continued

| | | | | | | |
|---|---|---|---|---|---|---|
| F | Cl | CH$_2$ | 1 | 2 | CO$_2$CH$_3$ | CH$_2$Cl |
| F | Cl | CH$_2$ | 1 | 2 | CO$_2$CH$_3$ | CH$_2$Br |
| F | Cl | CH$_2$ | 1 | 2 | CH$_2$C≡CH | CH$_2$Cl |
| F | Cl | CH$_2$ | 1 | 2 | CH$_2$C≡CH | CH$_2$Br |
| F | Cl | CHF | 1 | 1 | H | CH$_2$Cl |
| F | Cl | CHF | 1 | 1 | H | CH$_2$Br |
| F | Cl | CHF | 1 | 1 | C(=O)CH$_3$ | CH$_2$Cl |
| F | Cl | CHF | 1 | 1 | C(=O)CH$_3$ | CH$_2$Br |
| F | Cl | CHF | 1 | 1 | CO$_2$CH$_3$ | CH$_2$Cl |
| F | Cl | CHF | 1 | 1 | CO$_2$CH$_3$ | CH$_2$Br |
| F | Cl | CHF | 1 | 1 | CH$_2$C≡CH | CH$_2$Cl |
| F | Cl | CHF | 1 | 1 | CH$_2$C≡CH | CH$_2$Br |
| F | Cl | CHF | 1 | 2 | H | CH$_2$Cl |
| F | Cl | CHF | 1 | 2 | H | CH$_2$Br |
| F | Cl | CHF | 1 | 2 | C(=O)CH$_3$ | CH$_2$Cl |
| F | Cl | CHF | 1 | 2 | C(=O)CH$_3$ | CH$_2$Br |
| F | Cl | CHF | 1 | 2 | CO$_2$CH$_3$ | CH$_2$Cl |
| F | Cl | CHF | 1 | 2 | CO$_2$CH$_3$ | CH$_2$Br |
| F | Cl | CHF | 1 | 2 | CH$_2$C≡CH | CH$_2$Cl |
| F | Cl | CHF | 1 | 2 | CH$_2$C≡CH | CH$_2$Br |
| F | Cl | CHCl | 1 | 1 | H | CH$_2$Cl |
| F | Cl | CHCl | 1 | 1 | H | CH$_2$Br |
| F | Cl | CHCl | 1 | 1 | C(=O)CH$_3$ | CH$_2$Cl |
| F | Cl | CHCl | 1 | 1 | C(=O)CH$_3$ | CH$_2$Br |
| F | Cl | CHCl | 1 | 1 | CO$_2$CH$_3$ | CH$_2$Cl |
| F | Cl | CHCl | 1 | 1 | CO$_2$CH$_3$ | CH$_2$Br |
| F | Cl | CHCl | 1 | 1 | CH$_2$C≡CH | CH$_2$Cl |
| F | Cl | CHCl | 1 | 1 | CH$_2$C≡CH | CH$_2$Br |
| F | Cl | CHCl | 1 | 2 | H | CH$_2$Cl |
| F | Cl | CHCl | 1 | 2 | H | CH$_2$Br |
| F | Cl | CHCl | 1 | 2 | C(=O)CH$_3$ | CH$_2$Cl |
| F | Cl | CHCl | 1 | 2 | C(=O)CH$_3$ | CH$_2$Br |
| F | Cl | CHCl | 1 | 2 | CO$_2$CH$_3$ | CH$_2$Cl |
| F | Cl | CHCl | 1 | 2 | CO$_2$CH$_3$ | CH$_2$Br |
| F | Cl | CHCl | 1 | 2 | CH$_2$C≡CH | CH$_2$Cl |
| F | Cl | CHCl | 1 | 2 | CH$_2$C≡CH | CH$_2$Br |
| F | Br | CH$_2$ | 1 | 1 | H | CH$_2$Cl |
| F | Br | CH$_2$ | 1 | 1 | H | CH$_2$Br |
| F | Br | CH$_2$ | 1 | 1 | C(=O)CH$_3$ | CH$_2$Cl |
| F | Br | CH$_2$ | 1 | 1 | C(=O)CH$_3$ | CH$_2$Br |
| F | Br | CH$_2$ | 1 | 1 | CO$_2$CH$_3$ | CH$_2$Cl |
| F | Br | CH$_2$ | 1 | 1 | CO$_2$CH$_3$ | CH$_2$Br |
| F | Br | CH$_2$ | 1 | 1 | CH$_2$C≡CH | CH$_2$Cl |
| F | Br | CH$_2$ | 1 | 1 | CH$_2$C≡CH | CH$_2$Br |
| F | Br | CH$_2$ | 1 | 2 | H | CH$_2$Cl |
| F | Br | CH$_2$ | 1 | 2 | H | CH$_2$Br |
| F | Br | CH$_2$ | 1 | 2 | C(=O)CH$_3$ | CH$_2$Cl |
| F | Br | CH$_2$ | 1 | 2 | C(=O)CH$_3$ | CH$_2$Br |
| F | Br | CH$_2$ | 1 | 2 | CO$_2$CH$_3$ | CH$_2$Cl |
| F | Br | CH$_2$ | 1 | 2 | CO$_2$CH$_3$ | CH$_2$Br |
| F | Br | CH$_2$ | 1 | 2 | CH$_2$C≡CH | CH$_2$Cl |
| F | Br | CH$_2$ | 1 | 2 | CH$_2$C≡CH | CH$_2$Br |
| F | Br | CHF | 1 | 1 | H | CH$_2$Cl |
| F | Br | CHF | 1 | 1 | H | CH$_2$Br |
| F | Br | CHF | 1 | 1 | C(=O)CH$_3$ | CH$_2$Cl |
| F | Br | CHF | 1 | 1 | C(=O)CH$_3$ | CH$_2$Br |
| F | Br | CHF | 1 | 1 | CO$_2$CH$_3$ | CH$_2$Cl |
| F | Br | CHF | 1 | 1 | CO$_2$CH$_3$ | CH$_2$Br |
| F | Br | CHF | 1 | 1 | CH$_2$C≡CH | CH$_2$Cl |
| F | Br | CHF | 1 | 1 | CH$_2$C≡CH | CH$_2$Br |
| F | Br | CHF | 1 | 2 | H | CH$_2$Cl |
| F | Br | CHF | 1 | 2 | H | CH$_2$Br |
| F | Br | CHF | 1 | 2 | C(=O)CH$_3$ | CH$_2$Cl |
| F | Br | CHF | 1 | 2 | C(=O)CH$_3$ | CH$_2$Br |
| F | Br | CHF | 1 | 2 | CO$_2$CH$_3$ | CH$_2$Cl |
| F | Br | CHF | 1 | 2 | CO$_2$CH$_3$ | CH$_2$Br |
| F | Br | CHF | 1 | 2 | CH$_2$C≡CH | CH$_2$Cl |
| F | Br | CHF | 1 | 2 | CH$_2$C≡CH | CH$_2$Br |
| F | Br | CHCl | 1 | 1 | H | CH$_2$Cl |
| F | Br | CHCl | 1 | 1 | H | CH$_2$Br |
| F | Br | CHCl | 1 | 1 | C(=O)CH$_3$ | CH$_2$Cl |
| F | Br | CHCl | 1 | 1 | C(=O)CH$_3$ | CH$_2$Br |
| F | Br | CHCl | 1 | 1 | CO$_2$CH$_3$ | CH$_2$Cl |
| F | Br | CHCl | 1 | 1 | CO$_2$CH$_3$ | CH$_2$Br |
| F | Br | CHCl | 1 | 1 | CH$_2$C≡CH | CH$_2$Cl |
| F | Br | CHCl | 1 | 1 | CH$_2$C≡CH | CH$_2$Br |
| F | Br | CHCl | 1 | 2 | H | CH$_2$Cl |
| F | Br | CHCl | 1 | 2 | H | CH$_2$Br |
| F | Br | CHCl | 1 | 2 | C(=O)CH$_3$ | CH$_2$Cl |
| F | Br | CHCl | 1 | 2 | C(=O)CH$_3$ | CH$_2$Br |
| F | Br | CHCl | 1 | 2 | CO$_2$CH$_3$ | CH$_2$Cl |
| F | Br | CHCl | 1 | 2 | CO$_2$CH$_3$ | CH$_2$Br |
| F | Br | CHCl | 1 | 2 | CH$_2$C≡CH | CH$_2$Cl |
| F | Br | CHCl | 1 | 2 | CH$_2$C≡CH | CH$_2$Br |
| F | CN | CH$_2$ | 1 | 1 | H | CH$_2$Cl |
| F | CN | CH$_2$ | 1 | 1 | H | CH$_2$Br |
| F | CN | CH$_2$ | 1 | 1 | C(=O)CH$_3$ | CH$_2$Cl |
| F | CN | CH$_2$ | 1 | 1 | C(=O)CH$_3$ | CH$_2$Br |
| F | CN | CH$_2$ | 1 | 1 | CO$_2$CH$_3$ | CH$_2$Cl |
| F | CN | CH$_2$ | 1 | 1 | CO$_2$CH$_3$ | CH$_2$Br |
| F | CN | CH$_2$ | 1 | 1 | CH$_2$C≡CH | CH$_2$Cl |
| F | CN | CH$_2$ | 1 | 1 | CH$_2$C≡CH | CH$_2$Br |
| F | CN | CH$_2$ | 1 | 2 | H | CH$_2$Cl |
| F | CN | CH$_2$ | 1 | 2 | H | CH$_2$Br |
| F | CN | CH$_2$ | 1 | 2 | C(=O)CH$_3$ | CH$_2$Cl |
| F | CN | CH$_2$ | 1 | 2 | C(=O)CH$_3$ | CH$_2$Br |
| F | CN | CH$_2$ | 1 | 2 | CO$_2$CH$_3$ | CH$_2$Cl |
| F | CN | CH$_2$ | 1 | 2 | CO$_2$CH$_3$ | CH$_2$Br |
| F | CN | CH$_2$ | 1 | 2 | CH$_2$C≡CH | CH$_2$Cl |
| F | CN | CH$_2$ | 1 | 2 | CH$_2$C≡CH | CH$_2$Br |
| F | CN | CHF | 1 | 1 | H | CH$_2$Cl |
| F | CN | CHF | 1 | 1 | H | CH$_2$Br |
| F | CN | CHF | 1 | 1 | C(=O)CH$_3$ | CH$_2$Cl |
| F | CN | CHF | 1 | 1 | C(=O)CH$_3$ | CH$_2$Br |
| F | CN | CHF | 1 | 1 | CO$_2$CH$_3$ | CH$_2$Cl |
| F | CN | CHF | 1 | 1 | CO$_2$CH$_3$ | CH$_2$Br |
| F | CN | CHF | 1 | 1 | CH$_2$C≡CH | CH$_2$Cl |
| F | CN | CHF | 1 | 1 | CH$_2$C≡CH | CH$_2$Br |
| F | CN | CHF | 1 | 2 | H | CH$_2$Cl |
| F | CN | CHF | 1 | 2 | H | CH$_2$Br |
| F | CN | CHF | 1 | 2 | C(=O)CH$_3$ | CH$_2$Cl |
| F | CN | CHF | 1 | 2 | C(=O)CH$_3$ | CH$_2$Br |
| F | CN | CHF | 1 | 2 | CO$_2$CH$_3$ | CH$_2$Cl |
| F | CN | CHF | 1 | 2 | CO$_2$CH$_3$ | CH$_2$Br |
| F | CN | CHF | 1 | 2 | CH$_2$C≡CH | CH$_2$Cl |
| F | CN | CHF | 1 | 2 | CH$_2$C≡CH | CH$_2$Br |
| F | CN | CHCl | 1 | 1 | H | CH$_2$Cl |
| F | CN | CHCl | 1 | 1 | H | CH$_2$Br |
| F | CN | CHCl | 1 | 1 | C(=O)CH$_3$ | CH$_2$Cl |
| F | CN | CHCl | 1 | 1 | C(=O)CH$_3$ | CH$_2$Br |
| F | CN | CHCl | 1 | 1 | CO$_2$CH$_3$ | CH$_2$Cl |
| F | CN | CHCl | 1 | 1 | CO$_2$CH$_3$ | CH$_2$Br |
| F | CN | CHCl | 1 | 1 | CH$_2$C≡CH | CH$_2$Cl |
| F | CN | CHCl | 1 | 1 | CH$_2$C≡CH | CH$_2$Br |
| F | CN | CHCl | 1 | 2 | H | CH$_2$Cl |
| F | CN | CHCl | 1 | 2 | H | CH$_2$Br |
| F | CN | CHCl | 1 | 2 | C(=O)CH$_3$ | CH$_2$Cl |
| F | CN | CHCl | 1 | 2 | C(=O)CH$_3$ | CH$_2$Br |
| F | CN | CHCl | 1 | 2 | CO$_2$CH$_3$ | CH$_2$Cl |
| F | CN | CHCl | 1 | 2 | CO$_2$CH$_3$ | CH$_2$Br |
| F | CN | CHCl | 1 | 2 | CH$_2$C≡CH | CH$_2$Cl |
| F | CN | CHCl | 1 | 2 | CH$_2$C≡CH | CH$_2$Br |
| Cl | H | CH$_2$ | 1 | 1 | H | CH$_2$Cl |
| Cl | H | CH$_2$ | 1 | 1 | H | CH$_2$Br |
| Cl | H | CH$_2$ | 1 | 2 | H | CH$_2$Cl |
| Cl | H | CH$_2$ | 1 | 2 | H | CH$_2$Br |
| Cl | H | CHF | 1 | 1 | H | CH$_2$Cl |
| Cl | H | CHF | 1 | 1 | H | CH$_2$Br |
| Cl | H | CHF | 1 | 2 | H | CH$_2$Cl |
| Cl | H | CHF | 1 | 2 | H | CH$_2$Br |
| Cl | H | CHCl | 1 | 1 | H | CH$_2$Cl |
| Cl | H | CHCl | 1 | 1 | H | CH$_2$Br |
| Cl | H | CHCl | 1 | 2 | H | CH$_2$Cl |
| Cl | H | CHCl | 1 | 2 | H | CH$_2$Br |
| Cl | Cl | CH$_2$ | 1 | 1 | H | CH$_2$Cl |
| Cl | Cl | CH$_2$ | 1 | 1 | H | CH$_2$Br |
| Cl | Cl | CH$_2$ | 1 | 1 | C(=O)CH$_3$ | CH$_2$Cl |
| Cl | Cl | CH$_2$ | 1 | 1 | C(=O)CH$_3$ | CH$_2$Br |
| Cl | Cl | CH$_2$ | 1 | 1 | CO$_2$CH$_3$ | CH$_2$Cl |
| Cl | Cl | CH$_2$ | 1 | 1 | CO$_2$CH$_3$ | CH$_2$Br |
| Cl | Cl | CH$_2$ | 1 | 1 | CH$_2$C≡CH | CH$_2$Cl |
| Cl | Cl | CH$_2$ | 1 | 1 | CH$_2$C≡CH | CH$_2$Br |
| Cl | Cl | CH$_2$ | 1 | 2 | H | CH$_2$Cl |
| Cl | Cl | CH$_2$ | 1 | 2 | H | CH$_2$Br |
| Cl | Cl | CH$_2$ | 1 | 2 | C(=O)CH$_3$ | CH$_2$Cl |
| Cl | Cl | CH$_2$ | 1 | 2 | C(=O)CH$_3$ | CH$_2$Br |
| Cl | Cl | CH$_2$ | 1 | 2 | CO$_2$CH$_3$ | CH$_2$Cl |
| Cl | Cl | CH$_2$ | 1 | 2 | CO$_2$CH$_3$ | CH$_2$Br |

TABLE 1-continued

| X | Y | Z | n | m | R¹ | R² |
|---|---|---|---|---|---|---|
| Cl | Cl | CH₂ | 1 | 2 | CH₂C≡CH | CH₂Cl |
| Cl | Cl | CH₂ | 1 | 2 | CH₂C≡CH | CH₂Br |
| Cl | Cl | CHF | 1 | 1 | H | CH₂Cl |
| Cl | Cl | CHF | 1 | 1 | H | CH₂Br |
| Cl | Cl | CHF | 1 | 1 | C(=O)CH₃ | CH₂Cl |
| Cl | Cl | CHF | 1 | 1 | C(=O)CH₃ | CH₂Br |
| Cl | Cl | CHF | 1 | 1 | CO₂CH₃ | CH₂Cl |
| Cl | Cl | CHF | 1 | 1 | CO₂CH₃ | CH₂Br |
| Cl | Cl | CHF | 1 | 1 | CH₂C≡CH | CH₂Cl |
| Cl | Cl | CHF | 1 | 1 | CH₂C≡CH | CH₂Br |
| Cl | Cl | CHF | 1 | 2 | H | CH₂Cl |
| Cl | Cl | CHF | 1 | 2 | H | CH₂Br |
| Cl | Cl | CHF | 1 | 2 | C(=O)CH₃ | CH₂Cl |
| Cl | Cl | CHF | 1 | 2 | C(=O)CH₃ | CH₂Br |
| Cl | Cl | CHF | 1 | 2 | CO₂CH₃ | CH₂Cl |
| Cl | Cl | CHF | 1 | 2 | CO₂CH₃ | CH₂Br |
| Cl | Cl | CHF | 1 | 2 | CH₂C≡CH | CH₂Cl |
| Cl | Cl | CHF | 1 | 2 | CH₂C≡CH | CH₂Br |
| Cl | Cl | CHCl | 1 | 1 | H | CH₂Cl |
| Cl | Cl | CHCl | 1 | 1 | H | CH₂Br |
| Cl | Cl | CHCl | 1 | 1 | C(=O)CH₃ | CH₂Cl |
| Cl | Cl | CHCl | 1 | 1 | C(=O)CH₃ | CH₂Br |
| Cl | Cl | CHCl | 1 | 1 | CO₂CH₃ | CH₂Cl |
| Cl | Cl | CHCl | 1 | 1 | CO₂CH₃ | CH₂Br |
| Cl | Cl | CHCl | 1 | 1 | CH₂C≡CH | CH₂Cl |
| Cl | Cl | CHCl | 1 | 1 | CH₂C≡CH | CH₂Br |
| Cl | Cl | CHCl | 1 | 2 | H | CH₂Cl |
| Cl | Cl | CHCl | 1 | 2 | H | CH₂Br |
| Cl | Cl | CHCl | 1 | 2 | C(=O)CH₃ | CH₂Cl |
| Cl | Cl | CHCl | 1 | 2 | C(=O)CH₃ | CH₂Br |
| Cl | Cl | CHCl | 1 | 2 | CO₂CH₃ | CH₂Cl |
| Cl | Cl | CHCl | 1 | 2 | CO₂CH₃ | CH₂Br |
| Cl | Cl | CHCl | 1 | 2 | CH₂C≡CH | CH₂Cl |
| Cl | Cl | CHCl | 1 | 2 | CH₂C≡CH | CH₂Br |
| Cl | Br | CH₂ | 1 | 1 | H | CH₂Cl |
| Cl | Br | CH₂ | 1 | 1 | H | CH₂Br |
| Cl | Br | CH₂ | 1 | 1 | C(=O)CH₃ | CH₂Cl |
| Cl | Br | CH₂ | 1 | 1 | C(=O)CH₃ | CH₂Br |
| Cl | Br | CH₂ | 1 | 1 | CO₂CH₃ | CH₂Cl |
| Cl | Br | CH₂ | 1 | 1 | CO₂CH₃ | CH₂Br |
| Cl | Br | CH₂ | 1 | 1 | CH₂C≡CH | CH₂Cl |
| Cl | Br | CH₂ | 1 | 1 | CH₂C≡CH | CH₂Br |
| Cl | Br | CH₂ | 1 | 2 | H | CH₂Cl |
| Cl | Br | CH₂ | 1 | 2 | H | CH₂Br |
| Cl | Br | CH₂ | 1 | 2 | C(=O)CH₃ | CH₂Cl |
| Cl | Br | CH₂ | 1 | 2 | C(=O)CH₃ | CH₂Br |
| Cl | Br | CH₂ | 1 | 2 | CO₂CH₃ | CH₂Cl |
| Cl | Br | CH₂ | 1 | 2 | CO₂CH₃ | CH₂Br |
| Cl | Br | CH₂ | 1 | 2 | CH₂C≡CH | CH₂Cl |
| Cl | Br | CH₂ | 1 | 2 | CH₂C≡CH | CH₂Br |
| Cl | Br | CHF | 1 | 1 | H | CH₂Cl |
| Cl | Br | CHF | 1 | 1 | H | CH₂Br |
| Cl | Br | CHF | 1 | 1 | C(=O)CH₃ | CH₂Cl |
| Cl | Br | CHF | 1 | 1 | C(=O)CH₃ | CH₂Br |
| Cl | Br | CHF | 1 | 1 | CO₂CH₃ | CH₂Cl |
| Cl | Br | CHF | 1 | 1 | CO₂CH₃ | CH₂Br |
| Cl | Br | CHF | 1 | 1 | CH₂C≡CH | CH₂Cl |
| Cl | Br | CHF | 1 | 1 | CH₂C≡CH | CH₂Br |
| Cl | Br | CHF | 1 | 2 | H | CH₂Cl |
| Cl | Br | CHF | 2 | 2 | H | CH₂Br |
| Cl | Br | CHF | 1 | 2 | C(=O)CH₃ | CH₂Cl |
| Cl | Br | CHF | 1 | 2 | C(=O)CH₃ | CH₂Br |
| Cl | Br | CHF | 1 | 2 | CO₂CH₃ | CH₂Cl |
| Cl | Br | CHF | 1 | 2 | CO₂CH₃ | CH₂Br |
| Cl | Br | CHF | 1 | 2 | CH₂C≡CH | CH₂Cl |
| Cl | Br | CHF | 1 | 2 | CH₂C≡CH | CH₂Br |
| Cl | Br | CHCl | 1 | 1 | H | CH₂Cl |
| Cl | Br | CHCl | 1 | 1 | H | CH₂Br |
| Cl | Br | CHCl | 1 | 1 | C(=O)CH₃ | CH₂Cl |
| Cl | Br | CHCl | 1 | 1 | C(=O)CH₃ | CH₂Br |
| Cl | Br | CHCl | 1 | 1 | CO₂CH₃ | CH₂Cl |
| Cl | Br | CHCl | 1 | 1 | CO₂CH₃ | CH₂Br |
| Cl | Br | CHCl | 1 | 1 | CH₂C≡CH | CH₂Cl |
| Cl | Br | CHCl | 1 | 1 | CH₂C≡CH | CH₂Br |
| Cl | Br | CHCl | 1 | 2 | H | CH₂Cl |
| Cl | Br | CHCl | 1 | 2 | H | CH₂Br |
| Cl | Br | CHCl | 1 | 2 | C(=O)CH₃ | CH₂Cl |
| Cl | Br | CHCl | 1 | 2 | C(=O)CH₃ | CH₂Br |
| Cl | Br | CHCl | 1 | 2 | CO₂CH₃ | CH₂Cl |
| Cl | Br | CHCl | 1 | 2 | CO₂CH₃ | CH₂Br |
| Cl | Br | CHCl | 1 | 2 | CH₂C≡CH | CH₂Cl |
| Cl | Br | CHCl | 1 | 2 | CH₂C≡CH | CH₂Br |
| Cl | CN | CH₂ | 1 | 1 | H | CH₂Cl |
| Cl | CN | CH₂ | 1 | 1 | H | CH₂Br |
| Cl | CN | CH₂ | 1 | 1 | C(=O)CH₃ | CH₂Cl |
| Cl | CN | CH₂ | 1 | 1 | C(=O)CH₃ | CH₂Br |
| Cl | CN | CH₂ | 1 | 1 | CO₂CH₃ | CH₂Cl |
| Cl | CN | CH₂ | 1 | 1 | CO₂CH₃ | CH₂Br |
| Cl | CN | CH₂ | 1 | 1 | CH₂C≡CH | CH₂Cl |
| Cl | CN | CH₂ | 1 | 1 | CH₂C≡CH | CH₂Br |
| Cl | CN | CH₂ | 1 | 2 | H | CH₂Cl |
| Cl | CN | CH₂ | 1 | 2 | H | CH₂Br |
| Cl | CN | CH₂ | 1 | 2 | C(=O)CH₃ | CH₂Cl |
| Cl | CN | CH₂ | 1 | 2 | C(=O)CH₃ | CH₂Br |
| Cl | CN | CH₂ | 1 | 2 | CO₂CH₃ | CH₂Cl |
| Cl | CN | CH₂ | 1 | 2 | CO₂CH₃ | CH₂Br |
| Cl | CN | CH₂ | 1 | 2 | CH₂C≡CH | CH₂Cl |
| Cl | CN | CH₂ | 1 | 2 | CH₂C≡CH | CH₂Br |
| Cl | CN | CHF | 1 | 1 | H | CH₂Cl |
| Cl | CN | CHF | 1 | 1 | H | CH₂Br |
| Cl | CN | CHF | 1 | 1 | C(=O)CH₃ | CH₂Cl |
| Cl | CN | CHF | 1 | 1 | C(=O)CH₃ | CH₂Br |
| Cl | CN | CHF | 1 | 1 | CO₂CH₃ | CH₂Cl |
| Cl | CN | CHF | 1 | 1 | CO₂CH₃ | CH₂Br |
| Cl | CN | CHF | 1 | 1 | CH₂C≡CH | CH₂Cl |
| Cl | CN | CHF | 1 | 1 | CH₂C≡CH | CH₂Br |
| Cl | CN | CHF | 1 | 2 | H | CH₂Cl |
| Cl | CN | CHF | 1 | 2 | H | CH₂Br |
| Cl | CN | CHF | 1 | 2 | C(=O)CH₃ | CH₂Cl |
| Cl | CN | CHF | 1 | 2 | C(=O)CH₃ | CH₂Br |
| Cl | CN | CHF | 1 | 2 | CO₂CH₃ | CH₂Cl |
| Cl | CN | CHF | 1 | 2 | CO₂CH₃ | CH₂Br |
| Cl | CN | CHF | 1 | 2 | CH₂C≡CH | CH₂Cl |
| Cl | CN | CHF | 1 | 2 | CH₂C≡CH | CH₂Br |
| Cl | CN | CHCl | 1 | 1 | H | CH₂Cl |
| Cl | CN | CHCl | 1 | 1 | H | CH₂Br |
| Cl | CN | CHCl | 1 | 1 | C(=O)CH₃ | CH₂Cl |
| Cl | CN | CHCl | 1 | 1 | C(=O)CH₃ | CH₂Br |
| Cl | CN | CHCl | 1 | 1 | CO₂CH₃ | CH₂Cl |
| Cl | CN | CHCl | 1 | 1 | CO₂CH₃ | CH₂Br |
| Cl | CN | CHCl | 1 | 1 | CH₂C≡CH | CH₂Cl |
| Cl | CN | CHCl | 1 | 1 | CH₂C≡CH | CH₂Br |
| Cl | CN | CHCl | 1 | 2 | H | CH₂Cl |
| Cl | CN | CHCl | 1 | 2 | H | CH₂Br |
| Cl | CN | CHCl | 1 | 2 | C(=O)CH₃ | CH₂Cl |
| Cl | CN | CHCl | 1 | 2 | C(=O)CH₃ | CH₂Br |
| Cl | CN | CHCl | 1 | 2 | CO₂CH₃ | CH₂Cl |
| Cl | CN | CHCl | 1 | 2 | CO₂CH₃ | CH₂Br |
| Cl | CN | CHCl | 1 | 2 | CH₂C≡CH | CH₂Cl |
| Cl | CN | CHCl | 1 | 2 | CH₂C≡CH | CH₂Br |

| J = 11 and R²¹ = Br | | | | | | |
|---|---|---|---|---|---|---|
| X | Y | Z | n | m | R¹ | R² |
| F | H | CH₂ | 1 | 1 | H | CH₂Cl |
| F | H | CH₂ | 1 | 1 | H | CH₂Br |
| F | H | CH₂ | 1 | 2 | H | CH₂Cl |
| F | H | CH₂ | 1 | 2 | H | CH₂Br |
| F | H | CHF | 1 | 1 | H | CH₂Cl |
| F | H | CHF | 1 | 1 | H | CH₂Br |
| F | H | CHF | 1 | 2 | H | CH₂Cl |
| F | H | CHF | 1 | 2 | H | CH₂Br |
| F | H | CHCl | 1 | 1 | H | CH₂Cl |
| F | H | CHCl | 1 | 1 | H | CH₂Br |
| F | H | CHCl | 1 | 2 | H | CH₂Cl |
| F | H | CHCl | 1 | 2 | H | CH₂Br |
| F | Cl | CH₂ | 1 | 1 | H | CH₂Cl |
| F | Cl | CH₂ | 1 | 1 | H | CH₂Br |
| F | Cl | CH₂ | 1 | 1 | C(=O)CH₃ | CH₂Cl |
| F | Cl | CH₂ | 1 | 1 | C(=O)CH₃ | CH₂Br |
| F | Cl | CH₂ | 1 | 1 | CO₂CH₃ | CH₂Cl |
| F | Cl | CH₂ | 1 | 1 | CO₂CH₃ | CH₂Br |
| F | Cl | CH₂ | 1 | 1 | CH₂C≡CH | CH₂Cl |
| F | Cl | CH₂ | 1 | 1 | CH₂C≡CH | CH₂Br |
| F | Cl | CH₂ | 1 | 2 | H | CH₂Cl |
| F | Cl | CH₂ | 1 | 2 | H | CH₂Br |
| F | Cl | CH₂ | 1 | 2 | C(=O)CH₃ | CH₂Cl |

TABLE 1-continued

| | | | | | | |
|---|---|---|---|---|---|---|
| F | Cl | CH$_2$ | 1 | 2 | C(=O)CH$_3$ | CH$_2$Br |
| F | Cl | CH$_2$ | 1 | 2 | CO$_2$CH$_3$ | CH$_2$Cl |
| F | Cl | CH$_2$ | 1 | 2 | CO$_2$CH$_3$ | CH$_2$Br |
| F | Cl | CH$_2$ | 1 | 2 | CH$_2$C≡CH | CH$_2$Cl |
| F | Cl | CH$_2$ | 1 | 2 | CH$_2$C≡CH | CH$_2$Br |
| F | Cl | CHF | 1 | 1 | H | CH$_2$Cl |
| F | Cl | CHF | 1 | 1 | H | CH$_2$Br |
| F | Cl | CHF | 1 | 1 | C(=O)CH$_3$ | CH$_2$Cl |
| F | Cl | CHF | 1 | 1 | C(=O)CH$_3$ | CH$_2$Br |
| F | Cl | CHF | 1 | 1 | CO$_2$CH$_3$ | CH$_2$Cl |
| F | Cl | CHF | 1 | 1 | CO$_2$CH$_3$ | CH$_2$Br |
| F | Cl | CHF | 1 | 1 | CH$_2$C≡CH | CH$_2$Cl |
| F | Cl | CHF | 1 | 1 | CH$_2$C≡CH | CH$_2$Br |
| F | Cl | CHF | 1 | 2 | H | CH$_2$Cl |
| F | Cl | CHF | 1 | 2 | H | CH$_2$Br |
| F | Cl | CHF | 1 | 2 | C(=O)CH$_3$ | CH$_2$Cl |
| F | Cl | CHF | 1 | 2 | C(=O)CH$_3$ | CH$_2$Br |
| F | Cl | CHF | 1 | 2 | CO$_2$CH$_3$ | CH$_2$Cl |
| F | Cl | CHF | 1 | 2 | CO$_2$CH$_3$ | CH$_2$Br |
| F | Cl | CHF | 1 | 2 | CH$_2$C≡CH | CH$_2$Cl |
| F | Cl | CHF | 1 | 2 | CH$_2$C≡CH | CH$_2$Br |
| F | Cl | CHCl | 1 | 1 | H | CH$_2$Cl |
| F | Cl | CHCl | 1 | 1 | H | CH$_2$Br |
| F | Cl | CHCl | 1 | 1 | C(=O)CH$_3$ | CH$_2$Cl |
| F | Cl | CHCl | 1 | 1 | C(=O)CH$_3$ | CH$_2$Br |
| F | Cl | CHCl | 1 | 1 | CO$_2$CH$_3$ | CH$_2$Cl |
| F | Cl | CHCl | 1 | 1 | CO$_2$CH$_3$ | CH$_2$Br |
| F | Cl | CHCl | 1 | 1 | CH$_2$C≡CH | CH$_2$Cl |
| F | Cl | CHCl | 1 | 1 | CH$_2$C≡CH | CH$_2$Br |
| F | Cl | CHCl | 1 | 2 | H | CH$_2$Cl |
| F | Cl | CHCl | 1 | 2 | H | CH$_2$Br |
| F | Cl | CHCl | 1 | 2 | C(=O)CH$_3$ | CH$_2$Cl |
| F | Cl | CHCl | 1 | 2 | C(=O)CH$_3$ | CH$_2$Br |
| F | Cl | CHCl | 1 | 2 | CO$_2$CH$_3$ | CH$_2$Cl |
| F | Cl | CHCl | 1 | 2 | CO$_2$CH$_3$ | CH$_2$Br |
| F | Cl | CHCl | 1 | 2 | CH$_2$C≡CH | CH$_2$Cl |
| F | Cl | CHCl | 1 | 2 | CH$_2$C≡CH | CH$_2$Br |
| F | Br | CH$_2$ | 1 | 1 | H | CH$_2$Cl |
| F | Br | CH$_2$ | 1 | 1 | H | CH$_2$Br |
| F | Br | CH$_2$ | 1 | 1 | C(=O)CH$_3$ | CH$_2$Cl |
| F | Br | CH$_2$ | 1 | 1 | C(=O)CH$_3$ | CH$_2$Br |
| F | Br | CH$_2$ | 1 | 1 | CO$_2$CH$_3$ | CH$_2$Cl |
| F | Br | CH$_2$ | 1 | 1 | CO$_2$CH$_3$ | CH$_2$Br |
| F | Br | CH$_2$ | 1 | 1 | CH$_2$C≡CH | CH$_2$Cl |
| F | Br | CH$_2$ | 1 | 1 | CH$_2$C≡CH | CH$_2$Br |
| F | Br | CH$_2$ | 1 | 2 | H | CH$_2$Cl |
| F | Br | CH$_2$ | 1 | 2 | H | CH$_2$Br |
| F | Br | CH$_2$ | 1 | 2 | C(=O)CH$_3$ | CH$_2$Cl |
| F | Br | CH$_2$ | 1 | 2 | C(=O)CH$_3$ | CH$_2$Br |
| F | Br | CH$_2$ | 1 | 2 | CO$_2$CH$_3$ | CH$_2$Cl |
| F | Br | CH$_2$ | 1 | 2 | CO$_2$CH$_3$ | CH$_2$Br |
| F | Br | CH$_2$ | 1 | 2 | CH$_2$C≡CH | CH$_2$Cl |
| F | Br | CH$_2$ | 1 | 2 | CH$_2$C≡CH | CH$_2$Br |
| F | Br | CHF | 1 | 1 | H | CH$_2$Cl |
| F | Br | CHF | 1 | 1 | H | CH$_2$Br |
| F | Br | CHF | 1 | 1 | C(=O)CH$_3$ | CH$_2$Cl |
| F | Br | CHF | 1 | 1 | C(=O)CH$_3$ | CH$_2$Br |
| F | Br | CHF | 1 | 1 | CO$_2$CH$_3$ | CH$_2$Cl |
| F | Br | CHF | 1 | 1 | CO$_2$CH$_3$ | CH$_2$Br |
| F | Br | CHF | 1 | 1 | CH$_2$=CH | CH$_2$Cl |
| F | Br | CHF | 1 | 1 | CH$_2$=CH | CH$_2$Br |
| F | Br | CHF | 1 | 2 | H | CH$_2$Cl |
| F | Br | CHF | 1 | 2 | H | CH$_2$Br |
| F | Br | CHF | 1 | 2 | C(=O)CH$_3$ | CH$_2$Cl |
| F | Br | CHF | 1 | 2 | C(=O)CH$_3$ | CH$_2$Br |
| F | Br | CHF | 1 | 2 | CO$_2$CH$_3$ | CH$_2$Cl |
| F | Br | CHF | 1 | 2 | CO$_2$CH$_3$ | CH$_2$Br |
| F | Br | CHF | 1 | 2 | CH$_2$C≡CH | CH$_2$Cl |
| F | Br | CHF | 1 | 2 | CH$_2$C≡CH | CH$_2$Br |
| F | Br | CHCl | 1 | 1 | H | CH$_2$Cl |
| F | Br | CHCl | 1 | 1 | H | CH$_2$Br |
| F | Br | CHCl | 1 | 1 | C(=O)CH$_3$ | CH$_2$Cl |
| F | Br | CHCl | 1 | 1 | C(=O)CH$_3$ | CH$_2$Br |
| F | Br | CHCl | 1 | 1 | CO$_2$CH$_3$ | CH$_2$Cl |
| F | Br | CHCl | 1 | 1 | CO$_2$CH$_3$ | CH$_2$Br |
| F | Br | CHCl | 1 | 1 | CH$_2$=CH | CH$_2$Cl |
| F | Br | CHCl | 1 | 1 | CH$_2$=CH | CH$_2$Br |
| F | Br | CHCl | 1 | 2 | H | CH$_2$Cl |
| F | Br | CHCl | 1 | 2 | H | CH$_2$Br |
| F | Br | CHCl | 1 | 2 | C(=O)CH$_3$ | CH$_2$Cl |
| F | Br | CHCl | 1 | 2 | C(=O)CH$_3$ | CH$_2$Br |
| F | Br | CHCl | 1 | 2 | CO$_2$CH$_3$ | CH$_2$Cl |
| F | Br | CHCl | 1 | 2 | CO$_2$CH$_3$ | CH$_2$Br |
| F | Br | CHCl | 1 | 2 | CH$_2$=CH | CH$_2$Cl |
| F | Br | CHCl | 1 | 2 | CH$_2$=CH | CH$_2$Br |
| F | CN | CH$_2$ | 1 | 1 | H | CH$_2$Cl |
| F | CN | CH$_2$ | 1 | 1 | H | CH$_2$Br |
| F | CN | CH$_2$ | 1 | 1 | C(=O)CH$_3$ | CH$_2$Cl |
| F | CN | CH$_2$ | 1 | 1 | C(=O)CH$_3$ | CH$_2$Br |
| F | CN | CH$_2$ | 1 | 1 | CO$_2$CH$_3$ | CH$_2$Cl |
| F | CN | CH$_2$ | 1 | 1 | CO$_2$CH$_3$ | CH$_2$Br |
| F | CN | CH$_2$ | 1 | 1 | CH$_2$=CH | CH$_2$Cl |
| F | CN | CH$_2$ | 1 | 1 | CH$_2$=CH | CH$_2$Br |
| F | CN | CH$_2$ | 1 | 2 | H | CH$_2$Cl |
| F | CN | CH$_2$ | 1 | 2 | H | CH$_2$Br |
| F | CN | CH$_2$ | 1 | 2 | C(=O)CH$_3$ | CH$_2$Cl |
| F | CN | CH$_2$ | 1 | 2 | C(=O)CH$_3$ | CH$_2$Br |
| F | CN | CH$_2$ | 1 | 2 | CO$_2$CH$_3$ | CH$_2$Cl |
| F | CN | CH$_2$ | 1 | 2 | CO$_2$CH$_3$ | CH$_2$Br |
| F | CN | CH$_2$ | 1 | 2 | CH$_2$C≡CH | CH$_2$Cl |
| F | CN | CH$_2$ | 1 | 2 | CH$_2$C≡CH | CH$_2$Br |
| F | CN | CHF | 1 | 1 | H | CH$_2$Cl |
| F | CN | CHF | 1 | 1 | H | CH$_2$Br |
| F | CN | CHF | 1 | 1 | C(=O)CH$_3$ | CH$_2$Cl |
| F | CN | CHF | 1 | 1 | C(=O)CH$_3$ | CH$_2$Br |
| F | CN | CHF | 1 | 1 | CO$_2$CH$_3$ | CH$_2$Cl |
| F | CN | CHF | 1 | 1 | CO$_2$CH$_3$ | CH$_2$Br |
| F | CN | CHF | 1 | 1 | CH$_2$C≡CH | CH$_2$Cl |
| F | CN | CHF | 1 | 1 | CH$_2$C≡CH | CH$_2$Br |
| F | CN | CHF | 1 | 2 | H | CH$_2$Cl |
| F | CN | CHF | 1 | 2 | H | CH$_2$Br |
| F | CN | CHF | 1 | 2 | C(=O)CH$_3$ | CH$_2$Cl |
| F | CN | CHF | 1 | 2 | C(=O)CH$_3$ | CH$_2$Br |
| F | CN | CHF | 1 | 2 | CO$_2$CH$_3$ | CH$_2$Cl |
| F | CN | CHF | 1 | 2 | CO$_2$CH$_3$ | CH$_2$Br |
| F | CN | CHF | 1 | 2 | CH$_2$C≡CH | CH$_2$Cl |
| F | CN | CHF | 1 | 2 | CH$_2$C≡CH | CH$_2$Br |
| F | CN | CHCl | 1 | 1 | H | CH$_2$Cl |
| F | CN | CHCl | 1 | 1 | H | CH$_2$Br |
| F | CN | CHCl | 1 | 1 | C(=O)CH$_3$ | CH$_2$Cl |
| F | CN | CHCl | 1 | 1 | C(=O)CH$_3$ | CH$_2$Br |
| F | CN | CHCl | 1 | 1 | CO$_2$CH$_3$ | CH$_2$Cl |
| F | CN | CHCl | 1 | 1 | CO$_2$CH$_3$ | CH$_2$Br |
| F | CN | CHCl | 1 | 1 | CH$_2$C≡CH | CH$_2$Cl |
| F | CN | CHCl | 1 | 1 | CH$_2$C≡CH | CH$_2$Br |
| F | CN | CHCl | 1 | 2 | H | CH$_2$Cl |
| F | CN | CHCl | 1 | 2 | H | CH$_2$Br |
| F | CN | CHCl | 1 | 2 | C(=O)CH$_3$ | CH$_2$Cl |
| F | CN | CHCl | 1 | 2 | C(=O)CH$_3$ | CH$_2$Br |
| F | CN | CHCl | 1 | 2 | CO$_2$CH$_3$ | CH$_2$Cl |
| F | CN | CHCl | 1 | 2 | CO$_2$CH$_3$ | CH$_2$Br |
| F | CN | CHCl | 1 | 2 | CH$_2$C≡CH | CH$_2$Cl |
| F | CN | CHCl | 1 | 2 | CH$_2$C≡CH | CH$_2$Br |
| Cl | H | CH$_2$ | 1 | 1 | H | CH$_2$Cl |
| Cl | H | CH$_2$ | 1 | 1 | H | CH$_2$Br |
| Cl | H | CH$_2$ | 1 | 2 | H | CH$_2$Cl |
| Cl | H | CH$_2$ | 1 | 2 | H | CH$_2$Br |
| Cl | H | CHF | 1 | 1 | H | CH$_2$Cl |
| Cl | H | CHF | 1 | 1 | H | CH$_2$Br |
| Cl | H | CHF | 1 | 2 | H | CH$_2$Cl |
| Cl | H | CHF | 1 | 2 | H | CH$_2$Br |
| Cl | H | CHCl | 1 | 1 | H | CH$_2$Cl |
| Cl | H | CHCl | 1 | 1 | H | CH$_2$Br |
| Cl | H | CHCl | 1 | 2 | H | CH$_2$Cl |
| Cl | H | CHCl | 1 | 2 | H | CH$_2$Br |
| Cl | Cl | CH$_2$ | 1 | 1 | H | CH$_2$Cl |
| Cl | Cl | CH$_2$ | 1 | 1 | H | CH$_2$Br |
| Cl | Cl | CH$_2$ | 1 | 1 | C(=O)CH$_3$ | CH$_2$Cl |
| Cl | Cl | CH$_2$ | 1 | 1 | C(=O)CH$_3$ | CH$_2$Br |
| Cl | Cl | CH$_2$ | 1 | 1 | CO$_2$CH$_3$ | CH$_2$Cl |
| Cl | Cl | CH$_2$ | 1 | 1 | CO$_2$CH$_3$ | CH$_2$Br |
| Cl | Cl | CH$_2$ | 1 | 1 | CH$_2$C≡CH | CH$_2$Cl |
| Cl | Cl | CH$_2$ | 1 | 1 | CH$_2$C≡CH | CH$_2$Br |
| Cl | Cl | CH$_2$ | 1 | 2 | H | CH$_2$Cl |
| Cl | Cl | CH$_2$ | 1 | 2 | H | CH$_2$Br |
| Cl | Cl | CH$_2$ | 1 | 2 | C(=O)CH$_3$ | CH$_2$Cl |
| Cl | Cl | CH$_2$ | 1 | 2 | C(=O)CH$_3$ | CH$_2$Br |
| Cl | Cl | CH$_2$ | 1 | 2 | CO$_2$CH$_3$ | CH$_2$Cl |

TABLE 1-continued

| | | | | | | |
|---|---|---|---|---|---|---|
| Cl | Cl | CH$_2$ | 1 | 2 | CO$_2$CH$_3$ | CH$_2$Br |
| Cl | Cl | CH$_2$ | 1 | 2 | CH$_2$C≡CH | CH$_2$Cl |
| Cl | Cl | CH$_2$ | 1 | 2 | CH$_2$C≡CH | CH$_2$Br |
| Cl | Cl | CHF | 1 | 1 | H | CH$_2$Cl |
| Cl | Cl | CHF | 1 | 1 | H | CH$_2$Br |
| Cl | Cl | CHF | 1 | 1 | C(=O)CH$_3$ | CH$_2$Cl |
| Cl | Cl | CHF | 1 | 1 | C(=O)CH$_3$ | CH$_2$Br |
| Cl | Cl | CHF | 1 | 1 | CO$_2$CH$_3$ | CH$_2$Cl |
| Cl | Cl | CHF | 1 | 1 | CO$_2$CH$_3$ | CH$_2$Br |
| Cl | Cl | CHF | 1 | 1 | CH$_2$C≡CH | CH$_2$Cl |
| Cl | Cl | CHF | 1 | 1 | CH$_2$C≡CH | CH$_2$Br |
| Cl | Cl | CHF | 1 | 2 | H | CH$_2$Cl |
| Cl | Cl | CHF | 1 | 2 | H | CH$_2$Br |
| Cl | Cl | CHF | 1 | 2 | C(=O)CH$_3$ | CH$_2$Cl |
| Cl | Cl | CHF | 1 | 2 | C(=O)CH$_3$ | CH$_2$Br |
| Cl | Cl | CHF | 1 | 2 | CO$_2$CH$_3$ | CH$_2$Cl |
| Cl | Cl | CHF | 1 | 2 | CO$_2$CH$_3$ | CH$_2$Br |
| Cl | Cl | CHF | 1 | 2 | CH$_2$C≡CH | CH$_2$Cl |
| Cl | Cl | CHF | 1 | 2 | CH$_2$C≡CH | CH$_2$Br |
| Cl | Cl | CHCl | 1 | 1 | H | CH$_2$Cl |
| Cl | Cl | CHCl | 1 | 1 | H | CH$_2$Br |
| Cl | Cl | CHCl | 1 | 1 | C(=O)CH$_3$ | CH$_2$Cl |
| Cl | Cl | CHCl | 1 | 1 | C(=O)CH$_3$ | CH$_2$Br |
| Cl | Cl | CHCl | 1 | 1 | CO$_2$CH$_3$ | CH$_2$Cl |
| Cl | Cl | CHCl | 1 | 1 | CO$_2$CH$_3$ | CH$_2$Br |
| Cl | Cl | CHCl | 1 | 1 | CH$_2$C≡CH | CH$_2$Cl |
| Cl | Cl | CHCl | 1 | 1 | CH$_2$C≡CH | CH$_2$Br |
| Cl | Cl | CHCl | 1 | 2 | H | CH$_2$Cl |
| Cl | Cl | CHCl | 1 | 2 | H | CH$_2$Br |
| Cl | Cl | CHCl | 1 | 2 | C(=O)CH$_3$ | CH$_2$Cl |
| Cl | Cl | CHCl | 1 | 2 | C(=O)CH$_3$ | CH$_2$Br |
| Cl | Cl | CHCl | 1 | 2 | CO$_2$CH$_3$ | CH$_2$Cl |
| Cl | Cl | CHCl | 1 | 2 | CO$_2$CH$_3$ | CH$_2$Br |
| Cl | Cl | CHCl | 1 | 2 | CH$_2$C≡CH | CH$_2$Cl |
| Cl | Cl | CHCl | 1 | 2 | CH$_2$C≡CH | CH$_2$Br |
| Cl | Br | CH$_2$ | 1 | 1 | H | CH$_2$Cl |
| Cl | Br | CH$_2$ | 1 | 1 | H | CH$_2$Br |
| Cl | Br | CH$_2$ | 1 | 1 | C(=O)CH$_3$ | CH$_2$Cl |
| Cl | Br | CH$_2$ | 1 | 1 | C(=O)CH$_3$ | CH$_2$Br |
| Cl | Br | CH$_2$ | 1 | 1 | CO$_2$CH$_3$ | CH$_2$Cl |
| Cl | Br | CH$_2$ | 1 | 1 | CO$_2$CH$_3$ | CH$_2$Br |
| Cl | Br | CH$_2$ | 1 | 1 | CH$_2$C≡CH | CH$_2$Cl |
| Cl | Br | CH$_2$ | 1 | 1 | CH$_2$C≡CH | CH$_2$Br |
| Cl | Br | CH$_2$ | 1 | 2 | H | CH$_2$Cl |
| Cl | Br | CH$_2$ | 1 | 2 | H | CH$_2$Br |
| Cl | Br | CH$_2$ | 1 | 2 | C(=O)CH$_3$ | CH$_2$Cl |
| Cl | Br | CH$_2$ | 1 | 2 | C(=O)CH$_3$ | CH$_2$Br |
| Cl | Br | CH$_2$ | 1 | 2 | CO$_2$CH$_3$ | CH$_2$Cl |
| Cl | Br | CH$_2$ | 1 | 2 | CO$_2$CH$_3$ | CH$_2$Br |
| Cl | Br | CH$_2$ | 1 | 2 | CH$_2$C≡CH | CH$_2$Cl |
| Cl | Br | CH$_2$ | 1 | 2 | CH$_2$C≡CH | CH$_2$Br |
| Cl | Br | CHF | 1 | 1 | H | CH$_2$Cl |
| Cl | Br | CHF | 1 | 1 | H | CH$_2$Br |
| Cl | Br | CHF | 1 | 1 | C(=O)CH$_3$ | CH$_2$Cl |
| Cl | Br | CHF | 1 | 1 | C(=O)CH$_3$ | CH$_2$Br |
| Cl | Br | CHF | 1 | 1 | CO$_2$CH$_3$ | CH$_2$Cl |
| Cl | Br | CHF | 1 | 1 | CO$_2$CH$_3$ | CH$_2$Br |
| Cl | Br | CHF | 1 | 1 | CH$_2$C≡CH | CH$_2$Cl |
| Cl | Br | CHF | 1 | 1 | CH$_2$C≡CH | CH$_2$Br |
| Cl | Br | CHF | 1 | 2 | H | CH$_2$Cl |
| Cl | Br | CHF | 1 | 2 | H | CH$_2$Br |
| Cl | Br | CHF | 1 | 2 | C(=O)CH$_3$ | CH$_2$Cl |
| Cl | Br | CHF | 1 | 2 | C(=O)CH$_3$ | CH$_2$Br |
| Cl | Br | CHF | 1 | 2 | CO$_2$CH$_3$ | CH$_2$Cl |
| Cl | Br | CHF | 1 | 2 | CO$_2$CH$_3$ | CH$_2$Br |
| Cl | Br | CHF | 1 | 2 | CH$_2$C≡CH | CH$_2$Cl |
| Cl | Br | CHF | 1 | 2 | CH$_2$C≡CH | CH$_2$Br |
| Cl | Br | CHCl | 1 | 1 | H | CH$_2$Cl |
| Cl | Br | CHCl | 1 | 1 | H | CH$_2$Br |
| Cl | Br | CHCl | 1 | 1 | C(=O)CH$_3$ | CH$_2$Cl |
| Cl | Br | CHCl | 1 | 1 | C(=O)CH$_3$ | CH$_2$Br |
| Cl | Br | CHCl | 1 | 1 | CO$_2$CH$_3$ | CH$_2$Cl |
| Cl | Br | CHCl | 1 | 1 | CO$_2$CH$_3$ | CH$_2$Br |
| Cl | Br | CHCl | 1 | 1 | CH$_2$C≡CH | CH$_2$Cl |
| Cl | Br | CHCl | 1 | 1 | CH$_2$C≡CH | CH$_2$Br |
| Cl | Br | CHCl | 1 | 2 | H | CH$_2$Cl |
| Cl | Br | CHCl | 1 | 2 | H | CH$_2$Br |
| Cl | Br | CHCl | 1 | 2 | C(=O)CH$_3$ | CH$_2$Cl |
| Cl | Br | CHCl | 1 | 2 | C(=O)CH$_3$ | CH$_2$Br |
| Cl | Br | CHCl | 1 | 2 | CO$_2$CH$_3$ | CH$_2$Cl |
| Cl | Br | CHCl | 1 | 2 | CO$_2$CH$_3$ | CH$_2$Br |
| Cl | Br | CHCl | 1 | 2 | CH$_2$C≡CH | CH$_2$Cl |
| Cl | Br | CHCl | 1 | 2 | CH$_2$C≡CH | CH$_2$Br |
| Cl | CN | CH$_2$ | 1 | 1 | H | CH$_2$Cl |
| Cl | CN | CH$_2$ | 1 | 1 | H | CH$_2$Br |
| Cl | CN | CH$_2$ | 1 | 1 | C(=O)CH$_3$ | CH$_2$Cl |
| Cl | CN | CH$_2$ | 1 | 1 | C(=O)CH$_3$ | CH$_2$Br |
| Cl | CN | CH$_2$ | 1 | 1 | CO$_2$CH$_3$ | CH$_2$Cl |
| Cl | CN | CH$_2$ | 1 | 1 | CO$_2$CH$_3$ | CH$_2$Br |
| Cl | CN | CH$_2$ | 1 | 1 | CH$_2$C≡CH | CH$_2$Cl |
| Cl | CN | CH$_2$ | 1 | 1 | CH$_2$C≡CH | CH$_2$Br |
| Cl | CN | CH$_2$ | 1 | 2 | H | CH$_2$Cl |
| Cl | CN | CH$_2$ | 1 | 2 | H | CH$_2$Br |
| Cl | CN | CH$_2$ | 1 | 2 | C(=O)CH$_3$ | CH$_2$Cl |
| Cl | CN | CH$_2$ | 1 | 2 | C(=O)CH$_3$ | CH$_2$Br |
| Cl | CN | CH$_2$ | 1 | 2 | CO$_2$CH$_3$ | CH$_2$Cl |
| Cl | CN | CH$_2$ | 1 | 2 | CO$_2$CH$_3$ | CH$_2$Br |
| Cl | CN | CH$_2$ | 1 | 2 | CH$_2$C≡CH | CH$_2$Cl |
| Cl | CN | CH$_2$ | 1 | 2 | CH$_2$C≡CH | CH$_2$Br |
| Cl | CN | CHF | 1 | 1 | H | CH$_2$Cl |
| Cl | CN | CHF | 1 | 1 | H | CH$_2$Br |
| Cl | CN | CHF | 1 | 1 | C(=O)CH$_3$ | CH$_2$Cl |
| Cl | CN | CHF | 1 | 1 | C(=O)CH$_3$ | CH$_2$Br |
| Cl | CN | CHF | 1 | 1 | CO$_2$CH$_3$ | CH$_2$Cl |
| Cl | CN | CHF | 1 | 1 | CO$_2$CH$_3$ | CH$_2$Br |
| Cl | CN | CHF | 1 | 1 | CH$_2$C≡CH | CH$_2$Cl |
| Cl | CN | CHF | 1 | 1 | CH$_2$C≡CH | CH$_2$Br |
| Cl | CN | CHF | 1 | 2 | H | CH$_2$Cl |
| Cl | CN | CHF | 1 | 2 | H | CH$_2$Br |
| Cl | CN | CHF | 1 | 2 | C(=O)CH$_3$ | CH$_2$Cl |
| Cl | CN | CHF | 1 | 2 | C(=O)CH$_3$ | CH$_2$Br |
| Cl | CN | CHF | 1 | 2 | CO$_2$CH$_3$ | CH$_2$Cl |
| Cl | CN | CHF | 1 | 2 | CO$_2$CH$_3$ | CH$_2$Br |
| Cl | CN | CHF | 1 | 2 | CH$_2$C≡CH | CH$_2$Cl |
| Cl | CN | CHF | 1 | 2 | CH$_2$C≡CH | CH$_2$Br |
| Cl | CN | CHCl | 1 | 1 | H | CH$_2$Cl |
| Cl | CN | CHCl | 1 | 1 | H | CH$_2$Br |
| Cl | CN | CHCl | 1 | 1 | C(=O)CH$_3$ | CH$_2$Cl |
| Cl | CN | CHCl | 1 | 1 | C(=O)CH$_3$ | CH$_2$Br |
| Cl | CN | CHCl | 1 | 1 | CO$_2$CH$_3$ | CH$_2$Cl |
| Cl | CN | CHCl | 1 | 1 | CO$_2$CH$_3$ | CH$_2$Br |
| Cl | CN | CHCl | 1 | 1 | CH$_2$C≡CH | CH$_2$Cl |
| Cl | CN | CHCl | 1 | 1 | CH$_2$C≡CH | CH$_2$Br |
| Cl | CN | CHCl | 1 | 2 | H | CH$_2$Cl |
| Cl | CN | CHCl | 1 | 2 | H | CH$_2$Br |
| Cl | CN | CHCl | 1 | 2 | C(=O)CH$_3$ | CH$_2$Cl |
| Cl | CN | CHCl | 1 | 2 | C(=O)CH$_3$ | CH$_2$Br |
| Cl | CN | CHCl | 1 | 2 | CO$_2$CH$_3$ | CH$_2$Cl |
| Cl | CN | CHCl | 1 | 2 | CO$_2$CH$_3$ | CH$_2$Br |
| Cl | CN | CHCl | 1 | 2 | CH$_2$C≡CH | CH$_2$Cl |
| Cl | CN | CHCl | 1 | 2 | CH$_2$C≡CH | CH$_2$Br |

J = 12, Y = Cl, and R$^2$ = CH$_2$Cl

| X | R$^1$ | Z | n | m | R$^{22}$ |
|---|---|---|---|---|---|
| F | H | CH$_2$ | 1 | 1 | CH$_3$ |
| F | C(=O)CH$_3$ | CH$_2$ | 1 | 1 | CH$_3$ |
| F | CO$_2$CH$_3$ | CH$_2$ | 1 | 1 | CH$_3$ |
| F | H | CHF | 1 | 1 | CH$_3$ |
| F | C(=O)CH$_3$ | CHF | 1 | 1 | CH$_3$ |
| F | CO$_2$CH$_3$ | CHF | 1 | 1 | CH$_3$ |
| F | H | CH$_2$ | 1 | 2 | CH$_3$ |
| F | C(=O)CH$_3$ | CH$_2$ | 1 | 2 | CH$_3$ |
| F | CO$_2$CH$_3$ | CH$_2$ | 1 | 2 | CH$_3$ |
| F | H | CHF | 1 | 2 | CH$_3$ |
| F | C(=O)CH$_3$ | CHF | 1 | 2 | CH$_3$ |
| F | CO$_2$CH$_3$ | CHF | 1 | 2 | CH$_3$ |
| Cl | H | CH$_2$ | 1 | 1 | CH$_3$ |
| Cl | C(=O)CH$_3$ | CH$_2$ | 1 | 1 | CH$_3$ |
| Cl | CO$_2$CH$_3$ | CH$_2$ | 1 | 1 | CH$_3$ |
| Cl | H | CHF | 1 | 1 | CH$_3$ |
| Cl | C(=O)CH$_3$ | CHF | 1 | 1 | CH$_3$ |
| Cl | CO$_2$CH$_3$ | CHF | 1 | 1 | CH$_3$ |
| Cl | H | CH$_2$ | 1 | 2 | CH$_3$ |
| Cl | C(=O)CH$_3$ | CH$_2$ | 1 | 2 | CH$_3$ |
| Cl | CO$_2$CH$_3$ | CH$_2$ | 1 | 2 | CH$_3$ |
| Cl | H | CHF | 1 | 2 | CH$_3$ |

TABLE 1-continued

| X | R¹ | Z¹ | n | m | R²¹ |
|---|---|---|---|---|---|
| Cl | C(=O)CH₃ | CHF | 1 | 2 | CH₃ |
| Cl | CO₂CH₃ | CHF | 1 | 2 | CH₃ |
| F | H | CH₂ | 1 | 1 | CH₂CH₃ |
| F | C(=O)CH₃ | CH₂ | 1 | 1 | CH₂CH₃ |
| F | CO₂CH₃ | CH₂ | 1 | 1 | CH₂CH₃ |
| F | H | CHF | 1 | 1 | CH₂CH₃ |
| F | C(=O)CH₃ | CHF | 1 | 1 | CH₂CH₃ |
| F | CO₂CH₃ | CHF | 1 | 1 | CH₂CH₃ |
| F | H | CH₂ | 1 | 2 | CH₂CH₃ |
| F | C(=O)CH₃ | CH₂ | 1 | 2 | CH₂CH₃ |
| F | CO₂CH₃ | CH₂ | 1 | 2 | CH₂CH₃ |
| F | H | CHF | 1 | 2 | CH₂CH₃ |
| F | C(=O)CH₃ | CHF | 1 | 2 | CH₂CH₃ |
| F | CO₂CH₃ | CHF | 1 | 2 | CH₂CH₃ |
| Cl | H | CH₂ | 1 | 1 | CH₂CH₃ |
| Cl | C(=O)CH₃ | CH₂ | 1 | 1 | CH₂CH₃ |
| Cl | CO₂CH₃ | CH₂ | 1 | 1 | CH₂CH₃ |
| Cl | H | CHF | 1 | 1 | CH₂CH₃ |
| Cl | C(=O)CH₃ | CHF | 1 | 1 | CH₂CH₃ |
| Cl | CO₂CH₃ | CHF | 1 | 1 | CH₂CH₃ |
| Cl | H | CH₂ | 1 | 2 | CH₂CH₃ |
| Cl | C(=O)CH₃ | CH₂ | 1 | 2 | CH₂CH₃ |
| Cl | CO₂CH₃ | CH₂ | 1 | 2 | CH₂CH₃ |
| Cl | H | CHF | 1 | 2 | CH₂CH₃ |
| Cl | C(=O)CH₃ | CHF | 1 | 2 | CH₂CH₃ |
| Cl | CO₂CH₃ | CHF | 1 | 2 | CH₂CH₃ |

$J = 13$, $Y = Cl$, and $R^2 = CH_2Cl$

| X | R¹ | Z¹ | n | m | R²¹ |
|---|---|---|---|---|---|
| F | H | CH₂ | 1 | 1 | Cl |
| F | C(=O)CH₃ | CH₂ | 1 | 1 | Cl |
| F | CO₂CH₃ | CH₂ | 1 | 1 | Cl |
| F | H | CHF | 1 | 1 | Cl |
| F | C(=O)CH₃ | CHF | 1 | 1 | Cl |
| F | CO₂CH₃ | CHF | 1 | 1 | Cl |
| F | H | CH₂ | 1 | 2 | Cl |
| F | C(=O)CH₃ | CH₂ | 1 | 2 | Cl |
| F | CO₂CH₃ | CH₂ | 1 | 2 | Cl |
| F | H | CHF | 1 | 2 | Cl |
| F | C(=O)CH₃ | CHF | 1 | 2 | Cl |
| F | CO₂CH₃ | CHF | 1 | 2 | Cl |
| Cl | H | CH₂ | 1 | 1 | Cl |
| Cl | C(=O)CH₃ | CH₂ | 1 | 1 | Cl |
| Cl | CO₂CH₃ | CH₂ | 1 | 1 | Cl |
| Cl | H | CHF | 1 | 1 | Cl |
| Cl | C(=O)CH₃ | CHF | 1 | 1 | Cl |
| Cl | CO₂CH₃ | CHF | 1 | 1 | Cl |
| Cl | H | CH₂ | 1 | 2 | Cl |
| Cl | C(=O)CH₃ | CH₂ | 1 | 2 | Cl |
| Cl | CO₂CH₃ | CH₂ | 1 | 2 | Cl |
| Cl | H | CHF | 1 | 2 | Cl |
| Cl | C(=O)CH₃ | CHF | 1 | 2 | Cl |
| Cl | CO₂CH₃ | CHF | 1 | 2 | Cl |
| F | H | CH₂ | 1 | 1 | Br |
| F | C(=O)CH₃ | CH₂ | 1 | 1 | Br |
| F | CO₂CH₃ | CH₂ | 1 | 1 | Br |
| F | H | CHF | 1 | 1 | Br |
| F | C(=O)CH₃ | CHF | 1 | 1 | Br |
| F | CO₂CH₃ | CHF | 1 | 1 | Br |
| F | H | CH₂ | 1 | 2 | Br |
| F | C(=O)CH₃ | CH₂ | 1 | 2 | Br |
| F | CO₂CH₃ | CH₂ | 1 | 2 | Br |
| F | H | CHF | 1 | 2 | Br |
| F | C(=O)CH₃ | CHF | 1 | 2 | Br |
| F | CO₂CH₃ | CHF | 1 | 2 | Br |
| Cl | H | CH₂ | 1 | 1 | Br |
| Cl | C(=O)CH₃ | CH₂ | 1 | 1 | Br |
| Cl | CO₂CH₃ | CH₂ | 1 | 1 | Br |
| Cl | H | CHF | 1 | 1 | Br |
| Cl | C(=O)CH₃ | CHF | 1 | 1 | Br |
| Cl | CO₂CH₃ | CHF | 1 | 1 | Br |
| Cl | H | CH₂ | 1 | 2 | Br |
| Cl | C(=O)CH₃ | CH₂ | 1 | 2 | Br |
| Cl | CO₂CH₃ | CH₂ | 1 | 2 | Br |
| Cl | H | CHF | 1 | 2 | Br |
| Cl | C(=O)CH₃ | CHF | 1 | 2 | Br |
| Cl | CO₂CH₃ | CHF | 1 | 2 | Br |

$J = 14$, $Y = Cl$, $R^2 = CH_2Cl$, and $R^{17} = R^{18} = CH_3$

| X | R¹ |
|---|---|
| F | H |
| F | C(=O)CH₃ |
| F | CO₂CH₃ |
| Cl | H |
| Cl | C(=O)CH₃ |
| Cl | CO₂CH₃ |

$J = 15$, $Y = Cl$, $R^2 = CH_2Cl$, and $R^{19} = CH_3$

| X | R¹ | R¹⁸ |
|---|---|---|
| F | H | CH₃ |
| F | C(=O)CH₃ | CH₃ |
| F | CO₂CH₃ | CH₃ |
| F | H | CF₃ |
| F | C(=O)CH₃ | CF₃ |
| F | CO₂CH₃ | CF₃ |
| Cl | H | CH₃ |
| Cl | C(=O)CH₃ | CH₃ |
| Cl | CO₂CH₃ | CH₃ |
| Cl | H | CF₃ |
| Cl | C(=O)CH₃ | CF₃ |
| Cl | CO₂CH₃ | CF₃ |

$J = 16$, $Y = Cl$, and $R^2 = CH_2Cl$

| X | R¹ | R¹⁷ |
|---|---|---|
| F | H | CH₃ |
| F | C(=O)CH₃ | CH₃ |
| F | CO₂CH₃ | CH₃ |
| F | H | CF₃ |
| F | C(=O)CH₃ | CF₃ |
| F | CO₂CH₃ | CF₃ |
| Cl | H | CH₃ |
| Cl | C(=O)CH₃ | CH₃ |
| Cl | CO₂CH₃ | CH₃ |
| Cl | H | CF₃ |
| Cl | C(=O)CH₃ | CF₃ |
| Cl | CO₂CH₃ | CF₃ |

$J = 17$, $Q \equiv O$, and $R^{19} = CH_3$

| X | Y | W | R¹ | R² | R¹⁴ |
|---|---|---|---|---|---|
| F | H | N | H | CH₂Cl | CH₃ |
| F | H | N | H | CH₂Br | CH₃ |
| F | H | N | H | CH₂Cl | CF₃ |
| F | H | N | H | CH₂Br | CF₃ |
| F | H | N | H | CH₂Cl | N(CH₃)₂ |
| F | H | N | H | CH₂Br | N(CH₃)₂ |
| F | H | CCH₃ | H | CH₂Cl | CH₃ |
| F | H | CCH₃ | H | CH₂Br | CH₃ |
| F | H | CCH₃ | H | CH₂Cl | CF₃ |
| F | H | CCH₃ | H | CH₂Br | CF₃ |
| F | H | CCH₃ | H | CH₂Cl | N(CH₃)₂ |
| F | H | CCH₃ | H | CH₂Br | N(CH₃)₂ |
| F | Cl | N | H | CH₂Cl | CH₃ |
| F | Cl | N | H | CH₂Br | CH₃ |
| F | Cl | N | C(=O)CH₃ | CH₂Cl | CH₃ |
| F | Cl | N | C(=O)CH₃ | CH₂Br | CH₃ |
| F | Cl | N | CO₂CH₃ | CH₂Cl | CH₃ |
| F | Cl | N | CO₂CH₃ | CH₂Br | CH₃ |
| F | Cl | N | CH₂C≡CH | CH₂Cl | CH₃ |
| F | Cl | N | CH₂C≡CH | CH₂Br | CH₃ |
| F | Cl | N | H | CH₂Cl | CF₃ |
| F | Cl | N | H | CH₂Br | CF₃ |
| F | Cl | N | C(=O)CH₃ | CH₂Cl | CF₃ |
| F | Cl | N | C(=O)CH₃ | CH₂Br | CF₃ |
| F | Cl | N | CO₂CH₃ | CH₂Cl | CF₃ |
| F | Cl | N | CO₂CH₃ | CH₂Br | CF₃ |
| F | Cl | N | CH₂C≡CH | CH₂Cl | CF₃ |

TABLE 1-continued

| | | | | | |
|---|---|---|---|---|---|
| F | Cl | N | CH$_2$C≡CH | CH$_2$Br | CP3 |
| F | Cl | N | H | CH$_2$Cl | N(CH$_3$)$_2$ |
| F | Cl | N | H | CH$_2$Br | N(CH$_3$)$_2$ |
| F | Cl | N | C(=O)CH$_3$ | CH$_2$Cl | N(CH$_3$)$_2$ |
| F | Cl | N | C(=O)CH$_3$ | CH$_2$Br | N(CH$_3$)$_2$ |
| F | Cl | N | CO$_2$CH$_3$ | CH$_2$Cl | N(CH$_3$)$_2$ |
| F | Cl | N | CO$_2$CH$_3$ | CH$_2$Br | N(CH$_3$)$_2$ |
| F | Cl | N | CH$_2$C≡CH | CH$_2$Cl | N(CH$_3$)$_2$ |
| F | Cl | N | CH$_2$C≡CH | CH$_2$Br | N(CH$_3$)$_2$ |
| F | Cl | CCH$_3$ | H | CH$_2$Cl | CH$_3$ |
| F | Cl | CCH$_3$ | H | CH$_2$Br | CH$_3$ |
| F | Cl | CCH$_3$ | C(=O)CH$_3$ | CH$_2$Cl | CH$_3$ |
| F | Cl | CCH$_3$ | C(=O)CH$_3$ | CH$_2$Br | CH$_3$ |
| F | Cl | CCH$_3$ | CO$_2$CH$_3$ | CH$_2$Cl | CH$_3$ |
| F | Cl | CCH$_3$ | CO$_2$CH$_3$ | CH$_2$Br | CH$_3$ |
| F | Cl | CCH$_3$ | CH$_2$C≡CH | CH$_2$Cl | CH$_3$ |
| F | Cl | CCH$_3$ | CH$_2$C≡CH | CH$_2$Br | CH$_3$ |
| F | Cl | CCH$_3$ | H | CH$_2$Cl | CF$_3$ |
| F | Cl | CCH$_3$ | H | CH$_2$Br | CF$_3$ |
| F | Cl | CCH$_3$ | C(=O)CH$_3$ | CH$_2$Cl | CF$_3$ |
| F | Cl | CCH$_3$ | C(=O)CH$_3$ | CH$_2$Br | CF$_3$ |
| F | Cl | CCH$_3$ | CO$_2$CH$_3$ | CH$_2$Cl | CF$_3$ |
| F | Cl | CCH$_3$ | CO$_2$CH$_3$ | CH$_2$Br | CF$_3$ |
| F | Cl | CCH$_3$ | CH$_2$C≡CH | CH$_2$Cl | CF$_3$ |
| F | Cl | CCH$_3$ | CH$_2$C≡CH | CH$_2$Br | CF$_3$ |
| F | Cl | CCH$_3$ | H | CH$_2$Cl | N(CH$_3$)$_2$ |
| F | Cl | CCH$_3$ | H | CH$_2$Br | N(CH$_3$)$_2$ |
| F | Cl | CCH$_3$ | C(=O)CH$_3$ | CH$_2$Cl | N(CH$_3$)$_2$ |
| F | Cl | CCH$_3$ | C(=O)CH$_3$ | CH$_2$Br | N(CH$_3$)$_2$ |
| F | Cl | CCH$_3$ | CO$_2$CH$_3$ | CH$_2$Cl | N(CH$_3$)$_2$ |
| F | Cl | CCH$_3$ | CO$_2$CH$_3$ | CH$_2$Br | N(CH$_3$)$_2$ |
| F | Cl | CCH$_3$ | CH$_2$C≡CH | CH$_2$Cl | N(CH$_3$)$_2$ |
| F | Cl | CCH$_3$ | CH$_2$C≡CH | CH$_2$Br | N(CH$_3$)$_2$ |
| F | Br | N | H | CH$_2$Cl | CH$_3$ |
| F | Br | N | H | CH$_2$Br | CH$_3$ |
| F | Br | N | C(=O)CH$_3$ | CH$_2$Cl | CH$_3$ |
| F | Br | N | C(=O)CH$_3$ | CH$_2$Br | CH$_3$ |
| F | Br | N | CO$_2$CH$_3$ | CH$_2$Cl | CH$_3$ |
| F | Br | N | CO$_2$CH$_3$ | CH$_2$Br | CH$_3$ |
| F | Br | N | CH$_2$C≡CH | CH$_2$Cl | CH$_3$ |
| F | Br | N | CH$_2$C≡CH | CH$_2$Br | CH$_3$ |
| F | Br | N | H | CH$_2$Cl | CF$_3$ |
| F | Br | N | H | CH$_2$Br | CF$_3$ |
| F | Br | N | C(=O)CH$_3$ | CH$_2$Cl | CF$_3$ |
| F | Br | N | C(=O)CH$_3$ | CH$_2$Br | CF$_3$ |
| F | Br | N | CO$_2$CH$_3$ | CH$_2$Cl | CF$_3$ |
| F | Br | N | CO$_2$CH$_3$ | CH$_2$Br | CF$_3$ |
| F | Br | N | CH$_2$C≡CH | CH$_2$Cl | CF$_3$ |
| F | Br | N | CH$_2$C≡CH | CH$_2$Br | CF$_3$ |
| F | Br | N | H | CH$_2$Cl | N(CH$_3$)$_2$ |
| F | Br | N | H | CH$_2$Br | N(CH$_3$)$_2$ |
| F | Br | N | C(=O)CH$_3$ | CH$_2$Cl | N(CH$_3$)$_2$ |
| F | Br | N | C(=O)CH$_3$ | CH$_2$Br | N(CH$_3$)$_2$ |
| F | Br | N | CO$_2$CH$_3$ | CH$_2$Cl | N(CH$_3$)$_2$ |
| F | Br | N | CO$_2$CH$_3$ | CH$_2$Br | N(CH$_3$)$_2$ |
| F | Br | N | CH$_2$C≡CH | CH$_2$Cl | N(CH$_3$)$_2$ |
| F | Br | N | CH$_2$C≡CH | CH$_2$Br | N(CH$_3$)$_2$ |
| F | Br | CCH$_3$ | H | CH$_2$Cl | CH$_3$ |
| F | Br | CCH$_3$ | H | CH$_2$Br | CH$_3$ |
| F | Br | CCH$_3$ | C(=O)CH$_3$ | CH$_2$Cl | CH$_3$ |
| F | Br | CCH$_3$ | C(=O)CH$_3$ | CH$_2$Br | CH$_3$ |
| F | Br | CCH$_3$ | CO$_2$CH$_3$ | CH$_2$Cl | CH$_3$ |
| F | Br | CCH$_3$ | CO$_2$CH$_3$ | CH$_2$Br | CH$_3$ |
| F | Br | CCH$_3$ | CH$_2$C≡CH | CH$_2$Cl | CH$_3$ |
| F | Br | CCH$_3$ | CH$_2$C≡CH | CH$_2$Br | CH$_3$ |
| F | Br | CCH$_3$ | H | CH$_2$Cl | CF$_3$ |
| F | Br | CCH$_3$ | H | CH$_2$Br | CF$_3$ |
| F | Br | CCH$_3$ | C(=O)CH$_3$ | CH$_2$Cl | CF$_3$ |
| F | Br | CCH$_3$ | C(=O)CH$_3$ | CH$_2$Br | CF$_3$ |
| F | Br | CCH$_3$ | CO$_2$CH$_3$ | CH$_2$Cl | CF$_3$ |
| F | Br | CCH$_3$ | CO$_2$CH$_3$ | CH$_2$Br | CF$_3$ |
| F | Br | CCH$_3$ | CH$_2$C≡CH | CH$_2$Cl | CF$_3$ |
| F | Br | CCH$_3$ | CH$_2$C≡CH | CH$_2$Br | CF$_3$ |
| F | Br | CCH$_3$ | H | CH$_2$Cl | N(CH$_3$)$_2$ |
| F | Br | CCH$_3$ | H | CH$_2$Br | N(CH$_3$)$_2$ |
| F | Br | CCH$_3$ | C(=O)CH$_3$ | CH$_2$Cl | N(CH$_3$)$_2$ |
| F | Br | CCH$_3$ | C(=O)CH$_3$ | CH$_2$Br | N(CH$_3$)$_2$ |
| F | Br | CCH$_3$ | CO$_2$CH$_3$ | CH$_2$Cl | N(CH$_3$)$_2$ |
| F | Br | CCH$_3$ | CO$_2$CH$_3$ | CH$_2$Br | N(CH$_3$)$_2$ |
| F | Br | CCH$_3$ | CH$_2$C≡CH | CH$_2$Cl | N(CH$_3$)$_2$ |
| F | Br | CCH$_3$ | CH$_2$C≡CH | CH$_2$Br | N(CH$_3$)$_2$ |
| F | CN | N | H | CH$_2$Cl | CH$_3$ |
| F | CN | N | H | CH$_2$Br | CH$_3$ |
| F | CN | N | C(=O)CH$_3$ | CH$_2$Cl | CH$_3$ |
| F | CN | N | C(=O)CH$_3$ | CH$_2$Br | CH$_3$ |
| F | CN | N | CO$_2$CH$_3$ | CH$_2$Cl | CH$_3$ |
| F | CN | N | CO$_2$CH$_3$ | CH$_2$Br | CH$_3$ |
| F | CN | N | CH$_2$C≡CH | CH$_2$Cl | CH$_3$ |
| F | CN | N | CH$_2$C≡CH | CH$_2$Br | CH$_3$ |
| F | CN | N | H | CH$_2$Cl | CF$_3$ |
| F | CN | N | H | CH$_2$Br | CF$_3$ |
| F | CN | N | C(=O)CH$_3$ | CH$_2$Cl | CF$_3$ |
| F | CN | N | C(=O)CH$_3$ | CH$_2$Br | CF$_3$ |
| F | CN | N | CO$_2$CH$_3$ | CH$_2$Cl | CF$_3$ |
| F | CN | N | CO$_2$CH$_3$ | CH$_2$Br | CF$_3$ |
| F | CN | N | CH$_2$C≡CH | CH$_2$Cl | CF$_3$ |
| F | CN | N | CH$_2$C≡CH | CH$_2$Br | CF$_3$ |
| F | CN | N | H | CH$_2$Cl | N(CH$_3$)$_2$ |
| F | CN | N | H | CH$_2$Br | N(CH$_3$)$_2$ |
| F | CN | N | C(=O)CH$_3$ | CH$_2$Cl | N(CH$_3$)$_2$ |
| F | CN | N | C(=O)CH$_3$ | CH$_2$Br | N(CH$_3$)$_2$ |
| F | CN | N | CO$_2$CH$_3$ | CH$_2$Cl | N(CH$_3$)$_2$ |
| F | CN | N | CO$_2$CH$_3$ | CH$_2$Br | N(CH$_3$)$_2$ |
| F | CN | N | CH$_2$C≡CH | CH$_2$Cl | N(CH$_3$)$_2$ |
| F | CN | N | CH$_2$C≡CH | CH$_2$Br | N(CH$_3$)$_2$ |
| F | CN | CCH$_3$ | H | CH$_2$Cl | CH$_3$ |
| F | CN | CCH$_3$ | H | CH$_2$Br | CH$_3$ |
| F | CN | CCH$_3$ | C(=O)CH$_3$ | CH$_2$Cl | CH$_3$ |
| F | CN | CCH$_3$ | C(=O)CH$_3$ | CH$_2$Br | CH$_3$ |
| F | CN | CCH$_3$ | CO$_2$CH$_3$ | CH$_2$Cl | CH$_3$ |
| F | CN | CCH$_3$ | CO$_2$CH$_3$ | CH$_2$Br | CH$_3$ |
| F | CN | CCH$_3$ | CH$_2$C≡CH | CH$_2$Cl | CH$_3$ |
| F | CN | CCH$_3$ | CH$_2$C≡CH | CH$_2$Br | CH$_3$ |
| F | CN | CCH$_3$ | H | CH$_2$Cl | CF$_3$ |
| F | CN | CCH$_3$ | H | CH$_2$Br | CF$_3$ |
| F | CN | CCH$_3$ | C(=O)CH$_3$ | CH$_2$Cl | CF$_3$ |
| F | CN | CCH$_3$ | C(=O)CH$_3$ | CH$_2$Br | CF$_3$ |
| F | CN | CCH$_3$ | CO$_2$CH$_3$ | CH$_2$Cl | CF$_3$ |
| F | CN | CCH$_3$ | CO$_2$CH$_3$ | CH$_2$Br | CF$_3$ |
| F | CN | CCH$_3$ | CH$_2$C≡CH | CH$_2$Cl | CF$_3$ |
| F | CN | CCH$_3$ | CH$_2$C≡CH | CH$_2$Br | CF$_3$ |
| F | CN | CCH$_3$ | H | CH$_2$Cl | N(CH$_3$)$_2$ |
| F | CN | CCH$_3$ | H | CH$_2$Br | N(CH$_3$)$_2$ |
| F | CN | CCH$_3$ | C(=O)CH$_3$ | CH$_2$Cl | N(CH$_3$)$_2$ |
| F | CN | CCH$_3$ | C(=O)CH$_3$ | CH$_2$Br | N(CH$_3$)$_2$ |
| F | CN | CCH$_3$ | CO$_2$CH$_3$ | CH$_2$Cl | N(CH$_3$)$_2$ |
| F | CN | CCH$_3$ | CO$_2$CH$_3$ | CH$_2$Br | N(CH$_3$)$_2$ |
| F | CN | CCH$_3$ | CH$_2$C≡CH | CH$_2$Cl | N(CH$_3$)$_2$ |
| F | CN | CCH$_3$ | CH$_2$C≡CH | CH$_2$Br | N(CH$_3$)$_2$ |
| Cl | H | N | H | CH$_2$Cl | CH$_3$ |
| Cl | H | N | H | CH$_2$Br | CH$_3$ |
| Cl | H | N | H | CH$_2$Cl | CF$_3$ |
| Cl | H | N | H | CH$_2$Br | CF$_3$ |
| Cl | H | N | H | CH$_2$Cl | N(CH$_3$)$_2$ |
| Cl | H | N | H | CH$_2$Br | N(CH$_3$)$_2$ |
| Cl | H | CCH$_3$ | H | CH$_2$Cl | CH$_3$ |
| Cl | H | CCH$_3$ | H | CH$_2$Br | CH$_3$ |
| Cl | H | CCH$_3$ | H | CH$_2$Cl | CF$_3$ |
| Cl | H | CCH$_3$ | H | CH$_2$Br | CF$_3$ |
| Cl | H | CCH$_3$ | H | CH$_2$Cl | N(CH$_3$)$_2$ |
| Cl | H | CCH$_3$ | H | CH$_2$Br | N(CH$_3$)$_2$ |
| Cl | Cl | N | H | CH$_2$Cl | CH$_3$ |
| Cl | Cl | N | H | CH$_2$Br | CH$_3$ |
| Cl | Cl | N | C(=O)CH$_3$ | CH$_2$Cl | CH$_3$ |
| Cl | Cl | N | C(=O)CH$_3$ | CH$_2$Br | CH$_3$ |
| Cl | Cl | N | CO$_2$CH$_3$ | CH$_2$Cl | CH$_3$ |
| Cl | Cl | N | CO$_2$CH$_3$ | CH$_2$Br | CH$_3$ |
| Cl | Cl | N | CH$_2$C≡CH | CH$_2$Cl | CH$_3$ |
| Cl | Cl | N | CH$_2$C≡CH | CH$_2$Br | CH$_3$ |
| Cl | Cl | N | H | CH$_2$Cl | CF$_3$ |
| Cl | Cl | N | H | CH$_2$Br | CF$_3$ |
| Cl | Cl | N | C(=O)CH$_3$ | CH$_2$Cl | CF$_3$ |
| Cl | Cl | N | C(=O)CH$_3$ | CH$_2$Br | CF$_3$ |
| Cl | Cl | N | CO$_2$CH$_3$ | CH$_2$Cl | CF$_3$ |
| Cl | Cl | N | CO$_2$CH$_3$ | CH$_2$Br | CF$_3$ |
| Cl | Cl | N | CH$_2$C≡CH | CH$_2$Cl | CF$_3$ |
| Cl | Cl | N | CH$_2$C≡CH | CH$_2$Br | CF$_3$ |
| Cl | Cl | N | H | CH$_2$Cl | N(CH$_3$)$_2$ |

TABLE 1-continued

| | | | | | |
|---|---|---|---|---|---|
| Cl | Cl | N | H | CH₂Br | N(CH₃)₂ |
| Cl | Cl | N | C(=O)CH₃ | CH₂Cl | N(CH₃)₂ |
| Cl | Cl | N | C(=O)CH₃ | CH₂Br | N(CH₃)₂ |
| Cl | Cl | N | CO₂CH₃ | CH₂Cl | N(CH₃)₂ |
| Cl | Cl | N | CO₂CH₃ | CH₂Br | N(CH₃)₂ |
| Cl | Cl | N | CH₂C≡CH | CH₂Cl | N(CH₃)₂ |
| Cl | Cl | N | CH₂C≡CH | CH₂Br | N(CH₃)₂ |
| Cl | Cl | CCH₃ | H | CH₂Cl | CH₃ |
| Cl | Cl | CCH₃ | H | CH₂Br | CH₃ |
| Cl | Cl | CCH₃ | C(=O)CH₃ | CH₂Cl | CH₃ |
| Cl | Cl | CCH₃ | C(=O)CH₃ | CH₂Br | CH₃ |
| Cl | Cl | CCH₃ | CO₂CH₃ | CH₂Cl | CH₃ |
| Cl | Cl | CCH₃ | CO₂CH₃ | CH₂Br | CH₃ |
| Cl | Cl | CCH₃ | CH₂C≡CH | CH₂Cl | CH₃ |
| Cl | Cl | CCH₃ | CH₂C≡CH | CH₂Br | CH₃ |
| Cl | Cl | CCH₃ | H | CH₂Cl | CF₃ |
| Cl | Cl | CCH₃ | H | CH₂Br | CF₃ |
| Cl | Cl | CCH₃ | C(=O)CH₃ | CH₂Cl | CF₃ |
| Cl | Cl | CCH₃ | C(=O)CH₃ | CH₂Br | CF₃ |
| Cl | Cl | CCH₃ | CO₂CH₃ | CH₂Cl | CF₃ |
| Cl | Cl | CCH₃ | CO₂CH₃ | CH₂Br | CF₃ |
| Cl | Cl | CCH₃ | CH₂C≡CH | CH₂Cl | CF₃ |
| Cl | Cl | CCH₃ | CH₂C≡CH | CH₂Br | CF₃ |
| Cl | Cl | CCH₃ | H | CH₂Cl | N(CH₃)₂ |
| Cl | Cl | CCH₃ | H | CH₂Br | N(CH₃)₂ |
| Cl | Cl | CCH₃ | C(=O)CH₃ | CH₂Cl | N(CH₃)₂ |
| Cl | Cl | CCH₃ | C(=O)CH₃ | CH₂Br | N(CH₃)₂ |
| Cl | Cl | CCH₃ | CO₂CH₃ | CH₂Cl | N(CH₃)₂ |
| Cl | Cl | CCH₃ | CO₂CH₃ | CH₂Br | N(CH₃)₂ |
| Cl | Cl | CCH₃ | CH₂C≡CH | CH₂Cl | N(CH₃)₂ |
| Cl | Cl | CCH₃ | CH₂C≡CH | CH₂Br | N(CH₃)₂ |
| Cl | Br | N | H | CH₂Cl | CH₃ |
| Cl | Br | N | H | CH₂Br | CH₃ |
| Cl | Br | N | C(=O)CH₃ | CH₂Cl | CH₃ |
| Cl | Br | N | C(=O)CH₃ | CH₂Br | CH₃ |
| Cl | Br | N | CO₂CH₃ | CH₂Cl | CH₃ |
| Cl | Br | N | CO₂CH₃ | CH₂Br | CH₃ |
| Cl | Br | N | CH₂C≡CH | CH₂Cl | CH₃ |
| Cl | Br | N | CH₂C≡CH | CH₂Br | CH₃ |
| Cl | Br | N | H | CH₂Cl | CF₃ |
| Cl | Br | N | H | CH₂Br | CF₃ |
| Cl | Br | N | C(=O)CH₃ | CH₂Cl | CF₃ |
| Cl | Br | N | C(=O)CH₃ | CH₂Br | CF₃ |
| Cl | Br | N | CO₂CH₃ | CH₂Cl | CF₃ |
| Cl | Br | N | CO₂CH₃ | CH₂Br | CF₃ |
| Cl | Br | N | CH₂C≡CH | CH₂Cl | CF₃ |
| Cl | Br | N | CH₂C≡CH | CH₂Br | CF₃ |
| Cl | Br | N | H | CH₂Cl | N(CH₃)₂ |
| Cl | Br | N | H | CH₂Br | N(CH₃)₂ |
| Cl | Br | N | C(=O)CH₃ | CH₂Cl | N(CH₃)₂ |
| Cl | Br | N | C(=O)CH₃ | CH₂Br | N(CH₃)₂ |
| Cl | Br | N | CO₂CH₃ | CH₂Cl | N(CH₃)₂ |
| Cl | Br | N | CO₂CH₃ | CH₂Br | N(CH₃)₂ |
| Cl | Br | N | CH₂C≡CH | CH₂Cl | N(CH₃)₂ |
| Cl | Br | N | CH₂C≡CH | CH₂Br | N(CH₃)₂ |
| Cl | Br | CCH₃ | H | CH₂Cl | CH₃ |
| Cl | Br | CCH₃ | H | CH₂Br | CH₃ |
| Cl | Br | CCH₃ | C(=O)CH₃ | CH₂Cl | CH₃ |
| Cl | Br | CCH₃ | C(=O)CH₃ | CH₂Br | CH₃ |
| Cl | Br | CCH₃ | CO₂CH₃ | CH₂Cl | CH₃ |
| Cl | Br | CCH₃ | CO₂CH₃ | CH₂Br | CH₃ |
| Cl | Br | CCH₃ | CH₂C≡CH | CH₂Cl | CH₃ |
| Cl | Br | CCH₃ | CH₂C≡CH | CH₂Br | CH₃ |
| Cl | Br | CCH₃ | H | CH₂Cl | CF₃ |
| Cl | Br | CCH₃ | H | CH₂Br | CF₃ |
| Cl | Br | CCH₃ | C(=O)CH₃ | CH₂Cl | CF₃ |
| Cl | Br | CCH₃ | C(=O)CH₃ | CH₂Br | CF₃ |
| Cl | Br | CCH₃ | CO₂CH₃ | CH₂Cl | CF₃ |
| Cl | Br | CCH₃ | CO₂CH₃ | CH₂Br | CF₃ |
| Cl | Br | CCH₃ | CH₂C≡CH | CH₂Cl | CF₃ |
| Cl | Br | CCH₃ | CH₂C≡CH | CH₂Br | CF₃ |
| Cl | Br | CCH₃ | H | CH₂Cl | N(CH₃)₂ |
| Cl | Br | CCH₃ | H | CH₂Br | N(CH₃)₂ |
| Cl | Br | CCH₃ | C(=O)CH₃ | CH₂Cl | N(CH₃)₂ |
| Cl | Br | CCH₃ | C(=O)CH₃ | CH₂Br | N(CH₃)₂ |
| Cl | Br | CCH₃ | CO₂CH₃ | CH₂Cl | N(CH₃)₂ |
| Cl | Br | CCH₃ | CO₂CH₃ | CH₂Br | N(CH₃)₂ |
| Cl | Br | CCH₃ | CH₂C≡CH | CH₂Cl | N(CH₃)₂ |
| Cl | Br | CCH₃ | CH₂C≡CH | CH₂Br | N(CH₃)₂ |
| Cl | CN | N | H | CH₂Cl | CH₃ |
| Cl | CN | N | H | CH₂Br | CH₃ |
| Cl | CN | N | C(=O)CH₃ | CH₂Cl | CH₃ |
| Cl | CN | N | C(=O)CH₃ | CH₂Br | CH₃ |
| Cl | CN | N | CO₂CH₃ | CH₂Cl | CH₃ |
| Cl | CN | N | CO₂CH₃ | CH₂Br | CH₃ |
| Cl | CN | N | CH₂C≡CH | CH₂Cl | CH₃ |
| Cl | CN | N | CH₂C≡CH | CH₂Br | CH₃ |
| Cl | CN | N | H | CH₂Cl | CF₃ |
| Cl | CN | N | H | CH₂Br | CF₃ |
| Cl | CN | N | C(=O)CH₃ | CH₂Cl | CF₃ |
| Cl | CN | N | C(=O)CH₃ | CH₂Br | CF₃ |
| Cl | CN | N | CO₂CH₃ | CH₂Cl | CF₃ |
| Cl | CN | N | CO₂CH₃ | CH₂Br | CF₃ |
| Cl | CN | N | CH₂C≡CH | CH₂Cl | CF₃ |
| Cl | CN | N | CH₂C≡CH | CH₂Br | CF₃ |
| Cl | CN | N | H | CH₂Cl | N(CH₃)₂ |
| Cl | CN | N | H | CH₂Br | N(CH₃)₂ |
| Cl | CN | N | C(=O)CH₃ | CH₂Cl | N(CH₃)₂ |
| Cl | CN | N | C(=O)CH₃ | CH₂Br | N(CH₃)₂ |
| Cl | CN | N | CO₂CH₃ | CH₂Cl | N(CH₃)₂ |
| Cl | CN | N | CO₂CH₃ | CH₂Br | N(CH₃)₂ |
| Cl | CN | N | CH₂C≡CH | CH₂Cl | N(CH₃)₂ |
| Cl | CN | N | CH₂C≡CH | CH₂Br | N(CH₃)₂ |
| Cl | CN | CCH₃ | H | CH₂Cl | CH₃ |
| Cl | CN | CCH₃ | H | CH₂Br | CH₃ |
| Cl | CN | CCH₃ | C(=O)CH₃ | CH₂Cl | CH₃ |
| Cl | CN | CCH₃ | C(=O)CH₃ | CH₂Br | CH₃ |
| Cl | CN | CCH₃ | CO₂CH₃ | CH₂Cl | CH₃ |
| Cl | CN | CCH₃ | CO₂CH₃ | CH₂Br | CH₃ |
| Cl | CN | CCH₃ | CH₂C≡CH | CH₂Cl | CH₃ |
| Cl | CN | CCH₃ | CH₂C≡CH | CH₂Br | CH₃ |
| Cl | CN | CCH₃ | H | CH₂Cl | CF₃ |
| Cl | CN | CCH₃ | H | CH₂Br | CF₃ |
| Cl | CN | CCH₃ | C(=O)CH₃ | CH₂Cl | CF₃ |
| Cl | CN | CCH₃ | C(=O)CH₃ | CH₂Br | CF₃ |
| Cl | CN | CCH₃ | CO₂CH₃ | CH₂Cl | CF₃ |
| Cl | CN | CCH₃ | CO₂CH₃ | CH₂Br | CF₃ |
| Cl | CN | CCH₃ | CH₂C≡CH | CH₂Cl | CF₃ |
| Cl | CN | CCH₃ | CH₂C≡CH | CH₂Br | CF₃ |
| Cl | CN | CCH₃ | H | CH₂Cl | N(CH₃)₂ |
| Cl | CN | CCH₃ | H | CH₂Br | N(CH₃)₂ |
| Cl | CN | CCH₃ | C(=O)CH₃ | CH₂Cl | N(CH₃)₂ |
| Cl | CN | CCH₃ | C(=O)CH₃ | CH₂Br | N(CH₃)₂ |
| Cl | CN | CCH₃ | CO₂CH₃ | CH₂Cl | N(CH₃)₂ |
| Cl | CN | CCH₃ | CO₂CH₃ | CH₂Br | N(CH₃)₂ |
| Cl | CN | CCH₃ | CH₂C≡CH | CH₂Cl | N(CH₃)₂ |
| Cl | CN | CCH₃ | CH₂C≡CH | CH₂Br | N(CH₃)₂ |

| J = 18, Q = O, Y = Cl, and R² = CH₂Cl | | | | |
|---|---|---|---|---|
| X | R¹ | Z | n | m |
| F | H | CH₂ | 1 | 1 |
| F | C(=O)CH₃ | CH₂ | 1 | 1 |
| F | CO₂CH₃ | CH₂ | 1 | 1 |
| F | H | CHF | 1 | 1 |
| F | C(=O)CH₃ | CHF | 1 | 1 |
| F | CO₂CH₃ | CHF | 1 | 1 |
| F | H | CH₂ | 1 | 2 |
| F | C(=O)CH₃ | CH₂ | 1 | 2 |
| F | CO₂CH₃ | CH₂ | 1 | 2 |
| F | H | CHF | 1 | 2 |
| F | C(=O)CH₃ | CHF | 1 | 2 |
| F | CO₂CH₃ | CHF | 1 | 2 |
| Cl | H | CH₂ | 1 | 1 |
| Cl | C(=O)CH₃ | CH₂ | 1 | 1 |
| Cl | CO₂CH₃ | CH₂ | 1 | 1 |
| Cl | H | CHF | 1 | 1 |
| Cl | C(=O)CH₃ | CHF | 1 | 1 |
| Cl | CO₂CH₃ | CHF | 1 | 1 |
| Cl | H | CH₂ | 1 | 2 |
| Cl | C(=O)CH₃ | CH₂ | 2 | |
| Cl | CO₂CH₃ | CH₂ | 1 | 2 |
| Cl | H | CHF | 1 | 2 |
| Cl | C(=O)CH₃ | CHF | 1 | 2 |
| Cl | CO₂CH₃ | CHF | 1 | 2 |

TABLE 1-continued

J = 19, Q = O, and $R^{24}$ = $CO_2CH_3$

| X | Y | Z | n | m | $R^1$ | $R^2$ |
|---|---|---|---|---|---|---|
| F | H | $CH_2$ | 1 | 1 | H | $CH_2Cl$ |
| F | H | $CH_2$ | 1 | 1 | H | $CH_2Br$ |
| F | H | $CH_2$ | 1 | 1 | C(=O)$CH_3$ | $CH_2Cl$ |
| F | H | $CH_2$ | 1 | 1 | C(=O)$CH_3$ | $CH_2Br$ |
| F | H | $CH_2$ | 1 | 1 | $CO_2CH_3$ | $CH_2Cl$ |
| F | H | $CH_2$ | 1 | 1 | $CO_2CH_3$ | $CH_2Br$ |
| F | H | $CH_2$ | 1 | 1 | $CH_2C\equiv CH$ | $CH_2Cl$ |
| F | H | $CH_2$ | 1 | 1 | $CH_2C\equiv CH$ | $CH_2Br$ |
| F | H | $CH_2$ | 1 | 2 | H | $CH_2Cl$ |
| F | H | $CH_2$ | 1 | 2 | H | $CH_2Br$ |
| F | H | $CH_2$ | 1 | 2 | C(=O)$CH_3$ | $CH_2Cl$ |
| F | H | $CH_2$ | 1 | 2 | C(=O)$CH_3$ | $CH_2Br$ |
| F | H | $CH_2$ | 1 | 2 | $CO_2CH_3$ | $CH_2Cl$ |
| F | H | $CH_2$ | 1 | 2 | $CO_2CH_3$ | $CH_2Br$ |
| F | H | $CH_2$ | 1 | 2 | $CH_2C\equiv CH$ | $CH_2Cl$ |
| F | H | $CH_2$ | 1 | 2 | $CH_2C\equiv CH$ | $CH_2Br$ |
| F | H | CHF | 1 | 1 | H | $CH_2Cl$ |
| F | H | CHF | 1 | 1 | H | $CH_2Br$ |
| F | H | CHF | 1 | 1 | C(=O)$CH_3$ | $CH_2Cl$ |
| F | H | CHF | 1 | 1 | C(=O)$CH_3$ | $CH_2Br$ |
| F | H | CHF | 1 | 1 | $CO_2CH_3$ | $CH_2Cl$ |
| F | H | CHF | 1 | 1 | $CO_2CH_3$ | $CH_2Br$ |
| F | H | CHF | 1 | 1 | $CH_2C\equiv CH$ | $CH_2Cl$ |
| F | H | CHF | 1 | 1 | $CH_2C\equiv CH$ | $CH_2Br$ |
| F | H | CHF | 1 | 2 | H | $CH_2Cl$ |
| F | H | CHF | 1 | 2 | H | $CH_2Br$ |
| F | H | CHF | 1 | 2 | C(=O)$CH_3$ | $CH_2Cl$ |
| F | H | CHF | 1 | 2 | C(=O)$CH_3$ | $CH_2Br$ |
| F | H | CHF | 1 | 2 | $CO_2CH_3$ | $CH_2Cl$ |
| F | H | CHF | 1 | 2 | $CO_2CH_3$ | $CH_2Br$ |
| F | H | CHF | 1 | 2 | $CH_2C\equiv CH$ | $CH_2Cl$ |
| F | H | CHF | 1 | 2 | $CH_2C\equiv CH$ | $CH_2Br$ |
| F | H | CHCl | 1 | 1 | H | $CH_2Cl$ |
| F | H | CHCl | 1 | 1 | H | $CH_2Br$ |
| F | H | CHCl | 1 | 1 | C(=O)$CH_3$ | $CH_2Cl$ |
| F | H | CHCl | 1 | 1 | C(=O)$CH_3$ | $CH_2Br$ |
| F | H | CHCl | 1 | 1 | $CO_2CH_3$ | $CH_2Cl$ |
| F | H | CHCl | 1 | 1 | $CO_2CH_3$ | $CH_2Br$ |
| F | H | CHCl | 1 | 1 | $CH_2C\equiv CH$ | $CH_2Cl$ |
| F | H | CHCl | 1 | 1 | $CH_2C\equiv CH$ | $CH_2Br$ |
| F | H | CHCl | 1 | 2 | H | $CH_2Cl$ |
| F | H | CHCl | 1 | 2 | H | $CH_2Br$ |
| F | H | CHCl | 1 | 2 | C(=O)$CH_3$ | $CH_2Cl$ |
| F | H | CHCl | 1 | 2 | C(=O)$CH_3$ | $CH_2Br$ |
| F | H | CHCl | 1 | 2 | $CO_2CH_3$ | $CH_2Cl$ |
| F | H | CHCl | 1 | 2 | $CO_2CH_3$ | $CH_2Br$ |
| F | H | CHCl | 1 | 2 | $CH_2C\equiv CH$ | $CH_2Cl$ |
| F | H | CHCl | 1 | 2 | $CH_2C\equiv CH$ | $CH_2Br$ |
| F | Cl | $CH_2$ | 1 | 1 | H | $CH_2Cl$ |
| F | Cl | $CH_2$ | 1 | 1 | H | $CH_2Br$ |
| F | Cl | $CH_2$ | 1 | 1 | C(=O)$CH_3$ | $CH_2Cl$ |
| F | Cl | $CH_2$ | 1 | 1 | C(=O)$CH_3$ | $CH_2Br$ |
| F | Cl | $CH_2$ | 1 | 1 | $CO_2CH_3$ | $CH_2Cl$ |
| F | Cl | $CH_2$ | 1 | 1 | $CO_2CH_3$ | $CH_2Br$ |
| F | Cl | $CH_2$ | 1 | 1 | $CH_2C\equiv CH$ | $CH_2Cl$ |
| F | Cl | $CH_2$ | 1 | 1 | $CH_2C\equiv CH$ | $CH_2Br$ |
| F | Cl | $CH_2$ | 1 | 2 | H | $CH_2Cl$ |
| F | Cl | $CH_2$ | 1 | 2 | H | $CH_2Br$ |
| F | Cl | $CH_2$ | 1 | 2 | C(=O)CH | $CH_2Cl$ |
| F | Cl | $CH_2$ | 1 | 2 | C(=O)$CH_3$ | $CH_2Br$ |
| F | Cl | $CH_2$ | 1 | 2 | $CO_2CH_3$ | $CH_2Cl$ |
| F | Cl | $CH_2$ | 1 | 2 | $CO_2CH_3$ | $CH_2Br$ |
| F | Cl | $CH_2$ | 1 | 2 | $CH_2C\equiv CH$ | $CH_2Cl$ |
| F | Cl | $CH_2$ | 1 | 2 | $CH_2C\equiv CH$ | $CH_2Br$ |
| F | Cl | CHF | 1 | 1 | H | $CH_2Cl$ |
| F | Cl | CHF | 1 | 1 | H | $CH_2Br$ |
| F | Cl | CHF | 1 | 1 | C(=O)$CH_3$ | $CH_2Cl$ |
| F | Cl | CHF | 1 | 1 | C(=O)$CH_3$ | $CH_2Br$ |
| F | Cl | CHF | 1 | 1 | $CO_2CH_3$ | $CH_2Cl$ |
| F | Cl | CHF | 1 | 1 | $CO_2CH_3$ | $CH_2Br$ |
| F | Cl | CHF | 1 | 1 | $CH_2C\equiv CH$ | $CH_2Cl$ |
| F | Cl | CHF | 1 | 1 | $CH_2C\equiv CH$ | $CH_2Br$ |
| F | Cl | CHF | 1 | 2 | H | $CH_2Cl$ |
| F | Cl | CHF | 1 | 2 | H | $CH_2Br$ |
| F | Cl | CHF | 1 | 2 | C(=O)$CH_3$ | $CH_2Cl$ |
| F | Cl | CHF | 1 | 2 | C(=O)$CH_3$ | $CH_2Br$ |
| F | Cl | CHF | 1 | 2 | $CO_2CH_3$ | $CH_2Cl$ |
| F | Cl | CHF | 1 | 2 | $CO_2CH_3$ | $CH_2Br$ |
| F | Cl | CHF | 1 | 2 | $CH_2C\equiv CH$ | $CH_2Cl$ |
| F | Cl | CHF | 1 | 2 | $CH_2C\equiv CH$ | $CH_2Br$ |
| F | Cl | CHCl | 1 | 1 | H | $CH_2Cl$ |
| F | Cl | CHCl | 1 | 1 | H | $CH_2Br$ |
| F | Cl | CHCl | 1 | 1 | C(=O)$CH_3$ | $CH_2Cl$ |
| F | Cl | CHCl | 1 | 1 | C(=O)$CH_3$ | $CH_2Br$ |
| F | Cl | CHCl | 1 | 1 | $CO_2CH_3$ | $CH_2Cl$ |
| F | Cl | CHCl | 1 | 1 | $CO_2CH_3$ | $CH_2Br$ |
| F | Cl | CHCl | 1 | 1 | $CH_2C\equiv CH$ | $CH_2Cl$ |
| F | Cl | CHCl | 1 | 1 | $CH_2C\equiv CH$ | $CH_2Br$ |
| F | Cl | CHCl | 1 | 2 | H | $CH_2Cl$ |
| F | Cl | CHCl | 1 | 2 | H | $CH_2Br$ |
| F | Cl | CHCl | 1 | 2 | C(=O)$CH_3$ | $CH_2Cl$ |
| F | Cl | CHCl | 1 | 2 | C(=O)$CH_3$ | $CH_2Br$ |
| F | Cl | CHCl | 1 | 2 | $CO_2CH_3$ | $CH_2Cl$ |
| F | Cl | CHCl | 1 | 2 | $CO_2CH_3$ | $CH_2Br$ |
| F | Cl | CHCl | 1 | 2 | $CH_2C\equiv CH$ | $CH_2Cl$ |
| F | Cl | CHCl | 1 | 2 | $CH_2C\equiv CH$ | $CH_2Br$ |
| F | Br | $CH_2$ | 1 | 1 | H | $CH_2Cl$ |
| F | Br | $CH_2$ | 1 | 1 | H | $CH_2Br$ |
| F | Br | $CH_2$ | 1 | 1 | C(=O)$CH_3$ | $CH_2Cl$ |
| F | Br | $CH_2$ | 1 | 1 | C(=O)$CH_3$ | $CH_2Br$ |
| F | Br | $CH_2$ | 1 | 1 | $CO_2CH_3$ | $CH_2Cl$ |
| F | Br | $CH_2$ | 1 | 1 | $CO_2CH_3$ | $CH_2Br$ |
| F | Br | $CH_2$ | 1 | 1 | $CH_2C\equiv CH$ | $CH_2Cl$ |
| F | Br | $CH_2$ | 1 | 1 | $CH_2C\equiv CH$ | $CH_2Br$ |
| F | Br | $CH_2$ | 1 | 2 | H | $CH_2Cl$ |
| F | Br | $CH_2$ | 1 | 2 | H | $CH_2Br$ |
| F | Br | $CH_2$ | 1 | 2 | C(=O)$CH_3$ | $CH_2Cl$ |
| F | Br | $CH_2$ | 1 | 2 | C(=O)$CH_3$ | $CH_2Br$ |
| F | Br | $CH_2$ | 1 | 2 | $CO_2CH_3$ | $CH_2Cl$ |
| F | Br | $CH_2$ | 1 | 2 | $CO_2CH_3$ | $CH_2Br$ |
| F | Br | $CH_2$ | 1 | 2 | $CH_2C\equiv CH$ | $CH_2Cl$ |
| F | Br | $CH_2$ | 1 | 2 | $CH_2C\equiv CH$ | $CH_2Br$ |
| F | Br | CHF | 1 | 1 | H | $CH_2Cl$ |
| F | Br | CHF | 1 | 1 | H | $CH_2Br$ |
| F | Br | CHF | 1 | 1 | C(=O)$CH_3$ | $CH_2Cl$ |
| F | Br | CHF | 1 | 1 | C(=O)$CH_3$ | $CH_2Br$ |
| F | Br | CHF | 1 | 1 | $CO_2CH_3$ | $CH_2Cl$ |
| F | Br | CHF | 1 | 1 | $CO_2CH_3$ | $CH_2Br$ |
| F | Br | CHF | 1 | 1 | $CH_2C\equiv CH$ | $CH_2Cl$ |
| F | Br | CHF | 1 | 1 | $CH_2C\equiv CH$ | $CH_2Br$ |
| F | Br | CHF | 1 | 2 | H | $CH_2Cl$ |
| F | Br | CHF | 1 | 2 | H | $CH_2Br$ |
| F | Br | CHF | 1 | 2 | C(=O)$CH_3$ | $CH_2Cl$ |
| F | Br | CHF | 1 | 2 | C(=O)$CH_3$ | $CH_2Br$ |
| F | Br | CHF | 1 | 2 | $CO_2CH_3$ | $CH_2Cl$ |
| F | Br | CHF | 1 | 2 | $CO_2CH_3$ | $CH_2Br$ |
| F | Br | CHF | 1 | 2 | $CH_2C\equiv CH$ | $CH_2Cl$ |
| F | Br | CHF | 1 | 2 | $CH_2C\equiv CH$ | $CH_2Br$ |
| F | Br | CHCl | 1 | 1 | H | $CH_2Cl$ |
| F | Br | CHCl | 1 | 1 | H | $CH_2Br$ |
| F | Br | CHCl | 1 | 1 | C(=O)$CH_3$ | $CH_2Cl$ |
| F | Br | CHCl | 1 | 1 | C(=O)$CH_3$ | $CH_2Br$ |
| F | Br | CHCl | 1 | 1 | $CO_2CH_3$ | $CH_2Cl$ |
| F | Br | CHCl | 1 | 1 | $CO_2CH_3$ | $CH_2Br$ |
| F | Br | CHCl | 1 | 1 | $CH_2=CH$ | $CH_2Cl$ |
| F | Br | CHCl | 1 | 1 | $CH_2=CH$ | $CH_2Br$ |
| F | Br | CHCl | 1 | 2 | H | $CH_2Cl$ |
| F | Br | CHCl | 1 | 2 | H | $CH_2Br$ |
| F | Br | CHCl | 1 | 2 | C(=O)$CH_3$ | $CH_2Cl$ |
| F | Br | CHCl | 1 | 2 | C(=O)$CH_3$ | $CH_2Br$ |
| F | Br | CHCl | 1 | 2 | $CO_2CH_3$ | $CH_2Cl$ |
| F | Br | CHCl | 1 | 2 | $CO_2CH_3$ | $CH_2Br$ |
| F | Br | CHCl | 1 | 2 | $CH_2=CH$ | $CH_2Cl$ |
| F | Br | CHCl | 1 | 2 | $CH_2C\equiv CH$ | $CH_2Br$ |
| F | CN | $CH_2$ | 1 | 1 | H | $CH_2Cl$ |
| F | CN | $CH_2$ | 1 | 1 | H | $CH_2Br$ |
| F | CN | $CH_2$ | 1 | 1 | C(=O)$CH_3$ | $CH_2Cl$ |
| F | CN | $CH_2$ | 1 | 1 | C(=O)$CH_3$ | $CH_2Br$ |
| F | CN | $CH_2$ | 1 | 1 | $CO_2CH_3$ | $CH_2Cl$ |
| F | CN | $CH_2$ | 1 | 1 | $CO_2CH_3$ | $CH_2Br$ |
| F | CN | $CH_2$ | 1 | 1 | $CH_2C\equiv CH$ | $CH_2Cl$ |
| F | CN | $CH_2$ | 1 | 1 | $CH_2C\equiv CH$ | $CH_2Br$ |
| F | CN | $CH_2$ | 1 | 2 | H | $CH_2Cl$ |
| F | CN | $CH_2$ | 1 | 2 | H | $CH_2Br$ |

TABLE 1-continued

| | | | | | | |
|---|---|---|---|---|---|---|
| F | CN | CH$_2$ | 1 | 2 | C(=O)CH$_3$ | CH$_2$Cl |
| F | CN | CH$_2$ | 1 | 2 | C(=O)CH$_3$ | CH$_2$Br |
| F | CN | CH$_2$ | 1 | 2 | CO$_2$CH$_3$ | CH$_2$Cl |
| F | CN | CH$_2$ | 1 | 2 | CO$_2$CH$_3$ | CH$_2$Br |
| F | CN | CH$_2$ | 1 | 2 | CH$_2$C≡CH | CH$_2$Cl |
| F | CN | CH$_2$ | 1 | 2 | CH$_2$C≡CH | CH$_2$Br |
| F | CN | CHF | 1 | 1 | H | CH$_2$Cl |
| F | CN | CHF | 1 | 1 | H | CH$_2$Br |
| F | CN | CHF | 1 | 1 | C(=O)CH$_3$ | CH$_2$Cl |
| F | CN | CHF | 1 | 1 | C(=O)CH$_3$ | CH$_2$Br |
| F | CN | CHF | 1 | 1 | CO$_2$CH$_3$ | CH$_2$Cl |
| F | CN | CHF | I | 1 | CO$_2$CH$_3$ | CH$_2$Br |
| F | CN | CHF | 1 | 1 | CH$_2$C≡CH | CH$_2$Cl |
| F | CN | CHF | 1 | 1 | CH$_2$C≡CH | CH$_2$Br |
| F | CN | CHF | 1 | 2 | H | CH$_2$Cl |
| F | CN | CHF | 1 | 2 | H | CH$_2$Br |
| F | CN | CHF | 1 | 2 | C(=O)CH$_3$ | CH$_2$Cl |
| F | CN | CHF | 1 | 2 | C(=O)CH$_3$ | CH$_2$Br |
| F | CN | CHF | 1 | 2 | CO$_2$CH$_3$ | CH$_2$Cl |
| F | CN | CHF | 1 | 2 | CO$_2$CH$_3$ | CH$_2$Br |
| F | CN | CHF | 1 | 2 | CH$_2$C≡CH | CH$_2$Cl |
| F | CN | CHF | 1 | 2 | CH$_2$C≡CH | CH$_2$Br |
| F | CN | CHCl | 1 | 1 | H | CH$_2$Cl |
| F | CN | CHCl | 1 | 1 | H | CH$_2$Br |
| F | CN | CHCl | 1 | 1 | C(=O)CH$_3$ | CH$_2$Cl |
| F | CN | CHCl | 1 | 1 | C(=O)CH$_3$ | CH$_2$Br |
| F | CN | CHCl | 1 | 1 | CO$_2$CH$_3$ | CH$_2$Cl |
| F | CN | CHCl | 1 | 1 | CO$_2$CH$_3$ | CH$_2$Br |
| F | CN | CHCl | 1 | 1 | CH$_2$C≡CH | CH$_2$Cl |
| F | CN | CHCl | 1 | 1 | CH$_2$C≡CH | CH$_2$Br |
| F | CN | CHCl | 1 | 2 | H | CH$_2$Cl |
| F | CN | CHCl | 1 | 2 | H | CH$_2$Br |
| F | CN | CHCl | 1 | 2 | C(=O)CH$_3$ | CH$_2$Cl |
| F | CN | CHCl | 1 | 2 | C(=O)CH$_3$ | CH$_2$Br |
| F | CN | CHCl | 1 | 2 | CO$_2$CH$_3$ | CH$_2$Cl |
| F | CN | CHCl | 1 | 2 | CO$_2$CH$_3$ | CH$_2$Br |
| F | CN | CHCl | 1 | 2 | CH$_2$C≡CH | CH$_2$Cl |
| F | CN | CHCl | 1 | 2 | CH$_2$C≡CH | CH$_2$Br |
| Cl | H | CH$_2$ | 1 | 1 | H | CH$_2$Cl |
| Cl | H | CH$_2$ | 1 | 1 | H | CH$_2$Br |
| Cl | H | CH$_2$ | 1 | 1 | C(=O)CH$_3$ | CH$_2$Cl |
| Cl | H | CH$_2$ | 1 | 1 | C(=O)CH$_3$ | CH$_2$Br |
| Cl | H | CH$_2$ | 1 | 1 | CO$_2$CH$_3$ | CH$_2$Cl |
| Cl | H | CH$_2$ | 1 | 1 | CO$_2$CH$_3$ | CH$_2$Br |
| Cl | H | CH$_2$ | 1 | 1 | CH$_2$C≡CH | CH$_2$Cl |
| Cl | H | CH$_2$ | 1 | 1 | CH$_2$C≡CH | CH$_2$Br |
| Cl | H | CH$_2$ | 1 | 2 | H | CH$_2$Cl |
| Cl | H | CH$_2$ | 1 | 2 | H | CH$_2$Br |
| Cl | H | CH$_2$ | 1 | 2 | C(=O)CH$_3$ | CH$_2$Cl |
| Cl | H | CH$_2$ | 1 | 2 | C(=O)CH$_3$ | CH$_2$Br |
| Cl | H | CH$_2$ | 1 | 2 | CO$_2$CH$_3$ | CH$_2$Cl |
| Cl | H | CH$_2$ | 1 | 2 | CO$_2$CH$_3$ | CH$_2$Br |
| Cl | H | CH$_2$ | 1 | 2 | CH$_2$C≡CH | CH$_2$Cl |
| Cl | H | CH$_2$ | 1 | 2 | CH$_2$C≡CH | CH$_2$Br |
| Cl | H | CHF | 1 | 1 | H | CH$_2$Cl |
| Cl | H | CHF | 1 | 1 | H | CH$_2$Br |
| Cl | H | CHF | 1 | 1 | C(=O)CH$_3$ | CH$_2$Cl |
| Cl | H | CHF | 1 | 1 | C(=O)CH$_3$ | CH$_2$Br |
| Cl | H | CHF | 1 | 1 | CO$_2$CH$_3$ | CH$_2$Cl |
| Cl | H | CHF | 1 | 1 | CO$_2$CH$_3$ | CH$_2$Br |
| Cl | H | CHF | 1 | 1 | CH$_2$C≡CH | CH$_2$Cl |
| Cl | H | CHF | 1 | 1 | CH$_2$C≡CH | CH$_2$Br |
| Cl | H | CHF | 1 | 2 | H | CH$_2$Cl |
| Cl | H | CHF | 1 | 2 | H | CH$_2$Br |
| Cl | H | CHF | 1 | 2 | C(=O)CH$_3$ | CH$_2$Cl |
| Cl | H | CHF | 1 | 2 | C(=O)CH$_3$ | CH$_2$Br |
| Cl | H | CHF | 1 | 2 | CO$_2$CH$_3$ | CH$_2$Cl |
| Cl | H | CHF | 1 | 2 | CO$_2$CH$_3$ | CH$_2$Br |
| Cl | H | CHF | 1 | 2 | CH$_2$C≡CH | CH$_2$Cl |
| Cl | H | CHF | 1 | 2 | CH$_2$C≡CH | CH$_2$Br |
| Cl | H | CHCl | 1 | 1 | H | CH$_2$Cl |
| Cl | H | CHCl | 1 | 1 | H | CH$_2$Br |
| Cl | H | CHCl | 1 | 1 | C(=O)CH$_3$ | CH$_2$Cl |
| Cl | H | CHCl | 1 | 1 | C(=O)CH$_3$ | CH$_2$Br |
| Cl | H | CHCl | 1 | 1 | CO$_2$CH$_3$ | CH$_2$Cl |
| Cl | H | CHCl | 1 | 1 | CO$_2$CH$_3$ | CH$_2$Br |
| Cl | H | CHCl | 1 | 1 | CH$_2$C≡CH | CH$_2$Cl |
| Cl | H | CHCl | 1 | 1 | CH$_2$C≡CH | CH$_2$Br |
| Cl | H | CHCl | 1 | 2 | H | CH$_2$Cl |
| Cl | R | CHCl | 1 | 2 | H | CH$_2$Br |
| Cl | H | CHCl | 1 | 2 | C(=O)CH$_3$ | CH$_2$Cl |
| Cl | H | CHCl | 1 | 2 | C(=O)CH$_3$ | CH$_2$Br |
| Cl | H | CHCl | 1 | 2 | CO$_2$CH$_3$ | CH$_2$Cl |
| Cl | R | CHCl | 1 | 2 | CO$_2$CH$_3$ | CH$_2$Br |
| Cl | R | CHCl | 1 | 2 | CH$_2$C≡CH | CH$_2$Cl |
| Cl | H | CHCl | 1 | 2 | CH$_2$C≡CH | CH$_2$Br |
| Cl | Cl | CH$_2$ | 1 | 1 | H | CH$_2$Cl |
| Cl | Cl | CH$_2$ | 1 | 1 | H | CH$_2$Br |
| Cl | Cl | CH$_2$ | 1 | 1 | C(=O)CH$_3$ | CH$_2$Cl |
| Cl | Cl | CH$_2$ | 1 | 1 | C(=O)CH$_3$ | CH$_2$Br |
| Cl | Cl | CH$_2$ | 1 | 1 | CO$_2$CH$_3$ | CH$_2$Cl |
| Cl | Cl | CH$_2$ | 1 | 1 | CO$_2$CH$_3$ | CH$_2$Br |
| Cl | Cl | CH$_2$ | 1 | 1 | CH$_2$C≡CH | CH$_2$Cl |
| Cl | Cl | CH$_2$ | 1 | 1 | CH$_2$C≡CH | CH$_2$Br |
| Cl | Cl | CH$_2$ | 1 | 2 | H | CH$_2$Cl |
| Cl | Cl | CH$_2$ | 1 | 2 | H | CH$_2$Br |
| Cl | Cl | CH$_2$ | 1 | 2 | C(=O)CH$_3$ | CH$_2$Cl |
| Cl | Cl | CH$_2$ | 1 | 2 | C(=O)CH$_3$ | CH$_2$Br |
| Cl | Cl | CH$_2$ | 1 | 2 | CO$_2$CH$_3$ | CH$_2$Cl |
| Cl | Cl | CH$_2$ | 1 | 2 | CO$_2$CH$_3$ | CH$_2$Br |
| Cl | Cl | CH$_2$ | 1 | 2 | CH$_2$C≡CH | CH$_2$Cl |
| Cl | Cl | CH$_2$ | 1 | 2 | CH$_2$C≡CH | CH$_2$Br |
| Cl | Cl | CHF | 1 | 1 | H | CH$_2$Cl |
| Cl | Cl | CHF | 1 | 1 | H | CH$_2$Br |
| Cl | Cl | CHF | 1 | 1 | C(=O)CH$_3$ | CH$_2$Cl |
| Cl | Cl | CHF | 1 | 1 | C(=O)CH$_3$ | CH$_2$Br |
| Cl | Cl | CHF | 1 | 1 | CO$_2$CH$_3$ | CH$_2$Cl |
| Cl | Cl | CHF | 1 | 1 | CO$_2$CH$_3$ | CH$_2$Br |
| Cl | Cl | CRF | 1 | 1 | CH$_2$C≡CH | CH$_2$Cl |
| Cl | Cl | CHF | 1 | 1 | CH$_2$C≡CH | CH$_2$Br |
| Cl | Cl | CRF | 1 | 2 | H | CH$_2$Cl |
| Cl | Cl | CHF | 1 | 2 | H | CH$_2$Br |
| Cl | Cl | CHF | 1 | 2 | C(=O)CH$_3$ | CH$_2$Cl |
| Cl | Cl | CHF | 1 | 2 | C(=O)CH$_3$ | CH$_2$Br |
| Cl | Cl | CHF | 1 | 2 | CO$_2$CH$_3$ | CH$_2$Cl |
| Cl | Cl | CHF | I | 2 | CO$_2$CH$_3$ | CH$_2$Br |
| Cl | Cl | CHF | 1 | 2 | CH$_2$C≡CH | CH$_2$Cl |
| Cl | Cl | CHF | 1 | 2 | CH$_2$C≡CH | CH$_2$Br |
| Cl | Cl | CHCl | 1 | 1 | H | CH$_2$Cl |
| Cl | Cl | CHCl | 1 | 1 | H | CH$_2$Br |
| Cl | Cl | CHCl | 1 | 1 | C(=O)CH$_3$ | CH$_2$Cl |
| Cl | Cl | CHCl | 1 | 1 | C(=O)CH$_3$ | CH$_2$Br |
| Cl | Cl | CHCl | 1 | 1 | CO$_2$CH$_3$ | CH$_2$Cl |
| Cl | Cl | CHCl | 1 | 1 | CO$_2$CH$_3$ | CH$_2$Br |
| Cl | Cl | CHCl | 1 | 1 | CH$_2$C≡CH | CH$_2$Cl |
| Cl | Cl | CHCl | 1 | 1 | CH$_2$C≡CH | CH$_2$Br |
| Cl | Cl | CHCl | 1 | 2 | H | CH$_2$Cl |
| Cl | Cl | CHCl | 1 | 2 | H | CH$_2$Br |
| Cl | Cl | CHCl | 1 | 2 | C(=O)CH$_3$ | CH$_2$Cl |
| Cl | Cl | CHCl | 1 | 2 | C(=O)CH$_3$ | CH$_2$Br |
| Cl | Cl | CHCl | 1 | 2 | CO$_2$CH$_3$ | CH$_2$Cl |
| Cl | Cl | CHCl | 1 | 2 | CO$_2$CH$_3$ | CH$_2$Br |
| Cl | Cl | CHCl | 1 | 2 | CH$_2$C≡CH | CH$_2$Cl |
| Cl | Cl | CHCl | 1 | 2 | CH$_2$C≡CH | CH$_2$Br |
| Cl | Br | CH$_2$ | 1 | 1 | H | CH$_2$Cl |
| Cl | Br | CH$_2$ | 1 | 1 | H | CH$_2$Br |
| Cl | Br | CH$_2$ | 1 | 1 | C(=O)CH$_3$ | CH$_2$Cl |
| Cl | Br | CH$_2$ | 1 | 1 | C(=O)CH$_3$ | CH$_2$Br |
| Cl | Br | CH$_2$ | 1 | 1 | CO$_2$CH$_3$ | CH$_2$Cl |
| Cl | Br | CH$_2$ | 1 | 1 | CO$_2$CH$_3$ | CH$_2$Br |
| Cl | Br | CH$_2$ | 1 | 1 | CH$_2$C≡CH | CH$_2$Cl |
| Cl | Br | CH$_2$ | 1 | 1 | CH$_2$C≡CH | CH$_2$Br |
| Cl | Br | CH$_2$ | 1 | 2 | H | CH$_2$Cl |
| Cl | Br | CH$_2$ | 1 | 2 | H | CH$_2$Br |
| Cl | Br | CH$_2$ | 1 | 2 | C(=O)CH$_3$ | CH$_2$Cl |
| Cl | Br | CH$_2$ | 1 | 2 | C(=O)CH$_3$ | CH$_2$Br |
| Cl | Br | CH$_2$ | 1 | 2 | CO$_2$CH$_3$ | CH$_2$Cl |
| Cl | Br | CH$_2$ | 1 | 2 | CO$_2$CH$_3$ | CH$_2$Br |
| Cl | Br | CH$_2$ | 1 | 2 | CH$_2$C≡CH | CH$_2$Cl |
| Cl | Br | CH$_2$ | 1 | 2 | CH$_2$C≡CH | CH$_2$Br |
| Cl | Br | CHF | 1 | 1 | H | CH$_2$Cl |
| Cl | Br | CHF | 1 | 1 | H | CH$_2$Br |
| Cl | Br | CHF | 1 | 1 | C(=O)CH$_3$ | CH$_2$Cl |
| Cl | Br | CHF | 1 | 1 | C(=O)CH$_3$ | CH$_2$Br |
| Cl | Br | CHF | 1 | 1 | CO$_2$CH$_3$ | CH$_2$Cl |
| Cl | Br | CHF | 1 | 1 | CO$_2$CH$_3$ | CH$_2$Br |
| Cl | Br | CHF | 1 | 1 | CH$_2$C≡CH | CH$_2$Cl |
| Cl | Br | CHF | 1 | 1 | CH$_2$C≡CH | CH$_2$Br |

TABLE 1-continued

| X | Y | Z | n | m | R¹ | R² |
|---|---|---|---|---|----|----|
| Cl | Br | CHF | 1 | 2 | H | CH$_2$Cl |
| Cl | Br | CHF | 1 | 2 | H | CH$_2$Br |
| Cl | Br | CHF | 1 | 2 | C(=O)CH$_3$ | CH$_2$Cl |
| Cl | Br | CHF | 1 | 2 | C(=O)CH$_3$ | CH$_2$Br |
| Cl | Br | CHF | 1 | 2 | CO$_2$CH$_3$ | CH$_2$Cl |
| Cl | Br | CHF | 1 | 2 | CO$_2$CH$_3$ | CH$_2$Br |
| Cl | Br | CHF | 1 | 2 | CH$_2$C≡CH | CH$_2$Cl |
| Cl | Br | CHF | 1 | 2 | CH$_2$C≡CH | CH$_2$Br |
| Cl | Br | CHCl | 1 | 1 | H | CH$_2$Cl |
| Cl | Br | CHCl | 1 | 1 | H | CH$_2$Br |
| Cl | Br | CHCl | 1 | 1 | C(=O)CH$_3$ | CH$_2$Cl |
| Cl | Br | CHCl | 1 | 1 | C(=O)CH$_3$ | CH$_2$Br |
| Cl | Br | CHCl | 1 | 1 | CO$_2$CH$_3$ | CH$_2$Cl |
| Cl | Br | CHCl | 1 | 1 | CO$_2$CH$_3$ | CH$_2$Br |
| Cl | Br | CHCl | 1 | 1 | CH$_2$C≡CH | CH$_2$Cl |
| Cl | Br | CHCl | 1 | 1 | CH$_2$C≡CH | CH$_2$Br |
| Cl | Br | CHCl | 1 | 2 | H | CH$_2$Cl |
| Cl | Br | CHCl | 1 | 2 | H | CH$_2$Br |
| Cl | Br | CHCl | 1 | 2 | C(=O)CH$_3$ | CH$_2$Cl |
| Cl | Br | CHCl | 1 | 2 | C(=O)CH$_3$ | CH$_2$Br |
| Cl | Br | CHCl | 1 | 2 | CO$_2$CH$_3$ | CH$_2$Cl |
| Cl | Br | CHCl | 1 | 2 | CO$_2$CH$_3$ | CH$_2$Br |
| Cl | Br | CHCl | 1 | 2 | CH$_2$C≡CH | CH$_2$Cl |
| Cl | Br | CHCl | 1 | 2 | CH$_2$C≡CH | CH$_2$Br |
| Cl | CN | CH$_2$ | 1 | 1 | H | CH$_2$Cl |
| Cl | CN | CH$_2$ | 1 | 1 | H | CH$_2$Br |
| Cl | CN | CH$_2$ | 1 | 1 | C(=O)CH$_3$ | CH$_2$Cl |
| Cl | CN | CH$_2$ | 1 | 1 | C(=O)CH$_3$ | CH$_2$Br |
| Cl | CN | CH$_2$ | 1 | 1 | CO$_2$CH$_3$ | CH$_2$Cl |
| Cl | CN | CH$_2$ | 1 | 1 | CO$_2$CH$_3$ | CH$_2$Br |
| Cl | CN | CH$_2$ | 1 | 1 | CH$_2$C≡CH | CH$_2$Cl |
| Cl | CN | CH$_2$ | 1 | 1 | CH$_2$C≡CH | CH$_2$Br |
| Cl | CN | CH$_2$ | 1 | 2 | H | CH$_2$Cl |
| Cl | CN | CH$_2$ | 1 | 2 | H | CH$_2$Br |
| Cl | CN | CH$_2$ | 1 | 2 | C(=O)CH$_3$ | CH$_2$Cl |
| Cl | CN | CH$_2$ | 1 | 2 | C(=O)CH$_3$ | CH$_2$Br |
| Cl | CN | CH$_2$ | 1 | 2 | CO$_2$CH$_3$ | CH$_2$Cl |
| Cl | CN | CH$_2$ | 1 | 2 | CO$_2$CH$_3$ | CH$_2$Br |
| Cl | CN | CH$_2$ | 1 | 2 | CH$_2$C≡CH | CH$_2$Cl |
| Cl | CN | CH$_2$ | 1 | 2 | CH$_2$C≡CH | CH$_2$Br |
| Cl | CN | CHF | 1 | 1 | H | CH$_2$Cl |
| Cl | CN | CHF | 1 | 1 | H | CH$_2$Br |
| Cl | CN | CHF | 1 | 1 | C(=O)CH$_3$ | CH$_2$Cl |
| Cl | CN | CHF | 1 | 1 | C(=O)CH$_3$ | CH$_2$Br |
| Cl | CN | CHF | 1 | 1 | CO$_2$CH$_3$ | CH$_2$Cl |
| Cl | CN | CHF | 1 | 1 | CO$_2$CH$_3$ | CH$_2$Br |
| Cl | CN | CHF | 1 | 1 | CH$_2$C≡CH | CH$_2$Cl |
| Cl | CN | CHF | 1 | 1 | CH$_2$C≡CH | CH$_2$Br |
| Cl | CN | CHF | 1 | 2 | H | CH$_2$Cl |
| Cl | CN | CHF | 1 | 2 | H | CH$_2$Br |
| Cl | CN | CHF | 1 | 2 | C(=O)CH$_3$ | CH$_2$Cl |
| Cl | CN | CHF | 1 | 2 | C(=O)CH$_3$ | CH$_2$Br |
| Cl | CN | CHF | 1 | 2 | CO$_2$CH$_3$ | CH$_2$Cl |
| Cl | CN | CHF | 1 | 2 | CO$_2$CH$_3$ | CH$_2$Br |
| Cl | CN | CHF | 1 | 2 | CH$_2$C≡CH | CH$_2$Cl |
| Cl | CN | CHF | 1 | 2 | CH$_2$C≡CH | CH$_2$Br |
| Cl | CN | CHCl | 1 | 1 | H | CH$_2$Cl |
| Cl | CN | CHCl | 1 | 1 | H | CH$_2$Br |
| Cl | CN | CHCl | 1 | 1 | C(=O)CH$_3$ | CH$_2$Cl |
| Cl | CN | CHCl | 1 | 1 | C(=O)CH$_3$ | CH$_2$Br |
| Cl | CN | CHCl | 1 | 1 | CO$_2$CH$_3$ | CH$_2$Cl |
| Cl | CN | CHCl | 1 | 1 | CO$_2$CH$_3$ | CH$_2$Br |
| Cl | CN | CHCl | 1 | 1 | CH$_2$C≡CH | CH$_2$Cl |
| Cl | CN | CHCl | 1 | 1 | CH$_2$C≡CH | CH$_2$Br |
| Cl | CN | CHCl | 1 | 2 | H | CH$_2$Cl |
| Cl | CN | CHCl | 1 | 2 | H | CH$_2$Br |
| Cl | CN | CHCl | 1 | 2 | C(=O)CH$_3$ | CH$_2$Cl |
| Cl | CN | CHCl | 1 | 2 | C(=O)CH$_3$ | CH$_2$Br |
| Cl | CN | CHCl | 1 | 2 | CO$_2$CH$_3$ | CH$_2$Cl |
| Cl | CN | CHCl | 1 | 2 | CO$_2$CH$_3$ | CH$_2$Br |
| Cl | CN | CHCl | 1 | 2 | CH$_2$C≡CH | CH$_2$Cl |
| Cl | CN | CHCl | 1 | 2 | CH$_2$C≡CH | CH$_2$Br |

J = 19, Q = O, and R²⁴ = C(O)N(OCH$_3$)(CH$_3$)

| X | Y | Z | n | m | R¹ | R² |
|---|---|---|---|---|----|----|
| F | H | CH$_2$ | 1 | 1 | H | CH$_2$Cl |
| F | H | CH$_2$ | 1 | 1 | H | CH$_2$Br |
| F | H | CH$_2$ | 1 | 1 | C(=O)CH$_3$ | CH$_2$Cl |
| F | H | CH$_2$ | 1 | 1 | C(=O)CH$_3$ | CH$_2$Br |
| F | H | CH$_2$ | 1 | 1 | CO$_2$CH$_3$ | CH$_2$Cl |
| F | H | CH$_2$ | 1 | 1 | CO$_2$CH$_3$ | CH$_2$Br |
| F | H | CH$_2$ | 1 | 1 | CH$_2$C≡CH | CH$_2$Cl |
| F | H | CH$_2$ | 1 | 1 | CH$_2$C≡CH | CH$_2$Br |
| F | H | CH$_2$ | 1 | 2 | H | CH$_2$Cl |
| F | H | CH$_2$ | 1 | 2 | H | CH$_2$Br |
| F | H | CH$_2$ | 1 | 2 | C(=O)CH$_3$ | CH$_2$Cl |
| F | H | CH$_2$ | 1 | 2 | C(=O)CH$_3$ | CH$_2$Br |
| F | H | CH$_2$ | 1 | 2 | CO$_2$CH$_3$ | CH$_2$Cl |
| F | H | CH$_2$ | 1 | 2 | CO$_2$CH$_3$ | CH$_2$Br |
| F | H | CH$_2$ | 1 | 2 | CH$_2$C≡CH | CH$_2$Cl |
| F | H | CH$_2$ | 1 | 2 | CH$_2$C≡CH | CH$_2$Br |
| F | H | CHF | 1 | 1 | H | CH$_2$Cl |
| F | H | CHF | 1 | 1 | H | CH$_2$Br |
| F | H | CHF | 1 | 1 | C(=O)CH$_3$ | CH$_2$Cl |
| F | H | CHF | 1 | 1 | C(=O)CH$_{33}$ | CH$_2$Br |
| F | H | CHF | 1 | 1 | CO$_2$CH$_3$ | CH$_2$Cl |
| F | H | CHF | 1 | 1 | CO$_2$CH$_3$ | CH$_2$Br |
| F | H | CHF | 1 | 1 | CH$_2$C≡CH | CH$_2$Cl |
| F | H | CHF | 1 | 1 | CH$_2$C≡CH | CH$_2$Br |
| F | H | CHF | 1 | 2 | H | CH$_2$Cl |
| F | H | CHF | 1 | 2 | H | CH$_2$Br |
| F | H | CHF | 1 | 2 | C(=O)CH$_3$ | CH$_2$Cl |
| F | H | CHF | 1 | 2 | C(=O)CH$_3$ | CH$_2$Br |
| F | H | CHF | 1 | 2 | CO$_2$CH$_3$ | CH$_2$Cl |
| F | H | CHF | 1 | 2 | CO$_2$CH$_3$ | CH$_2$Br |
| F | H | CHF | 1 | 2 | CH$_2$C≡CH | CH$_2$Cl |
| F | H | CHF | 1 | 2 | CH$_2$C≡CH | CH$_2$Br |
| F | H | CHCl | 1 | 1 | H | CH$_2$Cl |
| F | H | CHCl | 1 | 1 | H | CH$_2$Br |
| F | H | CHCl | 1 | 1 | C(=O)CH$_3$ | CH$_2$Cl |
| F | H | CHCl | 1 | 1 | C(=O)CH$_3$ | CH$_2$Br |
| F | H | CHCl | 1 | 1 | CO$_2$CH$_3$ | CH$_2$Cl |
| F | H | CHCl | 1 | 1 | CO$_2$CH$_3$ | CH$_2$Br |
| F | H | CHCl | 1 | 1 | CH$_2$C≡CH | CH$_2$Cl |
| F | H | CHCl | 1 | 1 | CH$_2$C≡CH | CH$_2$Br |
| F | H | CHCl | 1 | 2 | H | CH$_2$Cl |
| F | H | CHCl | 1 | 2 | H | CH$_2$Br |
| F | H | CHCl | 1 | 2 | C(=O)CH$_3$ | CH$_2$Cl |
| F | H | CHCl | 1 | 2 | C(=O)CH$_3$ | CH$_2$Br |
| F | H | CHCl | 1 | 2 | CO$_2$CH$_3$ | CH$_2$Cl |
| F | H | CHCl | 1 | 2 | CO$_2$CH$_3$ | CH$_2$Br |
| F | H | CHCl | 1 | 2 | CH$_2$C≡CH | CH$_2$Cl |
| F | H | CHCl | 1 | 2 | CH$_2$C≡CH | CH$_2$Br |
| F | Cl | CH$_2$ | 1 | 1 | H | CH$_2$Cl |
| F | Cl | CH$_2$ | 1 | 1 | H | CH$_2$Br |
| F | Cl | CH$_2$ | 1 | 1 | C(=O)CH$_3$ | CH$_2$Cl |
| F | Cl | CH$_2$ | 1 | 1 | C(=O)CH$_3$ | CH$_2$Br |
| F | Cl | CH$_2$ | 1 | 1 | CO$_2$CH$_3$ | CH$_2$Cl |
| F | Cl | CH$_2$ | 1 | 1 | CO$_2$CH$_3$ | CH$_2$Br |
| F | Cl | CH$_2$ | 1 | 1 | CH$_2$C≡CH | CH$_2$Cl |
| F | Cl | CH$_2$ | 1 | 1 | CH$_2$C≡CH | CH$_2$Br |
| F | Cl | CH$_2$ | 1 | 2 | H | CH$_2$Cl |
| F | Cl | CH$_2$ | 1 | 2 | H | CH$_2$Br |
| F | Cl | CH$_2$ | 1 | 2 | C(=O)CH$_3$ | CH$_2$Cl |
| F | Cl | CH$_2$ | 1 | 2 | C(=O)CH$_3$ | CH$_2$Br |
| F | Cl | CH$_2$ | 1 | 2 | CO$_2$CH$_3$ | CH$_2$Cl |
| F | Cl | CH$_2$ | 1 | 2 | CO$_2$CH$_3$ | CH$_2$Br |
| F | Cl | CH$_2$ | 1 | 2 | CH$_2$C≡CH | CH$_2$Cl |
| F | Cl | CH$_2$ | 1 | 2 | CH$_2$C≡CH | CH$_2$Br |
| F | Cl | CHF | 1 | 1 | H | CH$_2$Cl |
| F | Cl | CHF | 1 | 1 | H | CH$_2$Br |
| F | Cl | CHF | 1 | 1 | C(=O)CH$_3$ | CH$_2$Cl |
| F | Cl | CHF | 1 | 1 | C(=O)CH$_3$ | CH$_2$Br |
| F | Cl | CHF | 1 | 1 | CO$_2$CH$_3$ | CH$_2$Cl |
| F | Cl | CHF | 1 | 1 | CO$_2$CH$_3$ | CH$_2$Br |
| F | Cl | CHF | 1 | 1 | CH$_2$C≡CH | CH$_2$Cl |
| F | Cl | CHF | 1 | 1 | CH$_2$C≡CH | CH$_2$Br |
| F | Cl | CHF | 1 | 2 | H | CH$_2$Cl |
| F | Cl | CHF | 1 | 2 | H | CH$_2$Br |
| F | Cl | CHF | 1 | 2 | C(=O)CH$_3$ | CH$_2$Cl |
| F | Cl | CHF | 1 | 2 | C(=O)CH$_3$ | CH$_2$Br |
| F | Cl | CHF | 1 | 2 | CO$_2$CH$_3$ | CH$_2$Cl |
| F | Cl | CHF | 1 | 2 | CO$_2$CH$_3$ | CH$_2$Br |
| F | Cl | CHF | 1 | 2 | CH$_2$C≡CH | CH$_2$Cl |
| F | Cl | CHF | 1 | 2 | CH$_2$C≡CH | CH$_2$Br |
| F | Cl | CHCl | 1 | 1 | H | CH$_2$Cl |

TABLE 1-continued

| | | | | | | |
|---|---|---|---|---|---|---|
| F | Cl | CHCl | 1 | 1 | H | CH$_2$Cl |
| F | Cl | CHCl | 1 | 1 | H | CH$_2$Br |
| F | Cl | CHCl | 1 | 1 | C(=O)CH$_3$ | CH$_2$Cl |
| F | Cl | CHCl | 1 | 1 | C(=O)CH$_3$ | CH$_2$Br |
| F | Cl | CHCl | 1 | 1 | CO$_2$CH$_3$ | CH$_2$Cl |
| F | Cl | CHCl | 1 | 1 | CO$_2$CH$_3$ | CH$_2$Br |
| F | Cl | CHCl | 1 | 1 | CH$_2$C≡CH | CH$_2$Cl |
| F | Cl | CHCl | 1 | 1 | CH$_2$C≡CH | CH$_2$Br |
| F | Cl | CHCl | 1 | 2 | H | CH$_2$Cl |
| F | Cl | CHCl | 1 | 2 | H | CH$_2$Br |
| F | Cl | CHCl | 1 | 2 | C(=O)CH$_3$ | CH$_2$Cl |
| F | Cl | CHCl | 1 | 2 | C(=O)CH$_3$ | CH$_2$Br |
| F | Cl | CHCl | 1 | 2 | CO$_2$CH$_3$ | CH$_2$Cl |
| F | Cl | CHCl | 1 | 2 | CO$_2$CH$_3$ | CH$_2$Br |
| F | Cl | CHCl | 1 | 2 | CH$_2$C≡CH | CH$_2$Cl |
| F | Cl | CHCl | 1 | 2 | CH$_2$C≡CH | CH$_2$Br |
| F | Br | CH$_2$ | 1 | 1 | H | CH$_2$Cl |
| F | Br | CH$_2$ | 1 | 1 | H | CH$_2$Br |
| F | Br | CH$_2$ | 1 | 1 | C(=O)CH$_3$ | CH$_2$Cl |
| F | Br | CH$_2$ | 1 | 1 | C(=O)CH$_3$ | CH$_2$Br |
| F | Br | CH$_2$ | 1 | 1 | CO$_2$CH$_3$ | CH$_2$Cl |
| F | Br | CH$_2$ | 1 | 1 | CO$_2$CH$_3$ | CH$_2$Br |
| F | Br | CH$_2$ | 1 | 1 | CH$_2$C≡CH | CH$_2$Cl |
| F | Br | CH$_2$ | 1 | 1 | CH$_2$C≡CH | CH$_2$Br |
| F | Br | CH$_2$ | 1 | 2 | H | CH$_2$Cl |
| F | Br | CH$_2$ | 1 | 2 | H | CH$_2$Br |
| F | Br | CH$_2$ | 1 | 2 | C(=O)CH$_3$ | CH$_2$Cl |
| F | Br | CH$_2$ | 1 | 2 | C(=O)CH$_3$ | CH$_2$Br |
| F | Br | CH$_2$ | 1 | 2 | CO$_2$CH$_3$ | CH$_2$Cl |
| F | Br | CH$_2$ | 1 | 2 | CO$_2$CH$_3$ | CH$_2$Br |
| F | Br | CH$_2$ | 1 | 2 | CH$_2$C≡CH | CH$_2$Cl |
| F | Br | CH$_2$ | 1 | 2 | CH$_2$C≡CH | CH$_2$Br |
| F | Br | CHF | 1 | 1 | H | CH$_2$Cl |
| F | Br | CHF | 1 | 1 | H | CH$_2$Br |
| F | Br | CHF | 1 | 1 | C(=O)CH$_3$ | CH$_2$Cl |
| F | Br | CHF | 1 | 1 | C(=O)CH$_3$ | CH$_2$Br |
| F | Br | CHF | 1 | 1 | CO$_2$CH$_3$ | CH$_2$Cl |
| F | Br | CHF | 1 | 1 | CO$_2$CH$_3$ | CH$_2$Br |
| F | Br | CHF | 1 | 1 | CH$_2$C≡CH | CH$_2$Cl |
| F | Br | CHF | 1 | 1 | CH$_2$C≡CH | CH$_2$Br |
| F | Br | CHF | 1 | 2 | H | CH$_2$Cl |
| F | Br | CHF | 1 | 2 | H | CH$_2$Br |
| F | Br | CHF | 1 | 2 | C(=O)CH$_3$ | CH$_2$Cl |
| F | Br | CHF | 1 | 2 | C(=O)CH$_3$ | CH$_2$Br |
| F | Br | CHF | 1 | 2 | CO$_2$CH$_3$ | CH$_2$Cl |
| F | Br | CHF | 1 | 2 | CO$_2$CH$_3$ | CH$_2$Br |
| F | Br | CHF | 1 | 2 | CH$_2$C≡CH | CH$_2$Cl |
| F | Br | CHF | 1 | 2 | CH$_2$C≡CH | CH$_2$Br |
| F | Br | CHCl | 1 | 1 | H | CH$_2$Cl |
| F | Br | CHCl | 1 | 1 | H | CH$_2$Br |
| F | Br | CHCl | 1 | 1 | C(=O)CH$_3$ | CH$_2$Cl |
| F | Br | CHCl | 1 | 1 | C(=O)CH$_3$ | CH$_2$Br |
| F | Br | CHCl | 1 | 1 | CO$_2$CH$_3$ | CH$_2$Cl |
| F | Br | CHCl | 1 | 1 | CO$_2$CH$_3$ | CH$_2$Br |
| F | Br | CHCl | 1 | 1 | CH$_2$C≡CH | CH$_2$Cl |
| F | Br | CHCl | 1 | 1 | CH$_2$C≡CH | CH$_2$Br |
| F | Br | CHCl | 1 | 2 | H | CH$_2$Cl |
| F | Br | CHCl | 1 | 2 | H | CH$_2$Br |
| F | Br | CHCl | 1 | 2 | C(=O)CH$_3$ | CH$_2$Cl |
| F | Br | CHCl | 1 | 2 | C(=O)CH$_3$ | CH$_2$Br |
| F | Br | CHCl | 1 | 2 | CO$_2$CH$_3$ | CH$_2$Cl |
| F | Br | CHCl | 1 | 2 | CO$_2$CH$_3$ | CH$_2$Br |
| F | Br | CHCl | 1 | 2 | CH$_2$C≡CH | CH$_2$Cl |
| F | Br | CHCl | 1 | 2 | CH$_2$C≡CH | CH$_2$Br |
| F | CN | CH$_2$ | 1 | 1 | H | CH$_2$Cl |
| F | CN | CH$_2$ | 1 | 1 | H | CH$_2$Br |
| F | CN | CH$_2$ | 1 | 1 | C(=O)CH$_3$ | CH$_2$Cl |
| F | CN | CH$_2$ | 1 | 1 | C(=O)CH$_3$ | CH$_2$Br |
| F | CN | CH$_2$ | 1 | 1 | CO$_2$CH$_3$ | CH$_2$Cl |
| F | CN | CH$_2$ | 1 | 1 | CO$_2$CH$_3$ | CH$_2$Br |
| F | CN | CH$_2$ | 1 | 1 | CH$_2$C≡CH | CH$_2$Cl |
| F | CN | CH$_2$ | 1 | 1 | CH$_2$C≡CH | CH$_2$Br |
| F | CN | CH$_2$ | 1 | 2 | H | CH$_2$Cl |
| F | CN | CH$_2$ | 1 | 2 | H | CH$_2$Br |
| F | CN | CH$_2$ | 1 | 2 | C(=O)CH$_3$ | CH$_2$Cl |
| F | CN | CH$_2$ | 1 | 2 | C(=O)CH$_3$ | CH$_2$Br |
| F | CN | CH$_2$ | 1 | 2 | CO$_2$CH$_3$ | CH$_2$Cl |
| F | CN | CH$_2$ | 1 | 2 | CO$_2$CH$_3$ | CH$_2$Br |
| F | CN | CH$_2$ | 1 | 2 | CH$_2$C≡CH | CH$_2$Cl |
| F | CN | CH$_2$ | 1 | 2 | CH$_2$C≡CH | CH$_2$Br |
| F | CN | CHF | 1 | 1 | H | CH$_2$Cl |
| F | CN | CHF | 1 | 1 | H | CH$_2$Br |
| F | CN | CHF | 1 | 1 | C(=O)CH$_3$ | CH$_2$Cl |
| F | CN | CHF | 1 | 1 | C(=O)CH$_3$ | CH$_2$Br |
| F | CN | CHF | 1 | 1 | CO$_2$CH$_3$ | CH$_2$Cl |
| F | CN | CHF | 1 | 1 | CO$_2$CH$_3$ | CH$_2$Br |
| F | CN | CHF | 1 | 1 | CH$_2$C≡CH | CH$_2$Cl |
| F | CN | CHF | 1 | 1 | CH$_2$C≡CH | CH$_2$Br |
| F | CN | CHF | 1 | 2 | H | CH$_2$Cl |
| F | CN | CHF | 1 | 2 | H | CH$_2$Br |
| F | CN | CHF | 1 | 2 | C(=O)CH$_3$ | CH$_2$Cl |
| F | CN | CHF | 1 | 2 | C(=O)CH$_3$ | CH$_2$Br |
| F | CN | CHF | 1 | 2 | CO$_2$CH$_3$ | CH$_2$Cl |
| F | CN | CHF | 1 | 2 | CO$_2$CH$_3$ | CH$_2$Br |
| F | CN | CHF | 1 | 2 | CH$_2$C≡CH | CH$_2$Cl |
| F | CN | CHF | 1 | 2 | CH$_2$C≡CH | CH$_2$Br |
| F | CN | CHCl | 1 | 1 | H | CH$_2$Cl |
| F | CN | CHCl | 1 | 1 | H | CH$_2$Br |
| F | CN | CHCl | 1 | 1 | C(=O)CH$_3$ | CH$_2$Cl |
| F | CN | CHCl | 1 | 1 | C(=O)CH$_3$ | CH$_2$Br |
| F | CN | CHCl | 1 | 1 | CO$_2$CH$_3$ | CH$_2$Cl |
| F | CN | CHCl | 1 | 1 | CO$_2$CH$_3$ | CH$_2$Br |
| F | CN | CHCl | 1 | 1 | CH$_2$C≡CH | CH$_2$Cl |
| F | CN | CHCl | 1 | 1 | CH$_2$C≡CH | CH$_2$Br |
| F | CN | CHCl | 1 | 2 | H | CH$_2$Cl |
| F | CN | CHCl | 1 | 2 | H | CH$_2$Br |
| F | CN | CHCl | 1 | 2 | C(=O)CH$_3$ | CH$_2$Cl |
| F | CN | CHCl | 1 | 2 | C(=O)CH$_3$ | CH$_2$Br |
| F | CN | CHCl | 1 | 2 | CO$_2$CH$_3$ | CH$_2$Cl |
| F | CN | CHCl | 1 | 2 | CO$_2$CH$_3$ | CH$_2$Br |
| F | CN | CHCl | 1 | 2 | CH$_2$C≡CH | CH$_2$Cl |
| F | CN | CHCl | 1 | 2 | CH$_2$C≡CH | CH$_2$Br |
| Cl | H | CH$_2$ | 1 | 1 | H | CH$_2$Cl |
| Cl | H | CH$_2$ | 1 | 1 | H | CH$_2$Br |
| Cl | H | CH$_2$ | 1 | 1 | C(=O)CH$_3$ | CH$_2$Cl |
| Cl | H | CH$_2$ | 1 | 1 | C(=O)CH$_3$ | CH$_2$Br |
| Cl | H | CH$_2$ | 1 | 1 | CO$_2$CH$_3$ | CH$_2$Cl |
| Cl | H | CH$_2$ | 1 | 1 | CO$_2$CH$_3$ | CH$_2$Br |
| Cl | H | CH$_2$ | 1 | 1 | CH$_2$C≡CH | CH$_2$Cl |
| Cl | H | CH$_2$ | 1 | 1 | CH$_2$C≡CH | CH$_2$Br |
| Cl | H | CH$_2$ | 1 | 2 | H | CH$_2$Cl |
| Cl | H | CH$_2$ | 1 | 2 | H | CH$_2$Br |
| Cl | H | CH$_2$ | 1 | 2 | C(=O)CH$_3$ | CH$_2$Cl |
| Cl | H | CH$_2$ | 1 | 2 | C(=O)CH$_3$ | CH$_2$Br |
| Cl | H | CH$_2$ | 1 | 2 | CO$_2$CH$_3$ | CH$_2$Cl |
| Cl | H | CH$_2$ | 1 | 2 | CO$_2$CH$_3$ | CH$_2$Br |
| Cl | H | CH$_2$ | 1 | 2 | CH$_2$C≡CH | CH$_2$Cl |
| Cl | H | CH$_2$ | 1 | 2 | CH$_2$C≡CH | CH$_2$Br |
| Cl | H | CHF | 1 | 1 | H | CH$_2$Cl |
| Cl | H | CHF | 1 | 1 | H | CH$_2$Br |
| Cl | H | CHF | 1 | 1 | C(=O)CH$_3$ | CH$_2$Cl |
| Cl | H | CHF | 1 | 1 | C(=O)CH$_3$ | CH$_2$Br |
| Cl | H | CHF | 1 | 1 | CO$_2$CH$_3$ | CH$_2$Cl |
| Cl | H | CHF | 1 | 1 | CO$_2$CH$_3$ | CH$_2$Br |
| Cl | H | CHF | 1 | 1 | CH$_2$C≡CH | CH$_2$Cl |
| Cl | H | CHF | 1 | 1 | CH$_2$C≡CH | CH$_2$Br |
| Cl | H | CHF | 1 | 2 | H | CH$_2$Cl |
| Cl | H | CHF | 1 | 2 | H | CH$_2$Br |
| Cl | H | CHF | 1 | 2 | C(=O)CH$_3$ | CH$_2$Cl |
| Cl | H | CHF | 1 | 2 | C(=O)CH$_3$ | CH$_2$Br |
| Cl | H | CHF | 1 | 2 | CO$_2$CH$_3$ | CH$_2$Cl |
| Cl | H | CHF | 1 | 2 | CO$_2$CH$_3$ | CH$_2$Br |
| Cl | H | CHF | 1 | 2 | CH$_2$C≡CH | CH$_2$Cl |
| Cl | H | CHF | 1 | 2 | CH$_2$C≡CH | CH$_2$Br |
| Cl | H | CHCl | 1 | 1 | H | CH$_2$Cl |
| Cl | H | CHCl | 1 | 1 | H | CH$_2$Br |
| Cl | H | CHCl | 1 | 1 | C(=O)CH$_3$ | CH$_2$Cl |
| Cl | H | CHCl | 1 | 1 | C(=O)CH$_3$ | CH$_2$Br |
| Cl | H | CHCl | 1 | 1 | CO$_2$CH$_3$ | CH$_2$Cl |
| Cl | H | CHCl | 1 | 1 | CO$_2$CH$_3$ | CH$_2$Br |
| Cl | H | CHCl | 1 | 1 | CH$_2$C≡CH | CH$_2$Cl |
| Cl | H | CHCl | 1 | 1 | CH$_2$C≡CH | CH$_2$Br |
| Cl | H | CHCl | 1 | 2 | H | CH$_2$Cl |
| Cl | H | CHCl | 1 | 2 | H | CH$_2$Br |
| Cl | H | CHCl | 1 | 2 | C(=O)CH$_3$ | CH$_2$Cl |
| Cl | H | CHCl | 1 | 2 | C(=O)CH$_3$ | CH$_2$Br |
| Cl | H | CHCl | 1 | 2 | CO$_2$CH$_3$ | CH$_2$Cl |
| Cl | H | CHCl | 1 | 2 | CO$_2$CH$_3$ | CH$_2$Br |
| Cl | H | CHCl | 1 | 2 | CH$_2$C≡CH | CH$_2$Cl |

TABLE 1-continued

| X | Y | Z | n | m | R¹ | R² |
|---|---|---|---|---|---|---|
| Cl | H | CHCl | 1 | 2 | CH₂C≡CH | CH₂Br |
| Cl | Cl | CH₂ | 1 | 1 | H | CH₂Cl |
| Cl | Cl | CH₂ | 1 | 1 | H | CH₂Br |
| Cl | Cl | CH₂ | 1 | 1 | C(=O)CH₃ | CH₂Cl |
| Cl | Cl | CH₂ | 1 | 1 | C(=O)CH₃ | CH₂Br |
| Cl | Cl | CH₂ | 1 | 1 | CO₂CH₃ | CH₂Cl |
| Cl | Cl | CH₂ | 1 | 1 | CO₂CH₃ | CH₂Br |
| Cl | Cl | CH₂ | 1 | 1 | CH₂C≡CH | CH₂Cl |
| Cl | Cl | CH₂ | 1 | 1 | CH₂C≡CH | CH₂Br |
| Cl | Cl | CH₂ | 1 | 2 | H | CH₂Cl |
| Cl | Cl | CH₂ | 1 | 2 | H | CH₂Br |
| Cl | Cl | CH₂ | 1 | 2 | C(=O)CH₃ | CH₂Cl |
| Cl | Cl | CH₂ | 1 | 2 | C(=O)CH₃ | CH₂Br |
| Cl | Cl | CH₂ | 1 | 2 | CO₂CH₃ | CH₂Cl |
| Cl | Cl | CH₂ | 1 | 2 | CO₂CH₃ | CH₂Br |
| Cl | Cl | CH₂ | 1 | 2 | CH₂C≡CH | CH₂Cl |
| Cl | Cl | CH₂ | 1 | 2 | CH₂C≡CH | CH₂Br |
| Cl | Cl | CHF | 1 | 1 | H | CH₂Cl |
| Cl | Cl | CHF | 1 | 1 | H | CH₂Br |
| Cl | Cl | CHF | 1 | 1 | C(=O)CH₃ | CH₂Cl |
| Cl | Cl | CHF | 1 | 1 | C(=O)CH₃ | CH₂Br |
| Cl | Cl | CHF | 1 | 1 | CO₂CH₃ | CH₂Cl |
| Cl | Cl | CHF | 1 | 1 | CO₂CH₃ | CH₂Br |
| Cl | Cl | CHF | 1 | 1 | CH₂C≡CH | CH₂Cl |
| Cl | Cl | CHF | 1 | 1 | CH₂C≡CH | CH₂Br |
| Cl | Cl | CHF | 1 | 2 | H | CH₂Cl |
| Cl | Cl | CHF | 1 | 2 | H | CH₂Br |
| Cl | Cl | CHF | 1 | 2 | C(=O)CH₃ | CH₂Cl |
| Cl | Cl | CHF | 1 | 2 | C(=O)CH₃ | CH₂Br |
| Cl | Cl | CHF | 1 | 2 | CO₂CH₃ | CH₂Cl |
| Cl | Cl | CHF | 1 | 2 | CO₂CH₃ | CH₂Br |
| Cl | Cl | CHF | 1 | 2 | CH₂C≡CH | CH₂Cl |
| Cl | Cl | CHF | 1 | 2 | CH₂C≡CH | CH₂Br |
| Cl | Cl | CHCl | 1 | 1 | H | CH₂Cl |
| Cl | Cl | CHCl | 1 | 1 | H | CH₂Br |
| Cl | Cl | CHCl | 1 | 1 | C(=O)CH₃ | CH₂Cl |
| Cl | Cl | CHCl | 1 | 1 | C(=O)CH₃ | CH₂Br |
| Cl | Cl | CHCl | 1 | 1 | CO₂CH₃ | CH₂Cl |
| Cl | Cl | CHCl | 1 | 1 | CO₂CH₃ | CH₂Br |
| Cl | Cl | CHCl | 1 | 1 | CH₂C≡CH | CH₂Cl |
| Cl | Cl | CHCl | 1 | 1 | CH₂C≡CH | CH₂Br |
| Cl | Cl | CHCl | 1 | 2 | H | CH₂Cl |
| Cl | Cl | CHCl | 1 | 2 | H | CH₂Br |
| Cl | Cl | CHCl | 1 | 2 | C(=O)CH₃ | CH₂Cl |
| Cl | Cl | CHCl | 1 | 2 | C(=O)CH₃ | CH₂Br |
| Cl | Cl | CHCl | 1 | 2 | CO₂CH₃ | CH₂Cl |
| Cl | Cl | CHCl | 1 | 2 | CO₂CH₃ | CH₂Br |
| Cl | Cl | CHCl | 1 | 2 | CH₂C≡CH | CH₂Cl |
| Cl | Cl | CHCl | 1 | 2 | CH₂C≡CH | CH₂Br |
| Cl | Br | CH₂ | 1 | 1 | H | CH₂Cl |
| Cl | Br | CH₂ | 1 | 1 | H | CH₂Br |
| Cl | Br | CH₂ | 1 | 1 | C(=O)CH₃ | CH₂Cl |
| Cl | Br | CH₂ | 1 | 1 | C(=O)CH₃ | CH₂Br |
| Cl | Br | CH₂ | 1 | 1 | CO₂CH₃ | CH₂Cl |
| Cl | Br | CH₂ | 1 | 1 | CO₂CH₃ | CH₂Br |
| Cl | Br | CH₂ | 1 | 1 | CH₂C≡CH | CH₂Cl |
| Cl | Br | CH₂ | 1 | 1 | CH₂C≡CH | CH₂Br |
| Cl | Br | CH₂ | 1 | 2 | H | CH₂Cl |
| Cl | Br | CH₂ | 1 | 2 | H | CH₂Br |
| Cl | Br | CH₂ | 1 | 2 | C(=O)CH₃ | CH₂Cl |
| Cl | Br | CH₂ | 1 | 2 | C(=O)CH₃ | CH₂Br |
| Cl | Br | CH₂ | 1 | 2 | CO₂CH₃ | CH₂Cl |
| Cl | Br | CH₂ | 1 | 2 | CO₂CH₃ | CH₂Br |
| Cl | Br | CH₂ | 1 | 2 | CH₂C≡CH | CH₂Cl |
| Cl | Br | CH₂ | 1 | 2 | CH₂C≡CH | CH₂Br |
| Cl | Br | CHF | 1 | 1 | H | CH₂Cl |
| Cl | Br | CHF | 1 | 1 | H | CH₂Br |
| Cl | Br | CHF | 1 | 1 | C(=O)CH₃ | CH₂Cl |
| Cl | Br | CHF | 1 | 1 | C(=O)CH₃ | CH₂Br |
| Cl | Br | CHF | 1 | 1 | CO₂CH₃ | CH₂Cl |
| Cl | Br | CHF | 1 | 1 | CO₂CH₃ | CH₂Br |
| Cl | Br | CHF | 1 | 1 | CH₂C≡CH | CH₂Cl |
| Cl | Br | CHF | 1 | 1 | CH₂C≡CH | CH₂Br |
| Cl | Br | CHF | 1 | 2 | H | CH₂Cl |
| Cl | Br | CHF | 1 | 2 | H | CH₂Br |
| Cl | Br | CHF | 1 | 2 | C(=O)CH₃ | CH₂Cl |
| Cl | Br | CHF | 1 | 2 | C(=O)CH₃ | CH₂Br |
| Cl | Br | CHF | 1 | 2 | CO₂CH₃ | CH₂Cl |
| Cl | Br | CHF | 1 | 2 | CO₂CH₃ | CH₂Br |
| Cl | Br | CHF | 1 | 2 | CH₂C≡CH | CH₂Cl |
| Cl | Br | CHF | 1 | 2 | CH₂C≡CH | CH₂Br |
| Cl | Br | CHCl | 1 | 1 | H | CH₂Cl |
| Cl | Br | CHCl | 1 | 1 | H | CH₂Br |
| Cl | Br | CHCl | 1 | 1 | C(=O)CH₃ | CH₂Cl |
| Cl | Br | CHCl | 1 | 1 | C(=O)CH₃ | CH₂Br |
| Cl | Br | CHCl | 1 | 1 | CO₂CH₃ | CH₂Cl |
| Cl | Br | CHCl | 1 | 1 | CO₂CH₃ | CH₂Br |
| Cl | Br | CHCl | 1 | 1 | CH₂C≡CH | CH₂Cl |
| Cl | Br | CHCl | 1 | 1 | CH₂C≡CH | CH₂Br |
| Cl | Br | CHCl | 1 | 2 | H | CH₂Cl |
| Cl | Br | CHCl | 1 | 2 | H | CH₂Br |
| Cl | Br | CHCl | 1 | 2 | C(=O)CH₃ | CH₂Cl |
| Cl | Br | CHCl | 1 | 2 | C(=O)CH₃ | CH₂Br |
| Cl | Br | CHCl | 1 | 2 | CO₂CH₃ | CH₂Cl |
| Cl | Br | CHCl | 1 | 2 | CO₂CH₃ | CH₂Br |
| Cl | Br | CHCl | 1 | 2 | CH₂C≡CH | CH₂Cl |
| Cl | Br | CHCl | 1 | 2 | CH₂C≡CH | CH₂Br |
| Cl | CN | CH₂ | 1 | 1 | H | CH₂Cl |
| Cl | CN | CH₂ | 1 | 1 | H | CH₂Br |
| Cl | CN | CH₂ | 1 | 1 | C(=O)CH₃ | CH₂Cl |
| Cl | CN | CH₂ | 1 | 1 | C(=O)CH₃ | CH₂Br |
| Cl | CN | CH₂ | 1 | 1 | CO₂CH₃ | CH₂Cl |
| Cl | CN | CH₂ | 1 | 1 | CO₂CH₃ | CH₂Br |
| Cl | CN | CH₂ | 1 | 1 | CH₂C≡CH | CH₂Cl |
| Cl | CN | CH₂ | 1 | 1 | CH₂C≡CH | CH₂Br |
| Cl | CN | CH₂ | 1 | 2 | H | CH₂Cl |
| Cl | CN | CH₂ | 1 | 2 | H | CH₂Br |
| Cl | CN | CH₂ | 1 | 2 | C(=O)CH₃ | CH₂Cl |
| Cl | CN | CH₂ | 1 | 2 | C(=O)CH₃ | CH₂Br |
| Cl | CN | CH₂ | 1 | 2 | CO₂CH₃ | CH₂Cl |
| Cl | CN | CH₂ | 1 | 2 | CO₂CH₃ | CH₂Br |
| Cl | CN | CH₂ | 1 | 2 | CH₂C≡CH | CH₂Cl |
| Cl | CN | CH₂ | 1 | 2 | CH₂C≡CH | CH₂Br |
| Cl | CN | CHF | 1 | 1 | H | CH₂Cl |
| Cl | CN | CHF | 1 | 1 | H | CH₂Br |
| Cl | CN | CHF | 1 | 1 | C(=O)CH₃ | CH₂Cl |
| Cl | CN | CHF | 1 | 1 | C(=O)CH₃ | CH₂Br |
| Cl | CN | CHF | 1 | 1 | CO₂CH₃ | CH₂Cl |
| Cl | CN | CHF | 1 | 1 | CO₂CH₃ | CH₂Br |
| Cl | CN | CHF | 1 | 1 | CH₂C≡CH | CH₂Cl |
| Cl | CN | CHF | 1 | 1 | CH₂C≡CH | CH₂Br |
| Cl | CN | CHF | 1 | 2 | H | CH₂Cl |
| Cl | CN | CHF | 1 | 2 | H | CH₂Br |
| Cl | CN | CHF | 1 | 2 | C(=O)CH₃ | CH₂Cl |
| Cl | CN | CHF | 1 | 2 | C(=O)CH₃ | CH₂Br |
| Cl | CN | CHF | 1 | 2 | CO₂CH₃ | CH₂Cl |
| Cl | CN | CHF | 1 | 2 | CO₂CH₃ | CH₂Br |
| Cl | CN | CHF | 1 | 2 | CH₂C≡CH | CH₂Cl |
| Cl | CN | CHF | 1 | 2 | CH₂C≡CH | CH₂Br |
| Cl | CN | CHCl | 1 | 1 | H | CH₂Cl |
| Cl | CN | CHCl | 1 | 1 | H | CH₂Br |
| Cl | CN | CHCl | 1 | 1 | C(=O)CH₃ | CH₂Cl |
| Cl | CN | CHCl | 1 | 1 | C(=O)CH₃ | CH₂Br |
| Cl | CN | CHCl | 1 | 1 | CO₂CH₃ | CH₂Cl |
| Cl | CN | CHCl | 1 | 1 | CO₂CH₃ | CH₂Br |
| Cl | CN | CHCl | 1 | 1 | CH₂C≡CH | CH₂Cl |
| Cl | CN | CHCl | 1 | 1 | CH₂C≡CH | CH₂Br |
| Cl | CN | CHCl | 1 | 2 | H | CH₂Cl |
| Cl | CN | CHCl | 1 | 2 | H | CH₂Br |
| Cl | CN | CHCl | 1 | 2 | C(=O)CH₃ | CH₂Cl |
| Cl | CN | CHCl | 1 | 2 | C(=O)CH₃ | CH₂Br |
| Cl | CN | CHCl | 1 | 2 | CO₂CH₃ | CH₂Cl |
| Cl | CN | CHCl | 1 | 2 | CO₂CH₃ | CH₂Br |
| Cl | CN | CHCl | 1 | 2 | CH₂C≡CH | CH₂Cl |
| Cl | CN | CHCl | 1 | 2 | CH₂C≡CH | CH₂Br |

J = 19, Q = O, and R²⁴ = C(O)N(CH₃)₂

| X | Y | Z | n | m | R¹ | R² |
|---|---|---|---|---|---|---|
| F | H | CH₂ | 1 | 1 | H | CH₂Cl |
| F | H | CH₂ | 1 | 1 | H | CH₂Br |
| F | H | CH₂ | 1 | 1 | C(=O)CH₃ | CH₂Cl |
| F | H | CH₂ | 1 | 1 | C(=O)CH₃ | CH₂Br |
| F | H | CH₂ | 1 | 1 | CO₂CH₃ | CH₂Cl |
| F | H | CH₂ | 1 | 1 | CO₂CH₃ | CH₂Br |
| F | H | CH₂ | 1 | 1 | CH₂C≡CH | CH₂Cl |
| F | H | CH₂ | 1 | 1 | CH₂C≡CH | CH₂Br |

TABLE 1-continued

| | | | | | | |
|---|---|---|---|---|---|---|
| F | H | CH$_2$ | 1 | 2 | H | CH$_2$Cl |
| F | H | CH$_2$ | 1 | 2 | H | CH$_2$Br |
| F | H | CH$_2$ | 1 | 2 | C(=O)CH$_3$ | CH$_2$Cl |
| F | H | CH$_2$ | 1 | 2 | C(=O)CH$_3$ | CH$_2$Br |
| F | H | CH$_2$ | 1 | 2 | CO$_2$CH$_3$ | CH$_2$Cl |
| F | H | CH$_2$ | 1 | 2 | CO$_2$CH$_3$ | CH$_2$Br |
| F | H | CH$_2$ | 1 | 2 | CH$_2$C≡CH | CH$_2$Cl |
| F | H | CH$_2$ | 1 | 2 | CH$_2$C≡CH | CH$_2$Br |
| F | H | CHF | 1 | 1 | H | CH$_2$Cl |
| F | H | CHF | 1 | 1 | H | CH$_2$Br |
| F | H | CHF | 1 | 1 | C(=O)CH$_3$ | CH$_2$Cl |
| F | H | CHF | 1 | 1 | C(=O)CH$_3$ | CH$_2$Br |
| F | H | CHF | 1 | 1 | CO$_2$CH$_3$ | CH$_2$Cl |
| F | H | CHF | 1 | 1 | CO$_2$CH$_3$ | CH$_2$Br |
| F | H | CHF | 1 | 1 | CH$_2$C≡CH | CH$_2$Cl |
| F | H | CHF | 1 | 1 | CH$_2$C≡CH | CH$_2$Br |
| F | H | CHF | 1 | 2 | H | CH$_2$Cl |
| F | H | CHF | 1 | 2 | H | CH$_2$Br |
| F | H | CHF | 1 | 2 | C(=O)CH$_3$ | CH$_2$Cl |
| F | H | CHF | 1 | 2 | C(=O)CH$_3$ | CH$_2$Br |
| F | H | CHF | 1 | 2 | CO$_2$CH$_3$ | CH$_2$Cl |
| F | H | CHF | 1 | 2 | CO$_2$CH$_3$ | CH$_2$Br |
| F | H | CHF | 1 | 2 | CH$_2$C≡CH | CH$_2$Cl |
| F | H | CHF | 1 | 2 | CH$_2$C≡CH | CH$_2$Br |
| F | H | CHCl | 1 | 1 | H | CH$_2$Cl |
| F | H | CHCl | 1 | 1 | H | CH$_2$Br |
| F | H | CHCl | 1 | 1 | C(=O)CH$_3$ | CH$_2$Cl |
| F | H | CHCl | 1 | 1 | C(=O)CH$_3$ | CH$_2$Br |
| F | H | CHCl | 1 | 1 | CO$_2$CH$_3$ | CH$_2$Cl |
| F | H | CHCl | 1 | 1 | CO$_2$CH$_3$ | CH$_2$Br |
| F | H | CHCl | 1 | 1 | CH$_2$C≡CH | CH$_2$Cl |
| F | H | CHCl | 1 | 1 | CH$_2$C≡CH | CH$_2$Br |
| F | H | CHCl | 1 | 2 | H | CH$_2$Cl |
| F | H | CHCl | 1 | 2 | H | CH$_2$Br |
| F | H | CHCl | 1 | 2 | C(=O)CH$_3$ | CH$_2$Cl |
| F | H | CHCl | 1 | 2 | C(=O)CH$_3$ | CH$_2$Br |
| F | H | CHCl | 1 | 2 | CO$_2$CH$_3$ | CH$_2$Cl |
| F | H | CHCl | 1 | 2 | CO$_2$CH$_3$ | CH$_2$Br |
| F | H | CHCl | 1 | 2 | CH$_2$C≡CH | CH$_2$Cl |
| F | H | CHCl | 1 | 2 | CH$_2$C≡CH | CH$_2$Br |
| F | Cl | CH$_2$ | 1 | 1 | H | CH$_2$Cl |
| F | Cl | CH$_2$ | 1 | 1 | H | CH$_2$Br |
| F | Cl | CH$_2$ | 1 | 1 | C(=O)CH$_3$ | CH$_2$Cl |
| F | Cl | CH$_2$ | 1 | 1 | C(=O)CH$_3$ | CH$_2$Br |
| F | Cl | CH$_2$ | 1 | 1 | CO$_2$CH$_3$ | CH$_2$Cl |
| F | Cl | CH$_2$ | 1 | 1 | CO$_2$CH$_3$ | CH$_2$Br |
| F | Cl | CH$_2$ | 1 | 1 | CH$_2$C≡CH | CH$_2$Cl |
| F | Cl | CH$_2$ | 1 | 1 | CH$_2$C≡CH | CH$_2$Br |
| F | Cl | CH$_2$ | 1 | 2 | H | CH$_2$Cl |
| F | Cl | CH$_2$ | 1 | 2 | H | CH$_2$Br |
| F | Cl | CH$_2$ | 1 | 2 | C(=O)CH$_3$ | CH$_2$Cl |
| F | Cl | CH$_2$ | 1 | 2 | C(=O)CH$_3$ | CH$_2$Br |
| F | Cl | CH$_2$ | 1 | 2 | CO$_2$CH$_3$ | CH$_2$Cl |
| F | Cl | CH$_2$ | 1 | 2 | CO$_2$CH$_3$ | CH$_2$Br |
| F | Cl | CH$_2$ | 1 | 2 | CH$_2$C≡CH | CH$_2$Cl |
| F | Cl | CH$_2$ | 1 | 2 | CH$_2$C≡CH | CH$_2$Br |
| F | Cl | CHF | 1 | 1 | H | CH$_2$Cl |
| F | Cl | CHF | 1 | 1 | H | CH$_2$Br |
| F | Cl | CHF | 1 | 1 | C(=O)CH$_3$ | CH$_2$Cl |
| F | Cl | CHF | 1 | 1 | C(=O)CH$_3$ | CH$_2$Br |
| F | Cl | CHF | 1 | 1 | CO$_2$CH$_3$ | CH$_2$Cl |
| F | Cl | CHF | 1 | 1 | CO$_2$CH$_3$ | CH$_2$Br |
| F | Cl | CHF | 1 | 1 | CH$_2$C≡CH | CH$_2$Cl |
| F | Cl | CHF | 1 | 1 | CH$_2$C≡CH | CH$_2$Br |
| F | Cl | CHF | 1 | 2 | H | CH$_2$Cl |
| F | Cl | CHF | 1 | 2 | H | CH$_2$Br |
| F | Cl | CHF | 1 | 2 | C(=O)CH$_3$ | CH$_2$Cl |
| F | Cl | CHF | 1 | 2 | C(=O)CH$_3$ | CH$_2$Br |
| F | Cl | CHF | 1 | 2 | CO$_2$CH$_3$ | CH$_2$Cl |
| F | Cl | CHF | 1 | 2 | CO$_2$CH$_3$ | CH$_2$Br |
| F | Cl | CHF | 1 | 2 | CH$_2$C≡CH | CH$_2$Cl |
| F | Cl | CHF | 1 | 2 | CH$_2$C≡CH | CH$_2$Br |
| F | Cl | CHCl | 1 | 1 | H | CH$_2$Cl |
| F | Cl | CHCl | 1 | 1 | H | CH$_2$Br |
| F | Cl | CHCl | 1 | 1 | C(=O)CH$_3$ | CH$_2$Cl |
| F | Cl | CHCl | 1 | 1 | C(=O)CH$_3$ | CH$_2$Br |
| F | Cl | CHCl | 1 | 1 | CO$_2$CH$_3$ | CH$_2$Cl |
| F | Cl | CHCl | 1 | 1 | CO$_2$CH$_3$ | CH$_2$Br |
| F | Cl | CHCl | 1 | 1 | CH$_2$C≡CH | CH$_2$Cl |
| F | Cl | CHCl | 1 | 1 | CH$_2$C≡CH | CH$_2$Br |
| F | Cl | CHCl | 1 | 2 | H | CH$_2$Cl |
| F | Cl | CHCl | 1 | 2 | H | CH$_2$Br |
| F | Cl | CHCl | 1 | 2 | C(=O)CH$_3$ | CH$_2$Cl |
| F | Cl | CHCl | 1 | 2 | C(=O)CH$_3$ | CH$_2$Br |
| F | Cl | CHCl | 1 | 2 | CO$_2$CH$_3$ | CH$_2$Cl |
| F | Cl | CHCl | 1 | 2 | CO$_2$CH$_3$ | CH$_2$Br |
| F | Cl | CHCl | 1 | 2 | CH$_2$C≡CH | CH$_2$Cl |
| F | Cl | CHCl | 1 | 2 | CH$_2$C≡CH | CH$_2$Br |
| F | Br | CH$_2$ | 1 | 1 | H | CH$_2$Cl |
| F | Br | CH$_2$ | 1 | 1 | H | CH$_2$Br |
| F | Br | CH$_2$ | 1 | 1 | C(=O)CH$_3$ | CH$_2$Cl |
| F | Br | CH$_2$ | 1 | 1 | C(=O)CH$_3$ | CH$_2$Br |
| F | Br | CH$_2$ | 1 | 1 | CO$_2$CH$_3$ | CH$_2$Cl |
| F | Br | CH$_2$ | 1 | 1 | CO$_2$CH$_3$ | CH$_2$Br |
| F | Br | CH$_2$ | 1 | 1 | CH$_2$=CH | CH$_2$Cl |
| F | Br | CH$_2$ | 1 | 1 | CH$_2$=CH | CH$_2$Br |
| F | Br | CH$_2$ | 1 | 2 | H | CH$_2$Cl |
| F | Br | CH$_2$ | 1 | 2 | H | CH$_2$Br |
| F | Br | CH$_2$ | 1 | 2 | C(=O)CH$_3$ | CH$_2$Cl |
| F | Br | CH$_2$ | 1 | 2 | C(=O)CH$_3$ | CH$_2$Br |
| F | Br | CH$_2$ | 1 | 2 | CO$_2$CH$_3$ | CH$_2$Cl |
| F | Br | CH$_2$ | 1 | 2 | CO$_2$CH$_3$ | CH$_2$Br |
| F | Br | CH$_2$ | 1 | 2 | CH$_2$C≡CH | CH$_2$Cl |
| F | Br | CH$_2$ | 1 | 2 | CH$_2$C≡CH | CH$_2$Br |
| F | Br | CHF | 1 | 1 | H | CH$_2$Cl |
| F | Br | CHF | 1 | 1 | H | CH$_2$Br |
| F | Br | CHF | 1 | 1 | C(=O)CH$_3$ | CH$_2$Cl |
| F | Br | CHF | 1 | 1 | C(=O)CH$_3$ | CH$_2$Br |
| F | Br | CHF | 1 | 1 | CO$_2$CH$_3$ | CH$_2$Cl |
| F | Br | CHF | 1 | 1 | CO$_2$CH$_3$ | CH$_2$Br |
| F | Br | CHF | 1 | 1 | CH$_2$C≡CH | CH$_2$Cl |
| F | Br | CHF | 1 | 1 | CH$_2$C≡CH | CH$_2$Br |
| F | Br | CHF | 1 | 2 | H | CH$_2$Cl |
| F | Br | CHF | 1 | 2 | H | CH$_2$Br |
| F | Br | CHF | 1 | 2 | C(=O)CH$_3$ | CH$_2$Cl |
| F | Br | CHF | 1 | 2 | C(=O)CH$_3$ | CH$_2$Br |
| F | Br | CHF | 1 | 2 | CO$_2$CH$_3$ | CH$_2$Cl |
| F | Br | CHF | 1 | 2 | CO$_2$CH$_3$ | CH$_2$Br |
| F | Br | CHF | 1 | 2 | CH$_2$C≡CH | CH$_2$Cl |
| F | Br | CHF | 1 | 2 | CH$_2$C≡CH | CH$_2$Br |
| F | Br | CHCl | 1 | 1 | H | CH$_2$Cl |
| F | Br | CHCl | 1 | 1 | H | CH$_2$Br |
| F | Br | CHCl | 1 | 1 | C(=O)CH$_3$ | CH$_2$Cl |
| F | Br | CHCl | 1 | 1 | C(=O)CH$_3$ | CH$_2$Br |
| F | Br | CHCl | 1 | 1 | CO$_2$CH$_3$ | CH$_2$Cl |
| F | Br | CHCl | 1 | 1 | CO$_2$CH$_3$ | CH$_2$Br |
| F | Br | CHCl | 1 | 1 | CH$_2$C≡CH | CH$_2$Cl |
| F | Br | CHCl | 1 | 1 | CH$_2$C≡CH | CH$_2$Br |
| F | Br | CHCl | 1 | 2 | H | CH$_2$Cl |
| F | Br | CHCl | 1 | 2 | H | CH$_2$Br |
| F | Br | CHCl | 1 | 2 | C(=O)CH$_3$ | CH$_2$Cl |
| F | Br | CHCl | 1 | 2 | C(=O)CH$_3$ | CH$_2$Br |
| F | Br | CHCl | 1 | 2 | CO$_2$CH$_3$ | CH$_2$Cl |
| F | Br | CHCl | 1 | 2 | CO$_2$CH$_3$ | CH$_2$Br |
| F | Br | CHCl | 1 | 2 | CH$_2$C≡CH | CH$_2$Cl |
| F | Br | CHCl | 1 | 2 | CH$_2$C≡CH | CH$_2$Br |
| F | CN | CH$_2$ | 1 | 1 | H | CH$_2$Cl |
| F | CN | CH$_2$ | 1 | 1 | H | CH$_2$Br |
| F | CN | CH$_2$ | 1 | 1 | C(=O)CH$_3$ | CH$_2$Cl |
| F | CN | CH$_2$ | 1 | 1 | C(=O)CH$_3$ | CH$_2$Br |
| F | CN | CH$_2$ | 1 | 1 | CO$_2$CH$_3$ | CH$_2$Cl |
| F | CN | CH$_2$ | 1 | 1 | CO$_2$CH$_3$ | CH$_2$Br |
| F | CN | CH$_2$ | 1 | 1 | CH$_2$C≡CH | CH$_2$Cl |
| F | CN | CH$_2$ | 1 | 1 | CH$_2$C≡CH | CH$_2$Br |
| F | CN | CH$_2$ | 1 | 2 | H | CH$_2$Cl |
| F | CN | CH$_2$ | 1 | 2 | H | CH$_2$Br |
| F | CN | CH$_2$ | 1 | 2 | C(=O)CH$_3$ | CH$_2$Cl |
| F | CN | CH$_2$ | 1 | 2 | C(=O)CH$_3$ | CH$_2$Br |
| F | CN | CH$_2$ | 1 | 2 | CO$_2$CH$_3$ | CH$_2$Cl |
| F | CN | CH$_2$ | 1 | 2 | CO$_2$CH$_3$ | CH$_2$Br |
| F | CN | CH$_2$ | 1 | 2 | CH$_2$C≡CH | CH$_2$Cl |
| F | CN | CH$_2$ | 1 | 2 | CH$_2$C≡CH | CH$_2$Br |
| F | CN | CHF | 1 | 1 | H | CH$_2$Cl |
| F | CN | CHF | 1 | 1 | H | CH$_2$Br |
| F | CN | CHF | 1 | 1 | C(=O)CH$_3$ | CH$_2$Cl |
| F | CN | CHF | 1 | 1 | C(=O)CH$_3$ | CH$_2$Br |
| F | CN | CHF | 1 | 1 | CO$_2$CH$_3$ | CH$_2$Cl |
| F | CN | CHF | 1 | 1 | CO$_2$CH$_3$ | CH$_2$Br |

TABLE 1-continued

| | | | | | | |
|---|---|---|---|---|---|---|
| F | CN | CHF | 1 | 1 | CH₂C≡CH | CH₂Cl |
| F | CN | CHF | 1 | 1 | CH₂C≡CH | CH₂Br |
| F | CN | CHF | 1 | 2 | H | CH₂Cl |
| F | CN | CHF | 1 | 2 | H | CH₂Br |
| F | CN | CHF | 1 | 2 | C(=O)CH₃ | CH₂Cl |
| F | CN | CHF | 1 | 2 | C(=O)CH₃ | CH₂Br |
| F | CN | CHF | 1 | 2 | CO₂CH₃ | CH₂Cl |
| F | CN | CHF | 1 | 2 | CO₂CH₃ | CH₂Br |
| F | CN | CHF | 1 | 2 | CH₂C≡CH | CH₂Cl |
| F | CN | CHF | 1 | 2 | CH₂C≡CH | CH₂Br |
| F | CN | CHCl | 1 | 1 | H | CH₂Cl |
| F | CN | CHCl | 1 | 1 | H | CH₂Br |
| F | CN | CHCl | 1 | 1 | C(=O)CH₃ | CH₂Cl |
| F | CN | CHCl | 1 | 1 | C(=O)CH₃ | CH₂Br |
| F | CN | CHCl | 1 | 1 | CO₂CH₃ | CH₂Cl |
| F | CN | CHCl | 1 | 1 | CO₂CH₃ | CH₂Br |
| F | CN | CHCl | 1 | 1 | CH₂C≡CH | CH₂Cl |
| F | CN | CHCl | 1 | 1 | CH₂C≡CH | CH₂Br |
| F | CN | CHCl | 1 | 2 | H | CH₂Cl |
| F | CN | CHCl | 1 | 2 | H | CH₂Br |
| F | CN | CHCl | 1 | 2 | C(=O)CH₃ | CH₂Cl |
| F | CN | CHCl | 1 | 2 | C(=O)CH₃ | CH₂Br |
| F | CN | CHCl | 1 | 2 | CO₂CH₃ | CH₂Cl |
| F | CN | CHCl | 1 | 2 | CO₂CH₃ | CH₂Br |
| F | CN | CHCl | 1 | 2 | CH₂C≡CH | CH₂Cl |
| F | CN | CHCl | 1 | 2 | CH₂C≡CH | CH₂Br |
| Cl | H | CH₂ | 1 | 1 | H | CH₂Cl |
| Cl | H | CH₂ | 1 | 1 | H | CH₂Br |
| Cl | H | CH₂ | 1 | 1 | C(=O)CH₃ | CH₂Cl |
| Cl | H | CH₂ | 1 | 1 | C(=O)CH₃ | CH₂Br |
| Cl | H | CH₂ | 1 | 1 | CO₂CH₃ | CH₂Cl |
| Cl | H | CH₂ | 1 | 1 | CO₂CH₃ | CH₂Br |
| Cl | H | CH₂ | 1 | 1 | CH₂C≡CH | CH₂Cl |
| Cl | H | CH₂ | 1 | 1 | CH₂C≡CH | CH₂Br |
| Cl | H | CH₂ | 1 | 2 | H | CH₂Cl |
| Cl | H | CH₂ | 1 | 2 | H | CH₂Br |
| Cl | H | CH₂ | 1 | 2 | C(=O)CH₃ | CH₂Cl |
| Cl | H | CH₂ | 1 | 2 | C(=O)CH₃ | CH₂Br |
| Cl | H | CH₂ | 1 | 2 | CO₂CH₃ | CH₂Cl |
| Cl | H | CH₂ | 1 | 2 | CO₂CH₃ | CH₂Br |
| Cl | H | CH₂ | 1 | 2 | CH₂C≡CH | CH₂Cl |
| Cl | H | CH₂ | 1 | 2 | CH₂C≡CH | CH₂Br |
| Cl | H | CHF | 1 | 1 | H | CH₂Cl |
| Cl | H | CHF | 1 | 1 | H | CH₂Br |
| Cl | H | CHF | 1 | 1 | C(=O)CH₃ | CH₂Cl |
| Cl | H | CHF | 1 | 1 | C(=O)CH₃ | CH₂Br |
| Cl | H | CHF | 1 | 1 | CO₂CH₃ | CH₂Cl |
| Cl | H | CHF | 1 | 1 | CO₂CH₃ | CH₂Br |
| Cl | H | CHF | 1 | 1 | CH₂C≡CH | CH₂Cl |
| Cl | H | CHF | 1 | 1 | CH₂C≡CH | CH₂Br |
| Cl | H | CHF | 1 | 2 | H | CH₂Cl |
| Cl | H | CHF | 1 | 2 | H | CH₂Br |
| Cl | H | CHF | 1 | 2 | C(=O)CH₃ | CH₂Cl |
| Cl | H | CHF | 1 | 2 | C(=O)CH₃ | CH₂Br |
| Cl | H | CHF | 1 | 2 | CO₂CH₃ | CH₂Cl |
| Cl | H | CHF | 1 | 2 | CO₂CH₃ | CH₂Br |
| Cl | H | CHF | 1 | 2 | CH₂C≡CH | CH₂Cl |
| Cl | H | CHF | 1 | 2 | CH₂C≡CH | CH₂Br |
| Cl | H | CHCl | 1 | 1 | H | CH₂Cl |
| Cl | H | CHCl | 1 | 1 | H | CH₂Br |
| Cl | H | CHCl | 1 | 1 | C(=O)CH₃ | CH₂Cl |
| Cl | H | CHCl | 1 | 1 | C(=O)CH₃ | CH₂Br |
| Cl | H | CHCl | 1 | 1 | CO₂CH₃ | CH₂Cl |
| Cl | H | CHCl | 1 | 1 | CO₂CH₃ | CH₂Br |
| Cl | H | CHCl | 1 | 1 | CH₂C≡CH | CH₂Cl |
| Cl | H | CHCl | 1 | 1 | CH₂C≡CH | CH₂Br |
| Cl | H | CHCl | 1 | 2 | H | CH₂Cl |
| Cl | H | CHCl | 1 | 2 | H | CH₂Br |
| Cl | H | CHCl | 1 | 2 | C(=O)CH₃ | CH₂Cl |
| Cl | H | CHCl | 1 | 2 | C(=O)CH₃ | CH₂Br |
| Cl | H | CHCl | 1 | 2 | CO₂CH₃ | CH₂Cl |
| Cl | H | CHCl | 1 | 2 | CO₂CH₃ | CH₂Br |
| Cl | H | CHCl | 1 | 2 | CH₂C≡CH | CH₂Cl |
| Cl | H | CHCl | 1 | 2 | CH₂C≡CH | CH₂Br |
| Cl | Cl | CH₂ | 1 | 1 | H | CH₂Cl |
| Cl | Cl | CH₂ | 1 | 1 | H | CH₂Br |
| Cl | Cl | CH₂ | 1 | 1 | C(=O)CH₃ | CH₂Cl |
| Cl | Cl | CH₂ | 1 | 1 | C(=O)CH₃ | CH₂Br |
| Cl | Cl | CH₂ | 1 | 1 | CO₂CH₃ | CH₂Cl |
| Cl | Cl | CH₂ | 1 | 1 | CO₂CH₃ | CH₂Br |
| Cl | Cl | CH₂ | 1 | 1 | CH₂C≡CH | CH₂Cl |
| Cl | Cl | CH₂ | 1 | 1 | CH₂C≡CH | CH₂Br |
| Cl | Cl | CH₂ | 1 | 2 | H | CH₂Cl |
| Cl | Cl | CH₂ | 1 | 2 | H | CH₂Br |
| Cl | Cl | CH₂ | 1 | 2 | C(=O)CH₃ | CH₂Cl |
| Cl | Cl | CH₂ | 1 | 2 | C(=O)CH₃ | CH₂Br |
| Cl | Cl | CH₂ | 1 | 2 | CO₂CH₃ | CH₂Cl |
| Cl | Cl | CH₂ | 1 | 2 | CO₂CH₃ | CH₂Br |
| Cl | Cl | CH₂ | 1 | 2 | CH₂C≡CH | CH₂Cl |
| Cl | Cl | CH₂ | 1 | 2 | CH₂C≡CH | CH₂Br |
| Cl | Cl | CHF | 1 | 1 | H | CH₂Cl |
| Cl | Cl | CHF | 1 | 1 | H | CH₂Br |
| Cl | Cl | CHF | 1 | 1 | C(=O)CH₃ | CH₂Cl |
| Cl | Cl | CHF | 1 | 1 | C(=O)CH₃ | CH₂Br |
| Cl | Cl | CHF | 1 | 1 | CO₂CH₃ | CH₂Cl |
| Cl | Cl | CHF | 1 | 1 | CO₂CH₃ | CH₂Br |
| Cl | Cl | CHF | 1 | 1 | CH₂C≡CH | CH₂Cl |
| Cl | Cl | CHF | 1 | 1 | CH₂C≡CH | CH₂Br |
| Cl | Cl | CHF | 1 | 2 | H | CH₂Cl |
| Cl | Cl | CHF | 1 | 2 | H | CH₂Br |
| Cl | Cl | CHF | 1 | 2 | C(=O)CH₃ | CH₂Cl |
| Cl | Cl | CHF | 1 | 2 | C(=O)CH₃ | CH₂Br |
| Cl | Cl | CHF | 1 | 2 | CO₂CH₃ | CH₂Cl |
| Cl | Cl | CHF | 1 | 2 | CO₂CH₃ | CH₂Br |
| Cl | Cl | CHF | 1 | 2 | CH₂C≡CH | CH₂Cl |
| Cl | Cl | CHF | 1 | 2 | CH₂C≡CH | CH₂Br |
| Cl | Cl | CHCl | 1 | 1 | H | CH₂Cl |
| Cl | Cl | CHCl | 1 | 1 | H | CH₂Br |
| Cl | Cl | CHCl | 1 | 1 | C(=O)CH | CH₂Cl |
| Cl | Cl | CHCl | 1 | 1 | C(=O)CH | CH₂Br |
| Cl | Cl | CHCl | 1 | 1 | CO₂CH₃ | CH₂Cl |
| Cl | Cl | CHCl | 1 | 1 | CO₂CH₃ | CH₂Br |
| Cl | Cl | CHCl | 1 | 1 | CH₂C≡CH | CH₂Cl |
| Cl | Cl | CHCl | 1 | 1 | CH₂C≡CH | CH₂Br |
| Cl | Cl | CHCl | 1 | 2 | H | CH₂Cl |
| Cl | Cl | CHCl | 1 | 2 | H | CH₂Br |
| Cl | Cl | CHCl | 1 | 2 | C(=O)CH₃ | CH₂Cl |
| Cl | Cl | CHCl | 1 | 2 | C(=O)CH₃ | CH₂Br |
| Cl | Cl | CHCl | 1 | 2 | CO₂CH₃ | CH₂Cl |
| Cl | Cl | CHCl | 1 | 2 | CO₂CH₃ | CH₂Br |
| Cl | Cl | CHCl | 1 | 2 | CH₂C≡CH | CH₂Cl |
| Cl | Cl | CHCl | 1 | 2 | CH₂C≡CH | CH₂Br |
| Cl | Br | CH₂ | 1 | 1 | H | CH₂Cl |
| Cl | Br | CH₂ | 1 | 1 | H | CH₂Br |
| Cl | Br | CH₂ | 1 | 1 | C(=O)CH₃ | CH₂Cl |
| Cl | Br | CH₂ | 1 | 1 | C(=O)CH₃ | CH₂Br |
| Cl | Br | CH₂ | 1 | 1 | CO₂CH₃ | CH₂Cl |
| Cl | Br | CH₂ | 1 | 1 | CO₂CH₃ | CH₂Br |
| Cl | Br | CH₂ | 1 | 1 | CH₂C≡CH | CH₂Cl |
| Cl | Br | CH₂ | 1 | 1 | CH₂C≡CH | CH₂Br |
| Cl | Br | CH₂ | 1 | 2 | H | CH₂Cl |
| Cl | Br | CH₂ | 1 | 2 | H | CH₂Br |
| Cl | Br | CH₂ | 1 | 2 | C(=O)CH₃ | CH₂Cl |
| Cl | Br | CH₂ | 1 | 2 | C(=O)CH₃ | CH₂Br |
| Cl | Br | CH₂ | 1 | 2 | CO₂CH₃ | CH₂Cl |
| Cl | Br | CH₂ | 1 | 2 | CO₂CH₃ | CH₂Br |
| Cl | Br | CH₂ | 1 | 2 | CH₂C≡CH | CH₂Cl |
| Cl | Br | CH₂ | 1 | 2 | CH₂C≡CH | CH₂Br |
| Cl | Br | CHF | 1 | 1 | H | CH₂Cl |
| Cl | Br | CHF | 1 | 1 | H | CH₂Br |
| Cl | Br | CHF | 1 | 1 | C(=O)CH₃ | CH₂Cl |
| Cl | Br | CHF | 1 | 1 | C(=O)CH₃ | CH₂Br |
| Cl | Br | CHF | 1 | 1 | CO₂CH₃ | CH₂Cl |
| Cl | Br | CHF | 1 | 1 | CO₂CH₃ | CH₂Br |
| Cl | Br | CHF | 1 | 1 | CH₂C≡CH | CH₂Cl |
| Cl | Br | CHF | 1 | 1 | CH₂C≡CH | CH₂Br |
| Cl | Br | CHF | 1 | 2 | H | CH₂Cl |
| Cl | Br | CHF | 1 | 2 | H | CH₂Br |
| Cl | Br | CHF | 1 | 2 | C(=O)CH₃ | CH₂Cl |
| Cl | Br | CHF | 1 | 2 | C(=O)CH₃ | CH₂Br |
| Cl | Br | CHF | 1 | 2 | CO₂CH₃ | CH₂Cl |
| Cl | Br | CHF | 1 | 2 | CO₂CH₃ | CH₂Br |
| Cl | Br | CHF | 1 | 2 | CH₂C≡CH | CH₂Cl |
| Cl | Br | CHF | 1 | 2 | CH₂C≡CH | CH₂Br |
| Cl | Br | CHCl | 1 | 1 | H | CH₂Cl |
| Cl | Br | CHCl | 1 | 1 | H | CH₂Br |
| Cl | Br | CHCl | 1 | 1 | C(=O)CH₃ | CH₂Cl |
| Cl | Br | CHCl | 1 | 1 | C(=O)CH₃ | CH₂Br |

TABLE 1-continued

| | | | | | | |
|---|---|---|---|---|---|---|
| Cl | Br | CHCl | 1 | 1 | CO$_2$CH$_3$ | CH$_2$Cl |
| Cl | Br | CHCl | 1 | 1 | CO$_2$CH$_3$ | CH$_2$Br |
| Cl | Br | CHCl | 1 | 1 | CH$_2$C≡CH | CH$_2$Cl |
| Cl | Br | CHCl | 1 | 1 | CH$_2$C≡CH | CH$_2$Br |
| Cl | Br | CHCl | 1 | 2 | H | CH$_2$Cl |
| Cl | Br | CHCl | 1 | 2 | H | CH$_2$Br |
| Cl | Br | CHCl | 1 | 2 | C(=O)CH$_3$ | CH$_2$Cl |
| Cl | Br | CHCl | 1 | 2 | C(=O)CH$_3$ | CH$_2$Br |
| Cl | Br | CHCl | 1 | 2 | CO$_2$CH$_3$ | CH$_2$Cl |
| Cl | Br | CHCl | 1 | 2 | CO$_2$CH$_3$ | CH$_2$Br |
| Cl | Br | CHCl | 1 | 2 | CH$_2$C≡CH | CH$_2$Cl |
| Cl | Br | CHCl | 1 | 2 | CH$_2$C≡CH | CH$_2$Br |
| Cl | CN | CH$_2$ | 1 | 1 | H | CH$_2$Cl |
| Cl | CN | CH$_2$ | 1 | 1 | H | CH$_2$Br |
| Cl | CN | CH$_2$ | 1 | 1 | C(=O)CH$_3$ | CH$_2$Cl |
| Cl | CN | CH$_2$ | 1 | 1 | C(=O)CH$_3$ | CH$_2$Br |
| Cl | CN | CH$_2$ | 1 | 1 | CO$_2$CH$_3$ | CH$_2$Cl |
| Cl | CN | CH$_2$ | 1 | 1 | CO$_2$CH$_3$ | CH$_2$Br |
| Cl | CN | CH$_2$ | 1 | 1 | CH$_2$C≡CH | CH$_2$Cl |
| Cl | CN | CH$_2$ | 1 | 1 | CH$_2$C≡CH | CH$_2$Br |
| Cl | CN | CH$_2$ | 1 | 2 | H | CH$_2$Cl |
| Cl | CN | CH$_2$ | 1 | 2 | H | CH$_2$Br |
| Cl | CN | CH$_2$ | 1 | 2 | C(=O)CH$_3$ | CH$_2$Cl |
| Cl | CN | CH$_2$ | 1 | 2 | C(=O)CH$_3$ | CH$_2$Br |
| Cl | CN | CH$_2$ | 1 | 2 | CO$_2$CH$_3$ | CH$_2$Cl |
| Cl | CN | CH$_2$ | 1 | 2 | CO$_2$CH$_3$ | CH$_2$Br |
| Cl | CN | CH$_2$ | 1 | 2 | CH$_2$C≡CH | CH$_2$Cl |
| Cl | CN | CH$_2$ | 1 | 2 | CH$_2$C≡CH | CH$_2$Br |
| Cl | CN | CHF | 1 | 1 | H | CH$_2$Cl |
| Cl | CN | CHF | 1 | 1 | H | CH$_2$Br |
| Cl | CN | CHF | 1 | 1 | C(=O)CH$_3$ | CH$_2$Cl |
| Cl | CN | CHF | 1 | 1 | C(=O)CH$_3$ | CH$_2$Br |
| Cl | CN | CHF | 1 | 1 | CO$_2$CH$_3$ | CH$_2$Cl |
| Cl | CN | CHF | 1 | 1 | CO$_2$CH$_3$ | CH$_2$Br |
| Cl | CN | CHF | 1 | 1 | CH$_2$C≡CH | CH$_2$Cl |
| Cl | CN | CHF | 1 | 1 | CH$_2$C≡CH | CH$_2$Br |
| Cl | CN | CHF | 1 | 2 | H | CH$_2$Cl |
| Cl | CN | CHF | 1 | 2 | H | CH$_2$Br |
| Cl | CN | CHF | 1 | 2 | C(=O)CH$_3$ | CH$_2$Cl |
| Cl | CN | CHF | 1 | 2 | C(=O)CH$_3$ | CH$_2$Br |
| Cl | CN | CHF | 1 | 2 | CO$_2$CH$_3$ | CH$_2$Cl |
| Cl | CN | CHF | 1 | 2 | CO$_2$CH$_3$ | CH$_2$Br |
| Cl | CN | CHF | 1 | 2 | CH$_2$C≡CH | CH$_2$Cl |
| Cl | CN | CHF | 1 | 2 | CH$_2$C≡CH | CH$_2$Br |
| Cl | CN | CHCl | 1 | 1 | H | CH$_2$Cl |
| Cl | CN | CHCl | 1 | 1 | H | CH$_2$Br |
| Cl | CN | CHCl | 1 | 1 | C(=O)CH$_3$ | CH$_2$Cl |
| Cl | CN | CHCl | 1 | 1 | C(=O)CH$_3$ | CH$_2$Br |
| Cl | CN | CHCl | 1 | 1 | CO$_2$CH$_3$ | CH$_2$Cl |
| Cl | CN | CHCl | 1 | 1 | CO$_2$CH$_3$ | CH$_2$Br |
| Cl | CN | CHCl | 1 | 1 | CH$_2$C≡CH | CH$_2$Cl |
| Cl | CN | CHCl | 1 | 1 | CH$_2$C≡CH | CH$_2$Br |
| Cl | CN | CHCl | 1 | 2 | H | CH$_2$Cl |
| Cl | CN | CHCl | 1 | 2 | H | CH$_2$Br |
| Cl | CN | CHCl | 1 | 2 | C(=O)CH$_3$ | CH$_2$Cl |
| Cl | CN | CHCl | 1 | 2 | C(=O)CH$_3$ | CH$_2$Br |
| Cl | CN | CHCl | 1 | 2 | CO$_2$CH$_3$ | CH$_2$Cl |
| Cl | CN | CHCl | 1 | 2 | CO$_2$CH$_3$ | CH$_2$Br |
| Cl | CN | CHCl | 1 | 2 | CH$_2$C≡CH | CH$_2$Cl |
| Cl | CN | CHCl | 1 | 2 | CH$_2$C≡CH | CH$_2$Br |

J = 19, Q = O, and R$^{24}$ = CN

| X | Y | Z | n | m | R$^1$ | R$^2$ |
|---|---|---|---|---|---|---|
| F | H | CH$_2$ | 1 | 1 | H | CH$_2$Cl |
| F | H | CH$_2$ | 1 | 1 | H | CH$_2$Br |
| F | H | CH$_2$ | 1 | 1 | C(=O)CH$_3$ | CH$_2$Cl |
| F | H | CH$_2$ | 1 | 1 | C(=O)CH$_3$ | CH$_2$Br |
| F | H | CH$_2$ | 1 | 1 | CO$_2$CH$_3$ | CH$_2$Cl |
| F | H | CH$_2$ | 1 | 1 | CO$_2$CH$_3$ | CH$_2$Br |
| F | H | CH$_2$ | 1 | 1 | CH$_2$C≡CH | CH$_2$Cl |
| F | H | CH$_2$ | 1 | 1 | CH$_2$C≡CH | CH$_2$Br |
| F | H | CH$_2$ | 1 | 2 | H | CH$_2$Cl |
| F | H | CH$_2$ | 1 | 2 | H | CH$_2$Br |
| F | H | CH$_2$ | 1 | 2 | C(=O)CH$_3$ | CH$_2$Cl |
| F | H | CH$_2$ | 1 | 2 | C(=O)CH$_3$ | CH$_2$Br |
| F | H | CH$_2$ | 1 | 2 | CO$_2$CH$_3$ | CH$_2$Cl |
| F | H | CH$_2$ | 1 | 2 | CO$_2$CH$_3$ | CH$_2$Br |

TABLE 1-continued

| | | | | | | |
|---|---|---|---|---|---|---|
| F | H | CH$_2$ | 1 | 2 | CH$_2$C≡CH | CH$_2$Cl |
| F | H | CH$_2$ | 1 | 2 | CH$_2$C≡CH | CH$_2$Br |
| F | H | CHF | 1 | 1 | H | CH$_2$Cl |
| F | H | CHF | 1 | 1 | H | CH$_2$Br |
| F | H | CHF | 1 | 1 | C(=O)CH$_3$ | CH$_2$Cl |
| F | H | CHF | 1 | 1 | C(=O)CH$_3$ | CH$_2$Br |
| F | H | CHF | 1 | 1 | CO$_2$CH$_3$ | CH$_2$Cl |
| F | H | CHF | 1 | 1 | CO$_2$CH$_3$ | CH$_2$Br |
| F | H | CHF | 1 | 1 | CH$_2$C≡CH | CH$_2$Cl |
| F | H | CHF | 1 | 1 | CH$_2$C≡CH | CH$_2$Br |
| F | H | CHF | 1 | 2 | H | CH$_2$Cl |
| F | H | CHF | 1 | 2 | H | CH$_2$Br |
| F | H | CHF | 1 | 2 | C(=O)CH$_3$ | CH$_2$C |
| F | H | CHF | 1 | 2 | C(=O)CH$_3$ | CH$_2$Br |
| F | H | CHF | 1 | 2 | CO$_2$CH$_3$ | CH$_2$Cl |
| F | H | CHF | 1 | 2 | CO$_2$CH$_3$ | CH$_2$Br |
| F | H | CHF | 1 | 2 | CH$_2$C≡CH | CH$_2$Cl |
| F | H | CHF | 1 | 2 | CH$_2$C≡CH | CH$_2$Br |
| F | H | CHCl | 1 | 1 | H | CH$_2$Cl |
| F | H | CHCl | 1 | 1 | H | CH$_2$Br |
| F | H | CHCl | 1 | 1 | C(=O)CH$_3$ | CH$_2$Cl |
| F | H | CHCl | 1 | 1 | C(=O)CH$_3$ | CH$_2$Br |
| F | H | CHCl | 1 | 1 | CO$_2$CH$_3$ | CH$_2$Cl |
| F | H | CHCl | 1 | 1 | CO$_2$CH$_3$ | CH$_2$Br |
| F | H | CHCl | 1 | 1 | CH$_2$=CH | CH$_2$Cl |
| F | H | CHCl | 1 | 1 | CH$_2$=CH | CH$_2$Br |
| F | H | CHCl | 1 | 2 | H | CH$_2$Cl |
| F | H | CHCl | 1 | 2 | H | CH$_2$Br |
| F | H | CHCl | 1 | 2 | C(=O)CH$_3$ | CH$_2$Cl |
| F | H | CHCl | 1 | 2 | C(=O)CH$_3$ | CH$_2$Br |
| F | H | CHCl | 1 | 2 | CO$_2$CH$_3$ | CH$_2$Cl |
| F | H | CHCl | 1 | 2 | CO$_2$CH$_3$ | CH$_2$Br |
| F | H | CHCl | 1 | 2 | CH$_2$=CH | CH$_2$Cl |
| F | H | CHCl | 1 | 2 | CH$_2$=CH | CH$_2$Br |
| F | Cl | CH$_2$ | 1 | 1 | H | CH$_2$Cl |
| F | Cl | CH$_2$ | 1 | 1 | H | CH$_2$Br |
| F | Cl | CH$_2$ | 1 | 1 | C(=O)CH$_3$ | CH$_2$Cl |
| F | Cl | CH$_2$ | 1 | 1 | C(=O)CH$_3$ | CH$_2$Br |
| F | Cl | CH$_2$ | I | 1 | CO$_2$CH$_3$ | CH$_2$Cl |
| F | Cl | CH$_2$ | 1 | 1 | CO$_2$CH$_3$ | CH$_2$Br |
| F | Cl | CH$_2$ | 1 | 1 | CH$_2$C≡CH | CH$_2$Cl |
| F | Cl | CH$_2$ | 1 | 1 | CH$_2$C≡CH | CH$_2$Br |
| F | Cl | CH$_2$ | 1 | 2 | H | CH$_2$Cl |
| F | Cl | CH$_2$ | 1 | 2 | H | CH$_2$Br |
| F | Cl | CH$_2$ | 1 | 2 | C(=O)CH$_3$ | CH$_2$Cl |
| F | Cl | CH$_2$ | 1 | 2 | C(=O)CH$_3$ | CH$_2$Br |
| F | Cl | CH$_2$ | 1 | 2 | CO$_2$CH$_2$ | CH$_2$Cl |
| F | Cl | CH$_2$ | 1 | 2 | CO$_2$CH$_3$ | CH$_2$Br |
| F | Cl | CH$_2$ | 1 | 2 | CH$_2$C≡CH | CH$_2$Cl |
| F | Cl | CH$_2$ | 1 | 2 | CH$_2$C≡CH | CH$_2$Br |
| F | Cl | CHF | 1 | 1 | H | CH$_2$Cl |
| F | Cl | CHF | 1 | 1 | H | CH$_2$Br |
| F | Cl | CHF | 1 | 1 | C(=O)CH$_3$ | CH$_2$Cl |
| F | Cl | CHF | 1 | 1 | C(=O)CH$_3$ | CH$_2$Br |
| F | Cl | CHF | 1 | 1 | CO$_2$CH$_3$ | CH$_2$Cl |
| F | Cl | CHF | 1 | 1 | CO$_2$CH$_3$ | CH$_2$Br |
| P | Cl | CHF | 1 | 1 | CH$_2$C≡CH | CH$_2$Cl |
| F | Cl | CHF | 1 | 1 | CH$_2$C≡CH | CH$_2$Br |
| F | Cl | CHF | 1 | 2 | H | CH$_2$Cl |
| F | Cl | CHF | 1 | 2 | H | CH$_2$Br |
| F | Cl | CHF | 1 | 2 | C(=O)CH$_3$ | CH$_2$Cl |
| F | Cl | CHF | 1 | 2 | C(=O)CH$_3$ | CH$_2$Br |
| F | Cl | CHF | 1 | 2 | CO$_2$CH$_3$ | CH$_2$Cl |
| F | Cl | CHF | 1 | 2 | CO$_2$CH$_3$ | CH$_2$Br |
| F | Cl | CHF | 1 | 2 | CH$_2$C≡CH | CH$_2$Cl |
| F | Cl | CHF | 1 | 2 | CH$_2$C≡CH | CH$_2$Br |
| F | Cl | CHCl | 1 | 1 | H | CH$_2$Cl |
| F | Cl | CHCl | 1 | 1 | H | CH$_2$Br |
| F | Cl | CHCl | 1 | 1 | C(=O)CH$_3$ | CH$_2$Cl |
| F | Cl | CHCl | 1 | 1 | C(=O)CH$_3$ | CH$_2$Br |
| F | Cl | CHCl | 1 | 1 | CO$_2$CH$_3$ | CH$_2$Cl |
| F | Cl | CHCl | 1 | 1 | CO$_2$CH$_3$ | CH$_2$Br |
| F | Cl | CHCl | 1 | 1 | CH$_2$C≡CH | CH$_2$Cl |
| F | Cl | CHCl | 1 | 1 | CH$_2$C≡CH | CH$_2$Br |
| F | Cl | CHCl | 1 | 2 | H | CH$_2$Cl |
| F | Cl | CHCl | 1 | 2 | H | CH$_2$Br |
| F | Cl | CHCl | 1 | 2 | C(=O)CH$_3$ | CH$_2$Cl |
| F | Cl | CHCl | 1 | 2 | C(=O)CH$_3$ | CH$_2$Br |
| F | Cl | CHCl | 1 | 2 | CO$_2$CH | CH$_2$Cl |

TABLE 1-continued

| | | | | | | |
|---|---|---|---|---|---|---|
| F | Cl | CHCl | 1 | 2 | CO$_2$CH$_3$ | CH$_2$Br |
| F | Cl | CHCl | 1 | 2 | CH$_2$C≡CH | CH$_2$Cl |
| F | Cl | CHCl | 1 | 2 | CH$_2$C≡CH | CH$_2$Br |
| F | Br | CH$_2$ | 1 | 1 | H | CH$_2$Cl |
| F | Br | CH$_2$ | 1 | 1 | H | CH$_2$Br |
| F | Br | CH$_2$ | 1 | 1 | C(=O)CH$_3$ | CH$_2$Cl |
| F | Br | CH$_2$ | 1 | 1 | C(=O)CH$_3$ | CH$_2$Br |
| F | Br | CH$_2$ | 1 | 1 | CO$_2$CH$_3$ | CH$_2$Cl |
| F | Br | CH$_2$ | 1 | 1 | CO$_2$CH$_3$ | CH$_2$Br |
| F | Br | CH$_2$ | 1 | 1 | CH$_2$C≡CH | CH$_2$Cl |
| F | Br | CH$_2$ | 1 | 1 | CH$_2$C≡CH | CH$_2$Br |
| F | Br | CH$_2$ | 1 | 2 | H | CH$_2$Cl |
| F | Br | CH$_2$ | 1 | 2 | H | CH$_2$Br |
| F | Br | CH$_2$ | 1 | 2 | C(=O)CH$_3$ | CH$_2$Cl |
| F | Br | CH$_2$ | 1 | 2 | C(=O)CH$_3$ | CH$_2$Br |
| F | Br | CH$_2$ | 1 | 2 | CO$_2$CH$_3$ | CH$_2$Cl |
| F | Br | CH$_2$ | 1 | 2 | CO$_2$CH$_3$ | CH$_2$Br |
| F | Br | CH$_2$ | 1 | 2 | CH$_2$C≡CH | CH$_2$Cl |
| F | Br | CH$_2$ | 1 | 2 | CH$_2$C≡CH | CH$_2$Br |
| F | Br | CHF | 1 | 1 | H | CH$_2$Cl |
| F | Br | CHF | 1 | 1 | H | CH$_2$Br |
| F | Br | CHF | 1 | 1 | C(=O)CH$_3$ | CH$_2$Cl |
| F | Br | CHF | 1 | 1 | C(=O)CH$_3$ | CH$_2$Br |
| F | Br | CHF | 1 | 1 | CO$_2$CH$_3$ | CH$_2$Cl |
| F | Br | CHF | 1 | 1 | CO$_2$CH$_3$ | CH$_2$Br |
| F | Br | CHF | 1 | 1 | CH$_2$C≡CH | CH$_2$Cl |
| F | Br | CHF | 1 | 1 | CH$_2$C≡CH | CH$_2$Br |
| F | Br | CHF | 1 | 2 | H | CH$_2$Cl |
| F | Br | CHF | 1 | 2 | H | CH$_2$Br |
| F | Br | CHF | 1 | 2 | C(=O)CH$_3$ | CH$_2$Cl |
| F | Br | CHF | 1 | 2 | C(=O)CH$_3$ | CH$_2$Br |
| F | Br | CHF | 1 | 2 | CO$_2$CH$_3$ | CH$_2$Cl |
| F | Br | CHF | 1 | 2 | CO$_2$CH$_3$ | CH$_2$Br |
| F | Br | CHF | 1 | 2 | CH$_2$C≡CH | CH$_2$Cl |
| F | Br | CHF | 1 | 2 | CH$_2$C≡CH | CH$_2$Br |
| F | Br | CHCl | 1 | 1 | H | CH$_2$Cl |
| F | Br | CHCl | 1 | 1 | H | CH$_2$Br |
| F | Br | CHCl | 1 | 1 | C(=O)CH$_3$ | CH$_2$Cl |
| F | Br | CHCl | 1 | 1 | C(=O)CH$_3$ | CH$_2$Br |
| F | Br | CHCl | 1 | 1 | CO$_2$CH$_3$ | CH$_2$Cl |
| F | Br | CHCl | 1 | 1 | CO$_2$CH$_3$ | CH$_2$Br |
| F | Br | CHCl | 1 | 1 | CH$_2$C≡CH | CH$_2$Cl |
| F | Br | CHCl | 1 | 1 | CH$_2$C≡CH | CH$_2$Br |
| F | Br | CHCl | 1 | 2 | H | CH$_2$Cl |
| F | Br | CHCl | 1 | 2 | H | CH$_2$Br |
| F | Br | CHCl | 1 | 2 | C(=O)CH$_3$ | CH$_2$Cl |
| F | Br | CHCl | 1 | 2 | C(=O)CH$_3$ | CH$_2$Br |
| F | Br | CHCl | 1 | 2 | CO$_2$CH$_3$ | CH$_2$Cl |
| F | Br | CHCl | 1 | 2 | CO$_2$CH$_3$ | CH$_2$Br |
| F | Br | CHCl | 1 | 2 | CH$_2$C≡CH | CH$_2$Cl |
| F | Br | CHCl | 1 | 2 | CH$_2$C≡CH | CH$_2$Br |
| F | CN | CH$_2$ | 1 | 1 | H | CH$_2$Cl |
| F | CN | CH$_2$ | 1 | 1 | H | CH$_2$Br |
| F | CN | CH$_2$ | 1 | 1 | C(=O)CH$_3$ | CH$_2$Cl |
| F | CN | CH$_2$ | 1 | 1 | C(=O)CH$_3$ | CH$_2$Br |
| F | CN | CH$_2$ | 1 | 1 | CO$_2$CH$_3$ | CH$_2$Cl |
| F | CN | CH$_2$ | 1 | 1 | CO$_2$CH$_3$ | CH$_2$Br |
| F | CN | CH$_2$ | 1 | 1 | CH$_2$C≡CH | CH$_2$Cl |
| F | CN | CH$_2$ | 1 | 1 | CH$_2$C≡CH | CH$_2$Br |
| F | CN | CH$_2$ | 1 | 2 | H | CH$_2$Cl |
| F | CN | CH$_2$ | 1 | 2 | H | CH$_2$Br |
| F | CN | CH$_2$ | 1 | 2 | C(=O)CH$_3$ | CH$_2$Cl |
| F | CN | CH$_2$ | 1 | 2 | C(=O)CH$_3$ | CH$_2$Br |
| F | CN | CH$_2$ | 1 | 2 | CO$_2$CH$_3$ | CH$_2$Cl |
| F | CN | CH$_2$ | 1 | 2 | CO$_2$CH$_3$ | CH$_2$Br |
| F | CN | CH$_2$ | 1 | 2 | CH$_2$C≡CH | CH$_2$Cl |
| F | CN | CH$_2$ | 1 | 2 | CH$_2$C≡CH | CH$_2$Br |
| F | CN | CHF | 1 | 1 | H | CH$_2$Cl |
| F | CN | CHF | 1 | 1 | H | CH$_2$Br |
| F | CN | CHF | 1 | 1 | C(=O)CH$_3$ | CH$_2$Cl |
| F | CN | CHF | 1 | 1 | C(=O)CH$_3$ | CH$_2$Br |
| F | CN | CHF | 1 | 1 | CO$_2$CH$_3$ | CH$_2$Cl |
| F | CN | CHF | 1 | 1 | CO$_2$CH$_3$ | CH$_2$Br |
| F | CN | CHF | 1 | 1 | CH$_2$C≡CH | CH$_2$Cl |
| F | CN | CHF | 1 | 1 | CH$_2$C≡CH | CH$_2$Br |
| F | CN | CHF | 1 | 2 | H | CH$_2$Cl |
| F | CN | CHF | 1 | 2 | H | CH$_2$Br |
| F | CN | CHF | 1 | 2 | C(=O)CH$_3$ | CH$_2$Cl |
| F | CN | CHF | 1 | 2 | C(=O)CH$_3$ | CH$_2$Br |
| F | CN | CHF | 1 | 2 | CO$_2$CH$_3$ | CH$_2$Cl |
| F | CN | CHF | 1 | 2 | CO$_2$CH$_3$ | CH$_2$Br |
| F | CN | CHF | 1 | 2 | CH$_2$C≡CH | CH$_2$Cl |
| F | CN | CHF | 1 | 2 | CH$_2$C≡CH | CH$_2$Br |
| F | CN | CHCl | 1 | 1 | H | CH$_2$Cl |
| F | CN | CHCl | 1 | 1 | H | CH$_2$Br |
| F | CN | CHCl | 1 | 1 | C(=O)CH$_3$ | CH$_2$Cl |
| F | CN | CHCl | 1 | 1 | C(=O)CH$_3$ | CH$_2$Br |
| F | CN | CHCl | 1 | 1 | CO$_2$CH$_3$ | CH$_2$Cl |
| F | CN | CHCl | 1 | 1 | CO$_2$CH$_3$ | CH$_2$Br |
| F | CN | CHCl | 1 | 1 | CH$_2$C≡CH | CH$_2$Cl |
| F | CN | CHCl | 1 | 1 | CH$_2$C≡CH | CH$_2$Br |
| F | CN | CHCl | 1 | 2 | H | CH$_2$Cl |
| F | CN | CHCl | 1 | 2 | H | CH$_2$Br |
| F | CN | CHCl | 1 | 2 | C(=O)CH$_3$ | CH$_2$Cl |
| F | CN | CHCl | 1 | 2 | C(=O)CH$_3$ | CH$_2$Br |
| F | CN | CHCl | 1 | 2 | CO$_2$CH$_3$ | CH$_2$Cl |
| F | CN | CHCl | 1 | 2 | CO$_2$CH$_3$ | CH$_2$Br |
| F | CN | CHCl | 1 | 2 | CH$_2$C≡CH | CH$_2$Cl |
| F | CN | CHCl | 1 | 2 | CH$_2$C≡CH | CH$_2$Br |
| Cl | H | CH$_2$ | 1 | 1 | H | CH$_2$Cl |
| Cl | H | CH$_2$ | 1 | 1 | H | CH$_2$Br |
| Cl | H | CH$_2$ | 1 | 1 | C(=O)CH$_3$ | CH$_2$Cl |
| Cl | H | CH$_2$ | 1 | 1 | C(=O)CH$_3$ | CH$_2$Br |
| Cl | H | CH$_2$ | 1 | 1 | CO$_2$CH$_3$ | CH$_2$Cl |
| Cl | H | CH$_2$ | 1 | 1 | CO$_2$CH$_3$ | CH$_2$Br |
| Cl | H | CH$_2$ | 1 | 1 | CH$_2$C≡CH | CH$_2$Cl |
| Cl | H | CH$_2$ | 1 | 1 | CH$_2$C≡CH | CH$_2$Br |
| Cl | H | CH$_2$ | 1 | 2 | H | CH$_2$Cl |
| Cl | H | CH$_2$ | 1 | 2 | H | CH$_2$Br |
| Cl | H | CH$_2$ | 1 | 2 | C(=O)CH$_3$ | CH$_2$Cl |
| Cl | H | CH$_2$ | 1 | 2 | C(=O)CH$_3$ | CH$_2$Br |
| Cl | H | CH$_2$ | 1 | 2 | CO$_2$CH$_3$ | CH$_2$Cl |
| Cl | H | CH$_2$ | 1 | 2 | CO$_2$CH$_3$ | CH$_2$Br |
| Cl | H | CH$_2$ | 1 | 2 | CH$_2$C≡CH | CH$_2$Cl |
| Cl | H | CH$_2$ | 1 | 2 | CH$_2$C≡CH | CH$_2$Br |
| Cl | H | CHF | 1 | 1 | H | CH$_2$Cl |
| Cl | H | CHF | 1 | 1 | H | CH$_2$Br |
| Cl | H | CHF | 1 | 1 | C(=O)CH$_3$ | CH$_2$Cl |
| Cl | H | CHF | 1 | 1 | C(=O)CH$_3$ | CH$_2$Br |
| Cl | H | CHF | 1 | 1 | CO$_2$CH$_3$ | CH$_2$Cl |
| Cl | H | CHF | 1 | 1 | CO$_2$CH$_3$ | CH$_2$Br |
| Cl | H | CHF | 1 | 1 | CH$_2$C≡CH | CH$_2$Cl |
| Cl | H | CHF | 1 | 1 | CH$_2$C≡CH | CH$_2$Br |
| Cl | H | CHF | 1 | 2 | H | CH$_2$Cl |
| Cl | H | CHF | 1 | 2 | H | CH$_2$Br |
| Cl | H | CHF | 1 | 2 | C(=O)CH$_3$ | CH$_2$Cl |
| Cl | H | CHF | 1 | 2 | C(=O)CH$_3$ | CH$_2$Br |
| Cl | H | CHF | 1 | 2 | CO$_2$CH$_3$ | CH$_2$Cl |
| Cl | H | CHF | 1 | 2 | CO$_2$CH$_3$ | CH$_2$Br |
| Cl | H | CHF | 1 | 2 | CH$_2$C≡CH | CH$_2$Cl |
| Cl | H | CHF | 1 | 2 | CH$_2$C≡CH | CH$_2$Br |
| Cl | H | CHCl | 1 | 1 | H | CH$_2$Cl |
| Cl | H | CHCl | 1 | 1 | H | CH$_2$Br |
| Cl | H | CHCl | 1 | 1 | C(=O)CH$_3$ | CH$_2$Cl |
| Cl | H | CHCl | 1 | 1 | C(=O)CH$_3$ | CH$_2$Br |
| Cl | H | CHCl | 1 | 1 | CO$_2$CH$_3$ | CH$_2$Cl |
| Cl | H | CHCl | 1 | 1 | CO$_2$CH$_3$ | CH$_2$Br |
| Cl | H | CHCl | 1 | 1 | CH$_2$C≡CH | CH$_2$Cl |
| Cl | H | CHCl | 1 | 1 | CH$_2$C≡CH | CH$_2$Br |
| Cl | H | CHCl | 1 | 2 | H | CH$_2$Cl |
| Cl | H | CHCl | 1 | 2 | H | CH$_2$Br |
| Cl | H | CHCl | 1 | 2 | C(=O)CH$_3$ | CH$_2$Cl |
| Cl | H | CHCl | 1 | 2 | C(=O)CH$_3$ | CH$_2$Br |
| Cl | H | CHCl | 1 | 2 | CO$_2$CH$_3$ | CH$_2$Cl |
| Cl | H | CHCl | 1 | 2 | CO$_2$CH$_3$ | CH$_2$Br |
| Cl | H | CHCl | 1 | 2 | CH$_2$C≡CH | CH$_2$Cl |
| Cl | H | CHCl | 1 | 2 | CH$_2$C≡CH | CH$_2$Br |
| Cl | Cl | CH$_2$ | 1 | 1 | H | CH$_2$Cl |
| Cl | Cl | CH$_2$ | 1 | 1 | H | CH$_2$Br |
| Cl | Cl | CH$_2$ | 1 | 1 | C(=O)CH$_3$ | CH$_2$Cl |
| Cl | Cl | CH$_2$ | 1 | 1 | C(=O)CH$_3$ | CH$_2$Br |
| Cl | Cl | CH$_2$ | 1 | 1 | CO$_2$CH$_3$ | CH$_2$Cl |
| Cl | Cl | CH$_2$ | 1 | 1 | CO$_2$CH$_3$ | CH$_2$Br |
| Cl | Cl | CH$_2$ | 1 | 1 | CH$_2$C≡CH | CH$_2$Cl |
| Cl | Cl | CH$_2$ | 1 | 1 | CH$_2$C≡CH | CH$_2$Br |
| Cl | Cl | CH$_2$ | 1 | 2 | H | CH$_2$Cl |
| Cl | Cl | CH$_2$ | 1 | 2 | H | CH$_2$Br |
| Cl | Cl | CH$_2$ | 1 | 2 | C(=O)CH$_3$ | CH$_2$Cl |

TABLE 1-continued

| | | | | | | |
|---|---|---|---|---|---|---|
| Cl | Cl | CH$_2$ | 1 | 2 | C(=O)CH$_3$ | CH$_2$Br |
| Cl | Cl | CH$_2$ | 1 | 2 | CO$_2$CH$_3$ | CH$_2$Cl |
| Cl | Cl | CH$_2$ | 1 | 2 | CO$_2$CH$_3$ | CH$_2$Br |
| Cl | Cl | CH$_2$ | 1 | 2 | CH$_2$C≡CH | CH$_2$Cl |
| Cl | Cl | CH$_2$ | 1 | 2 | CH$_2$C≡CH | CH$_2$Br |
| Cl | Cl | CHF | 1 | 1 | H | CH$_2$Cl |
| Cl | Cl | CHF | 1 | 1 | H | CH$_2$Br |
| Cl | Cl | CHF | 1 | 1 | C(=O)CH$_3$ | CH$_2$Cl |
| Cl | Cl | CHF | 1 | 1 | C(=O)CH$_3$ | CH$_2$Br |
| Cl | Cl | CHF | 1 | 1 | CO$_2$CH$_3$ | CH$_2$Cl |
| Cl | Cl | CHF | 1 | 1 | CO$_2$CH$_3$ | CH$_2$Br |
| Cl | Cl | CHF | 1 | 1 | CH$_2$C≡CH | CH$_2$Cl |
| Cl | Cl | CHF | 1 | 1 | CH$_2$C≡CH | CH$_2$Br |
| Cl | Cl | CHF | 1 | 2 | H | CH$_2$Cl |
| Cl | Cl | CHF | 1 | 2 | H | CH$_2$Br |
| Cl | Cl | CHF | 1 | 2 | C(=O)CH$_3$ | CH$_2$Cl |
| Cl | Cl | CHF | 1 | 2 | C(=O)CH$_3$ | CH$_2$Br |
| Cl | Cl | CHF | 1 | 2 | CO$_2$CH$_3$ | CH$_2$Cl |
| Cl | Cl | CHF | 1 | 2 | CO$_2$CH$_3$ | CH$_2$Br |
| Cl | Cl | CHF | 1 | 2 | CH$_2$C≡CH | CH$_2$Cl |
| Cl | Cl | CHF | 1 | 2 | CH$_2$C≡CH | CH$_2$Br |
| Cl | Cl | CHCl | 1 | 1 | H | CH$_2$Cl |
| Cl | Cl | CHCl | 1 | 1 | H | CH$_2$Br |
| Cl | Cl | CHCl | 1 | 1 | C(=O)CH$_3$ | CH$_2$Cl |
| Cl | Cl | CHCl | 1 | 1 | C(=O)CH$_3$ | CH$_2$Br |
| Cl | Cl | CHCl | 1 | 1 | CO$_2$CH$_3$ | CH$_2$Cl |
| Cl | Cl | CHCl | 1 | 1 | CO$_2$CH$_3$ | CH$_2$Br |
| Cl | Cl | CHCl | 1 | 1 | CH$_2$C≡CH | CH$_2$Cl |
| Cl | Cl | CHCl | 1 | 1 | CH$_2$C≡CH | CH$_2$Br |
| Cl | Cl | CHCl | 1 | 2 | H | CH$_2$Cl |
| Cl | Cl | CHCl | 1 | 2 | H | CH$_2$Br |
| Cl | Cl | CHCl | 1 | 2 | C(=O)CH$_3$ | CH$_2$Cl |
| Cl | Cl | CHCl | 1 | 2 | C(=O)CH$_3$ | CH$_2$Br |
| Cl | Cl | CHCl | 1 | 2 | CO$_2$CH$_3$ | CH$_2$Cl |
| Cl | Cl | CHCl | 1 | 2 | CO$_2$CH$_3$ | CH$_2$Br |
| Cl | Cl | CHCl | 1 | 2 | CH$_2$C≡CH | CH$_2$Cl |
| Cl | Cl | CHCl | 1 | 2 | CH$_2$C≡CH | CH$_2$Br |
| Cl | Br | CH$_2$ | 1 | 1 | H | CH$_2$Cl |
| Cl | Br | CH$_2$ | 1 | 1 | H | CH$_2$Br |
| Cl | Br | CH$_2$ | 1 | 1 | C(=O)CH$_3$ | CH$_2$Cl |
| Cl | Br | CH$_2$ | 1 | 1 | C(=O)CH$_3$ | CH$_2$Br |
| Cl | Br | CH$_2$ | 1 | 1 | CO$_2$CH$_3$ | CH$_2$Cl |
| Cl | Br | CH$_2$ | 1 | 1 | CO$_2$CH$_3$ | CH$_2$Br |
| Cl | Br | CH$_2$ | 1 | 1 | CH$_2$C≡CH | CH$_2$Cl |
| Cl | Br | CH$_2$ | 1 | 1 | CH$_2$C≡CH | CH$_2$Br |
| Cl | Br | CH$_2$ | 1 | 2 | H | CH$_2$Cl |
| Cl | Br | CH$_2$ | 1 | 2 | H | CH$_2$Br |
| Cl | Br | CH$_2$ | 1 | 2 | C(=O)CH$_3$ | CH$_2$Cl |
| Cl | Br | CH$_2$ | 1 | 2 | C(=O)CH$_3$ | CH$_2$Br |
| Cl | Br | CH$_2$ | 1 | 2 | CO$_2$CH$_3$ | CH$_2$Cl |
| Cl | Br | CH$_2$ | 1 | 2 | CO$_2$CH$_3$ | CH$_2$Br |
| Cl | Br | CH$_2$ | 1 | 2 | CH$_2$C≡CH | CH$_2$Cl |
| Cl | Br | CH$_2$ | 1 | 2 | CH$_2$C≡CH | CH$_2$Br |
| Cl | Br | CHF | 1 | 1 | H | CH$_2$Cl |
| Cl | Br | CHF | 1 | 1 | H | CH$_2$Br |
| Cl | Br | CHF | 1 | 1 | C(=O)CH$_3$ | CH$_2$Cl |
| Cl | Br | CHF | 1 | 1 | C(=O)CH$_3$ | CH$_2$Br |
| Cl | Br | CHF | 1 | 1 | CO$_2$CH$_3$ | CH$_2$Cl |
| Cl | Br | CHF | 1 | 1 | CO$_2$CH$_3$ | CH$_2$Br |
| Cl | Br | CHF | 1 | 1 | CH$_2$C≡CH | CH$_2$Cl |
| Cl | Br | CHF | 1 | 1 | CH$_2$C≡CH | CH$_2$Br |
| Cl | Br | CHF | 1 | 2 | H | CH$_2$Cl |
| Cl | Br | CHF | 1 | 2 | H | CH$_2$Br |
| Cl | Br | CHF | 1 | 2 | C(=O)CH$_3$ | CH$_2$Cl |
| Cl | Br | CHF | 1 | 2 | C(=O)CH$_3$ | CH$_2$Br |
| Cl | Br | CHF | 1 | 2 | CO$_2$CH$_3$ | CH$_2$Cl |
| Cl | Br | CHF | 1 | 2 | CO$_2$CH$_3$ | CH$_2$Br |
| Cl | Br | CHF | 1 | 2 | CH$_2$C≡CH | CH$_2$Cl |
| Cl | Br | CHF | 1 | 2 | CH$_2$C≡CH | CH$_2$Br |
| Cl | Br | CHCl | 1 | 1 | H | CH$_2$Cl |
| Cl | Br | CHCl | 1 | 1 | H | CH$_2$Br |
| Cl | Br | CHCl | 1 | 1 | C(=O)CH$_3$ | CH$_2$Cl |
| Cl | Br | CHCl | 1 | 1 | C(=O)CH$_3$ | CH$_2$Br |
| Cl | Br | CHCl | 1 | 1 | CO$_2$CH$_3$ | CH$_2$Cl |
| Cl | Br | CHCl | 1 | 1 | CO$_2$CH$_3$ | CH$_2$Br |
| Cl | Br | CHCl | 1 | 1 | CH$_2$C≡CH | CH$_2$Cl |
| Cl | Br | CHCl | 1 | 1 | CH$_2$C≡CH | CH$_2$Br |
| Cl | Br | CHCl | 1 | 2 | H | CH$_2$Cl |
| Cl | Br | CHCl | 1 | 2 | H | CH$_2$Br |
| Cl | Br | CHCl | 1 | 2 | C(=O)CH$_3$ | CH$_2$Cl |
| Cl | Br | CHCl | 1 | 2 | C(=O)CH$_3$ | CH$_2$Br |
| Cl | Br | CHCl | 1 | 2 | CO$_2$CH$_3$ | CH$_2$Cl |
| Cl | Br | CHCl | 1 | 2 | CO$_2$CH$_3$ | CH$_2$Br |
| Cl | Br | CHCl | 1 | 2 | CH$_2$C≡CH | CH$_2$Cl |
| Cl | Br | CHCl | 1 | 2 | CH$_2$C≡CH | CH$_2$Br |
| Cl | CN | CH$_2$ | 1 | 1 | H | CH$_2$Cl |
| Cl | CN | CH$_2$ | 1 | 1 | H | CH$_2$Br |
| Cl | CN | CH$_2$ | 1 | 1 | C(=O)CH$_3$ | CH$_2$Cl |
| Cl | CN | CH$_2$ | 1 | 1 | C(=O)CH$_3$ | CH$_2$Br |
| Cl | CN | CH$_2$ | 1 | 1 | CO$_2$CH$_3$ | CH$_2$Cl |
| Cl | CN | CH$_2$ | 1 | 1 | CO$_2$CH$_3$ | CH$_2$Br |
| Cl | CN | CH$_2$ | 1 | 1 | CH$_2$C≡CH | CH$_2$Cl |
| Cl | CN | CH$_2$ | 1 | 1 | CH$_2$C≡CH | CH$_2$Br |
| Cl | CN | CH$_2$ | 1 | 2 | H | CH$_2$Cl |
| Cl | CN | CH$_2$ | 1 | 2 | H | CH$_2$Br |
| Cl | CN | CH$_2$ | 1 | 2 | C(=O)CH$_3$ | CH$_2$Cl |
| Cl | CN | CH$_2$ | 1 | 2 | C(=O)CH$_3$ | CH$_2$Br |
| Cl | CN | CH$_2$ | 1 | 2 | CO$_2$CH$_3$ | CH$_2$Cl |
| Cl | CN | CH$_2$ | 1 | 2 | CO$_2$CH$_3$ | CH$_2$Br |
| Cl | CN | CH$_2$ | 1 | 2 | CH$_2$C≡CH | CH$_2$Cl |
| Cl | CN | CH$_2$ | 1 | 2 | CH$_2$C≡CH | CH$_2$Br |
| Cl | CN | CHF | 1 | 1 | H | CH$_2$Cl |
| Cl | CN | CHF | 1 | 1 | H | CH$_2$Br |
| Cl | CN | CHF | 1 | 1 | C(=O)CH$_3$ | CH$_2$Cl |
| Cl | CN | CHF | 1 | 1 | C(=O)CH$_3$ | CH$_2$Br |
| Cl | CN | CHF | 1 | 1 | CO$_2$CH$_3$ | CH$_2$Cl |
| Cl | CN | CHF | 1 | 1 | CO$_2$CH$_3$ | CH$_2$Br |
| Cl | CN | CHF | 1 | 1 | CH$_2$C≡CH | CH$_2$Cl |
| Cl | CN | CHF | 1 | 1 | CH$_2$C≡CH | CH$_2$Br |
| Cl | CN | CHF | 1 | 2 | H | CH$_2$Cl |
| Cl | CN | CHF | 1 | 2 | H | CH$_2$Br |
| Cl | CN | CHF | 1 | 2 | C(=O)CH$_3$ | CH$_2$Cl |
| Cl | CN | CHF | 1 | 2 | C(=O)CH$_3$ | CH$_2$Br |
| Cl | CN | CHF | 1 | 2 | CO$_2$CH$_3$ | CH$_2$Cl |
| Cl | CN | CHF | 1 | 2 | CO$_2$CH$_3$ | CH$_2$Br |
| Cl | CN | CHF | 1 | 2 | CH$_2$C≡CH | CH$_2$Cl |
| Cl | CN | CHF | 1 | 2 | CH$_2$C≡CH | CH$_2$Br |
| Cl | CN | CHCl | 1 | 1 | H | CH$_2$Cl |
| Cl | CN | CHCl | 1 | 1 | H | CH$_2$Br |
| Cl | CN | CHCl | 1 | 1 | C(=O)CH$_3$ | CH$_2$Cl |
| Cl | CN | CHCl | 1 | 1 | C(=O)CH$_3$ | CH$_2$Br |
| Cl | CN | CHCl | 1 | 1 | CO$_2$CH$_3$ | CH$_2$Cl |
| Cl | CN | CHCl | 1 | 1 | CO$_2$CH$_3$ | CH$_2$Br |
| Cl | CN | CHCl | 1 | 1 | CH$_2$C≡CH | CH$_2$Cl |
| Cl | CN | CHCl | 1 | 1 | CH$_2$C≡CH | CH$_2$Br |
| Cl | CN | CHCl | 1 | 2 | H | CH$_2$Cl |
| Cl | CN | CHCl | 1 | 2 | H | CH$_2$Br |
| Cl | CN | CHCl | 1 | 2 | C(=O)CH$_3$ | CH$_2$Cl |
| Cl | CN | CHCl | 1 | 2 | C(=O)CH$_3$ | CH$_2$Br |
| Cl | CN | CHCl | 1 | 2 | CO$_2$CH$_3$ | CH$_2$Cl |
| Cl | CN | CHCl | 1 | 2 | CO$_2$CH$_3$ | CH$_2$Br |
| Cl | CN | CHCl | 1 | 2 | CH$_2$C≡CH | CH$_2$Cl |
| Cl | CN | CHCl | 1 | 2 | CH$_2$C≡CH | CH$_2$Br |

| J = 19, X = F, Y = Cl, n = m = 1 | | | |
|---|---|---|---|
| Z | R$^1$ | R$^2$ | R$^{24}$ |
| CHF | H | CH$_2$Cl | CO$_2$CH$_2$CH$_3$ |
| CHF | H | CH$_2$Cl | C(O)N(CH$_2$CH$_3$)$_2$ |
| CHF | H | CH$_2$Cl | C(O)NHCH$_3$ |
| CHF | H | CH$_2$Cl |  |
| CHF | H | CH$_2$Cl |  |
| CHF | H | CH$_2$Br | CO$_2$CH$_2$CH$_3$ |
| CHF | H | CH$_2$Br | C(O)N(CH$_2$CH$_3$)$_2$ |
| CHF | H | CH$_2$Br | C(O)NHCH$_3$ |

TABLE 1-continued

| | | | |
|---|---|---|---|
| CHF | H | CH₂Br | 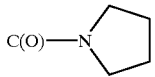 |
| CHF | H | CH₂Br | 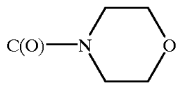 |
| CHF | H | CH₂F | CO₂CH₂CH₃ |
| CHF | H | CH₂F | C(O)N(CH₂CH₃)₂ |
| CHF | H | CH₂F | C(O)NHCH₃ |
| CHF | H | CH₂F | 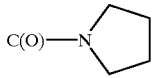 |
| CHF | H | CH₂F | 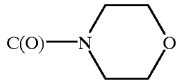 |
| CHF | H | CH₂OCH₃ | CO₂CH₂CH₃ |
| CHF | H | CH₂OCH₃ | C(O)N(CH₂CH₃)₂ |
| CHF | H | CH₂OCH₃ | C(O)NHCH₃ |
| CHF | H | CH₂OCH₃ | 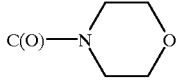 |
| CHF | H | CH₂OCH₃ | 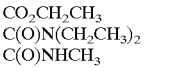 |
| CHF | H | CH₂CN | CO₂CH₂CH₃ |
| CHF | H | CH₂CN | C(O)N(CH₂CH₃)₂ |
| CHF | H | CH₂CN | C(O)NHCH₃ |
| CHF | H | CH₂CN | 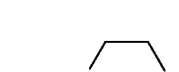 |
| CHF | H | CH₂CN | 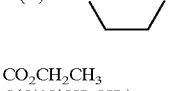 |
| CHF | H | CH₂SCH₃ | CO₂CH₂CH₃ |
| CHF | H | CH₂SCH₃ | C(O)N(CH₂CH₃)₂ |
| CHF | H | CH₂SCH₃ | C(O)NHCH₃ |
| CHF | H | CH₂SCH₃ | 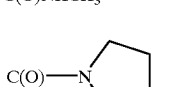 |
| CHF | H | CH₂SCH₃ | 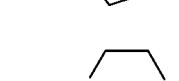 |
| CHF | H | CH₂SO₂CH₃ | CO₂CH₂CH₃ |
| CHF | H | CH₂SO₂CH₃ | C(O)N(CH₂CH₃)₂ |
| CHF | H | CH₂SO₂CH₃ | C(O)NHCH₃ |
| CHF | H | CH₂SO₂CH₃ | 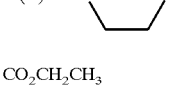 |

TABLE 1-continued

| | | | |
|---|---|---|---|
| CHF | H | CH₂SO₂CH₃ | 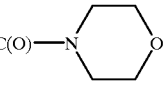 |
| CHCl | H | CH₂Cl | CO₂CH₂CH₃ |
| CHCl | H | CH₂Cl | C(O)N(CH₂CH₃)₂ |
| CHCl | H | CH₂Cl | C(O)NHCH₃ |
| CHCl | H | CH₂Cl | 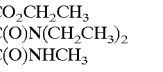 |
| CHCl | H | CH₂Cl | 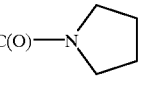 |
| CHCl | H | CH₂Br | CO₂CH₂CH₃ |
| CHCl | H | CH₂Br | C(O)N(CH₂CH₃)₂ |
| CHCl | H | CH₂Br | C(O)NHCH₃ |
| CHCl | H | CH₂Br | 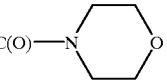 |
| CHCl | H | CH₂Br | 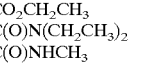 |
| CHCl | H | CH₂F | CO₂CH₂CH₃ |
| CHCl | H | CH₂F | C(O)N(CH₂CH₃)₂ |
| CHCl | H | CH₂F | C(O)NHCH₃ |
| CHCl | H | CH₂F | 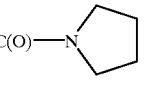 |
| CHCl | H | CH₂F | 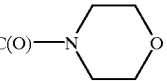 |
| CHCl | H | CH₂OCH₃ | CO₂CH₂CH₃ |
| CHCl | H | CH₂OCH₃ | C(O)N(CH₂CH₃)₂ |
| CHCl | H | CH₂OCH₃ | C(O)NHCH₃ |
| CHCl | H | CH₂OCH₃ | 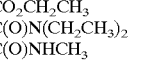 |
| CHCl | H | CH₂OCH₃ | 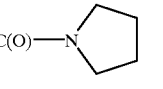 |
| CHCl | H | CH₂CN | CO₂CH₂CH₃ |
| CHCl | H | CH₂CN | C(O)N(CH₂CH₃)₂ |
| CHCl | H | CH₂CN | C(O)NHCH₃ |
| CHCl | H | CH₂CN | 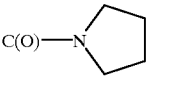 |
| CHCl | H | CH₂CN | 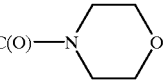 |

TABLE 1-continued

| | | | |
|---|---|---|---|
| CHCl | H | CH$_2$SCH$_3$ | CO$_2$CH$_2$CH$_3$ |
| CHCl | H | CH$_2$SCH$_3$ | C(O)N(CH$_2$CH$_3$)$_2$ |
| CHCl | H | CH$_2$SCH$_3$ | C(O)NHCH$_3$ |
| CHCl | H | CH$_2$SCH$_3$ | C(O)—pyrrolidinyl |
| CHCl | H | CH$_2$SCH$_3$ | C(O)—morpholinyl |
| CHCl | H | CH$_2$SO$_2$CH$_3$ | CO$_2$CH$_2$CH$_3$ |
| CHCl | H | CH$_2$SO$_2$CH$_3$ | C(O)N(CH$_2$CH$_3$)$_2$ |
| CHCl | H | CH$_2$SO$_2$CH$_3$ | C(O)NHCH$_3$ |
| CHCl | H | CH$_2$SO$_2$CH$_3$ | C(O)—pyrrolidinyl |
| CHCl | H | CH$_2$SO$_2$CH$_3$ | C(O)—morpholinyl |
| CHBr | H | CH$_2$Cl | CO$_2$CH$_2$CH$_3$ |
| CHBr | H | CH$_2$Cl | C(O)N(CH$_2$CH$_3$)$_2$ |
| CHBr | H | CH$_2$Cl | C(O)NHCH$_3$ |
| CHBr | H | CH$_2$Cl | C(O)—pyrrolidinyl |
| CHBr | H | CH$_2$Cl | C(O)—morpholinyl |
| CHBr | H | CH$_2$Br | CO$_2$CH$_2$CH$_3$ |
| CHBr | H | CH$_2$Br | C(O)N(CH$_2$CH$_3$)$_2$ |
| CHBr | H | CH$_2$Br | C(O)NHCH$_3$ |
| CHBr | H | CH$_2$Br | C(O)—pyrrolidinyl |
| CHBr | R | CH$_2$Br | C(O)—morpholinyl |
| CHBr | H | CH$_2$F | CO$_2$CH$_2$CH$_3$ |
| CHBr | H | CH$_2$F | C(O)N(CH$_2$CH$_3$)$_2$ |
| CHBr | H | CH$_2$F | C(O)NHCH$_3$ |
| CHBr | H | CH$_2$F | C(O)—pyrrolidinyl |
| CHBr | H | CH$_2$F | C(O)—morpholinyl |
| CHBr | H | CH$_2$OCH$_3$ | CO$_2$CH$_2$CH$_3$ |
| CHBr | H | CH$_2$OCH$_3$ | C(O)N(CH$_2$CH$_3$)$_2$ |
| CHBr | H | CH$_2$OCH$_3$ | C(O)NHCH$_3$ |
| CHBr | H | CH$_2$OCH$_3$ | C(O)—pyrrolidinyl |
| CHBr | H | CH$_2$OCH$_3$ | C(O)—morpholinyl |
| CHBr | H | CH$_2$CN | CO$_2$CH$_2$CH$_3$ |
| CHBr | H | CH$_2$CN | C(O)N(CH$_2$CH$_3$)$_2$ |
| CHBr | H | CH$_2$CN | C(O)NHCH$_3$ |
| CHBr | H | CH$_2$CN | C(O)—pyrrolidinyl |
| CHBr | H | CH$_2$CN | C(O)—morpholinyl |
| CHBr | H | CH$_2$SCH$_3$ | CO$_2$CH$_2$CH$_3$ |
| CHBr | H | CH$_2$SCH$_3$ | C(O)N(CH$_2$CH$_3$)$_2$ |
| CHBr | H | CH$_2$SCH$_3$ | C(O)NHCH$_3$ |
| CHBr | H | CH$_2$SCH$_3$ | C(O)—pyrrolidinyl |
| CHBr | H | CH$_2$SCH$_3$ | C(O)—morpholinyl |
| CHBr | H | CH$_2$SO$_2$CH$_3$ | CO$_2$CH$_2$CH$_3$ |
| CHBr | H | CH$_2$SO$_2$CH$_3$ | C(O)N(CH$_2$CH$_3$)$_2$ |
| CHBr | H | CH$_2$SO$_2$CH$_3$ | C(O)NHCH$_3$ |
| CHBr | H | CH$_2$SO$_2$CH$_3$ | C(O)—pyrrolidinyl |
| CHBr | H | CH$_2$SO$_2$CH$_3$ | C(O)—morpholinyl |

Formulation/Utility

Compounds of this invention will generally be used as a formulation or composition with an agriculturally suitable carrier comprising at least one of a liquid diluent, a solid diluent or a surfactant. The formulation or composition ingredients are selected to be consistent with the physical properties of the active ingredient, mode of application and environmental factors such as soil type, moisture and temperature. Useful formulations include liquids such as solutions (including emulsifiable concentrates), suspensions, emulsions (including microemulsions and/or suspoemulsions) and the like which optionally can be thickened into gels. Useful formulations further include solids such as dusts, powders, granules, pellets, tablets, films, and the like which can be water-dispersible ("wettable") or water-soluble. Active ingredient can be (micro)encapsulated and further formed into a suspension or solid formulation; alternatively the entire formulation of active ingredient can be encapsulated (or "overcoated"). Encapsulation can control or delay release of the active ingredient. Sprayable formulations can be extended in suitable media and used at spray volumes from about one to several hundred liters per hectare. High-strength compositions are primarily used as intermediates for further formulation.

The formulations will typically contain effective amounts of active ingredient, diluent and surfactant within the following approximate ranges which add up to 100 percent by weight.

|  | Weight Percent | | |
|---|---|---|---|
|  | Active Ingredient | Diluent | Surfactant |
| Water-Dispersible and Water-soluble Granules, Tablets and Powders. | 5–90 | 0–94 | 1–15 |
| Suspensions, Emulsions, Solutions (including Emulsifiable Concentrates) | 5–50 | 40–95 | 0–15 |
| Dusts | 1–25 | 70–99 | 0–5 |
| Granules and Pellets | 0.01n99 | 5–99.99 | 0–15 |
| High Strength Compositions | 90–99 | 0–10 | 0–2 |

Typical solid diluents are described in Watkins, et al., *Handbook of Insecticide Dust Diluents and Carriers*, 2nd Ed., Dorland Books, Caldwell, N.J. Typical liquid diluents are described in Marsden, *Solvents Guide*, 2nd Ed., Interscience, New York, 1950. *McCutcheon's Detergents and Emulsifiers Annual*, Allured Publ. Corp., Ridgewood, N.J. as well as Sisely and Wood, *Encyclopedia of Surface Active Agents*, Chemical Publ. Co., Inc., New York, 1964, list surfactants and recommended uses. All formulations can contain minor amounts of additives to reduce foam, caking, corrosion, microbiological growth and the like, or thickeners to increase viscosity.

Surfactants include, for example, polyethoxylated alcohols, polyethoxylated alkylphenols, polyethoxylated sorbitan fatty acid esters, dialkyl sulfosuccinates, alkyl sulfates, alkylbenzene sulfonates, organosilicones, N,N-dialkyltaurates, lignin sulfonates, naphthalene sulfonate formaldehyde condensates, polycarboxylates, and polyoxyethylene/polyoxypropylene block copolymers. Solid diluents include, for example, clays such as bentonite, montmorillonite, attapulgite and kaolin, starch, sugar, silica, talc, diatomaceous earth, urea, calcium carbonate, sodium carbonate and bicarbonate, and sodium sulfate. Liquid diluents include, for example, water, N,N-dimethylformamide, dimethyl sulfoxide, N-alkylpyrrolidone, ethylene glycol, polypropylene glycol, paraffins, alkylbenzenes, alkylnaphthalenes, oils of olive, castor, linseed, tung, sesame, corn, peanut, cotton-seed, soybean, rape-seed and coconut, fatty acid esters, ketones such as cyclohexanone, 2-heptanone, isophorone and 4-hydroxy-4-methyl-2-pentanone, and alcohols such as methanol, cyclohexanol, decanol and tetrahydrofurfuryl alcohol.

Solutions, including emulsifiable concentrates, can be prepared by simply mixing the ingredients. Dusts and powders can be prepared by blending and, usually, grinding as in a hammer mill or fluid-energy mill. Suspensions are usually prepared by wet-milling; see, for example, U.S. Pat. No. 3,060,084. Granules and pellets can be prepared by spraying the active material upon preformed granular carriers or by agglomeration techniques. See Browning, "Agglomeration", *Chemical Engineering, Dec.* 4, 1967, pp 147–48, *Perry's Chemical Engineer's Handbook*, 4th Ed., McGraw-Hill, New York, 1963, pages 8–57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see U.S. Pat. No. 3,235,361, Col. 6, line 16 through Col. 7, line 19 and Examples 10–41; U.S. Pat. No. 3,309,192, Col. 5, line 43 through Col. 7, line 62 and Examples 8, 12, 15, 39, 41, 52, 53, 58, 132, 138–140, 162–164, 166, 167 and 169–182; U.S. Pat. No. 2,891,855, Col. 3, line 66 through Col. 5, line 17 and Examples 1–4; Klingman, *Weed Control as a Science*, John Wiley and Sons, Inc., New York, 1961, pp 81–96; and Hance et al., *Weed Control Handbook*, 8th Ed., Blackwell Scientific Publications, Oxford, 1989.

In the following Examples, all percentages are by weight and all formulations are prepared in conventional ways. Compound numbers refer to compounds in Index Tables A–J.

| Example A | |
|---|---|
| High Strength Concentrate | |
| Compound 23 | 98.5% |
| silica aerogel | 0.5% |
| synthetic amorphous fine silica | 1.0%. |
| Example B | |
| Wettable Powder | |
| Compound 25 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0%. |
| Example C | |
| Granule | |
| Compound 21 | 10.0% |
| attapulgite granules (low volatile matter, 0.71/0.30 mm; U.S.S. No. 25–50 sieves) | 90.0%. |
| Example D | |
| Extruded Pellet | |
| Compound 52 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0%. |

Test results indicate that the compounds of the present invention are highly active preemergent and postemergent herbicides or plant growth regulants. Many of them have utility for broad-spectrum pre- and/or postemergence weed control in areas where complete control of all vegetation is desired such as around fuel storage tanks, industrial storage areas, parking lots, drive-in theaters, air fields, river banks, irrigation and other waterways, around billboards and highway and railroad structures. Some of the compounds are useful for the control of selected grass and broadleaf weeds with tolerance to important agronomic crops which include but are not limited to alfalfa, barley, cotton, wheat, rape, sugar beets, corn (maize), sorghum, soybeans, rice, oats, peanuts, vegetables, tomato, potato, perennial plantation crops including coffee, cocoa, oil palm, rubber, sugarcane, citrus, grapes, fruit trees, nut trees, banana, plantain, pineapple, hops, tea and forests such as eucalyptus and conifers (e.g., loblolly pine), and turf species (e.g., Kentucky bluegrass, St. Augustine grass, Kentucky fescue and Bermuda grass). Those skilled in the art will appreciate that not all compounds are equally effective against all weeds. Alternatively, the subject compounds are useful to modify plant growth.

Compounds of this invention can be used alone or in combination with other commercial herbicides, insecticides or fungicides. Compounds of this invention can also be used in combination with commercial herbicide safeners such as benoxacor, dichlormid and furilazole to increase safety to certain crops. A mixture of one or more of the following herbicides with a compound of this invention may be particularly useful for weed control: acetochlor, acifluorfen and its sodium salt, aclonifen, acrolein (2-propenal), alachlor, ametryn, amidosulfuron, amitrole, ammonium sulfamate, anilofos, asulam, atrazine, azimsulfuron, benazolin, benazolin-ethyl, benfluralin, benfuresate, bensulfuron-methyl, bensulide, bentazone, bifenox, bromacil, bromoxynil, bromoxynil octanoate, butachlor, butralin, butylate, chlomethoxyfen, chloramben, chlorbromuron, chloridazon, chlorimuron-ethyl, chlornitrofen, chlorotoluron, chlorpropham, chiorsulfuron, chlorthal-dimethyl, cinmethylin, cinosulfuron, clethodim, clomazone, clopyralid, clopyralid-olamine, cyanazine, cycloate, cyclosulfamuron, 2,4-D and its butotyl, butyl, isoctyl and isopropyl esters and its dimethylammonium, diolamine and trolamine salts, daimuron, dalapon, dalapon-sodium, dazomet, 2,4-DB and its dimethylammonium, potassium and sodium salts, desmedipham, desmetryn, dicamba and its diglycolammonium, dimethylammonium, potassium and sodium salts, dichlobenil, dichlorprop, diclofop-methyl, 2-[4,5-dihydro-4-methyl-4-(1-methyl-ethyl)-5-oxo-1H-imidazol-2-yl]-5-methyl-3-pyridinecarboxylic acid (AC 263,222), difenzoquat metilsulfate, diflufenican, dimepiperate, dimethenamid, dimethylarsinic acid and its sodium salt, dinitramine, diphenamid, diquat dibromide, dithiopyr, diuron, DNOC, endothal, EPTC, esprocarb, ethalfluralin, ethametsulfuron-methyl, ethofumesate, ethyl α,2-dichloro-5-[4-(difluoromethyl)-4,5-dihydro-3-methyl-5-oxo-1H-1,2,4-triazol-1-yl]-4-fluorobenzenepropanoate (F8426), fenoxaprop-ethyl, fenoxaprop-P-ethyl, fenuron, fenuron-TCA, flamprop-methyl, flamprop-M-isopropyl, flamprop-M-methyl, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, fluridone, flurochloridone, fluroxypyr, fomesafen, fosamine-ammonium, glufosinate, glufosinate-armonium, glyphosate, glyphosate-isopropylammonium, glyphosate-sesquisodium, glyphosate-trimesium, halosulfuron-methyl, haloxyfop-ethyl, haloxyfop-methyl, hexazinone, imazamethabenz-methyl, imazamox (AC 299 263), imazapyr, imazaquin, imazaquin-ammonium, imazethapyr, imazethapyr-ammonium, imazosulfuron, ioxynil, ioxynil octanoate, ioxynil-sodium, isoproturon, isouron, isoxaben, isoxaflutole (RPA 201772), lactofen, lenacil, linuron, maleic hydrazide, MCPA and its dimethylammonium, potassium and sodium salts, MCPA-isoctyl, mecoprop, mecoprop-P, mefenacet, mefluidide, metam-sodium, methabenzthiazuron, methyl [[2-chloro-4-fluoro-5-[(tetrahydro-3-oxo-1H,3H-[1,3,4] thiadiazolo[3,4-a]pyridazin-1-ylidene)amino]phenyl] thioacetate (K1H 9201), methylarsonic acid and its calcium, monoammonium, monosodium and disodium salts, methyl [[[1-[5-[2-chloro-4-(trifluoromethyl)phenoxy]-2-nitrophenyl]-2-methoxyethylidene]amino]oxy]acetate (AKH-7088), methyl 5-[[[[(4,6-dimethyl-2-pyrimidinyl) amino]carbonyl]amino]sulfonyl]-1-(2-pyridinyl)-1H-pyrazole-4-carboxylate (NC-330), metobenzuron, metolachlor, metosulaam, metoxuron, metribuzin, metsulfuron-methyl, molinate, monolinuron, napropamide, naptalam, neburon, nicosulfuron, norflurazon, oryzalin, oxadiazon, 3-oxetanyl 2-[[[[(4,6-dimethyl-2-pyrimidinyl) amino]carbonyl]amino]sulfonyl]benzoate (CGA 277476), oxyfluorfen, paraquat dichloride, pebulate, pendimethalin, perfluidone, phenmedipham, picloram, picloram-potassium, pretilachlor, primisulfuron-methyl, prometon, prometryn, propachlor, propanil, propaquizafop, propazine, propham, propyzarnide, prosulfuron, pyrazolynate, pyrazosulfuron-ethyl, pyridate, pyrithiobac, pyrithiobac-sodium, quinclorac, quizalofop-ethyl, quizalofop-P-ethyl, quizalofop-P-tefuryl, rimsulfuron, sethoxydim, siduron, simazine, sulcotrione (ICIA0051), sulfentrazone, sulfometuron-methyl, TCA, TCA-sodium, tebuthiuron, terbacil, terbuthylazine, terbutryn, thenylchlor, thiafluamide (BAY 11390), thifensulfuron-methyl, thiobencarb, tralkoxydim, tri-allate, triasulfuron, tribenuron-methyl, triclopyr, triclopyr-butotyl, triclopyr-triethylammonium, tridiphane, trifluralin, triflusulfuron-methyl, and vemolate.

In certain instances, combinations with other herbicides having a similar spectrum of control but a different mode of action will be particularly advantageous for preventing the development of resistant weeds.

Certain combinations of compounds of this invention with other herbicides may provide synergistic herbicidal effects on weeds or may provide enhanced crop safety.

Preferred for better control of undesired vegetation in corn (e.g., lower use rate, broader spectrum of weeds controlled, or enhanced crop safety) or for preventing the development of resistant weeds in corn are mixtures of a compound of this invention with one or more of the herbicides selected from the group rimsulfuron, thifensulfuron-methyl, chlorimuron-ethyl, nicosulfuron, prosulfuron, primsulfuron, atrazine, terbuthylazine, dicamba, 2,4-D, bomoxynil, pyridate, sulcotrione, glufosinate, glyphosate, glyphosate-trimesium, fluthiacet-methyl, quizalofop-p-ethyl, bentazone, clopyralid, flumetsulam, halosulfuron, sethoxydim, flumiclorac-pentyl, imozamox, acetachlor, alachlor, dimethenarrid, isoxaflutole, metolachlor, metribuzin, pendimethalin, and thiafluimid.

Preferred for better control of undesired vegetation in soybeans (e.g., lower use rate, broader spectrum of weeds controlled, or enhanced crop safety) or for preventing the development of resistant weeds in soybeans are mixtures of a compound of this invention with one or more of the herbicides selected from the group chlorimuron-ethyl, thifensulfuron-methyl, clethodim, sethoxydim, fluazifop-p-butyl, haloxyfop, imazethapyr, imozamox, imazaquin, glufosinate, glyphosate, glyphosate-trimesium, lactofen, fluthiacet-methyl, quizalofop-p-ethyl, acifluorfen-sodium, oxasulfuron, imazameth, flumiclorac-pentyl, and bentazone.

Preferred for better control of undesired vegetation in winter wheat, winter barley, spring wheat, spring barley, and peas (e.g., lower use rate, broader spectrum of weeds controlled, or enhanced crop safety) or for preventing the development of resistant weeds in winter wheat, winter barley, spring wheat, spring barley, and peas are mixtures of a compound of this invention with one or more of the herbicides selected from the group tribenuron-methyl, thifensulfuron-methyl, metsulfuron-methyl, chlorsulfuron, triasulfuron, 2,4-D, dicamba, bromoxynil, MCPA, fluroxypyr, clopyralid, fenoxaprop, fenchlorazole, diclofop, tralkoxydim, clodinafop, cloquintocet-mexyl, imazamethabenz, sulfosulfuron, difenzoquat, propanil, prosulfuron, metribuzin, glyphosate, triallate, trifluralin, paraquat, diallate, linuron, diflufenican, pendimethalin, cyanazine, neburon, terbutryn, prosulfocarb, isoproturon, chlortoluron, methabenzthiazuron, metoxuron, simazine, ioxynil, mecoprop, metosulam, fluroglycophen-ethyl, flamprop-M-isopropyl, and benzoylpropethyl.

Specifically preferred mixtures for use in corn are selected from the group:

a) (6S-cis)-1-chloro-N-[2-chloro-4-fluoro-5-(6-fluorotetrahydro-1,3-dioxo-1H-pyrrrolo[2-c]imidazol-2(3H)-yl)phenyl]methanesulfonamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | rimsulfuron | 2 | thifensulfuron-methyl |
| 3 | chlorimuron-ethyl | 4 | rimsulfuron (B1) in combination with thifensulfuron-methyl (B2) |
| 5 | nicosulfuron | 6 | rimsulfuron (B3) in combination with nicosulfuron (B4) |
| 7 | rimsulfuron (B5) in combination with nicosulfuron (B6) in combination with thifensulfuron-methyl (B7) | 8 | prosulfuron |
| 9 | prosulfuron (B8) in combination with primsulfuron (B9) | 10 | atrazine |
| 11 | terbuthylazine | 12 | dicamba |
| 13 | 2,4-D | 14 | bromoxynil |
| 15 | pyridate | 16 | sulcotrione |
| 17 | glufosinate | 18 | glyphosate |
| 19 | glyphosate-trimesium | | |

Combination 1 is generally used in a ratio of A to B of 1:500 to 50:1, preferably 1:20 to 4:1, with B being applied at a rate of 1 to 50 g/ha, preferably 5 to 20 g/ha. Combination 2 is generally used in a ratio of A to B of 1:500 to 50:1, preferably 1:10 to 20:1, with B being applied at a rate of 1 to 50 g/ha, preferably 1 to 10 g/ha. Combination 3 is generally used in a ratio of A to B of 1:1,000 to 50:1, preferably 1:20 to 20:1 with B being applied at a rate of 1 to 100 g/ha, preferably 1 to 20 g/ha. Combination 4 is generally used in a ratio of A to B1 of 1:500 to 50:1, preferably 1:20 to 4:1, and a ratio of A to B2 of 1:500 to 50:1, preferably 1:10 to 20:1, with B1 being applied a rate of 1 to 50 g/ha, preferably 5 to 20 g/ha, and B2 being applied at a rate of 1 to 50 g/ha, preferably 1 to 10 g/ha. Combination 5 is generally used in a ratio of A to B of 1:2,000 to 5:1, preferably 1:50 to 2:1, with B being applied at a rate of 10 to 200 g/ha, preferably 10 to 50 g/ha. Combination 6 is generally used in a ratio of A to B3 of 1:500 to 50:1, preferably 1:20 to 4:1, and a ratio of A to B4 of 1:2,000 to 5:1, preferably 1:50 to 2:1, with B3 being applied at a rate of 1 to 50 g/ha, preferably 5 to 20 g/ha, and B4 being applied at a rate of 10 to 200 g/ha, preferably 10 to 50 g/ha. Combination 7 is generally used in a ratio of A to B5 of 1:500 to 50:1, preferably 1:20 to 4:1, and a ratio of A to B6 of 1:2,000 to 5:1, preferably 1:50 to 2:1, and a ratio of A to B7 of 1:500 to 50:1, preferably 1:10 to 20:1, with B5 being applied at a rate of 1 to 50 g/ha, preferably 5 to 20 g/ha, and B6 being applied at a rate of 10 to 200 g/ha, preferably 10 to 50 g/ha, and B7 being applied at a rate of 1 to 50 g/ha, preferably 1 to 10 g/ha. Combination 8 is generally used in a ratio of A to B of 1:1,000 to 5:1, preferably 1:60 to 1:1, with B being applied at a rate of 10 to 100 g/ha, preferably 20 to 60 g/ha. Combination 9 is generally used in a ratio of A to B8 of 1:1,000 to 5:1, preferably 1:60 to 1:1, and a ratio of A to B9 of 1:1,000 to 5:1, preferably 1:60 to 1:1, with B8 being applied at a rate of 10 to 100 g/ha, preferably 20 to 60 g/ha, and B9 being applied at a rate of 10 to 100 g/ha, preferably 20 to 60 g/ha. Combination 10 is generally used in a ratio of A to B of 1:30,000 to 1:10, preferably 1:1,000 to 1:25, with B being applied at a rate of 500 to 3,000 g/ha, preferably 500 to 1,000 g/ha. Combination 11 is generally used in a ratio of A to B of 1:50,000 to 1:10, preferably 1:2,000 to 1:25, with B being applied at a rate of 500 to 5,000 g/ha, preferably 500 to 2,000 g/ha. Combination 12 is generally used in a ratio of A to B of 1:10,000 to 1:2, preferably 1:500 to 1:5, with B being applied at a rate of 100 to 1,000 g/ha, preferably 100 to 500 g/ha. Combination 13 is generally used in a ratio of A to B of 1:10,000 to 1:2, preferably 1:500 to 1:5, with B being applied at a rate of 100 to 1,000 g/ha, preferably 100 to 500 g/ha. Combination 14 is generally used in a ratio of A to B of 1:10,000 to 1:2, preferably 1:500 to 1:5, with B being applied at a rate of 100 to 1,000 g/ha, preferably 100 to 500 g/ha. Combination 15 is generally used in a ratio of A to B of 1:30,000 to 1:40, preferably 1:1,000 to 1:10, with B being applied at a rate of 200 to 3,000 g/ha, preferably 200 to 1,000 g/ha. Combination 16 is generally used in a ratio of A to B of 1:30,000 to 1:40, preferably 1:1,000 to 1:10, with B being applied at a rate of 200 to 3,000 g/ha, preferably 200 to 1,000 g/ha. Combination 17 is generally used in a ratio of A to B of 1:30,000 to 1:40, preferably 1:1,000 to 1:10, with B being applied at a rate of 200 to 3,000 g/ha, preferably 200 to 1,000 g/ha. Combination 18 is generally used in a ratio of A to B of 1:30,000 to 1:40, preferably 1:1,000 to 1:10, with B being applied at a rate of 200 to 3,000 g/ha, preferably 200 to 1,000 g/ha. Combination 19 is generally used in a ratio of A to B of 1:30,000 to 1:40, preferably 1:1,000 to 1:10, with B being applied at a rate of 200 to 3,000 g/ha, preferably 200 to 1,000 g/ha.

b) (6S-cis)-N-[2-chloro-fluoro-5-(6-fluorotetrahydro-1,3-dioxo-1H-pyrrolo[1,2-c]imidazol-2(3H)-yl)phenyl]-N-[(chloromethyl)sulfonyl]acetamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | rimsulfuron | 2 | thifensulfuron-methyl |
| 3 | chlorimuron-ethyl | 4 | rimsulfuron (B1) in combination with thifensulfuron-methyl (B2) |
| 5 | nicosulfuron | 6 | rimsulfuron (B3) in combination with nicosulfuron (B4) |
| 7 | rimsulfuron (B5) in combination with nicosulfuron (B6) in combination with thifensulfuron-methyl (B7) | 8 | prosulfuron |
| 9 | prosulfuron (B8) in combination with primsulfuron (B9) | 10 | atrazine |
| 11 | terbuthylazine | 12 | dicamba |
| 13 | 2,4-D | 14 | bromoxynil |
| 15 | pyridate | 16 | sulcotrione |

| Combination Number | Mixture partner B | Combination Number | Mixture partner B |
| --- | --- | --- | --- |
| 17 | glufosinate | 18 | glyphosate |
| 19 | glyphosate-trimesium | | |

Combination 1 is generally used in a ratio of A to B of 1:500 to 50:1, preferably 1:20 to 4:1, with B being applied at a rate of 1 to 50 g/ha, preferably 5 to 20 g/ha. Combination 2 is generally used in a ratio of A to B of 1:500 to 50:1, preferably 1:10 to 20:1, with B being applied at a rate of 1 to 50 g/ha, preferably 1 to 10 g/ha. Combination 3 is generally used in a ratio of A to B of 1:1,000 to 50:1, preferably 1:20 to 20:1 with B being applied at a rate of 1 to 100 g/ha, preferably 1 to 20 g/ha. Combination 4 is generally used in a ratio of A to B 1 of 1:500 to 50:1, preferably 1:20 to 4:1, and a ratio of A to B2 of 1:500 to 50:1, preferably 1:10 to 20:1, with B1 being applied at a rate of 1 to 50 g/ha, preferably 5 to 20 g/ha, and B2 being applied at a rate of 1 to 50 g/ha, preferably 1 to 10 g/ha. Combination 5 is generally used in a ratio of A to B of 1:2,000 to 5:1, preferably 1:50 to 2:1, with B being applied at a rate of 10 to 200 g/ha, preferably 10 to 50 g/ha. Combination 6 is generally used in a ratio of A to B3 of 1:500 to 50:1, preferably 1:20 to 4:1, and a ratio of A to B4 of 1:2,000 to 5:1, preferably 1:50 to 2:1, with B3 being applied at a rate of 1 to 50 g/ha, preferably 5 to 20 g/ha, and B4 being applied at a rate of 10 to 200 g/ha, preferably 10 to 50 g/ha. Combination 7 is generally used in a ratio of A to B5 of 1:500 to 50:1, preferably 1:20 to 4:1, and a ratio of A to B6 of 1:2,000 to 5:1, preferably 1:50 to 2:1, and a ratio of A to B7 of 1:500 to 50:1, preferably 1:10 to 20:1, with B5 being applied at a rate of 1 to 50 g/ha, preferably 5 to 20 g/ha, and B6 being applied at a rate of 10 to 200 g/ha, preferably 10 to 50 g/ha, and B7 being applied at a rate of 1 to 50 g/ha, preferably 1 to 10 g/ha. Combination 8 is generally used in a ratio of A to B of 1:1,000 to 5:1, preferably 1:60 to 1:1, with B being applied at a rate of 10 to 100 g/ha, preferably 20 to 60 g/ha. Combination 9 is generally used in a ratio of A to B8 of 1:1,000 to 5:1, preferably 1:60 to l:1, and a ratio of A to B9 of 1:1,000 to 5:1, preferably 1:60 to 1:1, with B8 being applied at a rate of 10 to 100 g/ha, preferably 20 to 60 g/ha, and B9 being applied at a rate of 10 to 100 g/ha, preferably 20 to 60 g/ha. Combination 10 is generally used in a ratio of A to B of 1:30,000 to 1:10, preferably 1:1,000 to 1:25, with B being applied at a rate of 500 to 3,000 g/ha, preferably 500 to 1,000 g/ha. Combination 11 is generally used in a ratio of A to B of 1:50,000 to 1:10, preferably 1:2,000 to 1:25, with B being applied at a rate of 500 to 5,000 g/ha, preferably 500 to 2,000 g/ha. Combination 12 is generally used in a ratio of A to B of 1:10,000 to 1:2, preferably 1:500 to 1:5, with B being applied at a rate of 100 to 1,000 g/ha, preferably 100 to 500 g/ha. Combination 13 is generally used in a ratio of A to B of 1:10,000 to 1:2, preferably 1:500 to 1:5, with B being applied at a rate of 100 to 1,000 g/ha, preferably 100 to 500 g/ha. Combination 14 is generally used in a ratio of A to B of 1:10,000 to 1:2, preferably 1:500 to 1:5, with B being applied at a rate of 100 to 1,000 g/ha, preferably 100 to 500 g/ha. Combination 15 is generally used in a ratio of A to B of 1:30,000 to 1:40, preferably 1:1,000 to 1:10, with B being applied at a rate of 200 to 3,000 g/ha, preferably 200 to 1,000 g/ha. Combination 16 is generally used in a ratio of A to B of 1:30,000 to 1:40, preferably 1:1,000 to 1:10, with B being applied at a rate of 200 to 3,000 g/ha, preferably 200 to 1,000 g/ha. Combination 17 is generally used in a ratio of A to B of 1:30,000 to 1:40, preferably 1:1,000 to 1:10, with B being applied at a rate of 200 to 3,000 g/ha, preferably 200 to 1,000 g/ha. Combination 18 is generally used in a ratio of A to B of 1:30,000 to 1:40, preferably 1:1,000 to 1:10, with B being applied at a rate of 200 to 3,000 g/ha, preferably 200 to 1,000 g/ha. Combination 19 is generally used in a ratio of A to B of 1:30,000 to 1:40, preferably 1:1,000 to 1:10, with B being applied at a rate of 200 to 3,000 g/ha, preferably 200 to 1,000 g/ha.

c) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide (mixture partner A, generally applied at a rate of 0.1 to 50 g/ha, preferably applied at a rate of 1 to 20 g/ha in combination with:

| Combination Number | Mixture partner B | Combination Number | Mixture partner B |
| --- | --- | --- | --- |
| 1 | rimsulfuron | 2 | thifensulfuron-methyl |
| 3 | chlorimuron-ethyl | 4 | rimsulfuron (B1) in combination with thifensulfuron-methyl (B2) |
| 5 | nicosulfuron | 6 | rimsulfuron (B3) in combination with nicosulfuron (B4) |
| 7 | rimsulfuron (B5) in combination with nicosulfuron (B6) in combination with thifensulfuron-methyl (B7) | 8 | prosulfuron |
| 9 | prosulfuron (B8) in combination with primsulfuron (B9) | 10 | atrazine |
| 11 | terbuthylazine | 12 | dicamba |
| 13 | 2,4-D | 14 | bromoxynil |
| 15 | pyridate | 16 | sulcotrione |
| 17 | glufosinate | 18 | glyphosate |
| 19 | glyphosate-trimesium | | |

Combination 1 is generally used in a ratio of A to B of 1:500 to 50:1, preferably 1:20 to 4:1, with B being applied at a rate of 1 to 50 g/ha, preferably 5 to 20 g/ha. Combination 2 is generally used in a ratio of A to B of 1:500 to 50:1, preferably 1:10 to 20:1, with B being applied at a rate of 1 to 50 g/ha, preferably 1 to 10 g/ha. Combination 3 is generally used in a ratio of A to B of 1:1,000 to 50:1, preferably 1:20 to 20:1, with B being applied at a rate of 1 to 100 g/ha, preferably 1 to 20 g/ha. Combination 4 is generally used in a ratio of A to B1 of 1:500 to 50:1, preferably 1:20 to 4:1, and a ratio of A to B2 of 1:500 to 50:1, preferably 1:10 to 20:1, with B1 being applied at a rate of 1 to 50 g/ha, preferably 5 to 20 g/ha, and B2 being applied at a rate of 1 to 50 g/ha, preferably 1 to 10 g/ha. Combination 5 is generally used in a ratio of A to B of 1:2,000 to 5:1, preferably 1:50 to 2:1, with B being applied at a rate of 10 to 200 g/ha, preferably 10 to 50 g/ha. Combination 6 is generally used in a ratio of A to B3 of 1:500 to 50:1, preferably 1:20 to 4:1, and a ratio of A to B4 of 1:2,000 to 5:1, preferably 1:50 to 2:1, with B3 being applied at a rate of 1 to 50 g/ha, preferably 5 to 20 g/ha, and B4 being applied at a rate of 10 to 200 g/ha, preferably 10 to 50 g/ha. Combination 7 is generally used in a ratio of A to B5 of 1:500 to 50:1, preferably 1:20 to 4:1, and a ratio of A to B6 of 1:2,000 to 5:1, preferably 1:50 to 2:1, and a ratio of A to B7 of 1:500 to 50:1, preferably 1:10 to 20:1, with B5 being applied at a rate of 1 to 50 g/ha, preferably 5 to 20 g/ha, and B6 being applied at a rate of 10 to 200 g/ha, preferably 10 to 50 g/ha, and B7 being applied at a rate of 1 to 50 g/ha, preferably 1 to 10 g/ha. Combination 8 is generally used in a ratio of A to B of 1:1,000 to 5:1, preferably 1:60 to 1:1, with B being applied at a rate of 10 to 100 g/ha, preferably 20 to 60 g/ha Combination 9 is generally used in a ratio of A to B8 of 1:1,000 to 5:1, preferably 1:60 to 1:1, and a ratio of A to B9 of 1:1,000 to 5:1, preferably 1:60 to 1:1, with B8 being applied at a rate of 10 to 100 g/ha, preferably 20 to 60 g/ha, and B9 being applied at a rate of 10 to 100 g/ha, preferably 20 to 60 g/ha. Combination 10 is generally used in a ratio of A to B of 1:30,000 to 1:10, preferably 1:1,000 to 1:25, with B being applied at a rate of 500 to 3,000 g/ha, preferably 500 to 1,000 g/ha. Combination 11 is generally used in a ratio of A to B of 1:50,000 to 1:10, preferably 1:2,000 to 1:25, with B being applied at a rate of 500 to 5,000 g/ha, preferably 500 to 2,000 g/ha. Combination 12 is generally used in a ratio of A to B of 1:10,000 to 1:2, preferably 1:500 to 1:5, with B being applied at a rate of 100 to 1,000 g/ha, preferably 100 to 500 g/ha. Combination 13 is generally used in a ratio of A to B of 1:10,000 to 1:2, preferably 1:500 to 1:5, with B being applied at a rate of 100 to 1,000 g/ha, preferably 100 to 500 g/ha Combination 14 is generally used in a ratio of A to B of 1:10,000 to 1:2, preferably 1:500 to 1:5, with B being applied at a rate of 100 to 1,000 g/ha, preferably 100 to 500 g/ha. Combination 15 is generally used in a ratio of A to B of 1:30,000 to 1:40, preferably 1:1,000 to 1:10, with B being applied at a rate of 200 to 3,000 g/ha, preferably 200 to 1,000 g/ha. Combination 16 is generally used in a ratio of A to B of 1:30,000 to 1:40, preferably 1:1,000 to 1:10, with B being applied at a rate of 200 to 3,000 g/ha, preferably 200 to 1,000 g/ha. Combination 17 is generally used in a ratio of A to B of 1:30,000 to 1:40, preferably 1:1,000 to 1:10, with B being applied at a rate of 200 to 3,000 g/ha, preferably 200 to 1,000 g/ha. Combination 18 is generally used in a ratio of A to B of 1:30,000 to 1:40, preferably 1:1,000 to 1:10, with B being applied at a rate of 200 to 3,000 g/ha, preferably 200 to 1,000 g/ha. Combination 19 is generally used in a ratio of A to B of 1:30,000 to 1:40, preferably 1:1,000 to 1:10, with B being applied at a rate of 200 to 3,000 g/ha, preferably 200 to 1,000 g/ha.

d) (6S-cis)-N-[2-chloro-5-(6-chlorotetrahydro-1,3-dioxo-1H-pyrrolo[1,2-c]imidazol-2(3H)-yl)-4-fluorophenyl)-N-[(chloromethyl)sulfonyl]acetamide (mixture partner A, generally applied at a rate of 0.1 to 50 g/ha, preferably applied at a rate of 1 to in combination with:

| Combination Number | Mixture partner B | Combination Number | Mixture partner B |
|---|---|---|---|
| 1 | rimsulfuron | 2 | thifensulfuron-methyl |
| 3 | chlorimuron-ethyl | 4 | rimsulfuron (B1) in combination with thifensulfuron-methyl (B2) |
| 5 | nicosulfuron | 6 | rimsulfuron (B3) in combination with nicosulfuron (B4) |
| 7 | rimsulfuron (B5) in combination with nicosulfuron (B6) in combination with thifensulfuron-methyl (B7) | 8 | prosulfuron |
| 9 | prosulfuron (B8) in combination with primsulfuron (B9) | 10 | atrazine |

| Combination Number | Mixture partner B | Combination Number | Mixture partner B |
|---|---|---|---|
| 11 | terbuthylazine | 12 | dicamba |
| 13 | 2,4-D | 14 | bromoxynil |
| 15 | pyridate | 16 | sulcotrione |
| 17 | glufosinate | 18 | glyphosate |
| 19 | glyphosate-trimesium | | |

Combination 1 is generally used in a ratio of A to B of 1:500 to 50:1, preferably 1:20 to 4:1, with B being applied at a rate of 1 to 50 g/ha, preferably 5 to 20 g/ha. Combination 2 is generally used in a ratio of A to B of 1:500 to 50:1, preferably 1:10 to 20:1, with B being applied at a rate of 1 to 50 g/ha, preferably 1 to 10 g/ha. Combination 3 is generally used in a ratio of A to B of 1:1,000 to 50:1, preferably 1:20 to 20:1, with B being applied at a rate of 1 to 100 g/ha, preferably 1 to 20 g/ha. Combination 4 is generally used in a ratio of A to B 1 of 1:500 to 50:1, preferably 1:20 to 4:1, and a ratio of A to B2 of 1:500 to 50:1, preferably 1:10 to 20:1, with B1 being applied at a rate of 1 to 50 g/ha, preferably 5 to 20 g/ha, and B2 being applied at a rate of 1 to 50 g/ha, preferably 1 to 10 g/ha. Combination 5 is generally used in a ratio of A to B of 1:2,000 to 5:1, preferably 1:50 to 2:1, with B being applied at a rate of 10 to 200 g/ha, preferably 10 to 50 g/ha. Combination 6 is generally used in a ratio of A to B3 of 1:500 to 50:1, preferably 1:20 to 4:1, and a ratio of A to B4 of 1:2,000 to 5:1, preferably 1:50 to 2:1, with B3 being applied at a rate of 1 to 50 g/ha, preferably 5 to 20 g/ha, and B4 being applied at a rate of 10 to 200 g/ha, preferably 10 to 50 g/ha. Combination 7 is generally used in a ratio of A to B5 of 1:500 to 50:1, preferably 1:20 to 4:1, and a ratio of A to B6 of 1:2,000 to 5:1, preferably 1:50 to 2:1, and a ratio of A to B7 of 1:500 to 50:1, preferably 1:10 to 20:1, with B5 being applied at a rate of 1 to 50 g/ha, preferably 5 to 20 g/ha, and B6 being applied at a rate of 10 to 200 g/ha, preferably 10 to 50 g/ha, and B7 being applied at a rate of 1 to 50 g/ha, preferably 1 to 10 g/ha. Combination 8 is generally used in a ratio of A to B of 1:1,000 to 5:1, preferably 1:60 to 1:1, with B being applied at a rate of 10 to 100 g/ha, preferably 20 to 60 g/hfa Combination 9 is generally used in a ratio of A to B8 of 1:1,000 to 5:1, preferably 1:60 to 1:1, and a ratio of A to B9 of 1:1,000 to 5:1, preferably 1:60 to 1:1, with B8 being applied at a rate of 10 to 100 g/ha, preferably 20 to 60 g/ha, and B9 being applied at a rate of 10 to 100 g/ha, preferably 20 to 60 g/ha. Combination 10 is generally used in a ratio of A to B of 1:30,000 to 1:10, preferably 1:1,000 to 1:25, with B being applied at a rate of 500 to 3,000 g/ha, preferably 500 to 1,000 g/ha. Combination 11 is generally used in a ratio of A to B of 1:50,000 to 1:10, preferably 1:2,000 to 1:25, with B being applied at a rate of 500 to 5,000 g/ha, preferably 500 to 2,000 g/ha. Combination 12 is generally used in a ratio of A to B of 1:10,000 to 1:2, preferably 1:500 to 1:5, with B being applied at a rate of 100 to 1,000 g/ha, preferably 100 to 500 g/ha. Combination 13 is generally used in a ratio of A to B of 1:10,000 to 1:2, preferably 1:500 to 1:5, with B being applied at a rate of 100 to 1,000 g/ha, preferably 100 to 500 g/ha. Combination 14 is generally used in a ratio of A to B of 1:10,000 to 1:2, preferably 1:500 to 1:5, with B being applied at a rate of 100 to 1,000 g/ha, preferably 100 to 500 g/ha. Combination 15 is generally used in a ratio of A to B of 1:30,000 to 1:40, preferably 1:1,000 to 1:10, with B being applied at a rate of 200 to 3,000 g/ha, preferably 200 to 1,000 g/ha Combination 16 is generally used in a ratio of A to B of 1:30,000 to 1:40, preferably 1:1,000 to 1:10, with B being applied at a rate of 200 to 3,000 g/ha, preferably 200 to 1,000 g/ha. Combination 17 is generally used in a ratio of A to B of 1:30,000 to 1:40, preferably 1:1,000 to 1:10, with B being applied at a rate of 200 to 3,000 g/ha, preferably 200 to 1,000 g/ha. Combination I8 is generally used in a ratio of A to B of 1:30,000 to 1:40, preferably 1:1,000 to 1:10, with B being applied at a rate of 200 to 3,000 g/ha, preferably 200 to 1,000 g/ha. Combination 19 is generally used in a ratio of A to B of 1:30,000 to 1:40, preferably 1:1,000 to 1:10, with B being applied at a rate of 200 to 3,000 g/ha, preferably 200 to 1,000 g/ha.

e) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide monosodium salt (mixture partner A, generally applied at a rate of 0.1 to 50 g/ha, preferably applied at a rate of 1 to 20 g/ha in combination with:

| Combination Number | Mixture partner B | Combination Number | Mixture partner B |
|---|---|---|---|
| 1 | rimsulfuron | 2 | thifensulfuron-methyl |
| 3 | chlorimuron-ethyl | 4 | rimsulfuron (B1) in combination with thifensulfuron-methyl (B2) |
| 5 | nicosulfuron | 6 | nicosulfuron (B3) in combination with nicosulfuron (B4) |
| 7 | rimsulfuron (B5) in combination with nicosulfuron (B6) in combination with thifensulfuron-methyl (B7) | 8 | prosulfuron |
| 9 | prosulfuron (B8) in combination with primsulfuron (B9) | 10 | atrazine |
| 11 | terbuthylazine | 12 | dicamba |
| 13 | 2,4-D | 14 | bromoxynil |
| 15 | pyridate | 16 | sulcotrione |
| 17 | glufosinate | 18 | glyphosate |
| 19 | glyphosate-trimesium | | |

Combination 1 is generally used in a ratio of A to B of 1:500 to 50:1, preferably 1:20 to 4:1, with B being applied at a rate of 1 to 50 g/ha, preferably 5 to 20 g/ha. Combination 2 is generally used in a ratio of A to B of 1:500 to 50:1, preferably 1:10 to 20:1, with B being applied at a rate of 1 to 50 g/ha, preferably 1 to 10 g/ha. Combination 3 is generally used in a ratio of A to B of 1:1,000 to 50:1, preferably 1:20 to 20:1, with B being applied at a rate of 1 to 100 g/ha, preferably 1 to 20 g/ha. Combination 4 is generally used in a ratio of A to B1 of 1:500 to 50:1, preferably 1:20 to 4:1, and a ratio of A to B2 of 1:500 to 50:1, preferably 1:10 to 20:1, with B1 being applied at a rate of 1 to 50 g/ha, preferably 5 to 20 g/ha, and B2 being applied at a rate of 1 to 50 g/ha, preferably 1 to 10 g/ha. Combination 5 is generally used in a ratio of A to B of 1:2,000 to 5:1, preferably 1:50 to 2:1, with B being applied at a rate of 10 to 200 g/ha, preferably 10 to 50 g/ha. Combination 6 is generally used in a ratio of A to B3 of 1:500 to 50:1, preferably 1:20 to 4:1, and a ratio of A to B4 of 1:2,000 to 5:1, preferably 1:50 to 2:1, with B3 being applied at a rate of 1 to 50 g/ha, preferably 5 to 20 g/ha, and B4 being applied at a rate of 10 to 200 g/ha, preferably 10 to 50 g/ha. Combination 7 is generally used in a ratio of A to B5 of 1:500 to 50:1, preferably 1:20 to 4:1, and a ratio of A to B6 of 1:2,000 to 5:1, preferably 1:50 to 2:1, and a ratio of A to B7 of 1:500 to 50:1, preferably 1:10 to 20:1, with B5 being applied at a rate of 1 to 50 g/ha, preferably 5 to 20 g/ha, and B6 being applied at a rate of 10 to 200 g/ha, preferably 10 to 50 g/ha, and B7 being applied at a rate of 1 to 50 g/ha, preferably 1 to 10 g/ha. Combination 8 is generally used in a ratio of A to B of 1:1,000 to 5:1, preferably 1:60 to 1:1, with B being applied at a rate of 10 to 100 g/ha, preferably 20 to 60 g/ha. Combination 9 is generally used in a ratio of A to B8 of 1:1,000 to 5:1, preferably 1:60 to 1:1, and a ratio of A to B9 of 1:1,000 to 5:1, preferably 1:60 to 1:1, with B8 being applied at a rate of 10 to 100 g/ha, preferably 20 to 60 g/ha, and B9 being applied at a rate of 10 to 100 g/ha, preferably 20 to 60 g/ha. Combination 10 is generally used in a ratio of A to B of 1:30,000 to 1:10, preferably 1:1,000 to 1:25, with B being applied at a rate of 500 to 3,000 g/ha, preferably 500 to 1,000 g/ha. Combination 11 is generally used in a ratio of A to B of 1:50,000 to 1:10, preferably 1:2,000 to 1:25, with B being applied at a rate of 500 to 5,000 g/ha, preferably 500 to 2,000 g/ha. Combination 12 is generally used in a ratio of A to B of 1:10,000 to 1:2, preferably 1:500 to 1:5, with B being applied at a rate of 100 to 1,000 g/ha, preferably 100 to 500 g/ha. Combination 13 is generally used in a ratio of A to B of 1:10,000 to 1:2, preferably 1:500 to 1:5, with B being applied at a rate of 100 to 1,000 g/ha, preferably 100 to 500 g/ha. Combination 14 is generally used in a ratio of A to B of 1:10,000 to 1:2, preferably 1:500 to 1:5, with B being applied at a rate of 100 to 1,000 g/ha, preferably 100 to 500 g/ha. Combination 15 is generally used in a ratio of A to B of 1:30,000 to 1:40, preferably 1:1,000 to 1:10, with B being applied at a rate of 200 to 3,000 g/ha, preferably 200 to 1,000 g/ha. Combination 16 is generally used in a ratio of A to B of 1:30,000 to 1:40, preferably 1:1,000 to 1:10, with B being applied at a rate of 200 to 3,000 g/ha, preferably 200 to 1,000 g/ha. Combination 17 is generally used in a ratio of A to B of 1:30,000 to 1:40, preferably 1:1,000 to 1:10, with B being applied at a rate of 200 to 3,000 g/ha, preferably 200 to 1,000 g/ha. Combination 18 is generally used in a ratio of A to B of 1:30,000 to 1:40, preferably 1:1,000 to 1:10, with B being applied at a rate of 200 to 3,000 g/ha, preferably 200 to 1,000 g/ha. Combination 19 is generally used in a ratio of A to B of 1:30,000 to 1:40, preferably 1:1,000 to 1:10, with B being applied at a rate of 200 to 3,000 g/ha, preferably 200 to 1,000 g/ha.

f) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide monopotassium salt (mixture partner A, generally applied at a rate of 0.1 to 50 g/ha, preferably applied at a to 20 g/ha) in combination with:

| Combination Number | Mixture partner B | Combination Number | Mixture partner B |
|---|---|---|---|
| 1 | rimsulfuron | 2 | thifensulfuron-methyl |
| 3 | chlorimuron-ethyl | 4 | rimsulfuron (B1) in combination with thifensulfuron-methyl (B2) |
| 5 | nicosulfuron | 6 | rimsulfuron (B3) in combination with nicosulfuron (B4) |

-continued

| Combination Number | Mixture partner B | Combination Number | Mixture partner B |
|---|---|---|---|
| 7 | rimsulfuron (B5) in combination with nicosulfuron (B6) in combination with thifensulfuron-methyl (B7) | 8 | prosulfuron |
| 9 | prosulfuron (B8) in combination with primsulfuron (B9) | 10 | atrazine |
| 11 | terbuthylazine | 12 | dicamba |
| 13 | 2,4-D | 14 | bromoxynil |
| 15 | pyridate | 16 | sulcotrione |
| 17 | glufosinate | 18 | glyphosate |
| 19 | glyphosate-trimesium | | |

Combination 1 is generally used in a ratio of A to B of 1:500 to 50:1, preferably 1:20 to 4:1, with B being applied at a rate of 1 to 50 g/ha, preferably 5 to 20 g/ha. Combination 2 is generally used in a ratio of A to B of 1:500 to 50:1, preferably 1:10 to 20:1, with B being applied at a rate of 1 to 50 g/ha, preferably 1 to 10 g/ha. Combination 3 is generally used in a ratio of A to B of 1:1,000 to 50:1, preferably 1:20 to 20:1, with B being applied at a rate of 1 to 100 g/ha, preferably 1 to 20 g/ha. Combination 4 is generally used in a ratio of A to B1 of 1:500 to 50:1, preferably 1:20 to 4:1, and a ratio of A to B2 of 1:500 to 50:1, preferably 1:10 to 20:1, with B1 being applied at a rate of 1 to 50 g/ha, preferably 5 to 20 g/ha, and B2 being applied at a rate of 1 to 50 g/ha, preferably 1 to 10 g/ha. Combination 5 is generally used in a ratio of A to B of 1:2,000 to 5:1, preferably 1:50 to 2:1, with B being applied at a rate of 10 to 200 g/ha, preferably 10 to 50 g/ha. Combination 6 is generally used in a ratio of A to B3 of 1:500 to 50:1, preferably 1:20 to 4:1, and a ratio of A to B4 of 1:2,000 to 5:1, preferably 1:50 to 2:1, with B3 being applied at a rate of 1 to 50 g/ha, preferably 5 to 20 g/ha, and B4 being applied at a rate of 10 to 200 g/ha, preferably 10 to 50 g/ha. Combination 7 is generally used in a ratio of A to B5 of 1:500 to 50:1, preferably 1:20 to 4:1, and a ratio of A to B6 of 1:2,000 to 5:1, preferably 1:50 to 2:1, and a ratio of A to B7 of 1:500 to 50:1, preferably 1:10 to 20:1, with B5 being applied at a rate of 1 to 50 g/ha, preferably 5 to 20 g/ha, and B6 being applied at a rate of 10 to 200 g/ha, preferably 10 to 50 g/ha, and B7 being applied at a rate of 1 to 50 g/ha, preferably 1 to 10 g/ha. Combination 8 is generally used in a ratio of A to B of 1:1,000 to 5:1, preferably 1:60 to 1:1, with B being applied at a rate of 10 to 100 g/ha, preferably 20 to 60 g/ha. Combination 9 is generally used in a ratio of A to B8 of 1:1,000 to 5:1, preferably 1:60 to 1:1, and a ratio of A to B9 of 1:1,000 to 5:1, preferably 1:60 to 1:1, with B8 being applied at a rate of 10 to 100 g/ha, preferably 20 to 60 g/ha, and B9 being applied at a rate of 10 to 100 g/ha, preferably 20 to 60 g/ha. Combination 10 is generally used in a ratio of A to B of 1:30,000 to 1:10, preferably 1:1,000 to 1:25, with B being applied at a rate of 500 to 3,000 g/ha, preferably 500 to 1,000 g/ha. Combination 11 is generally used in a ratio of A to B of 1:50,000 to 1:10, preferably 1:2,000 to 1:25, with B being applied at a rate of 500 to 5,000 g/ha, preferably 500 to 2,000 g/ha. Combination 12 is generally used in a ratio of A to B of 1:10,000 to 1:2, preferably 1:500 to 1:5, with B being applied at a rate of 100 to 1,000 g/ha, preferably 100 to 500 g/ha. Combination 13 is generally used in a ratio of A to B of 1:10,000 to 1:2, preferably 1:500 to 1:5, with B being applied at a rate of 100 to 1,000 g/ha, preferably 100 to 500 g/ha. Combination 14 is generally used in a ratio of A to B of 1:10,000 to 1:2, preferably 1:500 to 1:5, with B being applied at a rate of 100 to 1,000 g/ha, preferably 100 to 500 g/ha. Combination 15 is generally used in a ratio of A to B of 1:30,000 to 1:40, preferably 1:1,000 to 1:10, with B being applied at a rate of 200 to 3,000 g/ha, preferably 200 to 1,000 g/ha. Combination 16 is generally used in a ratio of A to B of 1:30,000 to 1:40, preferably 1:1,000 to 1:10, with B being applied at a rate of 200 to 3,000 g/ha, preferably 200 to 1,000 g/ha. Combination 17 is generally used in a ratio of A to B of 1:30,000 to 1:40, preferably 1:1,000 to 1:10, with B being applied at a rate of 200 to 3,000 g/ha, preferably 200 to 1,000 g/ha. Combination 18 is generally used in a ratio of A to B of 1:30,000 to 1:40, preferably 1:1,000 to 1:10, with B being applied at a rate of 200 to 3,000 g/ha, preferably 200 to 1,000 g/ha. Combination 19 is generally used in a ratio of A to B of 1:30,000 to 1:40, preferably 1:1,000 to 1:10, with B being applied at a rate of 200 to 3,000 g/ha, preferably 200 to 1,000 g/ha.

g) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide monosodium salt (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | rimsulfuron | 2 | thifensulfuron-methyl |
| 3 | chlorimuron-ethyl | 4 | rimsulfuron (B1) in combination with thifensulfuron-methyl (B2) |
| 5 | nicosulfuron | 6 | rimsulfuron (B3) in combination with nicosulfuron (B4) |
| 7 | rimsulfuron (B5) in combination with nicosulfuron (B6) in combination with thifensulfuron-methyl (B7) | 8 | prosulfuron |
| 9 | prosulfuron (B8) in combination with primsulfuron (B9) | 10 | atrazine |
| 11 | terbuthylazine | 12 | dicamba |
| 13 | 2,4-D | 14 | bromoxynil |
| 15 | pyridate | 16 | sulcotrione |
| 17 | glufosinate | 18 | glyphosate |
| 19 | glyphosate-trimesium | | |

Combination 1 is generally used in a ratio of A to B of 1:500 to 50:1, preferably 1:20 to 4:1, with B being applied at a rate of 1 to 50 g/ha, preferably 5 to 20 g/ha. Combination 2 is generally used in a ratio of A to B of 1:500 to 50:1, preferably 1:10 to 20:1, with B being applied at a rate of 1 to 50 g/ha, preferably 1 to 10 g/ha. Combination 3 is generally used in a ratio of A to B of 1:1,000 to 50:1, preferably 1:20 to 20:1, with B being applied at a rate of 1 to 100 g/ha, preferably 1 to 20 g/ha. Combination 4 is generally used in a ratio of A to B1 of 1:500 to 50:1, preferably 1:20 to 4:1, and a ratio of A to B2 of 1:500 to 50:1, preferably 1:10 to 20:1, with B1 being applied at a rate of 1 to 50 g/ha, preferably 5 to 20 g/ha, and B2 being applied at a rate of 1 to 50 g/ha, preferably 1 to 10 g/ha. Combination 5 is generally used in a ratio of A to B of 1:2,000 to 5:1, preferably 1:50 to 2:1, with B being applied at a rate of 10 to 200 g/ha, preferably 10 to 50 g/ha. Combination 6 is generally used in a ratio of A to B3 of 1:500 to 50:1, preferably 1:20 to 4:1, and a ratio of A to B4 of 1:2,000 to 5:1, preferably 1:50 to 2:1, with B3 being applied at a rate of 1 to 50 g/ha, preferably 5 to 20 g/ha, and B4 being applied at a rate of 10 to 200 g/ha, preferably 10 to 50 g/ha. Combination 7 is generally used in a ratio of A to B5 of 1:500 to 50:1, preferably 1:20 to 4:1, and a ratio of A to B6 of 1:2,000 to 5:1, preferably 1:50 to 2:1, and a ratio of A to B7 of 1:500 to 50:1, preferably 1:10 to 20:1, with B5 being applied at a rate of 1 to 50 g/ha, preferably 5 to 20 g/ha, and B6 being applied at a rate of 10 to 200 g/ha, preferably 10 to 50 g/ha, and B7 being applied at a rate of 1 to 50 g/ha, preferably 1 to 10 g/ha. Combination 8 is generally used in a ratio of A to B of 1:1,000 to 5:1, preferably 1:60 to 1:1, with B being applied at a rate of 10 to 100 g/ha, preferably 20 to 60 g/ha. Combination 9 is generally used in a ratio of A to B8 of 1:1,000 to 5:1, preferably 1:60 to 1:1, and a ratio of A to B9 of 1:1,000 to 5:1, preferably 1:60 to 1:1, with B8 being applied at a rate of 10 to 100 g/ha, preferably 20 to 60 g/ha, and B9 being applied at a rate of 10 to 100 g/ha, preferably 20 to 60 g/ha. Combination 10 is generally used in a ratio of A to B of 1:30,000 to 1:10, preferably 1:1,000 to 1:25, with B being applied at a rate of 500 to 3,000 g/ha, preferably 500 to 1,000 g/ha. Combination 11 is generally used in a ratio of A to B of 1:50,000 to 1:10, preferably 1:2,000 to 1:25, with B being applied at a rate of 500 to 5,000 g/ha, preferably 500 to 2,000 g/ha. Combination 12 is generally used in a ratio of A to B of 1:10,000 to 1:2, preferably 1:500 to 1:5, with B being applied at a rate of 100 to 1,000 g/ha, preferably 100 to 500 g/ha. Combination 13 is generally used in a ratio of A to B of 1:10,000 to 1:2, preferably 1:500 to 1:5, with B being applied at a rate of 100 to 1,000 g/ha, preferably 100 to 500 g/ha. Combination 14 is generally used in a ratio of A to B of 1:10,000 to 1:2, preferably 1:500 to 1:5, with B being applied at a rate of 100 to 1,000 g/ha, preferably 100 to 500 g/ha. Combination 15 is generally used in a ratio of A to B of 1:30,000 to 1:40, preferably 1:1,000 to 1:10, with B being applied at a rate of 200 to 3,000 g/ha, preferably 200 to 1,000 g/ha. Combination 16 is generally used in a ratio of A to B of 1:30,000 to 1:40, preferably 1:1,000 to 1:10, with B being applied at a rate of 200 to 3,000 g/ha, preferably 200 to 1,000 g/ha. Combination 17 is generally used in a ratio of A to B of 1:30,000 to 1:40, preferably 1:1,000 to 1:10, with B being applied at a rate of 200 to 3,000 g/ha, preferably 200 to 1,000 g/ha. Combination 18 is generally used in a ratio of A to B of 1:30,000 to 1:40, preferably 1:1,000 to 1:10, with B being applied at a rate of 200 to 3,000 g/ha, preferably 200 to 1,000 g/ha. Combination 19 is generally used in a ratio of A to B of 1:30,000 to 1:40, preferably 1:1,000 to 1:10, with B being applied at a rate of 200 to 3,000 g/ha, preferably 200 to 1,000 g/ha.

h) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide monopotassium salt mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | rimsulfuron | 2 | thifensulfuron-methyl |
| 3 | chlorimuron-ethyl | 4 | rimsulfuron (B1) in combination with thifensulfuron-methyl (B2) |
| 5 | nicosulfuron | 6 | rimsulfuron (B3) in combination with nicosulfuron (B4) |
| 7 | rimsulfuron (B5) in combination with nicosulfuron (B6) in combination with thifensulfuron-methyl (B7) | 8 | prosulfuron |
| 9 | prosulfuron (B8) in combination with primsulfuron (B9) | 10 | atrazine |
| 11 | terbuthylazine | 12 | dicamba |
| 13 | 2,4-D | 14 | bromoxynil |
| 15 | pyridate | 16 | sulcotrione |
| 17 | glufosinate | 18 | glyphosate |
| 19 | glyphosate-trimesium | | |

Combination 1 is generally used in a ratio of A to B of 1:500 to 50:1, preferably 1:20 to 4:1, with B being applied at a rate of 1 to 50 g/ha, preferably 5 to 20 g/ha. Combination 2 is generally used in a ratio of A to B of 1:500 to 50:1, preferably 1:10 to 20:1, with B being applied at a rate of 1 to 50 g/ha, preferably 1 to 10 g/ha. Combination 3 is generally used in a ratio of A to B of 1:1,000 to 50:1, preferably 1:20 to 20:1, with B being applied at a rate of 1 to 100 g/ha, preferably 1 to 20 g/ha. Combination 4 is generally used in a ratio of A to B1 of 1:500 to 50:1, preferably 1:20 to 4:1, and a ratio of A to B2 of 1:500 to 50:1, preferably 1:10 to 20:1, with B1 being applied at a rate of 1 to 50 g/ha, preferably 5 to 20 g/ha, and B2 being applied at a rate of 1 to 50 g/ha, preferably 1 to 10 g/ha. Combination 5 is generally used in a ratio of A to B of 1:2,000 to 5:1, preferably 1:50 to 2:1, with B being applied at a rate of 10 to 200 g/ha, preferably 10 to 50 g/ha. Combination 6 is generally used in a ratio of A to B3 of 1:500 to 50:1, preferably 1:20 to 4:1, and a ratio of A to B4 of 1:2,000 to 5:1, preferably 1:50 to 2:1, with B3 being applied at a rate of 1 to 50 g/ha, preferably 5 to 20 g/ha, and B4 being applied at a rate of 10 to 200 g/ha, preferably 10 to 50 g/ha. Combination 7 is generally used in a ratio of A to B5 of 1:500 to 50:1, preferably 1:20 to 4:1, and a ratio of A to B6 of 1:2,000 to 5:1, preferably 1:50 to 2:1, and a ratio of A to B7 of 1:500 to 50:1, preferably 1:10 to 20:1, with B5 being applied at a rate of 1 to 50 g/ha, preferably 5 to 20 g/ha, and B6 being applied at a rate of 10 to 200 g/ha, preferably 10 to 50 g/ha, and B7 being applied at a rate of 1 to 50 g/ha, preferably 1 to 10 g/ha. Combination 8 is generally used in a ratio of A to B of 1:1,000 to 5:1, preferably 1:60 to 1:1, with B being applied at a rate of 10 to 100 g/ha, preferably 20 to 60 g/ha. Combination 9 is generally used in a ratio of A to B8 of 1:1,000 to 5:1, preferably 1:60 to 1:1, and a ratio of A to B9 of 1:1,000 to 5:1, preferably 1:60 to 1:1, with B8 being applied at a rate of 10 to 100 g/ha, preferably 20 to 60 g/ha, and B9 being applied at a rate of 10 to 100 g/ha, preferably 20 to 60 g/ha. Combination 10 is generally used in a ratio of A to B of 1:30,000 to 1:10, preferably 1:1,000 to 1:25, with B being applied at a rate of 500 to 3,000 g/ha, preferably 500 to 1,000 g/ha. Combination 11 is generally used in a ratio of A to B of 1:50,000 to 1:10, preferably 1:2,000 to 1:25, with B being applied at a rate of 500 to 5,000 g/ha, preferably 500 to 2,000 g/ha. Combination 12 is generally used in a ratio of A to B of 1:10,000 to 1:2, preferably 1:500 to 1:5, with B being applied at a rate of 100 to 1,000 g/ha, preferably 100 to 500 g/ha. Combination 13 is generally used in a ratio of A to B of 1:10,000 to 1:2, preferably 1:500 to 1:5, with B being applied at a rate of 100 to 1,000 g/ha, preferably 100 to 500 g/ha. Combination 14 is generally used in a ratio of A to B of 1:10,000 to 1:2, preferably 1:500 to 1:5, with B being applied at a rate of 100 to 1,000 g/ha, preferably 100 to 500 g/ha. Combination 15 is generally used in a ratio of A to B of 1:30,000 to 1:40, preferably 1:1,000 to 1:10, with B being applied at a rate of 200 to 3,000 g/ha, preferably 200 to 1,000 g/ha. Combination 16 is generally used in a ratio of A to B of 1:30,000 to 1:40, preferably 1:1,000 to 1:10, with B being applied at a rate of 200 to 3,000 g/ha, preferably 200 to 1,000 g/ha. Combination 17 is generally used in a ratio of A to B of 1:30,000 to 1:40, preferably 1:1,000 to 1:10, with B being applied at a rate of 200 to 3,000 g/ha, preferably 200 to 1,000 g/ha. Combination 18 is generally used in a ratio of A to B of 1:30,000 to 1:40, preferably 1:1,000 to 1:10, with B being applied at a rate of 200 to 3,000 g/ha, preferably 200 to 1,000 g/ha. Combination 19 is generally used in a ratio of A to B of 1:30,000 to 1:40, preferably 1:1,000 to 1:10, with B being applied at a rate of 200 to 3,000 g/ha, preferably 200 to 1,000 g/ha.

Specifically preferred mixtures for use in soybeans are selected from the group:

a) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | chlorimuron-ethyl | 2 | thifensulfuron-methyl |
| 3 | chlorimuron-ethyl (B1) in combination with thifensulfuron-methyl (B2) | 4 | clethodim |
| 5 | sethoxydim | 6 | fluazifop-p-butyl |
| 7 | haloxyfop | 8 | imazethapyr |
| 9 | imozamox | 10 | imazaquin |
| 11 | glufosinate | 12 | glyphosate |
| 13 | glyphosate-trimesium | 14 | lactofen |

Combination 1 is generally used in a ratio of A to B of 1:1,000 to 10:1, preferably 1:25 to 4:1, with B being applied at a rate of 5 to 100 g/ha, preferably 5 to 25 g/ha. Combination 2 is generally used in a ratio of A to B of 1:1,000 to 50:1, preferably 1:10 to 10:1, with B being applied at a rate of 1 to 100 g/ha, preferably 1 to 10 g/ha. Combination 3 is generally used in a ratio of A to B 1 of 1:1,000 to 50:1, preferably 1:50 to 4:1, and ratio of A to B2 of 1:500 to 50:1, preferably 1:10 to 20:1, with B1 being applied at a rate of 1 to 100 g/ha, preferably 5 to 50 g/ha, and B2 being applied at a rate of 1 to 50 g/ha, preferably 1 to 10 g/ha. Combination 4 is generally used in a ratio of A to B of 1:5,000 to 50:1, preferably 1:50 to 2:1, with B being applied at a rate of 1 to 500 g/ha, preferably 10 to 50 g/ha. Combination 5 is generally used in a ratio of A to B of 1:5,000 to 5:1, preferably 1:200 to 1:2, with B being applied at a rate of 10 to 500 g/ha, preferably 50 to 200 g/ha. Combination 6 is generally used in a ratio of A to B of 1:5,000 to 5:1, preferably 1:200 to 1:2, with B being applied at a rate of 10 to 500 g/ha, preferably 50 to 200 g/ha. Combination 7 is generally used in a ratio of A to B of 1:5,000 to 5:1, preferably 1:200 to 1:2, with B being applied at a rate of 10 to 500 g/ha, preferably 50 to 200 g/ha. Combination 8 is generally used in a ratio of A to B of 1:5,000 to 5:1, preferably 1:200 to 1:2, with B being applied at a rate of 10 to 500 g/ha, preferably 50 to 200 g/ha. Combination 9 is generally used in a ratio of A to B of 1:5,000 to 5:1, preferably 1:100 to 2:1, with B being applied at a rate of 10 to 500 g/ha, preferably 10 to 100 g/ha. Combination 10 is generally used in a ratio of A to B of 1:10,000 to 1:2, preferably 1:400 to 1:5, with B being applied at a rate of 100 to 1,000 g/ha preferably 100 to 400 g/ha. Combination 11 is generally used in a ratio of A to B of 1:40,000 to 1:2, preferably 1:1,000 to 1:10, with B being applied at a rate of 100 to 4,000 g/ha, preferably 200 to 1,000 g/ha. Combination 12 is generally used in a ratio of A to B of 1:40,000 to 1:2, preferably 1:1,000 to 1:10, with B being applied at a rate of 100 to 4,000 g/ha, preferably 200 to 1,000 g/ha. Combination 13 is generally used in a ratio of A to B of 1:40,000 to 1:2, preferably 1:1,000 to 1:10, with B being applied at a rate of 100 to 4,000 g/ha, preferably 200 to 1,000 g/ha. Combination 14 is generally used in a ratio of A to B of 1:5,000 to 50:1, preferably 1:200 to 1:2, with B being applied at a rate of 10 to 500 g/ha, preferably 50 to 200 g/ha.

b) (6S-cis)-N-[2-chloro-4-fluoro-5-(6-fluorotetrahydro-1,3-dioxo-1H-pyrrolo[2-c]imidazol-2(3H)-yl)phenyl]-N-[(chloromethyl)sulfonyl]acetamide (mixture partner A, generally applied at a rate of 0.1 to 50 g/ha, perferably applied at a rate of 1 to 20 g/ha)in combination with:

| Combination Number | Mixture partner B | Combination Number | Mixture partner B |
|---|---|---|---|
| 1 | chlorimuron-ethyl | 2 | thifensulfuron-methyl |
| 3 | chlorimuron-ethyl (B1) in combination with thifensulfuron-methyl (B2) | 4 | clethodim |
| 5 | sethoxydim | 6 | fluazifop-p-butyl |
| 7 | haloxyfop | 8 | imazethapyr |
| 9 | imozamox | 10 | imazaquin |
| 11 | glufosinate | 12 | glyphosate |
| 13 | glyphosate-trimesium | 14 | lactofen |

Combination 1 is generally used in a ratio of A to B of 1:1,000 to 10:1, preferably 1.25 to 4:1, with B being applied at a rate of 5 to 100 g/ha, preferably 5 to 25 g/ha. Combination 2 is generally used in a ratio of A to B of 1:1,000 to 50:1, preferably 1:10 to 10:1, with B being applied at a rate of 1 to 100 g/ha, preferably 1 to 10 g/ha. Combination 3 is generally used in a ratio of A to B1 of 1:1,000 to 50:1, preferably 1:50 to 4:1, and ratio of A to B2 of 1:500 to 50:1, preferably 1:10 to 20:1, with B1 being applied at a rate of 1 to 100 g/ha, preferably 5 to 50 g/ha, and B2 being applied at a rate of 1 to 50 g/ha, preferably 1 to 10 g/ha. Combination 4 is generally used in a ratio of A to B of 1:5,000 to 50:1, preferably 1:50 to 2:1, with B being applied at a rate of 1 to 500 g/ha, preferably 10 to 50 g/ha. Combination 5 is generally used in a ratio of A to B of 1:5000 to 5:1, preferably 1:200 to 1:2, with B being applied at a rate of 10 to 500 g/ha, preferably 50 to 200 g/ha. Combination 6 is generally used in a ratio of A to B of 1:5,000 to 5:1, preferably 1:200 to 1:2, with B being applied at a rate of 10 to 500 g/ha, preferably 50 to 200 g/ha. Combination 7 is generally used in a ratio of A to B of 1:5,000 to 5:1, preferably 1:200 to 1:2, with B being applied at a rate of 10 to 500 g/ha, preferably 50 to 200 g/ha. Combination 8 is generally used in a ratio of A to B of 1:5,000 to 5:1, preferably 1:200 to 1:2, with B being applied at a rate of 10 to 500 g/ha, preferably 50 to 200 g/ha. Combination 9 is generally used in a ratio of A to B of 1:5,000 to 5:1, preferably 1:100 to 2:1, with B being applied at a rate of 10 to 500 g/ha, preferably 10 to 100 g/ha. Combination 10 is generally used in a ratio of A to B of 1:10,000 to 1:2, preferably 1:400 to 1:5, with B being applied at a rate of 100 to 1,000 g/ha, preferably 100 to 400 g/ha. Combination 11 is generally used in a ratio of A to B of 1:40,000 to 1:2, preferably 1:1,000 to 1:10, with B being applied at a rate of 100 to 4,000 g/ha, preferably 200 to 1,000 g/ha. Combination 12 is generally used in a ratio of A to B of 1:40,000 to 1:2, preferably 1:1,000 to 1:10, with B being applied at a rate of 100 to 4,000 g/ha, preferably 200 to 1,000 g/ha. Combination 13 is generally used in a ratio of A to B of 1:40,000 to 1:2, preferably 1:1,000 to 1:10, with B being applied at a rate of 100 to 4,000 g/ha, preferably 200 to 1,000 g/ha. Combination 14 is generally used in a ratio of A to B of 1:5,000 to 50:1, preferably 1:200 to 1:2, with B being applied at a rate of 10 to 500 g/ha, preferably 50 to 200 g/ha.

c) (6S-cis)-1-chloro-N-[2-chloro-5-(6-chlorotetrahydro-1,3-dioxo-1H-pyrrolo[1,2-c]imidazol-2(3H)-yl)4-fluorophenyl]methanesulfonamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
| --- | --- | --- | --- |
| 1 | chlorimuron-ethyl | 2 | thifensulfuron-methyl |
| 3 | chlorimuron-ethyl (B1) in combination with thifensulfuron-methyl (B2) | 4 | clethodim |
| 5 | sethoxydim | 6 | fluazifop-p-butyl |
| 7 | haloxyfop | 8 | imazethapyr |
| 9 | imozamox | 10 | imazaquin |
| 11 | glufosinate | 12 | glyphosate |
| 13 | glyphosate-trimesium | 14 | lactofen |

Combination 1 is generally used in a ratio of A to B of 1:1,000 to 10:1, preferably 1:25 to 4:1, with B being applied at a rate of 5 to 100 g/ha, preferably 5 to 25 g/ha. Combination 2 is generally used in a ratio of A to B of 1:1,000 to 50:1, preferably 1:10 to 10:1, with B being applied at a rate of 1 to 100 g/ha, preferably 1 to 10 g/ha. Combination 3 is generally used in a ratio of A to B1 of 1:1,000 to 50:1, preferably 1:50 to 4:1, and ratio of A to B2 of 1:500 to 50:1, preferably 1:10 to 20:1, with B1 being applied at a rate of 1 to 100 g/ha, preferably 5 to 50 g/ha, and B2 being applied at a rate of 1 to 50 g/ha, preferably 1 to 10 g/ha. Combination 4 is generally used in a ratio of A to B of 1:5,000 to 50:1, preferably 1:50 to 2:1, with B being applied at a rate of 1 to 500 g/ha, preferably 10 to 50 g/ha. Combination 5 is generally used in a ratio of A to B of 1:5,000 to 5:1, preferably 1:200 to 1:2, with B being applied at a rate of 10 to 500 g/ha, preferably 50 to 200 g/ha. Combination 6 is generally used in a ratio of A to B of 1:5,000 to 5:1, preferably 1:200 to 1:2, with B being applied at a rate of 10 to 500 g/ha, preferably 50 to 200 g/ha. Combination 7 is generally used in a ratio of A to B of 1:5,000 to 5:1, preferably 1:200 to 1:2, with B being applied at a rate of 10 to 500 g/ha, preferably 50 to 200 g/ha. Combination 8 is generally used in a ratio of A to B of 1:5,000 to 5:1, preferably 1:200 to 1:2, with B being applied at a rate of 10 to 500 g/ha, preferably 50 to 200 g/ha. Combination 9 is generally used in a ratio of A to B of 1:5,000 to 5:1, preferably 1:100 to 2:1, with B being applied at a rate of 10 to 500 g/ha, preferably 10 to 100 g/ha. Combination 10 is generally used in a ratio of A to B of 1:10,000 to 1:2, preferably 1:400 to 1:5, with B being applied at a rate of 100 to 1,000 g/ha, preferably 100 to 400 g/ha. Combination 11 is generally used in a ratio of A to B of 1:40,000 to 1:2, preferably 1:1,000 to 1:10, with B being applied at a rate of 100 to 4,000 g/ha, preferably 200 to 1,000 g/ha. Combination 12 is generally used in a ratio of A to B of 1:40,000 to 1:2, preferably 1:1,000 to 1:10, with B being applied at a rate of 100 to 4,000 g/ha, preferably 200 to 1,000 g/ha Combination 13 is generally used in a ratio of A to B of 1:40,000 to 1:2, preferably 1:1,000 to 1:10, with B being applied at a rate of 100 to 4,000 g/ha, preferably 200 to 1,000 g/ha Combination 14 is generally used in a ratio of A to B of 1:5,000 to 50:1, preferably 1:200 to 1:2, with B being applied at a rate of 10 to 500 g/ha, preferably 50 to 200 g/ha.

d) (6S-cis)-N-[2-chloro-5-(6-chlorotetrahydro-1,3-dioxo-1H-pyrrolo[1,2-c]imidazol-2(3H)-yl)-4-fluorophenyl)-N-[(chloromethyl)sulfonyl]acetamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
| --- | --- | --- | --- |
| 1 | chlorimuron-ethyl | 2 | thifensulfuron-methyl |
| 3 | chlorimuron-ethyl (B1) in combination with thifensulfuron-methyl (B2) | 4 | clethodim |
| 5 | sethoxydim | 6 | fluazifop-p-butyl |
| 7 | haloxyfop | 8 | imazethapyr |
| 9 | imozamox | 10 | imazaquin |
| 11 | glufosinate | 12 | glyphosate |
| 13 | glyphosate-trimesium | 14 | lactofen |

Combination 1 is generally used in a ratio of A to B of 1:1,000 to 10:1, preferably 1:25 to 4:1, with B being applied at a rate of 5 to 100 g/ha, preferably 5 to 25 g/ha. Combination 2 is generally used in a ratio of A to B of 1:1,000 to 50:1, preferably 1:10 to 10:1, with B being applied at a rate of 1 to 100 g/ha, preferably 1 to 10 g/ha. Combination 3 is generally used in a ratio of A to B1 of 1:1,000 to 50:1, preferably 1:50 to 4:1, and ratio of A to B2 of 1:500 to 50:1, preferably 1:10 to 20: 1, with B1 being applied at a rate of 1 to 100 g/ha, preferably 5 to 50 g/ha, and B2 being applied at a rate of 1 to 50 g/ha, preferably 1 to 10 g/ha. Combination 4 is generally used in a ratio of A to B of 1:5,000 to 50:1, preferably 1:50 to 2:1, with B being applied at a rate of 1 to 500 g/ha, preferably 10 to 50 g/ha. Combination 5 is generally used in a ratio of A to B of 1:5,000 to 5:1, preferably 1:200 to 1:2, with B being applied at a rate of 10 to 500 g/ha, preferably 50 to 200 g/ha. Combination 6 is generally used in a ratio of A to B of 1:5,000 to 5:1, preferably 1:200 to 1:2, with B being applied at a rate of 10 to 500 g/ha, preferably 50 to 200 g/ha. Combination 7 is generally used in a ratio of A to B of 1:5,000 to 5:1, preferably 1:200 to 1:2, with B being applied at a rate of 10 to 500 g/ha, preferably 50 to 200 g/ha. Combination 8 is generally used in a ratio of A to B of 1:5,000 to 5:1, preferably 1:200 to 1:2, with B being applied at a rate of 10 to 500 g/ha, preferably 50 to 200 g/ha. Combination 9 is generally used in a ratio of A to B of 1:5,000 to 5:1, preferably 1:100 to 2:1, with B being applied at a rate of 10 to 500 g/ha, preferably 10 to 100 g/ha. Combination 10 is generally used in a ratio of A to B of 1:10,000 to 1:2, preferably 1:400 to 1:5, with B being applied at a rate of 100 to 1,000 g/ha, preferably 100 to 400 g/ha. Combination 11 is generally used in a ratio of A to B of 1:40,000 to 1:2, preferably 1:1,000 to 1:10, with B being applied at a rate of 100 to 4,000 g/ha, preferably 200 to 1,000 g/ha. Combination 12 is generally used in a ratio of A to B of 1:40,000 to 1:2, preferably 1:1,000 to 1:10, with B being applied at a rate of 100 to 4,000 g/ha, preferably 200 to 1,000 g/ha. Combination 13 is generally used in a ratio of A to B of 1:40,000 to 1:2, preferably 1:1,000 to 1:10, with B being applied at a rate of 100 to 4,000 g/ha, preferably 200 to 1,000 g/ha Combination 14 is generally used in a ratio of A to B of 1:5,000 to 50:1, preferably 1:200 to 1:2, with B being applied at a rate of 10 to 500 g/ha, preferably 50 to 200 g/ha.

e) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide monosodium salt (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | chlorimuron-ethyl | 2 | thifensulfuron-methyl |
| 3 | chlorimuron-ethyl (B1) in combination with thifensulfuron-methyl (B2) | 4 | clethodim |
| 5 | sethoxydim | 6 | fluazifop-p-butyl |
| 7 | haloxyfop | 8 | imazethapyr |
| 9 | imozamox | 10 | imazaquin |
| 11 | glufosinate | 12 | glyphosate |
| 13 | glyphosate-trimesium | 14 | lactofen |

Combination 1 is generally used in a ratio of A to B of 1:1,000 to 10:1, preferably 1:25 to 4:1, with B being applied at a rate of 5 to 100 g/ha, preferably 5 to 25 g/ha. Combination 2 is generally used in a ratio of A to B of 1:1,000 to 50:1, preferably 1:10 to 10:1, with B being applied at a rate of 1 to 100 g/ha, preferably 1 to 10 g/ha. Combination 3 is generally used in a ratio of A to B1 of 1:1,000 to 50:1, preferably 1:50 to 4:1, and ratio of A to B2 of 1:500 to 50:1, preferably 1:10 to 20:1, with B1 being applied at a rate of 1 to 100 g/ha, preferably 5 to 50 g/ha, and B2 being applied at a rate of 1 to 50 g/ha, preferably 1 to 10 g/ha. Combination 4 is generally used in a ratio of A to B of 1:5,000 to 50:1, preferably 1:50 to 2:1, with B being applied at a rate of 1 to 500 g/ha, preferably 10 to 50 g/ha. Combination 5 is generally used in a ratio of A to B of 1:5,000 to 5:1, preferably 1:200 to 1:2, with B being applied at a rate of 10 to 500 g/ha, preferably 50 to 200 g/ha. Combination 6 is generally used in a ratio of A to B of 1:5,000 to 5:1, preferably 1:200 to 1:2, with B being applied at a rate of 10 to 500 g/ha, preferably 50 to 200 g/ha. Combination 7 is generally used in a ratio of A to B of 1:5,000 to 5:1, preferably 1:200 to 1:2, with B being applied at a rate of 10 to 500 g/ha. preferably 50 to 200 g/ha. Combination 8 is generally used in a ratio of A to B of 1:5,000 to 5:1, preferably 1:200 to 1:2, with B being applied at a rate of 10 to 500 g/ha, preferably 50 to 200 g/ha. Combination 9 is generally used in a ratio of A to B of 1:5,000 to 5:1, preferably 1:100 to 2:1, with B being applied at a rate of 10 to 500 g/ha, preferably 10 to 100 g/ha. Combination 10 is generally used in a ratio of A to B of 1:10,000 to 1:2, preferably 1:400 to 1:5, with B being applied at a rate of 100 to 1,000 g/ha, preferably 100 to 400 g/ha. Combination 11 is generally used in a ratio of A to B of 1:40,000 to 1:2, preferably 1:1,000 to 1:10, with B being applied at a rate of 100 to 4,000 g/ha, preferably 200 to 1,000 g/ha. Combination 12 is oenerallv used in a ratio of A to B of 1:40,000 to 1:2, preferably 1:1,000 to 1:10, with B being applied at a rate of 100 to 4,000 g/ha, preferably 200 to 1,000 g/ha. Combination 13 is generally used in a ratio of A to B of 1:40,000 to 1:2, preferably 1:1,000 to 1:10, with B being applied at a rate of 100 to 4,000 g/ha, preferably 200 to 1,000 g/ha. Combination 14 is generally used in a ratio of A to B of 1:5,000 to 50:1, preferably 1:200 to 1:2, with B being applied at a rate of 10 to 500 g/ha, preferably 50 to 200 g/ha.

f) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamnide monopotassium salt (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | chlorimuron-ethyl | 2 | thifensulfuron-methyl |
| 3 | chlorimuron-ethyl (B1) in combination with thifensulfuron-methyl (B2) | 4 | clethodim |
| 5 | sethoxydim | 6 | fluazifop-p-butyl |
| 7 | haloxyfop | 8 | imazethapyr |
| 9 | imozamox | 10 | imazaquin |
| 11 | glufosinate | 12 | glyphosate |
| 13 | glyphosate-trimesium | 14 | lactofen |

Combination 1 is generally used in a ratio of A to B of 1:1,000 to 10:1, preferably 1:25 to 4:1, with B being applied at a rate of 5 to 100 g/ha, preferably 5 to 25 g/ha. Combination 2 is generally used in a ratio of A to B of 1:1,000 to 50:1, preferably 1:10 to 10:1, with B being applied at a rate of 1 to 100 g/ha, preferably 1 to 10 g/ha. Combination 3 is generally used in a ratio of A to B1 of 1:1,000 to 50:1, preferably 1:50 to 4:1, and ratio of A to B2 of 1:500 to 50:1, preferably 1:10 to 20:1, with B1 being applied at a rate of 1 to 100 g/ha, preferably 5 to 50 g/ha, and B2 being applied at a rate of 1 to 50 g/ha, preferably 1 to 10 g/ha. Combination 4 is generally used in a ratio of A to B of 1:5,000 to 50:1, preferably 1:50 to 2:1, with B being applied at a rate of 1 to 500 g/ha, preferably 10 to 50 g/ha. Combination 5 is generally used in a ratio of A to B of 1:5,000 to 5:1, preferably 1:200 to 1:2, with B being applied at a rate of 10 to 500 g/ha, preferably 50 to 200 g/ha. Combination 6 is generally used in a ratio of A to B of 1:5,000 to 5:1, preferably 1:200 to 1:2, with B being applied at a rate of 10 to 500 g/ha, preferably 50 to 200 g/ha. Combination 7 is generally used in a ratio of A to B of 1:5,000 to 5:1, preferably 1:200 to 1:2, with B being applied at a rate of 10 to 500 g/ha, preferably 50 to 200 g/ha. Combination 8 is generally used in a ratio of A to B of 1:5,000 to 5:1, preferably 1:200 to 1:2, with B being applied at a rate of 10 to 500 g/ha, preferably 50 to 200 g/ha. Combination 9 is generally used in a ratio of A to B of 1:5,000 to 5:1, preferably 1:100 to 2:1, with B being applied at a rate of 10 to 500 g/ha, preferably 10 to 100 g/ha. Combination 10 is generally used in a ratio of A to B of 1:10,000 to 1:2, preferably 1:400 to 1:5, with B being applied at a rate of 100 to 1,000 g/ha, preferably 100 to 400 g/ha. Combination 11 is generally used in a ratio of A to B of 1:40,000 to 1:2, preferably 1:1,000 to 1:10, with B being applied at a rate of 100 to 4,000 g/ha, preferably 200 to 1,000 g/ha. Combination 12 is generally used in a ratio of A to B of 1:40,000 to 1:2, preferably 1:1,000 to 1:10, with B being applied at a rate of 100 to 4,000 g/ha, preferably 200 to 1,000 g/ha. Combination 13 is generally used in a ratio of A to B of 1:40,000 to 1:2, preferably 1:1,000 to 1:10, with B being applied at a rate of 100 to 4,000 g/ha, preferably 200 to 1,000 g/ha. Combination 14 is generally used in a ratio of A to B of 1:5,000 to 50:1, preferably 1:200 to 1:2, with B being applied at a rate of 10 to 500 g/ha, preferably 50 to 200 g/la.

g) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide monosodium salt (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | chlorimuron-ethyl | 2 | thifensulfuron-methyl |
| 3 | chlorimuron-ethyl (B1) in combination with thifensulfuron-methyl (B2) | 4 | clethodim |
| 5 | sethoxydim | 6 | fluazifop-p-butyl |
| 7 | haloxyfop | 8 | imazethapyr |
| 9 | imozamox | 10 | imazaquin |
| 11 | glufosinate | 12 | glyphosate |
| 13 | glyphosate-trimesium | 14 | lactofen |

Combination 1 is generally used in a ratio of A to B of 1:1,000 to 10:1, preferably 1:25 to 4:1, with B being applied at a rate of 5 to 100 g/ha, preferably 5 to 25 g/ha. Combination 2 is generally used in a ratio of A to B of 1:1,000 to 50:1, preferably 1:10 to 10:1, with B being applied at a rate of 1 to 100 g/ha, preferably 1 to 10 g/ha. Combination 3 is generally used in a ratio of A to B1 of 1:1,000 to 50:1, preferably 1:50 to 4:1, and ratio of A to B2 of 1:500 to 50:1, preferably 1:10 to 20:1, with B1 being applied at a rate of 1 to 100 g/ha, preferably 5 to 50 g/ha, and B2 being applied at a rate of 1 to 50 g/ha, preferably 1 to 10 g/ha. Combination 4 is generally used in a ratio of A to B of 1:5,000 to 50:1, preferably 1:50 to 2:1, with B being applied at a rate of 1 to 500 g/ha, preferably 10 to 50 g/ha. Combination 5 is generally used in a ratio of A to B of 1:5,000 to 5:1, preferably 1:200 to 1:2, with B being applied at a rate of 10 to 500 g/ha, preferably 50 to 200 g/ha. Combination 6 is generally used in a ratio of A to B of 1:5,000 to 5:1, preferably 1:200 to 1:2, with B being applied at a rate of 10 to 500 g/ha, preferably 50 to 200 g/ha. Combination 7 is generally used in a ratio of A to B of 1:5,000 to 5:1, preferably 1:200 to 1:2, with B being applied at a rate of 10 to 500 g/ha, preferably 50 to 200 g/ha. Combination 8 is generally used in a ratio of A to B of 1:5,000 to 5:1, preferably 1:200 to 1:2, with B being applied at a rate of 10 to 500 g/ha, preferably 50 to 200 g/ha. Combination 9 is generally used in a ratio of A to B of 1:5,000 to 5:1, preferably 1:100 to 2:1, with B being applied at a rate of 10 to 500 g/ha, preferably 10 to 100 g/ha. Combination 10 is generally used in a ratio of A to B of 1:10,000 to 1:2, preferably 1:400 to 1:5, with B being applied at a rate of 100 to 1,000 g/ha, preferably 100 to 400 g/ha. Combination 11 is generally used in a ratio of A to B of 1:40,000 to 1:2, preferably 1:1,000 to 1:10, with B being applied at a rate of 100 to 4,000 g/ha, preferably 200 to 1,000 g/ha. Combination 12 is generally used in a ratio of A to B of 1:40,000 to 1:2, preferably 1:1,000 to 1:10, with B being applied at a rate of 100 to 4,000 g/ha, preferably 200 to 1,000 g/ha. Combination 13 is generally used in a ratio of A to B of 1:40,000 to 1:2, preferably 1:1,000 to 1:10, with B being applied at a rate of 100 to 4,000 g/ha, preferably 200 to 1,000 g/ha. Combination 14 is generally used in a ratio of A to B of 1:5,000 to 50:1, preferably 1:200 to 1:2, with B being applied at a rate of 10 to 500 g/ha, preferably 50 to 200 g/ha.

h) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide monopotassium salt (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | chlorimuron-ethyl | 2 | thifensulfuron-methyl |
| 3 | chlorimuron-ethyl (B1) in combination with thifensulfuron-methyl (B2) | 4 | clethodim |
| 5 | sethoxydim | 6 | fluazifop-p-butyl |
| 7 | haloxyfop | 8 | imazethapyr |
| 9 | imozamox | 10 | imazaquin |
| 11 | glufosinate | 12 | glyphosate |
| 13 | glyphosate-trimesium | 14 | lactofen |

Combination 1 is generally used in a ratio of A to B of 1:1,000 to 10:1, preferably 1:25 to 4:1, with B being applied at a rate of 5 to 100 g/ha, preferably 5 to 25 g/ha. Combination 2 is generally used in a ratio of A to B of 1:1,000 to 50:1, preferably 1:10 to 10:1, with B being applied at a rate of 1 to 100 g/ha, preferably 1 to 10 g/ha. Combination 3 is generally used in a ratio of A to B1 of 1:1,000 to 50:1, preferably 1:50 to 4:1, and ratio of A to B2 of 1:500 to 50:1, preferably 1:10 to 20:1, with B1 being applied at a rate of 1 to 100 g/ha, preferably 5 to 50 g/ha, and B2 being applied at a rate of 1 to 50 g/ha, preferably 1 to 10 g/ha. Combination 4 is generally used in a ratio of A to B of 1:5,000 to 50:1, preferably 1:50 to 2:1, with B being applied at a rate of 1 to 500 g/ha, preferably 10 to 50 g/ha. Combination 5 is generally used in a ratio of A to B of 1:5,000 to 5:1, preferably 1:200 to 1:2, with B being applied at a rate of 10 to 500 g/ha, preferably 50 to 200 g/ha. Combination 6 is generally used in a ratio of A to B of 1:5,000 to 5:1, preferably 1:200 to 1:2, with B being applied at a rate of 10 to 500 g/ha, preferably 50 to 200 g/ha. Combination 7 is generally used in a ratio of A to B of 1:5,000 to 5:1, preferably 1:200 to 1:2, with B being applied at a rate of 10 to 500 g/ha, preferably 50 to 200 g/ha. Combination 8 is generally used in a ratio of A to B of 1:5,000 to 5:1, preferably 1:200 to 1:2, with B being applied at a rate of 10 to 500 g/ha, preferably 50 to 200 g/ha. Combination 9 is generally used in a ratio of A to B of 1:5,000 to 5:1, preferably 1:100 to 2:1, with B being applied at a rate of 10 to 500 g/ha, preferably 10 to 100 g/ha. Combination 10 is generally used in a ratio of A to B of 1:10,000 to 1:2, preferably 1:400 to 1:5, with B being applied at a rate of 100 to 1,000 g/ha, preferably 100 to 400 g/ha. Combination 11 is generally used in a ratio of A to B of 1:40,000 to 1:2, preferably 1:1,000 to 1:10, with B being applied at a rate of 100 to 4,000 g/ha, preferably 200 to 1,000 g/ha. Combination 12 is generally used in a ratio of A to B of 1:40,000 to 1:2, preferably 1:1,000 to 1:10, with B being applied at a rate of 100 to 4,000 g/ha, preferably 200 to 1,000 g/ha. Combination 13 is generally used in a ratio of A to B of 1:40,000 to 1:2, preferably 1:1,000 to 1:10, with B being applied at a rate of 100 to 4,000 g/ha, preferably 200 to 1,000 g/ha. Combination 14 is generally used in a ratio of A to B of 1:5,000 to 50:1, preferably 1:200 to 1:2, with B being applied at a rate of 10 to 500 g/ha, preferably 50 to 200 g/ha.

Specifically preferred mixtures for use in winter wheat, winter barley, spring wheat, spring barley, and peas are selected from the group:

a) 6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | tribenuron-methyl | 2 | thifensulfuron-methyl |
| 3 | thifensulfuron-methyl (B1) in combination with tribenuron-methyl (B2) | 4 | metsulfuron-methyl |
| 5 | thifensulfuron-methyl (B3) in combination with metsulfuron-methyl (B4) | 6 | thifensulfuron-methyl (B5) in combination with tribenuron-methyl (B6) in combination with metsulfuron-methyl (B7) |
| 7 | chlorsulfuron | 8 | chlorsulfuron (B8) in combination with metsulfuron-methyl (B9) |
| 9 | triasulfuron | 10 | 2,4-D |
| 11 | dicamba | 12 | bromoxynil |
| 13 | MCPA | 14 | bromoxynil (B10) in combination with MCPA (B11) |
| 15 | fluroxypyr | 16 | clopyralid |
| 17 | fenoxaprop (B12) in combination with fenchlorazole (B13) | 18 | diclofop |
| 19 | tralkoxydim | 20 | clodinafop (B14) in combination with cloquintocet-mexyl (B15) |
| 21 | imazamethabenz | 22 | sulfosulfuron |
| 23 | difenzoquat | 24 | propanil |
| 25 | prosulfuron | 26 | metribuzin |
| 27 | glyphosate | 28 | triallate |
| 29 | trifluralin | | |

Combination 1 is generally used in a ratio of A to B of 1:500 to 50:1, preferably 1:10 to 20:1, with B being applied at a rate of 1 to 50 g/ha, preferably 1 to 10 g/ha. Combination 2 is generally used in a ratio of A to B of 1:1,000 to 50:1, preferably 1:20 to 20:1, with B being applied at a rate of 1 to 100 g/ha, preferably 1 to 20 g/ha. Combination 3 is generally used in a ratio of A to B1 of 1:500 to 50:1, preferably 1:20 to 20:1, and ratio of A to B2 of 1:500 to 50:1, preferably 1:10 to 20:1. with B1 being applied at a rate of 1 to 50 g/ha, preferably 1 to 20 g/ha, and B2 being applied at a rate of 1 to 50 g/ha, preferably 1 to 10 g/ha. Combination 4 is generally used in a ratio of A to B of 1:200 to 50:1, preferably 1:20 to 20:1, with B being applied at a rate of 1 to 20 g/ha, preferably 1 to 10 g/ha. Combination 5 is generally used in a ratio of A to B3 of 1:1,000 to 50:1, preferably 1:20 to 20:1, and ratio of A to B4 of 1:200 to 50:1, preferably 1:20 to 20:1, with B3 being applied at a rate of 1 to 100 g/ha, preferably 1 to 20 g/ha, and B4 being applied at a rate of 1 to 20 g/ha, preferably 1 to 10 g/ha Combination 6 is generally used in a ratio of A to B5 of 1:1,000 to 50:1, preferably 1:20 to 20:1, and ratio of A to B6 of 1:500 to 50:1, preferably 1:10 to 20:1, and ratio of A to B7 of 1:200 to 50:1, preferably 1:20 to 20:1, with B5 being applied at a rate of 1 to 100 g/ha, preferably 1 to 20 g/ha, and B6 being applied at a rate of 1 to 50 g/ha, preferably 1 to 10 g/ha, and B7 being applied at a rate of 1 to 20 g/ha, preferably 1 to 10 g/ha. Combination 7 is generally used in a ratio of A to B of 1:500 to 50:1, preferably 1:10 to 20:1, with B being applied at a rate of 1 to 50 g/ha, preferably 1 to 10 g/ha. Combination 8 is generally used in a ratio of A to B8 of 1:500 to 50:1, preferably 1:10 to 20:1, and ratio of A to B9 of 1:200 to 50:1, preferably 1:20 to 20:1, with B5 being applied at a rate of 1 to 50 g/ha, preferably 1 to 20 g/ha, and B9 being applied at a rate of 1 to 20 g/ha, preferably 1 to 10 g/ha. Combination 9 is generally used in a ratio of A to B of 1:1,000 to 50:1, preferably 1:20 to 20:1, with B being applied at a rate of 1 to 100 g/ha, preferably 1 to 20 g/ha. Combination 10 is generally used in a ratio of A to B of 1:30,000 to 1:2, preferably 1:500 to 1:5, with B being applied at a rate of 100 to 3,000 g/ha, preferably 100 to 500 g/ha. Combination 11 is generally used in a ratio of A to B of 1:5,000 to 5:1, preferably 1:100 to 2:1, with B being applied at a rate of 10 to 500 g/ha, preferably 10 to 100 g/ha. Combination 12 is generally used in a ratio of A to B of 1:20,000 to 1:2, preferably 1:500 to 1:5, with B being applied at a rate of 100 to 2,000 g/ha, preferably 100 to 500 g/ha. Combination 13 is generally used in a ratio of A to B of 1:20,000 to 1:2, preferably 1:500 to 1:5, with B being applied at a rate of 100 to 2,000 g/ha, preferably 100 to 500 g/ha. Combination 14 is generally used in a ratio of A to B10 of 1:20,000 to 1:2, preferably 1:500 to 1:5, and ratio of A to B11 of 1:20,000 to 1:2, preferably 1:500 to 1:5, with B10 being applied at a rate of 100 to 2,000 g/ha, preferably 100 to 500 g/ha, and B11 being applied at a rate of 100 to 2,000 g/ha, preferably 100 to 500 g/ha. Combination 15 is generally used in a ratio of A to B of 1:5,000 to 5:1, preferably 1:100 to 2:1, with B being applied at a rate of 10 to 500 g/ha, preferably 10 to 100 g/ha. Combination 16 is generally used in a ratio of A to B of 1:5,000 to 5:1, preferably 1:100 to 2:1, with B being applied at a rate of 10 to 500 g/ha, preferably 10 to 100 g/ha. Combination 17 is generally used in a ratio of A to B12 of 1:5,000 to 5:1, preferably 1:500 to 1:5, and ratio of A to B1 3 of 1:1,000 to 50:1, preferably 1:20 to 20:1, with B12 being applied at a rate of 10 to 500 g/ha, preferably 10 to 100 g/ha, and B13 being applied at a rate of 1 to 100 g/ha, preferably 1 to 20 g/ha. Combination 18 is generally used in a ratio of A to B of 1:20,000 to 1:2, preferably 1:1,000 to 1:10, with B being applied at a rate of 100 to 2,000 g/ha, preferably 200 to 1,000 g/ha. Combination 19 is generally used in a ratio of A to B of 1:10,000 to 1:2, preferably 1:300 to 1:5. with B being applied at a rate of 100 to 1,000 g/ha, preferably 100 to 300 g/ha. Combination 20 is generally used in a ratio of A to B14 of 1:2,000 to 5:1, preferably 1:60 to 2:1, and ratio of A to B15 of 1:1,000 to 50:1, preferably 1:20 to 20:1, with B14 being applied at a rate of 10 to 200 g/ha, preferably 10 to 60 g/ha, and B15 being applied at a rate of 1 to 100 g/ha, preferably 1 to 20 g/ha. Combination 21 is generally used in a ratio of A to B of 1:10,000 to 1:2, preferably 1:300 to 1:5, with B being applied at a rate of 100 to 1,000 g/ha, preferably 100 to 300 g/ha. Combination 22 is generally used in a ratio of A to B of 1:1,000 to 50:1, preferably 1:20 to 20:1, with B being applied at a rate of 1 to 100 g/ha, preferably 1 to 20 g/ha. Combination 23 is generally used in a ratio of A to B of 1:20,000 to 1:2, preferably 1:1,000 to 1:10, with B being applied at a rate of 100 to 2,000 g/ha, preferably 200 to 1,000 g/ha. Combination 24 is generally used in a ratio of A to B of 1:20,000 to 1:2, preferably 1:1,000 to 1:10, with B being applied at a rate of 100 to 2,000 g/ha, preferably 200 to 1,000 g/ha. Combination 25 is generally used in a ratio of A to B of 1:1,000 to 5:1, preferably 1:50 to 2:1, with B being applied at a rate of 10 to 100 g/ha, preferably 10 to 50 g/ha. Combination 26 is generally used in a ratio of A to B of 1:10,000 to 5:1, preferably 1:100to 2:1, with B being applied at a rate of 10 to 1,000 g/ha, preferably 10 to 100 g/ha. Combination 27 is generally used in a ratio of A to B of 1:20,000 to 1:2, preferably 1:1,000 to 1:10, with B being applied at a rate of 100 to 2,000 g/ha, preferably 200 to 1,000 g/ha. Combination 28 is generally used in a ratio of A to B of 1:20,000 to 1:20, preferably 1:1,500 to 1:50, with B being applied at a rate of 1,000 to 2,000 g/ha, preferably 1,000 to 1,500 g/ha.

Combination 29 is generally used in a ratio of A to B of 1:20,000 to 1:2, preferably 1:1,000 to 1:10, with B being applied a rate of 100 to 2,000 g/ha, preferably 200 to 1,000 g/ha.

b) 6S-cis)-N-pyrrolo[1,2-chloro-4-fluoro-5-(6-fluorotetrahydro-1,3-dioxo-1H-[2-c]imidazol-2(3H)-yl)phenyl]-N-[(chloromethyl)sulfonyl]acetamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | tribenuron-methyl | 2 | thifensulfuron-methyl |
| 3 | thifensulfuron-methyl (B1) in combination with tribenuron-methyl (B2) | 4 | metsulfuron-methyl |
| 5 | thifensulfuron-methyl (B3) in combination with metsulfuron-methyl (B4) | 6 | thifensulfuron-methyl (B5) in combination with tribenuron-methyl (B6) in combination with metsulfuron-methyl (B7) |
| 7 | chlorsulfuron | 8 | chlorsulfuron (B8) in combination with metsulfuron-methyl (B9) |
| 9 | triasulfuron | 10 | 2,4-D |
| 11 | dicamba | 12 | bromoxynil |
| 13 | MCPA | 14 | bromoxynil (B10) in combination with MCPA (B11) |
| 15 | fluroxypyr | 16 | clopyralid |
| 17 | fenoxaprop (B12) in combination with fenchlorazole (B13) | 18 | diclofop |
| 19 | tralkoxydim | 20 | clodinafop (B14) in combination with cloquintocet-mexyl (B15) |
| 21 | imazamethabenz | 22 | sulfosulfuron |
| 23 | difenzoquat | 24 | propanil |
| 25 | prosulfuron | 26 | metribuzin |
| 27 | glyphosate | 28 | triallate |
| 29 | trifluralin | | |

Combination 1 is generally used in a ratio of A to B of 1:500 to 50:1, preferably 1:10 to 20:1, with B being applied at a rate of 1 to 50 g/ha, preferably 1 to 10 g/ha. Combination 2 is generally used in a ratio of A to B of 1:1,000 to 50:1, preferably 1:20 to 20:1, with B being applied at a rate of 1 to 100 g/ha, preferably 1 to 20 g/ha. Combination 3 is generally used in a ratio of A to B1 of 1:500 to 50:1, preferably 1:20 to 20:1, and ratio of A to B2 of 1:500 to 50:1, preferably 1:10 to 20:1. with B1 being applied at a rate of 1 to 50 g/ha, preferably 1 to 20 g/ha, and B2 being applied at a rate of 1 to 50 g/ha, preferably 1 to 10 g/ha. Combination 4 is generally used in a ratio of A to B of 1:200 to 50:1, preferably 1:20 to 20:1, with B being applied at a rate of 1 to 20 g/ha, preferably 1 to 10 g/ha. Combination 5 is generally used in a ratio of A to B3 of 1:1,000 to 50:1, preferably 1:20 to 20:1, and ratio of A to B4 of 1:200 to 50:1, preferably 1:20 to 20:1, with B3 being applied at a rate of 1 to 100 g/ha, preferably 1 to 20 g/ha, and B4 being applied at a rate of 1 to 20 g/ha, preferably 1 to 10 g/ha Combination 6 is generally used in a ratio of A to B5 of 1:1,000 to 50:1, preferably 1:20 to 20:1, and ratio of A to B6 of 1:500 to 50:1, preferably 1:10 to 20:1, and ratio of A to B7 of 1:200 to 50:1, preferably 1:20 to 20:1, with B5 being applied at a rate of 1 to 100 g/ha, preferably 1 to 20 g/ha, and B6 being applied at a rate of 1 to 50 g/ha, preferably 1 to 10 g/ha, and B7 being applied at a rate of 1 to 20 g/ha, preferably 1 to 10 g/ha. Combination 7 is generally used in a ratio of A to B of 1:500 to 50:1, preferably 1:10 to 20:1, with B being applied at a rate of 1 to 50 g/ha, preferably 1 to 10 g/ha. Combination 8 is generally used in a ratio of A to B8 of 1:500 to 50:1, preferably 1:10 to 20:1, and ratio of A to B9 of 1:200 to 50:1, preferably 1:20 to 20:1, with B5 being applied at a rate of 1 to 50 g/ha, preferably 1 to 10 g/ha, and B9 being applied at a rate of 1 to 20 g/ha, preferably 1 to 10 g/ha. Combination 9 is generally used in a ratio of A to B of 1:1,000 to 50:1, preferably 1:20 to 20:1, with B being applied at a rate of 1 to 100 g/ha, preferably 1 to 20 g/ha. Combination 10 is generally used in a ratio of A to B of 1:30,000 to 1:2, preferably 1:500 to 1:5, with B being applied at a rate of 100 to 3,000 g/ha, preferably 100 to 500 g/ha. Combination 11 is generally used in a ratio of A to B of 1:5,000 to 5:1, preferably 1:100 to 2:1, with B being applied at a rate of 10 to 500 g/ha, preferably 10 to 100 g/ha. Combination 12 is generally used in a ratio of A to B of 1:20,000 to 1:2, preferably 1:500 to 1:5, with B being applied at a rate of 100 to 2,000 g/ha, preferably 100 to 500 g/ha. Combination 13 is generally used in a ratio of A to B of 1:20,000 to 1:2, preferably 1:500 to 1:5, with B being applied at a rate of 100 to 2,000 g/ha, preferably 100 to 500 g/ha. Combination 14 is generally used in a ratio of A to B10 of 1:20,000 to 1:2, preferably 1:500 to 1:5, and ratio of A to B11 of 1:20,000 to 1:2, preferably 1:500 to 1:5, with B10 being applied at a rate of 100 to 2,000 g/ha, preferably 100 to 500 g/ha, and B11 being applied at a rate of 100 to 2,000 g/ha, preferably 100 to 500 g/ha. Combination 15 is generally used in a ratio of A to B of 1:5,000 to 5:1, preferably 1:100 to 2:1, with B being applied at a rate of 10 to 500 g/ha, preferably 10 to 100 g/ha. Combination 16 is generally used in a ratio of A to B of 1:5,000 to 5:1, preferably 1:100 to 2:1, with B being applied at a rate of 10 to 500 g/ha, preferably 10 to 100 g/ha. Combination 17 is generally used in a ratio of A to B12 of 1:5,000 to 5:1, preferably 1:500 to 1:5, and ratio of A to B1 3 of 1:1,000 to 50:1, preferably 1:20 to 20:1, with B12 being applied at a rate of 10 to 500 g/ha, preferably 10 to 100 g/ha, and B13 being applied at a rate of 1 to 100 g/ha, preferably 1 to 20 g/ha. Combination 18 is generally used in a ratio of A to B of 1:20,000 to 1:2, preferably 1:1,000 to 1:10, with B being applied at a rate of 100 to 2,000 g/ha, preferably 200 to 1,000 g/ha. Combination 19 is generally used in a ratio of A to B of 1:10,000 to 1:2, preferably 1:300 to 1:5. with B being applied at a rate of 100 to 1,000 g/ha, preferably 100 to 300 g/ha. Combination 20 is generally used in a ratio of A to B14 of 1:2,000 to 5:1, preferably 1:60 to 2:1, and ratio of A to B15 of 1:1,000 to 50:1, preferably 1:20 to 20:1, with B14 being applied at a rate of 10 to 200 g/ha, preferably 10 to 60 g/ha, and B15 being applied at a rate of 1 to 100 g/ha, preferably 1 to 20 g/ha. Combination 21 is generally used in a ratio of A to B of 1:10,000 to 1:2, preferably 1:300 to 1:5, with B being applied at a rate of 100 to 1,000 g/ha, preferably 100 to 300 g/ha. Combination 22 is generally used in a ratio of A to B of 1:1,000 to 50:1, preferably 1:20 to 20:1, with B being applied at a rate of 1 to 100 g/ha, preferably 1 to 20 g/ha. Combination 23 is generally used in a ratio of A to B of 1:20,000 to 1:2, preferably 1:1,000 to 1:10, with B being applied at a rate of 100 to 2,000 g/ha, preferably 200 to 1,000 g/ha. Combination 24 is generally used in a ratio of A to B of 1:20,000 to 1:2, preferably 1:1,000 to 1:10, with B being applied at a rate of 100 to 2,000 g/ha, preferably 200 to 1,000 g/ha. Combination 25 is generally used in a ratio of A to B of 1:1,000 to 5:1, preferably 1:50 to 2:1, with B being applied at a rate of 10 to 100 g/ha, preferably 10 to 50 g/ha. Combination 26 is generally used in a ratio of A to B of 1:10,000 to 5:1, preferably 1:100to 2:1, with B being applied at a rate of 10 to 1,000 g/ha, preferably 10 to 100 g/ha. Combination 27 is generally used in a ratio of A to B of 1:20,000 to 1:2, preferably 1:1,000 to 1:10, with B being applied at a rate of 100 to 2,000 g/ha, preferably 200 to 1,000 g/ha. Combination 28 is generally used in a ratio of A to B of 1:20,000 to 1:20, preferably 1:1,500 to 1:50, with B being applied at a rate of 1,000 to 2,000 g/ha, preferably 1,000 to 1,500 g/ha. Combination 29 is generally used in a ratio of A to B of 1:20,000 to 1:2, preferably 1:1,000 to 1:10, with B being applied a rate of 100 to 2,000 g/ha, preferably 200 to 1,000 g/ha.

c) 6S-cis)-N-[2-chloro-4-fluoro-5-(6-fluorotetrahydro-1, 3-dioxo-1H-pyrrolo[1,2-c]imidazol-2(3H)-yl)phenyl]-N-[(chloromethyl)sulfonyl]acetamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | tribenuron-methyl | 2 | thifensulfuron-methyl |
| 3 | thifensulfuron-methyl (B1) in combination with tribenuron-methyl (B2) | 4 | metsulfuron-methyl |
| 5 | thifensulfuron-methyl (B3) in combination with metsulfuron-methyl (B4) | 6 | thifensulfuron-methyl (B5) in combination with tribenuron-methyl (B6) in combination with metsulfuron-methyl (B7) |
| 7 | chlorsulfuron | 8 | chlorsulfuron (B8) in combination with metsulfuron-methyl (B9) |
| 9 | triasulfuron | 10 | 2,4-D |
| 11 | dicamba | 12 | bromoxynil |
| 13 | MCPA | 14 | bromoxynil (B10) in combination with MCPA (B11) |
| 15 | fluroxypyr | 16 | clopyralid |
| 17 | fenoxaprop (B12) in combination with fenchlorazole (B13) | 18 | diclofop |
| 19 | tralkoxydim | 20 | clodinafop (B14) in combination with cloquintocet-mexyl (B15) |
| 21 | imazamethabenz | 22 | sulfosulfuron |
| 23 | difenzoquat | 24 | propanil |
| 25 | prosulfuron | 26 | metribuzin |
| 27 | glyphosate | 28 | triallate |
| 29 | trifluralin | | |

Combination 1 is generally used in a ratio of A to B of 1:500 to 50:1, preferably 1:10 to 20:1, with B being applied at a rate of 1 to 50 g/ha, preferably 1 to 10 g/ha. Combination 2 is generally used in a ratio of A to B of 1:1,000 to 50:1, preferably 1:20 to 20:1, with B being applied at a rate of 1 to 100 g/ha, preferably 1 to 20 g/ha. Combination 3 is generally used in a ratio of A to B1 of 1:500 to 50:1, preferably 1:20 to 20:1, and ratio of A to B2 of 1:500 to 50:1, preferably 1:10 to 20:1, with B1 being applied at a rate of 1 to 50 g/ha, preferably 1 to 20 g/ha, and B2 being applied at a rate of 1 to 50 g/ha, preferably 1 to 10 g/ha. Combination 4 is generally used in a ratio of A to B of 1:200 to 50:1, preferably 1:20 to 20:1, with B being applied at a rate of 1 to 20 g/ha, preferably 1 to 10 g/ha. Combination 5 is generally used in a ratio of A to B3 of 1:1,000 to 50:1, preferably 1:20 to 20:1, and ratio of A to B4 of 1:200 to 50:1, preferably 1:20 to 20:1, with B3 being applied at a rate of 1 to 100 g/ha, preferably 1 to 20 g/ha, and B4 being applied at a rate of 1 to 20 g/ha, preferably 1 to 10 g/ha Combination 6 is generally used in a ratio of A to B5 of 1:1,000 to 50:1, preferably 1:20 to 20:1, and ratio of A to B6 of 1:500 to 50:1, preferably 1:10 to 20:1, and ratio of A to B7 of 1:200 to 50:1, preferably 1:20 to 20:1, with B5 being applied at a rate of 1 to 100 g/ha, preferably 1 to 20 g/ha, and B6 being applied at a rate of 1 to 50 g/ha, preferably 1 to 10 g/ha, and B7 being applied at a rate of 1 to 20 g/ha, preferably 1 to 10 g/ha. Combination 7 is generally used in a ratio of A to B of 1:500 to 50:1, preferably 1:10 to 20:1, with B being applied at a rate of 1 to 50 g/ha, preferably 1 to 10 g/ha. Combination 8 is generally used in a ratio of A to B8 of 1:500 to 50:1, preferably 1:10 to 20:1, and ratio of A to B9 of 1:200 to 50:1, preferably 1:20 to 20:1, with B5 being applied at a rate of 1 to 50 g/ha, preferably 1 to 10 g/ha, and B9 being applied at a rate of 1 to 20 g/ha, preferably 1 to 10 g/ha. Combination 9 is generally used in a ratio of A to B of 1:1,000 to 50:1, preferably 1:20 to 20:1, with B being applied at a rate of 1 to 100 g/ha, preferably 1 to 20 g/ha. Combination 10 is generally used in a ratio of A to B of 1:30,000 to 1:2, preferably 1:500 to 1:5, with B being applied at a rate of 100 to 3,000 g/ha, preferably 100 to 500 g/ha. Combination 11 is generally used in a ratio of A to B of 1:5,000 to 5:1, preferably 1:100 to 2:1, with B being applied at a rate of 10 to 500 g/ha, preferably 10 to 100 g/ha. Combination 12 is generally used in a ratio of A to B of 1:20,000 to 1:2, preferably 1:500 to 1:5, with B being applied at a rate of 100 to 2,000 g/ha, preferably 100 to 500 g/ha. Combination 13 is generally used in a ratio of A to B of 1:20,000 to 1:2, preferably 1:500 to 1:5, with B being applied at a rate of 100 to 2,000 g/ha, preferably 100 to 500 g/ha. Combination 14 is generally used in a ratio of A to B10 of 1:20,000 to 1:2, preferably 1:500 to 1:5, and ratio of A to B11 of 1:20,000 to 1:2, preferably 1:500 to 1:5, with B10 being applied at a rate of 100 to 2,000 g/ha, preferably 100 to 500 g/ha, and B11 being applied at a rate of 100 to 2,000 g/ha, preferably 100 to 500 g/ha. Combination 15 is generally used in a ratio of A to B of 1:5,000 to 5:1, preferably 1:100 to 2:1, with B being applied at a rate of 10 to 500 g/ha, preferably 10 to 100 g/ha. Combination 16 is generally used in a ratio of A to B of 1:5,000 to 5:1, preferably 1:100 to 2:1, with B being applied at a rate of 10 to 500 g/ha, preferably 10 to 100 g/ha. Combination 17 is generally used in a ratio of A to B12 of 1:5,000 to 5:1, preferably 1:500 to 1:5, and ratio of A to B13 of 1:1,000 to 50:1, preferably 1:20 to 20:1, with B12 being applied at a rate of 10 to 500 g/ha, preferably 10 to 100 g/ha, and B13 being applied at a rate of 1 to 100 g/ha, preferably 1 to 20 g/ha. Combination 18 is generally used in a ratio of A to B of 1:20,000 to 1:2, preferably 1:1,000 to 1:10, with B being applied at a rate of 100 to 2,000 g/ha, preferably 200 to 1,000 g/ha. Combination 19 is generally used in a ratio of A to B of 1:10,000 to 1:2, preferably 1:300 to 1:5. with B being applied at a rate of 100 to 1,000 g/ha, preferably 100 to 300 g/ha. Combination 20 is generally used in a ratio of A to B14 of 1:2,000 to 5:1, preferably 1:60 to 2:1, and ratio of A to B15 of 1:1,000 to 50:1, preferably 1:20 to 20:1, with B14 being applied at a rate of 10 to 200 g/ha, preferably 10 to 60 g/ha, and B15 being applied at a rate of 1 to 100 g/ha, preferably 1 to 20 g/ha. Combination 21 is generally used in a ratio of A to B of 1:10,000 to 1:2, preferably 1:300 to 1:5, with B being applied at a rate of 100 to 1,000 g/ha, preferably 100 to 300 g/ha. Combination 22 is generally used in a ratio of A to B of 1:1,000 to 50:1, preferably 1:20 to 20:1, with B being applied at a rate of 1 to 100 g/ha, preferably 1 to 20 g/ha. Combination 23 is generally used in a ratio of A to B of 1:20,000 to 1:2, preferably 1:1,000 to 1:10, with B being applied at a rate of 100 to 2,000 g/ha, preferably 200 to 1,000 g/ha. Combination 24 is generally used in a ratio of A to B of 1:20,000 to 1:2, preferably 1:1,000 to 1:10, with B being applied at a rate of 100 to 2,000 g/ha, preferably 200 to 1,000 g/ha. Combination 25 is generally used in a ratio of A to B of 1:1,000 to 5:1, preferably 1:50 to 2:1, with B being applied at a rate of 10 to 100 g/ha, preferably 10 to 50 g/ha. Combination 26 is generally used in a ratio of A to B of 1:10,000 to 5:1, preferably 1:100 to 2:1, with B being applied at a rate of 10 to 1,000 g/ha, preferably 10 to 100 g/ha. Combination 27 is generally used in a ratio of A to B of 1:20,000 to 1:2, preferably 1:1,000 to 1:10, with B being applied at a rate of 100 to 2,000 g/ha, preferably 200 to 1,000 g/ha. Combination 28 is generally used in a ratio of A to B of 1:20,000 to 1:20, preferably 1:1,500 to 1:50, with B being applied at a rate of 1,000 to 2,000 g/ha, preferably 1,000 to 1,500 g/ha. Combination 29 is generally used in a ratio of A to B of 1:20,000 to 1:2, preferably 1:1,000 to 1:10, with B being applied a rate of 100 to 2,000 g/ha, preferably 200 to 1,000 g/ha.

d) 6S-cis)-N-[2-chloro-4-fluoro-5-(6-fluorotetrahydro-1,3-dioxo-1H-pyrrolo[1,2-c]imidazol-2(3H)-yl)phenyl]-N-[(chloromethyl)sulfonyl]acetamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | tribenuron-methyl | 2 | thifensulfuron-methyl |
| 3 | thifensulfuron-methyl (B1) in combination with tribenuron-methyl (B2) | 4 | metsulfuron-methyl |
| 5 | thifensulfuron-methyl (B3) in combination with metsulfuron-methyl (B4) | 6 | thifensulfuron-methyl (B5) in combination with tribenuron-methyl (B6) in combination with metsulfuron-methyl (B7) |
| 7 | chlorsulfuron | 8 | chlorsulfuron (B8) in combination with metsulfuron-methyl (B9) |
| 9 | triasulfuron | 10 | 2,4-D |
| 11 | dicamba | 12 | bromoxynil |
| 13 | MCPA | 14 | bromoxynil (B10) in combination with MCPA (B11) |
| 15 | fluroxypyr | 16 | clopyralid |
| 17 | fenoxaprop (B12) in combination with fenchlorazole (B13) | 18 | diclofop |
| 19 | tralkoxydim | 20 | clodinafop (B14) in combination with cloquintocet-mexyl (B15) |
| 21 | imazamethabenz | 22 | sulfosulfuron |
| 23 | difenzoquat | 24 | propanil |
| 25 | prosulfuron | 26 | metribuzin |
| 27 | glyphosate | 28 | triallate |
| 29 | trifluralin | | |

Combination 1 is generally used in a ratio of A to B of 1:500 to 50:1, preferably 1:10 to 20:1, with B being applied at a rate of 1 to 50 g/ha, preferably 1 to 10 g/ha. Combination 2 is generally used in a ratio of A to B of 1:1,000 to 50:1, preferably 1:20 to 20:1, with B being applied at a rate of 1 to 100 g/ha, preferably 1 to 20 g/ha. Combination 3 is generally used in a ratio of A to B1 of 1:500 to 50:1, preferably 1:20 to 20:1, and ratio of A to B2 of 1:500 to 50:1, preferably 1:10 to 20:1. with B1 being applied at a rate of 1 to 50 g/ha, preferably 1 to 20 g/ha, and B2 being applied at a rate of 1 to 50 g/ha, preferably 1 to 10 g/ha. Combination 4 is generally used in a ratio of A to B of 1:200 to 50:1, preferably 1:20 to 20:1, with B being applied at a rate of 1 to 20 g/ha, preferably 1 to 10 g/ha. Combination 5 is generally used in a ratio of A to B3 of 1:1,000 to 50:1, preferably 1:20 to 20:1, and ratio of A to B4 of 1:200 to 50:1, preferably 1:20 to 20:1, with B3 being applied at a rate of 1 to 100 g/ha, preferably 1 to 20 g/ha, and B4 being applied at a rate of 1 to 20 g/ha, preferably 1 to 10 g/ha Combination 6 is generally used in a ratio of A to B5 of 1:1,000 to 50:1, preferably 1:20 to 20:1, and ratio of A to B6 of 1:500 to 50:1, preferably 1:10 to 20:1, and ratio of A to B7 of 1:200 to 50:1, preferably 1:20 to 20:1, with B5 being applied at a rate of 1 to 100 g/ha, preferably 1 to 20 g/ha, and B6 being applied at a rate of 1 to 50 g/ha, preferably 1 to 10 g/ha, and B7 being applied at a rate of 1 to 20 g/ha, preferably 1 to 10 g/ha. Combination 7 is generally used in a ratio of A to B of 1:500 to 50:1, preferably 1:10 to 20:1, with B being applied at a rate of 1 to 50 g/ha, preferably 1 to 10 g/ha. Combination 8 is generally used in a ratio of A to B8 of 1:500 to 50:1, preferably 1:10 to 20:1, and ratio of A to B9 of 1:200 to 50:1, preferably 1:20 to 20:1, with B5 being applied at a rate of 1 to 50 g/ha, preferably 1 to 10 g/ha, and B9 being applied at a rate of 1 to 20 g/ha, preferably 1 to 10 g/ha. Combination 9 is generally used in a ratio of A to B of 1:1,000 to 50:1, preferably 1:20 to 20:1, with B being applied at a rate of 1 to 100 g/ha, preferably 1 to 20 g/ha. Combination 10 is generally used in a ratio of A to B of 1:30,000 to 1:2, preferably 1:500 to 1:5, with B being applied at a rate of 100 to 3,000 g/ha, preferably 100 to 500 g/ha. Combination 11 is generally used in a ratio of A to B of 1:5,000 to 5:1, preferably 1:100 to 2:1, with B being applied at a rate of 10 to 500 g/ha, preferably 10 to 100 g/ha. Combination 12 is generally used in a ratio of A to B of 1:20,000 to 1:2, preferably 1:500 to 1:5, with B being applied at a rate of 100 to 2,000 g/ha, preferably 100 to 500 g/ha. Combination 13 is generally used in a ratio of A to B of 1:20,000 to 1:2, preferably 1:500 to 1:5, with B being applied at a rate of 100 to 2,000 g/ha, preferably 100 to 500 g/ha. Combination 14 is generally used in a ratio of A to B10 of 1:20,000 to 1:2, preferably 1:500 to 1:5, and ratio of A to B11 of 1:20,000 to 1:2, preferably 1:500 to 1:5, with B10 being applied at a rate of 100 to 2,000 g/ha, preferably 100 to 500 g/ha, and B11 being applied at a rate of 100 to 2,000 g/ha, preferably 100 to 500 g/ha. Combination 15 is generally used in a ratio of A to B of 1:5,000 to 5:1, preferably 1:100 to 2:1, with B being applied at a rate of 10 to 500 g/ha, preferably 10 to 100 g/ha. Combination 16 is generally used in a ratio of A to B of 1:5,000 to 5:1, preferably 1:100 to 2:1, with B being applied at a rate of 10 to 500 g/ha, preferably 10 to 100 g/ha. Combination 17 is generally used in a ratio of A to B12 of 1:5,000 to 5:1, preferably 1:500 to 1:5, and ratio of A to B13 of 1:1,000 to 50:1, preferably 1:20 to 20:1, with B12 being applied at a rate of 10 to 500 g/ha, preferably 10 to 100 g/ha, and B13 being applied at a rate of 1 to 100 g/ha, preferably 1 to 20 g/ha. Combination 18 is generally used in a ratio of A to B of 1:20,000 to 1:2, preferably 1:1,000 to 1:10, with B being applied at a rate of 100 to 2,000 g/ha, preferably 200 to 1,000 g/ha. Combination 19 is generally used in a ratio of A to B of 1:10,000 to 1:2, preferably 1:300 to 1:5. with B being applied at a rate of 100 to 1,000 g/ha, preferably 100 to 300 g/ha. Combination 20 is generally used in a ratio of A to B14 of 1:2,000 to 5:1, preferably 1:60 to 2:1, and ratio of A to B15 of 1:1,000 to 50:1, preferably 1:20 to 20:1, with B14 being applied at a rate of 10 to 200 g/ha, preferably 10 to 60 g/ha, and B15 being applied at a rate of 1 to 100 g/ha, preferably 1 to 20 g/ha. Combination 21 is generally used in a ratio of A to B of 1:10,000 to 1:2, preferably 1:300 to 1:5, with B being applied at a rate of 100 to 1,000 g/ha, preferably 100 to 300 g/ha. Combination 22 is generally used in a ratio of A to B of 1:1,000 to 50:1, preferably 1:20 to 20:1, with B being applied at a rate of 1 to 100 g/ha, preferably 1 to 20 g/ha. Combination 23 is generally used in a ratio of A to B of 1:20,000 to 1:2, preferably 1:1,000 to 1:10, with B being applied at a rate of 100 to 2,000 g/ha, preferably 200 to 1,000 g/ha. Combination 24 is generally used in a ratio of A to B of 1:20,000 to 1:2, preferably 1:1,000 to 1:10, with B being applied at a rate of 100 to 2,000 g/ha, preferably 200 to 1,000 g/ha. Combination 25 is generally used in a ratio of A to B of 1:1,000 to 5:1, preferably 1:50 to 2:1, with B being applied at a rate of 10 to 100 g/ha, preferably 10 to 50 g/ha. Combination 26 is generally used in a ratio of A to B of 1:10,000 to 5:1, preferably 1:100to 2:1, with B being applied at a rate of 10 to 1,000 g/ha, preferably 10 to 100 g/ha. Combination 27 is generally used in a ratio of A to B of 1:20,000 to 1:2, preferably 1:1,000 to 1:10, with B being applied at a rate of 100 to 2,000 g/ha, preferably 200 to 1,000 g/ha. Combination 28 is generally used in a ratio of A to B of 1:20,000 to 1:20, preferably 1:1,500 to 1:50, with B being applied at a rate of 1,000 to 2,000 g/ha, preferably 1,000 to 1,500 g/ha. Combination 29 is generally used in a ratio of A to B of 1:20,000 to 1:2, preferably 1:1,000 to 1:10, with B being applied a rate of 100 to 2,000 g/ha, preferably 200 to 1,000 g/ha.

e) 6S-cis)1-chloro-N-[2-chloro-4-fluoro-5-(6-fluorotetrahydro-1,3-dioxo-1H-pyrrolo[1,2-c]imidazol-2(3H)-yl)phenyl]-N-[(chloromethyl)sulfonyl]acetamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | tribenuron-methyl | 2 | thifensulfuron-methyl |
| 3 | thifensulfuron-methyl (B1) in combination with tribenuron-methyl (B2) | 4 | metsulfuron-methyl |
| 5 | thifensulfuron-methyl (B3) in combination with metsulfuron-methyl (B4) | 6 | thifensulfuron-methyl (B5) in combination with tribenuron-methyl (B6) in combination with metsulfuron-methyl (B7) |
| 7 | chlorsulfuron | 8 | chlorsulfuron (B8) in combination with metsulfuron-methyl (B9) |
| 9 | triasulfuron | 10 | 2,4-D |
| 11 | dicamba | 12 | bromoxynil |
| 13 | MCPA | 14 | bromoxynil (B10) in combination with MCPA (B11) |
| 15 | fluroxypyr | 16 | clopyralid |
| 17 | fenoxaprop (B12) in combination with fenchlorazole (B13) | 18 | diclofop |
| 19 | tralkoxydim | 20 | clodinafop (B14) in combination with cloquintocet-mexyl (B15) |
| 21 | imazamethabenz | 22 | sulfosulfuron |
| 23 | difenzoquat | 24 | propanil |
| 25 | prosulfuron | 26 | metribuzin |
| 27 | glyphosate | 28 | triallate |
| 29 | trifluralin | | |

Combination 1 is generally used in a ratio of A to B of 1:500 to 50:1, preferably 1:10 to 20:1, with B being applied at a rate of 1 to 50 g/ha, preferably 1 to 10 g/ha. Combination 2 is generally used in a ratio of A to B of 1:1,000 to 50:1, preferably 1:20 to 20:1, with B being applied at a rate of 1 to 100 g/ha, preferably 1 to 20 g/ha. Combination 3 is generally used in a ratio of A to B1 of 1:500 to 50:1, preferably 1:20 to 20:1, and ratio of A to B2 of 1:500 to 50:1, preferably 1:10 to 20:1. with B1 being applied at a rate of 1 to 50 g/ha, preferably 1 to 20 g/ha, and B2 being applied at a rate of 1 to 50 g/ha, preferably 1 to 10 g/ha. Combination 4 is generally used in a ratio of A to B of 1:200 to 50:1, preferably 1:20 to 20:1, with B being applied at a rate of 1 to 20 g/ha, preferably 1 to 10 g/ha. Combination 5 is generally used in a ratio of A to B3 of 1:1,000 to 50:1, preferably 1:20 to 20:1, and ratio of A to B4 of 1:200 to 50:1, preferably 1:20 to 20:1, with B3 being applied at a rate of 1 to 100 g/ha, preferably 1 to 20 g/ha, and B4 being applied at a rate of 1 to 20 g/ha, preferably 1 to 10 g/ha Combination 6 is generally used in a ratio of A to B5 of 1:1,000 to 50:1, preferably 1:20 to 20:1, and ratio of A to B6 of 1:500 to 50:1, preferably 1:10 to 20:1, and ratio of A to B7 of 1:200 to 50:1, preferably 1:20 to 20:1, with B5 being applied at a rate of 1 to 100 g/ha, preferably 1 to 20 g/ha, and B6 being applied at a rate of 1 to 50 g/ha, preferably 1 to 10 g/ha, and B7 being applied at a rate of 1 to 20 g/ha, preferably 1 to 10 g/ha. Combination 7 is generally used in a ratio of A to B of 1:500 to 50:1, preferably 1:10 to 20:1, with B being applied at a rate of 1 to 50 g/ha, preferably 1 to 10 g/ha. Combination 8 is generally used in a ratio of A to B8 of 1:500 to 50:1, preferably 1:10 to 20:1, and ratio of A to B9 of 1:200 to 50:1, preferably 1:20 to 20:1, with B5 being applied at a rate of 1 to 50 g/ha, preferably 1 to 10 g/ha, and B9 being applied at a rate of 1 to 20 g/ha, preferably 1 to 10 g/ha. Combination 9 is generally used in a ratio of A to B of 1:1,000 to 50:1, preferably 1:20 to 20:1, with B being applied at a rate of 1 to 100 g/ha, preferably 1 to 20 g/ha. Combination 10 is generally used in a ratio of A to B of 1:30,000 to 1:2, preferably 1:500 to 1:5, with B being applied at a rate of 100 to 3,000 g/ha, preferably 100 to 500 g/ha. Combination 11 is generally used in a ratio of A to B of 1:5,000 to 5:1, preferably 1:100 to 2:1, with B being applied at a rate of 10 to 500 g/ha, preferably 10 to 100 g/ha. Combination 12 is generally used in a ratio of A to B of 1:20,000 to 1:2, preferably 1:500 to 1:5, with B being applied at a rate of 100 to 2,000 g/ha, preferably 100 to 500 g/ha. Combination 13 is generally used in a ratio of A to B of 1:20,000 to 1:2, preferably 1:500 to 1:5, with B being applied at a rate of 100 to 2,000 g/ha, preferably 100 to 500 g/ha. Combination 14 is generally used in a ratio of A to B10 of 1:20,000 to 1:2, preferably 1:500 to 1:5, and ratio of A to B11 of 1:20,000 to 1:2, preferably 1:500 to 1:5, with B10 being applied at a rate of 100 to 2,000 g/ha, preferably 100 to 500 g/ha, and B11 being applied at a rate of 100 to 2,000 g/ha, preferably 100 to 500 g/ha. Combination 15 is generally used in a ratio of A to B of 1:5,000 to 5:1, preferably 1:100 to 2:1, with B being applied at a rate of 10 to 500 g/ha, preferably 10 to 100 g/ha. Combination 16 is generally used in a ratio of A to B of 1:5,000 to 5:1, preferably 1:100 to 2:1, with B being applied at a rate of 10 to 500 g/ha, preferably 10 to 100 g/ha. Combination 17 is generally used in a ratio of A to B12 of 1:5,000 to 5:1, preferably 1:500 to 1:5, and ratio of A to B1 3 of 1:1,000 to 50:1, preferably 1:20 to 20:1, with B12 being applied at a rate of 10 to 500 g/ha, preferably 10 to 100 g/ha, and B13 being applied at a rate of 1 to 100 g/ha, preferably 1 to 20 g/ha. Combination 18 is generally used in a ratio of A to B of 1:20,000 to 1:2, preferably 1:1,000 to 1:10, with B being applied at a rate of 100 to 2,000 g/ha, preferably 200 to 1,000 g/ha. Combination 19 is generally used in a ratio of A to B of 1:10,000 to 1:2, preferably 1:300 to 1:5. with B being applied at a rate of 100 to 1,000 g/ha, preferably 100 to 300 g/ha. Combination 20 is generally used in a ratio of A to B14 of 1:2,000 to 5:1, preferably 1:60 to 2:1, and ratio of A to B15 of 1:1,000 to 50:1, preferably 1:20 to 20:1, with B14 being applied at a rate of 10 to 200 g/ha, preferably 10 to 60 g/ha, and B15 being applied at a rate of 1 to 100 g/ha, preferably 1 to 20 g/ha. Combination 21 is generally used in a ratio of A to B of 1:10,000 to 1:2, preferably 1:300 to 1:5, with B being applied at a rate of 100 to 1,000 g/ha, preferably 100 to 300 g/ha. Combination 22 is generally used in a ratio of A to B of 1:1,000 to 50:1, preferably 1:20 to 20:1, with B being applied at a rate of 1 to 100 g/ha, preferably 1 to 20 g/ha. Combination 23 is generally used in a ratio of A to B of 1:20,000 to 1:2, preferably 1:1,000 to 1:10, with B being applied at a rate of 100 to 2,000 g/ha, preferably 200 to 1,000 g/ha. Combination 24 is generally used in a ratio of A to B of 1:20,000 to 1:2, preferably 1:1,000 to 1:10, with B being applied at a rate of 100 to 2,000 g/ha, preferably 200 to 1,000 g/ha. Combination 25 is generally used in a ratio of A to B of 1:1,000 to 5:1, preferably 1:50 to 2:1, with B being applied at a rate of 10 to 100 g/ha, preferably 10 to 50 g/ha. Combination 26 is generally used in a ratio of A to B of 1:10,000 to 5:1, preferably 1:100 to 2:1, with B being applied at a rate of 10 to 1,000 g/ha, preferably 10 to 100 g/ha. Combination 27 is generally used in a ratio of A to B of 1:20,000 to 1:2, preferably 1:1,000 to 1:10, with B being applied at a rate of 100 to 2,000 g/ha, preferably 200 to 1,000 g/ha. Combination 28 is generally used in a ratio of A to B of 1:20,000 to 1:20, preferably 1:1,500 to 1:50, with B being applied at a rate of 1,000 to 2,000 g/ha, preferably 1,000 to 1,500 g/ha. Combination 29 is generally used in a ratio of A to B of 1:20,000 to 1:2, preferably 1:1,000 to 1:10, with B being applied a rate of 100 to 2,000 g/ha, preferably 200 to 1,000 g/ha.

f) 6S-cis)-1-chloro-N-[2-chloro-4-fluoro-5-(6-fluorotetrahydro-1,3-dioxo-1H-pyrrolo[1,2-c]imidazol-2(3H)-yl)phenyl]-N-[(chloromethyl)sulfonyl]acetamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | tribenuron-methyl | 2 | thifensulfuron-methyl |
| 3 | thifensulfuron-methyl (B1) in combination with tribenuron-methyl (B2) | 4 | metsulfuron-methyl |
| 5 | thifensulfuron-methyl (B3) in combination with metsulfuron-methyl (B4) | 6 | thifensulfuron-methyl (B5) in combination with tribenuron-methyl (B6) in combination with metsulfuron-methyl (B7) |
| 7 | chlorsulfuron | 8 | chlorsulfuron (B8) in combination with metsulfuron-methyl (B9) |
| 9 | triasulfuron | 10 | 2,4-D |
| 11 | dicamba | 12 | bromoxynil |
| 13 | MCPA | 14 | bromoxynil (B10) in combination with MCPA (B11) |
| 15 | fluroxypyr | 16 | clopyralid |
| 17 | fenoxaprop (B12) in combination with fenchlorazole (B13) | 18 | diclofop |
| 19 | tralkoxydim | 20 | clodinafop (B14) in combination with cloquintocet-mexyl (B15) |
| 21 | imazamethabenz | 22 | sulfosulfuron |
| 23 | difenzoquat | 24 | propanil |
| 25 | prosulfuron | 26 | metribuzin |

-continued

| Combination Number | Mixture partner B | Combination Number | Mixture partner B |
|---|---|---|---|
| 27 | glyphosate | 28 | triallate |
| 29 | trifluralin | | |

Combination 1 is generally used in a ratio of A to B of 1:500 to 50:1, preferably 1:10 to 20:1, with B being applied at a rate of 1 to 50 g/ha, preferably 1 to 10 g/ha. Combination 2 is generally used in a ratio of A to B of 1:1,000 to 50:1, preferably 1:20 to 20:1, with B being applied at a rate of 1 to 100 g/ha, preferably 1 to 20 g/ha. Combination 3 is generally used in a ratio of A to B1 of 1:500 to 50:1, preferably 1:20 to 20:1, and ratio of A to B2 of 1:500 to 50:1, preferably 1:10 to 20:1. with B1 being applied at a rate of 1 to 50 g/ha, preferably 1 to 20 g/ha, and B2 being applied at a rate of 1 to 50 g/ha, preferably 1 to 10 g/ha. Combination 4 is generally used in a ratio of A to B of 1:200 to 50:1, preferably 1:20 to 20:1, with B being applied at a rate of 1 to 20 g/ha, preferably 1 to 10 g/ha. Combination 5 is generally used in a ratio of A to B3 of 1:1,000 to 50:1, preferably 1:20 to 20:1, and ratio of A to B4 of 1:200 to 50:1, preferably 1:20 to 20:1, with B3 being applied at a rate of 1 to 100 g/ha, preferably 1 to 20 g/ha, and B4 being applied at a rate of 1 to 20 g/ha, preferably 1 to 10 g/ha Combination 6 is generally used in a ratio of A to B5 of 1:1,000 to 50:1, preferably 1:20 to 20:1, and ratio of A to B6 of 1:500 to 50:1, preferably 1:10 to 20:1, and ratio of A to B7 of 1:200 to 50:1, preferably 1:20 to 20:1, with B5 being applied at a rate of 1 to 100 g/ha, preferably 1 to 20 g/ha, and B6 being applied at a rate of 1 to 50 g/ha, preferably 1 to 10 g/ha, and B7 being applied at a rate of 1 to 20 g/ha, preferably 1 to 10 g/ha. Combination 7 is generally used in a ratio of A to B of 1:500 to 50:1, preferably 1:10 to 20:1, with B being applied at a rate of 1 to 50 g/ha, preferably 1 to 10 g/ha. Combination 8 is generally used in a ratio of A to B8 of 1:500 to 50:1, preferably 1:10 to 20:1, and ratio of A to B9 of 1:200 to 50:1, preferably 1:20 to 20:1, with B5 being applied at a rate of 1 to 50 g/ha, preferably 1 to 10 g/ha, and B9 being applied at a rate of 1 to 20 g/ha, preferably 1 to 10 g/ha. Combination 9 is generally used in a ratio of A to B of 1:1,000 to 50:1, preferably 1:20 to 20:1, with B being applied at a rate of 1 to 100 g/ha, preferably 1 to 20 g/ha. Combination 10 is generally used in a ratio of A to B of 1:30,000 to 1:2, preferably 1:500 to 1:5, with B being applied at a rate of 100 to 3,000 g/ha, preferably 100 to 500 g/ha. Combination 11 is generally used in a ratio of A to B of 1:5,000 to 5:1, preferably 1:100 to 2:1, with B being applied at a rate of 10 to 500 g/ha, preferably 10 to 100 g/ha. Combination 12 is generally used in a ratio of A to B of 1:20,000 to 1:2, preferably 1:500 to 1:5, with B being applied at a rate of 100 to 2,000 g/ha, preferably 100 to 500 g/ha. Combination 13 is generally used in a ratio of A to B of 1:20,000 to 1:2, preferably 1:500 to 1:5, with B being applied at a rate of 100 to 2,000 g/ha, preferably 100 to 500 g/ha. Combination 14 is generally used in a ratio of A to B10 of 1:20,000 to 1:2, preferably 1:500 to 1:5, and ratio of A to B11 of 1:20,000 to 1:2, preferably 1:500 to 1:5, with B10 being applied at a rate of 100 to 2,000 g/ha, preferably 100 to 500 g/ha, and B11 being applied at a rate of 100 to 2,000 g/ha, preferably 100 to 500 g/ha. Combination 15 is generally used in a ratio of A to B of 1:5,000 to 5:1, preferably 1:100 to 2:1, with B being applied at a rate of 10 to 500 g/ha, preferably 10 to 100 g/ha. Combination 16 is generally used in a ratio of A to B of 1:5,000 to 5:1, preferably 1:100 to 2:1, with B being applied at a rate of 10 to 500 g/ha, preferably 10 to 100 g/ha. Combination 17 is generally used in a ratio of A to B12 of 1:5,000 to 5:1, preferably 1:500 to 1:5, and ratio of A to B1 3 of 1:1,000 to 50:1, preferably 1:20 to 20:1, with B12 being applied at a rate of 10 to 500 g/ha, preferably 10 to 100 g/ha, and B13 being applied at a rate of 1 to 100 g/ha, preferably 1 to 20 g/ha. Combination 18 is generally used in a ratio of A to B of 1:20,000 to 1:2, preferably 1:1,000 to 1:10, with B being applied at a rate of 100 to 2,000 g/ha, preferably 200 to 1,000 g/ha. Combination 19 is generally used in a ratio of A to B of 1:10,000 to 1:2, preferably 1:300 to 1:5. with B being applied at a rate of 100 to 1,000 g/ha, preferably 100 to 300 g/ha. Combination 20 is generally used in a ratio of A to B14 of 1:2,000 to 5:1, preferably 1:60 to 2:1, and ratio of A to B15 of 1:1,000 to 50:1, preferably 1:20 to 20:1, with B14 being applied at a rate of 10 to 200 g/ha, preferably 10 to 60 g/ha, and B15 being applied at a rate of 1 to 100 g/ha, preferably 1 to 20 g/ha. Combination 21 is generally used in a ratio of A to B of 1:10,000 to 1:2, preferably 1:300 to 1:5, with B being applied at a rate of 100 to 1,000 g/ha, preferably 100 to 300 g/ha. Combination 22 is generally used in a ratio of A to B of 1:1,000 to 50:1, preferably 1:20 to 20:1, with B being applied at a rate of 1 to 100 g/ha, preferably 1 to 20 g/ha. Combination 23 is generally used in a ratio of A to B of 1:20,000 to 1:2, preferably 1:1,000 to 1:10, with B being applied at a rate of 100 to 2,000 g/ha, preferably 200 to 1,000 g/ha. Combination 24 is generally used in a ratio of A to B of 1:20,000 to 1:2, preferably 1:1,000 to 1:10, with B being applied at a rate of 100 to 2,000 g/ha, preferably 200 to 1,000 g/ha. Combination 25 is generally used in a ratio of A to B of 1:1,000 to 5:1, preferably 1:50 to 2:1, with B being applied at a rate of 10 to 100 g/ha, preferably 10 to 50 g/ha. Combination 26 is generally used in a ratio of A to B of 1:10,000 to 5:1, preferably 1:100 to 2:1, with B being applied at a rate of 10 to 1,000 g/ha, preferably 10 to 100 g/ha. Combination 27 is generally used in a ratio of A to B of 1:20,000 to 1:2, preferably 1:1,000 to 1:10, with B being applied at a rate of 100 to 2,000 g/ha, preferably 200 to 1,000 g/ha. Combination 28 is generally used in a ratio of A to B of 1:20,000 to 1:20, preferably 1:1,500 to 1:50, with B being applied at a rate of 1,000 to 2,000 g/ha, preferably 1,000 to 1,500 g/ha. Combination 29 is generally used in a ratio of A to B of 1:20,000 to 1:2, preferably 1:1,000 to 1:10, with B being applied a rate of 100 to 2,000 g/ha, preferably 200 to 1,000 g/ha.

g) 6S-cis)-1-chloro-N-[2-chloro-4-fluoro-5-(6-fluorotetrahydro-1,3-dioxo-1H-pyrrolo[1,2-c]imidazol-2(3H)-yl)phenyl]-N-[(chloromethyl)sulfonyl]acetamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | tribenuron-methyl | 2 | thifensulfuron-methyl |
| 3 | thifensulfuron-methyl (B1) in combination with tribenuron-methyl (B2) | 4 | metsulfuron-methyl |
| 5 | thifensulfuron-methyl (B3) in combination with metsulfuron-methyl (B4) | 6 | thifensulfuron-methyl (B5) in combination with tribenuron-methyl (B6) in combination with metsulfuron-methyl (B7) |
| 7 | chlorsulfuron | 8 | chlorsulfuron (B8) in combination with metsulfuron-methyl (B9) |
| 9 | triasulfuron | 10 | 2,4-D |
| 11 | dicamba | 12 | bromoxynil |
| 13 | MCPA | 14 | bromoxynil (B10) in combination with MCPA (B11) |
| 15 | fluroxypyr | 16 | clopyralid |
| 17 | fenoxaprop (B12) in combination with fenchlorazole (B13) | 18 | diclofop |
| 19 | tralkoxydim | 20 | clodinafop (B14) in combination with cloquintocet-mexyl (B15) |
| 21 | imazamethabenz | 22 | sulfosulfuron |
| 23 | difenzoquat | 24 | propanil |
| 25 | prosulfuron | 26 | metribuzin |
| 27 | glyphosate | 28 | triallate |
| 29 | trifluralin | | |

Combination 1 is generally used in a ratio of A to B of 1:500 to 50:1, preferably 1:10 to 20:1, with B being applied at a rate of 1 to 50 g/ha, preferably 1 to 10 g/ha. Combination 2 is generally used in a ratio of A to B of 1:1,000 to 50:1, preferably 1:20 to 20:1, with B being applied at a rate of 1 to 100 g/ha, preferably 1 to 20 g/ha. Combination 3 is generally used in a ratio of A to B1 of 1:500 to 50:1, preferably 1:20 to 20:1, and ratio of A to B2 of 1:500 to 50:1, preferably 1:10 to 20:1. with B1 being applied at a rate of 1 to 50 g/ha, preferably 1 to 20 g/ha, and B2 being applied at a rate of 1 to 50 g/ha, preferably 1 to 10 g/ha. Combination 4 is generally used in a ratio of A to B of 1:200 to 50:1, preferably 1:20 to 20:1, with B being applied at a rate of 1 to 20 g/ha, preferably 1 to 10 g/ha. Combination 5 is generally used in a ratio of A to B3 of 1:1,000 to 50:1, preferably 1:20 to 20:1, and ratio of A to B4 of 1:200 to 50:1, preferably 1:20 to 20:1, with B3 being applied at a rate of 1 to 100 g/ha, preferably 1 to 20 g/ha, and B4 being applied at a rate of 1 to 20 g/ha, preferably 1 to 10 g/ha Combination 6 is generally used in a ratio of A to B5 of 1:1,000 to 50:1, preferably 1:20 to 20:1, and ratio of A to B6 of 1:500 to 50:1, preferably 1:10 to 20:1, and ratio of A to B7 of 1:200 to 50:1, preferably 1:20 to 20:1, with B5 being applied at a rate of 1 to 100 g/ha, preferably 1 to 20 g/ha, and B6 being applied at a rate of 1 to 50 g/ha, preferably 1 to 10 g/ha, and B7 being applied at a rate of 1 to 20 g/ha, preferably 1 to 10 g/ha. Combination 7 is generally used in a ratio of A to B of 1:500 to 50:1, preferably 1:10 to 20:1, with B being applied at a rate of 1 to 50 g/ha, preferably 1 to 10 g/ha. Combination 8 is generally used in a ratio of A to B8 of 1:500 to 50:1, preferably 1:10 to 20:1, and ratio of A to B9 of 1:200 to 50:1, preferably 1:20 to 20:1, with B5 being applied at a rate of 1 to 50 g/ha, preferably 1 to 10 g/ha, and B9 being applied at a rate of 1 to 20 g/ha, preferably 1 to 10 g/ha. Combination 9 is generally used in a ratio of A to B of 1:1,000 to 50:1, preferably 1:20 to 20:1, with B being applied at a rate of 1 to 100 g/ha, preferably 1 to 20 g/ha. Combination 10 is generally used in a ratio of A to B of 1:30,000 to 1:2, preferably 1:500 to 1:5, with B being applied at a rate of 100 to 3,000 g/ha, preferably 100 to 500 g/ha. Combination 11 is generally used in a ratio of A to B of 1:5,000 to 5:1, preferably 1:100 to 2:1, with B being applied at a rate of 10 to 500 g/ha, preferably 10 to 100 g/ha. Combination 12 is generally used in a ratio of A to B of 1:20,000 to 1:2, preferably 1:500 to 1:5, with B being applied at a rate of 100 to 2,000 g/ha, preferably 100 to 500 g/ha. Combination 13 is generally used in a ratio of A to B of 1:20,000 to 1:2, preferably 1:500 to 1:5, with B being applied at a rate of 100 to 2,000 g/ha, preferably 100 to 500 g/ha. Combination 14 is generally used in a ratio of A to B10 of 1:20,000 to 1:2, preferably 1:500 to 1:5, and ratio of A to B11 of 1:20,000 to 1:2, preferably 1:500 to 1:5, with B10 being applied at a rate of 100 to 2,000 g/ha, preferably 100 to 500 g/ha, and B11 being applied at a rate of 100 to 2,000 g/ha, preferably 100 to 500 g/ha. Combination 15 is generally used in a ratio of A to B of 1:5,000 to 5:1, preferably 1:100 to 2:1, with B being applied at a rate of 10 to 500 g/ha, preferably 10 to 100 g/ha. Combination 16 is generally used in a ratio of A to B of 1:5,000 to 5:1, preferably 1:100 to 2:1, with B being applied at a rate of 10 to 500 g/ha, preferably 10 to 100 g/ha. Combination 17 is generally used in a ratio of A to B12 of 1:5,000 to 5:1, preferably 1:500 to 1:5, and ratio of A to B1 3 of 1:1,000 to 50:1, preferably 1:20 to 20:1, with B12 being applied at a rate of 10 to 500 g/ha, preferably 10 to 100 g/ha, and B13 being applied at a rate of 1 to 100 g/ha, preferably 1 to 20 g/ha. Combination 18 is generally used in a ratio of A to B of 1:20,000 to 1:2, preferably 1:1,000 to 1:10, with B being applied at a rate of 100 to 2,000 g/ha, preferably 200 to 1,000 g/ha. Combination 19 is generally used in a ratio of A to B of 1:10,000 to 1:2, preferably 1:300 to 1:5. with B being applied at a rate of 100 to 1,000 g/ha, preferably 100 to 300 g/ha. Combination 20 is generally used in a ratio of A to B14 of 1:2,000 to 5:1, preferably 1:60 to 2:1, and ratio of A to B15 of 1:1,000 to 50:1, preferably 1:20 to 20:1, with B14 being applied at a rate of 10 to 200 g/ha, preferably 10 to 60 g/ha, and B15 being applied at a rate of 1 to 100 g/ha, preferably 1 to 20 g/ha. Combination 21 is generally used in a ratio of A to B of 1:10,000 to 1:2, preferably 1:300 to 1:5, with B being applied at a rate of 100 to 1,000 g/ha, preferably 100 to 300 g/ha. Combination 22 is generally used in a ratio of A to B of 1:1,000 to 50:1, preferably 1:20 to 20:1, with B being applied at a rate of 1 to 100 g/ha, preferably 1 to 20 g/ha. Combination 23 is generally used in a ratio of A to B of 1:20,000 to 1:2, preferably 1:1,000 to 1:10, with B being applied at a rate of 100 to 2,000 g/ha, preferably 200 to 1,000 g/ha. Combination 24 is generally used in a ratio of A to B of 1:20,000 to 1:2, preferably 1:1,000 to 1:10, with B being applied at a rate of 100 to 2,000 g/ha, preferably 200 to 1,000 g/ha. Combination 25 is generally used in a ratio of A to B of 1:1,000 to 5:1, preferably 1:50 to 2:1, with B being applied at a rate of 10 to 100 g/ha, preferably 10 to 50 g/ha. Combination 26 is generally used in a ratio of A to B of 1:10,000 to 5:1, preferably 1:100 to 2:1, with B being applied at a rate of 10 to 1,000 g/ha, preferably 10 to 100 g/ha. Combination 27 is generally used in a ratio of A to B of 1:20,000 to 1:2, preferably 1:1,000 to 1:10, with B being applied at a rate of 100 to 2,000 g/ha, preferably 200 to 1,000 g/ha. Combination 28 is generally used in a ratio of A to B of 1:20,000 to 1:20, preferably 1:1,500 to 1:50, with B being applied at a rate of 1,000 to 2,000 g/ha, preferably 1,000 to 1,500 g/ha. Combination 29 is generally used in a ratio of A to B of 1:20,000 to 1:2, preferably 1:1,000 to 1:10, with B being applied a rate of 100 to 2,000 g/ha, preferably 200 to 1,000 g/ha.

h) 6S-cis)-1-chloro-N-[2-chloro-4-fluoro-5-(6-fluorotetrahydro-1,3-dioxo-1H-pyrrolo[1,2-c]imidazol-2(3H)-yl)phenyl]-N-[(chloromethyl)sulfonyl]acetamide (mixture partner A, generally applied at a rate of 0.1 to 50 g/ha, preferably applied at a rate of 1 to 20 g/ha) in combination with:

| Combination Number | Mixture partner B | Combination Number | Mixture partner B |
|---|---|---|---|
| 1 | tribenuron-methyl | 2 | thifensulfuron-methyl |
| 3 | thifensulfuron-methyl (B1) in combination with tribenuron-methyl (B2) | 4 | metsulfuron-methyl |
| 5 | thifensulfuron-methyl (B3) in combination with metsulfuron-methyl (B4) | 6 | thifensulfuron-methyl (B5) in combination with tribenuron-methyl (B6) in combination with metsulfuron-methyl (B7) |
| 7 | chlorsulfuron | 8 | chlorsulfuron (B8) in combination with metsulfuron-methyl (B9) |
| 9 | triasulfuron | 10 | 2,4-D |
| 11 | dicamba | 12 | bromoxynil |
| 13 | MCPA | 14 | bromoxynil (B10) in combination with MCPA (B11) |
| 15 | fluroxypyr | 16 | clopyralid |
| 17 | fenoxaprop (B12) in combination with fenchlorazole (B13) | 18 | diclofop |
| 19 | tralkoxydim | 20 | clodinafop (B14) in combination with cloquintocet-mexyl (B15) |
| 21 | imazamethabenz | 22 | sulfosulfuron |
| 23 | difenzoquat | 24 | propanil |
| 25 | prosulfuron | 26 | metribuzin |
| 27 | glyphosate | 28 | triallate |
| 29 | trifluralin | | |

Combination 1 is generally used in a ratio of A to B of 1:500 to 50:1, preferably 1:10 to 20:1, with B being applied at a rate of 1 to 50 g/ha, preferably 1 to 10 g/ha. Combination 2 is generally used in a ratio of A to B of 1:1,000 to 50:1, preferably 1:20 to 20:1, with B being applied at a rate of 1 to 100 g/ha, preferably 1 to 20 g/ha. Combination 3 is generally used in a ratio of A to B1 of 1:500 to 50:1, preferably 1:20 to 20:1, and ratio of A to B2 of 1:500 to 50:1, preferably 1:10 to 20:1. with B1 being applied at a rate of 1 to 50 g/ha, preferably 1 to 20 g/ha, and B2 being applied at a rate of 1 to 50 g/ha, preferably 1 to 10 g/ha. Combination 4 is generally used in a ratio of A to B of 1:200 to 50:1, preferably 1:20 to 20:1, with B being applied at a rate of 1 to 20 g/ha, preferably 1 to 10 g/ha. Combination 5 is generally used in a ratio of A to B3 of 1:1,000 to 50:1, preferably 1:20 to 20:1, and ratio of A to B4 of 1:200 to 50:1, preferably 1:20 to 20:1, with B3 being applied at a rate of 1 to 100 g/ha, preferably 1 to 20 g/ha, and B4 being applied at a rate of 1 to 20 g/ha, preferably 1 to 10 g/ha Combination 6 is generally used in a ratio of A to B5 of 1:1,000 to 50:1, preferably 1:20 to 20:1, and ratio of A to B6 of 1:500 to 50:1, preferably 1:10 to 20:1, and ratio of A to B7 of 1:200 to 50:1, preferably 1:20 to 20:1, with B5 being applied at a rate of 1 to 100 g/ha, preferably 1 to 20 g/ha, and B6 being applied at a rate of 1 to 50 g/ha, preferably 1 to 10 g/ha, and B7 being applied at a rate of 1 to 20 g/ha, preferably 1 to 10 g/ha. Combination 7 is generally used in a ratio of A to B of 1:500 to 50:1, preferably 1:10 to 20:1, with B being applied at a rate of 1 to 50 g/ha, preferably 1 to 10 g/ha. Combination 8 is generally used in a ratio of A to B8 of 1:500 to 50:1, preferably 1:10 to 20:1, and ratio of A to B9 of 1:200 to 50:1, preferably 1:20 to 20:1, with B5 being applied at a rate of 1 to 50 g/ha, preferably 1 to 10 g/ha, and B9 being applied at a rate of 1 to 20 g/ha, preferably 1 to 10 g/ha. Combination 9 is generally used in a ratio of A to B of 1:1,000 to 50:1, preferably 1:20 to 20:1, with B being applied at a rate of 1 to 100 g/ha, preferably 1 to 20 g/ha. Combination 10 is generally used in a ratio of A to B of 1:30,000 to 1:2, preferably 1:500 to 1:5, with B being applied at a rate of 100 to 3,000 g/ha, preferably 100 to 500 g/ha. Combination 11 is generally used in a ratio of A to B of 1:5,000 to 5:1, preferably 1:100 to 2:1, with B being applied at a rate of 10 to 500 g/ha, preferably 10 to 100 g/ha. Combination 12 is generally used in a ratio of A to B of 1:20,000 to 1:2, preferably 1:500 to 1:5, with B being applied at a rate of 100 to 2,000 g/ha, preferably 100 to 500 g/ha. Combination 13 is generally used in a ratio of A to B of 1:20,000 to 1:2, preferably 1:500 to 1:5, with B being applied at a rate of 100 to 2,000 g/ha, preferably 100 to 500 g/ha. Combination 14 is generally used in a ratio of A to B10 of 1:20,000 to 1:2, preferably 1:500 to 1:5, and ratio of A to B11 of 1:20,000 to 1:2, preferably 1:500 to 1:5, with B10 being applied at a rate of 100 to 2,000 g/ha, preferably 100 to 500 g/ha, and B11 being applied at a rate of 100 to 2,000 g/ha, preferably 100 to 500 g/ha. Combination 15 is generally used in a ratio of A to B of 1:5,000 to 5:1, preferably 1:100 to 2:1, with B being applied at a rate of 10 to 500 g/ha, preferably 10 to 100 g/ha. Combination 16 is generally used in a ratio of A to B of 1:5,000 to 5:1, preferably 1:100 to 2:1, with B being applied at a rate of 10 to 500 g/ha, preferably 10 to 100 g/ha. Combination 17 is generally used in a ratio of A to B12 of 1:5,000 to 5:1, preferably 1:500 to 1:5, and ratio of A to B1 3 of 1:1,000 to 50:1, preferably 1:20 to 20:1, with B12 being applied at a rate of 10 to 500 g/ha, preferably 10 to 100 g/ha, and B13 being applied at a rate of 1 to 100 g/ha, preferably 1 to 20 g/ha. Combination 18 is generally used in a ratio of A to B of 1:20,000 to 1:2, preferably 1:1,000 to 1:10, with B being applied at a rate of 100 to 2,000 g/ha, preferably 200 to 1,000 g/ha. Combination 19 is generally used in a ratio of A to B of 1:10,000 to 1:2, preferably 1:300 to 1:5. with B being applied at a rate of 100 to 1,000 g/ha, preferably 100 to 300 g/ha. Combination 20 is generally used in a ratio of A to B14 of 1:2,000 to 5:1, preferably 1:60 to 2:1, and ratio of A to B15 of 1:1,000 to 50:1, preferably 1:20 to 20:1, with B14 being applied at a rate of 10 to 200 g/ha, preferably 10 to 60 g/ha, and B15 being applied at a rate of 1 to 100 g/ha, preferably 1 to 20 g/ha. Combination 21 is generally used in a ratio of A to B of 1:10,000 to 1:2, preferably 1:300 to 1:5, with B being applied at a rate of 100 to 1,000 g/ha, preferably 100 to 300 g/ha. Combination 22 is generally used in a ratio of A to B of 1:1,000 to 50:1, preferably 1:20 to 20:1, with B being applied at a rate of 1 to 100 g/ha, preferably 1 to 20 g/ha. Combination 23 is generally used in a ratio of A to B of 1:20,000 to 1:2, preferably 1:1,000 to 1:10, with B being applied at a rate of 100 to 2,000 g/ha, preferably 200 to 1,000 g/ha. Combination 24 is generally used in a ratio of A to B of 1:20,000 to 1:2, preferably 1:1,000 to 1:10, with B being applied at a rate of 100 to 2,000 g/ha, preferably 200 to 1,000 g/ha. Combination 25 is generally used in a ratio of A to B of 1:1,000 to 5:1, preferably 1:50 to 2:1, with B being applied at a rate of 10 to 100 g/ha, preferably 10 to 50 g/ha. Combination 26 is generally used in a ratio of A to B of 1:10,000 to 5:1, preferably 1: I00 to 2:1, with B being applied at a rate of 10 to 1,000 g/ha, preferably 10 to 100 g/ha. Combination 27 is generally used in a ratio of A to B of 1:20,000 to 1:2, preferably 1:1,000 to 1:10, with B being applied at a rate of 100 to 2,000 g/ha, preferably 200 to 1,000 g/ha. Combination 28 is generally used in a ratio of A to B of 1:20,000 to 1:20, preferably 1:1,500 to 1:50, with B being applied at a rate of 1,000 to 2,000 g/ha, preferably 1,000 to 1,500 g/ha. Combination 29 is generally used in a ratio of A to B of 1:20,000 to 1:2, preferably 1:1,000 to 1:10, with B being applied a rate of 100 to 2,000 g/ha, preferably 200 to 1,000 g/ha.

A herbicidally effective amount of the compounds of this invention is determined by a number of factors. These factors include: formulation selected, method of application, amount and type of vegetation present, growing conditions, etc. In general, a herbicidally effective amount of compounds of this invention is 0.001 to 20 kg/ha with a preferred range of 0.001 to 1.0 kg/ha. One skilled in the art can easily determine the herbicidally effective amount necessary for the desired level of weed control.

The following Tests demonstrate the control efficacy of the compounds of this invention against specific weeds. The weed control afforded by the compounds is not limited, however, to these species. See Index Tables A–K for compound descriptions. The following abbreviation is used in the Index Tables which follow: CN=cyano. The abbreviation "dec" indicates that the compound appeared to decompose on melting. The abbreviation "Ex." stands for "Example" and is followed by a number indicatin- in which example the compound is prepared.

Index Table A

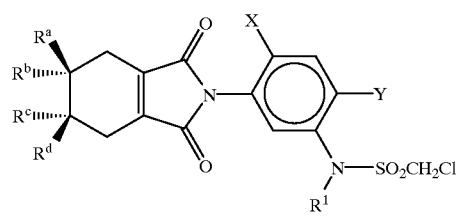

| Cmpd | $R^a$ | $R^b$ | $R^c$ | $R^d$ | X | Y | $R^1$ | m.p. (° C.) |
|---|---|---|---|---|---|---|---|---|
| 1 | H | H | H | H | F | Cl | H | 136–139 |
| 2 | H | H | H | H | F | Cl | $CH_2C\equiv CH$ | * |
| 3 | H | H | H | H | F | Cl | $SO_2CH_2Cl$ | 213–216 |
| 4 | H | H | H | H | F | Cl | $C(O)CH(CH_3)_2$ | 185 |
| 5 | H | H | H | H | F | Cl | $C(O)CH_3$ | 200 |
| 6 | Br | OH | H | H | F | Cl | H | 169–172 |
| 7 | Br | Br | H | H | F | Cl | H | 218–219 |
| 8 | Br | F | H | H | F | Cl | H | 202–205 |

Index Table B

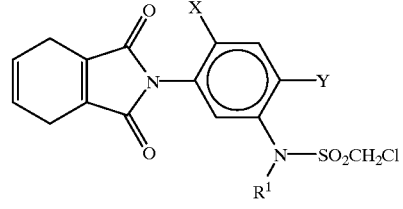

| Cmpd | X | Y | $R^1$ | m.p. (° C.) |
|---|---|---|---|---|
| 9 | F | Cl | H | 173–176 |
| 10 | F | Cl | $SO_2CH_2Cl$ | 210–214 |

Index Table C

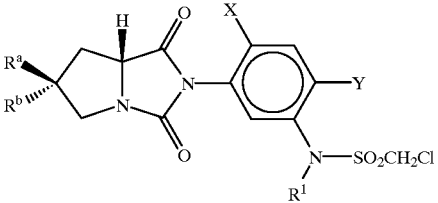

| Cmpd | X | Y | R¹ | R² | m.p. (° C.) |
|---|---|---|---|---|---|
| 11 | Cl | Cl | H | $CH_2Cl$ | 209–211 |
| 12 | Cl | Cl | $C(O)CH_3$ | $CH_2Cl$ | 89–90 |
| 13 | Cl | Cl | $CH_2C{\equiv}CH$ | $CH_2Cl$ | 78–80 |
| 14 | Cl | Cl | $C(O)CH_2Cl$ | $CH_2Cl$ | 204–206 |
| 15 | Cl | Cl | H | $CF_3$ | * |
| 16 | Cl | Cl | $SO_2CH_2CH_2CH_2Cl$ | $CH_2CH_2CH_2Cl$ | 148–152 |
| 17 | Cl | Cl | H | $CH_2CH_2CH_2Cl$ | 192–194 |
| 18 | Cl | Cl | H | $CH{=}CH_2$ | * |
| 19 | Cl | Cl | $SO_2CH{=}CH_2$ | $CH{=}CH_2$ | * |

Index Table D

| Cmpd | Rᵃ | Rᵇ | X | Y | R¹ | m.p. (° C.) |
|---|---|---|---|---|---|---|
| 20 | F | H | F | Cl | $CH_2C{\equiv}CH$ | * |
| 21 (Ex. 1) | F | H | F | Cl | H | 169–170* |
| 22 | F | H | F | Cl | $SO_2CH_2Cl$ | 200 (dec) |
| 23 (Ex. 3) | F | H | F | Cl | $C(O)CH_3$ | 198–200 |
| 24 | Cl | H | F | Cl | $SO_2CH_2Cl$ | * |
| 25 (Ex. 2) | Cl | H | F | Cl | H | 169–170 |
| 26 | H | H | F | Cl | H | 72–74 |
| 27 | H | H | F | Cl | $SO_2CH_2Cl$ | 216–217 |
| 28 | H | H | Cl | Cl | H | 216 |
| 29 | H | H | Cl | Cl | $SO_2CH_2Cl$ | 196 |
| 30 | F | H | Cl | Cl | H | 205 |
| 31 (Ex. 8) | Cl | H | F | Cl | $CH_3$ | 120–124 |
| 32 (Ex. 4) | Cl | H | F | Cl | $C(O)CH_3$ | 180–181 |
| 33 (Ex. 9) | Cl | H | F | Cl | $CH_2CH_3$ | 152–154 |
| 34 (Ex. 6) | F | H | F | Cl | $CH_2CH_3$ | 198–200 |
| 35 (Ex. 5) | F | H | F | Cl | $CH_3$ | 90–92 |

Index Table D -continued

| Cmpd | Rᵃ | Rᵇ | X | Y | R¹ | m.p. (° C.) |
|---|---|---|---|---|---|---|
| 36 (Ex. 10) | Cl | H | F | Cl | $CO_2CH_3$ | 117–124 |
| 37 (Ex.7) | F | H | F | Cl | $CO_2CH_3$ | 108–115 |
| 38 | H | OH | F | Cl | H | 207–209 |

Index Table E

| Cmpd | M⊕ | Rᵃ | m.p. (° C.) |
|---|---|---|---|
| 39 | Na | F | 198–200 |
| 40 | $HN(CH_2CH_3)_3$ | F | 73–76 |
| 41 | K | F | 194–196 |
| 42 | Li | F | 208–217 |
| 43 | $HN(CH_2CH_2OH)_3$ | F | 55–57 |
| 44 | $H_2N(CH(CH_3)_2)_2$ | F | 76–80 |
| 45 | ($H_2N$-cyclohexyl)₂ | Cl | 160–162 |

Index Table F

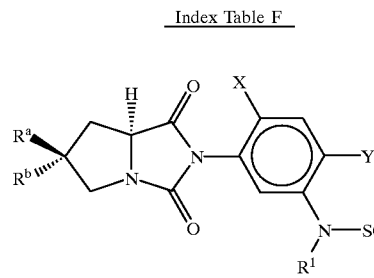

| Cmpd | Rᵃ | Rᵇ | X | Y | R¹ | m.p. (° C.) |
|---|---|---|---|---|---|---|
| 46 | F | H | F | Cl | H | 170–172 |
| 47 | F | H | F | Cl | $SO_2CH_2Cl$ | 110–111 |
| 48 | Cl | H | F | Cl | H | * |

-continued

Index Table F

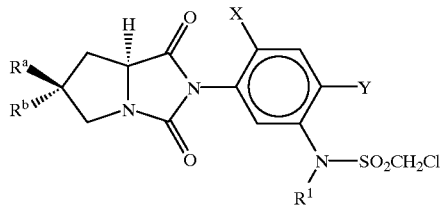

| Cmpd | $R^a$ | $R^b$ | X | Y | $R^1$ | m.p. (° C.) |
|---|---|---|---|---|---|---|
| 49 | H | F | F | Cl | H | 78 (dec) |
| 50 | H | F | F | Cl | $SO_2CH_2Cl$ | 101–203 (dec) |
| 51 | Cl | H | F | Cl | $SO_2CH_2Cl$ | 140–142 |

Index Table G

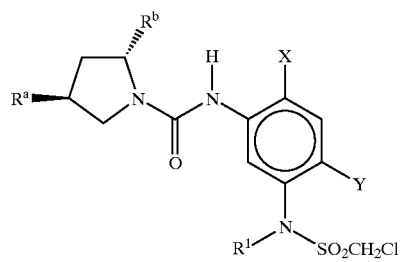

| Cmpd | $R^a$ | $R^b$ | X | Y | $R^1$ | m.p. (° C.) |
|---|---|---|---|---|---|---|
| 52 | F | $CO_2CH_3$ | F | Cl | H | 77 (dec) |
| 53 | Cl | $CO_2CH_3$ | F | Cl | H | 145–150 |
| 54 | F | $CO_2CH_2CH_3$ | F | Cl | H | * |
| 55 | Cl | $CO_2CH_2CH_3$ | F | Cl | H | * |
| 56 | F | C(O)—N⟩pyrrolidine | F | Cl | H | 129–130 |
| 57 | F | C(O)—N⟩morpholine | F | Cl | H | 108–110 |
| 58 | Cl | $CO_2CH_3$ | F | Cl | $C(O)CH_3$ | 115–118 |
| 59 | F | $CO_2CH_3$ | F | Cl | $CH_3$ | 76–77 (dec) |
| 60 | F | $C(O)NHOCH_3$ | F | Cl | H | 160 (dec) |
| 61 | Cl | $C(O)NHOCH_3$ | F | Cl | H | 66–70 |
| 62 | Cl | C(O)—N⟩morpholine | F | Cl | H | 68–72 |

Index Table G

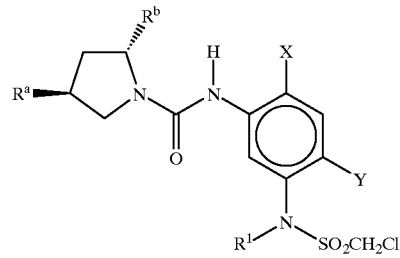

| Cmpd | $R^a$ | $R^b$ | X | Y | $R^1$ | m.p. (° C.) |
|---|---|---|---|---|---|---|
| 63 | Cl | C(O)—N⟩pyrrolidine | F | Cl | H | 80 |

Index Table H

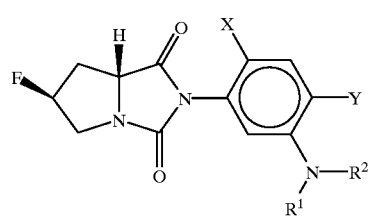

| Cmpd | X | Y | $R^1$ | $R^2$ | m.p. (° C.) |
|---|---|---|---|---|---|
| 64 | F | Cl | H | $SO_2CH_2Br$ | 60–65 (dec) |
| 65 | F | Cl | H | $SO_2CH_2SO_2CH_3$ | 90–95 (dec) |

Index Table I

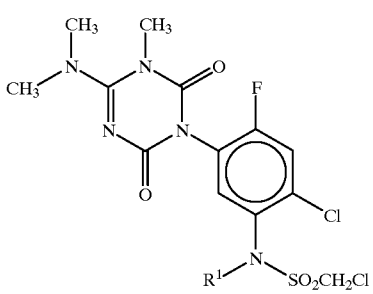

| Cmpd | $R^1$ | m.p. (° C.) |
|---|---|---|
| 66 (Ex. 13) | H | 234–237 |
| 67 | $SO_2CH_2Cl$ | 144–147 |

Index Table J

| Cmpd | Structure | m.p. (° C.) |
|---|---|---|
| 68 | 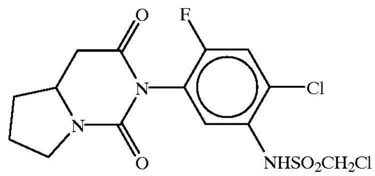 | 98–100 |
| 69 | 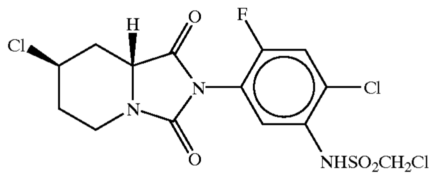 | * |
| 70 (Ex. 12) | 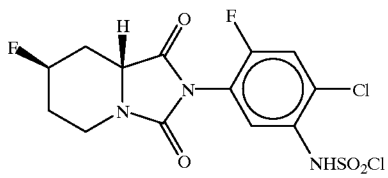 | 60–64 |
| 71 | 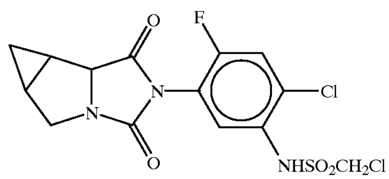 | 89–94 |
| 72 | 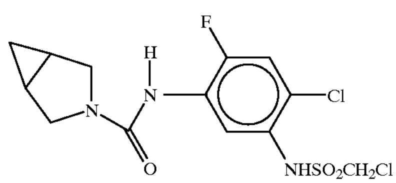 | 94–98 |
| 73 (Ex. 11) | 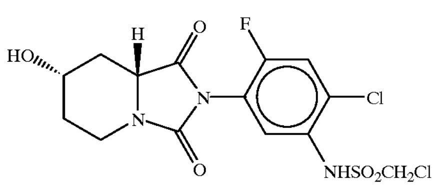 | * |

*See Index Table K for $^1$H NMR data.

INDEX TABLE K

| Cmpd No. | $^1$H NMR Data (CDCl$_3$ solution unless indicated otherwise)[a] |
|---|---|
| 2 | δ 7.56(d, 1H), 7.40(d, 1H), 4.68(m, 1H), 4.66(s, 2H), 4.29(m, 1H), 2.44 (m, 4H), 1.84(m, 4H). |
| 15 | δ 7.83(s, 1H), 7.54(s, 1H), 6.96(s, 1H), 3.70(m, 2H), 3.31(quintet, 1H), 2.78(t, 2H), 2.01(m, 4H), 1.39(d, 6H). |

INDEX TABLE K-continued

| Cmpd No. | $^1$H NMR Data (CDCl$_3$ solution unless indicated otherwise)[a] |
|---|---|
| 18 | (DMSO-d$_6$) δ 10.05(s, 1H), 7.92(d, 1H), 7.47(d, 1H), 6.96(ddd, 1H), 6.05 (dd, 2H), 3.57(t, 2H), 2.68(t, 2H), 1.78–1.99(m, 4H). |
| 19 | (DMSO-d$_6$) δ 8.14(s, 1H), 7.68(s, 1H), 7.25(dd, 2H), 6.45(dd, 2H), 6.35 (dd, 2H), 3.56(m, 2H), 2.69(t, 2H), 1.89(m, 2H), 1.81(m, 2H). |
| 20 | δ 7.9–7.7(m, 2H), 5.7–5.5(m, 1H), 4.7(dd, 1H), 4.5(s, 2H), 3.4(s, 1H), 3.5–3.3(m, 2H), 2.5–2.1(m, 2H). |
| 21 | δ 7.62(d, 1H), 7.34(d, 1H), 7.26(br s, 1H), 5.5(m, 1H), 4.60(dd, 1H), 4.52(s, 2H), 4.12(m, 1H), 3.62(dd, 1H), 2.64(m, 1H), 2.06(m, 1H). |
| 24 | δ 7.78(d, 1H), 7.42(d, 1H), 5.31(dd, 2H), 4.90(dd, 2H), 4.79(m, 2H), 4.22(dd, 1H), 3.62(dd, 1H), 2.60(m, 1H), 2.32(m, 1H). |
| 48 | δ 7.70(d, 1H), 7.38(d, 1H), 7.08(br s, 1H), 4.56(br s, 3H), 4.42(dd, 1H), 4.30(d, 1H), 3.52(dd, 1H), 2.36(m, 2H). |
| 54 | δ 8.42(d, 1H), 7.18(d, 1H), 6.96(br s, 1H), 5.32(m, 1H), 4.58(s, 2H), 4.22 (q, 2H), 4.06(m, 3H), 2.46(m, 2H). |
| 55 | δ 8.42(d, 1H), 7.21(d, 1H), 7.0(br s, 1H), 4.64(t, 1H), 4.60(s, 2H), 4.58 (m, 1H), 4.24(q, 2H), 3.92(m, 2H), 2.60(m, 2H). |
| 69 | δ 7.65(d, 1H), 7.35(d, 1H), 4.70(br s, 1H), 4.55(s, 3H), 4.10–4.00(m, 1H), 3.5–3.35(m, 1H), 2.6–2.5(br d, 1H), 2.1(m, 3H). |
| 73 | (DMSO-d$_6$) δ 10.1(br s, 1H), 7.75(m, 1H), 7.4(dd, 1H), 5.1(m, 1H), 4.9 (s, 2H), 4.1–3.9(m, 3H), 3.75(m, 1H), 2.95(m, 1H), 2.05(m, 1H), 1.9(br d, 1H), 1.2(m, 1H). |

[a] $^1$H NMR data are in ppm downfield from tetramethylsilane. Couplings are designated by(s)-singlet,(d)-doublet,(t)-triplet,(q)-quartet,(m)-multiplet,(dd)-doublet of doublets,(ddd)-doublet of doublet of doublets,(dt)-doublet of triplets,(br s)-broad singlet.

BIOLOGICAL EXAMPLES OF THE INVENTION

TEST A

Seeds of barnyardgrass (*Echinochloa crus-galli*), cocklebur (*Xanthium strumarium*), crabgrass (Digitaria spp.), downy brome (*Bromus tectorum*), giant foxtail (*Setaria faberii*), morningglory (Ipomoea spp.), sorghum (*Sorghum bicolor*), velvetleaf (*Abutilon theophrasti*), and wild oat (*Avena fatua*) were planted into a sandy loam soil and treated preemergence by soil drench (PDRN), with test chemicals formulated in a non-phytotoxic solvent mixture which included a surfactant. At the same time, these crop and weed species were also treated postemergence sprayed to runoff (STRO), with test chemicals formulated in the same manner.

Plants ranged in height from two to eighteen cm and were in the two to three leaf stage for the postemergence treatment. Treated plants and untreated controls were maintained in a greenhouse for approximately eleven days, after which all treated plants were compared to untreated controls and visually evaluated for injury. Plant response ratings, summarized in Table A, are based on a 0 to 10 scale where 0 is no effect and 10 is complete control. A dash (–) response means no test results.

TABLE A

| | COMPOUND | | | |
|---|---|---|---|---|
| | 45 | 50 | 59 | 68 |
| Rate 2000 g/ha PDRN | | | | |
| Barnyardgrass | 10 | 10 | 10 | 9 |
| Cocklebur | 10 | 10 | 10 | 10 |
| Crabgrass | 10 | 9 | 10 | 8 |
| Downy brome | 7 | 8 | 9 | 2 |
| Giant foxtail | 10 | 10 | 10 | 9 |
| Morningglory | 10 | 10 | 10 | 10 |
| Sorghum | 5 | 3 | 10 | 0 |
| Velvetleaf | 10 | 10 | 10 | 10 |
| Wild oats | 9 | 9 | 9 | 9 |

TABLE A-continued

| | COMPOUND | | | |
|---|---|---|---|---|
| | 45 | 50 | 59 | 68 |
| Rate 1000 g/ha STRO | | | | |
| Barnyardgrass | 10 | 10 | 10 | 8 |
| Cocklebur | 10 | 10 | 10 | 10 |
| Crabgrass | 6 | 8 | 9 | 3 |
| Downy brome | 4 | 10 | 8 | 3 |
| Giant foxtail | 7 | 7 | 9 | 3 |
| Morningglory | 10 | 10 | 10 | 10 |
| Sorghum | 6 | 5 | 7 | 3 |
| Velvetleaf | 10 | 10 | 10 | 10 |
| Wild oats | 5 | 9 | 5 | 2 |

TEST B

Seeds of barley (*Hordeum vulgare*), barnyardgrass (*Echinochloa crus-galli*), bedstraw (*Galium aparine*), blackgrass (*Alopecurus myosuroides*), chickweed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberii*), lambsquarters (*Chenopodium album*), morningglory (*Ipomoea hederacea*), rape (*Brassica napus*), rice (*Oryza sativa*), sorghum (*Sorghum bicolor*), soybean (*Glycine max*), sugar beet (*Beta vulgaris*), velvetleaf (*Abutilon theophrasti*), wheat (*Triticum aestivum*), wild buckwheat (*Polygonum convolvulus*), wild oat (*Avena fatua*) and purple nutsedge (*Cyperus rotundus*) tubers were planted and treated preemergence with test chemicals formulated in a non-phytotoxic solvent mixture which included a surfactant.

At the same time, these crop and weed species were also treated with postemergence applications of test chemicals formulated in the same manner. Plants ranged in height from two to eighteen cm (one to four leaf stage) for postemergence treatments. Treated plants and controls were maintained in a greenhouse for twelve to sixteen days, after which all species were compared to controls and visually evaluated. Plant response ratings, summarized in Table B, are based on a scale of 0 to 10 where 0 is no effect and 10 is complete control. A dash (–) response means no test result.

TABLE B

POSTEMERGENCE

Rate 1000 g/ha

| COMPOUND | 1 | 6 | 7 | 8 |
|---|---|---|---|---|
| Barley | 3 | 3 | 3 | 3 |
| Barnyardgrass | 9 | 4 | 9 | 9 |
| Bedstraw | 7 | 10 | — | 9 |
| Blackgrass | 3 | 4 | 4 | 3 |
| Chickweed | 6 | 9 | 10 | 10 |
| Cocklebur | 10 | 7 | 10 | 9 |
| Corn | 7 | 2 | 2 | 1 |
| Cotton | 10 | 10 | 10 | 10 |
| Crabgrass | 2 | 1 | 2 | 2 |
| Downy brome | 2 | 3 | 5 | 4 |
| Giant foxtail | 3 | 3 | 2 | 3 |
| Lambsquarter | 8 | 7 | 9 | 10 |
| Morningglory | 10 | 5 | 10 | 10 |
| Nutsedge | 3 | 2 | 4 | 4 |
| Rape | 10 | 8 | 10 | 10 |
| Rice | 5 | 3 | 4 | 4 |
| Sorghum | 3 | 2 | 2 | 2 |
| Soybean | 9 | 3 | 5 | 4 |
| Sugar beet | 10 | 7 | 10 | 10 |
| Velvetleaf | 10 | 10 | 10 | 10 |
| Wheat | 3 | 3 | 2 | 3 |
| Wild buckwheat | 10 | 5 | 10 | 10 |
| Wild oat | 2 | 3 | 4 | 4 |

Rate 400 g/ha

| COMPOUND | 9 | 10 | 38 | 65 | 66 | 67 | 70 |
|---|---|---|---|---|---|---|---|
| Barley | 3 | 3 | 0 | 3 | 1 | 1 | 4 |
| Barnyardgrass | 10 | 3 | 1 | 8 | 4 | 2 | 10 |
| Bedstraw | 10 | 10 | 2 | 9 | 7 | 3 | 10 |
| Blackgrass | 4 | 3 | 1 | 3 | 5 | 2 | 8 |
| Chickweed | 9 | 10 | 3 | 5 | 3 | 2 | 10 |
| Cocklebur | 10 | 10 | 1 | 10 | 3 | 2 | 10 |
| Corn | 5 | 1 | 1 | 5 | 1 | 1 | 7 |
| Cotton | 10 | 10 | 4 | 10 | 9 | 4 | 10 |
| Crabgrass | 3 | 3 | 1 | 2 | 2 | 1 | 4 |
| Downy brome | 4 | 3 | 1 | 3 | 4 | 2 | 4 |
| Giant foxtail | 3 | 2 | 2 | 3 | 6 | 2 | 6 |
| Lambsquarter | 9 | 9 | 3 | 10 | 4 | 4 | 10 |
| Morningglory | 10 | 10 | 3 | 3 | 2 | 3 | 10 |
| Nutsedge | 3 | 2 | 0 | 1 | 2 | 1 | 4 |
| Rape | 10 | 10 | 3 | 10 | 7 | 0 | 10 |
| Rice | 3 | 3 | 0 | 2 | 8 | 4 | 8 |
| Sorghum | 2 | 2 | 1 | 2 | 2 | 2 | 7 |
| Soybean | 4 | 6 | 1 | 6 | 4 | 4 | 7 |
| Sugar beet | 10 | 10 | 1 | 10 | 6 | 2 | 10 |
| Velvetleaf | 10 | 10 | 1 | 9 | 9 | 2 | 10 |
| Wheat | 3 | 2 | 0 | 2 | 3 | 4 | 8 |
| Wild buckwheat | 10 | 10 | 2 | 10 | 2 | 1 | 10 |
| Wild oat | 4 | 3 | 1 | 3 | 3 | 1 | 3 |

Rate 200 g/ha

| COMPOUND | 1 | 2 | 11 | 15 | 16 | 17 | 18 | 19 | 20 | 21 | 31 | 32 | 33 | 34 | 35 | 36 |
|---|---|---|---|---|---|---|---|---|---|---|---|---|---|---|---|---|
| Barley | 2 | 5 | 3 | 4 | 4 | 4 | 1 | 0 | 4 | 3 | 3 | 3 | 4 | 5 | 4 | 3 |
| Barnyardgrass | 7 | 6 | 9 | 4 | 2 | 6 | 3 | 4 | 9 | 9 | 3 | 10 | 5 | 10 | 5 | 7 |
| Bedstraw | 6 | 9 | 8 | 7 | 5 | 7 | 6 | 3 | 9 | 6 | 10 | 10 | 9 | 10 | 10 | 10 |
| Blackgrass | 3 | 3 | 2 | 3 | 5 | 5 | 5 | 0 | 5 | 10 | 3 | 3 | 4 | 6 | 5 | 4 |
| Chickweed | 7 | 8 | 8 | 2 | 3 | 7 | 1 | 0 | 9 | 10 | 9 | 10 | 10 | 10 | 10 | 10 |
| Cocklebur | 3 | 3 | 2 | 10 | 3 | 7 | 0 | 6 | 10 | 10 | 10 | 10 | 10 | 10 | 10 | 10 |
| Corn | 10 | 10 | 10 | 3 | 3 | 9 | 7 | 2 | 3 | 9 | 2 | 7 | 3 | 8 | 3 | 3 |
| Cotton | 10 | 10 | 9 | 3 | 10 | 10 | 2 | 8 | 10 | 10 | 10 | 10 | 10 | 10 | 10 | 10 |
| Crabgrass | 2 | 6 | 7 | 3 | 6 | 4 | 3 | 5 | 3 | 3 | 4 | 4 | 3 | 8 | 3 | 3 |
| Downy brome | 2 | 3 | 3 | 3 | 4 | 4 | 3 | 0 | 7 | 7 | 3 | 2 | 3 | 5 | 3 | 3 |
| Giant foxtail | 2 | 6 | 2 | 5 | 6 | 6 | 0 | 5 | 4 | 8 | 3 | 3 | 4 | 6 | 4 | 3 |
| Lambsquarter | 7 | 10 | 7 | 9 | 10 | 9 | 6 | 7 | 10 | 10 | 10 | 10 | 10 | 10 | 10 | 10 |
| Morningglory | 7 | 10 | 10 | 10 | 10 | 10 | 7 | 6 | 10 | 10 | 10 | 10 | 10 | 10 | 10 | 10 |
| Nutsedge | 2 | 2 | 2 | 5 | 2 | 6 | 3 | 0 | 1 | 3 | 3 | 2 | 3 | 4 | 5 | 5 |
| Rape | 2 | 10 | 10 | 10 | 9 | 9 | 3 | 3 | 10 | 10 | 10 | 10 | 10 | 10 | 10 | 10 |
| Rice | 5 | 6 | 5 | 3 | 5 | 5 | 4 | 4 | 6 | 6 | 6 | 3 | 4 | 9 | 6 | 4 |
| Sorghum | 4 | 4 | 4 | 4 | 3 | 3 | 3 | 4 | 5 | 3 | 3 | — | — | 8 | 7 | 2 |
| Soybean | 3 | 9 | 4 | 3 | 8 | 8 | 4 | 4 | 9 | 9 | 9 | 6 | 10 | 10 | 9 | 10 |
| Sugar beet | 8 | 10 | 5 | 6 | 8 | 10 | 2 | 3 | 6 | 6 | 10 | 10 | 10 | 10 | 10 | 10 |
| Velvetleaf | 9 | 10 | 10 | 9 | 9 | 10 | 4 | 4 | 10 | 10 | 10 | 10 | 10 | 10 | 10 | 10 |
| Wheat | 3 | 3 | 4 | 3 | 6 | 6 | 6 | 7 | 3 | 5 | 4 | 3 | 4 | 4 | 4 | 3 |
| Wild buckwheat | 1 | 10 | 10 | 3 | 10 | 10 | 0 | 2 | 10 | 10 | 10 | 10 | 10 | 10 | 10 | 10 |
| Wild oat | 0 | 2 | 3 | 2 | 3 | 3 | 0 | 0 | 4 | 3 | 3 | 3 | 3 | 4 | 3 | 4 |

Rate 200 g/ha

| COMPOUND | 37 | 47 | 53 | 58 | 61 | 62 | 63 | 65 | 66 | 67 | 70 | 1 | 8 |
|---|---|---|---|---|---|---|---|---|---|---|---|---|---|
| Barley | 5 | 4 | 3 | 3 | 3 | 1 | 1 | 3 | 3 | 0 | 3 | 2 | 3 |
| Barnyardgrass | 10 | 4 | 10 | 9 | 9 | 2 | 1 | 8 | 4 | 1 | 4 | 7 | 7 |
| Bedstraw | 10 | 3 | 9 | 10 | — | 2 | — | 9 | 7 | — | — | 6 | 9 |
| Blackgrass | 7 | 3 | 3 | 2 | 2 | 4 | 1 | 3 | 5 | 3 | 3 | 3 | 3 |
| Chickweed | 10 | 5 | 10 | 10 | 4 | 4 | 1 | 3 | 3 | 3 | 10 | 7 | 3 |
| Cocklebur | 10 | 10 | 10 | 10 | 10 | 3 | 2 | 10 | 3 | 5 | 10 | 9 | — |
| Corn | 6 | 3 | 4 | 2 | 6 | 6 | 5 | 10 | 1 | 5 | 10 | 10 | 9 |
| Cotton | 10 | 10 | 10 | 10 | 10 | 9 | 6 | 5 | 7 | 1 | 10 | 10 | 1 |
| Crabgrass | 2 | 2 | 1 | 2 | 4 | 2 | 1 | 2 | 2 | 0 | 1 | 2 | 1 |
| Downy brome | 5 | 3 | 3 | 2 | 10 | 1 | 7 | 10 | — | 5 | 1 | 3 | 1 |
| Giant foxtail | 8 | 2 | 2 | 2 | 4 | 1 | 0 | 3 | 2 | 0 | 3 | 2 | 1 |
| Lambsquarter | 10 | 9 | 10 | 10 | 9 | 6 | 2 | 10 | 5 | 5 | 9 | 9 | 10 |
| Morningglory | 10 | 10 | 10 | 10 | 10 | 6 | 4 | 2 | 5 | 5 | 2 | 10 | 1 |
| Nutsedge | 3 | — | 1 | 1 | 8 | 2 | 0 | 2 | 0 | 0 | 1 | 1 | 1 |
| Rape | 10 | 10 | 10 | 10 | 10 | 10 | 2 | 10 | 5 | 2 | 10 | 10 | 10 |

TABLE B-continued

| | 5 | 11 | 12 | 13 | 14 | 15 | 16 | 17 | 18 | 19 | 20 | 21 | 23 | 24 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|
| Rice | 6 | 2 | 2 | 2 | 3 | 4 | 3 | 2 | 4 | 1 | 4 | 4 | 0 | 2 | 2 | 2 | 3 | 3 | 3 | 5 | 3 | 3 | 1 | 8 | 4 | 4 | 3 |
| Sorghum | 2 | 2 | 2 | 2 | 2 | 3 | 2 | 1 | 7 | 2 | 6 | 2 | 0 | 2 | 2 | 5 | 3 | 4 | 6 | 2 | 2 | 1 | 6 | 4 | 4 | 4 |
| Soybean | 10 | 3 | 2 | 3 | 3 | 3 | 3 | 2 | 4 | 3 | 9 | 3 | 0 | 3 | 2 | 8 | 4 | 4 | 10 | 8 | 2 | 3 | 7 | 10 | 5 | 8 |
| Sugar beet | 10 | 10 | 10 | 10 | 10 | 7 | 10 | 3 | 10 | 10 | 10 | 10 | 1 | 10 | 10 | 10 | 10 | 10 | 10 | 10 | 6 | 6 | 10 | 10 | 10 | 10 |
| Velvetleaf | 10 | 10 | 10 | 10 | 10 | 8 | 10 | 6 | 10 | 7 | 10 | 10 | 0 | 10 | 10 | 10 | 10 | 10 | 10 | 10 | 4 | 4 | 2 | 10 | 8 | 9 | 10 |
| Wheat | 5 | 3 | 2 | 2 | 2 | 1 | 2 | 2 | 7 | 2 | 3 | 3 | 1 | 2 | 4 | 5 | 3 | 5 | 3 | 4 | 4 | 1 | 2 | 6 | 3 | 2 | 10 |
| Wild buckwheat | 10 | 10 | 10 | 10 | 10 | 10 | 10 | 4 | 10 | 9 | 7 | 6 | 0 | 10 | 9 | 10 | 10 | 10 | 10 | 10 | 1 | 3 | 10 | 10 | 9 | 10 |
| Wild oat | 7 | 2 | 3 | 3 | 3 | 2 | 3 | 2 | 2 | 2 | 2 | 3 | 2 | 3 | 2 | 3 | 3 | 3 | 3 | 3 | 2 | 1 | 2 | 2 | 2 | 2 |

Rate 50 g/ha

| COMPOUND | 5 | 11 | 12 | 13 | 14 | 15 | 16 | 17 | 18 | 19 | 20 | 21 | 23 | 24 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|
| Barley | 2 | 2 | 2 | 3 | 2 | 2 | 3 | 3 | 0 | 0 | 4 | 2 | 3 | 3 | 2 | 2 | 0 | 1 | 3 | 3 | 3 | 4 | 5 | 4 | 3 | 4 |
| Barnyardgrass | 7 | 8 | 6 | 2 | 9 | 2 | 2 | 4 | 2 | 2 | 6 | 10 | 6 | 4 | 5 | 5 | 2 | 2 | 9 | 1 | 6 | 3 | 4 | 4 | 2 | 10 |
| Bedstraw | 6 | 7 | 9 | 9 | 5 | 3 | 3 | 7 | 4 | 2 | 9 | 9 | 9 | 9 | 9 | 8 | 4 | 3 | 9 | 9 | 9 | 9 | 10 | 10 | 9 | 10 |
| Blackgrass | 1 | 2 | 2 | 4 | 4 | 2 | 3 | 3 | 0 | 2 | 4 | 3 | 4 | 1 | 9 | 8 | 4 | 1 | 3 | 7 | 2 | 3 | 4 | 3 | 3 | 3 |
| Chickweed | 3 | 3 | 3 | 4 | 4 | 2 | 3 | 7 | 0 | 0 | 10 | 10 | 10 | 2 | 9 | 6 | 1 | 1 | 10 | 7 | 10 | 8 | 10 | 9 | 10 | 10 |
| Cocklebur | 8 | 10 | 7 | 5 | 3 | 1 | 4 | 7 | 1 | 3 | 10 | 10 | 10 | 10 | 7 | 6 | 4 | 1 | 10 | 9 | 10 | 10 | 10 | 8 | 10 | 10 |
| Corn | 3 | 4 | 4 | 1 | 4 | 6 | 2 | 2 | 2 | 4 | 1 | 5 | 1 | 1 | 8 | 6 | 4 | 3 | 1 | 1 | 2 | 1 | 4 | 2 | 1 | 6 |
| Cotton | 10 | 10 | 10 | 10 | 6 | 10 | 10 | 10 | 2 | 0 | 10 | 10 | 10 | 10 | 2 | 10 | 9 | 9 | 10 | 9 | 10 | 10 | 10 | 10 | 10 | 10 |
| Crabgrass | 2 | 4 | 2 | 3 | 4 | 6 | 2 | 4 | 2 | 4 | 2 | 7 | 3 | 1 | 2 | 2 | 1 | 1 | 2 | 2 | 2 | 3 | 4 | 4 | 3 | 2 |
| Downy brome | 2 | 1 | 2 | 4 | 2 | 2 | 3 | 5 | 0 | 0 | 10 | 3 | 5 | 1 | 4 | 3 | 1 | 1 | 3 | 2 | 2 | 3 | 4 | 2 | 3 | 4 |
| Giant foxtail | 3 | 3 | 1 | 3 | 9 | 2 | 4 | 4 | 3 | 3 | 3 | 7 | 3 | 2 | 2 | 3 | 1 | 1 | 2 | 2 | 2 | 3 | 4 | 2 | 2 | 3 |
| Lambsquarter | 7 | 10 | 9 | 10 | 9 | 3 | 9 | 8 | 3 | 4 | 10 | 10 | 10 | 10 | 9 | 9 | 7 | 7 | 10 | 9 | 10 | 9 | 10 | 10 | 10 | 10 |
| Morningglory | 10 | 9 | 9 | 10 | 9 | 9 | 9 | 9 | 2 | 4 | 10 | 10 | 10 | 10 | 10 | 10 | 7 | 10 | 10 | 10 | 10 | 10 | 10 | 10 | 10 | 10 |
| Nutsedge | 2 | 1 | 1 | 0 | 0 | 0 | 4 | 1 | 0 | 0 | — | 1 | 1 | 1 | 2 | 1 | 1 | 2 | 1 | 3 | 1 | 2 | 2 | 2 | 1 | 2 |
| Rape | 6 | 9 | 9 | 8 | 9 | 6 | 7 | 6 | 3 | 3 | 10 | 10 | 10 | 10 | 3 | 2 | 1 | 1 | 9 | 9 | 10 | 10 | 10 | 10 | 10 | 10 |
| Rice | 4 | 3 | 3 | 4 | 0 | 3 | 4 | 5 | 3 | 3 | 2 | 4 | 3 | 2 | 4 | 1 | 1 | 1 | 2 | 9 | 3 | 3 | 6 | 5 | 2 | 2 |
| Sorghum | 4 | 3 | 3 | 4 | 3 | 2 | 4 | 2 | 2 | 3 | 3 | 3 | 3 | 3 | 3 | 1 | 1 | 1 | 2 | 3 | 3 | 4 | 3 | 3 | 2 | 3 |
| Soybean | 7 | 1 | 2 | 7 | 4 | 2 | 8 | 6 | 1 | 2 | 8 | 10 | 2 | 5 | 2 | 2 | 2 | 1 | 5 | 8 | 10 | 9 | 9 | 3 | 8 | 10 |
| Sugar beet | 10 | 10 | 10 | 10 | 9 | 3 | 10 | 10 | 3 | 2 | 10 | 10 | 10 | 10 | 10 | 10 | 2 | 2 | 10 | 10 | 10 | 10 | 10 | 10 | 10 | 10 |
| Velvetleaf | 10 | 10 | 10 | 10 | 10 | 10 | 9 | 3 | 1 | 1 | 10 | 10 | 10 | 10 | 8 | 7 | 5 | 3 | 10 | 8 | 10 | 10 | 10 | 8 | 10 | 10 |
| Wheat | 2 | 2 | 3 | 2 | 3 | 2 | 3 | 3 | 0 | 1 | 4 | 3 | 2 | 2 | 3 | 3 | 0 | 1 | 3 | 4 | 3 | 4 | 4 | 3 | 2 | 4 |
| Wild buckwheat | 10 | 10 | 7 | 9 | 9 | 9 | 8 | 10 | 2 | 1 | 10 | 10 | 10 | 10 | 8 | 7 | 3 | 2 | 10 | 10 | 10 | 10 | 10 | 10 | 10 | 10 |
| Wild oat | 1 | 1 | 2 | 3 | 1 | 2 | 3 | 3 | 0 | 0 | 2 | 2 | 3 | 2 | 2 | 3 | 1 | 0 | 3 | 2 | 3 | 2 | 3 | 2 | 3 | 4 |

Rate 50 g/ha

| COMPOUND | 45 | 47 | 48 | 50 | 51 | 53 | 58 | 59 | 61 | 62 | 63 | 65 | 68 |
|---|---|---|---|---|---|---|---|---|---|---|---|---|---|
| Barley | 2 | 1 | 2 | 1 | 0 | 3 | 3 | 1 | 1 | 1 | 0 | 2 | 2 |
| Barnyardgrass | 10 | 2 | 3 | 5 | 4 | 2 | 3 | 3 | 5 | 0 | 3 | 3 | 3 |
| Bedstraw | 10 | 2 | 8 | 4 | 4 | 4 | 10 | 6 | — | 1 | 1 | 6 | 6 |
| Blackgrass | 1 | 2 | 1 | 1 | 1 | 8 | 2 | 1 | 2 | 1 | 1 | 1 | 1 |
| Chickweed | 10 | 3 | 3 | 6 | 2 | 2 | 10 | 8 | 3 | 2 | 1 | 6 | 4 |
| Cocklebur | 10 | 8 | 5 | 9 | 6 | 9 | 10 | 10 | 10 | 8 | 3 | 9 | 2 |
| Corn | 2 | 2 | 1 | 1 | 1 | 1 | 2 | 1 | 3 | 0 | 0 | 1 | 1 |
| Cotton | 10 | 10 | 10 | 10 | 9 | 10 | 10 | 10 | 10 | 9 | 6 | 10 | 10 |
| Crabgrass | 1 | 1 | 1 | 3 | 1 | 1 | 2 | 2 | 4 | 1 | 0 | 2 | 2 |
| Downy brome | 1 | 2 | 0 | 1 | 0 | 3 | 2 | 4 | 3 | 0 | 0 | 2 | 1 |
| Giant foxtail | 2 | 1 | 2 | 2 | 1 | 1 | 2 | 3 | 3 | 1 | 0 | 2 | 1 |

Rate 20 g/ha | Rate 10 g/ha

| COMPOUND | 39 | 40 | 41 | 42 | 43 | 44 | 72 | 4 | 5 | 12 | 13 | 14 | 23 |
|---|---|---|---|---|---|---|---|---|---|---|---|---|---|
| Barley | 3 | 3 | 2 | 2 | 3 | 3 | 2 | 2 | 1 | 2 | 1 | 1 | 3 |
| Barnyardgrass | 10 | 10 | 10 | 10 | 8 | 10 | 10 | 1 | 3 | 1 | 3 | 3 | 3 |
| Bedstraw | 9 | 10 | 9 | 10 | 9 | 9 | 8 | 8 | 6 | 4 | 5 | 5 | 9 |
| Blackgrass | 2 | 10 | 2 | 1 | 2 | 2 | 1 | 1 | 1 | 0 | 2 | 1 | 2 |
| Chickweed | 10 | 10 | 9 | 10 | 10 | 10 | 7 | 7 | 3 | 7 | 1 | 0 | 9 |
| Cocklebur | 10 | 10 | 10 | 10 | 9 | 10 | 7 | 3 | 7 | 3 | 6 | 6 | 10 |
| Corn | 1 | 3 | 2 | 2 | 2 | 2 | 2 | 2 | 3 | 1 | 1 | 1 | 1 |
| Cotton | 2 | 2 | 2 | 2 | 2 | 3 | 1 | 4 | 10 | 10 | 10 | 10 | 10 |
| Crabgrass | 2 | 2 | 2 | 2 | 2 | 3 | 2 | 1 | 2 | 1 | 1 | 3 | 1 |
| Downy brome | 3 | 2 | 2 | 1 | 2 | 3 | 4 | 2 | 1 | 0 | 1 | 1 | 1 |
| Giant foxtail | 2 | 2 | 3 | 2 | 3 | 4 | 1 | 2 | 3 | 2 | 2 | 1 | 2 |

TABLE B-continued

| COMPOUND | 1 | 6 | 7 | 8 | 9 | 10 | 38 | 66 | 67 | 70 | 1 | 2 | 11 | 15 | 16 | 17 | 18 | 19 | 20 | 21 | 24 | 26 | 27 | 28 | 29 | 30 | 45 | 48 | 50 | 51 | 59 | 68 |
|---|---|---|---|---|---|---|---|---|---|---|---|---|---|---|---|---|---|---|---|---|---|---|---|---|---|---|---|---|---|---|---|---|
| Lambsquarter | 10 | 7 | 4 | 9 | 4 | 8 | 9 | 8 | 8 | 4 | 2 | 10 | 10 | 9 | 10 | 10 | 10 | 10 | 10 | 8 | | | | | | | | | | | | |
| Morningglory | 10 | 10 | 10 | 7 | 2 | 10 | 10 | 10 | 10 | 7 | 4 | 10 | 10 | 7 | 10 | 10 | 10 | 10 | 10 | 6 | | | | | | | | | | | | |
| Nutsedge | 1 | 0 | 1 | 1 | 1 | 1 | 0 | 2 | 3 | 1 | 0 | 1 | 1 | 0 | 1 | 1 | 1 | 1 | 1 | 1 | | | | | | | | | | | | |
| Rape | 10 | 9 | 9 | 10 | 2 | 10 | 10 | 10 | 10 | 7 | 1 | 10 | 10 | 3 | 10 | 10 | 10 | 10 | 10 | 2 | | | | | | | | | | | | |
| Rice | 2 | 1 | 2 | 2 | 1 | 1 | 2 | 4 | 3 | 0 | 0 | 2 | 3 | 2 | 2 | 3 | 2 | 2 | 2 | 2 | | | | | | | | | | | | |
| Sorghum | 2 | | 2 | 2 | 2 | 2 | 2 | 3 | 3 | 0 | 0 | 2 | 2 | 1 | 2 | 2 | 2 | 2 | 2 | 2 | | | | | | | | | | | | |
| Soybean | 2 | 2 | 3 | 3 | 2 | 1 | 3 | 6 | 4 | 2 | 0 | 3 | 3 | 2 | 3 | 3 | 3 | 3 | 3 | 3 | | | | | | | | | | | | |
| Sugar beet | 10 | 10 | 8 | 8 | 2 | 10 | 9 | 10 | 10 | 6 | 2 | 10 | 10 | 9 | 10 | 10 | 10 | 10 | 10 | 7 | | | | | | | | | | | | |
| Velvetleaf | 10 | 10 | 7 | 10 | 5 | 10 | 10 | 8 | 10 | 0 | 0 | 10 | 10 | 8 | 10 | 10 | 10 | 10 | 10 | 8 | | | | | | | | | | | | |
| Wheat | 2 | 3 | 2 | 1 | 0 | 2 | 2 | 1 | 2 | 2 | 1 | 3 | 3 | 1 | 3 | 3 | 3 | 4 | 3 | 1 | | | | | | | | | | | | |
| Wild buckwheat | 8 | 8 | 6 | 10 | 6 | 10 | 10 | 2 | 10 | 1 | 0 | 10 | 10 | 2 | 10 | 10 | 10 | 10 | 10 | 6 | | | | | | | | | | | | |
| Wild oat | 1 | 2 | 1 | 1 | 1 | 3 | 2 | 1 | 1 | 1 | 0 | 2 | 2 | 2 | 2 | 2 | 2 | 3 | 2 | 1 | | | | | | | | | | | | |

Rate 10 g/ha

| COMPOUND | 24 | 26 | 27 | 28 | 29 | 30 | 45 | 48 | 50 | 51 | 59 | 68 |
|---|---|---|---|---|---|---|---|---|---|---|---|---|
| Barley | 1 | 1 | 1 | 0 | 0 | 1 | 0 | 0 | 0 | 0 | 0 | 0 |
| Barnyardgrass | 3 | 4 | 2 | 1 | 1 | 3 | 4 | 1 | 1 | 1 | 2 | 1 |
| Bedstraw | 9 | 7 | 7 | 3 | 0 | 9 | — | 3 | 3 | 3 | 3 | 6 |
| Blackgrass | 1 | 1 | 1 | 0 | 0 | 1 | 1 | 0 | 0 | 1 | 1 | 2 |
| Chickweed | 9 | 3 | 2 | 0 | 0 | 1 | 10 | 1 | 1 | 0 | 8 | 1 |
| Cocklebur | 10 | 4 | 3 | 1 | 0 | 9 | 10 | 0 | 5 | 1 | 7 | 0 |
| Corn | 1 | 1 | 1 | 1 | 0 | 1 | 1 | 1 | 2 | 1 | 2 | 0 |
| Cotton | 10 | 10 | 9 | 8 | 0 | 10 | 10 | 9 | 9 | 9 | 8 | 8 |
| Crabgrass | 0 | 1 | 1 | 0 | 0 | 1 | 1 | 1 | 2 | 1 | 0 | 1 |
| Downy brome | 1 | 0 | 1 | 0 | 0 | 1 | 1 | 0 | 1 | 0 | 1 | 1 |
| Giant foxtail | 1 | 1 | 1 | 3 | 0 | 1 | 2 | 1 | 0 | 1 | 2 | 1 |
| Lambsquarter | 9 | 8 | 8 | 3 | 3 | 9 | 8 | 3 | 7 | 7 | 7 | 5 |
| Morningglory | 10 | 10 | 10 | 1 | 1 | 10 | 7 | 0 | 6 | 0 | 10 | 1 |
| Nutsedge | 0 | 0 | 0 | 0 | 0 | 0 | 0 | 0 | 0 | 0 | 0 | 0 |
| Rape | 10 | 8 | 10 | 8 | 0 | 8 | 9 | 9 | 2 | 0 | 1 | 2 |
| Rice | 2 | 1 | 1 | 0 | 0 | 2 | 2 | 2 | 10 | 9 | 3 | 0 |
| Sorghum | 2 | 1 | 1 | 1 | 1 | 1 | 2 | 1 | 1 | 2 | 2 | 0 |
| Soybean | 3 | 0 | 0 | 0 | 0 | 2 | 2 | 0 | 1 | 0 | 5 | 1 |
| Sugar beet | 10 | 9 | 6 | 6 | 1 | 10 | 10 | 1 | 5 | 1 | 8 | 6 |
| Velvetleaf | 10 | 8 | 8 | 8 | 1 | 10 | 10 | 3 | 5 | 2 | 4 | 6 |
| Wheat | 1 | 0 | 0 | 1 | 0 | 0 | 2 | 0 | 0 | 0 | 1 | 0 |
| Wild buckwheat | 10 | 4 | 5 | 1 | 0 | 9 | 6 | 2 | 6 | 1 | 3 | 1 |
| Wild oat | 1 | 0 | 1 | 0 | 0 | 1 | 1 | 0 | 0 | 0 | 1 | 1 |

PREEMERGENCE

| | Rate 1000 g/ha | | | | | Rate 400 g/ha | | | | | Rate 200 g/ha | | | | |
|---|---|---|---|---|---|---|---|---|---|---|---|---|---|---|---|
| COMPOUND | 1 | 6 | 7 | 8 | 9 | 10 | 38 | 66 | 67 | 70 | 17 | 18 | 32 | 33 | 34 | 35 | 36 |
| Barley | 0 | 0 | 0 | 0 | 0 | 0 | 0 | 0 | 0 | 0 | 0 | 0 | 0 | 0 | 3 | 3 | 0 |
| Barnyardgrass | 6 | 0 | 0 | 0 | 2 | 0 | 0 | 6 | 0 | 9 | 4 | 0 | 3 | 10 | 10 | 6 | 5 |
| Bedstraw | 10 | — | 9 | 3 | 8 | 10 | 0 | — | 3 | 10 | 3 | 0 | 10 | 10 | 10 | 10 | 10 |

TABLE B-continued

| | 1 | 3 | 6 | 7 | 8 | 9 | 10 | 37 | 47 | 53 | 58 | 61 | 62 | 63 | 65 |
|---|---|---|---|---|---|---|---|---|---|---|---|---|---|---|---|
| | | | | | | | | | | | Rate 200 g/ha | | | | |
| Blackgrass | 1 | 0 | 0 | 4 | 0 | 0 | 0 | 0 | 0 | 0 | 0 | 2 | 0 | 0 | 1 |
| Chickweed | 8 | 4 | 0 | 10 | 0 | 2 | 2 | 10 | 4 | 0 | 9 | 10 | 0 | 0 | 1 |
| Cocklebur | 8 | 2 | 0 | 0 | 0 | 3 | 0 | 7 | 2 | 10 | 3 | 7 | 0 | — | 0 |
| Corn | 0 | 0 | 0 | 0 | 5 | 0 | 0 | 0 | 0 | 0 | 0 | 0 | 0 | 0 | 0 |
| Cotton | 10 | 0 | 0 | 0 | 10 | 4 | 0 | 10 | 6 | 0 | 0 | 0 | 0 | 0 | 4 |
| Crabgrass | 3 | 6 | 0 | 0 | 0 | 8 | 2 | 8 | 1 | — | 0 | 2 | 0 | — | 0 |
| Downy brome | 2 | 0 | 0 | 2 | 0 | 2 | 0 | 10 | 3 | 0 | 0 | 1 | 0 | — | 0 |
| Giant foxtail | 10 | 1 | 0 | 10 | — | 0 | 0 | 10 | 9 | 10 | 10 | 0 | 3 | 10 | 3 |
| Lambsquarter | 6 | 3 | 0 | 10 | 10 | 10 | 10 | 10 | 10 | 10 | 10 | 10 | 0 | 0 | 4 |
| Morningglory | 0 | 0 | 0 | 10 | — | 9 | 3 | 10 | 7 | 10 | 10 | 10 | 0 | 0 | 0 |
| Nutsedge | 10 | 0 | 0 | 10 | 0 | 0 | 0 | 0 | 0 | 0 | 10 | 0 | 0 | 10 | 0 |
| Rape | 10 | 0 | 4 | 8 | 8 | 0 | 0 | 10 | 4 | 0 | 8 | 6 | 6 | 0 | 10 |
| Rice | 1 | 2 | 0 | 0 | 0 | 3 | 3 | 0 | 3 | 3 | 0 | 0 | 0 | 0 | 0 |
| Sorghum | 0 | 0 | 0 | 0 | 0 | 3 | 5 | 4 | 0 | 0 | 2 | 7 | 4 | 3 | 4 |
| Soybean | 1 | 0 | 0 | 0 | 0 | 3 | 3 | 3 | 1 | 0 | 8 | 0 | 0 | 1 | 9 |
| Sugar beet | 9 | 4 | 0 | 10 | 0 | 9 | 3 | 10 | 5 | 0 | 0 | 2 | 9 | 10 | 0 |
| Velvetleaf | 10 | 10 | 0 | 10 | 10 | 10 | 10 | 10 | 10 | 10 | 10 | 0 | 1 | 0 | 5 |
| Wheat | 0 | 0 | 0 | 0 | 0 | 7 | 0 | 6 | 0 | 3 | 0 | 8 | 0 | 8 | 0 |
| Wild buckwheat | 7 | 0 | 0 | 10 | 2 | 0 | 0 | 10 | 5 | 0 | 6 | 7 | 3 | — | 0 |
| Wild oat | 2 | 0 | 1 | 0 | 0 | 2 | 2 | 6 | 3 | 0 | 1 | 0 | 0 | 0 | 1 |

| COMPOUND | 37 | 38 | 39 | 40 | 41 | 42 | 43 | 44 | 66 | 67 | 70 | 72 | 2 | 4 |
|---|---|---|---|---|---|---|---|---|---|---|---|---|---|---|
| | | | | | Rate 100 g/ha | | | | | | | | Rate 50 g/ha | |
| Barley | 0 | 0 | 0 | 0 | 0 | 0 | 0 | 0 | 0 | 0 | 0 | 0 | 0 | 0 |
| Barnyardgrass | 10 | 0 | 4 | 8 | 5 | 6 | 8 | 8 | 0 | 0 | 9 | 0 | 3 | 0 |
| Bedstraw | 10 | 0 | 10 | 10 | 10 | 10 | 10 | 10 | 0 | — | 10 | — | 4 | 9 |
| Blackgrass | 6 | 0 | 0 | 2 | 1 | 0 | 1 | 0 | 0 | 0 | 0 | 0 | 0 | 0 |
| Chickweed | 10 | 0 | 10 | 10 | 10 | 10 | 10 | 10 | 0 | 0 | 10 | 0 | 0 | 0 |
| Cocklebur | 10 | 0 | 9 | 10 | 10 | 10 | 10 | 10 | 0 | 0 | 10 | 0 | 1 | 0 |
| Corn | 1 | 0 | 10 | 10 | 10 | 10 | 10 | 10 | 0 | 0 | 10 | 0 | 0 | 0 |
| Cotton | 10 | 0 | 10 | 10 | 10 | 10 | 10 | 10 | 0 | 0 | 10 | 2 | 0 | 0 |
| Crabgrass | 2 | 0 | 0 | 4 | 0 | 4 | 4 | 0 | 0 | 0 | 0 | 0 | 3 | 3 |
| Downy brome | 6 | 0 | 0 | 0 | 0 | 0 | 0 | 0 | 0 | 0 | 0 | 0 | 0 | 0 |
| Giant foxtail | 5 | 0 | 0 | 0 | 0 | 0 | 0 | 0 | 0 | 0 | 0 | 0 | 0 | 0 |
| Lambsquarter | 10 | 0 | 10 | 10 | 10 | 10 | 10 | 10 | 0 | 0 | 10 | 6 | 10 | 10 |
| Morningglory | 10 | 0 | 10 | 10 | 10 | 10 | 10 | 10 | 3 | 0 | 10 | 6 | 3 | 0 |
| Nutsedge | 0 | 0 | 0 | 0 | 0 | 0 | 0 | 0 | 0 | 0 | 0 | 0 | 0 | 0 |
| Rape | 10 | 0 | 9 | 4 | 10 | 10 | 10 | 10 | 0 | 0 | 10 | 1 | 0 | 0 |
| Rice | 4 | 0 | 0 | 0 | 0 | 0 | 0 | 0 | 0 | 0 | 5 | 3 | 3 | 1 |
| Sorghum | 1 | 0 | 0 | 0 | 0 | 0 | 0 | 0 | 0 | 0 | 2 | 0 | 0 | 0 |
| Soybean | 10 | 0 | 0 | 10 | 10 | 10 | 10 | 10 | 0 | 0 | 10 | 2 | 0 | 0 |
| Sugar beet | 10 | 0 | 10 | 10 | 10 | 10 | 10 | 10 | 0 | 0 | 10 | 0 | 4 | 0 |
| Velvetleaf | 10 | 0 | 9 | 10 | 10 | 10 | 10 | 10 | 3 | 0 | 8 | 0 | 4 | 9 |
| Wheat | 3 | 0 | 0 | 0 | 0 | 0 | 0 | 0 | 0 | 0 | 0 | 0 | 4 | 7 |
| Wild buckwheat | 10 | 0 | 9 | 10 | 10 | 6 | 8 | 9 | 0 | 0 | 8 | 0 | 0 | 0 |
| Wild oat | 8 | 0 | 0 | 0 | 0 | 0 | 0 | 0 | 0 | 0 | 0 | 0 | 0 | 0 |

TABLE B-continued

Rate 50 g/ha

| COMPOUND | 5 | 11 | 12 | 13 | 14 | 15 | 16 | 17 | 18 | 19 | 20 | 21 | 23 | 24 | 26 | 27 | 28 | 29 | 30 | 31 | 32 | 33 | 34 | 35 | 36 | 37 |
|---|---|---|---|---|---|---|---|---|---|---|---|---|---|---|---|---|---|---|---|---|---|---|---|---|---|---|
| Barley | 0 | 0 | 0 | 0 | 0 | 0 | 0 | 0 | 0 | 0 | 4 | 0 | 0 | 0 | 0 | 0 | 0 | 0 | 0 | 0 | 0 | 0 | 1 | 0 | 0 | 0 |
| Barnyardgrass | 0 | 2 | 0 | 0 | 3 | 0 | 0 | 0 | 0 | 0 | 3 | 3 | 3 | 1 | 2 | 3 | 0 | 0 | 9 | 1 | 0 | 3 | 8 | 0 | 2 | 6 |
| Bedstraw | 9 | 9 | 3 | 3 | 0 | 0 | 0 | 0 | 0 | — | 8 | 10 | 10 | 10 | 9 | 8 | 3 | 6 | 2 | 6 | 9 | 10 | 10 | 10 | 10 | 10 |
| Blackgrass | 0 | 0 | 0 | 0 | 0 | 0 | 0 | 0 | 0 | 0 | 0 | 8 | 2 | 0 | 0 | 0 | 0 | 0 | 7 | 9 | 9 | 0 | 6 | 1 | 1 | 2 |
| Chickweed | 0 | 0 | 0 | 0 | 0 | 0 | 0 | 0 | 0 | 0 | 9 | 0 | 9 | 10 | 9 | 1 | 3 | 0 | 0 | 0 | 9 | 9 | 10 | 9 | 10 | 10 |
| Cocklebur | 0 | 0 | 0 | 0 | 3 | 0 | 0 | 3 | 0 | 0 | 7 | 0 | 10 | 10 | 2 | 3 | 0 | 0 | 10 | 0 | 10 | 6 | 8 | 0 | 10 | 10 |
| Corn | 0 | 0 | 0 | 0 | 4 | 0 | 0 | 0 | 0 | 0 | 0 | 0 | 0 | 0 | 0 | 0 | 0 | 0 | 0 | 7 | 10 | 0 | 1 | 0 | 0 | 0 |
| Cotton | 7 | 0 | 0 | 2 | 0 | 0 | 0 | 5 | 0 | 0 | 8 | 10 | 10 | 10 | 10 | 1 | 0 | 0 | 10 | 3 | 0 | 7 | 1 | 10 | 10 | 10 |
| Crabgrass | 0 | 0 | 0 | 0 | 0 | 0 | 3 | 3 | 0 | 0 | 2 | 2 | 2 | 0 | 3 | 0 | 0 | 0 | 0 | 0 | 0 | 5 | 7 | 3 | 3 | 0 |
| Downy brome | 0 | 0 | 0 | 0 | 0 | 0 | 0 | 0 | 2 | 0 | 2 | 2 | 2 | 0 | 0 | 0 | 0 | 0 | 0 | 3 | 10 | 1 | 5 | 1 | 0 | 5 |
| Giant foxtail | 0 | 0 | 0 | 0 | 0 | 0 | 0 | 0 | 0 | 0 | 7 | 0 | 0 | 0 | 0 | 0 | 0 | 0 | 0 | 2 | 0 | 0 | 6 | 2 | 0 | 0 |
| Lambsquarter | 9 | 10 | 9 | 10 | 8 | 7 | 10 | 10 | 6 | 0 | 10 | 10 | 10 | 10 | 10 | 9 | 7 | 0 | 10 | 10 | 10 | 10 | 10 | 10 | 10 | 10 |
| Morningglory | 0 | 0 | 1 | 0 | 5 | — | 0 | 0 | 0 | 0 | 10 | 0 | 0 | 0 | 0 | 10 | 0 | 0 | 10 | 7 | 10 | 10 | 10 | 0 | 10 | 10 |
| Nutsedge | 0 | 3 | 0 | 0 | 5 | 0 | 0 | 0 | 0 | 0 | 0 | 0 | 8 | 10 | 10 | 0 | 0 | 0 | 0 | 0 | 10 | 0 | 1 | 0 | 10 | 0 |
| Rape | 0 | 1 | 0 | 0 | 0 | 0 | 0 | 2 | 0 | 0 | 0 | 0 | 0 | 9 | 10 | 9 | 7 | 8 | 8 | 6 | 0 | 3 | 5 | 5 | 10 | 3 |
| Rice | 0 | 3 | 0 | 0 | 0 | 0 | 0 | 2 | 2 | 0 | 9 | 2 | 0 | 0 | 3 | 10 | 0 | 0 | 0 | 0 | 0 | 1 | 2 | 7 | 2 | 0 |
| Sorghum | 0 | 0 | 0 | 0 | 2 | 0 | 0 | 0 | 0 | 0 | 0 | 0 | 1 | 0 | 0 | 0 | 0 | 0 | 0 | 6 | 0 | 6 | 9 | 0 | 4 | 3 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 10 | 2 | 7 | 3 | 0 |
| Sugar beet | 8 | 10 | 10 | 10 | 10 | 10 | 0 | 7 | 3 | 0 | 10 | 10 | 10 | 10 | 10 | 9 | 9 | 0 | 10 | 10 | 10 | 10 | 10 | 10 | 10 | 10 |
| Velvetleaf | 10 | 9 | 5 | 10 | 10 | 0 | 0 | 7 | 0 | 0 | 10 | 10 | 10 | 9 | 7 | 2 | 0 | 0 | 10 | 10 | 10 | 10 | 10 | 10 | 10 | 5 |
| Wheat | 1 | 0 | 0 | 0 | 0 | 0 | 0 | 0 | 0 | 0 | 3 | 5 | 0 | 0 | 0 | 0 | 0 | 0 | 0 | 8 | 7 | 4 | 2 | 0 | 2 | 3 |
| Wild buckwheat | 0 | 0 | 0 | 5 | 3 | 0 | 0 | 0 | 0 | 0 | 7 | 10 | 10 | 7 | 0 | 0 | 0 | 0 | 9 | 0 | 0 | 10 | 10 | 10 | 9 | 10 |
| Wild oat | 0 | 0 | 0 | 0 | 0 | 0 | 0 | 0 | 0 | 0 | 4 | 2 | 3 | 0 | 0 | 0 | 0 | 0 | 0 | 2 | 0 | 0 | 5 | 2 | 5 | 5 |

| COMPOUND | 45 | 47 | 48 | 50 | 51 | 53 | 58 | 59 | 61 | 62 | 63 | 65 | 68 | 39 | 40 | 41 | 42 | 43 | 44 | 72 | 4 | 5 | 12 | 13 | 14 | 23 |
|---|---|---|---|---|---|---|---|---|---|---|---|---|---|---|---|---|---|---|---|---|---|---|---|---|---|---|
| | | | | | | | Rate 50 g/ha | | | | | | | Rate 20 g/ha | | | | | | | Rate 10 g/ha | | | | | |
| Barley | 0 | 0 | 0 | 1 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | 0 | 0 | 0 | 0 | 0 | 0 | 0 | 2 | 0 | 0 | 0 | 0 | 1 | 2 | 3 | 3 | 1 | 4 | 0 | 0 | 0 | 0 | 0 | 0 | 0 |
| Bedstraw | 10 | 0 | 5 | 10 | — | 9 | 10 | 3 | 10 | 0 | 0 | — | 1 | 10 | 9 | 8 | 10 | 9 | 10 | 0 | 0 | 0 | 0 | 0 | 0 | 10 |
| Blackgrass | 2 | 0 | 0 | 2 | 0 | 0 | 0 | 2 | 0 | 0 | 0 | 0 | 2 | 0 | 0 | 0 | 0 | 0 | 10 | 0 | 0 | 0 | 0 | 0 | 0 | 0 |
| Chickweed | 10 | 3 | 0 | 9 | 0 | 9 | 10 | 9 | 10 | 0 | 6 | — | 6 | 10 | 10 | 10 | 10 | 10 | 10 | 0 | 0 | 0 | 0 | 0 | 0 | 0 |
| Cocklebur | 10 | 0 | 0 | 3 | 0 | 10 | 10 | 2 | 10 | 0 | 0 | 0 | 10 | 10 | 10 | 10 | 10 | 10 | 10 | 0 | 0 | 0 | 0 | 0 | 0 | 9 |
| Corn | 0 | 0 | 0 | 0 | 0 | 0 | 0 | 0 | 0 | 0 | 0 | 4 | 0 | 10 | 10 | 10 | 10 | 10 | 10 | 0 | 0 | 0 | 0 | 0 | 0 | 0 |
| Cotton | 2 | 0 | 0 | 0 | 0 | 3 | 0 | 2 | 9 | 0 | 6 | 0 | 3 | 10 | 10 | 10 | 10 | 10 | 10 | 0 | 0 | 0 | 0 | 0 | 0 | 0 |
| Crabgrass | 0 | 0 | 0 | 2 | 0 | 0 | 0 | 1 | 0 | 0 | 0 | 0 | 0 | 0 | 0 | 0 | 0 | 0 | 0 | 0 | 0 | 0 | 0 | 0 | 0 | 0 |
| Downy brome | 0 | 0 | 0 | 0 | 0 | 0 | 0 | 0 | 10 | 0 | 0 | — | 7 | 9 | 10 | 9 | 10 | 10 | 10 | 0 | 0 | 0 | 0 | 0 | 0 | 0 |
| Giant foxtail | 10 | 0 | 0 | 10 | 0 | 10 | 10 | 10 | 10 | 0 | 0 | 10 | 0 | 10 | 10 | 10 | 10 | 10 | 10 | 0 | 0 | 0 | 0 | 0 | 0 | 0 |
| Lambsquarter | 10 | 7 | 0 | 0 | 0 | 10 | 0 | 3 | 5 | 0 | 0 | 0 | 7 | 9 | 10 | 9 | 10 | 10 | 10 | 0 | 0 | 0 | 7 | 8 | 0 | 9 |
| Morningglory | 10 | 0 | 0 | 0 | 0 | 10 | 10 | 2 | 10 | 0 | 0 | 0 | 0 | 9 | 10 | 10 | 10 | 10 | 10 | 3 | 0 | 0 | 1 | 0 | 0 | 10 |
| Nutsedge | 0 | 0 | 0 | 0 | 0 | 0 | 0 | 0 | 0 | 0 | 0 | 10 | 3 | 10 | 10 | 10 | 10 | 10 | 9 | 0 | 0 | 0 | 0 | 0 | 0 | 0 |
| Rape | 10 | 3 | 0 | 3 | 0 | 8 | 0 | 0 | 10 | 0 | 2 | 0 | 3 | 9 | 10 | 10 | 10 | 10 | 0 | 0 | 0 | 0 | 0 | 0 | 0 | 10 |
| Rice | 0 | 0 | 0 | 0 | 0 | 0 | 0 | 1 | 0 | 0 | 0 | 0 | 0 | 10 | 10 | 10 | 10 | 10 | 0 | 0 | 0 | 0 | 0 | 0 | 0 | 0 |
| Sorghum | 0 | 0 | 0 | 0 | 0 | 0 | 0 | 0 | 10 | 0 | 0 | 0 | 3 | 10 | 10 | 10 | 10 | 10 | 0 | 0 | 0 | 0 | 0 | 0 | 0 | 0 |
| Soybean | 0 | 0 | 0 | 0 | 0 | 0 | 0 | 10 | 5 | 0 | 0 | 0 | 0 | 10 | 10 | 10 | 10 | 10 | 0 | 0 | 0 | 0 | 0 | 0 | 0 | 0 |
| Sugar beet | 9 | 4 | 0 | 10 | 0 | 7 | 9 | 10 | 10 | 5 | 0 | — | 8 | 10 | 10 | 10 | 10 | 10 | 10 | 0 | 0 | 0 | 0 | 6 | 3 | 7 |
| Velvetleaf | 10 | 3 | 0 | 0 | 0 | 10 | 10 | 10 | 10 | 3 | 2 | 10 | 8 | 10 | 10 | 10 | 10 | 10 | 10 | 0 | 0 | 0 | 0 | 0 | 0 | 10 |

TABLE B-continued

| | | | | | | | | | | | | | | | | | | | | |
|---|---|---|---|---|---|---|---|---|---|---|---|---|---|---|---|---|---|---|---|---|
| Wheat | 0 | 0 | 0 | 1 | 0 | 0 | 0 | 0 | 0 | 1 | 0 | 0 | 0 | 0 | 0 | 0 | 0 | 0 | 0 | 0 |
| Wild buckwheat | 8 | 1 | 0 | 0 | 4 | 5 | 9 | 4 | 0 | — | 3 | 6 | 0 | 2 | 4 | 6 | 9 | 2 | 9 | 0 |
| Wild oat | 1 | 0 | 0 | 3 | 2 | 0 | 2 | 0 | 3 | 0 | 3 | 0 | 0 | 0 | 0 | 0 | 0 | 0 | 0 | 0 |

Rate 10 g/ha

| COMPOUND | 24 | 26 | 27 | 28 | 29 | 30 | 45 | 48 | 50 | 51 | 59 | 68 |
|---|---|---|---|---|---|---|---|---|---|---|---|---|
| Barley | 0 | 0 | 0 | 0 | 0 | 0 | 0 | 0 | 0 | 0 | 0 | 0 |
| Barnyardgrass | 0 | 0 | 0 | 0 | 0 | 0 | 0 | 0 | 0 | 0 | 0 | 1 |
| Bedstraw | 0 | 0 | — | 0 | 2 | 3 | 10 | 0 | 0 | 0 | 0 | 1 |
| Blackgrass | 7 | 3 | 0 | 0 | 0 | 0 | 1 | 0 | 0 | 0 | 0 | 0 |
| Chickweed | 0 | 0 | 0 | 0 | 0 | 2 | 10 | 0 | 0 | 0 | 0 | 0 |
| Cocklebur | 4 | 0 | 0 | 0 | 0 | 3 | 5 | 0 | 0 | 0 | 0 | 0 |
| Corn | 0 | 0 | 0 | 0 | 0 | 0 | 0 | 0 | 0 | 0 | 0 | 0 |
| Cotton | 0 | 0 | 0 | 0 | 0 | 0 | 0 | 0 | 0 | 0 | 0 | 0 |
| Crabgrass | 0 | 0 | 0 | 0 | 0 | 0 | 0 | 0 | 0 | 0 | 0 | 0 |
| Downy brome | 0 | 0 | 0 | 0 | 0 | 0 | 0 | 0 | 0 | 0 | 0 | 0 |
| Giant foxtail | 0 | 0 | 0 | 0 | 4 | 0 | 0 | 0 | 0 | 0 | 0 | 0 |
| Lambsquarter | 8 | 9 | 6 | 0 | 0 | 9 | 9 | 0 | 8 | 0 | 10 | 0 |
| Morningglory | 2 | 0 | 10 | 0 | 0 | 3 | 5 | 0 | — | 0 | 0 | 0 |
| Nutsedge | 0 | 0 | 0 | 0 | 0 | 0 | 0 | 0 | 0 | 0 | 0 | 0 |
| Rape | 0 | 0 | 0 | 0 | 0 | 8 | 10 | 0 | 0 | 0 | 0 | 0 |
| Rice | 0 | 0 | 0 | 0 | 0 | 0 | 0 | 0 | 0 | 0 | 0 | 0 |
| Sorghum | 0 | 0 | 0 | 0 | 0 | 0 | 0 | 0 | 0 | 0 | 0 | 0 |
| Soybean | 0 | 0 | 0 | 0 | 0 | 0 | 0 | 0 | 0 | 0 | 0 | 0 |
| Sugar beet | 5 | 3 | 3 | 0 | 0 | 9 | 7 | 0 | 7 | 0 | 3 | 6 |
| Velvetleaf | 8 | 0 | 0 | 0 | 0 | 10 | 5 | 0 | 7 | 0 | 1 | 0 |
| Wheat | 0 | 0 | 0 | 0 | 0 | 0 | 0 | 0 | 0 | 0 | 0 | 0 |
| Wild buckwheat | 1 | 0 | 0 | 0 | 0 | 3 | 3 | 0 | 0 | 0 | 0 | 3 |
| Wild oat | 0 | 0 | 0 | 0 | 0 | 0 | 0 | 0 | 0 | 0 | 0 | 3 |

TEST C

The compounds evaluated in this test were formulated in a non-phytotoxic solvent mixture which included a surfactant and applied to the soil surface before plant seedlings emerged (preemergence application), to water that covered the soil surface (flood application), and to plants that were in the one-to-four leaf stage (postemergence application). A sandy loam soil was used for the preemergence and postemergence tests, while a silt loam soil was used in the flood test. Water depth was approximately 2.5 cm for the flood test and was maintained at this level for the duration of the test.

Plant species in the preemergence and postemergence tests consisted of barnyardgrass (*Echinochloa crus-galli*), barley (*Hordeun vulgare*), bedstraw (*Galium aparine*), blackgrass (*Alopecurus myosuroides*), chickwveed (*Stellaria media*), cocklebur (*Xanthium strumarium*), corn (*Zea mays*), cotton (*Gossypium hirsutum*), crabgrass (*Digitaria sanguinalis*), downy brome (*Bromus tectorum*), giant foxtail (*Setaria faberi*), johnsongrass (*Sorghum halpense*), lambsquarters (*Chenopodiun album*), morningglory (*Ipomoea hederacea*), pigweed (*Amaranthus retroflexus*), rape (*Brassica napus*), ryegrass (*Lolium multiflorum*), soybean (*Glycine max*), speedwell (*Veronica persica*), sugar beet (*Beta vulgaris*), velvetleaf (*Abutilon theophrasti*), wheat (*Triticum aestivum*), wild buckwNvheat (*Polygonum convolvulus*), and wild oat (*Avena fatua*). All plant species were planted one day before application of the compound for the preemergence portion of this test. Plantings of these species were adjusted to produce plants of appropriate size for the postemergence portion of the test. Plant species in the flood test consisted of rice (*Oryza saliva*), umbrella sedge (*Cyperus difformis*), duck salad (*Heteranthera limosa*), barnyardgrass (*Echinochloa crusgalli*, designated 'barnyard 2') and Late watergrass (*Echinocloa oryzicola*, designated 'watergrass 2') grown to the 2 leaf stage for testing.

All plant species were grown using normal greenhouse practices. Visual evaluations of injury expressed on treated plants, when compared to untreated controls, were recorded approximately fourteen to twenty one days after application of the test compound. Plant response this ratings, summarized in Table C, were recorded on a 0 to 100 scale where 0 is no effect and 100 is complete control. A dash (−) response means no test result.

TABLE C

POSTEMERGENCE

| COMPOUND | Rate 125 g/ha | | | | | | | | | | | | Rate 62 g/ha | | | | | | | | | | | | Rate 31 g/ha | | | | | | | | |
|---|---|---|---|---|---|---|---|---|---|---|---|---|---|---|---|---|---|---|---|---|---|---|---|---|---|---|---|---|---|---|---|---|
| | 2 | 1 | 2 | 3 | 4 | 5 | 7 | 8 | 9 | 10 | 11 | 12 | 13 | 14 | 20 | 21 | 45 | 65 | 70 | 1 | 2 | 3 | 4 | 5 | 7 | 8 | 9 | 10 | 11 |
| Barley Igri | 35 | 35 | 35 | 25 | 30 | 0 | 10 | 20 | 30 | 30 | 40 | 45 | 45 | 40 | 35 | 0 | 30 | 10 | 30 | 35 | 35 | 25 | 30 | 0 | 10 | 10 | 20 | 30 | — |
| Barnyard 2 | 35 | 20 | 30 | 25 | 20 | 15 | 0 | 0 | 20 | 10 | 30 | 10 | 65 | 0 | 20 | 35 | — | 0 | — | 20 | 30 | 0 | 20 | 15 | 0 | 0 | 0 | 10 | 25 |
| Barnyardgrass | 45 | 60 | 30 | 35 | 40 | 50 | 15 | 10 | 0 | 0 | 85 | 60 | 35 | 50 | 75 | 100 | 70 | 50 | 60 | 50 | 30 | 30 | 35 | 40 | 10 | 10 | 0 | 0 | 75 |
| Bedstraw | — | 100 | 100 | — | 100 | 100 | 50 | 70 | 100 | 35 | 50 | 45 | 40 | 55 | 100 | 10 | 100 | 80 | 100 | 80 | 100 | 100 | 50 | 100 | 40 | 10 | 50 | 35 | — |
| Blackgrass | 35 | 10 | 35 | 15 | 25 | 20 | 10 | 40 | 20 | 10 | 15 | 20 | 30 | 25 | 10 | 10 | 70 | 20 | 70 | 0 | 20 | 10 | 20 | 20 | 0 | 70 | 0 | 10 | 15 |
| Chickweed | 95 | 100 | 80 | 10 | 35 | 90 | — | — | 100 | 100 | 80 | 30 | 85 | 55 | 100 | 100 | 100 | 40 | 100 | 80 | 80 | 10 | 20 | 65 | — | 80 | 90 | 75 | 70 |
| Cocklebur | 100 | 100 | 90 | 90 | 100 | 100 | 100 | 90 | 100 | 100 | 100 | 50 | 60 | 70 | 100 | 100 | 100 | 100 | 100 | 90 | 90 | 90 | 90 | 95 | 10 | 15 | 70 | 80 | 90 |
| Corn | 20 | 30 | 15 | 25 | 35 | 35 | 15 | 20 | 20 | 15 | 50 | 80 | 35 | 50 | 35 | 55 | 10 | 10 | 40 | 100 | 15 | 20 | 30 | 30 | 10 | 15 | 15 | 10 | 35 |
| Cotton | 100 | 100 | 100 | 100 | 100 | 100 | 100 | 100 | 100 | 100 | 100 | 100 | 90 | — | 100 | 100 | 100 | 100 | 100 | 100 | 100 | 100 | 100 | 100 | 100 | 100 | 100 | 90 | 100 |
| Crabgrass | 65 | 35 | 50 | 40 | 30 | 50 | 30 | 20 | 15 | 20 | 50 | 35 | 35 | 50 | 35 | 50 | 30 | 20 | 50 | 30 | 40 | 40 | 30 | 40 | 20 | 20 | 10 | 20 | 35 |
| Downy Brome | 30 | 30 | 30 | 20 | 30 | 10 | 0 | 30 | 0 | 0 | 100 | 20 | 30 | 25 | 20 | 100 | 20 | 0 | 35 | 20 | 30 | 20 | 30 | 10 | 0 | 0 | 0 | 0 | 0 |
| Duck salad | 0 | 0 | 0 | 0 | 0 | 0 | 0 | 0 | 40 | 0 | 0 | 0 | 0 | 0 | 0 | 0 | 0 | 0 | — | 0 | 0 | 0 | 0 | 0 | 0 | 0 | 0 | 0 | 0 |
| Giant foxtail | 70 | 40 | 60 | 35 | 60 | 50 | 20 | 15 | 25 | 20 | 35 | 55 | 45 | 35 | 55 | 75 | 40 | 20 | 60 | 30 | 60 | — | 40 | 40 | 10 | 10 | 40 | 10 | 30 |
| Italn. Rygrass | 10 | 35 | 10 | 20 | 25 | 20 | 0 | 0 | 30 | 20 | 60 | 10 | 10 | 20 | 30 | 0 | 20 | 30 | 10 | 25 | 10 | 20 | 25 | 15 | 10 | 0 | 20 | 10 | 0 |
| Johnsongrass | 30 | — | 30 | 60 | 60 | 50 | 20 | 0 | 25 | 20 | 0 | 50 | 50 | 60 | 40 | 55 | 35 | 50 | 65 | — | 25 | 50 | 30 | 40 | 10 | 0 | 10 | 10 | 35 |
| Lambsquarter | 100 | 100 | 100 | — | 100 | 90 | 70 | 100 | 80 | 60 | 100 | 100 | 100 | 100 | 100 | 100 | 100 | 80 | 100 | 100 | 100 | 100 | 95 | 85 | 70 | 60 | 60 | 40 | 95 |
| Morningglory | 100 | 90 | 100 | 90 | 85 | 90 | 80 | 30 | 70 | 100 | 10 | 70 | 85 | 50 | 50 | 100 | 100 | 100 | 100 | 90 | 100 | 90 | 85 | 90 | 40 | 100 | 40 | 70 | — |
| Rape | 100 | 90 | 100 | 65 | 50 | 80 | 70 | 50 | 30 | 50 | 100 | 90 | 100 | 100 | 100 | 100 | 100 | 100 | 100 | 90 | 100 | 10 | 40 | 80 | 40 | 50 | 30 | 50 | 95 |
| Redroot Pigweed | 100 | 100 | 100 | 90 | 100 | 95 | 70 | 50 | 20 | 50 | 100 | 100 | 100 | 100 | 100 | 100 | 100 | 100 | 100 | 80 | 100 | 90 | 100 | 90 | 70 | 20 | 30 | 40 | 100 |
| Rice Japonica | 40 | — | 35 | 35 | 25 | 60 | 0 | 30 | 35 | 0 | 30 | 0 | 45 | 15 | 35 | 20 | 20 | 50 | — | 30 | 55 | 40 | 20 | 25 | 30 | 0 | 0 | 0 | 25 |
| Soybean | 70 | 50 | 70 | 40 | 70 | — | 40 | — | 20 | 35 | 70 | 35 | 70 | 40 | 80 | 40 | 40 | 50 | 50 | 40 | 90 | 100 | 60 | 40 | 90 | 30 | 20 | 30 | 25 |
| Speedwell | 95 | 100 | 90 | 100 | — | 95 | 90 | — | 100 | 60 | 100 | 85 | — | 100 | 100 | 100 | 100 | 100 | 100 | 95 | 100 | 100 | 100 | 100 | — | 50 | 100 | 60 | 0 |
| Sugar beet | 100 | 100 | 100 | 100 | 100 | 100 | 100 | — | 80 | 70 | 100 | 100 | 100 | 100 | 100 | 100 | 100 | 100 | 100 | 100 | 100 | 100 | 100 | 100 | 90 | — | 60 | 100 | 100 |
| Umbrella sedge | 0 | 0 | 0 | 0 | 0 | 0 | 0 | 0 | 0 | 0 | 0 | 0 | 0 | 0 | 0 | 0 | 0 | 0 | — | 0 | 0 | 0 | 0 | 0 | 0 | 0 | 0 | 0 | 0 |
| Velvetleaf | 100 | 100 | 100 | 100 | 100 | 100 | 100 | 90 | 100 | 90 | 100 | 100 | 100 | 100 | 100 | 100 | 100 | 100 | 100 | 100 | 100 | 100 | 100 | 100 | 90 | 90 | 100 | 60 | 100 |
| Watergrass 2 | 30 | 15 | 30 | 15 | 15 | 15 | 0 | 20 | 30 | 20 | 20 | 10 | 65 | 0 | 25 | 20 | 0 | 0 | 10 | 10 | 30 | 15 | 25 | 30 | 0 | 0 | 30 | — | 10 |
| Wheat | 25 | 35 | 25 | 30 | 25 | 30 | 50 | 0 | 0 | 40 | 20 | 35 | 40 | 40 | 30 | 25 | 35 | 0 | 100 | 30 | 20 | 30 | 25 | 30 | 35 | 0 | 10 | 10 | 15 |
| Wild buckwheat | 100 | 100 | 95 | 100 | 100 | 100 | 100 | 85 | 90 | 70 | 85 | 100 | 95 | 100 | 100 | 100 | 100 | 100 | 100 | 85 | 80 | 100 | 100 | 100 | 70 | 40 | 90 | 60 | 85 |
| *Wild oat | 30 | 35 | 35 | 25 | 25 | 10 | 40 | 20 | 40 | 10 | 35 | 45 | 40 | 35 | 35 | 0 | 30 | 30 | 30 | 35 | 35 | 25 | 25 | 0 | 35 | 0 | 30 | 10 | 35 |

| COMPOUND | 12 | 13 | 14 | 20 | 21 | 23 | 25 | 26 | 27 | 28 | 29 | 30 | 36 | 37 | 45 | 46 | 49 | 52 | 53 | 54 | 56 | 57 | 60 | 64 | 65 | 68 | 69 | 70 | 73 |
|---|---|---|---|---|---|---|---|---|---|---|---|---|---|---|---|---|---|---|---|---|---|---|---|---|---|---|---|---|---|
| Barley Igri | 25 | 40 | 35 | 40 | 35 | 30 | 40 | 20 | 20 | 10 | 0 | 25 | 20 | 20 | 0 | 20 | 30 | 30 | 35 | 30 | 25 | 30 | 20 | 20 | 20 | 0 | 30 | 20 | 0 |
| Barnyard 2 | 0 | 50 | 0 | 15 | 25 | 20 | 0 | 20 | 15 | 10 | 10 | 10 | — | — | — | 10 | — | 10 | 0 | 0 | 0 | 0 | — | 0 | 40 | 0 | 0 | — | 0 |
| Barnyardgrass | 50 | 30 | 40 | 50 | 90 | 100 | 100 | 85 | 70 | 60 | 60 | 100 | 20 | 80 | 60 | 55 | 95 | 100 | 100 | 100 | 55 | 90 | 55 | 60 | 40 | 10 | 80 | 80 | 0 |
| Bedstraw | 45 | 40 | 45 | 100 | 100 | 100 | 100 | 90 | 90 | 45 | 45 | 70 | 100 | 100 | 100 | 50 | 50 | 90 | 85 | 85 | 100 | 95 | 50 | 95 | 70 | 0 | 0 | 80 | — |
| Blackgrass | 10 | 30 | 25 | 10 | 10 | 25 | 15 | 20 | 15 | 45 | 15 | 15 | 0 | 30 | 50 | 0 | 25 | 25 | 20 | 25 | 15 | 10 | 10 | 10 | 20 | 0 | 10 | 40 | 0 |
| Chickweed | 30 | 30 | 55 | 100 | 100 | 100 | 100 | 70 | 50 | 40 | 0 | 90 | 100 | 100 | — | 10 | 95 | 100 | 100 | 95 | 60 | 100 | 100 | 95 | 70 | 0 | 95 | — | 0 |
| Cocklebur | 35 | 50 | 40 | 100 | 100 | 100 | 100 | 80 | 80 | 70 | 60 | 100 | 100 | 100 | 10 | 70 | 35 | 100 | 100 | 100 | 80 | 60 | 100 | 10 | 100 | 40 | 100 | 100 | — |
| Corn | 30 | 35 | 25 | 40 | 40 | 20 | 30 | 35 | 25 | 20 | 10 | 30 | 10 | 10 | 10 | 20 | 35 | 30 | 20 | 20 | 75 | 10 | 15 | 0 | 10 | 20 | 60 | 5 | 20 |
| Cotton | 95 | 90 | 90 | 100 | 100 | 100 | 100 | 100 | 100 | 90 | 90 | 100 | 100 | 100 | 100 | 100 | 100 | 100 | 100 | 100 | 80 | 100 | 100 | 100 | 100 | 80 | 100 | 100 | 10 |

TABLE C-continued

| | 1 | 2 | 3 | 4 | 5 | 7 | 8 | 9 | 10 | 11 | 12 | 13 | 14 | 20 | 21 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|
| Crabgrass | 30 | 25 | 50 | 35 | 40 | 60 | 50 | 35 | 35 | 20 | 20 | 30 | 10 | 20 | 30 | 30 | 30 | 30 | 50 | 50 | 60 | 60 | 20 | 30 | 15 | 10 | 30 | 50 | 0 |
| Downy Brome | 15 | 20 | 25 | 20 | 0 | 25 | 25 | 10 | 10 | 0 | 0 | 0 | 10 | 10 | 10 | 20 | 10 | 25 | 10 | 0 | 20 | 70 | 10 | 25 | 0 | 0 | 25 | 20 | 0 |
| Duck salad | 0 | 0 | 0 | 0 | 70 | 0 | 0 | 0 | 0 | 0 | 0 | 25 | 15 | 30 | 0 | 20 | — | 35 | 40 | 50 | 60 | 70 | 40 | 30 | 50 | 0 | 0 | 0 | 0 |
| Giant foxtail | 35 | 35 | 30 | 40 | 0 | 50 | 50 | 25 | 25 | 20 | 15 | 35 | 15 | 25 | 20 | 20 | 10 | 20 | 40 | 0 | 20 | 40 | 10 | 30 | 15 | 0 | 30 | 75 | 0 |
| Italn. Rygrass | 0 | 0 | 20 | 25 | 95 | 20 | — | 25 | 25 | 20 | 10 | 20 | 20 | 25 | 10 | 30 | 50 | 25 | 50 | 0 | 50 | 90 | 10 | 60 | 40 | 0 | 25 | 30 | 10 |
| Johnsongrass | 30 | 40 | 35 | 30 | 40 | — | 50 | 60 | 40 | 30 | 20 | 35 | 10 | 10 | 10 | 30 | 20 | 25 | 50 | 40 | 50 | 100 | 90 | 50 | 40 | 10 | 50 | 80 | 10 |
| Lambsquarter | 95 | — | 100 | 100 | 100 | 100 | 70 | 95 | 95 | 95 | 60 | 100 | 95 | 100 | 100 | 70 | 85 | 100 | 100 | 100 | 70 | 100 | 100 | 100 | 70 | 85 | 65 | 100 | 30 |
| Morningglory | 60 | 80 | 50 | 100 | 100 | 100 | 100 | 100 | 100 | 10 | 60 | 100 | 100 | 100 | 100 | 100 | 85 | 100 | 100 | 100 | 80 | 100 | 100 | 100 | 100 | 35 | 100 | 100 | 30 |
| Rape | 90 | 95 | 85 | 100 | 100 | 100 | 100 | 100 | 35 | 100 | 0 | 100 | 100 | 100 | 100 | 100 | 85 | 100 | 100 | 100 | 95 | 100 | 100 | 80 | 100 | 60 | 100 | 100 | 0 |
| Redroot Pigweed | 100 | 100 | 100 | 100 | 100 | 100 | 100 | 100 | 90 | 80 | 0 | 100 | 100 | 100 | 100 | 100 | 90 | 100 | 100 | 100 | 95 | 100 | 100 | 90 | 100 | 60 | 100 | 90 | 30 |
| Rice Japonica | 0 | 35 | 15 | 25 | 20 | 20 | 35 | 20 | 10 | 15 | 35 | 0 | 80 | 60 | 35 | 20 | 0 | 50 | 35 | 50 | 40 | 0 | 15 | 40 | 40 | 10 | 0 | 0 | 15 |
| Soybean | 35 | 60 | 35 | 80 | 40 | 35 | — | 20 | 65 | 40 | 0 | 40 | 100 | 60 | 35 | 40 | 25 | 50 | 35 | 50 | 40 | 25 | 25 | 40 | 40 | 30 | 60 | 60 | 0 |
| Speedwell | 80 | 80 | — | 100 | 80 | 100 | 100 | 100 | 100 | 90 | 80 | 100 | 100 | 100 | 100 | 40 | 100 | 100 | 35 | 50 | 40 | 0 | 100 | 70 | 0 | 10 | 100 | 40 | 30 |
| Sugar beet | 100 | 100 | 100 | 100 | 100 | 100 | 100 | 100 | 100 | 100 | 80 | 100 | 100 | 100 | 100 | 100 | 100 | 100 | 100 | 100 | 90 | 100 | 100 | 95 | 100 | 100 | 100 | 100 | 100 |
| *Umbrella sedge | 100 | 100 | 100 | 100 | 25 | 100 | 100 | 100 | 65 | 100 | — | 100 | — | — | — | 0 | — | 0 | — | 0 | 0 | 0 | 0 | 0 | 0 | 100 | 0 | — | — |
| Velvetleaf | 0 | 50 | 0 | 40 | 0 | 0 | — | 15 | 0 | 0 | 60 | 0 | — | 0 | 0 | 0 | 0 | 0 | 0 | 0 | 0 | 0 | 0 | 0 | 0 | 100 | 0 | — | 20 |
| Watergrass 2 | 20 | 40 | 30 | 20 | 15 | 20 | 35 | 20 | 15 | 20 | 10 | 20 | 10 | 10 | 25 | 40 | 30 | 30 | 30 | 25 | 25 | 30 | 25 | 25 | 35 | 35 | 30 | 20 | — |
| Wheat | 95 | 95 | 95 | 100 | 95 | 100 | 100 | 100 | 95 | 70 | 65 | 100 | 100 | 100 | 100 | 80 | 100 | 100 | 100 | 100 | 100 | 100 | 100 | 100 | 100 | 0 | 95 | 90 | 0 |
| Wild buckwheat | 35 | 45 | 35 | 35 | 30 | 25 | — | — | 15 | 10 | 0 | 25 | 10 | 25 | 10 | 25 | 20 | 35 | — | 25 | 30 | 45 | 10 | 25 | 10 | 0 | 25 | 0 | 0 |
| Wild oat | — | — | — | — | — | — | — | — | — | — | — | — | — | — | — | — | — | — | — | — | — | — | — | — | — | — | — | — | — |

Rate 16 g/ha

| COMPOUND | 1 | 2 | 3 | 4 | 5 | 7 | 8 | 9 | 10 | 11 | 12 | 13 | 14 | 20 | 21 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|
| Barley Igri | 30 | 35 | 35 | 25 | 30 | 0 | 0 | 10 | 20 | 20 | 10 | 40 | 25 | 30 | 30 | 30 | 0 | 35 | 15 | 15 | 10 | 10 | 25 | 30 | 20 | 25 | 30 | 30 | 20 |
| Barnyard 2 | 15 | 30 | 10 | 15 | 15 | 0 | 0 | 0 | 0 | 25 | 0 | 0 | 0 | 0 | 10 | 20 | 0 | 0 | 10 | 10 | 10 | 10 | 0 | 0 | 0 | 0 | 0 | 0 | 0 |
| Barnyardgrass | 35 | 30 | 25 | 35 | 35 | 40 | 50 | 30 | 20 | 60 | 50 | 25 | 40 | 30 | 70 | 95 | 30 | 100 | 80 | 60 | 40 | 40 | 90 | 30 | 50 | 15 | 10 | 10 | 10 |
| Bedstraw | 65 | 85 | 95 | 50 | 95 | 20 | — | 30 | 20 | 0 | 40 | 35 | 40 | 90 | 90 | 100 | 95 | 100 | 30 | 40 | 40 | 40 | 50 | 60 | 95 | 90 | 90 | 85 | 100 |
| Blackgrass | 0 | 30 | 10 | 20 | 20 | 40 | 50 | 20 | 20 | 10 | 10 | 30 | 20 | 10 | 10 | 20 | 10 | 20 | 10 | 30 | 10 | 10 | 10 | 10 | 10 | 10 | 10 | 20 | 25 |
| Chickweed | 10 | 45 | 40 | 20 | 60 | 40 | — | 50 | 40 | 45 | 40 | 30 | 55 | 95 | 100 | 100 | 95 | 100 | 50 | 50 | 25 | 0 | 85 | 90 | 100 | 95 | 95 | 80 | 100 |
| Cocklebur | 80 | 90 | 90 | 80 | 90 | 70 | 90 | 60 | 60 | 80 | 30 | 50 | 40 | 100 | 100 | 100 | 100 | 100 | 70 | 80 | 50 | 50 | 100 | 80 | 100 | 60 | 90 | 50 | 100 |
| Corn | 15 | 10 | 15 | 25 | 20 | 10 | 10 | 10 | 10 | 20 | 20 | 25 | 10 | 25 | 35 | 50 | 20 | 20 | 25 | 20 | 10 | 10 | 20 | 25 | 20 | 20 | 20 | 10 | 10 |
| Cotton | 90 | 100 | 100 | 90 | 100 | 90 | 90 | 90 | 70 | 100 | 80 | 90 | 85 | — | 30 | 25 | 100 | 50 | 100 | 100 | 80 | 90 | 100 | 60 | 60 | 20 | 100 | 30 | 100 |
| Crabgrass | 25 | 40 | 30 | 20 | 35 | 20 | 10 | 10 | 10 | 15 | 25 | 25 | 35 | 30 | 0 | 50 | 20 | 50 | 25 | 20 | 15 | 15 | 20 | 60 | 0 | 20 | 10 | 30 | 10 |
| Downy Brome | 20 | 30 | 10 | 25 | 0 | 0 | 0 | 0 | 0 | 0 | 10 | 20 | 15 | 0 | 30 | 25 | 30 | 40 | 10 | 15 | 0 | 0 | 15 | 60 | 35 | 20 | 30 | 0 | 10 |
| Duck salad | 0 | 0 | 30 | 0 | 0 | 0 | 50 | 15 | 0 | 0 | 25 | 30 | 25 | 35 | 0 | 50 | 30 | 40 | 25 | 15 | 20 | 15 | 25 | 50 | 60 | 20 | 30 | 30 | — |
| Giant foxtail | 25 | 50 | 30 | 35 | 40 | 40 | — | 0 | 25 | 20 | 10 | 30 | 25 | 35 | 60 | 50 | 30 | 40 | 90 | 80 | 20 | 15 | 10 | 40 | 35 | 20 | 20 | 30 | 10 |
| Italn. Rygrass | 25 | 10 | 0 | 20 | 15 | 10 | 25 | 15 | 25 | 25 | 25 | 20 | 20 | 20 | 25 | 15 | 20 | 50 | 30 | 30 | 20 | 10 | 10 | 30 | 10 | 10 | 10 | 30 | 10 |
| Johnsongrass | — | 25 | 40 | 30 | 30 | 40 | 30 | 0 | 40 | 20 | 20 | 35 | 20 | 10 | 10 | 50 | 20 | 50 | 30 | 30 | 20 | 10 | 100 | 100 | 100 | 30 | 40 | 20 | 90 |
| *Lambsquarter | 95 | 100 | 95 | 85 | 40 | 70 | 70 | 60 | 60 | 45 | 95 | 100 | 100 | 95 | 100 | 100 | 100 | 100 | 90 | 95 | 60 | 95 | 100 | 100 | 95 | 95 | 100 | 80 | 100 |
| Morningglory | 90 | 100 | 85 | 80 | 90 | 90 | 90 | 90 | 70 | 80 | 30 | 50 | 35 | 100 | 35 | 50 | 100 | 100 | 90 | 90 | 60 | 50 | 100 | 70 | 100 | 60 | 70 | 80 | 100 |
| Rape | 85 | 95 | 10 | 40 | 70 | 10 | 70 | 10 | 10 | 20 | 80 | 90 | 80 | 100 | 0 | 100 | 100 | 100 | 30 | 35 | 70 | 80 | 80 | 80 | 100 | 95 | 90 | 60 | 100 |
| Redroot Pigweed | 80 | 100 | 90 | 90 | 80 | 60 | 60 | — | 50 | 100 | 25 | 100 | 100 | — | 100 | 100 | 100 | 90 | 30 | 100 | 60 | 80 | 95 | 80 | 100 | 70 | 95 | 40 | 100 |
| Rice Japonica | 15 | 30 | 15 | 15 | 25 | 20 | 40 | 20 | 0 | 0 | 10 | 50 | 25 | 20 | 20 | 35 | 25 | 20 | 25 | 20 | 15 | 25 | 40 | 70 | 35 | 60 | 50 | 40 | 0 |
| Soybean | 30 | 50 | 35 | 50 | 35 | 20 | 25 | 0 | 25 | 25 | 35 | 25 | 25 | 25 | 35 | 35 | 35 | 40 | 45 | 80 | 25 | 25 | 85 | 95 | 100 | 75 | 90 | 40 | 100 |
| Sugar beet | 90 | 90 | 100 | 100 | 100 | 70 | 30 | 30 | 50 | 20 | 10 | 80 | 80 | 100 | 100 | 100 | 90 | 100 | 90 | 100 | 30 | 30 | 100 | 100 | 100 | 100 | 100 | 100 | 90 |
| Umbrella sedge | 100 | 100 | 100 | 100 | 95 | 80 | 80 | — | 60 | 100 | 35 | 100 | 100 | 100 | 100 | 100 | 100 | 100 | 100 | 100 | 75 | 95 | 100 | 70 | 100 | 100 | 100 | 100 | — |
| Velvetleaf | 0 | 100 | 100 | 100 | 0 | 0 | 0 | 0 | 0 | 10 | 95 | 10 | 10 | 0 | 100 | 100 | 100 | 0 | 100 | 100 | 10 | 30 | 10 | 20 | 0 | 30 | 40 | 20 | 90 |
| Watergrass 2 | 10 | 30 | 10 | 15 | 15 | 80 | 80 | — | 50 | 100 | 95 | 90 | 100 | 40 | 100 | 20 | 100 | 25 | 25 | 100 | 10 | 50 | 20 | 10 | 25 | 20 | 35 | 85 | — |
| Wheat | 25 | 15 | 25 | 25 | 30 | — | 0 | 0 | 0 | 10 | 10 | 40 | 10 | 10 | 10 | 25 | 0 | 25 | 15 | 10 | 0 | 0 | 10 | 20 | 25 | 30 | 35 | 30 | 0 |

TABLE C-continued

| Wild buckwheat | 65 | 75 | 90 | 100 | 95 | 50 | 40 | 50 | 50 | 70 | 50 | 95 | 95 | 100 | 95 | 70 | 30 | 100 | 80 | 90 | 90 | 100 | 95 | 100 |
|---|---|---|---|---|---|---|---|---|---|---|---|---|---|---|---|---|---|---|---|---|---|---|---|---|
| *Wild oat | 35 | 35 | 25 | 25 | 0 | 20 | 0 | 20 | 10 | 35 | 35 | 30 | 35 | 15 | 10 | 0 | 25 | 20 | 25 | 20 | 10 | 35 | 0 | 0 |

Rate 16 g/ha

| COMPOUND | 8 | 9 | 10 | 11 | 12 | 13 | 14 | 20 | 21 | 22 | 23 | 24 | 25 | 26 | 27 | 28 | 29 | 30 | 31 | 32 | 33 | 34 | 35 | 36 | 37 | 39 | 40 | 41 | 42 |
|---|---|---|---|---|---|---|---|---|---|---|---|---|---|---|---|---|---|---|---|---|---|---|---|---|---|---|---|---|---|
| Barley Igri | 37 | 39 | 40 | 41 | 42 | 43 | 44 | 45 | 46 | 48 | 49 | 52 | 53 | 54 | 56 | 57 | 58 | 60 | 64 | 65 | 68 | 69 | 70 | 73 | 1 | 3 | 4 | 5 | 7 |
| Barnyard 2 | 20 | 15 | 20 | 10 | 30 | 15 | 10 | 0 | 0 | 0 | 25 | 30 | 30 | 25 | 25 | 30 | 0 | 10 | 0 | 10 | 0 | 30 | 0 | 0 | 30 | 30 | 20 | 30 | 0 |
| Barnyardgrass | — | 45 | 50 | 0 | — | 0 | 0 | — | — | 40 | — | 0 | 0 | 35 | 35 | 0 | 20 | 25 | 40 | 30 | 0 | 0 | — | 0 | 35 | 10 | 15 | 10 | 0 |
| Bedstraw | 60 | 100 | 80 | 80 | 90 | 75 | 90 | 50 | 35 | 95 | 80 | 100 | 70 | 95 | 40 | 60 | 20 | 25 | 70 | 30 | 0 | 60 | 70 | 0 | 35 | 10 | 20 | 0 | 0 |
| Blackgrass | 100 | 100 | 100 | 100 | 70 | 75 | 100 | 80 | 0 | 45 | 50 | 85 | 85 | 85 | 85 | 100 | 65 | 40 | 70 | 60 | 0 | 90 | 60 | 0 | 50 | 50 | 50 | 80 | 30 |
| Blackgrass | 25 | 20 | 30 | 20 | 25 | 10 | 25 | 20 | 10 | 10 | 10 | 20 | 20 | 10 | 10 | 15 | 70 | 10 | 10 | 10 | 0 | 10 | 40 | 0 | 0 | 50 | 20 | 10 | 0 |
| Chickweed | 100 | 100 | 95 | 100 | 100 | 95 | 100 | 80 | 0 | 20 | 80 | 95 | 100 | 95 | 50 | 60 | 70 | 90 | 100 | 20 | 30 | 90 | 95 | 10 | 0 | 10 | 20 | 15 | 20 |
| Cocklebur | 100 | 90 | 100 | 100 | 100 | 30 | 55 | 25 | 50 | 45 | 90 | 100 | 100 | 100 | 70 | 30 | 10 | 10 | 100 | 90 | 30 | 65 | 70 | 5 | 75 | 90 | 50 | 85 | 50 |
| Corn | 10 | 35 | 25 | 10 | 20 | 45 | 25 | 80 | 10 | 40 | 20 | 30 | 15 | 15 | 10 | 35 | 10 | 10 | 10 | 5 | 30 | 15 | 15 | 10 | 100 | 90 | 40 | 50 | 20 |
| Cotton | 100 | 100 | 100 | 100 | 100 | 25 | 10 | 25 | 100 | 100 | 100 | 100 | 100 | 100 | 70 | 100 | 100 | 100 | 100 | 100 | 80 | 100 | 90 | 100 | 100 | 100 | 100 | 100 | 60 |
| Crabgrass | 15 | 35 | 50 | 20 | 20 | 20 | 55 | 100 | 25 | 30 | 15 | 20 | 30 | 40 | 40 | 60 | 20 | 10 | 20 | 40 | 10 | 25 | 0 | 10 | 25 | 30 | 20 | 30 | 0 |
| Downy Brome | 20 | 10 | 30 | 0 | 10 | 15 | 30 | 100 | 100 | 0 | 100 | 100 | 100 | 100 | 10 | 60 | 0 | 10 | 25 | 0 | 80 | 100 | 90 | 0 | 10 | 10 | 10 | 15 | 100 |
| Duck salad | — | 50 | 10 | 0 | — | 0 | 10 | 0 | 0 | 0 | 0 | 20 | 30 | 0 | 0 | 0 | 0 | 0 | 0 | 0 | 0 | 0 | 0 | 0 | 25 | 35 | 10 | 15 | 10 |
| Giant foxtail | 15 | 50 | 50 | 20 | 30 | 40 | 25 | — | 30 | 15 | 30 | 30 | 35 | 30 | 50 | 20 | 10 | 20 | 15 | 10 | 20 | 60 | 10 | 0 | 20 | 0 | 30 | 0 | — |

Rate 8 g/ha

| Sugar beet | 100 | 100 | 100 | 100 | 100 | 100 | 90 | — | 100 | 60 | 100 | 100 | 100 | 100 | 100 | 20 | 100 | 100 | 100 | — | 65 | 100 | — | 0 | | | | | |
| Umbrella sedge | — | 0 | 0 | — | — | 0 | 0 | — | 100 | — | 100 | 100 | 100 | 100 | — | 100 | 100 | 100 | 0 | 0 | 0 | 0 | — | 0 | | | | | |
| Velvetleaf | 100 | 100 | 100 | 100 | 100 | 100 | 0 | — | 100 | 80 | 100 | 100 | 100 | 90 | 90 | 100 | 100 | 100 | 100 | 90 | 90 | 100 | 100 | 0 | | | | | |
| Watergrass 2 | — | 65 | 50 | — | — | 10 | 25 | 90 | 0 | 45 | — | 25 | 20 | 20 | 20 | 20 | 30 | 10 | 25 | 25 | — | 25 | 15 | 0 | | | | | |
| Wheat | 0 | 20 | 15 | 20 | 35 | 10 | 0 | 0 | 30 | 0 | 30 | 100 | 100 | 100 | 95 | 100 | 100 | 100 | 85 | 100 | — | 85 | 80 | 0 | | | | | |
| Wild buckwheat | 100 | 90 | 100 | 100 | 95 | 100 | 90 | 90 | 70 | 65 | 95 | 100 | 100 | 100 | 20 | 100 | 100 | 10 | 0 | 100 | — | 25 | 0 | 0 | | | | | |
| Wild oat | 25 | 20 | 15 | 10 | 0 | 10 | 100 | 0 | 0 | 15 | 10 | 30 | 0 | 0 | 40 | 45 | 0 | 0 | 0 | 0 | — | 0 | — | 0 | | | | | |

Rate 8 g/ha

| COMPOUND | 8 | 9 | 10 | 11 | 12 | 13 | 14 | 20 | 21 | 22 | 23 | 24 | 25 | 26 | 27 | 28 | 29 | 30 | 31 | 32 | 33 | 34 | 35 | 36 | 37 | 39 | 40 | 41 | 42 |
|---|---|---|---|---|---|---|---|---|---|---|---|---|---|---|---|---|---|---|---|---|---|---|---|---|---|---|---|---|---|
| Barley Igri | 0 | 0 | 10 | 20 | 10 | 35 | 20 | 30 | 10 | 40 | 30 | 0 | 35 | 10 | 10 | 0 | 0 | 20 | 30 | 30 | 25 | 30 | 30 | 10 | 20 | 10 | 10 | 0 | 30 |
| Barnyard 2 | 0 | 0 | 0 | 25 | 0 | 0 | 0 | 0 | 0 | — | 15 | 0 | 0 | 10 | 10 | 10 | 10 | 10 | 0 | 0 | 0 | 0 | 0 | — | — | 35 | 40 | 0 | — |
| Barnyardgrass | 0 | 0 | 0 | 50 | 30 | 20 | 25 | 20 | 60 | 95 | 75 | 20 | 70 | 75 | 40 | 30 | 30 | 80 | 20 | 40 | 10 | 10 | 10 | 10 | 45 | 70 | 80 | 60 | 70 |
| Bedstraw | 20 | 0 | 20 | 0 | 40 | 20 | 20 | 20 | 10 | 45 | 100 | 95 | 85 | 30 | 25 | 25 | 40 | 50 | 60 | 60 | 80 | 60 | 85 | 100 | 70 | 909 | 80 | 100 | 70 |
| Blackgrass | 0 | 0 | 0 | 10 | 10 | 25 | 10 | 20 | 10 | 10 | 10 | 0 | 20 | 30 | 50 | 30 | 50 | 10 | 0 | 10 | 0 | 10 | 10 | 10 | 25 | 10 | 25 | 10 | 10 |
| Chickweed | — | 20 | 0 | 35 | 10 | 30 | 55 | 80 | 100 | 90 | 100 | 100 | 70 | 70 | 50 | 30 | 50 | 100 | 70 | 100 | 65 | 95 | 30 | 100 | 75 | 90 | 95 | 100 | 95 |
| Cocklebur | 70 | 40 | 60 | 70 | 20 | 45 | 25 | 80 | 100 | 100 | 100 | 100 | 100 | 50 | 70 | 30 | 100 | 100 | 100 | 100 | 60 | 70 | 10 | 100 | 100 | 90 | 100 | 100 | 100 |
| Corn | 10 | 10 | 10 | 10 | 20 | 25 | 10 | 25 | 25 | 30 | 15 | 10 | 10 | 15 | 15 | 30 | 50 | 0 | 15 | 15 | 15 | 15 | 10 | 5 | 5 | 20 | 15 | 10 | 15 |
| Cotton | 60 | 70 | 90 | 90 | 80 | 85 | 55 | 100 | 100 | 100 | 100 | 100 | 100 | 90 | 90 | 60 | 50 | 95 | 100 | 100 | 80 | 100 | 90 | 100 | 100 | 100 | 100 | 100 | 100 |
| Crabgrass | 10 | 10 | 10 | 10 | 20 | 25 | 30 | 25 | 30 | 0 | 50 | 15 | 35 | 10 | 20 | 60 | 50 | 15 | 50 | 40 | 10 | 10 | 20 | 10 | 15 | 10 | 10 | 15 | 15 |
| Downy Brome | 0 | 0 | 0 | 10 | 0 | 20 | 10 | 20 | 0 | 0 | 10 | 15 | 0 | 10 | 15 | 0 | 0 | 0 | 0 | 0 | 0 | 10 | 10 | 0 | 0 | 0 | 10 | 0 | 10 |
| Duck salad | 0 | 0 | 0 | 0 | 0 | 0 | 0 | 0 | 0 | — | 0 | 0 | 0 | 0 | 0 | 0 | 0 | 0 | 0 | 0 | 0 | 0 | 0 | — | — | 0 | 0 | — | — |

TABLE C-continued

Rate 8 g/ha

| COMPOUND | 5 | 10 | 15 | 20 | 25 | 30 | 35 | 40 |
|---|---|---|---|---|---|---|---|---|
| Giant foxtail | 5 | 10 | 0 | 20 | 15 | 30 | 15 | 40 |
| Italn. Rygrass | 0 | 0 | 0 | 0 | 0 | 0 | 0 | 0 |
| Johnsongrass | 0 | 0 | 0 | 10 | 10 | 25 | 10 | 10 |
| Lambsquarter | 40 | 20 | 50 | 95 | 100 | — | 30 | 100 |
| Morningglory | 40 | 100 | 20 | 80 | 30 | 50 | 100 | 100 |
| Rape | 10 | 0 | 20 | 80 | 65 | 90 | 100 | 100 |
| Redroot Pigweed | 40 | 20 | — | 90 | 100 | 100 | 100 | 100 |
| Rice Japonica | 0 | 0 | 0 | 25 | 0 | 0 | 25 | 25 |
| Soybean | 20 | 20 | 20 | 20 | 0 | 50 | 35 | 30 |
| Speedwell | — | 0 | 20 | 0 | 30 | 80 | 35 | 100 |
| Sugar beet | 0 | — | — | 100 | 100 | 100 | 100 | 100 |
| *Umbrella sedge | 0 | 0 | 60 | 0 | 0 | 0 | 0 | 0 |
| Velvetleaf | 60 | 50 | 0 | 100 | 95 | 100 | — | 100 |
| Watergrass 2 | 0 | — | 0 | 10 | 0 | 0 | 0 | 15 |
| Wheat | 0 | 0 | 0 | 10 | 25 | 20 | 35 | 25 |
| Wild buckwheat | 30 | 30 | 40 | 70 | 25 | 85 | 100 | 100 |
| Wild oat | 10 | 0 | 10 | 10 | 10 | 35 | 30 | 15 |

| COMPOUND | 43 | 44 | 45 | 46 | 48 | 49 | 52 | 53 | 54 | 56 | 57 | 58 | 60 | 64 | 65 | 68 | 69 | 70 | 73 |
|---|---|---|---|---|---|---|---|---|---|---|---|---|---|---|---|---|---|---|---|
| Barley Igri | 10 | 10 | — | 0 | 0 | 20 | 30 | 20 | 30 | 25 | 25 | 0 | 0 | 0 | 10 | 0 | 30 | 0 | 0 |
| Barnyard 2 | 0 | 80 | 30 | 0 | 0 | — | 0 | 60 | 95 | 15 | 30 | 10 | — | 30 | 20 | 0 | 50 | — | 0 |
| Barnyardgrass | 30 | 90 | 60 | 25 | 40 | 50 | 70 | 60 | 80 | 85 | 95 | 65 | 10 | 70 | 40 | 0 | — | 70 | 0 |
| Bedstraw | 40 | 90 | 0 | 0 | 0 | 50 | 50 | 70 | 20 | 10 | 15 | 45 | 20 | 10 | 0 | 0 | 0 | 20 | 20 |
| Blackgrass | 0 | 10 | 35 | 10 | 20 | 10 | 10 | 0 | 30 | 10 | 30 | 100 | 70 | 90 | 20 | 0 | 90 | 90 | 0 |
| Chickweed | 90 | 90 | — | 0 | 0 | 60 | 75 | 70 | 90 | 30 | 60 | 45 | 100 | 10 | 5 | 0 | 100 | 30 | 0 |
| Cocklebur | 100 | 100 | 100 | 50 | 30 | 50 | 100 | 100 | 100 | 70 | 80 | 100 | 5 | 90 | 50 | 20 | 100 | 100 | 0 |
| Corn | 5 | 10 | 5 | 75 | 0 | 10 | 20 | 10 | 10 | 10 | 20 | 10 | 0 | 100 | 20 | 70 | 10 | 0 | 0 |
| Cotton | 100 | 100 | 100 | 0 | 60 | 100 | 100 | 100 | 100 | 70 | 100 | 20 | 100 | 15 | 90 | 20 | 100 | 100 | 25 |
| Crabgrass | 20 | 10 | 10 | 90 | 20 | 15 | 20 | 20 | 30 | 10 | 40 | 0 | 5 | 10 | 5 | 10 | 35 | 0 | 25 |
| Downy Brome | 10 | 100 | 0 | 0 | 0 | 0 | 10 | 0 | 0 | 10 | 40 | 20 | 0 | 15 | 50 | 10 | 0 | 0 | 0 |
| Duck salad | 0 | 0 | — | 10 | 0 | — | 10 | 0 | 30 | 10 | 0 | 0 | 10 | 10 | 10 10 | 20 | 0 | 35 | 0 |
| Giant foxtail | 20 | 15 | 15 | 10 | 20 | 10 | 25 | 20 | 30 | 20 | 50 | 15 | 0 | 15 | 10 | 0 | 20 | 0 | 0 |
| Johnsongrass | 30 | 0 | 0 | 0 | 0 | 0 | 15 | 30 | 30 | 0 | 0 | 10 | 10 | 0 | 0 | 0 | 30 | 40 | 0 |
| Italn. Rygrass | 20 | 25 | 0 | 10 | — | 30 | 100 | 100 | 100 | 20 | 60 | 80 | 60 | 85 | 50 | 0 | 65 | 70 | 0 |
| Lambsquarter | 90 | 95 | 100 | 50 | 70 | 70 | 100 | 100 | 100 | 60 | 95 | 100 | 70 | 100 | 60 | 20 | 100 | 100 | 0 |
| Morningglory | 100 | 100 | 100 | 75 | 25 | 70 | 100 | 100 | 100 | — | 90 | 80 | 100 | 100 | 100 | 40 | 100 | 100 | 20 |
| Rape | 100 | 100 | 100 | 0 | 30 | 95 | 100 | 100 | 100 | 70 | 60 | 80 | 90 | 85 | 60 | 10 | 100 | 70 | 0 |
| Redroot Pigweed | 0 | 0 | 90 | 80 | 20 | 50 | 100 | 70 | 90 | 30 | 60 | 80 | 0 | 90 | 60 | 65 | 80 | 100 | 0 |
| Rice Japonica | 25 | 25 | 0 | 20 | 20 | 15 | 50 | 30 | 40 | 20 | 80 | 15 | 15 | 20 | 20 | 80 | 50 | 50 | 10 |
| Soybean | — | 90 | 10 | 20 | 20 | 75 | 100 | 100 | 100 | 20 | 95 | 55 | 95 | 50 | 80 | 0 | 100 | 90 | 0 |
| Speedwell | 100 | 80 | 100 | 30 | — | 100 | 100 | 100 | 100 | 15 | 100 | 100 | 95 | 100 | — | 0 | 100 | — | 0 |
| Sugar beet | 0 | 0 | — | 0 | — | — | 0 | 0 | — | — | — | — | 0 | 0 | 0 | — | — | 0 | — |
| Umbrella sedge | 100 | 100 | 100 | 80 | 0 | 90 | 100 | 100 | 100 | 10 | 25 | 85 | 90 | 0 | 50 | 0 | 25 | 10 | 0 |
| Velvetleaf | — | 0 | — | 0 | — | — | — | 10 | 10 | 95 | 100 | 0 | 100 | — | 100 | 0 | — | 80 | 0 |
| Watergrass 2 | 0 | 0 | 0 | 0 | 0 | 10 | 20 | 100 | 100 | 15 | 35 | 0 | 90 | 0 | 0 | 0 | — | 0 | 0 |
| Wheat | 100 | 90 | 80 | 30 | 40 | 80 | 100 | 100 | 0 | 10 | 25 | 0 | 0 | 0 | 100 | 0 | 20 | 0 | 0 |
| Wild buckwheat | 10 | 100 | 0 | 0 | 0 | 0 | 30 | 100 | 0 | 15 | 35 | 0 | 0 | 0 | 0 | 0 | 0 | 0 | 0 |

Rate 4 g/ha

| COMPOUND | 21 | 22 | 23 | 24 | 25 | 26 | 27 | 28 | 29 | 30 |
|---|---|---|---|---|---|---|---|---|---|---|
| Barley Igri | 20 | 40 | 25 | 0 | 20 | 0 | 0 | 0 | 0 | 20 |
| Barnyard 2 | 10 | — | 15 | 10 | 50 | 10 | 10 | 10 | 10 | 0 |
| Barnyardgrass | 60 | 75 | 60 | 80 | 85 | 35 | 30 | 20 | 20 | 60 |
| Bedstraw | 40 | 45 | 95 | 70 | 20 | 10 | 10 | 20 | 10 | 30 |
| Blackgrass | 10 | 10 | 20 | 5 | 100 | 30 | 10 | 0 | 0 | 10 |
| Chickweed | 100 | 35 | 90 | 90 | 10 | 30 | 30 | 30 | 0 | 65 |
| Cocklebur | 100 | 100 | 100 | 100 | 100 | 80 | 60 | 0 | 30 | 90 |
| Corn | 15 | 30 | 10 | 5 | 10 | 10 | 5 | 10 | 0 | 10 |
| Cotton | 100 | 100 | 100 | 90 | 100 | 80 | 90 | 40 | 40 | 90 |
| Crabgrass | 35 | 35 | 10 | 30 | 10 | 10 | 0 | 10 | 10 | 0 |
| Downy Brome | 0 | 0 | 0 | 10 | 0 | 10 | 0 | 0 | 0 | 0 |
| Duck salad | 0 | — | 40 | 0 | 25 | 10 | 10 | 10 | 10 | 10 |
| Giant foxtail | 35 | 25 | 0 | 10 | 20 | 10 | 10 | 10 | 10 | 10 |
| *Italn. Rygrass | 35 | 30 | 15 | 10 | 20 | 20 | 10 | 20 | 35 | 80 |
| Johnsongrass | 100 | 100 | 100 | 90 | 95 | 85 | 90 | 80 | 25 | 95 |
| Lambsquarter | 100 | 100 | 100 | 70 | 100 | 85 | 90 | 35 | 50 | 85 |
| Morningglory | 0 | — | 95 | 5 | 80 | 0 | 0 | 30 | 0 | 40 |
| Rape | 100 | 40 | 20 | 90 | 25 | 70 | 65 | 0 | 0 | 0 |
| Redroot Pigweed | 0 | 100 | 15 | 70 | 10 | 15 | 20 | 10 | 0 | 20 |
| Rice Japonica | 35 | 40 | 90 | 15 | 25 | 10 | 40 | 0 | 0 | 60 |
| Soybean | 100 | 100 | 100 | 95 | 100 | 80 | 0 | 0 | 0 | 100 |
| Speedwell | 100 | 100 | 100 | 90 | — | 90 | 95 | 20 | 10 | 0 |
| Sugar beet | 0 | — | 0 | 0 | 10 | 10 | 0 | 0 | 0 | 10 |
| Umbrella sedge | 20 | 20 | 15 | — | 100 | 10 | 80 | 20 | 0 | 0 |
| Velvetleaf | 100 | 100 | 100 | 0 | 0 | 10 | 10 | 10 | 10 | 0 |
| Watergrass 2 | 0 | — | 15 | — | — | 70 | 30 | 0 | 0 | 0 |
| Wheat | 20 | 20 | 10 | 0 | 100 | 10 | 0 | 25 | 10 | 95 |
| Wild buckwheat | 100 | 100 | 0 | 0 | 0 | 10 | 0 | 0 | 10 | 25 |
| Wild oat | 10 | 40 | 15 | 0 | 0 | 10 | 0 | 0 | 0 | |

TABLE C-continued

Rate 4 g/ha

| COMPOUND | 31 | 32 | 33 | 34 | 35 | 36 | 37 | 39 | 40 | 41 | 42 | 43 | 44 | 46 | 48 | 49 | 52 | 53 | 54 | 56 | 57 | 58 | 60 | 64 | 68 | 69 | 70 | 73 | Rate 2 g/ha 21 |
|---|---|---|---|---|---|---|---|---|---|---|---|---|---|---|---|---|---|---|---|---|---|---|---|---|---|---|---|---|---|
| Barley Igri | 30 | 0 | 10 | 25 | 25 | 10 | 10 | 10 | 10 | 0 | 25 | 0 | 10 | 0 | 0 | 0 | 25 | 10 | 0 | 0 | 25 | 0 | 0 | 0 | 0 | 30 | 0 | 0 | 10 |
| Barnyard 2 | 0 | 0 | 0 | 0 | 0 | — | — | 20 | 30 | 0 | — | 0 | 0 | 0 | 0 | — | 0 | 0 | 0 | 0 | 0 | 0 | — | 0 | 0 | 0 | — | 0 | 0 |
| Barnyardgrass | 20 | 30 | 10 | 10 | 0 | 10 | 40 | 50 | 70 | 30 | 50 | 25 | 60 | 10 | 20 | 35 | 50 | 30 | 70 | 10 | 10 | 10 | 10 | 10 | 0 | 35 | 40 | 0 | 35 |
| Bedstraw | 60 | 80 | 40 | 60 | 80 | 40 | 40 | 90 | 80 | 70 | 50 | 0 | 90 | 10 | 0 | 50 | 50 | 60 | 70 | 0 | 95 | 65 | 10 | 50 | 0 | 75 | 30 | 0 | 40 |
| Blackgrass | 0 | 0 | 0 | 0 | 10 | 0 | 20 | 10 | 80 | 10 | 5 | 0 | 10 | 0 | 0 | 60 | 10 | 0 | 20 | 0 | 10 | 0 | 0 | 0 | 0 | 0 | 10 | 0 | 10 |
| Chickweed | 70 | 95 | 65 | 70 | 45 | 70 | 75 | 70 | 80 | 100 | 85 | 90 | 90 | 0 | 30 | 30 | 30 | 55 | 80 | 85 | 55 | 45 | 40 | 85 | 0 | 85 | 10 | 0 | 80 |
| Cocklebur | 50 | 100 | 40 | 40 | 20 | 100 | 5 | 90 | 100 | 5 | 100 | 0 | 10 | 0 | 0 | 60 | 100 | 90 | 100 | 0 | 80 | 70 | 100 | 75 | 0 | 100 | — | 0 | 100 |
| Corn | 15 | 0 | 10 | 10 | 10 | 5 | 5 | 15 | 0 | 100 | 5 | 5 | 5 | 0 | 30 | 10 | 15 | 10 | 0 | 10 | 20 | 0 | 0 | 5 | 40 | 5 | 20 | 0 | 15 |
| Cotton | 100 | 100 | 80 | 90 | 85 | 90 | 100 | 100 | 100 | 100 | 100 | 100 | 100 | 90 | 50 | 90 | 100 | 100 | 100 | 0 | 80 | 100 | 100 | 100 | 5 | 100 | 80 | 0 | 100 |
| Crabgrass | 35 | 25 | 10 | 15 | 15 | 10 | 15 | 25 | 30 | 5 | 10 | 0 | 10 | 10 | 10 | 90 | 20 | 10 | 20 | 10 | 15 | 15 | 0 | 10 | 5 | 20 | 35 | 0 | 25 |
| Downy Brome | 0 | 0 | 0 | 0 | 0 | 0 | 0 | 0 | 10 | 0 | 0 | 0 | 0 | 0 | 0 | 0 | 10 | 0 | 0 | 0 | 10 | 0 | 0 | 0 | 0 | 0 | 0 | 0 | 0 |
| Giant foxtail | 40 | 40 | 10 | 15 | 0 | — | 10 | 30 | 10 | 10 | 15 | 10 | 15 | 0 | 10 | — | 15 | 15 | 25 | 0 | 20 | 10 | 10 | 10 | 0 | 15 | 35 | 0 | 25 |
| Italn. Rygrass | 0 | 0 | 0 | 0 | 0 | 10 | 0 | 0 | 10 | 0 | 0 | 0 | 0 | 0 | 0 | 5 | 0 | 0 | 0 | 0 | 25 | 0 | 0 | 0 | 0 | 0 | 0 | 0 | 0 |
| Johnsongrass | 15 | 5 | 20 | 20 | 10 | 10 | 0 | 15 | 30 | 10 | 5 | 10 | 15 | 0 | 0 | 20 | 10 | 0 | 20 | 0 | 30 | 10 | 0 | 10 | 0 | 20 | 0 | 0 | 30 |
| Lambsquarter | 100 | 100 | 80 | 90 | 90 | 70 | 100 | 100 | 100 | 100 | 100 | 100 | 90 | 50 | 0 | 70 | 100 | 85 | 95 | 0 | 85 | 75 | 45 | 80 | 0 | 60 | 30 | 0 | 100 |
| Morningglory | 90 | 100 | 80 | 90 | 90 | 70 | 100 | 100 | 100 | 100 | 100 | 100 | 100 | 35 | 50 | 70 | 100 | 100 | 100 | 0 | 80 | 50 | 100 | 100 | 20 | 100 | 50 | 0 | 100 |
| Rape | 30 | 100 | 65 | 40 | 10 | 80 | 100 | 95 | 100 | 100 | 100 | 100 | 100 | 0 | 10 | 95 | 95 | 60 | 100 | 0 | 30 | 95 | 90 | 85 | 0 | 100 | 100 | 0 | 100 |
| Redroot Pigweed | 45 | 100 | 60 | 70 | 50 | 70 | 90 | 100 | 100 | 100 | 85 | 100 | 100 | 0 | 20 | 40 | 95 | 60 | 80 | 0 | 90 | 70 | 85 | 80 | 30 | 70 | 70 | 0 | 100 |
| Rice Japonica | 0 | 0 | 0 | 0 | 0 | — | — | 20 | 25 | 0 | — | 0 | 0 | 0 | 0 | — | 0 | 0 | 0 | 0 | 0 | 0 | — | 0 | 0 | 0 | — | 0 | 0 |
| Soybean | 50 | 25 | 40 | 40 | 30 | 50 | 50 | 30 | 35 | 10 | 10 | 20 | 20 | 10 | 10 | 10 | 35 | 25 | 35 | 0 | 50 | 15 | 10 | 10 | 30 | 40 | 40 | 0 | 25 |
| Speedwell | 90 | — | 10 | 70 | 60 | 90 | 90 | 100 | 95 | 80 | 90 | 100 | 90 | 0 | 10 | 65 | 100 | 95 | 95 | 0 | 90 | 10 | 60 | 50 | 10 | 100 | 90 | 0 | 70 |
| Sugar beet | 95 | 100 | — | 100 | 95 | 80 | 95 | 100 | 100 | 100 | 100 | 100 | 70 | 0 | 10 | 65 | 100 | 100 | 100 | 0 | 10 | 45 | 95 | 100 | 0 | 80 | — | 0 | 100 |
| Umbrella sedge | 0 | 0 | 0 | 0 | 0 | — | — | 0 | 0 | 0 | 0 | 0 | 0 | 0 | 0 | — | 0 | 0 | 0 | 0 | 0 | 0 | — | 0 | 0 | 0 | — | 0 | 0 |
| Velvetleaf | 60 | 100 | 60 | 70 | 60 | 100 | 100 | 100 | 100 | 100 | 100 | 100 | 100 | 60 | 40 | 50 | 100 | 100 | 100 | 0 | 90 | 90 | 100 | 100 | 40 | 90 | 100 | 0 | 100 |
| Watergrass 2 | — | — | — | — | — | — | — | — | — | — | — | — | — | — | — | — | — | — | — | — | — | — | — | — | — | — | — | — | — |
| Wheat | 0 | 0 | 10 | 25 | 25 | 0 | 0 | 25 | 20 | 0 | 20 | 0 | 0 | 0 | 0 | 10 | 10 | 0 | 0 | 0 | 15 | 0 | 0 | 0 | 0 | 25 | 0 | 0 | 15 |
| Wild buckwheat | 30 | 90 | 75 | 80 | 90 | 70 | 90 | 90 | 90 | 90 | 90 | 90 | — | 0 | 20 | 60 | 95 | 95 | 0 | 0 | 95 | 65 | 70 | 85 | 0 | 70 | 50 | 0 | 100 |
| Wild oat | 20 | 10 | 10 | 0 | 0 | 0 | 0 | 10 | 10 | 0 | 0 | 10 | 20 | 0 | 0 | 0 | 25 | 0 | 0 | 0 | 30 | 0 | 0 | 0 | 0 | 10 | 0 | 0 | 10 |

Rate 2 g/ha

| COMPOUND | 22 | 23 | 24 | 25 | 26 | 28 | 30 | 31 | 32 | 33 | 34 | 35 | 39 | 40 | 41 | 42 | 43 | 44 | 46 | 48 | 52 | 53 | 54 | 56 | 57 | 58 | Rate 1 g/ha 21 | 22 | 39 |
|---|---|---|---|---|---|---|---|---|---|---|---|---|---|---|---|---|---|---|---|---|---|---|---|---|---|---|---|---|---|
| Barley Igri | 35 | 10 | 0 | 0 | 0 | 0 | 10 | 10 | 0 | 0 | 20 | 0 | 0 | 0 | 0 | 10 | 0 | 10 | 0 | 0 | 20 | 10 | 0 | — | — | 0 | 10 | 30 | 0 |
| Barnyard 2 | — | 15 | 0 | 0 | 10 | 0 | 0 | 0 | 0 | 0 | 0 | 0 | 10 | 20 | 0 | — | 0 | 0 | 20 | 0 | 0 | 0 | 50 | 0 | 0 | 0 | 0 | — | 0 |
| Barnyardgrass | 60 | 50 | 10 | 40 | 20 | 0 | 30 | 10 | 20 | 10 | 10 | 0 | 40 | 20 | 20 | 30 | 20 | 30 | 20 | 0 | 35 | 20 | 50 | — | — | 0 | 30 | 50 | 30 |
| Bedstraw | 40 | 85 | 80 | 55 | 0 | 0 | 30 | 30 | 75 | 40 | 40 | 0 | 75 | 80 | 40 | 30 | — | 80 | 0 | 0 | 10 | 30 | 70 | — | — | 50 | 40 | 30 | 70 |
| Blackgrass | 10 | 10 | 0 | 10 | 0 | 0 | 10 | 0 | 0 | 0 | 0 | 0 | 10 | 20 | 0 | 5 | 0 | 0 | 0 | 0 | 0 | 0 | 20 | — | — | 0 | 0 | 10 | 0 |
| Chickweed | 20 | 75 | 10 | 70 | 60 | 0 | 60 | 70 | 70 | 65 | 50 | 40 | 60 | 76 | 65 | 65 | 40 | 90 | 0 | 20 | 30 | 50 | 75 | — | — | 35 | 20 | 70 | 50 |
| Cocklebur | 80 | 100 | 70 | 100 | 0 | 0 | 40 | 35 | 100 | 30 | 20 | 20 | 90 | 90 | 80 | 5 | 20 | 100 | 0 | 0 | 100 | 75 | 100 | — | — | 70 | 90 | 25 | 90 |
| Corn | 25 | 10 | 0 | 0 | 0 | 0 | 0 | 0 | 0 | 0 | 5 | 0 | 10 | 10 | 5 | 5 | 5 | 5 | 10 | 20 | 10 | 10 | 5 | — | — | 0 | 10 | 10 | 50 |
| Cotton | 100 | 100 | 90 | 100 | 60 | 25 | 80 | 90 | 70 | 70 | 80 | 0 | 100 | 90 | 100 | 100 | 80 | 100 | 30 | 40 | 90 | 90 | 100 | 0 | 0 | 90 | 100 | 25 | 100 |
| Crabgrass | 30 | 25 | 5 | 10 | 10 | 0 | 10 | 25 | 15 | 5 | 15 | 10 | 20 | 20 | 20 | 5 | 10 | 0 | 0 | 0 | 20 | 0 | 20 | — | — | 10 | 20 | 0 | 10 |
| Downy Brome | — | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | — | 0 | 0 | — | 0 |
| Duck salad | — | — | 0 | 0 | 0 | 0 | 0 | 10 | 0 | 0 | 0 | 0 | 0 | 0 | 0 | — | 0 | 0 | 0 | 0 | 0 | 0 | 0 | 0 | 0 | 0 | 0 | — | 0 |

TABLE C-continued

| | | | | | | | | | | | | | | | | | | | | | | | |
|---|---|---|---|---|---|---|---|---|---|---|---|---|---|---|---|---|---|---|---|---|---|---|---|
| Giant foxtail | 20 | 35 | 10 | 20 | 0 | 0 | 0 | 20 | 35 | 10 | 10 | 25 | 30 | 10 | 10 | 10 | 10 | 10 | 0 | 10 | — | — | 5 | 20 | 10 | 20 |
| Italn. Rygrass | 0 | 0 | 0 | 0 | 0 | 0 | 0 | 0 | 0 | 0 | 0 | 0 | 0 | 0 | 0 | 0 | 0 | 10 | 0 | 10 | — | — | 0 | 0 | 0 | 0 |
| Johnsongrass | 25 | 10 | 10 | 10 | 10 | 10 | 10 | 10 | 5 | 15 | 10 | — | 20 | 20 | 5 | 10 | 0 | 10 | 10 | 20 | — | — | 45 | 20 | 25 | 10 |
| Lambsquarter | 95 | 100 | 70 | 95 | 85 | 40 | 80 | 80 | 95 | 35 | 45 | 90 | 100 | 70 | 50 | 65 | 90 | 95 | 45 | 0 | — | — | 45 | 30 | 95 | 90 |
| Morningglory | 85 | 100 | 40 | 100 | 65 | 15 | 95 | 30 | 100 | 40 | 70 | 100 | 100 | 100 | 100 | 90 | 95 | 95 | 20 | 10 | — | — | 30 | 100 | 70 | 95 |
| Rape | 100 | 95 | 90 | 100 | 0 | 0 | 70 | 40 | 100 | 50 | 40 | 100 | 100 | 100 | 100 | 100 | 100 | 100 | 10 | 75 | — | — | 70 | 100 | 90 | 90 |
| Redroot Pigweed | 100 | 100 | 70 | 80 | 35 | 20 | 10 | 0 | 95 | 50 | 60 | 100 | 90 | 85 | 80 | 100 | 80 | 95 | 10 | 95 | — | — | 60 | 100 | 85 | 100 |
| Rice Japonica | — | 20 | 0 | 0 | 15 | 10 | 0 | 0 | 0 | 30 | 0 | 15 | 0 | 0 | 0 | 0 | 0 | 0 | 0 | 0 | — | — | 0 | 0 | 0 | 10 |
| Soybean | 35 | 15 | 10 | 20 | 0 | 0 | 15 | 40 | 20 | 10 | 40 | 30 | 10 | 10 | 15 | 5 | 15 | 30 | 0 | 20 | 0 | 0 | 10 | 20 | 35 | 25 |
| Speedwell | 90 | 85 | 10 | 95 | 70 | 0 | 30 | 55 | 80 | 30 | 55 | 100 | 80 | 60 | 75 | 30 | 80 | 90 | 0 | 90 | — | — | 10 | 70 | 80 | 70 |
| Sugar beet | 100 | 100 | 70 | 100 | 90 | 0 | 100 | 50 | 55 | 10 | 100 | 80 | 100 | 100 | 60 | 100 | 100 | 100 | 0 | 100 | — | — | 40 | 100 | 95 | 70 |
| Umbrella sedge | — | 0 | 0 | 0 | 0 | 0 | 0 | 0 | 0 | 90 | 0 | 0 | 0 | 0 | 100 | 100 | 0 | 0 | 30 | 0 | — | — | 0 | 0 | 0 | 0 |
| Velvetleaf | 100 | 100 | 90 | 100 | 40 | 10 | 70 | 40 | 100 | 20 | 60 | 100 | 100 | 100 | 100 | 100 | 80 | 100 | 0 | 80 | 0 | 0 | 60 | 100 | 40 | 100 |
| Watergrass 2 | — | 10 | 0 | — | 10 | 10 | 0 | — | 0 | — | — | 15 | 10 | — | — | — | — | 0 | 10 | 0 | — | — | — | 0 | — | — |
| Wheat | 20 | 10 | 0 | 0 | 0 | 10 | 0 | 0 | 0 | 0 | 0 | 10 | 0 | 0 | 0 | 0 | 0 | 0 | 20 | 0 | 0 | 0 | 0 | 20 | 0 | 10 |
| Wild buckwheat | 95 | 100 | 55 | 100 | 45 | 10 | 90 | 30 | 85 | 65 | 75 | 80 | 80 | 80 | 80 | 95 | 95 | 80 | 20 | 95 | — | — | 65 | 85 | 90 | 65 |
| Wild oat | 35 | 10 | 0 | 0 | 0 | 0 | 10 | 10 | 0 | 0 | 0 | 10 | 10 | 10 | 10 | 0 | 0 | 15 | 0 | 0 | — | — | 0 | 0 | 25 | 0 |

| COMPOUND | Rate 1 g/ha 40 |
|---|---|
| Barley Igri | 0 |
| Barnyard 2 | 10 |
| Barnyardgrass | 30 |
| Bedstraw | 50 |
| Blackgrass | 15 |
| Chickweed | 70 |
| Cocklebur | 100 |
| Corn | 10 |
| Cotton | 100 |
| Crabgrass | 30 |
| Downy Brome | 0 |
| Duck salad | 0 |
| Giant foxtail | 20 |
| Italn. Rygrass | 0 |
| Johnsongrass | 10 |
| Lambsquarter | 100 |
| Morningglory | 100 |
| Rape | 90 |
| Redroot Pigweed | 90 |
| Rice Japonica | 10 |
| Soybean | 20 |
| Speedwell | 75 |
| Sugar beet | 100 |
| Umbrella sedge | 0 |
| Velvetleaf | 100 |
| Watergrass 2 | 0 |

TABLE C-continued

| | 1 | 2 | 3 | 4 | 5 | 7 | 8 | 9 | 10 | 11 | 12 | 13 | 14 | 20 | 21 | 23 | 24 | 25 | 26 | 27 | 28 | 29 | 30 | 31 | 32 | 33 | 34 | 35 | 36 |
|---|---|---|---|---|---|---|---|---|---|---|---|---|---|---|---|---|---|---|---|---|---|---|---|---|---|---|---|---|---|
| Italn. Rygrass | 0 | 0 | 0 | 0 | 20 | 0 | 0 | 0 | 0 | 0 | 0 | 0 | 20 | 0 | 0 | 10 | 0 | 0 | 0 | 0 | 10 | 85 | 0 | 0 | 0 | 0 | 0 | 0 | 0 |
| Johnsongrass | 0 | 20 | 0 | 30 | 0 | 0 | 0 | 0 | 10 | 30 | 40 | 0 | 0 | 40 | 0 | 0 | 0 | 0 | 0 | 0 | 40 | 95 | 0 | 0 | 0 | 30 | 0 | 0 | 0 |
| Lambsquarter | 95 | 100 | 100 | 100 | 100 | 100 | 100 | 95 | 90 | 25 | 70 | 100 | 100 | 100 | 100 | 90 | 95 | 100 | 100 | 100 | 100 | 100 | 100 | 100 | 100 | 95 | 80 | 100 | 20 |
| Morningglory | 0 | 0 | 0 | 100 | 100 | 100 | 100 | 100 | 10 | 50 | 0 | 15 | 95 | 100 | 100 | 0 | 0 | 0 | 75 | 95 | 30 | 85 | 100 | 95 | 10 | 0 | 0 | 100 | 0 |
| Rape | 0 | 0 | 20 | 100 | 100 | 100 | 100 | 100 | 10 | 0 | 0 | 100 | 100 | 100 | 100 | 100 | 90 | 100 | 100 | 100 | 100 | 90 | 100 | 80 | 10 | — | 100 | 100 | — |
| Redroot Pigweed | 40 | 20 | 40 | 100 | 100 | 100 | 100 | 100 | 10 | 80 | 95 | 100 | 100 | 100 | 100 | 30 | 20 | 10 | 95 | 100 | 100 | 100 | 100 | 100 | 80 | 0 | 100 | 100 | 70 |
| Soybean | 0 | 0 | 0 | 30 | 0 | 0 | 0 | 0 | 0 | 0 | 0 | 0 | 30 | 10 | 0 | 0 | 0 | 10 | 0 | 0 | 20 | 0 | 0 | 0 | 0 | — | 0 | 20 | 0 |
| Speedwell | 0 | 0 | 0 | 100 | 100 | 100 | 100 | 100 | 35 | 0 | 100 | 100 | 100 | 100 | 95 | 25 | 100 | 100 | 90 | 100 | 95 | 100 | 100 | 100 | 80 | 100 | 100 | 100 | 0 |
| Sugar beet | 100 | 100 | 100 | 100 | 100 | 100 | 100 | 100 | 0 | 0 | 10 | 100 | 100 | — | 100 | 10 | 100 | 100 | 100 | 100 | 90 | 100 | 100 | 100 | 100 | 100 | 100 | 100 | 0 |
| Velvetleaf | 70 | 10 | 40 | 100 | 0 | 100 | 100 | 100 | 35 | 0 | 0 | 100 | 100 | 100 | 100 | 100 | 100 | 100 | 100 | 100 | 100 | 100 | 100 | 100 | 100 | 100 | 100 | 100 | 0 |
| Wheat | 0 | 0 | 0 | 0 | 0 | 0 | 0 | 0 | 0 | 35 | 0 | 40 | 0 | 0 | 85 | 0 | 0 | 10 | 65 | 90 | 0 | 0 | 45 | 15 | 0 | 25 | 0 | 40 | 0 |
| Wild buckwheat | 0 | 0 | 0 | 90 | 90 | 100 | 100 | 0 | 0 | 0 | 20 | 0 | 60 | 0 | 30 | 0 | 10 | 0 | 90 | 10 | 95 | 100 | 0 | 0 | 25 | 0 | 25 | 0 | 0 |
| Wild oat | 0 | 0 | 0 | 0 | 0 | 10 | 100 | 0 | 0 | 35 | 0 | 0 | 0 | 0 | 0 | 0 | 0 | 0 | 0 | 0 | 0 | 90 | 0 | 0 | 0 | 0 | 0 | 0 | 0 |

Rate 16 g/ha

| COMPOUND | 37 | 39 | 40 | 41 | 42 | 43 | 44 | 45 | 46 | 48 | 49 | 52 | 53 | 54 | 56 | 57 | 58 | 60 | 64 | 65 | 68 | 69 | 70 | 73 | 1 | 31 | 32 | 33 | 34 | 35 | 36 |
|---|---|---|---|---|---|---|---|---|---|---|---|---|---|---|---|---|---|---|---|---|---|---|---|---|---|---|---|---|---|---|---|
| Barley Igri | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | — | 0 | 10 | 0 | 0 | 0 | 0 | 0 | — | 0 | 20 | 0 | 30 | 10 | 0 | 0 | 0 | 0 | — | 0 | 0 | 0 | 0 | 0 | 0 | 0 | 0 | 30 | 0 | 30 |
| Bedstraw | 15 | 70 | 55 | 70 | 10 | 25 | 30 | 0 | 20 | 0 | 0 | 10 | 30 | 95 | 60 | 100 | 90 | 25 | 0 | 0 | 0 | 0 | 100 | 0 | 0 | 0 | 100 | 0 | 100 | 0 | 0 |
| Blackgrass | 20 | 0 | 0 | 0 | 0 | 0 | 25 | 0 | 30 | 0 | 10 | 0 | 0 | 0 | 40 | 85 | 0 | 0 | 0 | 0 | 0 | 0 | 0 | 0 | 0 | 0 | 0 | 0 | 0 | 0 | 0 |
| Chickweed | 0 | 20 | 20 | 85 | 60 | 70 | 95 | 100 | 0 | 0 | 90 | 0 | 90 | 85 | 85 | 100 | 85 | 95 | 95 | 0 | 10 | 0 | 0 | 10 | 0 | 10 | 50 | 95 | 95 | 10 | 0 |
| Cocklebur | 60 | 80 | 90 | 70 | 100 | 100 | 10 | 30 | 0 | 0 | 0 | 30 | 80 | 60 | 70 | 70 | 0 | — | — | 30 | 100 | — | 0 | 10 | 0 | 0 | 100 | 0 | 40 | 0 | 0 |

Rate 8 g/ha

TABLE C-continued

| COMPOUND | 8 | 9 | 10 | 11 | 12 | 13 | 14 | 20 | 21 | 22 | 23 | 24 | 25 | 26 | 27 | 28 | 29 | 30 | 31 | 32 | 33 | 34 | 35 | 36 | 37 | 39 | 40 | 41 |
|---|---|---|---|---|---|---|---|---|---|---|---|---|---|---|---|---|---|---|---|---|---|---|---|---|---|---|---|---|
| Corn | 0 | 0 | 0 | 0 | 0 | 0 | 0 | 0 | 0 | 0 | 0 | 0 | 0 | 0 | 0 | 10 | 0 | 0 | 0 | 0 | 0 | 0 | 0 | 0 | 0 | 0 | 0 | 0 |
| Cotton | — | 20 | 100 | 10 | 100 | 80 | 70 | 20 | 20 | 40 | 0 | 100 | 100 | 90 | 10 | 95 | 30 | 70 | — | 30 | 0 | 30 | 60 | 0 | 0 | 10 | 0 | 0 |
| Crabgrass | 10 | 0 | 10 | 0 | 0 | 0 | 0 | 0 | 0 | 0 | 0 | 0 | 0 | 0 | 100 | 90 | 0 | 0 | 0 | 0 | 0 | 0 | 0 | 0 | 0 | 0 | 0 | — |
| Downy Brome | 0 | 0 | 0 | 0 | 0 | 0 | 10 | 0 | 10 | 0 | 0 | 0 | 0 | 0 | 0 | 25 | 0 | 0 | 0 | 0 | 0 | 0 | 0 | 0 | 0 | 0 | 0 | 0 |
| Giant foxtail | 10 | 20 | 10 | 0 | 0 | 0 | 0 | 0 | 0 | 0 | 0 | 0 | 0 | 0 | 100 | 100 | 0 | 0 | 0 | 0 | 0 | 0 | 0 | 0 | 0 | 0 | 0 | 0 |
| Italn. Rygrass | 0 | 0 | 0 | 0 | 0 | 0 | 0 | 0 | 0 | 0 | 0 | 0 | 0 | 0 | 0 | 60 | 0 | 0 | 0 | 0 | 0 | 0 | 0 | 0 | 0 | 0 | 0 | 0 |
| Johnsongrass | 30 | 0 | 80 | 0 | 10 | 0 | 0 | 0 | 0 | 0 | 0 | 0 | 0 | 0 | 20 | 95 | 0 | 0 | 0 | 0 | 0 | 0 | 0 | 0 | 0 | 0 | 0 | 0 |
| Lambsquarter | 100 | 100 | 100 | 100 | 100 | 100 | 100 | 100 | 100 | 70 | 95 | 95 | 100 | 100 | 95 | 100 | 100 | 80 | 100 | 100 | 95 | 100 | 100 | 60 | 60 | 90 | 95 | 95 |
| Morningglory | 100 | 100 | 100 | 50 | 100 | 50 | 100 | 100 | 0 | 0 | 0 | 100 | 0 | 60 | 10 | — | 0 | 95 | 100 100 | 0 | 70 | 90 | 0 | 0 | 0 | 0 | 0 | — |
| Rape | 90 | 100 | 100 | 100 | 100 | 100 | 100 | 95 | 0 | 0 | 10 | 35 | 30 | 70 | 100 | 30 | 0 | 100 | 90 | 100 | 100 | 100 | 100 | 60 | 60 | 0 | 50 | 0 |
| Redroot Pigweed | 100 | 100 | 100 | 90 | 100 | 100 | 100 | 100 | 30 | 10 | — | 10 | 80 | 90 | 100 | 100 | 100 | 80 | 100 | 20 | — | 70 | 10 | 0 | 95 | 95 | 100 | 95 |
| Soybean | 0 | 0 | 0 | 0 | 0 | 0 | 0 | 0 | — | 100 | 100 | 0 | — | 0 | 10 | 10 | 100 | 0 | 0 | 0 | 0 | 0 | — | 0 | 0 | 0 | 0 | 0 |
| Speedwell | 100 | 100 | 100 | 100 | 100 | 100 | 100 | — | 0 | 60 | 100 | 100 | 100 | 100 | 85 | 20 | 45 | 100 | 100 | — | 0 | 100 | — | 95 | 95 | 95 | 100 | 95 |
| Sugar beet | — | 100 | 100 | 100 | 100 | 100 | 100 | 90 | 0 | 0 | 100 | 100 | 90 | 100 | 85 | 100 | 10 | 80 | 100 | — | 0 | 100 | — | 20 | 20 | 10 | 45 | 20 |
| Velvetleaf | 100 | 100 | 100 | 100 | 100 | 100 | 100 | 100 | — | 0 | 30 | 100 | 0 | 100 | 40 | 100 | 0 | 100 | 100 | 100 | — | 80 | 70 | 50 | 50 | 0 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Wild buckwheat | 60 | 10 | 70 | 25 | 30 | 45 | 0 | 30 | 0 | 0 | 0 | 60 | 30 | 65 | 95 | 30 | 0 | 20 | 0 | — | 25 | 0 | 30 | 0 | 0 | 0 | 0 | 0 |
| Wild oat | 0 | 0 | 0 | 0 | 0 | 0 | 0 | 0 | 0 | 0 | 0 | 0 | 0 | 0 | 0 | 65 | 0 | 0 | 0 | 0 | 25 | 0 | 0 | 0 | 0 | 0 | 0 | 0 |

Rate 8 g/ha

| COMPOUND | 8 | 9 | 10 | 11 | 12 | 13 | 14 | 20 | 21 | 22 | 23 | 24 | 25 | 26 | 27 | 28 | 29 | 30 | 31 | 32 | 33 | 34 | 35 | 36 | 37 | 39 | 40 | 41 | 42 |
|---|---|---|---|---|---|---|---|---|---|---|---|---|---|---|---|---|---|---|---|---|---|---|---|---|---|---|---|---|---|
| Barley Igri | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | 0 | 0 | — | 0 | 0 | 0 | 0 | 0 | 0 | 0 | 0 | 0 | 0 | 0 | 0 | 0 | 0 | 0 | 0 | 0 | 10 | 0 | 0 | 0 | 0 | 0 | 0 | 0 |
| Bedstraw | 0 | 0 | 20 | 20 | 0 | 0 | 0 | 70 | 0 | 35 | 70 | 0 | 20 | 0 | 35 | 30 | 0 | 80 | 0 | 70 | 0 | 85 | 0 | 0 | 70 | 0 | 20 | 35 | 30 |
| *Blackgrass | 0 | 0 | 0 | 0 | 0 | 0 | 0 | 0 | 0 | 0 | 0 | 0 | 0 | 0 | 35 | 0 | 0 | 30 | 0 | 0 | 0 | — | 10 | 0 | 85 | 0 | 0 | 0 | 0 |
| Chickweed | 0 | 0 | 50 | 0 | 0 | 0 | 0 | 80 | 50 | 95 | 90 | 55 | 70 | 50 | 35 | 0 | 0 | 30 | 90 | 50 | 0 | 0 | 0 | 50 | 0 | 20 | 50 | 30 | 40 |
| Cocklebur | 0 | 0 | 0 | 0 | 0 | 0 | 0 | 60 | 100 | 35 | 100 | 10 | 100 | 0 | 0 | 0 | 0 | 0 | 0 | 0 | 0 | 0 | 0 | 0 | 0 | 50 | 0 | 0 | 0 |
| Corn | 0 | 0 | 0 | 0 | 0 | 0 | 0 | 0 | 0 | 0 | 0 | 0 | 0 | 0 | 0 | 0 | 0 | 40 | 20 | 60 | 0 | 0 | 0 | 0 | 50 | 20 | 30 | 0 | 60 |
| Cotton | 0 | 0 | 0 | 0 | 0 | 0 | 0 | 0 | 10 | 20 | 0 | 20 | 100 | 0 | 0 | 0 | 0 | 0 | 20 | 0 | 0 | 0 | 0 | 0 | 0 | 10 | 0 | 0 | 0 |
| *Crabgrass | 10 | 0 | 0 | 0 | 0 | 0 | 0 | 0 | 10 | 0 | 0 | 0 | 0 | 0 | 85 | 25 | 0 | 95 | 20 | 0 | 0 | 0 | 0 | 0 | 0 | 0 | 0 | 0 | 0 |
| Downy Brome | 0 | 0 | 0 | 0 | 0 | 0 | 0 | 0 | 10 | 0 | 0 | 0 | 70 | 0 | 0 | 0 | 0 | 100 | 0 | 50 | 0 | 0 | 0 | 0 | 0 | 0 | 10 | 0 | 0 |
| Giant foxtail | 0 | 0 | 0 | 0 | 0 | 0 | 0 | 0 | 10 | 0 | 0 | 0 | 0 | 0 | 0 | 40 | 50 | 100 | 30 | 90 | 0 | 50 | 0 | 20 | 50 | 10 | 0 | 0 | 0 |
| Italn. Rygrass | 0 | 0 | 0 | 0 | 0 | 0 | 0 | 0 | 20 | 0 | 0 | 0 | 90 | 80 | 90 | 0 | 0 | 100 | 30 | 0 | 0 | 0 | 0 | 0 | 0 | 0 | 0 | 0 | 0 |
| Johnsongrass | 0 | 0 | 0 | 0 | 0 | 0 | 0 | 10 | 0 | 0 | 0 | 0 | 0 | 10 | 35 | 0 | 100 | 30 | 95 | 100 | 0 | 0 | 0 | 0 | 10 | 0 | 0 | 0 | 0 |
| Lambsquarter | 10 | 0 | 0 | 20 | — | 0 | 70 | 100 | 100 | 100 | 95 | 100 | 100 | 70 | 85 | 25 | 0 | 95 | 55 | 50 | 100 | 0 | 0 | 50 | 50 | 100 | 100 | 100 | 90 |
| Morningglory | 0 | 0 | 0 | 0 | — | 100 | 0 | 100 | 10 | 0 | 60 | 20 | 70 | 10 | 0 | 0 | 70 | 100 | 60 | 90 | 100 | 0 | 0 | 0 | 0 | 20 | 30 | 30 | 0 |
| Rape | 0 | 0 | 0 | 0 | 0 | 0 | 0 | 0 | 100 | 20 | 100 | 0 | 100 | 80 | 0 | 40 | 50 | 100 | 30 | 0 | 0 | 50 | 0 | 20 | 50 | 20 | 10 | 0 | 80 |
| Redroot Pigweed | 0 | 0 | 0 | 20 | 20 | 0 | 0 | 35 | 10 | 100 | 95 | 100 | 90 | 80 | 90 | 0 | 0 | 100 | 95 | 100 | 100 | 100 | 0 | 70 | 100 | 100 | 95 | 80 | 35 |
| Soybean | 0 | 0 | 0 | 0 | 0 | 0 | 0 | 70 | 0 | 0 | 0 | 0 | 85 | 0 | 0 | 0 | 0 | 30 | 0 | 0 | 0 | 0 | 0 | 0 | 0 | 0 | 0 | 0 | 100 |
| Speedwell | 0 | 0 | 40 | 0 | 0 | 0 | 0 | 100 | 100 | 100 | 95 | 100 | 95 | 100 | 35 | 0 | 100 | 70 | 95 | 100 | 100 | 100 | 100 | 100 | 10 | 95 | 100 | 100 | 0 |
| Sugar beet | 0 | 0 | — | 0 | 0 | 0 | 0 | 70 | 100 | 100 | 100 | 100 | 100 | 10 | 10 | 0 | 0 | 100 | 55 | 90 | 70 | 100 | 0 | 100 | — | 100 | 100 | 80 | 10 |
| Velvetleaf | 0 | 0 | 0 | 10 | 20 | 0 | 0 | 85 | 100 | 100 | 100 | 100 | 100 | 10 | 35 | 0 | 10 | 60 | 100 | 100 | 0 | 0 | 0 | 0 | 50 | 100 | 100 | 100 | 100 |
| Wheat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | — | — | 0 | 0 | 0 | 0 |
| Wild buckwheat | 0 | 0 | 0 | 0 | 0 | 0 | 0 | 0 | 30 | 0 | 35 | 0 | 40 | 0 | 10 | 10 | 10 | 10 | 0 | 0 | 0 | 0 | 0 | 0 | 50 | 0 | 30 | 25 | 0 |
| Wild oat | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

TABLE C-continued

Rate 8 g/ha

| COMPOUND | 43 | 44 | 45 | 46 | 48 | 49 | 52 | 53 | 54 | 56 | 57 | 58 | 60 | 64 | 65 | 68 | 69 | 70 | 73 |
|---|---|---|---|---|---|---|---|---|---|---|---|---|---|---|---|---|---|---|---|
| Barley Igri | 0 | 0 | 0 | 0 | 0 | 0 | 0 | 0 | 0 | 0 | 10 | 0 | 0 | 0 | 0 | 0 | 0 | 0 | 0 |
| Barnyardgrass | 0 | 0 | 0 | 0 | 0 | 0 | 0 | 0 | 0 | 20 | 20 | 0 | 0 | 0 | 0 | 0 | 0 | 0 | 0 |
| Bedstraw | 70 | 0 | — | 0 | 0 | 0 | 0 | — | 0 | 75 | 25 | 0 | 20 | 0 | 20 | 10 | 95 | 100 | 0 |
| Blackgrass | 0 | 0 | 0 | 0 | 0 | 0 | 0 | 80 | 0 | 10 | 60 | 65 | 80 | 95 | 15 | 100 | 0 | 0 | 10 |
| Chickweed | — | 40 | 40 | 0 | 0 | 85 | 0 | 30 | 0 | 85 | 35 | 0 | 40 | 0 | 10 | 0 | 0 | 0 | — |
| Cocklebur | 30 | 10 | 0 | 0 | 0 | 0 | 20 | 10 | 10 | — | 50 | 65 | 0 | 0 | 15 | 100 | 0 | 0 | 0 |
| Corn | 0 | 0 | 0 | 0 | 0 | 0 | 0 | 0 | 0 | 0 | 0 | 0 | 0 | 0 | 0 | 0 | 0 | 0 | 0 |
| Cotton | 80 | 20 | 0 | 0 | 0 | 0 | 40 | 50 | 40 | 0 | 85 | 0 | 40 | 95 | 10 | 0 | 20 | 30 | 30 |
| Crabgrass | 0 | 0 | 0 | 0 | 30 | 0 | 0 | 0 | 0 | 10 | 35 | 0 | 0 | 0 | 0 | 0 | 0 | 0 | 0 |
| Downy Brome | 0 | 0 | 0 | 0 | 0 | 0 | 0 | 0 | 0 | 0 | 0 | 0 | 0 | 0 | 0 | 0 | 0 | 0 | 0 |
| Giant foxtail | 10 | 0 | 0 | 0 | 0 | 0 | 0 | 0 | 0 | 95 | 95 | 0 | 0 | 0 | 0 | 0 | 0 | 0 | 0 |
| Italn. Rygrass | 0 | 0 | 0 | 0 | 0 | 0 | 0 | 0 | 0 | 0 | 30 | 0 | 0 | 0 | 0 | 0 | 0 | 0 | 0 |
| Johnsongrass | 0 | 0 | 0 | 0 | 0 | 0 | 0 | 0 | 0 | 10 | 40 | 0 | 0 | 0 | 0 | 0 | 0 | 0 | 0 |
| Lambsquarter | 100 | 100 | 100 | 25 | 0 | 80 | 95 | 100 | 100 | 90 | 100 | 100 | 100 | 100 | 100 | 0 | 70 | 95 | 0 |
| Morningglory | 40 | 100 | 100 | 0 | 0 | 0 | 100 | 0 | 30 | 0 | 70 | 0 | 40 | 0 | 10 | 0 | 10 | 0 | 0 |
| Rape | 95 | 0 | 50 | 25 | 0 | 0 | 10 | 25 | 70 | 100 | 0 | 30 | 0 | 90 | 0 | 100 | 80 | 30 | 0 |
| Redroot Pigweed | 100 | 100 | 40 | 30 | 0 | 0 | 10 | 70 | 90 | 100 | 100 | 60 | 100 | 0 | 100 | — | 50 | 60 | 0 |
| Soybean | 0 | 0 | 0 | 0 | 0 | 0 | 0 | 0 | 0 | 0 | 15 | 0 | 0 | 0 | 10 | 100 | 0 | 0 | 0 |
| Speedwell | 100 | 95 | 0 | 25 | 0 | 100 | 0 | 90 | 100 | 80 | 100 | 100 | 100 | 0 | 0 | — | 100 | 90 | 0 |
| Sugar beet | 100 | 100 | 90 | 0 | 0 | 95 | 100 | 45 | 100 | 10 | 100 | 35 | 100 | 100 | — | 0 | 100 | — | 0 |
| Velvetleaf | 100 | 100 | 30 | 0 | 0 | 0 | 60 | 70 | 20 | 10 | 100 | 10 | 100 | 80 | 100 | 25 | 80 | 30 | 0 |
| Wheat | 0 | 0 | 0 | 0 | 0 | 0 | 0 | 0 | 0 | 0 | 0 | 0 | 0 | 0 | 0 | 0 | 0 | 0 | 0 |
| Wild buckwheat | 25 | 0 | 20 | 0 | 0 | 0 | 40 | 0 | 0 | 90 | 90 | 0 | 0 | 0 | 0 | 20 | 0 | 10 | 0 |
| Wild oat | 0 | 0 | 0 | 0 | 0 | 0 | 0 | 0 | 0 | 0 | 30 | 0 | 0 | 0 | 0 | 0 | 0 | 0 | 0 |

Rate 4 g/ha

| COMPOUND | 21 | 22 | 23 | 24 | 25 | 26 | 27 | 28 | 29 | 30 |
|---|---|---|---|---|---|---|---|---|---|---|
| Barley Igri | 0 | 0 | 0 | 0 | 0 | 0 | 0 | 0 | 0 | 0 |
| Barnyardgrass | 0 | 0 | 0 | 0 | 0 | 0 | 0 | 0 | 0 | 0 |
| Bedstraw | 0 | 35 | 0 | 0 | 0 | 0 | 0 | 0 | 0 | 0 |
| Blackgrass | 0 | 0 | 0 | 0 | 0 | 0 | 0 | 0 | 0 | 0 |
| Chickweed | 0 | 60 | 0 | 20 | 70 | 50 | 0 | 30 | 0 | 35 |
| Cocklebur | 90 | 0 | 30 | 0 | 90 | 0 | 0 | 0 | 0 | 0 |
| Corn | 40 | 0 | 50 | 20 | 0 | 0 | 0 | 0 | 0 | 0 |
| Cotton | — | 20 | 0 | 20 | 30 | 0 | 0 | 25 | 0 | 30 |
| Crabgrass | 0 | 10 | 0 | 0 | 0 | 0 | 0 | 0 | 0 | 0 |
| Downy Brome | 0 | 0 | 0 | 0 | 0 | 0 | 0 | 0 | 0 | 0 |
| Giant foxtail | 0 | 0 | 0 | 0 | 0 | 0 | 0 | 0 | 0 | 0 |
| Italn. Rygrass | 0 | 0 | 0 | 0 | 0 | 0 | 0 | 0 | 0 | 0 |
| Johnsongrass | 0 | 20 | 0 | 0 | 0 | 0 | 0 | 0 | 0 | 0 |
| Lambsquarter | 95 | 100 | 95 | 100 | 100 | 70 | 70 | 25 | 70 | 85 |
| Morningglory | 100 | 100 | 30 | 0 | 10 | 0 | 0 | 0 | 0 | 70 |
| Rape | 100 | 0 | 95 | 0 | 70 | 0 | 0 | 0 | 0 | 0 |
| Redroot Pigweed | 95 | 100 | 90 | 10 | 40 | 80 | 10 | 20 | 20 | 100 |
| Soybean | 0 | 0 | 0 | 0 | 0 | 0 | 0 | 0 | 0 | 30 |
| Speedwell | 100 | 100 | 85 | 100 | 85 | 0 | 0 | 0 | 65 | 70 |
| Sugar beet | 100 | 100 | 100 | 30 | 30 | 10 | 10 | 0 | 0 | 35 |
| Velvetleaf | 100 | 100 | 95 | 30 | 100 | 0 | 10 | 0 | 0 | 30 |
| Wheat | 0 | 0 | 0 | 0 | 0 | 0 | 0 | 0 | 0 | 0 |
| Wild buckwheat | 30 | 0 | — | 0 | 0 | 0 | 0 | 0 | 0 | 10 |
| Wild oat | 0 | 0 | 0 | 0 | 0 | 0 | 0 | 0 | 0 | 0 |

Rate 4 g/ha

| COMPOUND | 21 | 32 | 33 | 34 | 35 | 36 | 37 | 39 | 40 | 41 | 42 | 43 | 44 | 46 | 48 | 49 | 52 | 53 | 54 | 56 | 57 | 58 | 60 | 64 | 65 | 68 | 69 | 70 | 73 |
|---|---|---|---|---|---|---|---|---|---|---|---|---|---|---|---|---|---|---|---|---|---|---|---|---|---|---|---|---|---|
| Barley Igri | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Barnyardgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Bedstraw | 0 | 35 | 0 | 0 | 0 | 0 | — | 0 | 0 | 10 | 0 | 0 | 0 | 0 | 0 | 0 | 0 | 10 | 0 | 75 | 25 | 0 | 20 | 0 | 20 | 10 | 70 | 100 | 0 |
| Blackgrass | 0 | 0 | 0 | 0 | 0 | 0 | — | 0 | 0 | 0 | 10 | 0 | 0 | 0 | 0 | 0 | 0 | 0 | 0 | 10 | 35 | 10 | 0 | 0 | 0 | 0 | 0 | 0 | 0 |
| Chickweed | 0 | 0 | 0 | 0 | 0 | — | 30 | 20 | 0 | 85 | — | 0 | 70 | 0 | 0 | 70 | 0 | 20 | 30 | 85 | 0 | 70 | 85 | 0 | 0 | 70 | 0 | 0 | 0 |
| Cocklebur | 0 | 0 | 0 | 90 | 0 | 10 | 30 | 15 | 0 | 0 | 0 | 0 | 0 | 0 | 0 | 0 | 30 | 0 | 10 | 0 | 10 | 10 | 0 | 0 | 0 | 60 | 0 | 0 | 30 |
| Corn | 0 | 30 | 0 | 0 | 0 | 0 | 0 | 0 | 0 | 0 | 0 | 0 | 0 | 0 | 0 | 0 | 0 | 30 | 30 | 0 | 40 | 0 | 20 | 25 | 0 | 0 | 30 | 30 | 0 |
| Cotton | 0 | 20 | 0 | 0 | 0 | 0 | 0 | 0 | 0 | 0 | 10 | 0 | 0 | 0 | 0 | 0 | 0 | 0 | 10 | 0 | 10 | 0 | 0 | 0 | 0 | 0 | 0 | 0 | 0 |
| Crabgrass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Downy Brome | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Giant foxtail | 0 | 0 | 0 | 0 | 0 | 0 | 0 | 0 | 0 | 0 | 0 | 0 | 0 | 0 | 0 | 0 | 0 | 0 | 0 | 80 | 25 | 0 | 0 | 0 | 0 | 0 | 70 | 65 | 0 |
| Italn. Rygrass | 0 | 0 | 0 | 0 | 0 | 0 | 0 | 0 | 0 | 0 | 0 | 0 | 0 | 0 | 0 | 0 | 0 | 0 | 0 | 0 | 25 | 0 | 0 | 0 | 0 | 0 | 0 | 0 | 0 |
| Johnsongrass | 0 | 0 | 0 | 0 | 0 | 0 | 0 | 0 | 0 | 0 | 0 | 0 | 0 | 0 | 0 | 0 | 0 | 0 | 0 | 0 | 30 | 0 | 0 | 0 | 0 | 0 | 10 | 0 | 0 |
| Lambsquarter | — | 100 | 100 | 100 | 95 | 100 | 100 | 100 | 100 | 100 | 70 | 60 | 85 | 25 | 0 | 45 | 60 | 100 | 100 | 95 | 100 | 100 | 100 | 0 | 0 | 60 | 90 | 100 | 0 |
| Morningglory | 0 | — | 0 | 100 | 0 | 50 | 100 | 60 | 80 | 20 | 65 | 30 | 0 | 0 | 0 | 0 | 100 | 100 | 30 | 0 | 20 | 0 | 0 | 0 | 0 | 0 | 100 | 30 | 65 |
| Rape | 0 | 10 | 0 | 0 | 0 | 100 | 30 | 70 | 95 | 10 | 20 | 95 | 0 | 25 | 0 | 0 | 0 | 10 | 95 | 95 | 90 | 30 | 0 | 0 | 0 | 10 | 0 | 10 | 50 |
| Redroot Pigweed | 0 | 20 | 0 | 40 | 0 | 0 | 100 | 70 | 100 | 80 | 90 | 100 | — | 0 | 0 | 0 | 60 | 70 | 0 | 10 | 0 | 95 | 80 | 100 | 10 | 0 | 10 | 70 | 35 |
| Soybean | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |

Rate 2 g/ha

| COMPOUND | 21 |
|---|---|
| Barley Igri | 21 |
| Barnyardgrass | 0 |
| Bedstraw | 0 |
| Blackgrass | 0 |
| Chickweed | 0 |
| Cocklebur | 90 |
| Corn | 0 |
| Cotton | 0 |
| Crabgrass | 10 |
| Downy Brome | 0 |
| Giant foxtail | 0 |
| Italn. Rygrass | 0 |
| Johnsongrass | 0 |
| Lambsquarter | 90 |
| Morningglory | 100 |
| Rape | 80 |
| Redroot Pigweed | 95 |
| Soybean | 0 |

TABLE C-continued

Rate 2 g/ha

| COMPOUND | 22 | 23 | 24 | 25 | 26 | 28 | 30 | 31 | 32 | 33 | 34 | 35 | 39 | 40 | 41 | 42 | 43 | 44 | 46 | 48 | 52 | 53 | 54 | 58 |
|---|---|---|---|---|---|---|---|---|---|---|---|---|---|---|---|---|---|---|---|---|---|---|---|---|
| Speedwell | 95 | 100 | 95 | 100 | 40 | 0 | 95 | 100 | 100 | 100 | 100 | 0 | 0 | 0 | — | — | — | 90 | 70 | 20 | 95 | 100 | 20 | 0 |
| Sugar beet | 10 | 90 | 25 | 100 | — | — | 100 | 100 | 25 | 70 | 85 | 100 | 0 | — | 85 | 35 | 20 | 90 | 10 | 45 | 10 | 45 | 90 | 0 |
| Velvetleaf | 0 | 100 | 0 | 0 | 100 | 100 | 100 | 100 | 100 | 100 | 35 | 85 | 0 | — | 10 | — | 50 | 20 | 0 | 100 | 0 | 30 | 0 | 0 |
| Wheat | 0 | 0 | 0 | 0 | 0 | 0 | 0 | 0 | 0 | 0 | 0 | 0 | 0 | 0 | 0 | 0 | 0 | 0 | 85 | 85 | 0 | 0 | 0 | 25 |
| Wild buckwheat | 0 | 0 | 0 | 0 | 0 | 30 | 0 | — | 0 | 0 | 0 | 0 | 0 | 0 | 0 | 0 | 0 | 0 | 0 | 20 | 0 | 0 | 0 | 0 |
| Wild oat | 0 | 0 | 0 | 0 | 0 | 0 | 0 | 0 | 0 | 0 | — | 0 | 0 | 0 | 0 | 0 | 0 | 0 | 0 | 0 | 0 | 0 | 0 | 15 |

Rate 1 g/ha

| COMPOUND | 22 | 39 | 40 |
|---|---|---|---|
| Barley Igri | 0 | 0 | 0 |
| Barnyardgrass | 0 | 0 | 0 |
| Bedstraw | 35 | 0 | 0 |
| Blackgrass | 0 | 0 | 0 |
| Chickweed | 0 | 0 | 0 |
| Cocklebur | 0 | 10 | 20 |
| Corn | 0 | 0 | 0 |
| Cotton | 0 | 0 | 0 |
| Crabgrass | 10 | 0 | 0 |
| Downy Brome | 0 | 0 | 0 |
| Giant foxtail | 0 | 0 | 0 |
| Italn. Rygrass | 0 | 0 | 0 |
| Johnsongrass | 0 | 0 | 0 |
| Lambsquarter | 80 | 20 | 0 |
| Morningglory | 40 | 50 | 0 |
| Rape | 0 | — | — |
| Redroot Pigweed | 30 | 0 | 95 |
| Soybean | 0 | 20 | 20 |
| Speedwell | 95 | 20 | 20 |
| Sugar beet | 10 | 60 | 70 |
| Velvetleaf | — | 0 | 0 |
| Wheat | 0 | 0 | 0 |
| Wild buckwheat | 0 | 0 | 0 |
| Wild oat | 0 | 0 | 0 |

TEST D

Seeds of barnyardgrass (*Echinochloa crus-galli*), bindweed (*Concolculus arvensis*), black nightshade (*Solanum ptycanthum dunal*), cassia (*Cassia obtusifolia*), cocklebur (*Xanthium strumarium*), common ragweed (*Ambrosia artemsiifolia*), corn (*Zea mays*), cotton (*Gossypium hirsutam*), crabgrass (Digitaria spp.), fall panicum (*Panicum dichotomiflorum*), giant foxtail (*Setaria faberii*), green foxtail (*Setaria viridis*), jirnsonweed (*Datura stramonum*), johnsongrass (*Sorghum halepense*), lambsquarter (*Chenopodium album*), mornigglory (*Ipomoea* spp.), pigveed (*Amaranthus retroflexus*), prickly sida (*Sida spinosa*), shattercane (*Sorghwn vulgare*), signaigrass (*Brachiaria platyphylla*), smartveed (*Polygonwn pensylvanicum*), soybean (*Glycine max*), sunflower (*Helianthus annuus*), velvetleaf (*Abutilon theophrasti*), wild proso (*Pancium miliaceum*), woolly cupgrass (*Eriochloa villosa*), yellow foxtail (*Setaria lutescens*) and purple nutsedge (*Cyperus rotundus*) tubers were planted into a sandy loam soil. These crops and weeds were grown in the greenhouse until the plants ranged in height from two to eighteen cm (one to four leaf stage), then treated postemergence with the test chemicals formulated in a non-phytotoxic solvent mixture which included a surfactant. Pots receiving preemergence treatments were planted immediatley prior to test chemical application. Pots treated in this fashion were placed in the greenhouse and maintained according to routine greenhouse procedures.

Treated plants and untreated controls were maintained in the greenhouse approximately 14–21 days after application of the test compound. Visual evaluations of plant injury responses were then recorded. Plant response ratings, summarized in Table D, are reported on a 0 to 100 scale where 0 is no effect and 100 is complete control.

TABLE D

POSTEMERGENCE

| COMPOUND | Rate 35 g/ha 20 | 21 | Rate 17 g/ha 20 | 21 | Rate 8 g/ha 23 | 25 | 32 | Rate 4 g/ha 20 | 21 | 23 | 25 | 32 | Rate 2 g/ha 20 | 21 | 23 | 25 | 32 | Rate 1 g/ha 20 | 21 | 23 | 25 | 32 |
|---|---|---|---|---|---|---|---|---|---|---|---|---|---|---|---|---|---|---|---|---|---|---|
| Barnyardgrass | 50 | 100 | 30 | 100 | 100 | 55 | 60 | 10 | 90 | 50 | 5 | 40 | 10 | 40 | 30 | 0 | 10 | 5 | 0 | 0 | 0 | 0 |
| Bindweed | 100 | 100 | 100 | 100 | 100 | 100 | 100 | — | 100 | 100 | 100 | 100 | 100 | 100 | 100 | 100 | 100 | 100 | 100 | 100 | 50 | 100 |
| Blk Nightshade | 100 | 100 | 100 | 100 | 100 | 100 | 100 | 50 | 100 | 100 | 100 | 100 | 70 | 100 | 100 | 100 | 100 | 50 | 40 | 100 | — | 10 |
| Cassia | 70 | 60 | 0 | 50 | 0 | 50 | 0 | 50 | 50 | 0 | 5 | 0 | 50 | 5 | 0 | 5 | 5 | 5 | 0 | 5 | 0 | 0 |
| Cocklebur | 100 | 100 | 100 | 100 | 100 | 50 | 100 | 100 | 100 | 100 | 100 | 100 | 85 | 100 | 100 | 100 | 100 | 30 | 70 | 100 | 60 | 100 |
| Corn | 30 | 20 | 30 | 5 | 20 | 20 | 15 | 25 | 5 | 15 | 10 | 15 | 5 | 5 | 10 | 5 | 10 | 5 | 0 | 10 | 5 | 0 |
| Cotton | 100 | 100 | 100 | 100 | 100 | 100 | 100 | 100 | 100 | 100 | 100 | 100 | 95 | 100 | 100 | 100 | 100 | 60 | 80 | 100 | 60 | 100 |
| Crabgrass | 50 | 50 | 30 | 20 | 20 | 30 | 20 | 30 | 10 | 20 | 10 | 0 | 5 | 5 | 0 | 5 | 0 | 5 | 0 | 0 | 5 | 0 |
| Fall Panicum | 60 | 60 | 50 | 50 | 0 | 10 | 30 | 30 | 10 | 0 | 5 | 20 | 5 | 10 | 40 | 5 | 20 | 5 | 5 | 30 | 0 | 20 |
| Giant Foxtail | 40 | 50 | 30 | 40 | 50 | 20 | 50 | 30 | 30 | 45 | 20 | 70 | 5 | 30 | 10 | 10 | 5 | 5 | 5 | 5 | 5 | 15 |
| Green Foxtail | 50 | 60 | 30 | 50 | 50 | 50 | 50 | 20 | 20 | 20 | 20 | 5 | 10 | 5 | 10 | 60 | 70 | 5 | 20 | 80 | 40 | 60 |
| Jimsonweed | 100 | 100 | 90 | 100 | 100 | 100 | 100 | 85 | 100 | 100 | 100 | 100 | 70 | 70 | 100 | 60 | 100 | 70 | 70 | 100 | — | 5 |
| Johnson Grass | 70 | 40 | 40 | 5 | 50 | 10 | 40 | 40 | 5 | 5 | 5 | 5 | 40 | 5 | 5 | 0 | 5 | 10 | 0 | 5 | 5 | 5 |
| Lambsquarter | 100 | 100 | 90 | 100 | 70 | 80 | 100 | 80 | 100 | 70 | 70 | 30 | 75 | 90 | 50 | 20 | 30 | 45 | 50 | 30 | 40 | 100 |
| Morningglory | 100 | 100 | 100 | 100 | 100 | 100 | 100 | 100 | 100 | 100 | 100 | 100 | 100 | 100 | 100 | 100 | 100 | 100 | 100 | 100 | 100 | 100 |
| Nutsedge | 10 | 10 | 5 | 5 | 0 | 5 | 0 | 5 | 0 | 0 | 0 | 0 | 0 | 0 | 5 | 0 | 0 | 0 | 0 | 0 | 0 | 0 |
| Pigweed | 100 | 100 | 100 | 100 | 100 | 100 | 100 | 100 | 100 | 100 | 100 | 100 | 100 | 100 | 100 | 70 | 100 | 50 | 100 | 100 | 40 | 50 |
| Prickly Sida | 100 | 100 | 100 | 100 | 100 | 100 | 100 | 70 | 100 | 100 | 100 | 100 | 70 | 100 | 100 | 80 | 80 | 50 | 60 | 100 | 40 | 60 |
| Ragweed | 100 | 100 | 100 | 100 | 50 | 5 | 100 | 20 | 10 | 40 | 5 | 30 | 20 | 5 | 20 | 5 | 20 | 55 | 65 | 15 | 50 | 50 |
| Shattercane | 40 | 90 | 40 | 50 | 60 | 5 | 0 | 30 | 40 | 0 | 5 | 0 | 5 | 10 | 0 | 5 | 0 | 10 | 0 | 0 | 0 | 0 |
| Signalgrass | 50 | 70 | 30 | 40 | 0 | 5 | 50 | 30 | 40 | 20 | 5 | 0 | 10 | 40 | 50 | 0 | 40 | 10 | 20 | 50 | 5 | 20 |
| Smartweed | 100 | 100 | 100 | 100 | 80 | 40 | 60 | 70 | 70 | 70 | 35 | 40 | 50 | 60 | 50 | 10 | 30 | 5 | 5 | 75 | 30 | 20 |
| Soybean | 50 | 40 | 50 | 20 | 15 | 30 | 20 | 50 | 5 | 5 | 30 | 40 | 40 | 5 | 0 | 15 | 40 | 5 | 5 | 30 | 15 | 20 |
| Sunflower | 50 | 80 | 45 | 80 | 95 | 80 | 85 | 40 | 75 | 85 | 80 | 100 | 20 | 50 | 80 | 35 | 100 | 60 | 100 | 75 | 30 | 100 |
| Velvetleaf | 100 | 100 | 100 | 100 | 100 | 100 | 100 | 100 | 100 | 100 | 100 | 100 | 100 | 100 | 100 | 100 | 100 | 60 | 100 | 100 | 60 | 100 |
| Wild Proso | 50 | 30 | 40 | 30 | 40 | 20 | 60 | 10 | 10 | 30 | 10 | 10 | 10 | 5 | 10 | 10 | 5 | 5 | 5 | 10 | 10 | 5 |
| Woolly cupgrass | 35 | 60 | 10 | 60 | 50 | 30 | 50 | 10 | 50 | 40 | 10 | 30 | 5 | 20 | 5 | 5 | 5 | 5 | 5 | 5 | 5 | 5 |
| Yellow Foxtail | 65 | 80 | 50 | 60 | 50 | 50 | 60 | 10 | 30 | 15 | 10 | 60 | 10 | 10 | 5 | 5 | 5 | 5 | 5 | 5 | 5 | 5 |

PREEMERGENCE

| COMPOUND | Rate 35 g/ha 20 | 21 | Rate 17 g/ha 20 | 21 | Rate 8 g/ha 20 | 21 | Rate 4 g/ha 20 | 21 | Rate 2 g/ha 20 | 21 | Rate 1 g/ha 20 | 21 |
|---|---|---|---|---|---|---|---|---|---|---|---|---|
| Barnyardgrass | 50 | 10 | 0 | 0 | 0 | 0 | 0 | 0 | 0 | 0 | 0 | 0 |
| Bindweed | — | 100 | — | 100 | — | 100 | — | 100 | — | 100 | — | 0 |
| Blk Nightshade | — | 100 | — | 100 | — | 100 | — | 0 | — | 70 | — | 30 |
| Cassia | — | 100 | — | 100 | — | 100 | — | 0 | — | 0 | — | 0 |
| Cocklebur | — | 10 | — | 0 | — | 0 | — | 100 | — | 10 | — | 0 |
| Corn | 20 | 100 | 20 | 100 | 0 | 100 | 0 | 100 | 0 | 0 | 0 | 0 |
| Cotton | 70 | 20 | 100 | 0 | 0 | 0 | 0 | 0 | 0 | 50 | 0 | 30 |
| Crabgrass | 80 | 40 | 50 | 0 | 0 | 0 | 0 | 0 | 0 | 0 | 0 | 0 |
| Fall Panicum | 100 | 0 | 50 | 20 | 0 | 0 | 0 | 0 | 0 | 0 | 0 | 0 |
| Giant Foxtail | 50 | | 0 | | 0 | | 0 | | 0 | | 0 | |

TABLE D-continued

| | | | | | | | | | | | | |
|---|---|---|---|---|---|---|---|---|---|---|---|---|
| Green Foxtail | 100 | 20 | 50 | 0 | 0 | 0 | 0 | 0 | 0 | 0 | 0 | 0 |
| Jimsonweed | — | 100 | — | 100 | — | 100 | — | 100 | — | 100 | — | 0 |
| Johnson Grass | 70 | 20 | 80 | 0 | 10 | 0 | 0 | 0 | 0 | 0 | 0 | 0 |
| Lambsquarter | — | 100 | — | 100 | — | 100 | — | 100 | — | 50 | — | 100 |
| Morningglory | — | 100 | — | 100 | — | 100 | — | 100 | — | 0 | — | 0 |
| Nutsedge | — | 0 | — | 0 | — | 0 | — | 0 | — | 100 | — | 0 |
| Pigweed | — | 100 | — | 100 | — | 100 | — | 100 | — | 80 | — | 100 |
| Prickly Sida | — | 100 | — | 100 | — | 100 | — | 80 | — | 50 | — | 20 |
| Ragweed | 50 | 20 | 0 | 0 | 0 | 0 | 0 | 100 | 0 | 0 | 0 | 0 |
| Shattercane | 40 | 20 | 0 | — | 0 | — | 0 | 0 | 0 | 100 | 0 | 0 |
| Signalgrass | 100 | 100 | — | 100 | 0 | 100 | 0 | 0 | 0 | 0 | 0 | 0 |
| Smartweed | — | 0 | 100 | 0 | 0 | — | 0 | 0 | 0 | 0 | 0 | 0 |
| Soybean | 70 | 100 | 10 | 50 | 0 | 20 | 0 | 0 | 0 | 0 | 0 | 0 |
| Sunflower | — | 100 | — | 100 | 0 | 100 | 0 | 100 | 0 | 0 | 0 | 0 |
| Velvetleaf | 80 | 50 | 100 | 20 | 0 | 0 | 0 | 0 | 0 | 10 | 0 | 0 |
| Wild Proso | 80 | 30 | 50 | 30 | 0 | 10 | 0 | 0 | 0 | 0 | 0 | 0 |
| Woolly cupgrass | 50 | 10 | 50 | 0 | 0 | 0 | 0 | 0 | 0 | 0 | 0 | 0 |
| Yellow Foxtail | | | | | | | | | | | | |

TEST E

Compounds evaluated in this test were formulated in a non-phytotoxic solvent mixture which included a surfactant and applied to the soil surface before plant seedlings emerged (preemergence application) and to plants that were in the one- to four-leaf stage (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test.

Plantings of these crops and weed species were adjusted to produce plants of appropriate size for the postemergence test. All plant species were grown using normal greenhouse practices. Crop and weed species include annual bluegrass (*Poa annua*), black nightshade (*Solanum nigra*), blackgrass (*Alopecurus myosuroides*), chickweed (*Stellaria media*), deadnettle (*Lamium amplexicaule*), douwny brome (*Bromus tectorum*), field violet (*Viola arvensis*), galium (*Galium aparine*), green foxtail (*Setaria viridis*), jointed goatgrass (*Aegilops cylindrica*), kochia (*Kochia scoparia*), lambsquarters (*Chenopodium album*), littleseed canarygrass (*Phalaris minor*), rape (*Brassica napus*), redroot pigweed (*Amaranthus retroflexus*), Russian thistle (*Salsola kali*), ryegrass (*Lolium multiflorum*), sentless chamonile (*Matricaria inodora*), speedwell (*Veronica persica*), spring barely (*Hordeum vulgare* cy. 'Klages'), spring wheat (*Triticum aestivum* cy. 'ERA'), sugar beet (*Beta vulgaris* cy. 'US1'), sunflower (*Helianthus annuus* cy. 'Russian Giant'), *Veronica hederaefolia*, wild buckwheat (*Polygonum convolvulus*), wild mustard (*Sinapis arvensis*), wild oat (*Avena fatua*), winter barley (*Hordeum vulgare* cy. 'Igri') and winter wheat (*Triticumn aestivum* cy. 'Talent').

Treated plants and untreated controls were maintained in a greenhouse for approximately 21 to 28 days, after which all treated plants were compared to untreated controls and visually evaluated. Plant response ratings, summarized in Table E, are based upon a 0 to 100 scale where 0 is no effect and 100 is complete control. A dash response (–) means no test result.

TABLE E

POSTEMERGENCE

| COMPOUND | Rate 62 g/ha | Rate 31 g/ha | | | | | | | Rate 16 g/ha | | | | | | | | | | Rate 8 g/ha | | | | | |
|---|---|---|---|---|---|---|---|---|---|---|---|---|---|---|---|---|---|---|---|---|---|---|---|---|
| | 20 | 3 | 4 | 5 | 20 | 21 | 23 | 3 | 4 | 5 | 12 | 13 | 14 | 20 | 21 | 23 | 25 | 30 | 48 | 52 | 53 | 54 | 3 | 4 | 5 | 12 |
| Annual Bluegras | — | 10 | 20 | 20 | — | — | — | 10 | 10 | 20 | — | — | — | — | — | — | — | — | — | — | — | — | 10 | 10 | 10 | — |
| Blackgrass (2) | — | 10 | 20 | 10 | — | — | — | 20 | 20 | 20 | — | — | — | — | — | — | — | — | — | — | — | — | 10 | 20 | 10 | — |
| Blk Nightshade | 100 | 100 | 100 | 100 | 100 | 100 | 100 | 100 | 100 | 100 | 50 | — | — | 100 | 100 | 100 | 100 | 100 | 100 | 100 | 100 | 100 | 100 | 100 | 100 | 40 |
| Chickweed | 100 | 20 | 20 | 10 | 100 | 100 | 100 | 20 | 10 | 10 | 25 | 50 | 30 | 80 | 100 | 80 | 60 | 40 | 20 | 60 | 60 | 45 | 10 | 10 | 10 | — |
| Deadnettle | 100 | 30 | 20 | 20 | 80 | 100 | 100 | 30 | 20 | 30 | — | — | — | 100 | 100 | 100 | 100 | 100 | 15 | 100 | 100 | 100 | 15 | 10 | 30 | 40 |
| Downy brome | — | — | — | — | — | — | 20 | — | — | — | — | — | — | — | — | — | — | — | — | — | — | — | — | — | — | — |
| Field violet | 95 | 50 | 100 | 45 | 95 | 80 | 75 | 60 | 60 | 55 | 70 | 70 | 55 | 85 | 100 | 20 | 100 | 100 | 15 | 100 | 100 | 100 | 60 | 55 | 30 | 50 |
| Galium (2) | 100 | 30 | 50 | 30 | 100 | 100 | 100 | 60 | 60 | 35 | 30 | 30 | 30 | 100 | 100 | 80 | 60 | 50 | 30 | 100 | 95 | 100 | 40 | 35 | 40 | 40 |
| Green foxtail | — | — | — | — | — | — | 100 | — | — | — | — | — | — | — | — | 20 | — | — | — | — | — | — | — | — | — | — |
| Jointed Goatgra | — | — | — | — | — | — | 40 | — | — | — | — | — | — | — | 30 | 100 | — | — | 45 | 100 | 100 | 100 | — | — | — | — |
| Kochia | 100 | 100 | 100 | 100 | 100 | 100 | 100 | 100 | 100 | 100 | 100 | 100 | 100 | 100 | 100 | 100 | 100 | 100 | 40 | 100 | 100 | 100 | 30 | 80 | 100 | 50 |
| Lambsquarters | 100 | 60 | 65 | 30 | 100 | 100 | 100 | 55 | 60 | 30 | 100 | 100 | 70 | 100 | 100 | 80 | 100 | 100 | 45 | 100 | 100 | 100 | 20 | 50 | 10 | 70 |
| LS Canarygrass | — | 20 | 30 | 10 | — | 20 | — | 30 | 20 | 20 | 15 | — | — | 50 | 20 | 20 | 10 | 15 | 5 | 10 | 20 | — | 10 | 30 | 55 | — |
| Rape | — | 75 | 100 | 50 | — | — | 100 | 75 | 70 | 60 | — | — | — | — | — | — | — | — | — | — | — | — | 60 | 60 | 30 | — |
| Redroot Pigweed | 100 | 60 | 45 | 60 | 100 | 100 | 100 | 60 | 50 | 55 | 100 | 100 | 100 | 100 | 100 | 100 | 100 | 100 | 45 | 100 | 100 | 45 | 30 | 55 | — | 100 |
| Russian Thistle | — | — | — | — | — | — | — | — | — | — | 100 | — | 100 | — | — | — | — | — | — | — | — | — | — | — | — | 100 |
| Ryegrass | — | — | — | — | — | — | 30 | — | — | — | — | — | — | — | 30 | — | — | — | — | — | — | — | — | — | — | — |
| Scentless Chamo | 100 | 50 | 60 | 65 | — | 100 | 100 | 60 | 50 | 60 | 75 | 50 | 70 | 100 | 80 | 100 | 100 | 70 | 20 | 100 | 100 | 100 | 30 | 45 | 50 | 60 |
| Speedwell | 100 | 75 | 65 | 100 | 100 | 100 | 100 | 60 | 60 | 100 | 40 | 20 | 10 | 10 | — | 20 | — | 100 | 20 | 30 | 100 | 100 | 50 | 50 | 65 | 40 |
| Spring Barley | 45 | 10 | 15 | 10 | 45 | 20 | 20 | 10 | 10 | 10 | 15 | 30 | 10 | 50 | 20 | 20 | 10 | 15 | 5 | 10 | 10 | 20 | 10 | 10 | 10 | 0 |
| Sugar beet | — | 100 | 100 | 100 | — | — | 100 | 100 | 70 | 60 | — | — | 100 | — | — | — | — | — | — | — | — | — | 100 | 100 | 100 | — |
| Sunflower | — | 60 | 60 | 50 | — | — | 100 | 100 | 50 | 60 | — | — | — | — | — | — | — | — | 45 | — | — | — | 50 | 40 | 60 | — |
| Veronica hedera | — | — | — | — | — | — | 30 | — | — | — | — | — | — | — | — | — | — | — | — | — | — | — | — | — | — | — |
| Wheat (Spring) | 35 | 10 | 10 | 10 | 25 | 20 | 20 | 10 | 10 | 10 | 10 | 20 | 5 | 20 | 15 | 20 | 30 | 30 | 20 | 30 | 20 | 30 | 30 | 45 | 50 | 10 |
| Wheat (Winter) | 15 | 10 | 10 | 10 | 10 | 20 | 20 | 10 | 20 | 10 | 10 | 20 | 0 | 10 | 20 | 20 | 20 | 20 | 5 | 30 | 20 | 30 | 50 | 50 | 65 | 0 |
| Wild buckwheat | 100 | 100 | 100 | 55 | 100 | 100 | 100 | 100 | 100 | 60 | 60 | 75 | 70 | 85 | 100 | 100 | 100 | 100 | 55 | 100 | 100 | 100 | 10 | 10 | 10 | 40 |
| Wild mustard | — | 60 | 80 | 10 | — | — | — | 100 | 100 | — | — | — | — | — | — | — | — | — | — | — | — | — | — | — | — | — |
| Wild oat (2) | — | — | — | — | — | — | 30 | — | — | — | — | — | — | — | — | — | — | — | — | — | — | — | 10 | 10 | 10 | 0 |
| Winter Barley | 25 | 10 | 20 | 10 | 25 | 30 | 30 | 15 | 10 | 10 | 10 | 30 | 5 | 20 | 15 | 20 | 30 | 20 | 10 | 30 | 20 | 30 | 10 | 10 | 10 | 0 |

| COMPOUND | | | | | Rate 8 g/ha | | | | | | | | | | | Rate 4 g/ha | | | |
|---|---|---|---|---|---|---|---|---|---|---|---|---|---|---|---|---|---|---|---|
| | 13 | 14 | 20 | 21 | 23 | 30 | 32 | 33 | 34 | 35 | 43 | 48 | 49 | 52 | 53 | 54 | 55 | 12 | 13 | 14 | 20 | 21 | 23 | 25 | 30 |
| Annual Bluegras | — | — | — | — | — | — | — | — | — | — | — | — | — | — | — | — | — | — | — | — | — | — | — | — | 30 |
| Blackgrass (2) | — | — | — | — | — | — | — | — | — | — | — | — | — | — | — | — | — | — | — | — | — | — | — | — | — |
| Blk Nightshade | — | — | 100 | 100 | 100 | 100 | 100 | 100 | 100 | 100 | 100 | 10 | 100 | 100 | — | 100 | 100 | — | — | 100 | 100 | 100 | 100 | 100 | 100 |
| Chickweed | — | — | 85 | 100 | 100 | 100 | 100 | 100 | 100 | 60 | 100 | 50 | 70 | 50 | — | 75 | 50 | 10 | — | — | 75 | 100 | 100 | 100 | 25 |
| Deadnettle | 40 | 40 | 60 | 60 | 70 | 20 | 60 | 45 | 65 | 55 | 100 | 30 | 45 | 20 | 30 | 40 | 80 | 50 | 30 | 30 | 40 | 65 | 45 | 50 | 20 |
| Downy brome | — | — | — | — | — | — | — | — | — | — | — | — | — | — | — | — | 70 | — | — | — | — | — | 10 | — | — |
| Field violet | 60 | 35 | 75 | 70 | 70 | 70 | 100 | 100 | 100 | 100 | 100 | 40 | 60 | 50 | 30 | 30 | 40 | 50 | 40 | 30 | 30 | 65 | 60 | 100 | 60 |
| Galium (2) | 30 | 40 | 100 | 100 | 95 | 100 | 100 | 100 | 100 | 65 | 100 | 30 | 50 | 20 | 30 | 60 | 70 | 60 | 30 | 30 | 60 | 100 | 95 | 70 | 10 |
| Green foxtail | — | — | — | 40 | — | — | — | — | — | — | — | — | — | — | — | — | — | 10 | — | — | — | — | 70 | — | — |

TABLE E-continued

Rate 4 g/ha

| COMPOUND | 31 | 32 | 33 | 34 | 35 | 43 | 48 | 52 | 53 | 54 | 55 | 20 | 21 | 23 | 25 | 31 | 32 | 33 | 34 | 35 | 43 | 49 | 52 | 54 | 55 | Rate 1 g/ha |
|---|---|---|---|---|---|---|---|---|---|---|---|---|---|---|---|---|---|---|---|---|---|---|---|---|---|---|
| Jointed Goatgra | 100 | — | — | — | 10 | — | — | — | — | — | — | — | — | — | — | — | — | — | — | 15 | — | — | — | — | — | — |
| Kochia | 100 | 100 | 100 | 100 | 100 | 100 | 100 | 100 | 100 | 100 | 100 | 100 | 35 | 60 | 100 | 100 | 100 | 100 | 100 | 70 | 70 | 100 | 100 | 100 | 100 | 100 |
| Lambsquarters | 100 | 70 | 100 | 100 | 100 | 100 | 100 | 100 | 100 | 100 | 70 | 100 | 30 | 70 | 100 | 70 | 100 | 80 | 100 | 100 | 100 | 85 | 100 | 75 | 100 | 70 |
| LS Canarygrass | — | — | — | — | — | — | — | — | — | — | — | — | — | — | — | — | — | — | — | — | — | — | — | — | — | — |
| Rape | — | — | 100 | — | 100 | 100 | — | 100 | 100 | 100 | — | 100 | — | — | — | — | — | — | — | — | — | — | — | 100 | 100 | — |
| Redroot Pigweed | — | 100 | — | 100 | 100 | 100 | 20 | 100 | 100 | 100 | 70 | 100 | 10 | 50 | 100 | 60 | 100 | 100 | 70 | 70 | 90 | — | 50 | 100 | 100 | 100 |
| Russian Thistle | 100 | — | 100 | — | — | — | — | — | — | — | — | — | — | 100 | — | — | — | — | — | 100 | 100 | — | 100 | 100 | 100 | — |
| Ryegrass | — | — | — | — | 20 | — | — | — | — | — | — | — | — | — | — | — | — | — | — | — | — | — | — | — | — | — |
| Scentless Chamo | 40 | 60 | 70 | 60 | 100 | 65 | 65 | 70 | 60 | 100 | 50 | 35 | 10 | 70 | 65 | 100 | 70 | 100 | 100 | 30 | 70 | 55 | 55 | 10 | 60 | 50 |
| Speedwell | 40 | 0 | 85 | 0 | 100 | 20 | 100 | 100 | 65 | 60 | — | 30 | 10 | 100 | 10 | 100 | 100 | 100 | 30 | 10 | 60 | — | 100 | 100 | — | 35 |
| Spring Barley | 20 | 0 | 45 | 10 | 10 | 20 | 10 | 20 | 20 | 30 | 30 | 20 | 20 | 15 | 10 | 15 | 100 | 45 | 10 | 15 | 45 | 10 | 10 | 10 | 10 | 10 |
| Sugar beet | — | — | — | — | 100 | — | — | — | — | — | — | — | 5 | — | — | — | — | — | — | — | — | — | — | 100 | — | — |
| Sunflower | — | — | — | — | — | — | — | — | — | — | — | 100 | — | — | — | — | — | — | — | — | — | — | — | 80 | — | — |
| Veronica hedera | — | — | — | — | — | 95 | 5 | 30 | 60 | 100 | 100 | — | 20 | 20 | 20 | 20 | 20 | 20 | 10 | 10 | 5 | 5 | 5 | 10 | 55 | 10 |
| Wheat (Spring) | 20 | 0 | 20 | 20 | 20 | 20 | 20 | 20 | 30 | 30 | 20 | 20 | 0 | 10 | 10 | 10 | 20 | 15 | 20 | 20 | 5 | 5 | 10 | 10 | 10 | 10 |
| Wheat (Winter) | 10 | 0 | 5 | 10 | 10 | 20 | 10 | 10 | 25 | 20 | 20 | 20 | 2 | 10 | 20 | 20 | 10 | 30 | 10 | 10 | 5 | 5 | — | 10 | 10 | 10 |
| Wild buckwheat | 50 | 60 | 85 | 100 | 100 | 100 | 5 | 100 | 75 | 100 | 100 | 100 | 50 | 100 | 100 | 100 | 100 | 100 | 65 | 40 | 85 | 100 | 100 | 100 | 100 | 100 |
| Wild mustard | — | — | — | — | — | — | — | — | — | — | — | — | — | — | — | — | — | — | — | — | — | — | — | — | — | — |
| Wild oat (2) | — | — | — | — | 30 | — | — | — | — | — | — | — | — | 10 | — | — | — | — | — | — | — | 25 | 20 | 15 | — | — |
| Winter Barley | 20 | 0 | 20 | 20 | 15 | 20 | 10 | 30 | 20 | 30 | 30 | 20 | 5 | 10 | 20 | 10 | 20 | 15 | 15 | 0 | 15 | 0 | 0 | 10 | 10 | 10 |

Rate 2 g/ha

| COMPOUND | 31 | 32 | 33 | 34 | 35 | 43 | 49 | 52 | 54 | 55 | Rate 1 g/ha |
|---|---|---|---|---|---|---|---|---|---|---|---|
| Annual Bluegras | — | — | — | — | — | — | — | — | — | — | — |
| Blackgrass (2) | — | — | — | — | — | — | — | — | — | — | — |
| Blk Nightshade | 100 | 100 | 100 | 100 | 70 | 100 | 60 | 100 | 100 | 80 | 100 |
| Chickweed | 50 | 100 | 30 | 50 | 30 | 60 | 20 | 50 | 50 | 30 | 50 |
| Deadnettle | 30 | 50 | 45 | 55 | 40 | 40 | 30 | 30 | 70 | 30 | 30 |
| Downy brome | — | — | — | — | — | — | — | — | — | — | — |
| Field violet | 75 | 100 | 65 | 100 | 100 | 100 | 30 | 50 | 70 | 50 | 70 |
| Galium (2) | 30 | 50 | 25 | 60 | 30 | 100 | 20 | 50 | 50 | 50 | 30 |
| Green foxtail | — | — | — | — | — | — | — | — | — | — | — |
| Jointed Goatgra | — | — | — | — | — | — | — | — | — | — | — |
| Kochia | 60 | 100 | 70 | 70 | 65 | 100 | 40 | 100 | 100 | 50 | 75 |
| Lambsquarters | 70 | 100 | 60 | 70 | 60 | 100 | 50 | 100 | 90 | 30 | 70 |
| LS Canarygrass | — | — | — | — | — | — | — | — | — | — | — |
| Rape | — | — | 100 | — | — | — | — | — | — | — | — |
| Redroot Pigweed | 100 | 100 | 60 | 100 | 100 | 100 | 30 | 50 | 60 | 100 | 100 |
| Russian Thistle | 100 | 100 | 100 | 100 | 100 | 100 | 50 | 100 | 100 | 100 | 100 |
| Ryegrass | — | — | — | — | — | — | — | — | — | — | — |
| Scentless Chamo | 50 | 65 | 50 | 50 | 30 | 65 | 30 | 30 | 60 | 60 | 30 |
| Speedwell | 15 | 20 | 20 | 20 | 15 | 10 | 10 | — | 5 | 0 | 5 |
| Spring Barley | — | — | — | — | — | — | — | — | — | — | — |
| Sugar beet | — | — | — | — | — | — | — | — | — | — | — |
| Sunflower | — | — | — | — | — | — | — | — | — | — | — |
| Veronica hedera | 50 | 50 | 50 | 60 | 50 | 60 | 10 | 5 | 5 | 5 | 5 |
| Wheat (Spring) | 20 | 20 | 20 | 20 | 10 | 10 | 5 | 5 | 5 | 5 | 5 |
| Wheat (Winter) | 15 | 10 | 20 | 10 | 10 | 10 | 0 | 5 | 5 | 0 | — |

TABLE E-continued

| | | | | | | | | | | | | | | | | | | | |
|---|---|---|---|---|---|---|---|---|---|---|---|---|---|---|---|---|---|---|---|
| Wild buckwheat | 65 | 100 | 60 | 100 | 100 | 100 | 20 | 100 | 100 | 55 | 100 | 30 | 65 | 70 | 100 | 50 | 100 | 100 | 100 | 60 | 100 |
| Wild mustard | — | — | — | — | — | — | — | — | — | — | — | — | — | — | — | — | — | — | — | — | — |
| Wild oat (2) | — | — | — | — | — | — | — | — | — | — | — | — | — | — | — | — | — | — | — | — | — |
| Winter Barley | 20 | 20 | 20 | 20 | 20 | 20 | 5 | 10 | 20 | 10 | 10 | 20 | 20 | 20 | 10 | 10 | 5 | 5 | 5 | 0 | 10 |

Rate 1 g/ha

| COMPOUND | 31 | 32 | 52 | 54 | 55 |
|---|---|---|---|---|---|
| Annual Bluegras | — | — | — | — | — |
| Blackgrass (2) | — | — | — | — | — |
| Blk Nightshade | 60 | 100 | 100 | 100 | 30 |
| Chickweed | 10 | 50 | 20 | 50 | — |
| Deadnettle | 30 | 30 | 20 | 50 | 30 |
| Downy brome | — | — | — | — | — |
| Field violet | 50 | 65 | 50 | 60 | 30 |
| Galium (2) | 50 | 20 | 40 | 50 | 50 |
| Green foxtail | — | — | — | — | — |
| Jointed Goatgra | — | — | — | — | — |
| Kochia | 35 | 100 | 80 | 70 | 40 |
| Lambsquarters | 60 | 60 | 70 | 90 | 20 |
| LS Canarygrass | — | — | — | — | — |
| Rape | — | — | — | — | — |
| Redroot Pigweed | 100 | 100 | 100 | 100 | 30 |
| Russian Thistle | 70 | 75 | — | — | — |
| Ryegrass | — | — | — | — | — |
| Scentless Chamo | 55 | 55 | 50 | 50 | 20 |
| Speedwell | 5 | 5 | 50 | 0 | 50 |
| Spring Barley | — | — | 5 | 0 | 0 |
| Sugar beet | — | — | — | — | — |
| Sunflower | — | — | — | — | — |
| Veronica hedera | 30 | 50 | — | — | — |
| Wheat (Spring) | 5 | 10 | 5 | 5 | 5 |
| Wheat (Winter) | 5 | 2 | 5 | 0 | 0 |
| Wild buckwheat | 45 | 55 | 20 | 60 | 50 |
| Wild mustard | — | — | — | — | — |
| Wild oat (2) | — | — | — | — | — |
| Winter Barley | 10 | 10 | 5 | 0 | 0 |

PREEMERGENCE

| | Rate 62 g/ha | Rate 31 g/ha | | | | Rate 16 g/ha | | | | | Rate 8 g/ha | | | | | Rate 4 g/ha | | | | |
|---|---|---|---|---|---|---|---|---|---|---|---|---|---|---|---|---|---|---|---|---|
| COMPOUND | 20 | 20 | 21 | 31 | 32 | 20 | 21 | 25 | 30 | 31 | 32 | 20 | 21 | 25 | 30 | 31 | 32 | 52 | 53 | 54 | 20 | 21 | 25 |
| Blk Nightshade | 100 | 95 | 85 | 65 | 60 | 95 | 95 | 70 | 50 | 45 | 50 | 90 | 50 | 20 | 20 | 0 | 30 | 50 | 60 | 50 | 15 | 50 | 30 |
| Chickweed | 95 | 95 | 45 | 60 | 100 | 95 | 30 | 75 | 30 | 50 | 100 | 35 | 30 | 75 | 25 | 30 | 70 | 30 | 20 | 30 | 0 | 15 | 70 |
| Deadnettle | 100 | 95 | 15 | 60 | 60 | 70 | 10 | 20 | 30 | 30 | 65 | 10 | 0 | 10 | 20 | 20 | 60 | 10 | 0 | 50 | 0 | 10 | 10 |
| Field violet | 75 | 25 | 20 | 30 | 10 | 20 | 0 | 40 | 20 | 30 | 0 | 10 | 20 | 60 | 0 | 30 | 20 | 100 | 60 | 30 | 10 | 20 | 30 |
| Galium (2) | 100 | 100 | 100 | 75 | 100 | 100 | 100 | 100 | 50 | 25 | 100 | 80 | 65 | 60 | 40 | 10 | 50 | 60 | 60 | 50 | — | — | 30 |

TABLE E-continued

| | | | | | | | | | | | | | | | | | | | | | | | | | | | |
|---|---|---|---|---|---|---|---|---|---|---|---|---|---|---|---|---|---|---|---|---|---|---|---|---|---|---|---|
| Kochia | 100 | 90 | 100 | 50 | 45 | 100 | 100 | 100 | 30 | 30 | 30 | 50 | 30 | 30 | 90 | 100 | 100 | — | 30 | 10 | 20 | 20 | 0 | 0 | 5 | 85 | 95 |
| Lambsquarters | 100 | 100 | 100 | 65 | 60 | 100 | 90 | 100 | 60 | 60 | 60 | 100 | 100 | 100 | — | 90 | 100 | 100 | 70 | 50 | 70 | 30 | 100 | 100 | 100 | 100 | 100 |
| Redroot Pigweed | 100 | 100 | — | — | 85 | 65 | 100 | 50 | 50 | 55 | 55 | 100 | 100 | 30 | — | 90 | — | — | 30 | 30 | 35 | 50 | 70 | 20 | 5 | 50 | 0 |
| Russian Thistle | — | — | 100 | 100 | — | — | 100 | — | 75 | 75 | 75 | 10 | 20 | 10 | — | — | — | 75 | 70 | 70 | 70 | 90 | 20 | 75 | — | — | 70 |
| Scentless Chamo | — | — | 85 | 100 | — | — | 100 | 100 | 75 | 75 | 75 | 100 | 85 | 100 | 70 | 50 | 50 | — | 30 | 30 | 35 | 50 | 70 | — | 10 | — | — |
| Speedwell | 100 | 90 | — | 0 | 80 | 60 | 95 | 50 | 80 | — | — | — | — | — | — | 50 | — | 50 | 0 | — | 0 | 0 | 0 | 0 | 10 | 0 | 0 |
| Spring Barley | 30 | 10 | 100 | 10 | 10 | 0 | 50 | 30 | — | 0 | 0 | 10 | 10 | — | — | 0 | 0 | — | 0 | 0 | 0 | 0 | 0 | 10 | 5 | — | 100 |
| Veronica hedera | — | — | — | 100 | — | — | — | 0 | 0 | 65 | 65 | 100 | 100 | 100 | — | — | — | — | 70 | 70 | 40 | 0 | 65 | 75 | — | 0 | — |
| Wheat (Spring) | 5 | 0 | — | 10 | 10 | 0 | 10 | 10 | 85 | 30 | 65 | 20 | 10 | 100 | — | 50 | — | — | 10 | 10 | 0 | 10 | 0 | 0 | — | 10 | 10 |
| Wheat (Winter) | 5 | 5 | 5 | 10 | 0 | 0 | 10 | 10 | 10 | 0 | 0 | 10 | 10 | 10 | 0 | 0 | 0 | — | 0 | 0 | 0 | 0 | 0 | 0 | 0 | 0 | 0 |
| Wild buckwheat | 100 | 100 | 95 | 100 | 100 | 0 | 80 | 100 | 30 | 60 | 55 | 100 | 30 | — | 85 | 50 | 50 | 50 | 10 | — | 30 | 50 | 30 | 50 | 20 | 60 | 40 |
| Winter Barley | 30 | 5 | 5 | 0 | 5 | 5 | 10 | 30 | 20 | 30 | 10 | 30 | 20 | 20 | 0 | 0 | 10 | 10 | 0 | 20 | 0 | 25 | 10 | 10 | 0 | 15 | 20 |

| | Rate 4 g/ha | | | | | Rate 2 g/ha | | | | Rate 2 g/ha | |
|---|---|---|---|---|---|---|---|---|---|---|---|---|
| COMPOUND | 30 | 52 | 53 | 54 | 25 | 30 | 52 | 53 | 54 | 20 | 21 |
| Blk Nightshade | 10 | 0 | 30 | 0 | 30 | 10 | 0 | 30 | 0 | 0 | 50 |
| Chickweed | 20 | 50 | 0 | 10 | 70 | 20 | 50 | 0 | 10 | 0 | 0 |
| Deadnettle | 10 | 30 | 20 | 30 | 10 | 10 | 30 | 20 | 30 | 0 | 10 |
| Field violet | 0 | 0 | 0 | 0 | 0 | 0 | 0 | 0 | 0 | — | 10 |
| Galium (2) | 0 | 100 | 60 | 0 | 30 | 0 | 100 | 60 | 0 | 0 | 50 |
| Kochia | 30 | 100 | 0 | 0 | 95 | 30 | 100 | 0 | 0 | 0 | 50 |
| Lambsquarters | 30 | 70 | 100 | 50 | 100 | 30 | 70 | 100 | 50 | 15 | 100 |
| Redroot Pigweed | 40 | 60 | — | 100 | 100 | 40 | 60 | — | 100 | 0 | 80 |
| Russian Thistle | — | 0 | 10 | 10 | 0 | — | 0 | 10 | 10 | 0 | 70 |
| Scentless Chamo | 75 | 100 | — | — | 70 | 75 | 100 | — | — | — | — |
| Speedwell | — | — | — | — | — | — | — | — | — | — | 15 |
| Spring Barley | 10 | 0 | 60 | 0 | 100 | 10 | 0 | 60 | 0 | 0 | 0 |
| Veronica hedera | 0 | 100 | 10 | 100 | 10 | 10 | 100 | 10 | 100 | 0 | — |
| Wheat (Spring) | 0 | 20 | 10 | 0 | 10 | 0 | 20 | 10 | 0 | — | 10 |
| Wheat (Winter) | 0 | 0 | 0 | 0 | 0 | 0 | 0 | 0 | 0 | 0 | 0 |
| Wild buckwheat | — | 40 | 0 | 0 | 40 | — | 40 | 0 | 0 | 0 | 0 |
| Winter Barley | 20 | 25 | 10 | 0 | 20 | 25 | 10 | 20 | 0 | 10 | 30 |

TEST F

Compounds evaluated in this test were formulated in a non-phytotoxic solvent mixture which included a surfactant and applied to plants that were grown for various periods of time before treatment (postemergence application). A mixture of sandy loam soil and greenhouse potting mix in a 60:40 ratio was used for the postemergence test.

Plantings of these crops and weed species were adjusted to produce plants of appropriate size for the postemergence test. All plant species were grovn using normal greenhouse practices. Crop and weed species include arrowleaf sida (*Sida rhombifolia*), barnyardgrass (*Echinochloa crus-galli*), cocklebur (*Xanthium strumarium*), common lambsquarters (*Chenopodium album*), common ragweed (*Ambrosia artemisifolia*), corn (*Zea mays*), cotton (*Gossypium hirsutum*), eastern black nightshade (*Solanum ptycanthum*), fall panicum (*Panicun dichotomiflorum*), field bindweed (*Convolvulus arvensis*), Florida beggarweed (*Desmodium purpureum*), giant foxtail (*Setaria faberi*), hairy beggarticks (*Bidens pilosa*), ivyleaf morningglory (*Ipomoea hederacea*), johnsongrass (*Sorghum halepense*), ladysthumb (*Polygonum persicaria*), large crabgrass (*Digitaria sanguinalis*), purple nutsedge (*Cyperus rotundus*), redroot pigweed (*Amaranthus retroflexus*), soybean (*Glycine max*), surinam grass (*Brachiaria decumbens*), velvetleaf (*Abutilon theophrasti*) and wild poinsettia (*Euphorbia heterophylla*).

Treated plants and untreated controls were maintained in a greenhouse for approximately 14 to 21 days, after which all treated plants were compared to untreated controls and visually evaluated. Plant response ratings, summarized in Table F, were based upon a 0 to 100 scale where 0 was no effect and 100 was complete control. A dash response (−) means no test result.

TABLE F

POSTEMERGENCE

Rate 35 g/ha

| COMPOUND | 23 | 25 | 30 | 48 | 52 | 53 | 54 | 60 | 71 | 21 | 22 | 23 | 25 | 30 | 32 | 39 | 40 | 48 | 52 | 53 | 54 | 60 | 64 | 69 | 71 | Rate 8 g/ha 21 |
|---|---|---|---|---|---|---|---|---|---|---|---|---|---|---|---|---|---|---|---|---|---|---|---|---|---|---|
| Arrowleaw Sida | 100 | 100 | 75 | 45 | 100 | 100 | 100 | 70 | 25 | 100 | 100 | 100 | 85 | 35 | 100 | 100 | 100 | 20 | 100 | 90 | 100 | 70 | — | 10 | 10 | 80 |
| Barnyardgrass | 40 | 40 | 15 | 15 | 35 | 25 | 50 | 55 | 15 | 40 | 35 | 30 | 25 | 10 | 15 | 65 | 65 | 5 | 25 | 20 | 55 | 55 | 85 | 40 | 10 | 35 |
| Cocklebur | 100 | 100 | 75 | 25 | 100 | 100 | 100 | 100 | 25 | 100 | 100 | 100 | 100 | — | 100 | 100 | 100 | 15 | 100 | 100 | 100 | 100 | 100 | 100 | 15 | 100 |
| Common Ragweed | 100 | 100 | 100 | 30 | 100 | 100 | 100 | 85 | 40 | 100 | 100 | 100 | 100 | 10 | 100 | 100 | 100 | 0 | 100 | 100 | 100 | 100 | 100 | 85 | 35 | 100 |
| Corn | 25 | 10 | 10 | 5 | 10 | 15 | 10 | 20 | 10 | 20 | 25 | 20 | 10 | 10 | 15 | 15 | 15 | 0 | 15 | 10 | 10 | 15 | 20 | 20 | 5 | 15 |
| Cotton | 100 | 100 | 100 | 100 | 100 | 100 | 100 | 100 | 100 | 100 | 100 | 100 | 100 | 100 | 100 | 100 | 100 | 65 | 100 | 100 | 100 | 100 | 100 | 100 | 100 | 5 |
| Estrn Blknight | 100 | 100 | 95 | 25 | 100 | 100 | 100 | 100 | 85 | 40 | 35 | 90 | 65 | 75 | 100 | 100 | 100 | 0 | 100 | 100 | 100 | 100 | 100 | 100 | 35 | 100 |
| Fall Panicum | 45 | 25 | 15 | 15 | 20 | 15 | 20 | 20 | 10 | 40 | 35 | 30 | 10 | 60 | 35 | 15 | 15 | 10 | 10 | 10 | 15 | 20 | 20 | 5 | 5 | 20 |
| Field Bindweed | 100 | 100 | 100 | 70 | 80 | 100 | 100 | 100 | 35 | 100 | 100 | 100 | 100 | 75 | 100 | 100 | 100 | 20 | 70 | 80 | 70 | 60 | 80 | 100 | 25 | 100 |
| Fl Beggarweed | 65 | 85 | 80 | 20 | 80 | 100 | 75 | 70 | 40 | 100 | 100 | 50 | 70 | 60 | 70 | 90 | 85 | 15 | 25 | 15 | 25 | 25 | 25 | 15 | 35 | 100 |
| Giant Foxtail | 40 | 35 | 10 | 10 | 40 | 20 | 30 | 25 | 15 | 45 | 30 | 25 | 20 | 75 | 20 | 30 | 35 | 5 | 100 | 100 | 100 | 100 | 100 | 100 | 10 | 25 |
| Hairy Beggartic | 100 | 100 | 100 | 25 | 100 | 100 | 100 | 100 | 35 | 100 | 100 | 100 | 65 | 85 | 100 | 100 | 100 | 5 | 75 | 100 | 100 | 100 | 100 | 100 | 20 | 100 |
| Ivyleaw Mnglry | 100 | 100 | 95 | 85 | 85 | 100 | 100 | 80 | 20 | 95 | 85 | 100 | 75 | 35 | 100 | 100 | 35 | 25 | 100 | 45 | 35 | 70 | 95 | 50 | 10 | 25 |
| Johnsongrass | 30 | 25 | 15 | 5 | 15 | 20 | 15 | 15 | 5 | 20 | 25 | 15 | 20 | 10 | 15 | 30 | 35 | 5 | 10 | — | 20 | 15 | 50 | 10 | 55 | 75 |
| Ladysthumb | 100 | 60 | 60 | 20 | 90 | 50 | 65 | 10 | 20 | 65 | 30 | 25 | 50 | 55 | 100 | 100 | 0 | 15 | 60 | 45 | 35 | 0 | 0 | 0 | 10 | 80 |
| Lambsquarters | 100 | 100 | 95 | 30 | 100 | — | — | 80 | 65 | 100 | 100 | 90 | 90 | 90 | 100 | 100 | — | 10 | 100 | — | — | 100 | 100 | 100 | 15 | 15 |
| Large Crabgrass | 30 | 20 | 15 | 15 | 25 | 25 | 25 | 15 | 10 | 20 | 25 | 15 | 15 | 30 | 15 | 30 | 35 | 15 | 20 | 15 | 20 | 15 | 50 | 10 | 10 | 45 |
| Purple Nutsedge | 15 | 5 | 0 | 0 | 0 | 0 | 0 | 10 | 5 | 65 | 30 | 0 | 0 | 5 | 10 | 0 | 0 | 10 | 0 | 0 | 0 | 0 | 0 | 10 | 100 | 100 |
| Redroot Pigweed | 100 | 100 | 100 | 80 | 100 | 100 | 100 | 100 | 100 | 100 | 100 | 100 | 100 | 100 | 100 | — | — | 75 | 100 | 100 | 100 | 100 | 100 | 90 | 60 | 40 |
| Soybean | 40 | 50 | 75 | 20 | 60 | 45 | 30 | 35 | 15 | 45 | 35 | 50 | 50 | 30 | 15 | 45 | 50 | 5 | 35 | 40 | 25 | 50 | 50 | 60 | 10 | 20 |
| Surinam Grass | 25 | 30 | 10 | 15 | 30 | 25 | 30 | 45 | 15 | 25 | 35 | 15 | 25 | 5 | 15 | 25 | 30 | 10 | 20 | 20 | 25 | 40 | 25 | 10 | 25 | 100 |
| Velvetleaf | 100 | 100 | 100 | 50 | 100 | 100 | 100 | 90 | 40 | 100 | 100 | 100 | 100 | 100 | 100 | 100 | 100 | 15 | 100 | 100 | 100 | 90 | 100 | 100 | 60 | 100 |
| Wild Poinsettia | 100 | 100 | 100 | 65 | 100 | 100 | 100 | 100 | 100 | 100 | 100 | 100 | 100 | 80 | 100 | 100 | 100 | 10 | 100 | 100 | 100 | 100 | 100 | 100 | 30 | 100 |

Rate 17 g/ha / Rate 4 g/ha

| COMPOUND | 22 | 23 | 25 | 30 | 48 | 52 | 53 | 54 | 60 | 71 | 21 | 22 | 23 | 25 | 30 | 32 | 39 | 40 | 48 | 52 | 53 | 54 | 60 | 64 | 69 | 71 |
|---|---|---|---|---|---|---|---|---|---|---|---|---|---|---|---|---|---|---|---|---|---|---|---|---|---|---|
| Arrowleaw Sida | 100 | 50 | 80 | 20 | 25 | 25 | 10 | 60 | 90 | 35 | 75 | 55 | 20 | 0 | 10 | 0 | 90 | 75 | 20 | 25 | 0 | 0 | 25 |
| Barnyardgrass | 25 | 15 | 15 | 0 | 10 | 15 | 0 | 10 | 20 | 15 | 20 | 20 | 10 | 60 | 0 | 0 | 20 | 20 | 10 | 10 | 0 | 0 | 0 |
| Cocklebur | 100 | 100 | 100 | 40 | 100 | 100 | 25 | 85 | 80 | 100 | 100 | 100 | 100 | 75 | 25 | 10 | 100 | 100 | 100 | 100 | 0 | 0 | 90 |
| Common Ragweed | 100 | 100 | 100 | 100 | 15 | 100 | 50 | 100 | 70 | 100 | 100 | 95 | 100 | 20 | 50 | 20 | 100 | 100 | 100 | 100 | 0 | 0 | 100 |
| Corn | 15 | 15 | 10 | 5 | 15 | 5 | 5 | 10 | 10 | 10 | 10 | 10 | 15 | 0 | 5 | 5 | 10 | 10 | 15 | 5 | 0 | 0 | 10 |
| Cotton | 100 | 85 | 100 | 95 | 100 | 100 | 95 | 100 | 80 | 100 | 100 | 100 | 80 | 65 | 95 | 45 | 100 | 100 | 100 | 100 | 100 | 25 | 100 |
| Estrn Blknight | 20 | 15 | 5 | 65 | 10 | 5 | 30 | 40 | 70 | 10 | 100 | 15 | 5 | 10 | 30 | 25 | 20 | 20 | 80 | 85 | 5 | 0 | 80 |
| Fall Panicum | 100 | 100 | 100 | 10 | 100 | 100 | 45 | 100 | 20 | 100 | 100 | 15 | 10 | 25 | 45 | 10 | 15 | 10 | 5 | 5 | 0 | 0 | 0 |
| Fl Beggarweed | 100 | 50 | 65 | 90 | 30 | 45 | 30 | 50 | 60 | 60 | 60 | 100 | 30 | 10 | 30 | 25 | 70 | 60 | 30 | 45 | 0 | 0 | 100 |
| Giant Foxtail | 20 | 10 | 10 | 65 | 5 | 10 | 0 | 15 | 15 | 10 | 20 | 15 | 5 | 100 | 0 | 0 | 15 | 15 | 5 | 10 | 0 | 0 | 10 |
| Hairy Beggartic | 95 | 100 | 55 | 0 | 50 | 40 | 25 | 80 | 75 | 65 | 100 | 60 | 100 | 65 | 25 | 40 | 95 | 100 | 100 | 40 | 25 | 0 | 65 |
| Ivyleaw Mnglry | 100 | 100 | 65 | 50 | 20 | 50 | 15 | 100 | 85 | 25 | 80 | 15 | 30 | 50 | 15 | 50 | 15 | 15 | 80 | 50 | 0 | 0 | 25 |
| Johnsongrass | 25 | 15 | 15 | 10 | 10 | 10 | 5 | 10 | 10 | 0 | 10 | — | 5 | 10 | 5 | 10 | 40 | 20 | 10 | 10 | 0 | 0 | 0 |
| Ladysthumb | 65 | 45 | 35 | 40 | 30 | 30 | 25 | 25 | 70 | 30 | 50 | — | 45 | 25 | 25 | 10 | 40 | 60 | 45 | 30 | 25 | 0 | 30 |

TABLE F-continued

Rate 4 g/ha

| COMPOUND | 54 | 60 | 64 | 69 | 71 | 21 | 22 | 23 | 25 | 30 | 32 | 39 | 40 | 48 | 52 | 53 | 54 | 64 | 69 | 71 | 21 | 22 | 25 | 30 | 32 | 39 |
|---|---|---|---|---|---|---|---|---|---|---|---|---|---|---|---|---|---|---|---|---|---|---|---|---|---|---|
| Lambsquarters | 85 | 100 | 90 | 80 | 80 | 100 | 100 | 10 | 100 | — | — | — | 65 | 30 | 40 | 60 | 75 | 100 | 85 | 70 | 70 | 100 | 100 | 5 | 70 | — |
| Large Crabgrass | 15 | 5 | 15 | 0 | 15 | 15 | 20 | 5 | 15 | 10 | 15 | 10 | 10 | 10 | 5 | 10 | 10 | 5 | 10 | 15 | 15 | 10 | 15 | 0 | 10 | 5 |
| Purple Nutsedge | 20 | 0 | 0 | 10 | 10 | 0 | 0 | 0 | 0 | 0 | 0 | 0 | 0 | 75 | 35 | 100 | 100 | 100 | 100 | 0 | 0 | 0 | — | 10 | 0 | 0 |
| Redroot Pigweed | 100 | 100 | 100 | 100 | 100 | — | — | 45 | 100 | 15 | 100 | 100 | 100 | 50 | 5 | 35 | 100 | 100 | 100 | 40 | 100 | 25 | 30 | 0 | 100 | 100 |
| Soybean | 45 | 30 | 40 | 10 | 15 | 35 | 35 | 5 | 15 | 35 | 20 | 35 | 30 | 75 | 35 | 15 | 25 | 25 | 30 | 0 | 10 | 10 | 20 | 10 | 10 | 10 |
| Surinam Grass | 30 | 10 | 20 | 60 | 15 | 15 | 25 | 0 | 10 | 15 | 15 | 5 | 5 | 50 | 0 | 100 | 100 | 5 | 15 | 35 | 15 | 10 | 10 | 0 | 10 | 10 |
| Velvetleaf | 100 | 100 | 100 | 60 | 100 | 100 | 100 | 100 | 100 | 100 | 100 | 100 | 100 | 100 | 45 | 100 | 100 | 100 | 60 | 35 | 100 | 100 | 100 | 0 | 100 | 100 |
| Wild Poinsettia | 100 | 100 | 100 | 70 | 100 | 100 | 100 | 100 | 100 | 100 | 100 | 100 | 100 | 100 | — | 100 | 100 | 100 | 100 | 25 | 100 | 100 | 100 | 0 | 90 | 100 |

Rate 2 g/ha

| COMPOUND | 54 | 60 | 64 | 69 | 71 | 21 | 22 | 23 | 25 | 30 | 32 | 39 | 40 | 48 | 52 | 53 | 54 | 64 | 69 | 71 | 21 | 22 | 25 | 30 | 32 | 39 |
|---|---|---|---|---|---|---|---|---|---|---|---|---|---|---|---|---|---|---|---|---|---|---|---|---|---|---|
| Arrowleaf Sida | 90 | 50 | 0 | 0 | 0 | 70 | 50 | 15 | 15 | 0 | 45 | 70 | 35 | 0 | 10 | 10 | 100 | 0 | 0 | 0 | 60 | 40 | 10 | 0 | 0 | 60 |
| Barnyardgrass | 15 | 45 | 10 | 10 | 0 | 15 | 20 | 5 | 0 | 0 | 10 | 15 | 15 | 0 | 0 | 5 | 0 | 10 | 5 | 0 | 10 | 10 | 0 | 5 | 10 | 10 |
| Cocklebur | 100 | 75 | 100 | 75 | 0 | 100 | 90 | 100 | 100 | 15 | 75 | 90 | 95 | 0 | 65 | 25 | 55 | 100 | 45 | 0 | 100 | 80 | 35 | 40 | 60 | 80 |
| Common Ragweed | 100 | 60 | 20 | 0 | 0 | 100 | 80 | 100 | 85 | 35 | 100 | 100 | 90 | 10 | 5 | 100 | 100 | 20 | 0 | 0 | 30 | 55 | 20 | 0 | 20 | 75 |
| Corn | 5 | 10 | 10 | 15 | 0 | 5 | 5 | 5 | 5 | 5 | 10 | 10 | 5 | 0 | 5 | 5 | 10 | 10 | 5 | 5 | 5 | 10 | 10 | 5 | 10 | 5 |
| Cotton | 100 | 75 | 90 | 80 | 35 | 100 | 100 | 100 | 100 | 30 | 100 | 95 | 100 | 10 | 80 | 100 | 100 | 80 | 80 | 20 | 100 | 90 | 65 | 10 | 85 | 100 |
| Estrn Blknight | 95 | 60 | 100 | 80 | 10 | 100 | 100 | 80 | 40 | 5 | 100 | 100 | 100 | 0 | 75 | 50 | 90 | 5 | 40 | 5 | 100 | 5 | 5 | 10 | 100 | 85 |
| Fall Panicum | 5 | 15 | 5 | 5 | 0 | 5 | 10 | 5 | 0 | 15 | 40 | 10 | 5 | 10 | 0 | 5 | 0 | 5 | 0 | 0 | 0 | 55 | 15 | 0 | 30 | 5 |
| Field Bindweed | 100 | 40 | 95 | 90 | 0 | 100 | 95 | 100 | 25 | 0 | 90 | 100 | 100 | 0 | 100 | 20 | 60 | 100 | 60 | 0 | 75 | 50 | 0 | 15 | 85 | 90 |
| Fl Beggarweed | 35 | 50 | 55 | 10 | 0 | 40 | 60 | 20 | — | 15 | 40 | 65 | 55 | 0 | 35 | 25 | 25 | 5 | 0 | 0 | 25 | 20 | 15 | 0 | 15 | 50 |
| Giant Foxtail | 10 | 15 | 5 | 5 | 0 | 10 | 10 | 5 | 5 | 0 | 15 | 10 | 10 | 0 | 5 | 5 | 10 | 5 | 10 | 10 | 5 | 10 | 20 | 0 | 10 | 10 |
| Hairy Beggartic | 100 | 70 | 100 | 65 | 0 | 85 | 35 | 100 | 30 | 0 | 65 | 95 | 85 | 0 | 15 | 65 | 90 | 60 | 10 | 0 | 30 | 25 | 0 | 0 | 45 | 60 |
| Ivyleaw Mnglry | 100 | 85 | 100 | 75 | 5 | 100 | 100 | 100 | 30 | 5 | 80 | 100 | 100 | 0 | 20 | 35 | 95 | 100 | 65 | 0 | 80 | 95 | 15 | 0 | 70 | 70 |
| Johnsongrass | 5 | 10 | 5 | 10 | 0 | 0 | 10 | 5 | 5 | 0 | 10 | 15 | 10 | 0 | 5 | 5 | 15 | 10 | 5 | 0 | 5 | 5 | 10 | 0 | 10 | 5 |
| Ladysthumb | 20 | 70 | 20 | 40 | 5 | 30 | 50 | 20 | 20 | 20 | 25 | 30 | 35 | 10 | 10 | 25 | 15 | 10 | 10 | 0 | 25 | 20 | 5 | 10 | 25 | 25 |
| Lambsquarters | — | 60 | 80 | 20 | 20 | 55 | 65 | 65 | 80 | 50 | 65 | 100 | 85 | 0 | 55 | — | — | 75 | 5 | 10 | 40 | 40 | 75 | 35 | 50 | 90 |
| Large Crabgrass | 10 | 10 | 20 | 10 | 5 | 10 | 10 | 5 | 5 | 5 | 10 | 10 | 10 | 0 | 5 | 5 | 5 | 10 | 10 | 0 | 5 | 5 | 0 | 0 | 10 | 5 |
| Purple Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot Pigweed | 100 | 75 | 100 | 50 | 15 | 100 | 100 | 95 | 100 | 25 | 100 | — | — | 0 | 100 | 100 | 100 | 100 | 50 | 0 | 90 | 95 | 100 | 20 | 100 | — |
| Soybean | 15 | 15 | 30 | 50 | 0 | 25 | 35 | 25 | 25 | 0 | 10 | 25 | 25 | 0 | 15 | 10 | 10 | 20 | 20 | 10 | 20 | 25 | 10 | 0 | 0 | 15 |
| Surinam Grass | 10 | 20 | 5 | 10 | 5 | 10 | 10 | 5 | 10 | 15 | 15 | 10 | 10 | 0 | 5 | 10 | 5 | 5 | 5 | 0 | 10 | 5 | 10 | 10 | 10 | 5 |
| Velvetleaf | 100 | 45 | 100 | 100 | 0 | 100 | 100 | 100 | 100 | 10 | 100 | 100 | 100 | 0 | 100 | 100 | 100 | 100 | 50 | 35 | 100 | 90 | 20 | 0 | 50 | 75 |
| Wild Poinsettia | 100 | 100 | 100 | 100 | 0 | 100 | 95 | 100 | 100 | 15 | 100 | 100 | 100 | 0 | 75 | 80 | 95 | 100 | 95 | 25 | 80 | 80 | 35 | 10 | 80 | 95 |

Rate 1 g/ha

| COMPOUND | 40 | 48 | 52 | 53 | 54 | 64 | 69 | 71 |
|---|---|---|---|---|---|---|---|---|
| Arrowleaf Sida | 30 | 0 | 0 | 0 | 10 | 0 | 0 | 0 |
| Barnyardgrass | 10 | 0 | 0 | 0 | 0 | 5 | 5 | 0 |
| Cocklebur | 80 | 0 | 0 | 15 | 40 | 75 | 40 | 0 |
| Common Ragweed | 65 | 0 | 40 | 45 | 60 | 0 | 0 | 0 |
| Corn | 5 | 0 | 0 | 0 | 0 | 10 | 5 | 15 |
| Cotton | 80 | 0 | 35 | 100 | 80 | 80 | 40 | 0 |
| Estrn Blknight | 80 | 0 | 20 | 30 | 25 | 85 | 5 | 0 |
| Fall Panicum | 0 | 0 | 0 | 0 | 0 | 0 | 0 | 0 |
| Field Bindweed | 100 | 0 | 85 | — | 15 | 80 | 25 | 0 |
| Fl Beggarweed | 35 | 0 | — | 15 | 5 | 5 | 0 | 0 |
| Giant Foxtail | 10 | 0 | 5 | 0 | 5 | 0 | 0 | 0 |

TABLE F-continued

PREEMERGENCE

Rate 35 g/ha

| COMPOUND | 23 | 25 | 30 | 48 | 52 | 53 | 54 | 71 | 21 | 22 | 23 | 25 | 30 | 32 | 39 | 40 | 48 | 52 | 53 | 54 | 71 | 21 | 22 | 23 | 25 | 30 |
|---|---|---|---|---|---|---|---|---|---|---|---|---|---|---|---|---|---|---|---|---|---|---|---|---|---|---|
| Arrowleaf Sida | 100 | 100 | 65 | 0 | 100 | 100 | 100 | 15 | 100 | 100 | 100 | 65 | 50 | 90 | 100 | 100 | 0 | 100 | 100 | 100 | 0 | 15 | 90 | 25 | 40 | 15 |
| Barnyardgrass | 10 | 10 | 0 | 0 | 0 | 10 | 0 | 0 | 10 | 0 | 0 | 0 | 10 | 10 | 0 | 0 | 0 | 0 | 0 | 10 | 0 | 10 | 0 | 0 | 0 | 0 |
| Cocklebur | 30 | 100 | 100 | 0 | 100 | 100 | 15 | 0 | 100 | 0 | — | 100 | 25 | 60 | 100 | 100 | 0 | 100 | 45 | 50 | 0 | 100 | 35 | 15 | 100 | 0 |
| Common Ragweed | 100 | 100 | 100 | 15 | 100 | 100 | 95 | 45 | 100 | 40 | 70 | 100 | 75 | 100 | 100 | 100 | 5 | 100 | 100 | 100 | 20 | 50 | 0 | — | 0 | 50 |
| Corn | 0 | 0 | 0 | 0 | 0 | 0 | 0 | 0 | 0 | 10 | 0 | 0 | 0 | 10 | 0 | 0 | 0 | 0 | 0 | 0 | — | 0 | 5 | 0 | 0 | 0 |
| Cotton | 100 | 30 | 45 | 0 | 100 | 100 | 100 | 10 | 100 | 50 | 100 | 15 | 35 | 75 | 100 | 100 | 10 | 100 | 45 | 100 | 0 | 0 | 10 | 10 | 0 | 15 |
| Estrn Blknight | 0 | 100 | 100 | 20 | 100 | 100 | 100 | 90 | 0 | 30 | 10 | 100 | 100 | 100 | 100 | — | 0 | 100 | 100 | 100 | 55 | 100 | — | 0 | 100 | 95 |
| Fall Panicum | 50 | 10 | 15 | 10 | 10 | 0 | 15 | 25 | 100 | — | — | 100 | 70 | 0 | 40 | 15 | 0 | 100 | 100 | 100 | 10 | 0 | 0 | 0 | 0 | 40 |
| Field Bindweed | — | 100 | 100 | 0 | 100 | 100 | 100 | 20 | 0 | 20 | 0 | 100 | 25 | 10 | 100 | 10 | 0 | 100 | 100 | 100 | 5 | 100 | — | 0 | 100 | 10 |
| Fl Beggarweed | 20 | 10 | 40 | 0 | 20 | 15 | 10 | 10 | 35 | 0 | — | 0 | 0 | 0 | 25 | 0 | 0 | 0 | 0 | 0 | 0 | 15 | 0 | 0 | 0 | 0 |
| Giant Foxtail | — | 0 | 0 | 0 | 0 | 95 | 0 | 35 | 100 | 20 | — | 50 | 100 | 0 | 75 | 100 | 0 | 50 | 0 | 100 | 0 | 30 | 45 | 100 | 60 | 85 |
| Hairy Beggartic | 100 | 100 | 100 | 0 | 100 | 100 | 100 | 100 | 100 | 100 | 100 | 100 | 100 | 100 | — | 10 | 0 | 60 | 90 | 100 | 35 | 45 | 25 | 100 | 55 | 15 |
| Ivyleaw Mrnglry | 100 | 100 | 75 | 0 | 100 | 0 | 100 | 10 | 90 | 60 | 100 | 70 | 50 | 85 | 100 | 100 | 0 | 100 | 100 | 100 | 0 | 45 | 0 | 0 | 0 | 0 |
| Johnsongrass | — | 0 | 0 | 0 | 0 | 0 | 0 | 0 | 0 | 0 | 0 | 0 | 0 | 0 | 0 | 0 | 0 | 0 | 0 | — | 0 | 0 | 0 | — | 35 | — |
| Ladysthumb | — | 100 | 0 | 0 | 100 | 95 | 100 | 35 | 100 | 100 | 100 | 50 | 100 | 100 | 75 | 100 | 0 | 50 | 0 | 100 | 0 | 15 | 0 | 0 | 35 | 70 |
| Lambsquarters | 100 | 100 | 100 | 0 | 100 | 100 | 100 | 100 | 100 | 100 | 100 | 100 | 100 | 100 | — | 10 | 5 | 100 | 100 | 100 | 35 | 30 | 100 | 100 | 100 | 0 |
| Large Crabgrass | 0 | 0 | 0 | 0 | 0 | 15 | 10 | 10 | 20 | 60 | 0 | 0 | 0 | 10 | 15 | 0 | 0 | 0 | 15 | 5 | 0 | 15 | 25 | 0 | 0 | 0 |
| Purple Nutsedge | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Redroot Pigweed | 100 | 100 | 100 | 15 | 100 | 100 | 100 | 50 | 100 | 100 | 100 | 100 | 75 | 100 | 100 | 100 | 0 | 100 | 100 | 100 | 10 | 100 | 100 | 100 | 100 | 60 |
| Soybean | 0 | 0 | 0 | 0 | 0 | 0 | 20 | 10 | 20 | 15 | 0 | 0 | 0 | 10 | 10 | 10 | 0 | — | 5 | 10 | 0 | 10 | 25 | 0 | 0 | 0 |
| Surinam Grass | 10 | 0 | 10 | 0 | 20 | 15 | 5 | 0 | 10 | 100 | — | 50 | 20 | 0 | 10 | 10 | 0 | 0 | 100 | 100 | 20 | 10 | 0 | 0 | 0 | 35 |
| Velvetleaf | 100 | 100 | 100 | 0 | 100 | 100 | 100 | 35 | 100 | 100 | 100 | 45 | 90 | 100 | 100 | 100 | 0 | 80 | 80 | 100 | 20 | 100 | 100 | 100 | 100 | 35 |
| Wild Poinsettia | 100 | 100 | 45 | 0 | 100 | 100 | 100 | — | 100 | — | 55 | 45 | 35 | 0 | 100 | 100 | 0 | 0 | 0 | 0 | 0 | 100 | — | — | — | 20 |

Rate 8 g/ha

Rate 17 g/ha

Rate 8 g/ha

| COMPOUND | 32 | 39 | 40 | 48 | 52 | 53 | 54 | 71 | 21 | 22 | 23 | 25 | 30 |
|---|---|---|---|---|---|---|---|---|---|---|---|---|---|
| Arrowleaw Sida | 75 | 100 | 100 | 0 | 35 | 100 | 100 | 0 | 0 | 0 | 0 | 0 | 20 |
| Barnyardgrass | 0 | 0 | 0 | 0 | 0 | 0 | 0 | 0 | 0 | 0 | 0 | 0 | 0 |
| Cocklebur | — | 15 | 15 | 0 | 35 | 0 | 20 | 0 | 20 | — | 15 | 0 | 15 |
| Common Ragweed | 90 | 100 | 50 | 0 | 50 | 95 | 80 | 0 | 35 | 20 | 0 | 15 | 0 |
| Corn | 0 | 0 | 0 | 0 | 0 | 0 | 0 | 0 | 0 | 0 | 0 | 0 | 0 |

Rate 4 g/ha

Rate 2 g/ha

TABLE F-continued

| | | | | | | | | | | | | | | | | | | | | | | | | |
|---|---|---|---|---|---|---|---|---|---|---|---|---|---|---|---|---|---|---|---|---|---|---|---|---|
| Cotton | 45 | 100 | 100 | 0 | 40 | — | 0 | 20 | 35 | 0 | 0 | 0 | 0 | 100 | 0 | 0 | 25 | 0 | 15 | 0 | 0 | 0 | 0 | 0 |
| Estrn Blknight | 40 | — | — | 0 | 95 | 100 | 0 | 0 | — | 0 | 90 | 0 | 40 | 0 | — | 100 | 75 | 100 | 100 | 25 | — | 0 | — | 100 |
| Fall Panicum | 0 | 10 | 10 | 0 | 0 | 0 | 0 | 0 | 0 | 0 | 0 | 10 | 0 | 10 | 0 | 100 | 0 | 100 | 0 | 0 | 0 | 0 | 0 | 0 |
| Field Bindweed | 100 | 100 | 100 | 0 | 100 | 100 | 0 | 100 | 0 | 100 | 40 | 100 | 100 | 85 | 100 | 100 | 90 | 100 | 100 | 0 | 45 | 0 | 20 | 20 |
| Fl Beggarweed | 10 | 100 | 100 | 0 | 60 | 25 | 0 | 0 | 0 | 100 | 50 | 55 | 10 | 100 | 0 | 100 | 40 | 100 | 0 | 0 | 0 | 0 | 20 | 20 |
| Giant Foxtail | 0 | 0 | 10 | 0 | 0 | 0 | 0 | 10 | 0 | 0 | 45 | 0 | 0 | 0 | 0 | 0 | 0 | 0 | 0 | 0 | 0 | 0 | 0 | 0 |
| Hairy Beggartic | 30 | 100 | 100 | 0 | 35 | 55 | 0 | 50 | 0 | 45 | 30 | 45 | 15 | 100 | 0 | 50 | 20 | 55 | 30 | 0 | 0 | 20 | 15 | 15 |
| Ivyleaw Mrnglry | 70 | 25 | 0 | 0 | 100 | 70 | 0 | 10 | 0 | 30 | 0 | 15 | 30 | 15 | 0 | 0 | 50 | 50 | 0 | 0 | 0 | 0 | 25 | 25 |
| Johnsongrass | 0 | 0 | 0 | 0 | 0 | 0 | 0 | 0 | 0 | 0 | 0 | 0 | 60 | 0 | 0 | 0 | 0 | 0 | 0 | 0 | 0 | 0 | 0 | 0 |
| Ladysthumb | — | 65 | 100 | 0 | 10 | 0 | 0 | 0 | — | 0 | — | — | — | 15 | 45 | 0 | 0 | 100 | 0 | 0 | — | 0 | 10 | 10 |
| Lambsquarters | 100 | — | — | 0 | 95 | 100 | 0 | 100 | 40 | 100 | 100 | 50 | — | 0 | — | 70 | 0 | 100 | 10 | 0 | 0 | 0 | 80 | 80 |
| Large Crabgrass | 0 | 10 | 0 | 0 | 0 | 0 | 0 | 15 | 10 | 0 | 15 | 0 | 100 | 0 | 0 | 0 | 0 | 0 | 35 | 0 | 10 | 0 | 0 | 0 |
| Purple Nutsedge | 0 | 0 | 0 | 0 | 0 | 0 | 0 | — | 0 | — | 0 | 0 | 0 | 0 | 0 | 0 | 0 | 0 | 0 | 0 | 0 | 0 | 0 | 0 |
| Redroot Pigweed | 85 | 100 | 100 | 0 | 100 | 100 | 0 | 100 | 100 | 100 | 100 | 50 | 55 | 85 | 0 | 65 | 0 | 100 | 100 | 100 | 100 | 100 | 25 | 25 |
| Soybean | 10 | 0 | 0 | 0 | 0 | 5 | 0 | 0 | 0 | 0 | 0 | 10 | 10 | 0 | 0 | 0 | 0 | 0 | 0 | 0 | 0 | 0 | 0 | 0 |
| Surinam Grass | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 | 0 |
| Velvetleaf | 100 | 100 | 100 | 0 | 75 | 100 | 0 | 60 | 35 | 100 | 35 | 50 | 100 | 65 | 0 | 60 | 75 | 85 | 30 | 0 | 30 | 10 | 10 | 60 |
| Wild Poinsettia | 100 | 35 | 55 | 0 | 75 | 80 | 0 | 25 | — | 100 | — | 100 | 85 | 30 | 0 | 20 | 70 | 100 | 10 | 10 | 10 | 20 | 0 | 100 |

| | Rate 2 g/ha | | | | | | | | Rate 1 g/ha | | | | | | | | | | | |
|---|---|---|---|---|---|---|---|---|---|---|---|---|---|---|---|---|---|---|---|---|
| COMPOUND | 32 | 39 | 40 | 48 | 52 | 53 | 54 | 71 | 21 | 22 | 25 | 30 | 32 | 39 | 40 | 48 | 52 | 53 | 54 | 71 |
| Arrowleaw Sida | 65 | 0 | 85 | 0 | 0 | 60 | 100 | 0 | 0 | 0 | 0 | 0 | 60 | 0 | 0 | 0 | 0 | 50 | 95 | 0 |
| Barnyardgrass | 0 | 0 | 0 | 0 | 0 | 0 | 0 | 0 | 0 | 0 | 0 | 0 | 0 | 0 | 20 | 0 | 0 | 0 | 0 | 0 |
| Cocklebur | 35 | 0 | 0 | 0 | 0 | 0 | 55 | 0 | 0 | 0 | 0 | 0 | 25 | 0 | 0 | 0 | 0 | 0 | 0 | 0 |
| Common Ragweed | 55 | 0 | 0 | 30 | 30 | 70 | 55 | 0 | 0 | 10 | 0 | 0 | 55 | 0 | 0 | 0 | 0 | 0 | 50 | 0 |
| Corn | 0 | 0 | — | 0 | 0 | 0 | 0 | 0 | 0 | 0 | 0 | 0 | 0 | 0 | 0 | 0 | 0 | 0 | 0 | 0 |
| Cotton | 20 | 100 | 0 | 0 | 60 | 90 | 80 | 0 | 0 | 0 | 0 | 50 | 20 | 0 | 0 | 0 | 0 | 0 | 0 | 0 |
| Estrn Blknight | 30 | 0 | 0 | 0 | 0 | 0 | 0 | 0 | 0 | 0 | 50 | 0 | 30 | 0 | 0 | 0 | 40 | 90 | 65 | 0 |
| Fall Panicum | 0 | 0 | 90 | 0 | 15 | 0 | 100 | 0 | 0 | 0 | 0 | 0 | 50 | 20 | 0 | 0 | 0 | 0 | 0 | 0 |
| Field Bindweed | 100 | 100 | 20 | 0 | 0 | 100 | 100 | 0 | 0 | — | 0 | — | 10 | 0 | 0 | 0 | 0 | 0 | 45 | 0 |
| Fl Beggarweed | 10 | 35 | 0 | 0 | — | 0 | 0 | 0 | 0 | 0 | 0 | 0 | 30 | 0 | 0 | 0 | 0 | — | 30 | 0 |
| Giant Foxtail | 0 | 0 | 0 | 0 | 25 | 20 | 100 | 0 | 0 | 0 | 10 | — | 0 | 0 | 0 | 0 | 0 | 0 | 0 | 0 |
| Hairy Beggartic | 15 | 100 | 80 | 0 | 0 | 0 | 100 | 0 | 0 | 20 | 75 | 10 | 15 | 20 | 0 | 0 | 0 | 0 | 30 | 0 |
| Ivyleaw Mrnglry | 40 | 0 | — | 0 | 25 | 20 | 25 | 0 | 0 | — | 0 | 0 | 30 | 0 | 30 | 0 | 0 | 90 | 25 | 0 |
| Johnsongrass | 0 | 0 | 0 | 0 | 0 | 0 | 0 | 0 | 0 | 0 | 0 | 0 | 0 | 0 | — | 0 | 0 | — | 0 | 0 |
| Ladysthumb | 20 | 100 | 80 | 0 | 0 | 0 | 100 | 0 | 0 | — | 14 | — | 80 | — | — | 0 | 0 | 0 | 0 | 0 |
| Lambsquarters | 85 | — | 0 | 0 | 25 | 20 | 25 | 0 | 0 | 15 | 0 | 0 | 0 | — | 0 | 0 | 0 | 0 | 90 | 0 |
| Large Crabgrass | 0 | 0 | 0 | 0 | 0 | 0 | 50 | 0 | 0 | 0 | 75 | 0 | 15 | 0 | 0 | 0 | 0 | 0 | 0 | 0 |
| Purple Nutsedge | 0 | 0 | 0 | 0 | 0 | 0 | 0 | 0 | 0 | 0 | 0 | 10 | 30 | 0 | 30 | 0 | 0 | 0 | 0 | 0 |
| Redroot Pigweed | 40 | 45 | 95 | 0 | 50 | 15 | 80 | 0 | 0 | 60 | 14 | 0 | 40 | 0 | 90 | 0 | 15 | 0 | 20 | 0 |
| Soybean | 0 | 0 | 0 | 0 | 0 | 0 | 0 | 0 | 0 | 0 | 0 | 0 | 0 | 0 | 0 | 0 | 0 | 0 | 0 | 0 |
| Surinam Grass | 0 | 0 | 0 | 0 | 0 | 0 | 0 | 0 | 0 | 0 | 0 | 0 | 0 | 0 | — | 0 | 0 | 0 | 0 | 0 |
| Velvetleaf | 30 | 15 | 15 | 35 | 20 | 50 | 75 | 0 | 0 | 0 | 0 | 0 | 15 | 0 | 0 | 0 | 10 | 10 | 60 | 0 |
| Wild Poinsettia | 80 | 10 | 20 | — | 0 | 20 | 100 | 0 | 0 | 0 | 0 | 0 | 60 | 0 | 0 | 0 | 0 | 20 | 100 | 0 |

TEST G

Seeds, tubers, or plant parts of alexandergrass (*Brachiaria plantaginea*), bermudagrass (*Cynodon dactylon*), broadleaf signalgrass (*Brachiaria plantyphylla*), common purslane (*Portulaca oleracea*), common ragweed (*Ambrosia elatior*), cotton (*Gossypium hirsutum*), dallisgrass (*Paspalum dilatatum*), goosegrass (*Eleusine indica*), guineagrass (*Panicum maximum*), itchgrass (*Rottboellia exaltata*), johnson grass (*Sorghum halepense*), large crabgrass (*Digitaria sanguinalis*), peanuts (*Arachis hypogaea*), pitted morningglory (*Ipomoea lacunosa*), purple nutsedge (*Cyperus rotundus*), sandbur (*Cenchrus echinatus*), sourgrass (*Trichachne insularis*), and surinam grass (*Brachiaria decumbens*) were planted into greenhouse pots or flats containing greenhouse planting medium. Plant species were grown in separate pots or individual compartments. Preemergence applications were made within one day of planting the seed or plant part. Postemergence applications were applied when the plants were in the two to four leaf stage (three to twenty cm).

Test chemicals were formulated in a non-phytotoxic solvent mixture which included a surfactant and applied preemergence and postemergence to the plants. Untreated control plants and treated plants were placed in the greenhouse and visually evaluated for injury 13 to 21 days after herbicide application. Plant response ratings, summarized in Table G, are based on a 0 to 100 scale where 0 is no injury and 100 is complete control. A dash (–) response means no test result.

TABLE G

| | POSTEMERGENCE | | | | | | | | | | | | | | | |
|---|---|---|---|---|---|---|---|---|---|---|---|---|---|---|---|---|
| | Rate 250 g/ha | | | | Rate 125 g/ha | Rate 64 g/ha | | Rate 35 g/ha | Rate 32 g/ha | Rate 17.5 g/ha | Rate 16 g/ha | Rate 8 g/ha | | Rate 4 g/ha | | Rate 2 g/ha |
| COMPOUND | 21 | 23 | 52 | 57 | 57 | 22 | 57 | 21 | 57 | 21 | 57 | 21 | 57 | 21 | 57 | 21 |
| Alexandergrass | 30 | 0 | 0 | 0 | 0 | 10 | 0 | — | 0 | — | 0 | — | 0 | — | 0 | — |
| Bermudagrass | 0 | 20 | 0 | 0 | 0 | 80 | 0 | — | 0 | — | 0 | — | 0 | — | 0 | — |
| Brdlf Sgnlgrass | 100 | 75 | 0 | 0 | 0 | 90 | 0 | — | 0 | — | 0 | — | 0 | — | 0 | — |
| Cmn Purslane | 100 | 100 | 100 | 95 | 85 | 100 | 80 | — | 75 | — | 65 | — | 60 | — | 50 | — |
| Cmn Ragweed | 100 | 100 | — | — | 30 | 100 | 30 | — | 30 | — | 20 | — | 20 | — | 10 | — |
| Cotton | 100 | 100 | 100 | 98 | 75 | 100 | 50 | — | 0 | — | 0 | — | 0 | — | — | — |
| Dallisgrass | 25 | 20 | 35 | 0 | 0 | 70 | 0 | — | 0 | — | 0 | — | 0 | — | 0 | — |
| Goosegrass | 0 | 0 | 0 | 0 | 0 | 60 | 0 | — | 0 | — | 0 | — | 0 | — | 0 | — |
| Guineagrass | 60 | 0 | 0 | 0 | 0 | 45 | 0 | — | 0 | — | 0 | — | 0 | — | 0 | — |
| Itchgrass | 60 | — | — | — | — | 25 | — | — | — | — | — | — | — | — | — | — |
| Johnson grass | 50 | 0 | 40 | 0 | 0 | 20 | 0 | — | 0 | — | 0 | — | 0 | — | 0 | — |
| Large Crabgrass | 5 | 20 | 0 | 0 | 0 | 60 | 0 | — | 0 | — | 0 | — | 0 | — | 0 | — |
| Peanuts | 40 | 10 | 10 | 0 | 0 | 10 | 0 | 15 | 0 | — | 0 | 20 | 0 | 15 | 0 | 15 |
| Pit Morninglory | 100 | 100 | 100 | 75 | 60 | 100 | 50 | — | 40 | 10 | 35 | — | 30 | — | 30 | — |
| Purple Nutsedge | 10 | 10 | 0 | 0 | 0 | 98 | 0 | — | 0 | — | 0 | — | 0 | — | 0 | — |
| Sandbur | 20 | 40 | 65 | — | — | 45 | — | — | — | — | — | — | — | — | — | — |
| Sourgrass | 100 | 40 | 0 | 0 | 0 | 0 | 0 | — | 0 | — | — | — | 0 | — | 0 | — |
| Sugarcane | — | — | — | — | — | — | — | 15 | — | 65 | — | 15 | — | 10 | — | 5 |
| Surinam grass | 30 | 0 | 0 | 20 | 0 | 10 | 0 | — | 0 | — | 0 | — | 0 | — | 0 | — |

| | PREEMERGENCE | | | | | | | | | | | | | | | |
|---|---|---|---|---|---|---|---|---|---|---|---|---|---|---|---|---|
| | Rate 250 g/ha | | | | Rate 125 g/ha | Rate 64 g/ha | | Rate 35 g/ha | Rate 32 g/ha | Rate 17.5 g/ha | Rate 16 g/ha | Rate 8 g/ha | | Rate 4 g/ha | | Rate 2 g/ha |
| COMPOUND | 21 | 23 | 52 | 57 | 57 | 22 | 57 | 21 | 57 | 21 | 57 | 21 | 57 | 21 | 57 | 21 |
| Alexandergrass | 65 | 0 | 0 | 0 | 0 | 10 | 0 | — | 0 | — | 0 | — | 0 | — | 0 | — |
| Bermudagrass | 50 | 0 | 0 | 0 | 0 | 0 | 0 | — | 0 | — | 0 | — | 0 | — | 0 | — |
| Brdlf Sgnlgrass | 100 | 70 | 60 | 0 | 0 | 0 | 0 | — | 0 | — | 0 | — | 0 | — | 0 | — |
| Cmn Purslane | 100 | 100 | 100 | 100 | 100 | 100 | 0 | — | 0 | — | 0 | — | 0 | — | — | — |
| Cmn Ragweed | 100 | 100 | 100 | — | 0 | 100 | 0 | — | 0 | — | — | — | — | — | 0 | — |
| Cotton | 100 | 100 | 100 | 0 | 0 | 100 | 0 | — | 0 | — | 0 | — | 0 | — | 0 | — |
| Dallisgrass | 65 | 30 | 10 | 0 | 0 | 45 | 0 | — | 0 | — | 0 | — | 0 | — | 0 | — |
| Goosegrass | 98 | 40 | 20 | 0 | 0 | 0 | 0 | — | 0 | — | 0 | — | 0 | — | 0 | — |
| Guineagrass | 0 | 0 | 25 | 0 | 0 | 10 | 0 | — | 0 | — | 0 | — | 0 | — | 0 | — |
| Itchgrass | 35 | — | 0 | 0 | 0 | 0 | 0 | — | 0 | — | 0 | — | 0 | — | 0 | — |
| Johnson grass | 65 | 0 | 0 | 0 | 0 | 45 | 0 | — | 0 | — | 0 | — | 0 | — | 0 | — |
| Large Crabgrass | 40 | 0 | 0 | 0 | 0 | 30 | 0 | — | 0 | — | 0 | — | 0 | — | 0 | — |
| Peanuts | 10 | 20 | 10 | 20 | 0 | 30 | 98 | 40 | 30 | 30 | 0 | 35 | 0 | 20 | 0 | 20 |
| Pit Morninglory | 100 | 100 | 100 | 40 | 0 | 100 | 0 | — | 0 | — | 0 | — | 0 | — | 0 | — |
| Purple Nutsedge | 60 | 60 | 60 | 0 | 0 | 10 | 0 | — | 0 | — | 0 | — | 0 | — | 0 | — |
| Sandbur | 100 | 35 | 25 | 60 | 0 | 0 | 0 | — | 0 | — | 0 | — | 0 | — | 0 | — |
| Sourgrass | 100 | 100 | 70 | 0 | 0 | 0 | 0 | — | 0 | — | 0 | — | 0 | — | 0 | — |
| Sugarcane | — | — | — | — | — | — | — | 10 | — | 20 | — | 0 | — | 0 | — | 0 |
| Surinam grass | 70 | 65 | 65 | 0 | 0 | 0 | 0 | — | 0 | — | 0 | — | 0 | — | 0 | — |

TEST H

Compounds evaluated in this test were formulated in a non-phytotoxic solvent mixture which included a surfactant and applied to the soil surface before plant seedlings emerged (preemergence application) and to plants that were grown for various periods of time before treatment (postemergence application). A sandy loam soil was used for the preemergence test while a mixture of sandy loam soil and greenhouse potting mix in a 60:40 ratio was used for the postemergence test. Test compounds were applied within approximately one day after planting seeds for the preemergence test, and 13 days after the last postemergence planting.

Plantings of these crops and weed species were adjusted to produce plants of appropriate size for the postemergence test. All plant species were grown using normal greenhouse practices. Crop and weed species include *Acanthospermum hispidum*, alexandergrass (*Brachiaria plantaginea*), american black nightshade (*Solanum americanum*), apple-of-Peru (*Nicandra physaloides*), arrowleaf sida (*Sida rhombifolia*), brazilian sicklepod (*Cassia tora Brazilian*), brazilian signalgrass (*Brachiaria decumbens*), capim-colchao (*Digitaria horizontalis*), cristalina soybean (*Glycine max Cristalina*), florida beggarweed (*Desmodium purpureum*), hairy beggarticks (*Bidens pilosa*), slender amaranth (*Amaranthus viridis*), southern sandur (*Cenchrus echinatus*), tall morningglory (*Ipomoea purpurea*), tropical spiderwort (*Commelina benghalensis*), W20 Soybean (*Glycine max* W20), W4-4 Soybean (*Glycine max* W4-4) and wild pointsettia (*Euphorbia heterophylla*).

Treated plants and untreated controls were maintained in a greenhouse for approximately 13 days, after which all treated plants were compared to untreated controls and visually evaluated. Plant response ratings, summarized in Table H. are based upon a 0 to 100 scale where 0 is no effect and 100 is complete control. A dash response (–) means no test result.

TABLE H

POSTEMERGENCE

|  | Rate 35 g/ha | Rate 17 g/ha | | | | Rate 8 g/ha | | | |
|---|---|---|---|---|---|---|---|---|---|
| COMPOUND | 21 | 21 | 23 | 25 | 32 | 21 | 23 | 25 | 32 |
| Acanthospermum | 100 | 100 | 100 | 100 | 100 | 80 | 100 | 85 | 80 |
| Alexandergrass | 20 | 15 | 45 | 25 | 20 | 10 | 35 | 20 | 20 |
| Apple-of-Peru | 70 | 60 | 100 | 85 | 100 | 55 | 100 | 80 | 100 |
| Arrowleaf Sida | 100 | 100 | 100 | 85 | 100 | 85 | 100 | 80 | 100 |
| B. Signalgrass | 10 | 5 | 80 | 45 | 25 | 5 | 55 | 40 | 20 |
| Bl. Nightshade | 100 | 85 | 100 | 100 | 100 | 75 | 100 | 100 | 100 |
| Braz Sicklepod | 40 | 30 | 60 | 40 | 20 | 20 | 60 | 20 | 15 |
| Capim-Colch | 5 | 5 | 55 | 50 | 40 | 5 | 55 | 30 | 30 |
| Crist. Soybean | 60 | 50 | 70 | 25 | 30 | 15 | 60 | 25 | 20 |
| Fl. Beggarweed | 100 | 85 | 100 | 75 | 80 | 75 | 75 | 60 | 65 |
| H. Beggarticks | 100 | 100 | 100 | 100 | 100 | 100 | 100 | 100 | 100 |
| Morningglory | 100 | 85 | 100 | 100 | 100 | 80 | 100 | 100 | 100 |
| Sl. Amaranth | 85 | 75 | 100 | 85 | 80 | 70 | 100 | 75 | 75 |
| Southern Sandur | 10 | 5 | — | — | — | 5 | — | — | — |
| Tr. Spiderwort | 100 | 100 | 100 | 100 | — | 80 | 100 | 60 | — |
| Wld Pointsettia | 100 | 100 | 100 | 100 | 100 | 100 | 100 | 100 | 100 |
| W20 Soybean | 35 | 30 | 50 | 20 | 30 | 10 | 35 | 15 | 25 |
| W4-4 Soybean | 35 | 30 | 45 | 30 | 30 | 15 | 35 | 20 | 25 |

|  | Rate 4 g/ha | | | | Rate 2 g/ha | | | | Rate 1 g/ha | | | |
|---|---|---|---|---|---|---|---|---|---|---|---|---|
| COMPOUND | 21 | 23 | 25 | 32 | 21 | 23 | 25 | 32 | 21 | 23 | 25 | 32 |
| Acanthospermum | 80 | 100 | 80 | 75 | 60 | 100 | 70 | 60 | 60 | 100 | 70 | 60 |
| Alexandergrass | 5 | 30 | 15 | 15 | 0 | 25 | 10 | 10 | 10 | 20 | 10 | 10 |
| Apple-of-Peru | 50 | 100 | 80 | 100 | 40 | 100 | 60 | — | 90 | 100 | 55 | 100 |
| Arrowleaf Sida | 70 | 100 | 70 | 100 | 65 | 100 | 55 | 100 | 80 | 80 | 55 | 75 |
| B. Signalgrass | 0 | 50 | 40 | 20 | 0 | 40 | 20 | 20 | 0 | 30 | 15 | 10 |
| Bl. Nightshade | 65 | 100 | 100 | 100 | 55 | 100 | 85 | 100 | 70 | 80 | 80 | 100 |
| Braz Sicklepod | 0 | 20 | 0 | 15 | 0 | 20 | 0 | 15 | 15 | 15 | 50 | 10 |
| Capim-Colch | 5 | 55 | 25 | 30 | 5 | 15 | 25 | 30 | 0 | 10 | 20 | 15 |
| Crist. Soybean | 15 | 50 | 20 | 15 | 15 | 30 | 55 | 10 | 25 | 25 | 10 | 10 |
| Fl. Beggarweed | 55 | 55 | 50 | 65 | 50 | 35 | 50 | 55 | 15 | 70 | 20 | 55 |
| H. Beggarticks | 85 | 100 | 100 | 100 | 70 | 100 | 60 | 70 | 80 | 100 | 60 | 55 |
| Morningglory | 75 | 100 | 100 | 100 | 70 | 100 | 70 | 80 | 50 | 100 | 70 | 70 |
| Sl. Amaranth | 70 | 80 | 75 | 75 | 60 | 75 | 55 | 70 | 75 | 75 | 55 | 50 |
| Southern Sandur | 5 | — | — | — | 0 | — | — | — | — | — | — | — |
| Tr. Spiderwort | 70 | 100 | 60 | — | 70 | 100 | 15 | — | 65 | 80 | 10 | — |
| Wld Pointsettia | 100 | 100 | 100 | 100 | 80 | 100 | 70 | 100 | 75 | 75 | 100 | 100 |
| W20 Soybean | 10 | 25 | 15 | 20 | 10 | 20 | 10 | 15 | 20 | 15 | 0 | 15 |
| W4-4 Soybean | 10 | 30 | 20 | 20 | 10 | 25 | 15 | 15 | 25 | 20 | 10 | 20 |

PREEMERGENCE

|  | Rate 35 g/ha | Rate 17 g/ha | Rate 8 g/ha | Rate 4 g/ha | Rate 2 g/ha |
|---|---|---|---|---|---|
| COMPOUND | 21 | 21 | 21 | 21 | 21 |
| Acanthospermum | 100 | 100 | 100 | 100 | 60 |
| Alexandergrass | 5 | 5 | 5 | 0 | 0 |

TABLE H-continued

| | | | | | |
|---|---|---|---|---|---|
| Apple-of-Peru | 100 | 100 | 100 | 55 | 55 |
| Arrowleaf Sida | 100 | 100 | 100 | 0 | 0 |
| B. Signalgrass | 30 | 25 | 20 | 20 | 15 |
| Bl. Nightshade | 100 | 100 | 100 | 100 | 85 |
| Braz Sicklepod | 75 | 20 | 15 | 10 | — |
| Capim-Colch | 10 | 10 | 5 | 0 | 0 |
| Crist. Soybean | 10 | 5 | 0 | 0 | 0 |
| Fl. Beggarweed | 100 | 100 | 100 | 100 | 100 |
| H. Beggarticks | 100 | 100 | 100 | 75 | 60 |
| Morningglory | 100 | 100 | 90 | 85 | 55 |
| Sl. Amaranth | 100 | 100 | 100 | 100 | 100 |
| Southern Sandur | 75 | 40 | 10 | 5 | 0 |
| Tr. Spiderwort | 100 | 100 | 70 | 60 | 50 |
| Wld Pointsettia | 100 | 100 | 100 | 100 | 80 |
| W20 Soybean | 5 | 5 | 5 | 5 | 0 |
| W4-4 Soybean | 5 | 5 | 5 | 5 | 5 |

TEST I

Compounds evaluated in this test were formulated in a non-phytotoxic solvent mixture and applied to the surface of the water which was contained in each pot. Individual containers of barnyardgrass (*Echinochloa oryzicola*), small flower umbrella sedge (*Cyperus difformus*), common falsepimpernel (*Lindernia procumbens*), monochoria (*Monochoria vaginalis*) and bulrush (*Scirpus juncoides*) were seeded and allowed to grow until the 1.5 to 2.5 leaf stage of development. A Sultama clay loam soil was used for this propagation. Japonica rice (*Oryza sativa*) was transplanted at 0 and 2 cm depth five days before application of the test compound to the water surface. An early and late stage of each weed species was treated, the stage of development being related to the concurrent planting of Scirpus juncoides which was then treated at the 1.5 (early) and the 2.5 (late) leaf stage.

Treated plants and untreated controls were maintained under greenhouse conditions for twenty to thirty days at which time treated plants were compared to untreated controls and visually evaluated. Plant response ratings, summarized in Table I, are based upon a 0 to 100 scale where 0 is no effect and 100 is complete control. A dash response (–) indicated that no test result was recorded.

TABLE I

| | Rate 250 g/ha | | | Rate 125 g/ha | | | Rate 64 g/ha | | | Rate 32 g/ha | | |
|---|---|---|---|---|---|---|---|---|---|---|---|---|
| COMPOUND | 11 | 13 | 21 | 11 | 13 | 21 | 11 | 13 | 21 | 11 | 13 | 21 |
| Flood Saita soi | — | — | — | — | — | — | N | N | — | I | L | L |
| barnyard early | 0 | 100 | 95 | 0 | 90 | 85 | 0 | 60 | 65 | 0 | 30 | 60 |
| barnyard late | 30 | 100 | 90 | 0 | 70 | 85 | 0 | 50 | 60 | 0 | 40 | 50 |
| C. difformis ea | 100 | 100 | 100 | 40 | 100 | 100 | 0 | 100 | 100 | 0 | 70 | 100 |
| C. difformis la | 50 | 100 | 100 | 30 | 50 | 100 | 10 | 40 | 100 | 0 | 30 | 60 |
| Japoni rice 0 cm | 10 | 85 | 80 | 10 | 80 | 50 | 30 | 60 | 35 | 5 | 50 | 0 |
| Japoni rice 2 cm | 20 | 55 | 50 | 25 | 40 | 30 | 0 | 25 | 20 | 0 | 20 | 5 |
| L. procumben ea | 70 | 100 | 100 | 0 | 100 | 100 | 0 | 100 | 100 | 0 | 100 | 100 |
| L. procumben la | 100 | 100 | 100 | 20 | 85 | 100 | 0 | 95 | 100 | 0 | 100 | 100 |
| M. vaginalis ea | 20 | 80 | 100 | 0 | 75 | 100 | 0 | 40 | 100 | 0 | 30 | 100 |
| M. vaginalis la | 20 | 100 | 100 | 20 | 50 | 85 | 0 | 40 | 85 | 0 | 10 | 70 |
| S. juncoides 1. | 60 | 80 | 90 | 30 | 65 | 75 | 30 | 40 | 50 | 40 | 30 | 0 |
| S. juncoides 2. | 40 | 85 | 65 | 40 | 50 | 55 | 0 | 20 | 50 | 0 | 20 | 30 |

TEST J

Plastic pots were partially filled with silt loam soil. The soil was then saturated with water. Rice (*Oryza sativa*) seed or seedlings at the 2.0 to 3.5 leaf stage; seeds, tubers or plant parts selected from barnyardgrass (*Echinochloa crus-galli*, common waterplantain (*Alisma plantago-aquatica*), ducksalad (*Heteranthera limosa*), early watergrass (*Echinochloa oryzoides*), gooseweed (*Sphenoclea zeylanica*), junglerice (*Echinochloa colonum*), late watergrass (*Echinochloa oryzicola*), monochoria (*Monochoria vaginalis*), redstem (*Ammania* species), rice flatsedge (*Cyperus iria*), ricefield bulrush (*Scirpus mucronatus*), smallflower flatsedge (*Cyperus difformis*), tighthead sprangletop (*Leptochloa fasicularis*) and water-clover (*Marsilea quadrifolia*) into this soil. Plantings and waterings of these crops and weed species were adjusted to produce plants of appropriate size for the test. At the two leaf stage, water levels were raised to 3 cm above the soil surface and maintained at this level throughout the test. Chemical treatments were formulated in a non-phytotoxic solvent mixture which included a surfactant and applied directly to the paddy water, by pipette, or to the plant foliage, by an air-pressure assisted, calibrated belt-conveyer spray system. Treated plants and controls were maintained in a greenhouse for approximately 21 days, after which all species were compared to controls and visually evaluated. Plant response ratings, summarized in Table J, are reported on a 0 to 100 scale where 0 is no effect and 100 is complete control. A dash (–) response means no test result.

TABLE J

| | Rate 1000 g/ha | | | | | Rate 750 g/ha | | | | Rate 500 g/ha | | | | |
|---|---|---|---|---|---|---|---|---|---|---|---|---|---|---|
| COMPOUND | 12 | 21 | 25 | 39 | 40 | 21 | 25 | 39 | 40 | 12 | 21 | 25 | 39 | 40 |
| PD/TA | | | | | | | | | | | | | | |
| barnyardgrass | 60 | — | — | — | — | — | — | — | — | 40 | — | — | — | — |
| ducksalad | 100 | 0 | 20 | 60 | 50 | 0 | 0 | 60 | 0 | 100 | 0 | 0 | 30 | 10 |
| early watergrass | — | — | — | — | — | — | — | — | — | — | — | — | — | — |
| gooseweed | — | 100 | — | 100 | 95 | 90 | 100 | 85 | 85 | — | 98 | 85 | 80 | 85 |
| junglerice | 65 | — | — | — | — | — | — | — | — | 45 | — | — | — | — |
| late watergrass | 70 | — | — | — | — | — | — | — | — | 45 | — | — | — | — |
| monochoria | — | 65 | — | 85 | 65 | 55 | 60 | 60 | 55 | — | 55 | 45 | 40 | 60 |
| redstem | 100 | 10 | 0 | 40 | 30 | 0 | 0 | 30 | 20 | 100 | 0 | 0 | 0 | 20 |
| rice flatsedge | 100 | 85 | 80 | 75 | 90 | 75 | 75 | 80 | 90 | 100 | 55 | 60 | 30 | 20 |
| ricefield bulru | — | 60 | — | 65 | 50 | 60 | 60 | 60 | 35 | — | 50 | 30 | 60 | 40 |
| smallflower fla | 100 | 0 | 0 | 0 | 40 | 0 | 0 | 0 | 30 | 100 | 0 | 0 | 0 | 0 |
| tighthead spran | 0 | 0 | 20 | 30 | 25 | 0 | 60 | 0 | 40 | 65 | 0 | 0 | 0 | 40 |
| water-clover | — | 75 | 75 | 60 | 45 | 85 | 20 | 45 | 50 | — | 45 | 15 | 40 | 60 |
| A. plantago-aqu | — | 100 | — | 90 | 100 | 100 | 100 | 98 | 100 | — | 100 | 90 | 90 | 90 |
| 2 LF direct see | 30 | 15 | 20 | 20 | 40 | 15 | 20 | 10 | 35 | 35 | 15 | 15 | 10 | 20 |
| 2 LF transp. in | 45 | 10 | 15 | 15 | 35 | 10 | 15 | 10 | 25 | 35 | 10 | 10 | 10 | 20 |

| | Rate 375 g/ha | | | | Rate 250 g/ha | | | | | Rate 125 g/ha | | Rate 64 g/ha | | Rate 32 g/ha | Rate 16 g/ha |
|---|---|---|---|---|---|---|---|---|---|---|---|---|---|---|---|
| COMPOUND | 21 | 25 | 39 | 40 | 12 | 21 | 25 | 39 | 40 | 12 | 21 | 12 | 21 | 21 | 21 |
| PD/TA | | | | | | | | | | | | | | | |
| barnyardgrass | — | — | — | — | 35 | 30 | — | — | — | 15 | 15 | 10 | 0 | 0 | 0 |
| ducksalad | 20 | 0 | 0 | 0 | 100 | 60 | 0 | 0 | 0 | 80 | 40 | 50 | 20 | 0 | 0 |
| early watergrass | — | — | — | — | — | 35 | — | — | — | — | 45 | — | 15 | 0 | 20 |
| gooseweed | 80 | 45 | 90 | 85 | — | 60 | 75 | 75 | 60 | — | — | — | — | — | — |
| junglerice | — | — | — | — | 35 | — | — | — | — | 40 | — | 35 | — | — | — |
| late watergrass | — | — | — | — | 25 | 35 | — | — | — | 20 | 30 | 10 | 25 | 0 | 15 |
| monochoria | 40 | 40 | 25 | 40 | — | 35 | 40 | 25 | 30 | — | — | — | — | — | — |
| redstem | 0 | 0 | 0 | 10 | 95 | 85 | 0 | 0 | 10 | 75 | 55 | 10 | 40 | 35 | 25 |
| rice flatsedge | 35 | 30 | 70 | 15 | 95 | 98 | 30 | 20 | 60 | 85 | 85 | 80 | 98 | 40 | 20 |
| ricefield bulru | 40 | 15 | 65 | 35 | — | 30 | 10 | 20 | 10 | — | — | — | — | — | — |
| smallflower fla | 0 | 0 | 0 | 0 | 90 | 65 | 10 | 0 | 0 | 95 | 60 | 90 | 55 | 30 | 30 |
| tighthead spran | 0 | 0 | 0 | 0 | 50 | 20 | 0 | 10 | 0 | 40 | 45 | 30 | 0 | 0 | 75 |
| water-clover | 40 | 10 | 20 | 10 | — | 40 | 10 | 20 | 10 | — | — | — | — | — | — |
| A. plantago-aqu | 90 | 45 | 100 | 85 | — | 90 | 30 | 60 | 60 | — | — | — | — | — | — |
| 2 LF direct see | 15 | 10 | 10 | 20 | 15 | 10 | 10 | 15 | 20 | 20 | 15 | 15 | 10 | 0 | 10 |
| 2 LF transp. in | 10 | 10 | 10 | 20 | 20 | 10 | 0 | 10 | 20 | 20 | 0 | 10 | 0 | 0 | 10 |

The following protocol was used for the test in Table L. The data demonstrate the efficacy of mixtures of Compound 21 (Index Table D, page 188) and tribenuron-methyl, Compound 21 and thifensulfuron-methyl, Compound 21 and 2,4-D, Compound 21 and dicamba, Compound 21 and bromoxynil, Compound 21 and MCPA, Compound 21 and fluroxypyr, and Compound 21 and clopyralid against specific weeds. The weed control afforded by the mixtures of this invention are not limited, however, to these species.

Test L Protocol

*Kochia scoparia* (KCHSC), *Salsola kali* (SASKR), *Polygonwn convolvulus* (POLCO), *Stellaria media* (STEME), and *Galium aparine* (GALAP) were grown in a greenhouse to approximately 9–25 cm in height before treatment. Compound 21 was applied at 4 g ai/ha postemergence. A 1:2 ratio of tribenuron-methyl:thifensulfuron-methyl was applied at 8 g ai/ha postemergence. A mixture of Compound 21 at 4 g ai/ha and a 1:2 ratio of tribenuron methyl:thifensulfuron methyl at 8 g ai/ha was applied postemergence. Thifensulfuron methyl was applied at 8 g ai/ha postemergence. A mixture of Compound 21 at 4 g ai/ha and thifensulfuron methyl at 8 g ai/ha was applied postemergence. 2,4-D was applied at 250 g ai/ha postemergence. A mixture of Compound 21 at 4 g ai/ha and 2,4-D at 250 g ai/ha was applied postemergence. Dicamba was applied at 62 g ai/ha postemergence. A mixture of Compound 21 at 4 ai/ha and dicamba at 62 g ai/ha was applied postemergence. Bromoxynil was applied at 125 g ai/ha postemergence. A mixture of Compound 21 at 4 g ai/ha and bromoxynil at 125 g ai/ha was applied postemergence. MCPA was applied at 250 g ai/ha postemergence. A mixture of Compound 21 at 4 g ai/ha and bromoxynil at 250 g ai/ha was applied postemergence. Fluroxypyr was applied at 62 g ai/ha postemergence. A mixture of Compound 21 at 4 g ai/ha and fluroxypyr at 62 g ai/ha was applied postemergence. Clopyralid was applied at 125 g ai/ha post. A mixture of Compound 21 at 4 g ai/ha and clopyralid at 125 g ai/ha was applied postemergence. After treatment, the plants were maintained in a greenhouse and evaluated approximately 18 days after spraying. All sprayed plants were evaluated for injury as compared to control plants that were sprayed only with non-phytotoxic solvent. Injury was evaluated visually using a 0 to 100% scale where 0 indicates no effect and 100 indicates complete control.

For Test L, the mean response of each treatment was determined. Colby's equation was used to calculate the expected additive herbicidal effect of the mixtures of Compound 21 and the mixture partners listed above. Colby's equation (Colby, S. R. "Calculating Synergistic and Antagonistic Responses of Herbicide Combinations,"*Weeds*, 15(1), pp 20–22 (1967)) calculates the expected additive effect of herbicidal mixtures, and for two active ingredients is of the form:

$$P_{a+b} = P_a + P_b - (P_a P_b/100)$$

$P_{a+b}$ is the percentage effect of the mixture expected from additive contribution of the individual components, $P_a$ is the observed percentage effect of the first active ingredient at the same use rate as in the mixture, and $P_b$ is the observed percentage effect of the second active ingredient at the same use rate as in the mixture.

Results of Test L are shown in Table L, which lists the mean response of a specific weed to Compound 21 applied alone as a single active ingredient, applied as a mixture of Compound 21 and a specified mixture partner, and the expected additive effect of the herbicidal mixture of Compound 21 and that specified mixture partner (from Colby's equation). Weeds other than those specifically listed are also controlled by mixtures of Compound 21 and the above specified mixture partners. Different ratios of Compound 21 to the above specified mixture partners, and different formulation types, also provide useful weed control from the combination of the two herbicides.

TABLE L*

Effect of Compound 21 as Active Ingredient Alone and in Mixture

| Compound 21 (g ai/ha) | Mixture Partner | Mixture Partner Rate (g ai/ha) | | KCHSC | SASKR | POLCO | STEME | GALAP |
|---|---|---|---|---|---|---|---|---|
| 4 | none | | | 70 | 90 | 40 | 60 | 55 |
| 0 | 1:2 ratio of tribenuron-methyl:thifensulfuron-methyl | 8 | Mean | 65 | 100 | 75 | 90 | 75 |
| 4 | 1:2 ratio of tribenuron-methyl:thifensulfuron-methyl | 8 | Mean | 95 | 100 | 90 | 90 | 75 |
| 4 | 1:2 ratio of tribenuron-methyl:thifensulfuron-methyl | 8 | Exp.[1] | 90 | 100 | 85 | 96 | 89 |
| 0 | thifensulfuron-methyl | 8 | Mean | 10 | 100 | 95 | 80 | 60 |
| 4 | thifensulfuron-methyl | 8 | Mean | 90 | 100 | 95 | 85 | 80 |
| 4 | thifensulfuron-methyl | 8 | Exp. | 73 | 100 | 97 | 92 | 82 |
| 0 | 2,4-D | 250 | Mean | 35 | 70 | 30 | 20 | 30 |
| 4 | 2,4-D | 250 | Mean | 100 | 100 | 75 | 65 | 75 |
| 4 | 2,4-D | 250 | Exp. | 81 | 97 | 58 | 68 | 69 |
| 0 | dicamba | 62 | Mean | 40 | 60 | 40 | 30 | 70 |
| 4 | dicamba | 62 | Mean | 90 | 100 | 90 | 70 | 85 |
| 4 | dicamba | 62 | Exp. | 82 | 96 | 64 | 72 | 87 |
| 0 | bromoxynil | 125 | Mean | 50 | 95 | 65 | 10 | 20 |
| 4 | bromoxynil | 125 | Mean | 80 | 100 | 40 | 20 | 80 |
| 4 | bromoxynil | 125 | Exp. | 85 | 100 | 79 | 64 | 64 |
| 0 | MCPA | 250 | Mean | 15 | 20 | 20 | 20 | 5 |
| 4 | MCPA | 250 | Mean | 90 | 95 | 70 | 75 | 50 |
| 4 | MCPA | 250 | Exp. | 75 | 92 | 52 | 68 | 57 |
| 0 | fluroxypyr | 62 | Mean | 50 | 70 | 65 | 80 | 85 |
| 4 | fluroxypyr | 62 | Mean | 100 | 100 | 90 | 85 | 95 |
| 4 | fluroxypyr | 62 | Exp. | 85 | 97 | 79 | 92 | 93 |
| 0 | clopyralid | 125 | Mean | 0 | 20 | 65 | 5 | 5 |
| 4 | clopyralid | 125 | Mean | 90 | 100 | 85 | 35 | 50 |
| 4 | clopyralid | 125 | Exp. | 70 | 92 | 79 | 62 | 57 |

*Data are reported as percent control.
[1]"Exp." are expected responses calculated according to Colby, S. R. "Calculating Synergistic and Antagonistic Responses of Herbicide Combinations," Weeds, 15(1), pp 20–22 (1967).

The following protocol was used for the test in Table M. The data demonstrate the efficacy of mixtures of Compound 21 (Index Table D, page 188) and fenoxapropethyl, Compound 21 and diclofop-methyl, Compound 21 and tralkoxydim, Compound 21 and clodinafop, Compound 21 and imazamethabenz, Compound 21 and sulfosulfuron, Compound 21 and difenzoquat, Compound 21 and quinclorac, Compound 21 and prosulfuron, Compound 21 and metribuzin, Compound 21 and glyphosate, Compound 21 and triallate, and Compound 21 and trifluralin against specific weeds. The weed control afforded by the mixtures of this invention are not limited, however, to these species.

Test M Protocol

*Kochia scoparia* (KCHSC), *Salsola kali* (SASKR), *Polygonum convolvulus* (POLCO), *Stellaria media* (STEME), *Galium aparine* (GALAP), *Avena fatua* (AVEFA), and *Setaria viridis* (SETVI) were grown in a greenhouse to approximately 9–25 cm in height before treatment. Compound 21 was applied at 4 g ai/ha postemergence. Fenoxaprop-ethyl was applied at 62 g ai/ha postemergence. A mixture of Compound 21 at 4 g ai/ha and fenoxaprop-ethyl at 62 g ai/ha was applied postemergence. Diclofop-methyl was applied at 1000 g ai/ha postemergence. A mixture of Compound 21 at 4 g ai/ha and diclofop-methyl at 1000 g ai/ha was applied postemergence. Tralkoxydim was applied at 31 g ai/ha postemergence. A mixture of Compound 21 at 4 g ai/ha and tralkoxydim at 31 g ai/ha was applied postemergence. Clodinafop was applied at 31 g ai/ha postemergence. A mixture of Compound 21 at 4 g ai/ha and clodinafop at 31 g ai/ha was applied postemergence. Imazamethabenz was applied at 250 g ai/ha postemergence. A mixture of Compound 21 at 4 g ai/ha and imazamethabenz at 250 g ai/ha was applied postemergence. Sulfosulfuron was applied at 4 g ai/ha postemergence. A mixture of Compound 21 at 4 g ai/ha and sulfosulfuron at 4 g ai/ha was applied postemergence. Difenzoquat was applied at 2000 g ai/ha postemergence. A mixture of Compound 21 at 4 g ai/ha and difenzoquat at 2000 g ai/ha was applied postemergence. Quinclorac was applied at 250 g ai/ha postemergence. A mixture of Compound 21 at 4 g ai/ha and quinclorac at 250 g ai/ha was applied postemergence. Prosulfuron was applied at 8 g ai/ha postemergence. A mixture of Compound 21 at 4 g ai/ha and prosulfuron at 8 g ai/ha was applied postemergence. Metribuzin was applied at 62 g ai/ha postemergence. A mixture of Compound 21 at 4 g ai/ha and metribuzin at 62 g ai/ha was applied postemergence. Glyphosate was applied at 500 g ai/ha postemergence. A mixture of Compound 21 at 4 g ai/ha and glyphosate at 500 g ai/ha was applied postemergence. Triallate was applied at 500 g ai/ha preemergence. Triallate at 500 g ai/ha was applied preemergence followed by application of Compound 21 at 4 g ai/ha postemergence. Trifluralin was applied at 750 g ai/ha preemergence. Trifluralin at 750 g ai/ha was applied preemergence followed by application of Compound 21 at 4 g ai/ha postemergence. After treatment, the plants were maintained in a greenhouse and evaluated approximately 18 days after spraying. All sprayed plants were evaluated for injury as compared to control plants that were sprayed only with non-phytotoxic solvent. Injury was evaluated visually using a 0 to 100% scale where 0 indicates no effect and 100 indicates complete control.

Results of Test M are shown in Table M, which lists the mean response of a specific weed to Compound 21 applied alone as a single active ingredient, applied as a mixture of Compound 21 and a specified mixture partner, and the expected additive effect of the herbicidal mixture of Compound 21 and that specified mixture partner (from Colby's equation). Weeds other than those specifically listed are also controlled by mixtures of Compound 21 and the above specified mixture partners. Different ratios of Compound 21 to the above specified mixture partners, and different formulation types, also provide useful weed control from the combination of the two herbicides.

TABLE M*

Effect of Compound 21 as Active Ingredient Alone and in Mixture

| Cmpd. 21 (g ai/ha) | Mixture Partner | Mixture Partner Rate (g ai/ha) | | KCHSC | SASKR | POLCO | STEME | GALAP | AVEFA | SETVI |
|---|---|---|---|---|---|---|---|---|---|---|
| 4 | none | | | 90 | 60 | 45 | 75 | 60 | 2 | 25 |
| 0 | fenoxypropethyl | 62 | Mean | 0 | 30 | 0 | 0 | 15 | 60 | 100 |
| 4 | fenoxypropethyl | 62 | Mean | 85 | 90 | 50 | 80 | 70 | 65 | 95 |
| 4 | fenoxypropethyl | 62 | Exp.1 | 90 | 72 | 45 | 75 | 66 | 61 | 100 |
| 0 | diclofopmethyl | 1000 | Mean | 0 | 35 | 10 | 30 | 50 | 85 | 85 |
| 4 | diclofopmethyl | 1000 | Mean | 85 | 45 | 100 | 75 | 85 | 85 | 85 |
| 4 | diclofopmethyl | 1000 | Exp. | 90 | 74 | 51 | 83 | 80 | 85 | 89 |
| 0 | tralkoxydim | 31 | Mean | 0 | 5 | 5 | 25 | 0 | 40 | 20 |
| 4 | tralkoxydim | 31 | Mean | 90 | 70 | 55 | 75 | 80 | 55 | 60 |
| 4 | tralkoxydim | 31 | Exp. | 90 | 62 | 48 | 81 | 60 | 41 | 40 |
| 0 | clodinafop | 31 | Mean | 5 | 10 | 5 | 0 | 25 | 100 | 100 |
| 4 | clodinafop | 31 | Mean | 85 | 75 | 40 | 60 | 70 | 100 | 100 |
| 4 | clodinafop | 31 | Exp. | 91 | 64 | 48 | 75 | 70 | 100 | 100 |
| 0 | imazamethabenz | 250 | Mean | 5 | 30 | 50 | 10 | 75 | 90 | 25 |
| 4 | imazamethabenz | 250 | Mean | 90 | 50 | 90 | 50 | 75 | 90 | 30 |
| 4 | imazamethabenz | 250 | Exp. | 91 | 72 | 73 | 78 | 90 | 90 | 44 |
| 0 | sulfosulfuron | 4 | Mean | 30 | 65 | 50 | 75 | 60 | 70 | 75 |
| 4 | sulfosulfuron | 4 | Mean | 90 | 50 | 75 | 80 | 80 | 75 | 65 |
| 4 | sulfosulfuron | 4 | Exp. | 93 | 86 | 73 | 94 | 84 | 71 | 81 |
| 0 | difenzoquat | 2000 | Mean | 30 | 20 | 25 | 25 | 10 | 90 | 15 |
| 4 | difenzoquat | 2000 | Mean | 80 | 40 | 30 | 40 | 70 | 90 | 35 |
| 4 | difenzoquat | 2000 | Exp. | 93 | 68 | 59 | 81 | 64 | 90 | 36 |
| 0 | quinclorac | 250 | Mean | 5 | 35 | 0 | 30 | 55 | 0 | 75 |
| 4 | quinclorac | 250 | Mean | 85 | 45 | 50 | 85 | 85 | 3 | 70 |
| 4 | quinclorac | 250 | Exp. | 91 | 74 | 45 | 83 | 82 | 2 | 81 |
| 0 | prosulfuron | 8 | Mean | 90 | 90 | 100 | 90 | 60 | 15 | 10 |

TABLE M*-continued

Effect of Compound 21 as Active Ingredient Alone and in Mixture

| Cmpd. 21 (g ai/ha) | Mixture Partner | Mixture Partner Rate (g ai/ha) | | KCHSC | SASKR | POLCO | STEME | GALAP | AVEFA | SETVI |
|---|---|---|---|---|---|---|---|---|---|---|
| 4 | prosulfuron | 8 | Mean | 90 | 95 | 100 | 95 | 80 | 10 | 50 |
| 4 | prosulfuron | 8 | Exp. | 99 | 96 | 100 | 98 | 84 | 17 | 33 |
| 0 | metribuzin | 62 | Mean | 95 | 10 | 5 | 80 | 0 | 35 | 30 |
| 4 | metribuzin | 62 | Mean | 90 | 60 | 70 | 85 | 55 | 30 | 50 |
| 4 | metribuzin | 62 | Exp. | 100 | 64 | 48 | 95 | 60 | 36 | 48 |
| 0 | glyphosate | 500 | Mean | 20 | 20 | 15 | 80 | 50 | 80 | 100 |
| 4 | glyphosate | 500 | Mean | 95 | 85 | 85 | 100 | 85 | 80 | 100 |
| 4 | glyphosate | 500 | Exp. | 92 | 68 | 53 | 95 | 80 | 80 | 100 |
| 0 | triallate | 500 | Mean | 60 | 80 | 0 | 0 | 100 | —[2] | — |
| 4 | triallate | 500 | Mean | 80 | 100 | 100 | 100 | 100 | — | — |
| 4 | triallate | 500 | Exp. | 96 | 92 | 45 | 75 | 100 | — | — |
| 0 | trifluralin | 750 | Mean | 40 | 70 | 10 | 50 | 0 | — | — |
| 4 | trifluralin | 750 | Mean | 80 | 100 | 100 | 90 | 100 | — | — |
| 4 | trifluralin | 750 | Exp. | 94 | 88 | 51 | 88 | 60 | — | — |

*Data are reported as percent control.
[1]"Exp." are expected responses calculated according to Colby, S. R. "Calculating Synergistic and Antagonistic Responses of Herbicide Combinations," Weeds, 15(1), pp 20–22 (1967).
"—" represents no data available.

What is claimed is:

1. A compound selected from Formula I, N-oxides and agriculturally suitable salts thereof,

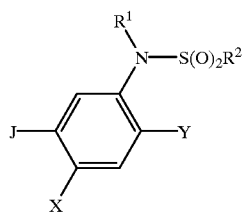

wherein

X is H, F or Cl;
Y is F, Cl, Br, nitro, $C_1$–$C_3$ haloalkyl, $C_1$–$C_3$ alkoxy, $C_1$–$C_3$ haloalkoxy or C(S)NH$_2$;
$R^1$ is H, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, $C_2$–$C_6$ alkoxyalkyl, $C_2$–$C_6$ haloalkoxyalkyl, formyl, $C_2$–$C_{20}$ alkylcarbonyl, $C_4$–$C_7$ cycloalkylcarbonyl, $C_2$–$C_6$ haloalkylcarbonyl, $C_2$–$C_6$ alkoxycarbonyl, $C_3$–$C_6$ alkoxyalkylcarbonyl, $C_2$–$C_6$ haloalkoxycarbonyl, $C_3$–$C_6$ cycloalkyl, $C_3$–$C_6$ halocycloalkyl, $C_4$–$C_7$ cycloalkylalklyl, $C_4$–$C_7$ halocycloalkylalkyl, $S(O)_2R^2$, $C(O)SR^3$, $C(O)NR^4R^5$ or benzoyl;
$R^2$ is $C_1$–$C_6$ monohaloalkyl;
$R^3$ is H, $C_1$–$C_3$ alkyl or $C_1$–$C_3$ haloalklyl; or $R^3$ is phenyl optionally substituted with $C_1$–$C_3$ alkyl, 1–3 halogen, 4–5 fluorine, 1–2 nitro, $C_1$–$C_3$ alkoxy or $CF_3$;
$R^4$ is H, $C_1$–$C_3$ alkyl or $C_1$–$C_3$ haloalkyl; or $R^4$ is phenyl optionally substituted with $C_1$–$C_3$ alkyl, 1–3 halogen, 4–5 fluorine, 1–2 nitro, $C_1$–$C_3$ alkoxy or $CF_3$;
$R^5$ is $C_1$–$C_3$ alkyl or $C_1$–$C_3$ haloalkyl;
$R^6$ is $C_1$–$C_3$ alkylsulfonyl, $C_1$–$C_3$ haloalkylsulfonyl or $P(=O)(OR^7)(OR^8)$; or $R^6$ is phenylsulfonyl optionally substituted with $C_1$–$C_6$ alkyl, 1–3 halogen, 4–5 fluorine, $C_1$–$C_6$ alkoxy, $CF_3$ or $C_2$–$C_4$ alkylcarbonyl;

$R^7$ and $R^8$ are each independently H, $C_1$–$C_3$ alkyl or $C_1$–$C_3$ haloalkyl;
J is

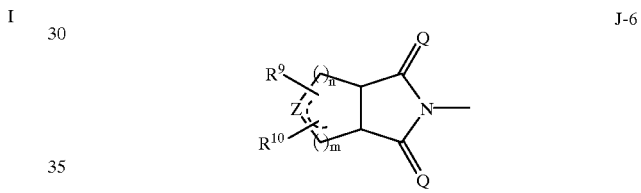

wherein the dashed line in J-6 indicates that the left-hand ring contains only single bonds or one bond in the ring is a carbon—carbon double bond;
m and n are each independently 0, 1, 2 or 3, provided that m+n is 2 or 3;
Z is $CR^9R^{10}$;
each $R^9$ is independently H, $C_1$–$C_6$ alkyl, halogen, hydroxy, $C_1$–$C_6$ alkoxy, $C_1$–$C_6$ haloalkyl, $C_1$–$C_6$ haloalkoxy, $C_2$–$C_6$ alkylcarbonyloxy or $C_2$–$C_6$ haloalkylcarbonyloxy;
each $R^{10}$ is independently H, $C_1$–$C_6$ alkyl, hydroxy or halogen; or
when $R^9$ and $R^{10}$ are bonded to adjacent carbon atoms they can be taken together with the carbons to which they are attached to form,

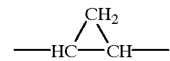

optionally substituted with at least one member selected from 1–2 halogen and 1–2 $C_1$–$C_3$ alkyl;
Q is independently O or S;
p is 1, 2 or 3; and
q is 0, 1, 2 or 3.

2. A compound of claim 1 wherein:
X is F or Cl;
Y is F, Cl or Br;

$R^1$ is H, $C_1$–$C_6$ alkyl, $C_3$–$C_6$ cycloalkyl, $C_3$–$C_6$ alkenyl, $C_3$–$C_6$ alkynyl, $C_1$–$C_6$ haloalkyl, $C_2$–$C_6$ alkoxyalkyl, $C_3$–$C_6$ haloalkenyl, $C_3$–$C_6$ alkoxyalkylcarbonyl, $C_2$–$C_6$ alkylcarbonyl, $C_2$–$C_6$ alkoxycarbonyl, $S(O)_2R^2$ or $C(O)NR^4R^5$;

$R^2$ is $C_1$–$C_6$ monohaloalkyl;

each $R^9$ is independently H, halogen or $C_1$–$C_6$ haloalkoxy;

each $R^{10}$ is independently H, hydroxy or halogen; and each Q is O.

3. A compound of claim 2 wherein:

Y is F or Cl;

$R^1$ is H, $C_1$–$C_6$ alkyl, $C_3$–$C_6$ cycloalkyl, $C_3$–$C_6$ alkenyl, $C_3$–$C_6$ alkynyl, $C_1$–$C_6$ haloalklyl, $C_2$–$C_6$ alkoxyalkyl, $C_3$–$C_6$ haloalkenyl, $C_2$–$C_6$ alkylcarbonyl or $C_2$–$C_6$ alkoxycarbonyl; and $R^2$ is $C_1$–$C_6$ monohaloalkyl.

4. The compound of claim 3 which is selected from the group:

a) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide;

b) (6S-cis)-N-[2-chloro-4-fluoro-5-(6-fluorotetrahydro-1,3-dioxo-1H-pyrrolo[1,2-c]imidazol-2(3H)phenyl]-N-[(chloromethyl)sulfonyl]acetamide;

c) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide;

d) (6S-cis)-N-[2-chloro-5-(6-chlorotetrahydro-1,3-dioxo-1H-pyrrolo[1,2-c]imidazol-2(3H)-yl)-4-fluorophenyl]-N-[(chloromethyl)sulfonyl]acetamide;

e) (6S-cis)-1-chloro-N-[2-chloro-4-fluoro-5-(6-fluorotetrahydro-1,3-dioxo-1H-pyrrolo[1,2-c]imidazol-2(3H)-yl)phenyl]methanesulfonamide monosodium salt;

f) (6S-cis)-1-chloro-N-[2-chloro-4-fluoro-5-(6-fluorotetrahydro-1,3)-dioxo-1H-pyrrolo[1,2-c]imidazol-2(3H)-yl)phenyl]methanesulfonamide monopotassium salt;

g) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide monosodium salt; and h) (6S-cis)-1-chloro-N-[2-chloro-5-(6-chlorotetrahydro-1,3-dioxo-1H-pyrrolo[1,2-c]imidazol-2(3H)-yl)-4-fluorophenyl]methanesulfonamide monopotassium salt.

5. A mixture comprising a herbicidally effective amount of a compound of claim 4 with a herbicidally effective amount of one or more compounds selected from rimsulfuron, thifensulfuron-methyl, chlorimuron-ethyl, nicosulfuron, prosulfuron, primisulfuron, atrazine, terbuthylazine, dicamba, 2,4-D, bomoxynil, pyridate, sulcotrione, glufosinate, glyphosate, glyphosate-trimesium, fluthiacet-methyl, quizalofop-p-ethyl, bentazone, clopyralid, flumetsulam, halosulfuron, sethoxydim, flumiclorac-pentyl, imazamox, acetochlor, alachlor, dimethenamid, isoxaflutole, metolachlor, metribuzin, pendimethalin, thiafluimid, clethodim, fluazifop-p-butyl, haloxyfop, imazethapyr, imazaquin, lactofen, acifluorfen-sodium, oxasulfuron, imazameth, tribenuron-methyl, metsulfuron-methyl, chlorsulfuron, triasulfuron, bromoxynil, MCPA, fluroxypyr, fenoxaprop, fenchlorazole, diclofop, tralkoxydim, clodinafop, cloquintocet-mexyl, imazamethabenz. sulfosulfuron, difenzoquat, propanil, triallate, trifluralin, paraquat, diallate, linuron, diflufenican, cyanazine, neburon, terbutryn, prosulfocarb, isoproturon, chlortoluron, methabenzthiazuron, metoxuron, simazine, ioxynil, mecoprop, metosulam, fluroglycophen-ethyl, flamprop-M-isopropyl, and benzoylpropethyl.

6. A herbicidal composition comprising a herbicidally effective amount of a compound of claim 1 and at least one of a surfactant, a solid diluent or a liquid diluent.

7. A herbicidal composition comprising a herbicidally effective amount of a mixture of claim 5 and at least one of a surfactant, a solid diluent or a liquid diluent.

8. A method for controlling the growth of undesired vegetation comprising contacting the vegetation or its environment with a herbicidally effective amount of a compound of claim 1.

9. A method for controlling the growth of undesired vegetation comprising contacting the vegetation or its environment with a herbicidally effective amount of a mixture of claim 5.

* * * * *

UNITED STATES PATENT AND TRADEMARK OFFICE
CERTIFICATE OF CORRECTION

PATENT NO.   : 6,060,432
DATED        : May 9, 2000
INVENTOR(S)  : Edward J. Adams et al.

Page 1 of 1

It is certified that error appears in the above-identified patent and that said Letters Patent is hereby corrected as shown below:

<u>Column 202,</u>
Compound J-6 " " should read -- --

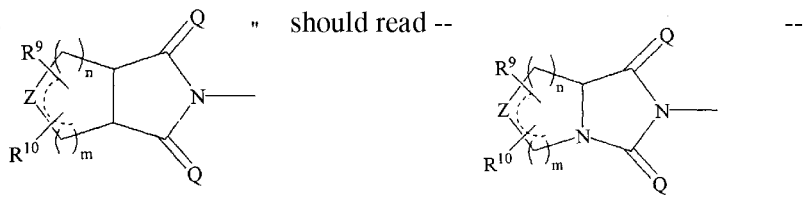

Signed and Sealed this

Thirty-first Day of August, 2004

*JON W. DUDAS*
*Director of the United States Patent and Trademark Office*